US 6,699,884 B2

(12) United States Patent
Brown et al.

(10) Patent No.: US 6,699,884 B2
(45) Date of Patent: Mar. 2, 2004

(54) FLUORO-SUBSTITUTED BENZENESULFONYL COMPOUNDS FOR THE TREATMENT OF INFLAMMATION

(75) Inventors: David L. Brown, Chesterfield, MO (US); Matthew J. Graneto, Chesterfield, MO (US); Cindy L. Ludwig, St. Louis, MO (US); John M. Molyneaux, St. Louis, MO (US); John J. Talley, Cambridge, MA (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 10/319,916

(22) Filed: Dec. 13, 2002

(65) Prior Publication Data

US 2003/0149078 A1 Aug. 7, 2003

Related U.S. Application Data

(63) Continuation of application No. 10/124,209, filed on Apr. 16, 2002.
(60) Provisional application No. 60/285,264, filed on Apr. 20, 2001.

(51) Int. Cl.$^7$ .................. A61K 31/40; A61K 31/44; C07C 317/32; C07D 213/02
(52) U.S. Cl. ............... 514/336; 514/357; 514/408; 514/520; 514/602; 514/709; 546/268.1; 546/339; 546/329; 546/330; 548/413; 548/577; 564/84; 564/85; 564/86; 568/29; 568/28
(58) Field of Search ................ 514/336, 357, 514/408, 520, 602, 709; 546/268.1, 339, 330, 329; 548/577, 413; 564/84, 85, 86; 568/28, 29

(56) References Cited

U.S. PATENT DOCUMENTS

| 4,146,721 A | 3/1979 | Rainer |
| 4,822,805 A | 4/1989 | Takasugi et al. |
| 4,914,121 A | 4/1990 | Sawai et al. |
| 5,051,518 A | 9/1991 | Murray et al. |
| 5,134,142 A | 7/1992 | Matsuo et al. |
| 5,338,749 A | 8/1994 | Wuest et al. |
| 5,344,991 A | 9/1994 | Reitz et al. |
| 5,380,738 A | 1/1995 | Norman et al. |
| 5,387,592 A | 2/1995 | Bradbury et al. |
| 5,389,635 A | 2/1995 | Olson |
| 5,393,790 A | 2/1995 | Reitz et al. |
| 5,401,765 A | 3/1995 | Lee |
| 5,418,254 A | 5/1995 | Huang et al. |
| 5,420,287 A | 5/1995 | Reitz et al. |

(List continued on next page.)

FOREIGN PATENT DOCUMENTS

| EP | 26928 A1 | 4/1981 |
| EP | 197704 A2 | 10/1986 |
| EP | 372445 B1 | 6/1990 |
| EP | 418 845 A1 | 3/1991 |
| EP | 745596 A1 | 12/1996 |
| EP | 799823 A1 | 10/1997 |
| EP | 1 064 964 A2 | 1/2001 |
| GB | 2294879 A | 5/1996 |
| JP | 1045374 A | 2/1989 |
| JP | 4277724 A | 10/1992 |
| JP | 5323522 A | 12/1993 |
| WO | WO 92/05162 A1 | 4/1992 |
| WO | WO 92/19604 A1 | 11/1992 |
| WO | WO 93/14082 A1 | 7/1993 |
| WO | WO 94/13635 A1 | 6/1994 |
| WO | WO 94/15932 A1 | 7/1994 |
| WO | WO 94/20480 A1 | 9/1994 |
| WO | WO 94/26731 A1 | 11/1994 |
| WO | WO 95/00501 A2 | 1/1995 |
| WO | WO 95/30652 A1 | 11/1995 |
| WO | WO 95/30656 A1 | 11/1995 |
| WO | WO 96/03387 A1 | 2/1996 |
| WO | WO 96/03388 A1 | 2/1996 |
| WO | WO 96/09293 A1 | 3/1996 |
| WO | WO 96/19462 A1 | 6/1996 |
| WO | WO 96/19463 A1 | 6/1996 |
| WO | WO 96/36617 A1 | 11/1996 |
| WO | WO 96/37467 A1 | 11/1996 |
| WO | WO 97/16435 A1 | 5/1997 |
| WO | WO 97/25045 A1 | 7/1997 |
| WO | WO 97/25047 A1 | 7/1997 |
| WO | WO 97/25048 A1 | 7/1997 |
| WO | WO 98/03484 A1 | 1/1998 |
| WO | WO 98/07425 A1 | 2/1998 |
| WO | WO 98/11080 A1 | 3/1998 |
| WO | WO 98/22442 A1 | 5/1998 |
| WO | WO 98/47890 A1 | 10/1998 |
| WO | WO 99/14205 A1 | 3/1999 |
| WO | WO 99/64415 A1 | 12/1999 |

OTHER PUBLICATIONS

Ahluwalia et al., "Mechanism of the Debromination in Heteocyclization Using α,α–Dibromocarbonyl Compounds as Synthons." Synth. Commun., 1989, pp. 619–626, vol. 19, Nos. 3&4.

(List continued on next page.)

Primary Examiner—Zinna Northington Davis

(57) ABSTRACT

Methods of treating cyclooxygenase-2 mediated disorders comprising administering to a subject a therapeutically effective amount of one or more fluoro-substituted benzenesulfonyl compounds corresponding to Formula I:

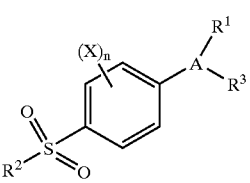

wherein A, X, n, $R^1$, $R^2$, and $R^3$ are as described in the specification, and novel fluoro-substituted benzenesulfonyl compounds within Formula I.

16 Claims, No Drawings

U.S. PATENT DOCUMENTS

| | | | |
|---|---|---|---|
| 5,434,178 | A | 7/1995 | Talley et al. |
| 5,466,823 | A | 11/1995 | Talley et al. |
| 5,475,018 | A | 12/1995 | Lee et al. |
| 5,486,534 | A | 1/1996 | Lee et al. |
| 5,504,215 | A | 4/1996 | Talley et al. |
| 5,508,426 | A | 4/1996 | Talley et al. |
| 5,510,496 | A | 4/1996 | Talley et al. |
| 5,516,907 | A | 5/1996 | Talley et al. |
| 5,521,193 | A | 5/1996 | Flynn et al. |
| 5,521,207 | A | 5/1996 | Graneto |
| 5,534,521 | A | 7/1996 | Flynn et al. |
| 5,565,482 | A | 10/1996 | Talley et al. |
| 5,576,339 | A | 11/1996 | Huang et al. |
| 5,596,008 | A | 1/1997 | Lee |
| 5,616,601 | A | 4/1997 | Khanna et al. |
| 5,639,777 | A | 6/1997 | Lee |
| 5,663,180 | A | 9/1997 | Reitz et al. |
| 5,668,161 | A | 9/1997 | Talley et al. |
| 5,670,510 | A | 9/1997 | Huang et al. |
| 5,672,626 | A | 9/1997 | Huang et al. |
| 5,672,627 | A | 9/1997 | Huang et al. |
| 5,719,163 | A | 2/1998 | Norman et al. |
| 5,736,579 | A | 4/1998 | Reitz et al. |
| 5,739,166 | A | 4/1998 | Reitz et al. |
| 5,756,529 | A | 5/1998 | Isakson et al. |
| 5,760,068 | A | 6/1998 | Talley et al. |
| 5,859,036 | A | 1/1999 | Sartori et al. |
| 5,859,257 | A | 1/1999 | Talley |
| 5,886,016 | A | 3/1999 | Talley et al. |
| 5,908,852 | A | 6/1999 | Talley et al. |
| 5,916,905 | A | 6/1999 | Weier et al. |
| 5,932,598 | A | 8/1999 | Talley et al. |
| 5,935,990 | A | 8/1999 | Khanna et al. |
| 5,994,381 | A | 11/1999 | Haruta et al. |

OTHER PUBLICATIONS

Bagetta et al., "HIV–1 gp120–Induced Apoptosis in the Rat Neocortex Involves Enhanced Expression of Cyclo–Oxygenase Type 2 (Cox–2)." Biochem. Biophys. Res. Commun., 1998, pp. 819–824, vol. 244.

Barnes et al., "Cyclooxygenase–2 Expression in Airway Cells." Lung Biol. Health Dis, 1998, pp. 111–127, vol. 114.

Bosch et al., "Efficacy and Tolerability of Intramuscular and Oral Meloxicam in Patients with Acute Lumbago: A Comparison with Intramuscular and Oral Piroxicam." Curr. Med. Res. Opin., 1997, pp 29–38, vol. 14, No. 1.

Buckman et al., "Cox–2 Expression in Induced by UVB Exposure in Human Skin: Implications for the development of skin cancer." Carcinogenesis, 1998, pp. 723–729, vol. 19, No. 5.

Bustos et al., "Modulation of Eicosanoid Metabolism in Endothellal Cells in a Xenograft Model." J. Clin. Invest., 1997, pp 1150–1158, vol. 100, No. 5.

Chu et al., "Synthesis of Sodium androst–5–ene–17–one–3β–methylene sulfonate." Steroids, 1997, pp 543–545, vol. 62.

Dikshit et al., "Synthesis and biological activity of 2,3– and 3,4–diarylfurans and 2,3,4–triaryl–2,5–dihydrofurans." Indian J. Chem, Sect. B, 1990, pp 954–960, vol. 29B, No. 10.

Dorofeenko et al., Khim. Farm. Zh., 1982, pp. 920–921, vol. 16.

Faid–Allah et al., "Pyrazole Derivatives with Possible Hypoglycemic Activity." Ind. J. Chem., Sect. B, 1988, pp. 245–249, vol. 27B, No. 3.

Gierse et al., "Expression and selective inhibition of the constitutive and inducible forms of human cyclo–oxygenase." Biochem J., 1995, pp. 479–484, vol. 305, Part 2.

Hargreaves et al., "A New and Sensitive Method for Measuring thermal Nociception in Cutaneous Hyperalgesia." Pain, 1988, pp. 77–88, vol. 32.

Hida et al., "Non–small Cell Lung Cancer Cyclooxygenase Activity and Proliferation are Inhibited by Non–steroidal Antiinflammatory Drugs." Anticancer Res., 1998, pp. 775–782, vol. 18, No. 1A.

Huang et al., "A Novel One–Pot Conversion of Methyl Sulfones to Sulfonamides." Tetrahedron Letters, 1994, pp. 7201–7204, vol. 35, No. 39.

Kawamori et al., "Chemopreventive Activity of Celecoxib, a Specific Cyclooxygenase–2 Inhibitor, against Colon Carcinogensis." Cancer Res., 1998, pp. 409–412, vol. 58, No. 3.

Kharasch et al., "Derivatives of Sulfenic Acids. V. 1–Fluorenone Sulfur Compounds." J. Am. Chem. Soc., 1951, pp. 3240–3244, vol. 73, No. 7.

Miyamoto et al., "The effect of cyclooxygenase–2 inhibitor on experimental allergic neuritis." Neuro Report, 1998, pp. 2331–2334, vol. 9, No. 10.

Miyaura et al., "The Palladium–Catalyzed Cross–Coupling Reaction of Phenylboronic Acid with Haloarenes in the Presence of Bases." Synth. Commun., 1981, pp. 513–519, vol. 11, No. 7.

Mukerjee et al., "Synthesis of Some Formazans and tetarazolium salts as antiviral agents." Acta. Pharma. Jugosl., 1981, pp. 151–158, vol. 31.

Nasjletti A. "The Role of Eicosanoids in Angiotensin–Dependent Hypertension." Hypertension, 1998, pp. 194–200, vol. 31, No. 1, Part 2.

Nogawa et al., "Interaction between inducible nitirc oxide synthase and cyclooxygenase–2 after cerebral ischemia." Proc. Natl. Acad. Sci., 1998, pp. 10966–10971, vol. 95, No. 18.

Reid et al., "Some New β–Diketones Containing the Trifluoromethyl Group." J. Amer. Chem. Soc., 1950, pp 2948–2952, vol. 72, No. 7.

Sandhya et al., "A light and electron microscopic study of cytoplasmic phospholipase $A_2$ and cyclooxygenase–2 in the hippocampus after kainate lesions." Brain Res., 1998, pp. 223–231, vol. 788.

Shoup et al., "Cyclooxygenase–2 Inhibitor NS–398 Improves Survival and Restores Leukocyte Counts in Burn Infection." J. Trauma: Inj., Infec., Crit Care, 1998, pp 215–221, vol. 45, No. 2.

Singer et al., "Cyclooxygenase 2 Is Induced in Colonic Epithelial Cells in Inflammatory Bowel Disease." Gastroenterology, 1998, pp. 297–306, vol. 115, No. 2.

Speir et al., "Aspirin Attenuates Cytomegalovirus Infectivity and Gene Expression Mediated by Cyclooxygenase–2 in Coronary Artery Smooth Muscle Cells." Circ. Res., 1998, pp. 210–216, vol. 83, No. 2.

Subbaramaiah et al., "Inhibition of Cyclooxygenase: A Novel Approach to Cancer Prevention (44170)." Proc. Soc. Exp. Biol. Med., 1997, pp. 201–210, vol. 216, No. 2.

Tsujii et al., "Cyclooxygenase Regulates Angiogenesis Induced by Colon Cancer Cells." Cell, 1998, pp. 705–716, vol. 93, No. 5.

Vleeschauwer et al., "Remarkably Mild and Simple Preparations of Sulfinates, Sulfonyl Chlorides and Sulfonamides from Thioanisoles." Syn. Lett., 1997, pp. 375–377, vol. 4.

Wilson et al., "Increased Expression of Inducible Nitric Oxide Synthase and Cyclooxygenase–2 in Barrett's Esophagus and Associated Adenocarcinomas." Cancer Res., 1998, pp. 2929–2934, vol. 58, No. 14.

Winter et al., "Carrageenin–Induced Edema in Hind Paw of the Rat as an Assay for Antiinflammatory Drugs." Proc. Soc. Exp. Biol. Med., 1962. pp. 544–547, vol. 111.

US 6,699,884 B2

FLUORO-SUBSTITUTED BENZENESULFONYL COMPOUNDS FOR THE TREATMENT OF INFLAMMATION

REFERENCE TO RELATED APPLICATION

This application claims priority from U.S. Provisional Application Serial No. 60/285,264, filed Apr. 20, 2001, the contents of which are hereby incorporated by reference in their entirety.

FIELD OF THE INVENTION

This invention is in the field of anti-inflammatory pharmaceutical agents and generally relates to compounds, compositions and methods for treating cyclooxygenase-2 mediated disorders, such as inflammation and inflammation-related disorders. The invention particularly relates to fluoro-substituted benzenesulfonyl compounds, compositions and methods for treating cyclooxygenase-2 mediated disorders.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. Common non-steroidal antiinflammatory drugs ("NSAIDs") that are active in reducing the prostaglandin-induced pain and swelling associated with the inflammation process are, however, also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

Recently, there has been significant research into some of the roles of cyclooxygenase-2. It has been found that COX-2 is upregulated in benign and malignant tumors (K. Subbaramaiah et al., *Proc. Soc. Exp. Biol. Med.*, 216, 201 (1997)) including lung cancer (T. Hida et al., *Anticancer Res.*, 18, 775–82 (1998)), Barrett's esophagus (K. Wilson, *Cancer Res.*, 58, 2929–34 (1998)) and skin cancer (S. Buckman et al., *Carcinogenesis*, 19, 723–29 (1998)). It is expressed in airway cells with implication in asthma (P. Barnes et al., *Lung Biol. Health Dis.*, 114, 111–27 (1998)). COX-2 also has a role in pre-term labor, angiogenesis (M. Tsujii et al., *Cell*, 93, 705–16 (1998)), vascular rejection (M. Bustos, *J. Clin. Invest.*, 100, 1150–58 (1997)), HIV induced apoptosis (G. Bagetta et al., *Biochem. Biophys. Res. Commun.*, 244, 819–24 (1998)), neurodegeneration (T. Sandhya et al., *Brain Res.*, 788, 223–31 (1998)), inflammatory bowel disease, colitis, (I. Singer et al., *Gastroenterology*, 115, 297–306 (1998)), cerebral ischemia (S. Nogawa et al., *Proc. Natl. Acad. Sci.*, 95, 10966–71 (1998)), and hypertension (A. Nasjletti, *Hypertension*, 31, 194–200 (1997)), among others.

Drugs that inhibit cyclooxygenase affect colon cancer (T. Kawamori et al., *Cancer Res.*, 58, 409–12 (1998)), allergic neuritis (K. Miyamoto et al., *Neuro. Report*, 9, 2331–34 (1998)), dementia, burn infections (M. Shoup, *J. Trauma: Inj., Infec., Crit. Care*, 45, 215–21 (1998)), cytomegalovirus infectivity (E. Speir et al., *Circ. Res.*, 83, 210–16 (1998)), and lumbago (H. Bosch, *Curr. Med. Res. Opin.*, 14, 29–38 (1997)), among others.

The references below disclose compounds having antiinflammatory activity and show that efforts are continuing to find a safe and effective antiinflammatory agent. WO96/19463 describes oxazoles substituted with a [(2- or 3)-halo-4-(alkylsulfonyl, aminosulfonyl or alkylaminosulfonyl)] phenyl group that selectively inhibit cyclooxygenase-2. U.S. Pat. No. 5,380,738 describes 4-fluoro-phenyl and 4-methylsulfonyl substituted oxazoles that selectively inhibit cyclooxygenase-2. U.S. Pat. No. 5,719,163 describes substituted oxazoles that selectively inhibit cyclooxygenase-2. WO96/36617 describes oxazoles that selectively inhibit cyclooxygenase-2. WO96/19462 describes oxazoles that selectively inhibit cyclooxygenase-2. WO98/11080 describes 3,4-diaryl-oxazolones that selectively inhibit cyclooxygenase-2.

EP 799,823 A1 describes 1- or 2-[3-halo-4-(methylsulfonyl, aminosulfonyl or substituted aminosulfonyl)phenyl]-pyrroles that selectively inhibit cyclooxygenase-2. U.S. Pat. No. 5,935,990 describes substituted pyrroles that selectively inhibit cyclooxygenase-2.

WO99/64415 describes 1-(4-bromophenyl)-2-[3-fluoro-4-(methylsulfonyl)phenyl]-5-methyl-1H-pyrrole; 5-(4-bromophenyl)-1-[3-fluoro-4-(methylsulfonyl)phenyl]-3-(hydrogen, cyano, nitro, trifluoromethyl or ethoxycarbonyl)-1H-pyrazole; 2-[(4-bromophenyl) or (3-methyl-4-bromophenyl)]-1-[3-fluoro-4-(methylsulfonyl)phenyl]-4-trifluoromethyl-1H-imidazole; 4-[2-(4-bromophenyl)-4-hydroxy-4-trifluoromethyl-1H-imidazol-1-yl]-2-fluorobenzene sulfonamide; 3-(4-bromophenyl)-4-[3-fluoro-4-(methylsulfonyl)phenyl]-2(5H)-furanone; 3-(4-bromophenyl)-4-[3-fluoro-4-(methylsulfonyl or aminosulfonyl)phenyl]-5-methylisoxazole; 4-(4-bromophenyl)-5-[3-fluoro-4-(methylsulfonyl or aminosulfonyl)phenyl]-2-methyl-1,3-oxazole; and 4-(3-methyl-4-bromophenyl)-5-[3-fluoro-4-(methylsulfonyl)phenyl]-2-methyl-1,3-oxazole as intermediates used in the preparation of sulfonylbenzene compounds comprising an aryl or heteroaryl substituted phenyl moiety. WO99/64415 states that the disclosed sulfonylbenzene compounds are useful in the treatment of cyclooxygenase mediated diseases.

U.S. Pat. Nos. 5,466,823, 5,504,215, 5,508,426, 5,510, 496, 5,516,907, 5,521,207 and 5,760,068 describe substituted pyrazolyl benzenesulfonamides that selectively inhibit cyclooxygenase-2. U.S. Pat. No. 5,475,018 describes 1,5-diphenyl pyrazoles that selectively inhibit cyclooxygenase-2. U.S. Pat. Nos. 5,486,534 and 5,756,529 describe 3,4-substituted pyrazoles that selectively inhibit cyclooxygenase-2. U.S. Pat. Nos. 5,401,765 and 5,639,777 describe 1,4,5-trisubstituted pyrazoles that selectively inhibit cyclooxygenase-2. U.S. Pat. Nos. 5,434,178 and 5,908,852 describe 1,3,5-trisubstituted pyrazoles that selectively inhibit cyclooxygenase-2.

WO94/15932 describes thiophene and furan derivatives that selectively inhibit cyclooxygenase-2. WO94/26731 describes thiophene compounds that selectively inhibit cyclooxygenase-2. WO97/16435 describes 3,4-diaryl-2-hydroxy-2,5-dihydrofurans as prodrugs of compounds that are cyclooxygenase-2 inhibitors. GB 2,294,879 describes substituted furanones as cyclooxygenase-2 inhibitors.

U.S. Pat. No. 5,859,257 describes substituted isoxazoles that selectively inhibit cyclooxygenase-2. EP 745,596 describes substituted isoxazoles that selectively inhibit cyclooxygenase-2.

U.S. Pat. Nos. 5,344,991, 5,420,287 and 5,663,180 describe substituted cyclopentenes that selectively inhibit cyclooxygenase-2.

U.S. Pat. No. 5,418,254 describes substituted cyclopentadienyls that selectively inhibit cyclooxygenase-2.

U.S. Pat. No. 5,916,905 describes 2,3-substituted pyridines that selectively inhibit cyclooxygenase-2. U.S. Pat. No. 5,596,008 describes 3,4-diaryl substituted pyridines that selectively inhibit cyclooxygenase-2. WO98/03484 describes substituted pyridines that selectively inhibit cyclooxygenase-2.

U.S. Pat. Nos. 5,393,790 and 5,736,579 describe substituted spiro compounds that selectively inhibit cyclooxygenase-2.

U.S. Pat. Nos. 5,670,510, 5,672,626 and 5,672,627 describe spirodienes that selectively inhibit cyclooxygenase-2.

U.S. Pat. No. 5,668,161 describes substituted thiazoles that selectively inhibit cyclooxygenase-2.

U.S. Pat. No. 5,616,601 describes 1,2-substituted imidazoles that selectively inhibit cyclooxygenase-2. WO96/03387 describes 4,5-substituted imidazoles that selectively inhibit cyclooxygenase-2. WO96/03388 describes 1,2-substituted imidazoles that selectively inhibit cyclooxygenase-2. U.S. Pat. Nos. 5,521,193 and 5,534,521 describe benzimidazoles that selectively inhibit cyclooxygenase-2.

WO94/13635 describes 5-methanesulfonamido-1-indanones that selectively inhibit cyclooxygenase-2. WO94/20480 describes alkanesulfonamido-1-indanones that selectively inhibit cyclooxygenase-2.

WO96/09293 describes benz[g]indazolyls that selectively inhibit cyclooxygenase-2.

WO98/47890 describes benzopyran derivatives that selectively inhibit cyclooxygenase-2. U.S. Pat. No. 5,886,016 describes benzopyranopyrazolyls that selectively inhibit cyclooxygenase-2. U.S. Pat. No. 5,565,482 describes heteroarylpyranopyrazolyls that selectively inhibit cyclooxygenase-2.

U.S. Pat. No. 5,739,166 describes substituted terphenyls that selectively inhibit cyclooxygenase-2.

Finally, various additional substituted sulfonamides have been described. Pyrazolyl-sulfonylureas have been described as having possible hypoglycemic activity [H. Faid-Allah and H. Mokhtar, *Ind. J. Chem.*, 27, 245 (1988)]. JP 1,045,374 describes water soluble tetrazolium compounds useful in assays for determining reducing substances. D. Mukerjee et al. [*Acta. Pharma. Jugosl.*, 31, 151 (1981)] describe tetrazolium sulfonamides as antiviral agents. JP 4,277,724 describes triphenyl pyrazolines as nonlinear optical material. JP 5,323,522 describes the use of heterocyclic compounds in black and white photographic material. U.S. Pat. No. 5,389,635 describes substituted imidazoles as angiotensin II antagonists. U.S. Pat. No. 5,387,592 describes substituted benzimidazole derivatives as angiotensin II antagonists. G. Dorofeenko et al. [*Khim. Farm. Zh.*, 16, 920 (1982)] describe pyridinium salts as antiviral agents. U.S. Pat. No. 5,338,749 describes diaryl-substituted heterocyclyl compounds as antiarthritis agents.

Compounds of the current invention, however, have not been described as antiinflammatory cyclooxygenase inhibitors.

DESCRIPTION OF THE INVENTION

The present invention comprises methods of treating cyclooxygenase-2 mediated disorders, such as inflammation, in a subject having or susceptible to such disorders by administering to the subject a therapeutically-effective amount of one or more compounds of Formulae I–VII as described below. The methods of the present invention also include prophylatic treatment of a subject. The compounds of Formulae I–VII comprise a class of fluoro-substituted benzene sulfonyl compounds that are safe and effective anti-inflammatory agents. These compounds generally exhibit improved selectivity and/or potency in inhibiting cyclooxygenase-2 over cyclooxygenase-1 relative to the corresponding sulfonamides or methylsulfones lacking such fluoro substituents. The present invention further comprises those novel fluoro-substituted benzene sulfonyl compounds within the class of compounds of Formulae I–VII.

More specifically, the present method of treating cyclooxygenase-2 mediated disorders comprises administering to the subject a therapeutically-effective amount of one or more compounds selected from the class of compounds defined by Formula I:

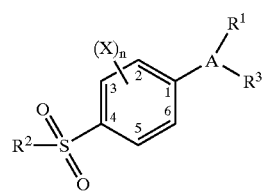

wherein:

A is a 5- or 6-member ring substituent selected from partially saturated or unsaturated heterocyclic and carbocyclic rings;

X is fluoro;

n is an integer greater than or equal to 2;

$R^1$ is cyclohexyl, pyridinyl, or phenyl, wherein said cyclohexyl, pyridinyl, and phenyl may be optionally substituted with one, two or three radicals selected from $C_{1-2}$-alkyl, $C_{1-2}$-haloalkyl, cyano, carboxyl, $C_{1-2}$-alkoxycarbonyl, hydroxyl, $C_{1-2}$-hydroxyalkyl, $C_{1-2}$-haloalkoxy, amino, $C_{1-2}$-alkylamino, phenylamino, nitro, $C_{1-2}$-alkoxy-$C_{1-2}$-alkyl, $C_{1-2}$-alkylsulfinyl, halo, $C_{1-2}$-alkoxy and $C_{1-3}$-alkylthio;

$R^2$ is alkyl (particularly methyl) or amino; and $R^3$ represents one or more radicals selected from hydrido, halo, $C_{1-2}$-alkyl, $C_{2-3}$-alkenyl, $C_{2-3}$-alkynyl, oxo, cyano, carboxyl, cyano-$C_{1-3}$-alkyl, heterocyclyloxy, $C_{1-3}$-alkoxy, $C_{1-3}$-alkylthio, alkylcarbonyl, cycloalkyl, phenyl, $C_{1-3}$-haloalkyl, heterocyclyl, cycloalkenyl, phenyl-$C_{1-3}$-alkyl, heterocyclyl-$C_{1-3}$-alkyl, $C_{1-3}$-alkylthio-$C_{1-3}$-alkyl, $C_{1-3}$-hydroxyalkyl, $C_{1-3}$-alkoxycarbonyl, phenylcarbonyl, phenyl-$C_{1-3}$-alkylcarbonyl, phenyl-$C_{2-3}$-alkenyl, $C_{1-3}$-alkoxy-$C_{1-3}$-alkyl, phenylthio-$C_{1-3}$-alkyl, phenyloxyalkyl, alkoxyphenylalkoxyalkyl, alkoxycarbonylalkyl, aminocarbonyl, aminocarbonyl-$C_{1-3}$-alkyl, $C_{1-3}$-alkylaminocarbonyl, N-phenylaminocarbonyl, N—($C_{1-3}$-alkyl)-N-phenylaminocarbonyl, $C_{1-3}$-alkylaminocarbonyl-$C_{1-3}$-alkyl, carboxy-$C_{1-3}$-alkyl, $C_{1-3}$-alkylamino, N-arylamino, N-aralkylamino, N—($C_{1-3}$-alkyl)-N-aralkylamino, N—($C_{1-3}$-alkyl)-N-arylamino, amino-$C_{1-3}$-alkyl, $C_{1-3}$-alkylaminoalkyl, N-phenylamino-$C_{1-3}$-alkyl, N-phenyl-$C_{1-3}$-alkylaminoalkyl, N—($C_{1-3}$-alkyl)-N-(phenyl-$C_{1-3}$-alkyl)amino-$C_{1-3}$-alkyl, N—($C_{1-3}$-alkyl)-N-phenylamino-$C_{1-3}$-alkyl, phenyloxy, phenylalkoxy, phenylthio, phenyl-$C_{1-3}$-alkylthio, $C_{1-3}$-alkylsulfinyl, $C_{1-3}$-alkylsulfonyl, aminosulfonyl, $C_{1-3}$-alkylaminosulfonyl, N-phenylaminosulfonyl, phenylsulfonyl, and N—($C_{1-3}$-alkyl)-N-phenylaminosulfonyl;

or a pharmaceutically-acceptable salt, tautomer or prodrug thereof.

In one embodiment, n is 2. Preferably, (a) one fluoro radical is present at the 2-position of the benzenesulfonyl compound (according to the numbering shown in Formula I above) and the other fluoro radical is present at the 5-position of the benzenesulfonyl compound, or (b) one fluoro radical is present at the 2-position of the benzenesulfonyl compound and the other fluoro radical is present at the 3-position of the benzenesulfonyl compound, or (c) one fluoro radical is present at the 3-position of the benzenesulfonyl compound and the other fluoro radical is present at the 5-position of the benzenesulfonyl compound.

In another embodiment, n is 3.

In another embodiment, n is 4.

In another embodiment, the present method of treating cyclooxygenase-2 mediated disorders comprises administering to the subject a therapeutically-effective amount of one or more compounds selected from a preferred class of compounds consisting of those compounds of Formula I wherein:

A is a 5- or 6-member ring substituent selected from partially saturated or unsaturated heterocyclic and carbocyclic rings;

X is fluoro;

n is an integer greater than or equal to 2;

$R^1$ is cyclohexyl, pyridinyl, or phenyl, wherein said cyclohexyl, pyridinyl, and phenyl may be optionally substituted with one, two or three radicals selected from $C_{1-2}$-alkyl, $C_{1-2}$-haloalkyl, cyano, carboxyl, $C_{1-2}$-alkoxycarbonyl, hydroxyl, $C_{1-2}$-hydroxyalkyl, $C_{1-2}$-haloalkoxy, amino, $C_{1-2}$-alkylamino, phenylamino, nitro, $C_{1-2}$-alkoxy-$C_{1-2}$-alkyl, $C_{1-2}$-alkylsulfinyl, halo, $C_{1-2}$-alkoxy and $C_{1-3}$-alkylthio;

$R^2$ is methyl or amino; and $R^3$ represents one or more radicals selected from hydrido, halo, $C_{1-2}$-alkyl, $C_{2-3}$-alkenyl, $C_{2-3}$-alkynyl, oxo, cyano, carboxyl, cyano-$C_{1-3}$-alkyl, (5- or 6-member ring heterocyclyl)oxy, $C_{1-3}$-alkoxy, $C_{1-3}$-alkylthio, $C_{1-3}$-alkylcarbonyl, $C_{3-6}$-cycloalkyl, phenyl, $C_{1-3}$-haloalkyl, 5- or 6-member ring heterocyclyl, $C_{3-6}$-cycloalkenyl, phenyl-$C_{1-3}$-alkyl, (5- or 6-member ring heterocyclyl)-$C_{1-3}$-alkyl, $C_{1-3}$-alkylthio-$C_{1-3}$-alkyl, $C_{1-3}$-hydroxyalkyl, $C_{1-3}$-alkoxycarbonyl, phenylcarbonyl, phenyl-$C_{1-3}$-alkylcarbonyl, phenyl-$C_{2-3}$-alkenyl, $C_{1-3}$-alkoxy-$C_{1-3}$-alkyl, phenylthio-$C_{1-3}$-alkyl, phenyloxy-$C_{1-3}$-alkyl, $C_{1-3}$-alkoxyphenyl-$C_{1-3}$-alkoxy-$C_{1-3}$-alkyl, $C_{1-3}$-alkoxycarbonyl-$C_{1-3}$-alkyl, aminocarbonyl, aminocarbonyl-$C_{1-3}$-alkyl, $C_{1-3}$-alkylaminocarbonyl, N-phenylaminocarbonyl, N—($C_{1-3}$-alkyl)-N-phenylaminocarbonyl, $C_{1-3}$-alkylaminocarbonyl-$C_{1-3}$-alkyl, carboxy-$C_{1-3}$-alkyl, $C_{1-3}$-alkylamino, N-phenylamino, N-(phenyl-$C_{1-3}$-alkyl)amino, N—($C_{1-3}$-alkyl)-N-(phenyl-$C_{1-3}$-alkyl)amino, N—($C_{1-3}$-alkyl)-N-phenylamino, amino-$C_{1-3}$-alkyl, $C_{1-3}$-alkylamino-$C_{1-3}$-alkyl, N-phenylamino-$C_{1-3}$-alkyl, N-phenyl-$C_{1-3}$-alkylamino-$C_{1-3}$-alkyl, N—($C_{1-3}$-alkyl)-N-phenyl-$C_{1-3}$-alkylamino-$C_{1-3}$-alkyl, N—($C_{1-3}$-alkyl)-N-phenylamino-$C_{1-3}$-alkyl, phenyloxy, phenyl-$C_{1-3}$-alkoxy, phenylthio, phenyl-$C_{1-3}$-alkylthio, $C_{1-3}$-alkylsulfinyl, $C_{1-3}$-alkylsulfonyl, aminosulfonyl, $C_{1-3}$-alkylaminosulfonyl, N-phenylaminosulfonyl, phenylsulfonyl, and N—($C_{1-3}$-alkyl)-N-phenylaminosulfonyl;

or a pharmaceutically-acceptable salt, tautomer or prodrug thereof.

Within this preferred class of compounds, A preferably is a radical selected from thienyl, furyl, furanone, thiazolyl, oxothiazolyl, thioxothiazolyl, imidazolyl, benzofuryl, indenyl, benzothienyl, isoxazolyl, oxooxazolyl, pyrazolyl, cyclopentenyl, cyclopentadienyl, benzindazolyl, benzopyranopyrazolyl, phenyl, and pyridyl. More preferably, A is a radical selected from thienyl, furyl, furanone, thiazolyl, oxothiazolyl, thioxothiazolyl, imidazolyl, benzofuryl, indenyl, benzothienyl, isoxazolyl, pyrazolyl, cyclopentenyl, cyclopentadienyl, benzindazolyl, benzopyranopyrazolyl, phenyl, and pyridyl. Still more preferably, A is a radical selected from thienyl, furanone, isoxazolyl, pyrazolyl, cyclopentenyl and pyridinyl. Still more preferably, A is a radical selected from furanone, isoxazolyl, and pyrazolyl.

In another embodiment, the present method of treating cyclooxygenase-2 mediated disorders comprises administering to the subject a therapeutically-effective amount of one or more compounds selected from a more preferred class of compounds consisting of compounds of Formula I wherein $R^1$ is cyclohexyl, pyridinyl, or phenyl, wherein said cyclohexyl, pyridinyl, and phenyl may be optionally substituted with one, two or three radicals selected from methyl, difluoromethyl, trifluoromethyl, cyano, carboxyl, methoxycarbonyl, hydroxyl, hydroxymethyl, trifluoromethoxy, amino, methylamino, phenylamino, nitro, methoxymethyl, methylsulfinyl, fluoro, chloro, bromo, methoxy and methylthio.

In another embodiment, the present method of treating cyclooxygenase-2 mediated disorders comprises administering to the subject a therapeutically-effective amount of one or more compounds selected from a more preferred class of compounds consisting of compounds of Formula I wherein $R^3$ is a radical selected from hydrido, fluoro, chloro, bromo, methyl, oxo, cyano, carboxyl, cyanomethyl, methoxy, methylthio, methylcarbonyl, phenyl, trifluoromethyl, difluoromethyl, phenylmethyl, methylthiomethyl, hydroxymethyl, methoxycarbonyl, ethoxycarbonyl, phenylcarbonyl, phenylmethylcarbonyl, methoxymethyl, phenylthiomethyl, phenyloxymethyl, methoxyphenylmethoxymethyl, methoxycarbonylmethyl, aminocarbonyl, aminocarbonylmethyl, methylaminocarbonyl, N-phenylaminocarbonyl, N-methyl-N-phenylaminocarbonyl, methylaminocarbonylmethyl, carboxymethyl, methylamino, N-phenylamino, N-(phenylmethyl)amino, N-methyl-N-(phenylmethyl)amino, N-methyl-N-phenylamino, aminomethyl, methylaminomethyl, N-phenylaminomethyl, N-phenylmethylaminomethyl, N-methyl-N-phenylmethylaminomethyl, N-methyl-N-phenylaminomethyl, phenyloxy, phenylmethoxy, phenylthio, phenylmethylthio, methylsulfinyl, methylsulfonyl, aminosulfonyl, methylaminosulfonyl, N-phenylaminosulfonyl, phenylsulfonyl, and N-methyl-N-phenylaminosulfonyl.

In another embodiment, the present method of treating cyclooxygenase-2 mediated disorders comprises administering to the subject a therapeutically-effective amount of one or more compounds selected from a more preferred class of compounds consisting of compounds of Formula I wherein $R^1$ and $R^3$ are defined as follows:

$R^1$ is cyclohexyl, pyridinyl, or phenyl, wherein said cyclohexyl, pyridinyl, and phenyl may be optionally substituted with one, two or three radicals selected from methyl, difluoromethyl, trifluoromethyl, cyano, carboxyl, methoxycarbonyl, hydroxyl, hydroxymethyl, trifluoromethoxy, amino, methylamino, phenylamino, nitro, methoxymethyl, methylsulfinyl, fluoro, chloro, bromo, methoxy and methylthio; and $R^3$ is a radical selected from hydrido, fluoro, chloro, bromo, methyl, oxo, cyano, carboxyl, cyanomethyl, methoxy, methylthio, methylcarbonyl, phenyl, trifluoromethyl, difluoromethyl, phenylmethyl, methylthiomethyl, hydroxymethyl, methoxycarbonyl, ethoxycarbonyl, phenylcarbonyl, phenylmethylcarbonyl, methoxymethyl, phenylthiomethyl, phenyloxymethyl, methoxyphenylmethoxymethyl, methoxycarbonylmethyl, aminocarbonyl, aminocarbonylmethyl, methylaminocarbonyl, N-phenylaminocarbonyl, N-methyl-N-phenylaminocarbonyl, methylaminocarbonylmethyl, carboxymethyl, methylamino, N-phenylamino, N-(phenylmethyl)amino, N-methyl-N-(phenylmethyl)amino, N-methyl-N-phenylamino, aminomethyl, methylaminomethyl, N-phenylaminomethyl, N-phenylmethylaminomethyl, N-methyl-N-phenylmethylaminomethyl, N-methyl-N-phenylaminomethyl, phenyloxy, phenylmethoxy, phenylthio, phenylmethylthio, methylsulfinyl, methylsulfonyl, aminosulfonyl, methylaminosulfonyl, N-phenylaminosulfonyl, phenylsulfonyl, and N-methyl-N-phenylaminosulfonyl.

In another embodiment, the present method of treating cyclooxygenase-2 mediated disorders comprises administering to the subject a therapeutically-effective amount of one or more compounds selected from a still more preferred class of compounds consisting of those compounds of Formula I wherein:

$R^1$ is cyclohexyl or phenyl, wherein said cyclohexyl and phenyl may be optionally substituted with one, two or three radicals selected from halo, cyano, $C_{1-2}$-alkyl, $C_{1-2}$-haloalkyl, $C_{1-2}$-alkoxy, and $C_{1-2}$-haloalkoxy; and $R^3$ is a radical selected from hydrido, $C_{1-2}$-alkyl, $C_{1-3}$-alkoxy, $C_{1-3}$-alkylcarbonyl, $C_{1-3}$-haloalkyl, and $C_{1-3}$-alkoxycarbonyl.

In another embodiment, the present method of treating cyclooxygenase-2 mediated disorders comprises administering to the subject a therapeutically-effective amount of one or more compounds selected from a still more preferred group of compounds consisting of those compounds of Formula I wherein:

$R^1$ is cyclohexyl or phenyl, wherein said cyclohexyl and phenyl may be optionally substituted with one, two or three radicals selected from methyl, difluoromethyl, trifluoromethyl, trifluoromethoxy, cyano, fluoro, chloro, bromo, and methoxy; and $R^3$ is a radical selected from hydrido, methyl, methoxy, methylcarbonyl, trifluoromethyl, difluoromethyl, and methoxycarbonyl.

Utility of Methods and Compounds

The methods and compounds of the present invention would be useful for, but not limited to, the treatment of inflammation in a subject, and for treatment of other cyclooxygenase-2 mediated disorders, such as, as an analgesic in the treatment of pain and headaches, or as an antipyretic for the treatment of fever. For example, the methods and compounds of the invention would be useful to treat arthritis, including but not limited to rheumatoid arthritis, spondyloarthropathies, gouty arthritis, osteoarthritis, systemic lupus erythematosus and juvenile arthritis. Such methods and compounds of the invention would be useful in the treatment of asthma, bronchitis, menstrual cramps, preterm labor, tendinitis, bursitis, allergic neuritis, cytomegalovirus infectivity, apoptosis including HIV induced apoptosis, lumbago, liver disease including hepatitis, skin-related conditions such as psoriasis, eczema, acne, UV damage, burns and dermatitis, and from post-operative inflammation including from ophthalmic surgery such as cataract surgery and refractive surgery.

The methods and compounds of the invention also would be useful to treat gastrointestinal conditions such as inflammatory bowel disease, Crohn's disease, gastritis, irritable bowel syndrome and ulcerative colitis.

The methods and compounds of the invention would be useful in treating inflammation in such diseases as migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like.

The methods and compounds would also be useful in the treatment of ophthalmic diseases, such as retinitis, conjunctivitis, retinopathies, uveitis, ocular photophobia, and of acute injury to the eye tissue.

The methods and compounds would also be useful in the treatment of pulmonary inflammation, such as that associated with viral infections and cystic fibrosis, and in bone resorption such as associated with osteoporosis.

The methods and compounds would also be useful for the treatment of certain central nervous system disorders, such as cortical dementias including Alzheimer's disease, neurodegeneration, and central nervous system damage resulting from stroke, ischemia and trauma. The term "treatment" includes partial or total inhibition of the dementia, including Alzheimer's disease, vascular dementia, multi-infarct dementia, pre-senile dementia, alcoholic dementia, and senile dementia.

The methods and compounds of the invention are useful as anti-inflammatory agents, such as for the treatment of arthritis, with the additional benefit of having significantly less harmful side effects. These methods and compounds would also be useful in the treatment of allergic rhinitis, respiratory distress syndrome, endotoxin shock syndrome, and liver disease. The methods and compounds would also be useful in the treatment of pain, but not limited to postoperative pain, dental pain, muscular pain, and pain resulting from cancer.

The methods and compounds above would be useful for, but not limited to, treating and preventing inflammation-related cardiovascular disorders in a subject. The methods and compounds would be useful for treatment and prevention of vascular diseases, coronary artery disease, aneurysm, vascular rejection, arteriosclerosis, atherosclerosis including cardiac transplant atherosclerosis, myocardial infarction, embolism, stroke, thrombosis, including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries.

The methods and compounds would be useful for, but not limited to, the treatment of angiogenesis-related disorders in a subject. According to the present invention, the methods and compounds can be used in the treatment of a subject in need of angiogenesis inhibition. The methods and compounds would be useful for treatment of neoplasia, including metastasis; ophthalmological conditions such as corneal graft rejection, ocular neovascularization, retinal neovascularization including neovascularization following injury or infection, diabetic retinopathy, macular degeneration, retrolental fibroplasia and neovascular glaucoma; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis.

The methods and compounds of the invention would be useful for the prevention or treatment of benign and malignant tumors/neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that affect epithelial cells throughout the body. Preferably, neoplasia is selected from gastrointestinal cancer, Barrett's esophagus, liver cancer, bladder cancer, pancreas cancer, ovary cancer, prostate cancer, cervical cancer, lung cancer, breast cancer and skin cancer, such as squamus cell and basal cell cancers. The methods and compounds can also be used to treat the fibrosis which occurs with radiation therapy. The methods and compounds can be used to treat subjects having adenomatous polyps, including those with familial adenomatous polyposis (FAP). Additionally, the methods and compounds can be used to prevent polyps from forming in patients at risk of FAP.

The methods and compounds of the present invention may be used alone or in conjunction with additional therapies and/or compounds known to those skilled in the art in the prevention or treatment of neoplasia. Alternatively, the methods and compounds described herein may be used in conjunctive therapy. By way of example, the compounds may be administered alone or in conjunction with other antineoplastic agents or other growth inhibiting agents or other drugs or nutrients.

The present methods and compounds may also be used in co-therapies, partially or completely, in addition to other antiinflammatories, such as together with steroids, NSAIDs, iNOS inhibitors, p-38 inhibitors, MMP inhibitors, TNF inhibitors, 5-lipoxygenase inhibitors, LTB$_4$ receptor antagonists and LTA$_4$ hydrolase inhibitors.

The present methods and compounds may also be used in combination therapies with opioids and other analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, Substance P antagonists, neurokinin-1 receptor antagonists and sodium channel blockers, among others. More preferred would be combinations with compounds selected from morphine, meperidine, codeine, pentazocine, buprenorphine, butorphanol, dezocine, meptazinol, hydrocodone, oxycodone, methadone, Tramadol [(+) enantiomer], DuP 747, Dynorphine A, Enadoline, RP-60180, HN-11608, E-2078, ICI-204448, acetominophen (paracetamol), propoxyphene, nalbuphine, E-4018, filenadol, mirfentanil, amitriptyline, DuP631, Tramadol [(−) enantiomer], GP-531, acadesine, AKI-1, AKI-2, GP-1683, GP-3269, 4030W92, tramadol racemate, Dynorphine A, E-2078, AXC3742, SNX-111, ADL2–1294, ICI-204448, CT-3, CP-99,994, and CP-99,994.

The methods and compounds can be used in co-therapies, in place of other conventional antiinflammatories, in combination with one or more antihistamines, decongestants, diuretics, antitussive agents or with other agents previously known to be effective in combination with antiinflammatory agents.

Subjects of Treatment

Besides being useful for human treatment, these methods and compounds are also useful for veterinary treatment of companion animals, exotic animals and farm animals, including mammals, rodents, and the like. More preferred animals include horses, dogs, and cats.

Selectivity of Compounds

The present novel methods preferably employ compounds which selectively inhibit cyclooxygenase-2 over cyclooxygenase-1. Preferably, the compounds have a cyclooxygenase-2 IC$_{50}$ of less than about 0.5 $\mu$M, and also have a selectivity ratio of cyclooxygenase-2 inhibition over cyclooxygenase-1 inhibition of at least 50, and more preferably of at least 100. Even more preferably, the compounds have a cyclooxygenase-1 IC$_{50}$ of greater than about 5 $\mu$M. Such preferred selectivity may indicate an ability to reduce the incidence of common NSAID-induced side effects.

Pyrazoles

In still another embodiment, the present method of treating cyclooxygenase-2 mediated disorders comprises administering to the subject a therapeutically-effective amount of one or more compounds selected from a subclass of compounds of Formula I corresponding to Formula II:

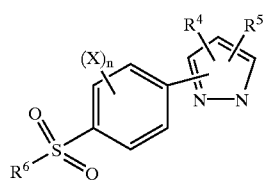

II wherein substituents X, n, R$^4$, R$^5$ and R$^6$ have the same definitions and sub-definitions as substituents X, n, R$^1$, R$^3$ and R$^2$, respectively, set forth above for the compounds of Formula I, and the pharmaceutically-acceptable salts, tautomers and prodrugs thereof.

Within this subclass of compounds, a preferred group of compounds consists of those compounds of Formula IIA or Formula IIB:

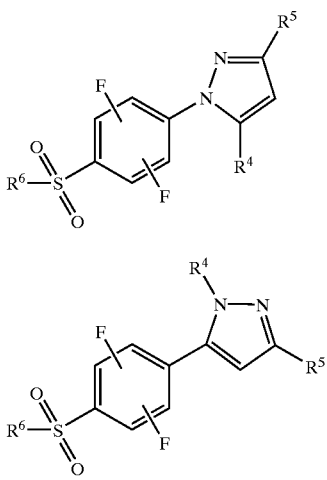

IIA

IIB wherein R⁴, R⁵ and R⁶ are as defined above, and the pharmaceutically-acceptable salts, tautomers and prodrugs thereof.

Within this subclass of compounds, a more preferred group of compounds consists of those compounds of Formula IIC or IID:

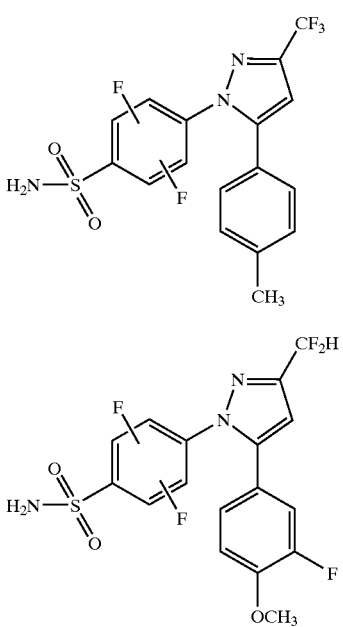

IIC

IID and the pharmaceutically-acceptable salts, tautomers and prodrugs thereof. Preferably, (a) one fluoro radical is present at the 2-position and the other fluoro radical is present at the 5-position, or (b) one fluoro radical is present at the 2-position and the other fluoro radical is present at the 3-position, or (c) one fluoro radical is present at the 3-position and the other fluoro radical is present at the 5-position.

Preferred species within this subclass include, but are not limited to:

5-phenyl-1-[3,5-difluoro-4-(methylsulfonyl)phenyl]-3-(trifluoromethyl)-1H-pyrazole;

5-(3-chloro-5-methylphenyl)-1-[3,5-difluoro-4-(methylsulfonyl)phenyl]-3-(trifluoromethyl)-1H-pyrazole;

5-(3,5-difluoro-5-methylphenyl)-1-[3,5-difluoro-4-(methylsulfonyl)phenyl]-3-(trifluoromethyl)-1H-pyrazole;

5-(3-chlorophenyl)-1-[3,5-difluoro-4-(methylsulfonyl)phenyl]-3-(trifluoromethyl)-1H-pyrazole;

5-(4-chlorophenyl)-1-[3,5-difluoro-4-(methylsulfonyl)phenyl]-3-(trifluoromethyl)-1H-pyrazole;

5-(3-bromophenyl)-1-[3,5-difluoro-4-(methylsulfonyl)phenyl]-3-(trifluoromethyl)-1H-pyrazole;

5-(4-bromophenyl)-1-[3,5-difluoro-4-(methylsulfonyl)phenyl]-3-(trifluoromethyl)-1H-pyrazole;

5-(3,5-difluorophenyl)-1-[3,5-difluoro-4-(methylsulfonyl)phenyl]-3-(trifluoromethyl)-1H-pyrazole;

5-(4-fluorophenyl)-1-[3,5-difluoro-4-(methylsulfonyl)phenyl]-3-(trifluoromethyl)-1H-pyrazole;

5-(4-methylphenyl)-1-[3,5-difluoro-4-(methylsulfonyl)phenyl]-3-(trifluoromethyl)-1H-pyrazole;

5-(3-methylphenyl)-1-[3,5-difluoro-4-(methylsulfonyl)phenyl]-3-(trifluoromethyl)-1H-pyrazole;

5-(3-bromo-5-methylphenyl)-1-[3,5-difluoro-4-(methylsulfonyl)phenyl]-3-(trifluoromethyl)-1H-pyrazole;

5-(3,4-dichlorophenyl)-1-[3,5-difluoro-4-(methylsulfonyl)phenyl]-3-(trifluoromethyl)-1H-pyrazole;

5-(3,4-dibromophenyl)-1-[3,5-difluoro-4-(methylsulfonyl)phenyl]-3-(trifluoromethyl)-1H-pyrazole;

5-(3,4-difluorophenyl)-1-[3,5-difluoro-4-(methylsulfonyl)phenyl]-3-(trifluoromethyl)-1H-pyrazole;

5-(3,5-dichlorophenyl)-1-[3,5-difluoro-4-(methylsulfonyl)phenyl]-3-(trifluoromethyl)-1H-pyrazole;

5-(3,5-dibromophenyl)-1-[3,5-difluoro-4-(methylsulfonyl)phenyl]-3-(trifluoromethyl)-1H-pyrazole;

5-(3,5-difluorophenyl)-1-[3,5-difluoro-4-(methylsulfonyl)phenyl]-3-(trifluoromethyl)-1H-pyrazole;

5-(3-chloro-4-fluorophenyl)-1-[3,5-difluoro-4-(methylsulfonyl)phenyl]-3-(trifluoromethyl)-1H-pyrazole;

5-(3-chloro-4-methylphenyl)-1-[3,5-difluoro-4-(methylsulfonyl)phenyl]-3-(trifluoromethyl)-1H-pyrazole;

5-(3-bromo-4-methylphenyl)-1-[3,5-difluoro-4-(methylsulfonyl)phenyl]-3-(trifluoromethyl)-1H-pyrazole;

5-(3,5-difluoro-4-methylphenyl)-1-[3,5-difluoro-4-(methylsulfonyl)phenyl]-3-(trifluoromethyl)-1H-pyrazole;

5-(3,4-dimethylphenyl)-1-[3,5-difluoro-4-(methylsulfonyl)phenyl]-3-(trifluoromethyl)-1H-pyrazole;

5-(4-trifluoromethoxyphenyl)-1-[3,5-difluoro-4-(methylsulfonyl)phenyl]-3-(trifluoromethyl)-1H-pyrazole;

5-(3-methyl-4-trifluoromethoxyphenyl)-1-[3,5-difluoro-4-(methylsulfonyl)phenyl]-3-(trifluoromethyl)-1H-pyrazole;

5-(4-methyl-3-trifluoromethoxyphenyl)-1-[3,5-difluoro-4-(methylsulfonyl)phenyl]-3-(trifluoromethyl)-1H-pyrazole;

5-(4-methyl-3-trifluoromethoxyphenyl)-1-[3,5-difluoro-4-(methylsulfonyl)phenyl]-3-(trifluoromethyl)-1H-pyrazole;
5-(3-cyano-4-methylphenyl)-1-[3,5-difluoro-4-(methylsulfonyl)phenyl]-3-(trifluoromethyl)-1H-pyrazole;
5-(4-cyano-3-methylphenyl)-1-[3,5-difluoro-4-(methylsulfonyl)phenyl]-3-(trifluoromethyl)-1H-pyrazole;
5-(3-cyanophenyl)-1-[3,5-difluoro-4-(methylsulfonyl)phenyl]-3-(trifluoromethyl)-1H-pyrazole;
5-(4-cyanophenyl)-1-[3,5-difluoro-4-(methylsulfonyl)phenyl]-3-(trifluoromethyl)-1H-pyrazole;
5-(3-chloro-4-methoxyphenyl)-1-[3,5-difluoro-4-(methylsulfonyl)phenyl]-3-(trifluoromethyl)-1H-pyrazole;
5-(4-chloro-3-methoxyphenyl)-1-[3,5-difluoro-4-(methylsulfonyl)phenyl]-3-(trifluoromethyl)-1H-pyrazole;
5-(2-methylpyridin-6-yl)-1-[3,5-difluoro-4-(methylsulfonyl)phenyl]-3-(trifluoromethyl)-1H-pyrazole;
5-(2-methylthiazol-4-yl)-1-[3,5-difluoro-4-(methylsulfonyl)phenyl]-3-(trifluoromethyl)-1H-pyrazole;
5-(4-methylthiazol-2-yl)-1-[3,5-difluoro-4-(methylsulfonyl)phenyl]-3-(trifluoromethyl)-1H-pyrazole;
5-(2-methylpyridin-3-yl)-1-[3,5-difluoro-4-(methylsulfonyl)phenyl]-3-(trifluoromethyl)-1H-pyrazole;
5-(2-methylpyridin-3-yl)-1-[3,5-difluoro-4-(methylsulfonyl)phenyl]-3-(trifluoromethyl)-1H-pyrazole;
5-(3-pyridinyl)-1-[3,5-difluoro-4-(methylsulfonyl)phenyl]-3-(trifluoromethyl)-1H-pyrazole;
5-(5-methylpyridin-3-yl)-1-[3,5-difluoro-4-(methylsulfonyl)phenyl]-3-(trifluoromethyl)-1H-pyrazole;
5-(2-methylpyridin-3-yl)-1-[3,5-difluoro-4-(methylsulfonyl)phenyl]-3-(trifluoromethyl)-1H-pyrazole;
3-cyclohexyl-1-[3,5-difluoro-4-(methylsulfonyl)phenyl]-3-(trifluoromethyl)-1H-pyrazole;
3-cyclopentyl-1-[3,5-difluoro-4-(methylsulfonyl)phenyl]-3-(trifluoromethyl)-1H-pyrazole;
5-phenyl-1-[3,5-difluoro-4-(methylsulfonyl)phenyl]-3-(difluoromethyl)-1H-pyrazole;
5-(3-chlorophenyl)-1-[3,5-difluoro-4-(methylsulfonyl)phenyl]-3-(difluoromethyl)-1H-pyrazole;
5-(4-chlorophenyl)-1-[3,5-difluoro-4-(methylsulfonyl)phenyl]-3-(difluoromethyl)-1H-pyrazole;
5-(3-bromophenyl)-1-[3,5-difluoro-4-(methylsulfonyl)phenyl]-3-(difluoromethyl)-1H-pyrazole;
5-(4-bromophenyl)-1-[3,5-difluoro-4-(methylsulfonyl)phenyl]-3-(difluoromethyl)-1H-pyrazole;
5-(3-fluorophenyl)-1-[3,5-difluoro-4-(methylsulfonyl)phenyl]-3-(difluoromethyl)-1H-pyrazole;
5-(4-fluorophenyl)-1-[3,5-difluoro-4-(methylsulfonyl)phenyl]-3-(difluoromethyl)-1H-pyrazole;
5-(3-methylphenyl)-1-[3,5-difluoro-4-(methylsulfonyl)phenyl]-3-(difluoromethyl)-1H-pyrazole;
5-(4-methylphenyl)-1-[3,5-difluoro-4-(methylsulfonyl)phenyl]-3-(difluoromethyl)-1H-pyrazole;
5-(3-cyanophenyl)-1-[3,5-difluoro-4-(methylsulfonyl)phenyl]-3-(difluoromethyl)-1H-pyrazole;
5-(4-cyanophenyl)-1-[3,5-difluoro-4-(methylsulfonyl)phenyl]-3-(difluoromethyl)-1H-pyrazole;
5-(3-trifluoromethylphenyl)-1-[3,5-difluoro-4-(methylsulfonyl)phenyl]-3-(difluoromethyl)-1H-pyrazole;
5-(4-trifluoromethylphenyl)-1-[3,5-difluoro-4-(methylsulfonyl)phenyl]-3-(difluoromethyl)-1H-pyrazole;
5-(3-trifluoromethoxyphenyl)-1-[3,5-difluoro-4-(methylsulfonyl)phenyl]-3-(difluoromethyl)-1H-pyrazole;
5-(4-trifluoromethoxyphenyl)-1-[3,5-difluoro-4-(methylsulfonyl)phenyl]-3-(difluoromethyl)-1H-pyrazole;
5-(3,4-dichlorophenyl)-1-[3,5-difluoro-4-(methylsulfonyl)phenyl]-3-(difluoromethyl)-1H-pyrazole;
5-(3,4-dibromophenyl)-1-[3,5-difluoro-4-(methylsulfonyl)phenyl]-3-(difluoromethyl)-1H-pyrazole;
5-(3,4-difluorophenyl)-1-[3,5-difluoro-4-(methylsulfonyl)phenyl]-3-(difluoromethyl)-1H-pyrazole;
5-(3,5-dichlorophenyl)-1-[3,5-difluoro-4-(methylsulfonyl)phenyl]-3-(difluoromethyl)-1H-pyrazole;
5-(3,5-dibromophenyl)-1-[3,5-difluoro-4-(methylsulfonyl)phenyl]-3-(difluoromethyl)-1H-pyrazole;
5-(3,5-difluorophenyl)-1-[3,5-difluoro-4-(methylsulfonyl)phenyl]-3-(difluoromethyl)-1H-pyrazole;
5-(3,4-dimethylphenyl)-1-[3,5-difluoro-4-(methylsulfonyl)phenyl]-3-(difluoromethyl)-1H-pyrazole;
5-(3,5-dimethylphenyl)-1-[3,5-difluoro-4-(methylsulfonyl)phenyl]-3-(difluoromethyl)-1H-pyrazole;
5-(3-methyl-4-chlorophenyl)-1-[3,5-difluoro-4-(methylsulfonyl)phenyl]-3-(difluoromethyl)-1H-pyrazole;
5-(4-methyl-3-chlorophenyl)-1-[3,5-difluoro-4-(methylsulfonyl)phenyl]-3-(difluoromethyl)-1H-pyrazole;
5-(3-methyl-4-fluorophenyl)-1-[3,5-difluoro-4-(methylsulfonyl)phenyl]-3-(difluoromethyl)-1H-pyrazole;
5-(4-methyl-3-fluorophenyl)-1-[3,5-difluoro-4-(methylsulfonyl)phenyl]-3-(difluoromethyl)-1H-pyrazole;
5-(3-methyl-4-bromophenyl)-1-[3,5-difluoro-4-(methylsulfonyl)phenyl]-3-(difluoromethyl)-1H-pyrazole;
5-(4-methyl-3-bromophenyl)-1-[3,5-difluoro-4-(methylsulfonyl)phenyl]-3-(difluoromethyl)-1H-pyrazole;
5-(3-methyl-4-trifluoromethylphenyl)-1-[3,5-difluoro-4-(methylsulfonyl)phenyl]-3-(difluoromethyl)-1H-pyrazole;
5-(4-methyl-3-trifluoromethylphenyl)-1-[3,5-difluoro-4-(methylsulfonyl)phenyl]-3-(difluoromethyl)-1H-pyrazole;

5-(3-methyl-4-trifluoromethoxyphenyl)-1-[3,5-difluoro-4-(methylsulfonyl)phenyl]-3-(difluoromethyl)-1H-pyrazole;

5-(4-methyl-3-trifluoromethoxyphenyl)-1-[3,5-difluoro-4-(methylsulfonyl)phenyl]-3-(difluoromethyl)-1H-pyrazole;

5-(3-cyano-4-methylphenyl)-1-[3,5-difluoro-4-(methylsulfonyl)phenyl]-3-(difluoromethyl)-1H-pyrazole;

5-(4-cyano-3-methylphenyl)-1-[3,5-difluoro-4-(methylsulfonyl)phenyl]-3-(difluoromethyl)-1H-pyrazole;

5-(3-chloro-4-methoxyphenyl)-1-[3,5-difluoro-4-(methylsulfonyl)phenyl]-3-(difluoromethyl)-1H-pyrazole;

5-(4-chloro-3-methoxyphenyl)-1-[3,5-difluoro-4-(methylsulfonyl)phenyl]-3-(difluoromethyl)-1H-pyrazole;

5-(2-methylpyridin-6-yl)-1-[3,5-difluoro-4-(methylsulfonyl)phenyl]-3-(difluoromethyl)-1H-pyrazole;

5-(2-methylthiazol-4-yl)-1-[3,5-difluoro-4-(methylsulfonyl)phenyl]-3-(difluoromethyl)-1H-pyrazole;

5-(4-methylthiazol-2-yl)-1-[3,5-difluoro-4-(methylsulfonyl)phenyl]-3-(difluoromethyl)-1H-pyrazole;

5-(2-methylpyridin-3-yl)-1-[3,5-difluoro-4-(methylsulfonyl)phenyl]-3-(difluoromethyl)-1H-pyrazole;

5-(2-methylpyridin-3-yl)-1-[3,5-difluoro-4-(methylsulfonyl)phenyl]-3-(difluoromethyl)-1H-pyrazole;

5-(3-pyridinyl)-1-[3,5-difluoro-4-(methylsulfonyl)phenyl]-3-(difluoromethyl)-1H-pyrazole;

5-(5-methylpyridin-3-yl)-1-[3,5-difluoro-4-(methylsulfonyl)phenyl]-3-(difluoromethyl)-1H-pyrazole;

5-(2-methylpyridin-3-yl)-1-[3,5-difluoro-4-(methylsulfonyl)phenyl]-3-(difluoromethyl)-1H-pyrazole;

5-cyclohexyl-1-[3,5-difluoro-4-(methylsulfonyl)phenyl]-3-(difluoromethyl)-1H-pyrazole;

5-cyclopentyl-1-[3,5-difluoro-4-(methylsulfonyl)phenyl]-3-(difluoromethyl)-1H-pyrazole;

1-phenyl-5-[3,5-difluoro-4-(methylsulfonyl)phenyl]-3-(trifluoromethyl)-1H-pyrazole;

1-(3-chlorophenyl)-5-[3,5-difluoro-4-(methylsulfonyl)phenyl]-3-(trifluoromethyl)-1H-pyrazole;

1-(4-chlorophenyl)-5-[3,5-difluoro-4-(methylsulfonyl)phenyl]-3-(trifluoromethyl)-1H-pyrazole;

1-(3-bromophenyl)-5-[3,5-difluoro-4-(methylsulfonyl)phenyl]-3-(trifluoromethyl)-1H-pyrazole;

1-(4-bromophenyl)-5-[3,5-difluoro-4-(methylsulfonyl)phenyl]-3-(trifluoromethyl)-1H-pyrazole;

1-(3-fluorophenyl)-5-[3,5-difluoro-4-(methylsulfonyl)phenyl]-3-(trifluoromethyl)-1H-pyrazole;

1-(4-fluorophenyl)-5-[3,5-difluoro-4-(methylsulfonyl)phenyl]-3-(trifluoromethyl)-1H-pyrazole;

1-(3-methylphenyl)-5-[3,5-difluoro-4-(methylsulfonyl)phenyl]-3-(trifluoromethyl)-1H-pyrazole;

1-(4-methylphenyl)-5-[3,5-difluoro-4-(methylsulfonyl)phenyl]-3-(trifluoromethyl)-1H-pyrazole;

1-(3-cyanophenyl)-5-[3,5-difluoro-4-(methylsulfonyl)phenyl]-3-(trifluoromethyl)-1H-pyrazole;

1-(4-cyanophenyl)-5-[3,5-difluoro-4-(methylsulfonyl)phenyl]-3-(trifluoromethyl)-1H-pyrazole;

1-(3-trifluoromethylphenyl)-5-[3,5-difluoro-4-(methylsulfonyl)phenyl]-3-(trifluoromethyl)-1H-pyrazole;

1-(4-trifluoromethylphenyl)-5-[3,5-difluoro-4-(methylsulfonyl)phenyl]-3-(trifluoromethyl)-1H-pyrazole;

1-(3-trifluoromethoxyphenyl)-5-[3,5-difluoro-4-(methylsulfonyl)phenyl]-3-(trifluoromethyl)-1H-pyrazole;

1-(4-trifluoromethoxyphenyl)-5-[3,5-difluoro-4-(methylsulfonyl)phenyl]-3-(trifluoromethyl)-1H-pyrazole;

1-(3,4-dichlorophenyl)-5-[3,5-difluoro-4-(methylsulfonyl)phenyl]-3-(trifluoromethyl)-1H-pyrazole;

1-(3,4-dibromophenyl)-5-[3,5-difluoro-4-(methylsulfonyl)phenyl]-3-(trifluoromethyl)-1H-pyrazole;

1-(3,4-difluorophenyl)-5-[3,5-difluoro-4-(methylsulfonyl)phenyl]-3-(trifluoromethyl)-1H-pyrazole;

1-(3,5-dichlorophenyl)-5-[3,5-difluoro-4-(methylsulfonyl)phenyl]-3-(trifluoromethyl)-1H-pyrazole;

1-(3,5-dibromophenyl)-5-[3,5-difluoro-4-(methylsulfonyl)phenyl]-3-(trifluoromethyl)-1H-pyrazole;

1-(3,5-difluorophenyl)-5-[3,5-difluoro-4-(methylsulfonyl)phenyl]-3-(trifluoromethyl)-1H-pyrazole;

1-(3,4-dimethylphenyl)-5-[3,5-difluoro-4-(methylsulfonyl)phenyl]-3-(trifluoromethyl)-1H-pyrazole;

1-(3,5-dimethylphenyl)-5-[3,5-difluoro-4-(methylsulfonyl)phenyl]-3-(trifluoromethyl)-1H-pyrazole;

1-(3-methyl-4-chlorophenyl)-5-[3,5-difluoro-4-(methylsulfonyl)phenyl]-3-(trifluoromethyl)-1H-pyrazole;

1-(4-methyl-3-chlorophenyl)-5-[3,5-difluoro-4-(methylsulfonyl)phenyl]-3-(trifluoromethyl)-1H-pyrazole;

1-(3-methyl-4-fluorophenyl)-5-[3,5-difluoro-4-(methylsulfonyl)phenyl]-3-(trifluoromethyl)-1H-pyrazole;

1-(4-methyl-3-fluorophenyl)-5-[3,5-difluoro-4-(methylsulfonyl)phenyl]-3-(trifluoromethyl)-1H-pyrazole;

1-(3-methyl-4-bromophenyl)-5-[3,5-difluoro-4-(methylsulfonyl)phenyl]-3-(trifluoromethyl)-1H-pyrazole;

1-(4-methyl-3-bromophenyl)-5-[3,5-difluoro-4-(methylsulfonyl)phenyl]-3-(trifluoromethyl)-1H-pyrazole;

1-(3-methyl-4-trifluoromethylphenyl)-5-[3,5-difluoro-4-(methylsulfonyl)phenyl]-3-(trifluoromethyl)-1H-pyrazole;

1-(4-methyl-3-trifluoromethylphenyl)-5-[3,5-difluoro-4-(methylsulfonyl)phenyl]-3-(trifluoromethyl)-1H-pyrazole;

1-(3-methyl-4-trifluoromethoxyphenyl)-5-[3,5-difluoro-4-(methylsulfonyl)phenyl]-3-(trifluoromethyl)-1H-pyrazole;

1-(4-methyl-3-trifluoromethoxyphenyl)-5-[3,5-difluoro-4-(methylsulfonyl)phenyl]-3-(trifluoromethyl)-1H-pyrazole;

1-(3-cyano-4-methylphenyl)-5-[3,5-difluoro-4-(methylsulfonyl)phenyl]-3-(trifluoromethyl)-1H-pyrazole;

1-(4-cyano-3-methylphenyl)-5-[3,5-difluoro-4-(methylsulfonyl)phenyl]-3-(trifluoromethyl)-1H-pyrazole;

1-(3-chloro-4-methoxyphenyl)-5-[3,5-difluoro-4-(methylsulfonyl)phenyl]-3-(trifluoromethyl)-1H-pyrazole;

1-(4-chloro-3-methoxyphenyl)-5-[3,5-difluoro-4-(methylsulfonyl)phenyl]-3-(trifluoromethyl)-1H-pyrazole;

1-(2-methylpyridin-6-yl)-5-[3,5-difluoro-4-(methylsulfonyl)phenyl]-3-(trifluoromethyl)-1H-pyrazole;

1-(2-methylthiazol-4-yl)-5-[3,5-difluoro-4-(methylsulfonyl)phenyl]-3-(trifluoromethyl)-1H-pyrazole;

1-(4-methylthiazol-2-yl)-5-[3,5-difluoro-4-(methylsulfonyl)phenyl]-3-(trifluoromethyl)-1H-pyrazole;

1-(2-methylpyridin-3-yl)-5-[3,5-difluoro-4-(methylsulfonyl)phenyl]-3-(trifluoromethyl)-1H-pyrazole;

1-(2-methylpyridin-3-yl)-5-[3,5-difluoro-4-(methylsulfonyl)phenyl]-3-(trifluoromethyl)-1H-pyrazole;

1-(3-pyridinyl)-5-[3,5-difluoro-4-(methylsulfonyl)phenyl]-3-(trifluoromethyl)-1H-pyrazole;

1-(5-methylpyridin-3-yl)-5-[3,5-difluoro-4-(methylsulfonyl)phenyl]-3-(trifluoromethyl)-1H-pyrazole;

1-(2-methylpyridin-3-yl)-5-[3,5-difluoro-4-(methylsulfonyl)phenyl]-3-(trifluoromethyl)-1H-pyrazole;

1-cyclohexyl-5-[3,5-difluoro-4-(methylsulfonyl)phenyl]-3-(trifluoromethyl)-1H-pyrazole;

1-cyclopentyl-5-[3,5-difluoro-4-(methylsulfonyl)phenyl]-3-(trifluoromethyl)-1H-pyrazole;

1-phenyl-5-[3,5-difluoro-4-(methylsulfonyl)phenyl]-3-(difluoromethyl)-1H-pyrazole;

1-(3-chlorophenyl)-5-[3,5-difluoro-4-(methylsulfonyl)phenyl]-3-(difluoromethyl)-1H-pyrazole;

1-(4-chlorophenyl)-5-[3,5-difluoro-4-(methylsulfonyl)phenyl]-3-(difluoromethyl)-1H-pyrazole;

1-(3-bromophenyl)-5-[3,5-difluoro-4-(methylsulfonyl)phenyl]-3-(difluoromethyl)-1H-pyrazole;

1-(4-bromophenyl)-5-[3,5-difluoro-4-(methylsulfonyl)phenyl]-3-(difluoromethyl)-1H-pyrazole;

1-(3-fluorophenyl)-5-[3,5-difluoro-4-(methylsulfonyl)phenyl]-3-(difluoromethyl)-1H-pyrazole;

1-(4-fluorophenyl)-5-[3,5-difluoro-4-(methylsulfonyl)phenyl]-3-(difluoromethyl)-1H-pyrazole;

1-(3-methylphenyl)-5-[3,5-difluoro-4-(methylsulfonyl)phenyl]-3-(difluoromethyl)-1H-pyrazole;

1-(4-methylphenyl)-5-[3,5-difluoro-4-(methylsulfonyl)phenyl]-3-(difluoromethyl)-1H-pyrazole;

1-(3-cyanophenyl)-5-[3,5-difluoro-4-(methylsulfonyl)phenyl]-3-(difluoromethyl)-1H-pyrazole;

1-(4-cyanophenyl)-5-[3,5-difluoro-4-(methylsulfonyl)phenyl]-3-(difluoromethyl)-1H-pyrazole;

1-(3-trifluoromethylphenyl)-5-[3,5-difluoro-4-(methylsulfonyl)phenyl]-3-(difluoromethyl)-1H-pyrazole;

1-(4-trifluoromethylphenyl)-5-[3,5-difluoro-4-(methylsulfonyl)phenyl]-3-(difluoromethyl)-1H-pyrazole;

1-(3-trifluoromethoxyphenyl)-5-[3,5-difluoro-4-(methylsulfonyl)phenyl]-3-(difluoromethyl)-1H-pyrazole;

1-(4-trifluoromethoxyphenyl)-5-[3,5-difluoro-4-(methylsulfonyl)phenyl]-3-(difluoromethyl)-1H-pyrazole;

1-(3,4-dichlorophenyl)-5-[3,5-difluoro-4-(methylsulfonyl)phenyl]-3-(difluoromethyl)-1H-pyrazole;

1-(3,4-dibromophenyl)-5-[3,5-difluoro-4-(methylsulfonyl)phenyl]-3-(difluoromethyl)-1H-pyrazole;

1-(3,4-difluorophenyl)-5-[3,5-difluoro-4-(methylsulfonyl)phenyl]-3-(difluoromethyl)-1H-pyrazole;

1-(3,5-dichlorophenyl)-5-[3,5-difluoro-4-(methylsulfonyl)phenyl]-3-(difluoromethyl)-1H-pyrazole;

1-(3,5-dibromophenyl)-5-[3,5-difluoro-4-(methylsulfonyl)phenyl]-3-(difluoromethyl)-1H-pyrazole;

1-(3,5-difluorophenyl)-5-[3,5-difluoro-4-(methylsulfonyl)phenyl]-3-(difluoromethyl)-1H-pyrazole;

1-(3,4-dimethylphenyl)-5-[3,5-difluoro-4-(methylsulfonyl)phenyl]-3-(difluoromethyl)-1H-pyrazole;

1-(3,5-dimethylphenyl)-5-[3,5-difluoro-4-(methylsulfonyl)phenyl]-3-(difluoromethyl)-1H-pyrazole;

1-(3-methyl-4-chlorophenyl)-5-[3,5-difluoro-4-(methylsulfonyl)phenyl]-3-(difluoromethyl)-1H-pyrazole;

1-(4-methyl-3-chlorophenyl)-5-[3,5-difluoro-4-(methylsulfonyl)phenyl]-3-(difluoromethyl)-1H-pyrazole;

1-(3-methyl-4-fluorophenyl)-5-[3,5-difluoro-4-(methylsulfonyl)phenyl]-3-(difluoromethyl)-1H-pyrazole;

1-(4-methyl-3-fluorophenyl)-5-[3,5-difluoro-4-(methylsulfonyl)phenyl]-3-(difluoromethyl)-1H-pyrazole;

1-(3-methyl-4-bromophenyl)-5-[3,5-difluoro-4-(methylsulfonyl)phenyl]-3-(difluoromethyl)-1H-pyrazole;

1-(4-methyl-3-bromophenyl)-5-[3,5-difluoro-4-(methylsulfonyl)phenyl]-3-(difluoromethyl)-1H-pyrazole;

1-(3-methyl-4-trifluoromethylphenyl)-5-[3,5-difluoro-4-(methylsulfonyl)phenyl]-3-(difluoromethyl)-1H-pyrazole;

1-(4-methyl-3-trifluoromethylphenyl)-5-[3,5-difluoro-4-(methylsulfonyl)phenyl]-3-(difluoromethyl)-1H-pyrazole;

1-(3-methyl-4-trifluoromethoxyphenyl)-5-[3,5-difluoro-4-(methylsulfonyl)phenyl]-3-(difluoromethyl)-1H-pyrazole;

1-(4-methyl-3-trifluoromethoxyphenyl)-5-[3,5-difluoro-4-(methylsulfonyl)phenyl]-3-(difluoromethyl)-1H-pyrazole;

1-(3-cyano-4-methylphenyl)-5-[3,5-difluoro-4-(methylsulfonyl)phenyl]-3-(difluoromethyl)-1H-pyrazole;

1-(4-cyano-3-methylphenyl)-5-[3,5-difluoro-4-(methylsulfonyl)phenyl]-3-(difluoromethyl)-1H-pyrazole;

1-(3-chloro-4-methoxyphenyl)-5-[3,5-difluoro-4-(methylsulfonyl)phenyl]-3-(difluoromethyl)-1H-pyrazole;

1-(4-chloro-3-methoxyphenyl)-5-[3,5-difluoro-4-(methylsulfonyl)phenyl]-3-(difluoromethyl)-1H-pyrazole;

1-(2-methylpyridin-6-yl)-5-[3,5-difluoro-4-(methylsulfonyl)phenyl]-3-(difluoromethyl)-1H-pyrazole;

1-(2-methylthiazol-4-yl)-5-[3,5-difluoro-4-(methylsulfonyl)phenyl]-3-(difluoromethyl)-1H-pyrazole;

1-(4-methylthiazol-2-yl)-5-[3,5-difluoro-4-(methylsulfonyl)phenyl]-3-(difluoromethyl)-1H-pyrazole;

1-(2-methylpyridin-3-yl)-5-[3,5-difluoro-4-(methylsulfonyl)phenyl]-3-(difluoromethyl)-1H-pyrazole;

1-(2-methylpyridin-3-yl)-5-[3,5-difluoro-4-(methylsulfonyl)phenyl]-3-(difluoromethyl)-1H-pyrazole;

1-(3-pyridinyl)-5-[3,5-difluoro-4-(methylsulfonyl)phenyl]-3-(difluoromethyl)-1H-pyrazole;

1-(5-methylpyridin-3-yl)-5-[3,5-difluoro-4-(methylsulfonyl)phenyl]-3-(difluoromethyl)-1H-pyrazole;

1-(2-methylpyridin-3-yl)-5-[3,5-difluoro-4-(methylsulfonyl)phenyl]-3-(difluoromethyl)-1H-pyrazole;

1-cyclohexyl-5-[3,5-difluoro-4-(methylsulfonyl)phenyl]-3-(difluoromethyl)-1H-pyrazole;

1-cyclopentyl-5-[3,5-difluoro-4-(methylsulfonyl)phenyl]-3-(difluoromethyl)-1H-pyrazole;

2,6-difluoro-4-[1-phenyl-3-(difluoromethyl)-1H-pyrazol-5-yl]benezenesulfonamide;

2,6-difluoro-4-[1-(3-chlorophenyl)-3-(difluoromethyl)-1H-pyrazol-5-yl]benezenesulfonamide;

2,6-difluoro-4-[1-(4-chlorophenyl)-3-(difluoromethyl)-1H-pyrazol-5-yl]benezenesulfonamide;

2,6-difluoro-4-[1-(3-bromophenyl)-3-(difluoromethyl)-1H-pyrazol-5-yl]benezenesulfonamide;

2,6-difluoro-4-[1-(4-bromophenyl)-3-(difluoromethyl)-1H-pyrazol-5-yl]benezenesulfonamide;

2,6-difluoro-4-[1-(3-fluorophenyl)-3-(difluoromethyl)-1H-pyrazol-5-yl]benezenesulfonamide;

2,6-difluoro-4-[1-(4-fluorophenyl)-3-(difluoromethyl)-1H-pyrazol-5-yl]benezenesulfonamide;

2,6-difluoro-4-[1-(3-methylphenyl)-3-(difluoromethyl)-1H-pyrazol-5-yl]benezenesulfonamide;

2,6-difluoro-4-[1-(4-methylphenyl)-3-(difluoromethyl)-1H-pyrazol-5-yl]benezenesulfonamide;

2,6-difluoro-4-[1-(3-cyanophenyl)-3-(difluoromethyl)-1H-pyrazol-5-yl]benezenesulfonamide;

2,6-difluoro-4-[1-(4-cyanophenyl)-3-(difluoromethyl)-1H-pyrazol-5-yl]benezenesulfonamide;

2,6-difluoro-4-[1-(3-trifluoromethylphenyl)-3-(difluoromethyl)-1H-pyrazol-5-yl]benezenesulfonamide;

2,6-difluoro-4-[1-(4-trifluoromethylphenyl)-3-(difluoromethyl)-1H-pyrazol-5-yl]benezenesulfonamide;

2,6-difluoro-4-[1-(3-trifluoromethoxyphenyl)-3-(difluoromethyl)-1H-pyrazol-5-yl]benezenesulfonamide;

2,6-difluoro-4-[1-(4-trifluoromethoxyphenyl)-3-(difluoromethyl)-1H-pyrazol-5-yl]benezenesulfonamide;

2,6-difluoro-4-[1-(3,4-dichlorophenyl)-3-(difluoromethyl)-1H-pyrazol-5-yl]benezenesulfonamide;

2,6-difluoro-4-[1-(3,4-dibromophenyl)-3-(difluoromethyl)-1H-pyrazol-5-yl]benezenesulfonamide 2,6-difluoro-4-[1-(3,4-difluorophenyl)-3-(difluoromethyl)-1H-pyrazol-5-yl]benezenesulfonamide;

2,6-difluoro-4-[1-(3,5-dichlorophenyl)-3-(difluoromethyl)-1H-pyrazol-5-yl]benezenesulfonamide;

2,6-difluoro-4-[1-(3,5-dibromophenyl)-3-(difluoromethyl)-1H-pyrazol-5-yl]benezenesulfonamide;

2,6-difluoro-4-[1-(3,5-difluorophenyl)-3-(difluoromethyl)-1H-pyrazol-5-yl]benezenesulfonamide;

2,6-difluoro-4-[1-(3,4-dimethylphenyl)-3-(difluoromethyl)-1H-pyrazol-5-yl]benezenesulfonamide;

2,6-difluoro-4-[1-(3,5-dimethylphenyl)-3-(difluoromethyl)-1H-pyrazol-5-yl]benezenesulfonamide;

2,6-difluoro-4-[1-(3-methyl-4-chlorophenyl)-3-(difluoromethyl)-1H-pyrazol-5-yl]benezenesulfonamide;

2,6-difluoro-4-[1-(4-methyl-3-chlorophenyl)-3-(difluoromethyl)-1H-pyrazol-5-yl]benezenesulfonamide;

2,6-difluoro-4-[1-(3-methyl-4-fluorophenyl)-3-(difluoromethyl)-1H-pyrazol-5-yl]benezenesulfonamide;

2,6-difluoro-4-[1-(4-methyl-3-fluorophenyl)-3-(difluoromethyl)-1H-pyrazol-5-yl]benezenesulfonamide;

2,6-difluoro-4-[1-(3-methyl-4-bromophenyl)-3-(difluoromethyl)-1H-pyrazol-5-yl]benezenesulfonamide;

2,6-difluoro-4-[1-(4-methyl-3-bromophenyl)-3-(difluoromethyl)-1H-pyrazol-5-yl]benezenesulfonamide;

2,6-difluoro-4-[1-(3-methyl-4-trifluoromethylphenyl)-3-(difluoromethyl)-1H-pyrazol-5-yl]benezenesulfonamide;

2,6-difluoro-4-[1-(4-methyl-3-trifluoromethylphenyl)-3-(difluoromethyl)-1H-pyrazol-5-yl]benezenesulfonamide;

2,6-difluoro-4-[1-(3-methyl-4-trifluoromethoxyphenyl)-3-(difluoromethyl)-1H-pyrazol-5-yl]benezenesulfonamide;
2,6-difluoro-4-[1-(4-methyl-3-trifluoromethoxyphenyl)-3-(difluoromethyl)-1H-pyrazol-5-yl]benezenesulfonamide;
2,6-difluoro-4-[1-(3-cyano-4-methylphenyl)-3-(difluoromethyl)-1H-pyrazol-5-yl]benezenesulfonamide;
2,6-difluoro-4-[1-(4-cyano-3-methylphenyl)-3-(difluoromethyl)-1H-pyrazol-5-yl]benezenesulfonamide;
2,6-difluoro-4-[1-(3-chloro-4-methoxyphenyl)-3-(difluoromethyl)-1H-pyrazol-5-yl]benezenesulfonamide;
2,6-difluoro-4-[1-(4-chloro-3-methoxyphenyl)-3-(difluoromethyl)-1H-pyrazol-5-yl]benezenesulfonamide;
2,6-difluoro-4-[1-(2-methylpyridin-6-yl)-3-(difluoromethyl)-1H-pyrazol-5-yl]benezenesulfonamide;
2,6-difluoro-4-[1-(2-methylthiazol-4-yl)-3-(difluoromethyl)-1H-pyrazol-5-yl]benezenesulfonamide;
2,6-difluoro-4-[1-(4-methylthiazol-2-yl)-3-(difluoromethyl)-1H-pyrazol-5-yl]benezenesulfonamide;
2,6-difluoro-4-[1-(2-methylpyridin-3-yl)-3-(difluoromethyl)-1H-pyrazol-5-yl]benezenesulfonamide;
2,6-difluoro-4-[1-(2-methylpyridin-3-yl)-3-(difluoromethyl)-1H-pyrazol-5-yl]benezenesulfonamide;
2,6-difluoro-4-[1-(3-pyridinyl)-3-(difluoromethyl)-1H-pyrazol-5-yl]benezenesulfonamide;
2,6-difluoro-4-[1-(5-methylpyridin-3-yl)-3-(difluoromethyl)-1H-pyrazol-5-yl]benezenesulfonamide;
2,6-difluoro-4-[1-(2-methylpyridin-3-yl)-3-(difluoromethyl)-1H-pyrazol-5-yl]benezenesulfonamide;
2,6-difluoro-4-[1-cyclohexyl-3-(difluoromethyl)-1H-pyrazol-5-yl]benezenesulfonamide;
2,6-difluoro-4-[1-cyclopentyl-3-(difluoromethyl)-1H-pyrazol-5-yl]benezenesulfonamide;
2,6-difluoro-4-[1-phenyl-3-(trifluoro)-1H-pyrazol-5-yl]benezenesulfonamide;
2,6-difluoro-4-[1-(3-chlorophenyl)-3-(trifluoro)-1H-pyrazol-5-yl]benezenesulfonamide;
2,6-difluoro-4-[1-(4-chlorophenyl)-3-(trifluoro)-1H-pyrazol-5-yl]benezenesulfonamide;
2,6-difluoro-4-[1-(3-bromophenyl)-3-(trifluoro)-1H-pyrazol-5-yl]benezenesulfonamide;
2,6-difluoro-4-[1-(4-bromophenyl)-3-(trifluoro)-1H-pyrazol-5-yl]benezenesulfonamide;
2,6-difluoro-4-[1-(3-fluorophenyl)-3-(trifluoro)-1H-pyrazol-5-yl]benezenesulfonamide;
2,6-difluoro-4-[1-(4-fluorophenyl)-3-(trifluoro)-1H-pyrazol-5-yl]benezenesulfonamide;
2,6-difluoro-4-[1-(3-methylphenyl)-3-(trifluoro)-1H-pyrazol-5-yl]benezenesulfonamide;
2,6-difluoro-4-[1-(4-methylphenyl)-3-(trifluoro)-1H-pyrazol-5-yl]benezenesulfonamide;
2,6-difluoro-4-[1-(3-cyanophenyl)-3-(trifluoro)-1H-pyrazol-5-yl]benezenesulfonamide;
2,6-difluoro-4-[1-(4-cyanophenyl)-3-(trifluoro)-1H-pyrazol-5-yl]benezenesulfonamide;
2,6-difluoro-4-[1-(3-trifluoromethylphenyl)-3-(trifluoro)-1H-pyrazol-5-yl]benezenesulfonamide;
2,6-difluoro-4-[1-(4-trifluoromethylphenyl)-3-(trifluoro)-1H-pyrazol-5-yl]benezenesulfonamide;
2,6-difluoro-4-[1-(3-trifluoromethoxyphenyl)-3-(trifluoro)-1H-pyrazol-5-yl]benezenesulfonamide;
2,6-difluoro-4-[1-(4-trifluoromethoxyphenyl)-3-(trifluoro)-1H-pyrazol-5-yl]benezenesulfonamide;
2,6-difluoro-4-[1-(3,4-dichlorophenyl)-3-(trifluoro)-1H-pyrazol-5-yl]benezenesulfonamide;
2,6-difluoro-4-[1-(3,4-dibromophenyl)-3-(trifluoro)-1H-pyrazol-5-yl]benezenesulfonamide;
2,6-difluoro-4-[1-(3,4-difluorophenyl)-3-(trifluoro)-1H-pyrazol-5-yl]benezenesulfonamide;
2,6-difluoro-4-[1-(3,5-dichlorophenyl)-3-(trifluoro)-1H-pyrazol-5-yl]benezenesulfonamide;
2,6-difluoro-4-[1-(3,5-dibromophenyl)-3-(trifluoro)-1H-pyrazol-5-yl]benezenesulfonamide;
2,6-difluoro-4-[1-(3,5-difluorophenyl)-3-(trifluoro)-1H-pyrazol-5-yl]benezenesulfonamide;
2,6-difluoro-4-[1-(3,4-dimethylphenyl)-3-(trifluoro)-1H-pyrazol-5-yl]benezenesulfonamide;
2,6-difluoro-4-[1-(3,5-dimethylphenyl)-3-(trifluoro)-1H-pyrazol-5-yl]benezenesulfonamide;
2,6-difluoro-4-[1-(3-methyl-4-chlorophenyl)-3-(trifluoro)-1H-pyrazol-5-yl]benezenesulfonamide;
2,6-difluoro-4-[1-(4-methyl-3-chlorophenyl)-3-(trifluoro)-1H-pyrazol-5-yl]benezenesulfonamide;
2,6-difluoro-4-[1-(3-methyl-4-fluorophenyl)-3-(trifluoro)-1H-pyrazol-5-yl]benezenesulfonamide;
2,6-difluoro-4-[1-(4-methyl-3-fluorophenyl)-3-(trifluoro)-1H-pyrazol-5-yl]benezenesulfonamide;
2,6-difluoro-4-[1-(3-methyl-4-bromophenyl)-3-(trifluoro)-1H-pyrazol-5-yl]benezenesulfonamide;
2,6-difluoro-4-[1-(4-methyl-3-bromophenyl)-3-(trifluoro)-1H-pyrazol-5-yl]benezenesulfonamide;
2,6-difluoro-4-[1-(3-methyl-4-trifluoromethylphenyl)-3-(trifluoro)-1H-pyrazol-5-yl]benezenesulfonamide;
2,6-difluoro-4-[1-(4-methyl-3-trifluoromethylphenyl)-3-(trifluoro)-1H-pyrazol-5-yl]benezenesulfonamide;
2,6-difluoro-4-[1-(3-methyl-4-trifluoromethoxyphenyl)-3-(trifluoro)-1H-pyrazol-5-yl]benezenesulfonamide;
2,6-difluoro-4-[1-(4-methyl-3-trifluoromethoxyphenyl)-3-(trifluoro)-1H-pyrazol-5-yl]benezenesulfonamide;
2,6-difluoro-4-[1-(3-cyano-4-methylphenyl)-3-(trifluoro)-1H-pyrazol-5-yl]benezenesulfonamide;
2,6-difluoro-4-[1-(4-cyano-3-methylphenyl)-3-(trifluoro)-1H-pyrazol-5-yl]benezenesulfonamide;
2,6-difluoro-4-[1-(3-chloro-4-methoxyphenyl)-3-(trifluoro)-1H-pyrazol-5-yl]benezenesulfonamide;
2,6-difluoro-4-[1-(4-chloro-3-methoxyphenyl)-3-(trifluoro)-1H-pyrazol-5-yl]benezenesulfonamide;
2,6-difluoro-4-[1-(2-methylpyridin-6-yl)-3-(trifluoro)-1H-pyrazol-5-yl]benezenesulfonamide;
2,6-difluoro-4-[1-(2-methylthiazol-4-yl)-3-(trifluoro)-1H-pyrazol-5-yl]benezenesulfonamide;
2,6-difluoro-4-[1-(4-methylthiazol-2-yl)-3-(trifluoro)-1H-pyrazol-5-yl]benezenesulfonamide;

2,6-difluoro-4-[1-(2-methylpyridin-3-yl)-3-(trifluoro)-1H-pyrazol-5-yl]benzenesulfonamide;
2,6-difluoro-4-[1-(2-methylpyridin-3-yl)-3-(trifluoro)-1H-pyrazol-5-yl]benzenesulfonamide;
2,6-difluoro-4-[1-(3-pyridinyl)-3-(trifluoro)-1H-pyrazol-5-yl]benzenesulfonamide;
2,6-difluoro-4-[1-(5-methylpyridin-3-yl)-3-(trifluoro)-1H-pyrazol-5-yl]benzenesulfonamide;
2,6-difluoro-4-[1-(2-methylpyridin-3-yl)-3-(trifluoro)-1H-pyrazol-5-yl]benzenesulfonamide;
2,6-difluoro-4-[1-cyclohexyl-3-(trifluoro)-1H-pyrazol-5-yl]benzenesulfonamide;
2,6-difluoro-4-[1-cyclopentyl-3-(trifluoro)-1H-pyrazol-5-yl]benzenesulfonamide;
2,6-difluoro-4-[1-phenyl-3-(trifluoro)-1H-pyrazol-5-yl]benzenesulfonamide;
2,6-difluoro-4-[1-(3-chlorophenyl)-3-(trifluoro)-1H-pyrazol-5-yl]benzenesulfonamide;
2,6-difluoro-4-[1-(4-chlorophenyl)-3-(trifluoro)-1H-pyrazol-5-yl]benzenesulfonamide;
2,6-difluoro-4-[1-(3-bromophenyl)-3-(trifluoro)-1H-pyrazol-5-yl]benzenesulfonamide;
2,6-difluoro-4-[1-(4-bromophenyl)-3-(trifluoro)-1H-pyrazol-5-yl]benzenesulfonamide;
2,6-difluoro-4-[1-(3-fluorophenyl)-3-(trifluoro)-1H-pyrazol-5-yl]benzenesulfonamide;
2,6-difluoro-4-[1-(4-fluorophenyl)-3-(trifluoro)-1H-pyrazol-5-yl]benzenesulfonamide;
2,6-difluoro-4-[1-(3-methylphenyl)-3-(trifluoro)-1H-pyrazol-5-yl]benzenesulfonamide;
2,6-difluoro-4-[1-(4-methylphenyl)-3-(trifluoro)-1H-pyrazol-5-yl]benzenesulfonamide;
2,6-difluoro-4-[1-(3-cyanophenyl)-3-(trifluoro)-1H-pyrazol-5-yl]benzenesulfonamide;
2,6-difluoro-4-[1-(4-cyanophenyl)-3-(trifluoro)-1H-pyrazol-5-yl]benzenesulfonamide;
2,6-difluoro-4-[1-(3-trifluoromethylphenyl)-3-(trifluoro)-1H-pyrazol-5-yl]benzenesulfonamide;
2,6-difluoro-4-[1-(4-trifluoromethylphenyl)-3-(trifluoro)-1H-pyrazol-5-yl]benzenesulfonamide;
2,6-difluoro-4-[1-(3-trifluoromethoxyphenyl)-3-(trifluoro)-1H-pyrazol-5-yl]benzenesulfonamide;
2,6-difluoro-4-[1-(4-trifluoromethoxyphenyl)-3-(trifluoro)-1H-pyrazol-5-yl]benzenesulfonamide;
2,6-difluoro-4-[1-(3,4-dichlorophenyl)-3-(trifluoro)-1H-pyrazol-5-yl]benzenesulfonamide;
2,6-difluoro-4-[1-(3,4-dibromophenyl)-3-(trifluoro)-1H-pyrazol-5-yl]benzenesulfonamide;
2,6-difluoro-4-[1-(3,4-difluorophenyl)-3-(trifluoro)-1H-pyrazol-5-yl]benzenesulfonamide;
2,6-difluoro-4-[1-(3,5-dichlorophenyl)-3-(trifluoro)-1H-pyrazol-5-yl]benzenesulfonamide;
2,6-difluoro-4-[1-(3,5-dibromophenyl)-3-(trifluoro)-1H-pyrazol-5-yl]benzenesulfonamide;
2,6-difluoro-4-[1-(3,5-difluorophenyl)-3-(trifluoro)-1H-pyrazol-5-yl]benzenesulfonamide;
2,6-difluoro-4-[1-(3,4-dimethylphenyl)-3-(trifluoro)-1H-pyrazol-5-yl]benzenesulfonamide;
2,6-difluoro-4-[1-(3,5-dimethylphenyl)-3-(trifluoro)-1H-pyrazol-5-yl]benzenesulfonamide;
2,6-difluoro-4-[1-(3-methyl-4-chlorophenyl)-3-(trifluoro)-1H-pyrazol-5-yl]benzenesulfonamide;
2,6-difluoro-4-[1-(4-methyl-3-chlorophenyl)-3-(trifluoro)-1H-pyrazol-5-yl]benzenesulfonamide;
2,6-difluoro-4-[1-(3-methyl-4-fluorophenyl)-3-(trifluoro)-1H-pyrazol-5-yl]benzenesulfonamide;
2,6-difluoro-4-[1-(4-methyl-3-fluorophenyl)-3-(trifluoro)-1H-pyrazol-5-yl]benzenesulfonamide;
2,6-difluoro-4-[1-(3-methyl-4-bromophenyl)-3-(trifluoro)-1H-pyrazol-5-yl]benzenesulfonamide;
2,6-difluoro-4-[1-(4-methyl-3-bromophenyl)-3-(trifluoro)-1H-pyrazol-5-yl]benzenesulfonamide;
2,6-difluoro-4-[1-(3-methyl-4-trifluoromethylphenyl)-3-(trifluoro)-1H-pyrazol-5-yl]benzenesulfonamide;
2,6-difluoro-4-[1-(4-methyl-3-trifluoromethylphenyl)-3-(trifluoro)-1H-pyrazol-5-yl]benzenesulfonamide;
2,6-difluoro-4-[1-(3-methyl-4-trifluoromethoxyphenyl)-3-(trifluoro)-1H-pyrazol-5-yl]benzenesulfonamide;
2,6-difluoro-4-[1-(4-methyl-3-trifluoromethoxyphenyl)-3-(trifluoro)-1H-pyrazol-5-yl]benzenesulfonamide;
2,6-difluoro-4-[1-(3-cyano-4-methylphenyl)-3-(trifluoro)-1H-pyrazol-5-yl]benzenesulfonamide;
2,6-difluoro-4-[1-(4-cyano-3-methylphenyl)-3-(trifluoro)-1H-pyrazol-5-yl]benzenesulfonamide;
2,6-difluoro-4-[1-(3-chloro-4-methoxyphenyl)-3-(trifluoro)-1H-pyrazol-5-yl]benzenesulfonamide;
2,6-difluoro-4-[1-(4-chloro-3-methoxyphenyl)-3-(trifluoro)-1H-pyrazol-5-yl]benzenesulfonamide;
2,6-difluoro-4-[1-(2-methylpyridin-6-yl)-3-(trifluoro)-1H-pyrazol-5-yl]benzenesulfonamide;
2,6-difluoro-4-[1-(2-methylthiazol-4-yl)-3-(trifluoro)-1H-pyrazol-5-yl]benzenesulfonamide;
2,6-difluoro-4-[1-(4-methylthiazol-2-yl)-3-(trifluoro)-1H-pyrazol-5-yl]benzenesulfonamide;
2,6-difluoro-4-[1-(2-methylpyridin-3-yl)-3-(trifluoro)-1H-pyrazol-5-yl]benzenesulfonamide;
2,6-difluoro-4-[1-(2-methylpyridin-3-yl)-3-(trifluoro)-1H-pyrazol-5-yl]benzenesulfonamide;
2,6-difluoro-4-[1-(3-pyridinyl)-3-(trifluoro)-1H-pyrazol-5-yl]benzenesulfonamide;
2,6-difluoro-4-[1-(5-methylpyridin-3-yl)-3-(trifluoro)-1H-pyrazol-5-yl]benzenesulfonamide;
2,6-difluoro-4-[1-(2-methylpyridin-3-yl)-3-(trifluoro)-1H-pyrazol-5-yl]benzenesulfonamide;
2,6-difluoro-4-[1-cyclohexyl-3-(trifluoro)-1H-pyrazol-5-yl]benzenesulfonamide;
2,6-difluoro-4-[1-cyclopentyl-3-(trifluoro)-1H-pyrazol-5-yl]benzenesulfonamide;
5-phenyl-1-[3,6-difluoro-4-(methylsulfonyl)phenyl]-3-(trifluoromethyl)-1H-pyrazole;
5-(3-chloro-5-methylphenyl)-1-[3,6-difluoro-4-(methylsulfonyl)phenyl]-3-(trifluoromethyl)-1H-pyrazole;
5-(3,6-difluoro-5-methylphenyl)-1-[3,6-difluoro-4-(methylsulfonyl)phenyl]-3-(trifluoromethyl)-1H-pyrazole;
5-(3-chlorophenyl)-1-[3,6-difluoro-4-(methylsulfonyl)phenyl]-3-(trifluoromethyl)-1H-pyrazole;
5-(4-chlorophenyl)-1-[3,6-difluoro-4-(methylsulfonyl)phenyl]-3-(trifluoromethyl)-1H-pyrazole;
5-(3-bromophenyl)-1-[3,6-difluoro-4-(methylsulfonyl)phenyl]-3-(trifluoromethyl)-1H-pyrazole;
5-(4-bromophenyl)-1-[3,6-difluoro-4-(methylsulfonyl)phenyl]-3-(trifluoromethyl)-1H-pyrazole;

5-(3,6-difluorophenyl)-1-[3,6-difluoro-4-(methylsulfonyl)phenyl]-3-(trifluoromethyl)-1H-pyrazole;

5-(4-fluorophenyl)-1-[3,6-difluoro-4-(methylsulfonyl)phenyl]-3-(trifluoromethyl)-1H-pyrazole;

5-(4-methylphenyl)-1-[3,6-difluoro-4-(methylsulfonyl)phenyl]-3-(trifluoromethyl)-1H-pyrazole;

5-(3-methylphenyl)-1-[3,6-difluoro-4-(methylsulfonyl)phenyl]-3-(trifluoromethyl)-1H-pyrazole;

5-(3-bromo-5-methylphenyl)-1-[3,6-difluoro-4-(methylsulfonyl)phenyl]-3-(trifluoromethyl)-1H-pyrazole;

5-(3,4-dichlorophenyl)-1-[3,6-difluoro-4-(methylsulfonyl)phenyl]-3-(trifluoromethyl)-1H-pyrazole;

5-(3,4-dibromophenyl)-1-[3,6-difluoro-4-(methylsulfonyl)phenyl]-3-(trifluoromethyl)-1H-pyrazole;

5-(3,4-difluorophenyl)-1-[3,6-difluoro-4-(methylsulfonyl)phenyl]-3-(trifluoromethyl)-1H-pyrazole;

5-(3,5-dichlorophenyl)-1-[3,6-difluoro-4-(methylsulfonyl)phenyl]-3-(trifluoromethyl)-1H-pyrazole;

5-(3,5-dibromophenyl)-1-[3,6-difluoro-4-(methylsulfonyl)phenyl]-3-(trifluoromethyl)-1H-pyrazole;

5-(3,6-difluorophenyl)-1-[3,6-difluoro-4-(methylsulfonyl)phenyl]-3-(trifluoromethyl)-1H-pyrazole;

5-(3-chloro-4-fluorophenyl)-1-[3,6-difluoro-4-(methylsulfonyl)phenyl]-3-(trifluoromethyl)-1H-pyrazole;

5-(3-chloro-4-methylphenyl)-1-[3,6-difluoro-4-(methylsulfonyl)phenyl]-3-(trifluoromethyl)-1H-pyrazole;

5-(3-bromo-4-methylphenyl)-1-[3,6-difluoro-4-(methylsulfonyl)phenyl]-3-(trifluoromethyl)-1H-pyrazole;

5-(3,6-difluoro-4-methylphenyl)-1-[3,6-difluoro-4-(methylsulfonyl)phenyl]-3-(trifluoromethyl)-1H-pyrazole;

5-(3,4-dimethylphenyl)-1-[3,6-difluoro-4-(methylsulfonyl)phenyl]-3-(trifluoromethyl)-1H-pyrazole;

5-(4-trifluoromethoxyphenyl)-1-[3,6-difluoro-4-(methylsulfonyl)phenyl]-3-(trifluoromethyl)-1H-pyrazole;

5-(3-methyl-4-trifluoromethoxyphenyl)-1-[3,6-difluoro-4-(methylsulfonyl)phenyl]-3-(trifluoromethyl)-1H-pyrazole;

5-(4-methyl-3-trifluoromethoxyphenyl)-1-[3,6-difluoro-4-(methylsulfonyl)phenyl]-3-(trifluoromethyl)-1H-pyrazole;

5-(4-methyl-3-trifluoromethoxyphenyl)-1-[3,6-difluoro-4-(methylsulfonyl)phenyl]-3-(trifluoromethyl)-1H-pyrazole;

5-(3-cyano-4-methylphenyl)-1-[3,6-difluoro-4-(methylsulfonyl)phenyl]-3-(trifluoromethyl)-1H-pyrazole;

5-(4-cyano-3-methylphenyl)-1-[3,6-difluoro-4-(methylsulfonyl)phenyl]-3-(trifluoromethyl)-1H-pyrazole;

5-(3-cyanophenyl)-1-[3,6-difluoro-4-(methylsulfonyl)phenyl]-3-(trifluoromethyl)-1H-pyrazole;

5-(4-cyanophenyl)-1-[3,6-difluoro-4-(methylsulfonyl)phenyl]-3-(trifluoromethyl)-1H-pyrazole;

5-(3-chloro-4-methoxyphenyl)-1-[3,6-difluoro-4-(methylsulfonyl)phenyl]-3-(trifluoromethyl)-1H-pyrazole;

5-(4-chloro-3-methoxyphenyl)-1-[3,6-difluoro-4-(methylsulfonyl)phenyl]-3-(trifluoromethyl)-1H-pyrazole;

5-(2-methylpyridin-6-yl)-1-[3,6-difluoro-4-(methylsulfonyl)phenyl]-3-(trifluoromethyl)-1H-pyrazole;

5-(2-methylthiazol-4-yl)-1-[3,6-difluoro-4-(methylsulfonyl)phenyl]-3-(trifluoromethyl)-1H-pyrazole;

5-(4-methylthiazol-2-yl)-1-[3,6-difluoro-4-(methylsulfonyl)phenyl]-3-(trifluoromethyl)-1H-pyrazole;

5-(2-methylpyridin-3-yl)-1-[3,6-difluoro-4-(methylsulfonyl)phenyl]-3-(trifluoromethyl)-1H-pyrazole;

5-(2-methylpyridin-3-yl)-1-[3,6-difluoro-4-(methylsulfonyl)phenyl]-3-(trifluoromethyl)-1H-pyrazole;

5-(3-pyridinyl)-1-[3,6-difluoro-4-(methylsulfonyl)phenyl]-3-(trifluoromethyl)-1H-pyrazole;

5-(5-methylpyridin-3-yl)-1-[3,6-difluoro-4-(methylsulfonyl)phenyl]-3-(trifluoromethyl)-1H-pyrazole;

5-(2-methylpyridin-3-yl)-1-[3,6-difluoro-4-(methylsulfonyl)phenyl]-3-(trifluoromethyl)-1H-pyrazole;

3-cyclohexyl-1-[3,6-difluoro-4-(methylsulfonyl)phenyl]-3-(trifluoromethyl)-1H-pyrazole;

3-cyclopentyl-1-[3,6-difluoro-4-(methylsulfonyl)phenyl]-3-(trifluoromethyl)-1H-pyrazole;

5-phenyl-1-[3,6-difluoro-4-(methylsulfonyl)phenyl]-3-(difluoromethyl)-1H-pyrazole;

5-(3-chlorophenyl)-1-[3,6-difluoro-4-(methylsulfonyl)phenyl]-3-(difluoromethyl)-1H-pyrazole;

5-(4-chlorophenyl)-1-[3,6-difluoro-4-(methylsulfonyl)phenyl]-3-(difluoromethyl)-1H-pyrazole;

5-(3-bromophenyl)-1-[3,6-difluoro-4-(methylsulfonyl)phenyl]-3-(difluoromethyl)-1H-pyrazole;

5-(4-bromophenyl)-1-[3,6-difluoro-4-(methylsulfonyl)phenyl]-3-(difluoromethyl)-1H-pyrazole;

5-(3-fluorophenyl)-1-[3,6-difluoro-4-(methylsulfonyl)phenyl]-3-(difluoromethyl)-1H-pyrazole;

5-(4-fluorophenyl)-1-[3,6-difluoro-4-(methylsulfonyl)phenyl]-3-(difluoromethyl)-1H-pyrazole;

5-(3-methylphenyl)-1-[3,6-difluoro-4-(methylsulfonyl)phenyl]-3-(difluoromethyl)-1H-pyrazole;

5-(4-methylphenyl)-1-[3,6-difluoro-4-(methylsulfonyl)phenyl]-3-(difluoromethyl)-1H-pyrazole;

5-(3-cyanophenyl)-1-[3,6-difluoro-4-(methylsulfonyl)phenyl]-3-(difluoromethyl)-1H-pyrazole;

5-(4-cyanophenyl)-1-[3,6-difluoro-4-(methylsulfonyl)phenyl]-3-(difluoromethyl)-1H-pyrazole;

5-(3-trifluoromethylphenyl)-1-[3,6-difluoro-4-(methylsulfonyl)phenyl]-3-(difluoromethyl)-1H-pyrazole;

5-(4-trifluoromethylphenyl)-1-[3,6-difluoro-4-(methylsulfonyl)phenyl]-3-(difluoromethyl)-1H-pyrazole;

5-(3-trifluoromethoxyphenyl)-1-[3,6-difluoro-4-(methylsulfonyl)phenyl]-3-(difluoromethyl)-1H-pyrazole;

5-(4-trifluoromethoxyphenyl)-1-[3,6-difluoro-4-(methylsulfonyl)phenyl]-3-(difluoromethyl)-1H-pyrazole;

5-(3,4-dichlorophenyl)-1-[3,6-difluoro-4-(methylsulfonyl)phenyl]-3-(difluoromethyl)-1H-pyrazole;

5-(3,4-dibromophenyl)-1-[3,6-difluoro-4-(methylsulfonyl)phenyl]-3-(difluoromethyl)-1H-pyrazole;

5-(3,4-difluorophenyl)-1-[3,6-difluoro-4-(methylsulfonyl)phenyl]-3-(difluoromethyl)-1H-pyrazole;

5-(3,5-dichlorophenyl)-1-[3,6-difluoro-4-(methylsulfonyl)phenyl]-3-(difluoromethyl)-1H-pyrazole;

5-(3,5-dibromophenyl)-1-[3,6-difluoro-4-(methylsulfonyl)phenyl]-3-(difluoromethyl)-1H-pyrazole;

5-(3,5-difluorophenyl)-1-[3,6-difluoro-4-(methylsulfonyl)phenyl]-3-(difluoromethyl)-1H-pyrazole;

5-(3,4-dimethylphenyl)-1-[3,6-difluoro-4-(methylsulfonyl)phenyl]-3-(difluoromethyl)-1H-pyrazole;

5-(3,5-dimethylphenyl)-1-[3,6-difluoro-4-(methylsulfonyl)phenyl]-3-(difluoromethyl)-1H-pyrazole;

5-(3-methyl-4-chlorophenyl)-1-[3,6-difluoro-4-(methylsulfonyl)phenyl]-3-(difluoromethyl)-1H-pyrazole;

5-(4-methyl-3-chlorophenyl)-1-[3,6-difluoro-4-(methylsulfonyl)phenyl]-3-(difluoromethyl)-1H-pyrazole;

5-(3-methyl-4-fluorophenyl)-1-[3,6-difluoro-4-(methylsulfonyl)phenyl]-3-(difluoromethyl)-1H-pyrazole;

5-(4-methyl-3-fluorophenyl)-1-[3,6-difluoro-4-(methylsulfonyl)phenyl]-3-(difluoromethyl)-1H-pyrazole;

5-(3-methyl-4-bromophenyl)-1-[3,6-difluoro-4-(methylsulfonyl)phenyl]-3-(difluoromethyl)-1H-pyrazole;

5-(4-methyl-3-bromophenyl)-1-[3,6-difluoro-4-(methylsulfonyl)phenyl]-3-(difluoromethyl)-1H-pyrazole;

5-(3-methyl-4-trifluoromethylphenyl)-1-[3,6-difluoro-4-(methylsulfonyl)phenyl]-3-(difluoromethyl)-1H-pyrazole;

5-(4-methyl-3-trifluoromethylphenyl)-1-[3,6-difluoro-4-(methylsulfonyl)phenyl]-3-(difluoromethyl)-1H-pyrazole;

5-(3-methyl-4-trifluoromethoxyphenyl)-1-[3,6-difluoro-4-(methylsulfonyl)phenyl]-3-(difluoromethyl)-1H-pyrazole;

5-(4-methyl-3-trifluoromethoxyphenyl)-1-[3,6-difluoro-4-(methylsulfonyl)phenyl]-3-(difluoromethyl)-1H-pyrazole;

5-(3-cyano-4-methylphenyl)-1-[3,6-difluoro-4-(methylsulfonyl)phenyl]-3-(difluoromethyl)-1H-pyrazole;

5-(4-cyano-3-methylphenyl)-1-[3,6-difluoro-4-(methylsulfonyl)phenyl]-3-(difluoromethyl)-1H-pyrazole;

5-(3-chloro-4-methoxyphenyl)-1-[3,6-difluoro-4-(methylsulfonyl)phenyl]-3-(difluoromethyl)-1H-pyrazole;

5-(4-chloro-3-methoxyphenyl)-1-[3,6-difluoro-4-(methylsulfonyl)phenyl]-3-(difluoromethyl)-1H-pyrazole;

5-(2-methylpyridin-6-yl)-1-[3,6-difluoro-4-(methylsulfonyl)phenyl]-3-(difluoromethyl)-1H-pyrazole;

5-(2-methylthiazol-4-yl)-1-[3,6-difluoro-4-(methylsulfonyl)phenyl]-3-(difluoromethyl)-1H-pyrazole;

5-(4-methylthiazol-2-yl)-1-[3,6-difluoro-4-(methylsulfonyl)phenyl]-3-(difluoromethyl)-1H-pyrazole;

5-(2-methylpyridin-3-yl)-1-[3,6-difluoro-4-(methylsulfonyl)phenyl]-3-(difluoromethyl)-1H-pyrazole;

5-(2-methylpyridin-3-yl)-1-[3,6-difluoro-4-(methylsulfonyl)phenyl]-3-(difluoromethyl)-1H-pyrazole;

5-(3-pyridinyl)-1-[3,6-difluoro-4-(methylsulfonyl)phenyl]-3-(difluoromethyl)-1H-pyrazole;

5-(5-methylpyridin-3-yl)-1-[3,6-difluoro-4-(methylsulfonyl)phenyl]-3-(difluoromethyl)-1H-pyrazole;

5-(2-methylpyridin-3-yl)-1-[3,6-difluoro-4-(methylsulfonyl)phenyl]-3-(difluoromethyl)-1H-pyrazole;

5-cyclohexyl-1-[3,6-difluoro-4-(methylsulfonyl)phenyl]-3-(difluoromethyl)-1H-pyrazole;

5-cyclopentyl-1-[3,6-difluoro-4-(methylsulfonyl)phenyl]-3-(difluoromethyl)-1H-pyrazole;

1-phenyl-5-[3,6-difluoro-4-(methylsulfonyl)phenyl]-3-(trifluoromethyl)-1H-pyrazole;

1-(3-chlorophenyl)-5-[3,6-difluoro-4-(methylsulfonyl)phenyl]-3-(trifluoromethyl)-1H-pyrazole;

1-(4-chlorophenyl)-5-[3,6-difluoro-4-(methylsulfonyl)phenyl]-3-(trifluoromethyl)-1H-pyrazole;

1-(3-bromophenyl)-5-[3,6-difluoro-4-(methylsulfonyl)phenyl]-3-(trifluoromethyl)-1H-pyrazole;

1-(4-bromophenyl)-5-[3,6-difluoro-4-(methylsulfonyl)phenyl]-3-(trifluoromethyl)-1H-pyrazole;

1-(3-fluorophenyl)-5-[3,6-difluoro-4-(methylsulfonyl)phenyl]-3-(trifluoromethyl)-1H-pyrazole;

1-(4-fluorophenyl)-5-[3,6-difluoro-4-(methylsulfonyl)phenyl]-3-(trifluoromethyl)-1H-pyrazole;

1-(3-methylphenyl)-5-[3,6-difluoro-4-(methylsulfonyl)phenyl]-3-(trifluoromethyl)-1H-pyrazole;

1-(4-methylphenyl)-5-[3,6-difluoro-4-(methylsulfonyl)phenyl]-3-(trifluoromethyl)-1H-pyrazole;

1-(3-cyanophenyl)-5-[3,6-difluoro-4-(methylsulfonyl)phenyl]-3-(trifluoromethyl)-1H-pyrazole;

1-(4-cyanophenyl)-5-[3,6-difluoro-4-(methylsulfonyl)phenyl]-3-(trifluoromethyl)-1H-pyrazole;

1-(3-trifluoromethylphenyl)-5-[3,6-difluoro-4-(methylsulfonyl)phenyl]-3-(trifluoromethyl)-1H-pyrazole;

1-(4-trifluoromethylphenyl)-5-[3,6-difluoro-4-(methylsulfonyl)phenyl]-3-(trifluoromethyl)-1H-pyrazole;

1-(3-trifluoromethoxyphenyl)-5-[3,6-difluoro-4-(methylsulfonyl)phenyl]-3-(trifluoromethyl)-1H-pyrazole;

1-(4-trifluoromethoxyphenyl)-5-[3,6-difluoro-4-(methylsulfonyl)phenyl]-3-(trifluoromethyl)-1H-pyrazole;

1-(3,4-dichlorophenyl)-5-[3,6-difluoro-4-(methylsulfonyl)phenyl]-3-(trifluoromethyl)-1H-pyrazole;

1-(3,4-dibromophenyl)-5-[3,6-difluoro-4-(methylsulfonyl)phenyl]-3-(trifluoromethyl)-1H-pyrazole;

1-(3,4-difluorophenyl)-5-[3,6-difluoro-4-(methylsulfonyl)phenyl]-3-(trifluoromethyl)-1H-pyrazole;

1-(3,5-dichlorophenyl)-5-[3,6-difluoro-4-(methylsulfonyl)phenyl]-3-(trifluoromethyl)-1H-pyrazole;

1-(3,5-dibromophenyl)-5-[3,6-difluoro-4-(methylsulfonyl)phenyl]-3-(trifluoromethyl)-1H-pyrazole;

1-(3,5-difluorophenyl)-5-[3,6-difluoro-4-(methylsulfonyl)phenyl]-3-(trifluoromethyl)-1H-pyrazole;

1-(3,4-dimethylphenyl)-5-[3,6-difluoro-4-(methylsulfonyl)phenyl]-3-(trifluoromethyl)-1H-pyrazole;

1-(3,5-dimethylphenyl)-5-[3,6-difluoro-4-(methylsulfonyl)phenyl]-3-(trifluoromethyl)-1H-pyrazole;

1-(3-methyl-4-chlorophenyl)-5-[3,6-difluoro-4-(methylsulfonyl)phenyl]-3-(trifluoromethyl)-1H-pyrazole;

1-(4-methyl-3-chlorophenyl)-5-[3,6-difluoro-4-(methylsulfonyl)phenyl]-3-(trifluoromethyl)-1H-pyrazole;

1-(3-methyl-4-fluorophenyl)-5-[3,6-difluoro-4-(methylsulfonyl)phenyl]-3-(trifluoromethyl)-1H-pyrazole;

1-(4-methyl-3-fluorophenyl)-5-[3,6-difluoro-4-(methylsulfonyl)phenyl]-3-(trifluoromethyl)-1H-pyrazole;

1-(3-methyl-4-bromophenyl)-5-[3,6-difluoro-4-(methylsulfonyl)phenyl]-3-(trifluoromethyl)-1H-pyrazole;

1-(4-methyl-3-bromophenyl)-5-[3,6-difluoro-4-(methylsulfonyl)phenyl]-3-(trifluoromethyl)-1H-pyrazole;

1-(3-methyl-4-trifluoromethylphenyl)-5-[3,6-difluoro-4-(methylsulfonyl)phenyl]-3-(trifluoromethyl)-1H-pyrazole;

1-(4-methyl-3-trifluoromethylphenyl)-5-[3,6-difluoro-4-(methylsulfonyl)phenyl]-3-(trifluoromethyl)-1H-pyrazole;

1-(3-methyl-4-trifluoromethoxyphenyl)-5-[3,6-difluoro-4-(methylsulfonyl)phenyl]-3-(trifluoromethyl)-1H-pyrazole;

1-(4-methyl-3-trifluoromethoxyphenyl)-5-[3,6-difluoro-4-(methylsulfonyl)phenyl]-3-(trifluoromethyl)-1H-pyrazole;

1-(3-cyano-4-methylphenyl)-5-[3,6-difluoro-4-(methylsulfonyl)phenyl]-3-(trifluoromethyl)-1H-pyrazole;

1-(4-cyano-3-methylphenyl)-5-[3,6-difluoro-4-(methylsulfonyl)phenyl]-3-(trifluoromethyl)-1H-pyrazole;

1-(3-chloro-4-methoxyphenyl)-5-[3,6-difluoro-4-(methylsulfonyl)phenyl]-3-(trifluoromethyl)-1H-pyrazole;

1-(4-chloro-3-methoxyphenyl)-5-[3,6-difluoro-4-(methylsulfonyl)phenyl]-3-(trifluoromethyl)-1H-pyrazole;

1-(2-methylpyridin-6-yl)-5-[3,6-difluoro-4-(methylsulfonyl)phenyl]-3-(trifluoromethyl)-1H-pyrazole;

1-(2-methylthiazol-4-yl)-5-[3,6-difluoro-4-(methylsulfonyl)phenyl]-3-(trifluoromethyl)-1H-pyrazole;

1-(4-methylthiazol-2-yl)-5-[3,6-difluoro-4-(methylsulfonyl)phenyl]-3-(trifluoromethyl)-1H-pyrazole;

1-(2-methylpyridin-3-yl)-5-[3,6-difluoro-4-(methylsulfonyl)phenyl]-3-(trifluoromethyl)-1H-pyrazole;

1-(2-methylpyridin-3-yl)-5-[3,6-difluoro-4-(methylsulfonyl)phenyl]-3-(trifluoromethyl)-1H-pyrazole;

1-(3-pyridinyl)-5-[3,6-difluoro-4-(methylsulfonyl)phenyl]-3-(trifluoromethyl)-1H-pyrazole;

1-(5-methylpyridin-3-yl)-5-[3,6-difluoro-4-(methylsulfonyl)phenyl]-3-(trifluoromethyl)-1H-pyrazole;

1-(2-methylpyridin-3-yl)-5-[3,6-difluoro-4-(methylsulfonyl)phenyl]-3-(trifluoromethyl)-1H-pyrazole;

1-cyclohexyl-5-[3,6-difluoro-4-(methylsulfonyl)phenyl]-3-(trifluoromethyl)-1H-pyrazole;

1-cyclopentyl-5-[3,6-difluoro-4-(methylsulfonyl)phenyl]-3-(trifluoromethyl)-1H-pyrazole;

1-phenyl-5-[3,6-difluoro-4-(methylsulfonyl)phenyl]-3-(difluoromethyl)-1H-pyrazole;

1-(3-chlorophenyl)-5-[3,6-difluoro-4-(methylsulfonyl)phenyl]-3-(difluoromethyl)-1H-pyrazole;

1-(4-chlorophenyl)-5-[3,6-difluoro-4-(methylsulfonyl)phenyl]-3-(difluoromethyl)-1H-pyrazole;

1-(3-bromophenyl)-5-[3,6-difluoro-4-(methylsulfonyl)phenyl]-3-(difluoromethyl)-1H-pyrazole;

1-(4-bromophenyl)-5-[3,6-difluoro-4-(methylsulfonyl)phenyl]-3-(difluoromethyl)-1H-pyrazole;

1-(3-fluorophenyl)-5-[3,6-difluoro-4-(methylsulfonyl)phenyl]-3-(difluoromethyl)-1H-pyrazole;

1-(4-fluorophenyl)-5-[3,6-difluoro-4-(methylsulfonyl)phenyl]-3-(difluoromethyl)-1H-pyrazole;

1-(3-methylphenyl)-5-[3,6-difluoro-4-(methylsulfonyl)phenyl]-3-(difluoromethyl)-1H-pyrazole;

1-(4-methylphenyl)-5-[3,6-difluoro-4-(methylsulfonyl)phenyl]-3-(difluoromethyl)-1H-pyrazole;

1-(3-cyanophenyl)-5-[3,6-difluoro-4-(methylsulfonyl)phenyl]-3-(difluoromethyl)-1H-pyrazole;

1-(4-cyanophenyl)-5-[3,6-difluoro-4-(methylsulfonyl)phenyl]-3-(difluoromethyl)-1H-pyrazole;

1-(3-trifluoromethylphenyl)-5-[3,6-difluoro-4-(methylsulfonyl)phenyl]-3-(difluoromethyl)-1H-pyrazole;

1-(4-trifluoromethylphenyl)-5-[3,6-difluoro-4-(methylsulfonyl)phenyl]-3-(difluoromethyl)-1H-pyrazole;

1-(3-trifluoromethoxyphenyl)-5-[3,6-difluoro-4-(methylsulfonyl)phenyl]-3-(difluoromethyl)-1H-pyrazole;

1-(4-trifluoromethoxyphenyl)-5-[3,6-difluoro-4-(methylsulfonyl)phenyl]-3-(difluoromethyl)-1H-pyrazole;

1-(3,4-dichlorophenyl)-5-[3,6-difluoro-4-(methylsulfonyl)phenyl]-3-(difluoromethyl)-1H-pyrazole;

1-(3,4-dibromophenyl)-5-[3,6-difluoro-4-(methylsulfonyl)phenyl]-3-(difluoromethyl)-1H-pyrazole;

1-(3,4-difluorophenyl)-5-[3,6-difluoro-4-(methylsulfonyl)phenyl]-3-(difluoromethyl)-1H-pyrazole;

1-(3,5-dichlorophenyl)-5-[3,6-difluoro-4-(methylsulfonyl)phenyl]-3-(difluoromethyl)-1H-pyrazole;

1-(3,5-dibromophenyl)-5-[3,6-difluoro-4-(methylsulfonyl)phenyl]-3-(difluoromethyl)-1H-pyrazole;

1-(3,5-difluorophenyl)-5-[3,6-difluoro-4-(methylsulfonyl)phenyl]-3-(difluoromethyl)-1H-pyrazole;

1-(3,4-dimethylphenyl)-5-[3,6-difluoro-4-(methylsulfonyl)phenyl]-3-(difluoromethyl)-1H-pyrazole;

1-(3,5-dimethylphenyl)-5-[3,6-difluoro-4-(methylsulfonyl)phenyl]-3-(difluoromethyl)-1H-pyrazole;

1-(3-methyl-4-chlorophenyl)-5-[3,6-difluoro-4-(methylsulfonyl)phenyl]-3-(difluoromethyl)-1H-pyrazole;

1-(4-methyl-3-chlorophenyl)-5-[3,6-difluoro-4-(methylsulfonyl)phenyl]-3-(difluoromethyl)-1H-pyrazole;

1-(3-methyl-4-fluorophenyl)-5-[3,6-difluoro-4-(methylsulfonyl)phenyl]-3-(difluoromethyl)-1H-pyrazole;

1-(4-methyl-3-fluorophenyl)-5-[3,6-difluoro-4-(methylsulfonyl)phenyl]-3-(difluoromethyl)-1H-pyrazole;

1-(3-methyl-4-bromophenyl)-5-[3,6-difluoro-4-(methylsulfonyl)phenyl]-3-(difluoromethyl)-1H-pyrazole;

1-(4-methyl-3-bromophenyl)-5-[3,6-difluoro-4-(methylsulfonyl)phenyl]-3-(difluoromethyl)-1H-pyrazole;

1-(3-methyl-4-trifluoromethylphenyl)-5-[3,6-difluoro-4-(methylsulfonyl)phenyl]-3-(difluoromethyl)-1H-pyrazole;

1-(4-methyl-3-trifluoromethylphenyl)-5-[3,6-difluoro-4-(methylsulfonyl)phenyl]-3-(difluoromethyl)-1H-pyrazole;

1-(3-methyl-4-trifluoromethoxyphenyl)-5-[3,6-difluoro-4-(methylsulfonyl)phenyl]-3-(difluoromethyl)-1H-pyrazole;

1-(4-methyl-3-trifluoromethoxyphenyl)-5-[3,6-difluoro-4-(methylsulfonyl)phenyl]-3-(difluoromethyl)-1H-pyrazole;

1-(3-cyano-4-methylphenyl)-5-[3,6-difluoro-4-(methylsulfonyl)phenyl]-3-(difluoromethyl)-1H-pyrazole;

1-(4-cyano-3-methylphenyl)-5-[3,6-difluoro-4-(methylsulfonyl)phenyl]-3-(difluoromethyl)-1H-pyrazole;

1-(3-chloro-4-methoxyphenyl)-5-[3,6-difluoro-4-(methylsulfonyl)phenyl]-3-(difluoromethyl)-1H-pyrazole;

1-(4-chloro-3-methoxyphenyl)-5-[3,6-difluoro-4-(methylsulfonyl)phenyl]-3-(difluoromethyl)-1H-pyrazole;

1-(2-methylpyridin-6-yl)-5-[3,6-difluoro-4-(methylsulfonyl)phenyl]-3-(difluoromethyl)-1H-pyrazole;

1-(2-methylthiazol-4-yl)-5-[3,6-difluoro-4-(methylsulfonyl)phenyl]-3-(difluoromethyl)-1H-pyrazole;

1-(4-methylthiazol-2-yl)-5-[3,6-difluoro-4-(methylsulfonyl)phenyl]-3-(difluoromethyl)-1H-pyrazole;

1-(2-methylpyridin-3-yl)-5-[3,6-difluoro-4-(methylsulfonyl)phenyl]-3-(difluoromethyl)-1H-pyrazole;

1-(2-methylpyridin-3-yl)-5-[3,6-difluoro-4-(methylsulfonyl)phenyl]-3-(difluoromethyl)-1H-pyrazole;

1-(3-pyridinyl)-5-[3,6-difluoro-4-(methylsulfonyl)phenyl]-3-(difluoromethyl)-1H-pyrazole;

1-(5-methylpyridin-3-yl)-5-[3,6-difluoro-4-(methylsulfonyl)phenyl]-3-(difluoromethyl)-1H-pyrazole;

1-(2-methylpyridin-3-yl)-5-[3,6-difluoro-4-(methylsulfonyl)phenyl]-3-(difluoromethyl)-1H-pyrazole;

1-cyclohexyl-5-[3,6-difluoro-4-(methylsulfonyl)phenyl]-3-(difluoromethyl)-1H-pyrazole;

1-cyclopentyl-5-[3,6-difluoro-4-(methylsulfonyl)phenyl]-3-(difluoromethyl)-1H-pyrazole;

2,5-difluoro-4-[1-phenyl-3-(difluoromethyl)-1H-pyrazol-5-yl]benzenesulfonamide;

2,5-difluoro-4-[1-(3-chlorophenyl)-3-(difluoromethyl)-1H-pyrazol-5-yl]benzenesulfonamide;

2,5-difluoro-4-[1-(4-chlorophenyl)-3-(difluoromethyl)-1H-pyrazol-5-yl]benzenesulfonamide;

2,5-difluoro-4-[1-(3-bromophenyl)-3-(difluoromethyl)-1H-pyrazol-5-yl]benzenesulfonamide;

2,5-difluoro-4-[1-(4-bromophenyl)-3-(difluoromethyl)-1H-pyrazol-5-yl]benzenesulfonamide;

2,5-difluoro-4-[1-(3-fluorophenyl)-3-(difluoromethyl)-1H-pyrazol-5-yl]benzenesulfonamide;

2,5-difluoro-4-[1-(4-fluorophenyl)-3-(difluoromethyl)-1H-pyrazol-5-yl]benzenesulfonamide;

2,5-difluoro-4-[1-(3-methylphenyl)-3-(difluoromethyl)-1H-pyrazol-5-yl]benzenesulfonamide;

2,5-difluoro-4-[1-(4-methylphenyl)-3-(difluoromethyl)-1H-pyrazol-5-yl]benzenesulfonamide;

2,5-difluoro-4-[1-(3-cyanophenyl)-3-(difluoromethyl)-1H-pyrazol-5-yl]benzenesulfonamide;

2,5-difluoro-4-[1-(4-cyanophenyl)-3-(difluoromethyl)-1H-pyrazol-5-yl]benzenesulfonamide;

2,5-difluoro-4-[1-(3-trifluoromethylphenyl)-3-(difluoromethyl)-1H-pyrazol-5-yl]benzenesulfonamide;

2,5-difluoro-4-[1-(4-trifluoromethylphenyl)-3-(difluoromethyl)-1H-pyrazol-5-yl]benezenesulfonamide;

2,5-difluoro-4-[1-(3-trifluoromethoxyphenyl)-3-(difluoromethyl)-1H-pyrazol-5-yl]benezenesulfonamide;

2,5-difluoro-4-[1-(4-trifluoromethoxyphenyl)-3-(difluoromethyl)-1H-pyrazol-5-yl]benezenesulfonamide;

2,5-difluoro-4-[1-(3,4-dichlorophenyl)-3-(difluoromethyl)-1H-pyrazol-5-yl]benezenesulfonamide;

2,5-difluoro-4-[1-(3,4-dibromophenyl)-3-(difluoromethyl)-1H-pyrazol-5-yl]benezenesulfonamide;

2,5-difluoro-4-[1-(3,4-difluorophenyl)-3-(difluoromethyl)-1H-pyrazol-5-yl]benezenesulfonamide;

2,5-difluoro-4-[1-(3,5-dichlorophenyl)-3-(difluoromethyl)-1H-pyrazol-5-yl]benezenesulfonamide;

2,5-difluoro-4-[1-(3,5-dibromophenyl)-3-(difluoromethyl)-1H-pyrazol-5-yl]benezenesulfonamide;

2,5-difluoro-4-[1-(3,5-difluorophenyl)-3-(difluoromethyl)-1H-pyrazol-5-yl]benezenesulfonamide;

2,5-difluoro-4-[1-(3,4-dimethylphenyl)-3-(difluoromethyl)-1H-pyrazol-5-yl]benezenesulfonamide;

2,5-difluoro-4-[1-(3,5-dimethylphenyl)-3-(difluoromethyl)-1H-pyrazol-5-yl]benezenesulfonamide;

2,5-difluoro-4-[1-(3-methyl-4-chlorophenyl)-3-(difluoromethyl)-1H-pyrazol-5-yl]benezenesulfonamide;

2,5-difluoro-4-[1-(4-methyl-3-chlorophenyl)-3-(difluoromethyl)-1H-pyrazol-5-yl]benezenesulfonamide;

2,5-difluoro-4-[1-(3-methyl-4-fluorophenyl)-3-(difluoromethyl)-1H-pyrazol-5-yl]benezenesulfonamide;

2,5-difluoro-4-[1-(4-methyl-3-fluorophenyl)-3-(difluoromethyl)-1H-pyrazol-5-yl]benezenesulfonamide;

2,5-difluoro-4-[1-(3-methyl-4-bromophenyl)-3-(difluoromethyl)-1H-pyrazol-5-yl]benezenesulfonamide;

2,5-difluoro-4-[1-(4-methyl-3-bromophenyl)-3-(difluoromethyl)-1H-pyrazol-5-yl]benezenesulfonamide;

2,5-difluoro-4-[1-(3-methyl-4-trifluoromethylphenyl)-3-(difluoromethyl)-1H-pyrazol-5-yl]benezenesulfonamide;

2,5-difluoro-4-[1-(4-methyl-3-trifluoromethylphenyl)-3-(difluoromethyl)-1H-pyrazol-5-yl]benezenesulfonamide;

2,5-difluoro-4-[1-(3-methyl-4-trifluoromethoxyphenyl)-3-(difluoromethyl)-1H-pyrazol-5-yl]benezenesulfonamide;

2,5-difluoro-4-[1-(4-methyl-3-trifluoromethoxyphenyl)-3-(difluoromethyl)-1H-pyrazol-5-yl]benezenesulfonamide;

2,5-difluoro-4-[1-(3-cyano-4-methylphenyl)-3-(difluoromethyl)-1H-pyrazol-5-yl]benezenesulfonamide;

2,5-difluoro-4-[1-(4-cyano-3-methylphenyl)-3-(difluoromethyl)-1H-pyrazol-5-yl]benezenesulfonamide;

2,5-difluoro-4-[1-(3-chloro-4-methoxyphenyl)-3-(difluoromethyl)-1H-pyrazol-5-yl]benezenesulfonamide;

2,5-difluoro-4-[1-(4-chloro-3-methoxyphenyl)-3-(difluoromethyl)-1H-pyrazol-5-yl]benezenesulfonamide;

2,5-difluoro-4-[1-(2-methylpyridin-6-yl)-3-(difluoromethyl)-1H-pyrazol-5-yl]benezenesulfonamide;

2,5-difluoro-4-[1-(2-methylthiazol-4-yl)-3-(difluoromethyl)-1H-pyrazol-5-yl]benezenesulfonamide;

2,5-difluoro-4-[1-(4-methylthiazol-2-yl)-3-(difluoromethyl)-1H-pyrazol-5-yl]benezenesulfonamide;

2,5-difluoro-4-[1-(2-methylpyridin-3-yl)-3-(difluoromethyl)-1H-pyrazol-5-yl]benezenesulfonamide;

2,5-difluoro-4-[1-(2-methylpyridin-3-yl)-3-(difluoromethyl)-1H-pyrazol-5-yl]benezenesulfonamide;

2,5-difluoro-4-[1-(3-pyridinyl)-3-(difluoromethyl)-1H-pyrazol-5-yl]benezenesulfonamide;

2,5-difluoro-4-[1-(5-methylpyridin-3-yl)-3-(difluoromethyl)-1H-pyrazol-5-yl]benezenesulfonamide;

2,5-difluoro-4-[1-(2-methylpyridin-3-yl)-3-(difluoromethyl)-1H-pyrazol-5-yl]benezenesulfonamide;

2,5-difluoro-4-[1-cyclohexyl-3-(difluoromethyl)-1H-pyrazol-5-yl]benezenesulfonamide;

2,5-difluoro-4-[1-cyclopentyl-3-(difluoromethyl)-1H-pyrazol-5-yl]benezenesulfonamide;

2,5-difluoro-4-[1-phenyl-3-(trifluoro)-1H-pyrazol-5-yl]benezenesulfonamide;

2,5-difluoro-4-[1-(3-chlorophenyl)-3-(trifluoro)-1H-pyrazol-5-yl]benezenesulfonamide;

2,5-difluoro-4-[1-(4-chlorophenyl)-3-(trifluoro)-1H-pyrazol-5-yl]benezenesulfonamide;

2,5-difluoro-4-[1-(3-bromophenyl)-3-(trifluoro)-1H-pyrazol-5-yl]benezenesulfonamide;

2,5-difluoro-4-[1-(4-bromophenyl)-3-(trifluoro)-1H-pyrazol-5-yl]benezenesulfonamide;

2,5-difluoro-4-[1-(3-fluorophenyl)-3-(trifluoro)-1H-pyrazol-5-yl]benezenesulfonamide;

2,5-difluoro-4-[1-(4-fluorophenyl)-3-(trifluoro)-1H-pyrazol-5-yl]benezenesulfonamide;

2,5-difluoro-4-[1-(3-methylphenyl)-3-(trifluoro)-1H-pyrazol-5-yl]benezenesulfonamide;

2,5-difluoro-4-[1-(4-methylphenyl)-3-(trifluoro)-1H-pyrazol-5-yl]benezenesulfonamide;

2,5-difluoro-4-[1-(3-cyanophenyl)-3-(trifluoro)-1H-pyrazol-5-yl]benezenesulfonamide;

2,5-difluoro-4-[1-(4-cyanophenyl)-3-(trifluoro)-1H-pyrazol-5-yl]benezenesulfonamide;

2,5-difluoro-4-[1-(3-trifluoromethylphenyl)-3-(trifluoro)-1H-pyrazol-5-yl]benezenesulfonamide;

2,5-difluoro-4-[1-(4-trifluoromethylphenyl)-3-(trifluoro)-1H-pyrazol-5-yl]benezenesulfonamide;
2,5-difluoro-4-[1-(3-trifluoromethoxyphenyl)-3-(trifluoro)-1H-pyrazol-5-yl]benezenesulfonamide;
2,5-difluoro-4-[1-(4-trifluoromethoxyphenyl)-3-(trifluoro)-1H-pyrazol-5-yl]benezenesulfonamide;
2,5-difluoro-4-[1-(3,4-dichlorophenyl)-3-(trifluoro)-1H-pyrazol-5-yl]benezenesulfonamide;
2,5-difluoro-4-[1-(3,4-dibromophenyl)-3-(trifluoro)-1H-pyrazol-5-yl]benezenesulfonamide;
2,5-difluoro-4-[1-(3,4-difluorophenyl)-3-(trifluoro)-1H-pyrazol-5-yl]benezenesulfonamide;
2,5-difluoro-4-[1-(3,5-dichlorophenyl)-3-(trifluoro)-1H-pyrazol-5-yl]benezenesulfonamide;
2,5-difluoro-4-[1-(3,5-dibromophenyl)-3-(trifluoro)-1H-pyrazol-5-yl]benezenesulfonamide;
2,5-difluoro-4-[1-(3,5-difluorophenyl)-3-(trifluoro)-1H-pyrazol-5-yl]benezenesulfonamide;
2,5-difluoro-4-[1-(3,4-dimethylphenyl)-3-(trifluoro)-1H-pyrazol-5-yl]benezenesulfonamide;
2,5-difluoro-4-[1-(3,5-dimethylphenyl)-3-(trifluoro)-1H-pyrazol-5-yl]benezenesulfonamide;
2,5-difluoro-4-[1-(3-methyl-4-chlorophenyl)-3-(trifluoro)-1H-pyrazol-5-yl]benezenesulfonamide;
2,5-difluoro-4-[1-(4-methyl-3-chlorophenyl)-3-(trifluoro)-1H-pyrazol-5-yl]benezenesulfonamide;
2,5-difluoro-4-[1-(3-methyl-4-fluorophenyl)-3-(trifluoro)-1H-pyrazol-5-yl]benezenesulfonamide;
2,5-difluoro-4-[1-(4-methyl-3-fluorophenyl)-3-(trifluoro)-1H-pyrazol-5-yl]benezenesulfonamide;
2,5-difluoro-4-[1-(3-methyl-4-bromophenyl)-3-(trifluoro)-1H-pyrazol-5-yl]benezenesulfonamide;
2,5-difluoro-4-[1-(4-methyl-3-bromophenyl)-3-(trifluoro)-1H-pyrazol-5-yl]benezenesulfonamide;
2,5-difluoro-4-[1-(3-methyl-4-trifluoromethylphenyl)-3-(trifluoro)-1H-pyrazol-5-yl]benezenesulfonamide;
2,5-difluoro-4-[1-(4-methyl-3-trifluoromethylphenyl)-3-(trifluoro)-1H-pyrazol-5-yl]benezenesulfonamide;
2,5-difluoro-4-[1-(3-methyl-4-trifluoromethoxyphenyl)-3-(trifluoro)-1H-pyrazol-5-yl]benezenesulfonamide;
2,5-difluoro-4-[1-(4-methyl-3-trifluoromethoxyphenyl)-3-(trifluoro)-1H-pyrazol-5-yl]benezenesulfonamide;
2,5-difluoro-4-[1-(3-cyano-4-methylphenyl)-3-(trifluoro)-1H-pyrazol-5-yl]benezenesulfonamide;
2,5-difluoro-4-[1-(4-cyano-3-methylphenyl)-3-(trifluoro)-1H-pyrazol-5-yl]benezenesulfonamide;
2,5-difluoro-4-[1-(3-chloro-4-methoxyphenyl)-3-(trifluoro)-1H-pyrazol-5-yl]benezenesulfonamide;
2,5-difluoro-4-[1-(4-chloro-3-methoxyphenyl)-3-(trifluoro)-1H-pyrazol-5-yl]benezenesulfonamide;
2,5-difluoro-4-[1-(2-methylpyridin-6-yl)-3-(trifluoro)-1H-pyrazol-5-yl]benezenesulfonamide;
2,5-difluoro-4-[1-(2-methylthiazol-4-yl)-3-(trifluoro)-1H-pyrazol-5-yl]benezenesulfonamide;
2,5-difluoro-4-[1-(4-methylthiazol-2-yl)-3-(trifluoro)-1H-pyrazol-5-yl]benezenesulfonamide;
2,5-difluoro-4-[1-(2-methylpyridin-3-yl)-3-(trifluoro)-1H-pyrazol-5-yl]benezenesulfonamide;
2,5-difluoro-4-[1-(2-methylpyridin-3-yl)-3-(trifluoro)-1H-pyrazol-5-yl]benezenesulfonamide;
2,5-difluoro-4-[1-(3-pyridinyl)-3-(trifluoro)-1H-pyrazol-5-yl]benezenesulfonamide;
2,5-difluoro-4-[1-(5-methylpyridin-3-yl)-3-(trifluoro)-1H-pyrazol-5-yl]benezenesulfonamide;
2,5-difluoro-4-[1-(2-methylpyridin-3-yl)-3-(trifluoro)-1H-pyrazol-5-yl]benezenesulfonamide;
2,5-difluoro-4-[1-cyclohexyl-3-(trifluoro)-1H-pyrazol-5-yl]benezenesulfonamide;
2,5-difluoro-4-[1-cyclopentyl-3-(trifluoro)-1H-pyrazol-5-yl]benezenesulfonamide;

and the pharmaceutically-acceptable salts, tautomers and prodrugs thereof.

Thiophenes

In still another embodiment, the present method of treating cyclooxygenase-2 mediated disorders comprises administering to the subject a therapeutically-effective amount of one or more compounds selected from a subclass of compounds of Formula I corresponding to Formula III:

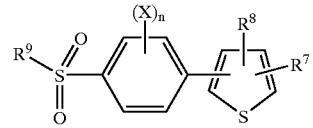

III wherein substituents X, n, $R^7$, $R^8$ and $R^9$ have the same definitions and sub-definitions as substituents X, n, $R^1$, $R^3$ and $R^2$, respectively, set forth above for the compounds of Formula I, and the pharmaceutically-acceptable salts, tautomers and prodrugs thereof.

Within this subclass of compounds, a more preferred group of compounds consists of those compounds of Formula IIIA:

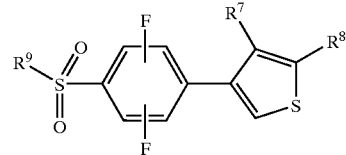

IIIA wherein $R^7$, $R^8$ and $R^9$ are as defined above, and the pharmaceutically-acceptable salts, tautomers and prodrugs thereof.

Within this subclass of compounds, another preferred group of compounds, in addition to those embodiments previously described with respect to compounds of Formula I, consists of those compounds of Formula III wherein:

$R^7$ is cyclohexyl or phenyl, wherein said cyclohexyl and phenyl may be optionally substituted with one, two or three radicals selected from halo, cyano, $C_{1-2}$-alkyl, $C_{1-2}$-haloalkyl, $C_{1-2}$-alkoxy, and $C_{1-2}$-haloalkoxy; and $R^8$ is a radical selected from hydrido, halogen, $C_{1-2}$-alkyl, $C_{1-3}$-alkoxy, $C_{1-3}$-alkylcarbonyl, $C_{1-3}$-haloalkyl, and $C_{1-3}$-alkoxycarbonyl.

Within this subclass of compounds, another preferred group of compounds, in addition to those embodiments previously described with respect to compounds of Formula I, consists of those compounds of Formula III wherein:

$R^7$ is cyclohexyl or phenyl, wherein said cyclohexyl and phenyl may be optionally substituted with one, two or three radicals selected from methyl, difluoromethyl, trifluoromethyl, trifluoromethoxy, cyano, fluoro, chloro, bromo, and methoxy; and $R^8$ is a radical selected from hydrido, chloro, fluoro, bromo, iodo, cyano, methyl, methoxy, methylcarbonyl, trifluoromethyl, difluoromethyl, and methoxycarbonyl.

Preferred species within this subclass include, but are not limited to:

3-phenyl-4-[3,5-difluoro-4-(methylsulfonyl)phenyl]thiophene;
3-(3-chlorophenyl)-4-[3,5-difluoro-4-(methylsulfonyl)phenyl]thiophene;
3-(4-chlorophenyl)-4-[3,5-difluoro-4-(methylsulfonyl)phenyl]thiophene;
3-(3-bromophenyl)-4-[3,5-difluoro-4-(methylsulfonyl)phenyl]thiophene;
3-(4-bromophenyl)-4-[3,5-difluoro-4-(methylsulfonyl)phenyl]thiophene;
3-(3-fluorophenyl)-4-[3,5-difluoro-4-(methylsulfonyl)phenyl]thiophene;
3-(4-fluorophenyl)-4-[3,5-difluoro-4-(methylsulfonyl)phenyl]thiophene;
3-(3-methylphenyl)-4-[3,5-difluoro-4-(methylsulfonyl)phenyl]thiophene;
3-(4-methylphenyl)-4-[3,5-difluoro-4-(methylsulfonyl)phenyl]thiophene;
3-(3-cyanophenyl)-4-[3,5-difluoro-4-(methylsulfonyl)phenyl]thiophene;
3-(4-cyanophenyl)-4-[3,5-difluoro-4-(methylsulfonyl)phenyl]thiophene;
3-(3-trifluoromethylphenyl)-4-[3,5-difluoro-4-(methylsulfonyl)phenyl]thiophene;
3-(4-trifluoromethylphenyl)-4-[3,5-difluoro-4-(methylsulfonyl)phenyl]thiophene;
3-(3-trifluoromethoxyphenyl)-4-[3,5-difluoro-4-(methylsulfonyl)phenyl]thiophene;
3-(4-trifluoromethoxyphenyl)-4-[3,5-difluoro-4-(methylsulfonyl)phenyl]thiophene;
3-(3,4-dichlorophenyl)-4-[3,5-difluoro-4-(methylsulfonyl)phenyl]thiophene;
3-(3,4-dibromophenyl)-4-[3,5-difluoro-4-(methylsulfonyl)phenyl]thiophene;
3-(3,4-difluorophenyl)-4-[3,5-difluoro-4-(methylsulfonyl)phenyl]thiophene;
3-(3,5-dichlorophenyl)-4-[3,5-difluoro-4-(methylsulfonyl)phenyl]thiophene;
3-(3,5-dibromophenyl)-4-[3,5-difluoro-4-(methylsulfonyl)phenyl]thiophene;
3-(3,5-difluorophenyl)-4-[3,5-difluoro-4-(methylsulfonyl)phenyl]thiophene;
3-(3,4-dimethylphenyl)-4-[3,5-difluoro-4-(methylsulfonyl)phenyl]thiophene;
3-(3,5-dimethylphenyl)-4-[3,5-difluoro-4-(methylsulfonyl)phenyl]thiophene;
3-(3-methyl-4-chlorophenyl)-4-[3,5-difluoro-4-(methylsulfonyl)phenyl]thiophene;
3-(4-methyl-3-chlorophenyl)-4-[3,5-difluoro-4-(methylsulfonyl)phenyl]thiophene;
3-(3-methyl-4-fluorophenyl)-4-[3,5-difluoro-4-(methylsulfonyl)phenyl]thiophene;
3-(4-methyl-3-fluorophenyl)-4-[3,5-difluoro-4-(methylsulfonyl)phenyl]thiophene;
3-(3-methyl-4-bromophenyl)-4-[3,5-difluoro-4-(methylsulfonyl)phenyl]thiophene;
3-(4-methyl-3-bromophenyl)-4-[3,5-difluoro-4-(methylsulfonyl)phenyl]thiophene;
3-(3-methyl-4-trifluoromethylphenyl)-4-[3,5-difluoro-4-(methylsulfonyl)phenyl]thiophene;
3-(4-methyl-3-trifluoromethylphenyl)-4-[3,5-difluoro-4-(methylsulfonyl)phenyl]thiophene;
3-(3-methyl-4-trifluoromethoxyphenyl)-4-[3,5-difluoro-4-(methylsulfonyl)phenyl]thiophene;
3-(4-methyl-3-trifluoromethoxyphenyl)-4-[3,5-difluoro-4-(methylsulfonyl)phenyl]thiophene;
3-(3-cyano-4-methylphenyl)-4-[3,5-difluoro-4-(methylsulfonyl)phenyl]thiophene;
3-(4-cyano-3-methylphenyl)-4-[3,5-difluoro-4-(methylsulfonyl)phenyl]thiophene;
3-(3-chloro-4-methoxyphenyl)-4-[3,5-difluoro-4-(methylsulfonyl)phenyl]thiophene;
3-(4-chloro-3-methoxyphenyl)-4-[3,5-difluoro-4-(methylsulfonyl)phenyl]thiophene;
3-(2-methylpyridin-6-yl)-4-[3,5-difluoro-4-(methylsulfonyl)phenyl]thiophene;
3-(2-methylthiazol-4-yl)-4-[3,5-difluoro-4-(methylsulfonyl)phenyl]thiophene;
3-(4-methylthiazol-2-yl)-4-[3,5-difluoro-4-(methylsulfonyl)phenyl]thiophene;
3-(2-methylpyridin-3-yl)-4-[3,5-difluoro-4-(methylsulfonyl)phenyl]thiophene;
3-(2-methylpyridin-3-yl)-4-[3,5-difluoro-4-(methylsulfonyl)phenyl]thiophene;
3-(3-pyridinyl)-4-[3,5-difluoro-4-(methylsulfonyl)phenyl]thiophene;
3-(5-methylpyridin-3-yl)-4-[3,5-difluoro-4-(methylsulfonyl)phenyl]thiophene;
3-(2-methylpyridin-3-yl)-4-[3,5-difluoro-4-(methylsulfonyl)phenyl]thiophene;
3-cyclohexyl-4-[3,5-difluoro-4-(methylsulfonyl)phenyl]thiophene;
3-cyclopentyl-4-[3,5-difluoro-4-(methylsulfonyl)phenyl]thiophene;
2,6-difluoro-4-[4-phenyl-3-thiophenyl]benezenesulfonamide;
2,6-difluoro-4-[4-(3-chlorophenyl)-3-thiophenyl]benezenesulfonamide;
2,6-difluoro-4-[4-(4-chlorophenyl)-3-thiophenyl]benezenesulfonamide;
2,6-difluoro-4-[4-(3-bromophenyl)-3-thiophenyl]benezenesulfonamide;
2,6-difluoro-4-[4-(4-bromophenyl)-3-thiophenyl]benezenesulfonamide;
2,6-difluoro-4-[4-(3-fluorophenyl)-3-thiophenyl]benezenesulfonamide;
2,6-difluoro-4-[4-(4-fluorophenyl)-3-thiophenyl]benezenesulfonamide;
2,6-difluoro-4-[4-(3-methylphenyl)-3-thiophenyl]benezenesulfonamide;
2,6-difluoro-4-[4-(4-methylphenyl)-3-thiophenyl]benezenesulfonamide;
2,6-difluoro-4-[4-(3-cyanophenyl)-3-thiophenyl]benezenesulfonamide;
2,6-difluoro-4-[4-(4-cyanophenyl)-3-thiophenyl]benezenesulfonamide;
2,6-difluoro-4-[4-(3-trifluoromethylphenyl)-3-thiophenyl]benezenesulfonamide;
2,6-difluoro-4-[4-(4-trifluoromethylphenyl)-3-thiophenyl]benezenesulfonamide;
2,6-difluoro-4-[4-(3-trifluoromethoxyphenyl)-3-thiophenyl]benezenesulfonamide;

2,6-difluoro-4-[4-(4-trifluoromethoxyphenyl)-3-thiophenyl]benezenesulfonamide;
2,6-difluoro-4-[4-(3,4-dichlorophenyl)-3-thiophenyl]benezenesulfonamide;
2,6-difluoro-4-[4-(3,4-dibromophenyl)-3-thiophenyl]benezenesulfonamide;
2,6-difluoro-4-[4-(3,4-difluorophenyl)-3-thiophenyl]benezenesulfonamide;
2,6-difluoro-4-[4-(3,5-dichlorophenyl)-3-thiophenyl]benezenesulfonamide;
2,6-difluoro-4-[4-(3,5-dibromophenyl)-3-thiophenyl]benezenesulfonamide;
2,6-difluoro-4-[4-(3,5-difluorophenyl)-3-thiophenyl]benezenesulfonamide;
2,6-difluoro-4-[4-(3,4-dimethylphenyl)-3-thiophenyl]benezenesulfonamide;
2,6-difluoro-4-[4-(3,5-dimethylphenyl)-3-thiophenyl]benezenesulfonamide;
2,6-difluoro-4-[4-(3-methyl-4-chlorophenyl)-3-thiophenyl]benezenesulfonamide;
2,6-difluoro-4-[4-(4-methyl-3-chlorophenyl)-3-thiophenyl]benezenesulfonamide;
2,6-difluoro-4-[4-(3-methyl-4-fluorophenyl)-3-thiophenyl]benezenesulfonamide;
2,6-difluoro-4-[4-(4-methyl-3-fluorophenyl)-3-thiophenyl]benezenesulfonamide;
2,6-difluoro-4-[4-(3-methyl-4-bromophenyl)-3-thiophenyl]benezenesulfonamide;
2,6-difluoro-4-[4-(4-methyl-3-bromophenyl)-3-thiophenyl]benezenesulfonamide;
2,6-difluoro-4-[4-(3-methyl-4-trifluoromethylphenyl)-3-thiophenyl]benezenesulfonamide;
2,6-difluoro-4-[4-(4-methyl-3-trifluoromethylphenyl)-3-thiophenyl]benezenesulfonamide;
2,6-difluoro-4-[4-(3-methyl-4-trifluoromethoxyphenyl)-3-thiophenyl]benezenesulfonamide;
2,6-difluoro-4-[4-(4-methyl-3-trifluoromethoxyphenyl)-3-thiophenyl]benezenesulfonamide;
2,6-difluoro-4-[4-(3-cyano-4-methylphenyl)-3-thiophenyl]benezenesulfonamide;
2,6-difluoro-4-[4-(4-cyano-3-methylphenyl)-3-thiophenyl]benezenesulfonamide;
2,6-difluoro-4-[4-(3-chloro-4-methoxyphenyl)-3-thiophenyl]benezenesulfonamide;
2,6-difluoro-4-[4-(4-chloro-3-methoxyphenyl)-3-thiophenyl]benezenesulfonamide;
2,6-difluoro-4-[4-(2-methylpyridin-6-yl)-3-thiophenyl]benezenesulfonamide;
2,6-difluoro-4-[4-(2-methylthiazol-4-yl)-3-thiophenyl]benezenesulfonamide;
2,6-difluoro-4-[4-(4-methylthiazol-2-yl)-3-thiophenyl]benezenesulfonamide;
2,6-difluoro-4-[4-(2-methylpyridin-3-yl)-3-thiophenyl]benezenesulfonamide;
2,6-difluoro-4-[4-(2-methylpyridin-3-yl)-3-thiophenyl]benezenesulfonamide;
2,6-difluoro-4-[4-(3-pyridinyl)-3-thiophenyl]benezenesulfonamide;
2,6-difluoro-4-[4-(5-methylpyridin-3-yl)-3-thiophenyl]benezenesulfonamide;
2,6-difluoro-4-[4-(2-methylpyridin-3-yl)-3-thiophenyl]benezenesulfonamide;
2,6-difluoro-4-[4-cyclohexyl-3-thiophenyl]benezenesulfonamide;
2,6-difluoro-4-[4-cyclopentyl-3-thiophenyl]benezenesulfonamide;

and the pharmaceutically-acceptable salts, tautomers and prodrugs thereof.

Isoxazoles

In still another embodiment, the present method of treating cyclooxygenase-2 mediated disorders comprises administering to the subject a therapeutically-effective amount of one or more compounds selected from a subclass of compounds of Formula I corresponding to Formula IV:

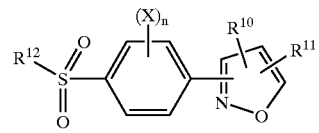

IV wherein substituents X, n, $R^{10}$, $R^{11}$ and $R^{12}$ have the same definitions and sub-definitions as substituents X, n, $R^1$, $R^3$ and $R^2$, respectively, set forth above for the compounds of Formula I, and the pharmaceutically-acceptable salts, tautomers and prodrugs thereof.

Within this subclass of compounds, a preferred group of compounds consists of those compounds of Formula IVA and IVB:

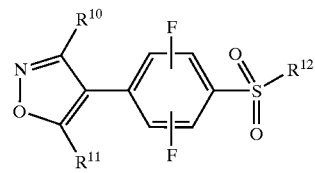

IVA

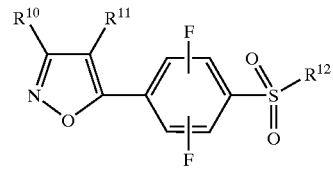

IVB wherein $R^{10}$, $R^{11}$ and $R^{12}$ are as defined above, and the pharmaceutically-acceptable salts, tautomers and prodrugs thereof.

Within this subclass of compounds, a more preferred group of compounds consists of those compounds of Formula IVC and IVD:

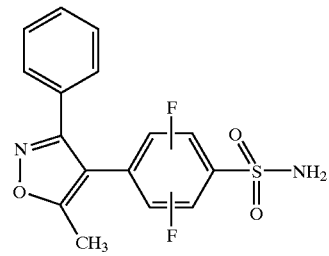

IVC

-continued

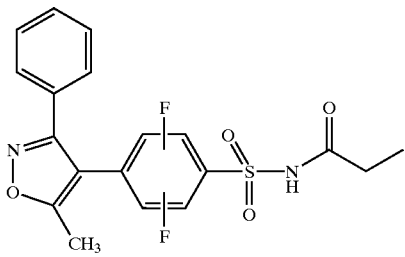

IVD and the pharmaceutically-acceptable salts, tautomers and prodrugs thereof. Preferably, (a) one fluoro radical is present at the 2-position and the other fluoro radical is present at the 5-position, or (b) one fluoro radical is present at the 2-position and the other fluoro radical is present at the 3-position, or (c) one fluoro radical is present at the 3-position and the other fluoro radical is present at the 5-position.

Preferred species within this subclass include, but are not limited to:

2,6-difluoro-4-[3-phenyl-5-fluoromethylisoxazol-4-yl]benezenesulfonamide;
2,6-difluoro-4-[3-(3-chlorophenyl)-5-fluoromethylisoxazol-4-yl]benezenesulfonamide;
2,6-difluoro-4-[3-(4-chlorophenyl)-5-fluoromethylisoxazol-4-yl]benezenesulfonamide;
2,6-difluoro-4-[3-(3-bromophenyl)-5-fluoromethylisoxazol-4-yl]benezenesulfonamide;
2,6-difluoro-4-[3-(4-bromophenyl)-5-fluoromethylisoxazol-4-yl]benezenesulfonamide;
2,6-difluoro-4-[3-(3-fluorophenyl)-5-fluoromethylisoxazol-4-yl]benezenesulfonamide;
2,6-difluoro-4-[3-(4-fluorophenyl)-5-fluoromethylisoxazol-4-yl]benezenesulfonamide;
2,6-difluoro-4-[3-(3-methylphenyl)-5-fluoromethylisoxazol-4-yl]benezenesulfonamide;
2,6-difluoro-4-[3-(4-methylphenyl)-5-fluoromethylisoxazol-4-yl]benezenesulfonamide;
2,6-difluoro-4-[3-(3-cyanophenyl)-5-fluoromethylisoxazol-4-yl]benezenesulfonamide;
2,6-difluoro-4-[3-(4-cyanophenyl)-5-fluoromethylisoxazol-4-yl]benezenesulfonamide;
2,6-difluoro-4-[3-(3-trifluoromethylphenyl)-5-fluoromethylisoxazol-4-yl]benezenesulfonamide;
2,6-difluoro-4-[3-(4-trifluoromethylphenyl)-5-fluoromethylisoxazol-4-yl]benezenesulfonamide;
2,6-difluoro-4-[3-(3-trifluoromethoxyphenyl)-5-fluoromethylisoxazol-4-yl]benezenesulfonamide;
2,6-difluoro-4-[3-(4-trifluoromethoxyphenyl)-5-fluoromethylisoxazol-4-yl]benezenesulfonamide;
2,6-difluoro-4-[3-(3,4-dichlorophenyl)-5-fluoromethylisoxazol-4-yl]benezenesulfonamide;
2,6-difluoro-4-[3-(3,4-dibromophenyl)-5-fluoromethylisoxazol-4-yl]benezenesulfonamide;
2,6-difluoro-4-[3-(3,4-difluorophenyl)-5-fluoromethylisoxazol-4-yl]benezenesulfonamide;
2,6-difluoro-4-[3-(3,5-dichlorophenyl)-5-fluoromethylisoxazol-4-yl]benezenesulfonamide;
2,6-difluoro-4-[3-(3,5-dibromophenyl)-5-fluoromethylisoxazol-4-yl]benezenesulfonamide;
2,6-difluoro-4-[3-(3,5-difluorophenyl)-5-fluoromethylisoxazol-4-yl]benezenesulfonamide;
2,6-difluoro-4-[3-(3,4-dimethylphenyl)-5-fluoromethylisoxazol-4-yl]benezenesulfonamide;
2,6-difluoro-4-[3-(3,5-dimethylphenyl)-5-fluoromethylisoxazol-4-yl]benezenesulfonamide;
2,6-difluoro-4-[3-(3-methyl-4-chlorophenyl)-5-fluoromethylisoxazol-4-yl]benezenesulfonamide;
2,6-difluoro-4-[3-(4-methyl-3-chlorophenyl)-5-fluoromethylisoxazol-4-yl]benezenesulfonamide;
2,6-difluoro-4-[3-(3-methyl-4-fluorophenyl)-5-fluoromethylisoxazol-4-yl]benezenesulfonamide;
2,6-difluoro-4-[3-(4-methyl-3-fluorophenyl)-5-fluoromethylisoxazol-4-yl]benezenesulfonamide;
2,6-difluoro-4-[3-(3-methyl-4-bromophenyl)-5-fluoromethylisoxazol-4-yl]benezenesulfonamide;
2,6-difluoro-4-[3-(4-methyl-3-bromophenyl)-5-fluoromethylisoxazol-4-yl]benezenesulfonamide;
2,6-difluoro-4-[3-(3-methyl-4-trifluoromethylphenyl)-5-fluoromethylisoxazol-4-yl]benezenesulfonamide;
2,6-difluoro-4-[3-(4-methyl-3-trifluoromethylphenyl)-5-fluoromethylisoxazol-4-yl]benezenesulfonamide;
2,6-difluoro-4-[3-(3-methyl-4-trifluoromethoxyphenyl)-5-fluoromethylisoxazol-4-yl]benezenesulfonamide;
2,6-difluoro-4-[3-(4-methyl-3-trifluoromethoxyphenyl)-5-fluoromethylisoxazol-4-yl]benezenesulfonamide;
2,6-difluoro-4-[3-(3-cyano-4-methylphenyl)-5-fluoromethylisoxazol-4-yl]benezenesulfonamide;
2,6-difluoro-4-[3-(4-cyano-3-methylphenyl)-5-fluoromethylisoxazol-4-yl]benezenesulfonamide;
2,6-difluoro-4-[3-(3-chloro-4-methoxyphenyl)-5-fluoromethylisoxazol-4-yl]benezenesulfonamide;
2,6-difluoro-4-[3-(4-chloro-3-methoxyphenyl)-5-fluoromethylisoxazol-4-yl]benezenesulfonamide;
2,6-difluoro-4-[3-(2-methylpyridin-6-yl)-5-fluoromethylisoxazol-4-yl]benezenesulfonamide;
2,6-difluoro-4-[3-(2-methylthiazol-4-yl)-5-fluoromethylisoxazol-4-yl]benezenesulfonamide;
2,6-difluoro-4-[3-(4-methylthiazol-2-yl)-5-fluoromethylisoxazol-4-yl]benezenesulfonamide;
2,6-difluoro-4-[3-(2-methylpyridin-3-yl)-5-fluoromethylisoxazol-4-yl]benezenesulfonamide;
2,6-difluoro-4-[3-(2-methylpyridin-3-yl)-5-fluoromethylisoxazol-4-yl]benezenesulfonamide;
2,6-difluoro-4-[3-(3-pyridinyl)-5-fluoromethylisoxazol-4-yl]benezenesulfonamide;
2,6-difluoro-4-[3-(5-methylpyridin-3-yl)-5-fluoromethylisoxazol-4-yl]benezenesulfonamide;
2,6-difluoro-4-[3-(2-methylpyridin-3-yl)-5-fluoromethylisoxazol-4-yl]benezenesulfonamide;
2,6-difluoro-4-[3-cyclohexyl-5-fluoromethylisoxazol-4-yl]benezenesulfonamide;
2,6-difluoro-4-[3-cyclopentyl-5-fluoromethylisoxazol-4-yl]benezenesulfonamide;
2,6-difluoro-4-[3-phenyl-5-difluoromethylisoxazol-4-yl]benezenesulfonamide;
2,6-difluoro-4-[3-(3-chloro-5-methylphenyl)-5-difluoromethylisoxazol-4-yl]benezenesulfonamide;
2,6-difluoro-4-[3-(3-fluoro-5-methylphenyl)-5-difluoromethylisoxazol-4-yl]benezenesulfonamide;
2,6-difluoro-4-[3-(3-chlorophenyl)-5-difluoromethylisoxazol-4-yl]benezenesulfonamide;
2,6-difluoro-4-[3-(4-chlorophenyl)-5-difluoromethylisoxazol-4-yl]benezenesulfonamide;

2,6-difluoro-4-[3-(3-bromophenyl)-5-difluoromethylisoxazol-4-yl]benezenesulfonamide;

2,6-difluoro-4-[3-(4-bromophenyl)-5-difluoromethylisoxazol-4-yl]benezenesulfonamide;

2,6-difluoro-4-[3-(3-fluorophenyl)-5-difluoromethylisoxazol-4-yl]benezenesulfonamide;

2,6-difluoro-4-[3-(4-fluorophenyl)-5-difluoromethylisoxazol-4-yl]benezenesulfonamide;

2,6-difluoro-4-[3-(4-methylphenyl)-5-difluoromethylisoxazol-4-yl]benezenesulfonamide;

2,6-difluoro-4-[3-(3-methylphenyl)-5-difluoromethylisoxazol-4-yl]benezenesulfonamide;

2,6-difluoro-4-[3-(3-bromo-5-methylphenyl)-5-difluoromethylisoxazol-4-yl]benezenesulfonamide;

2,6-difluoro-4-[3-(3,4-dichlorophenyl)-5-difluoromethylisoxazol-4-yl]benezenesulfonamide;

2,6-difluoro-4-[3-(3,4-dibromophenyl)-5-difluoromethylisoxazol-4-yl]benezenesulfonamide;

2,6-difluoro-4-[3-(3,4-difluorophenyl)-5-difluoromethylisoxazol-4-yl]benezenesulfonamide;

2,6-difluoro-4-[3-(3,5-dichlorophenyl)-5-difluoromethylisoxazol-4-yl]benezenesulfonamide;

2,6-difluoro-4-[3-(3,5-dibromophenyl)-5-difluoromethylisoxazol-4-yl]benezenesulfonamide;

2,6-difluoro-4-[3-(3,5-difluorophenyl)-5-difluoromethylisoxazol-4-yl]benezenesulfonamide;

2,6-difluoro-4-[3-(3-chloro-4-fluorophenyl)-5-difluoromethylisoxazol-4-yl]benezenesulfonamide;

2,6-difluoro-4-[3-(3-chloro-4-methylphenyl)-5-difluoromethylisoxazol-4-yl]benezenesulfonamide;

2,6-difluoro-4-[3-(3-bromo-4-methylphenyl)-5-difluoromethylisoxazol-4-yl]benezenesulfonamide;

2,6-difluoro-4-[3-(3-fluoro-4-methylphenyl)-5-difluoromethylisoxazol-4-yl]benezenesulfonamide;

2,6-difluoro-4-[3-(3,4-dimethylphenyl)-5-difluoromethylisoxazol-4-yl]benezenesulfonamide;

2,6-difluoro-4-[3-(4-trifluoromethoxyphenyl)-5-difluoromethylisoxazol-4-yl]benezenesulfonamide;

2,6-difluoro-4-[3-(3-methyl-4-trifluoromethoxyphenyl)-5-difluoromethylisoxazol-4-yl]benezenesulfonamide;

2,6-difluoro-4-[3-(4-methyl-3-trifluoromethoxyphenyl)-5-difluoromethylisoxazol-4-yl]benezenesulfonamide;

2,6-difluoro-4-[3-(3-trifluoromethylphenyl)-5-difluoromethylisoxazol-4-yl]benezenesulfonamide;

2,6-difluoro-4-[3-(4-trifluoromethylphenyl)-5-difluoromethylisoxazol-4-yl]benezenesulfonamide;

2,6-difluoro-4-[3-(3-methyl-4-trifluoromethylphenyl)-5-difluoromethylisoxazol-4-yl]benezenesulfonamide;

2,6-difluoro-4-[3-(4-methyl-3-trifluoromethylphenyl)-5-difluoromethylisoxazol-4-yl]benezenesulfonamide;

2,6-difluoro-4-[3-(3-cyano-4-methylphenyl)-5-difluoromethylisoxazol-4-yl]benezenesulfonamide;

2,6-difluoro-4-[3-(4-cyano-3-methylphenyl)-5-difluoromethylisoxazol-4-yl]benezenesulfonamide;

2,6-difluoro-4-[3-(3-cyanophenyl)-5-difluoromethylisoxazol-4-yl]benezenesulfonamide;

2,6-difluoro-4-[3-(4-cyanophenyl)-5-difluoromethylisoxazol-4-yl]benezenesulfonamide;

2,6-difluoro-4-[3-(3-chloro-4-methoxyphenyl)-5-difluoromethylisoxazol-4-yl]benezenesulfonamide;

2,6-difluoro-4-[3-(4-chloro-3-methoxyphenyl)-5-difluoromethylisoxazol-4-yl]benezenesulfonamide;

2,6-difluoro-4-[3-(2-methylpyridin-6-yl)-5-difluoromethylisoxazol-4-yl]benezenesulfonamide;

2,6-difluoro-4-[3-(2-methylthiazol-4-yl)-5-difluoromethylisoxazol-4-yl]benezenesulfonamide;

2,6-difluoro-4-[3-(4-methylthiazol-2-yl)-5-difluoromethylisoxazol-4-yl]benezenesulfonamide;

2,6-difluoro-4-[3-(2-methylpyridin-3-yl)-5-difluoromethylisoxazol-4-yl]benezenesulfonamide;

2,6-difluoro-4-[3-(2-methylpyridin-3-yl)-5-difluoromethylisoxazol-4-yl]benezenesulfonamide;

2,6-difluoro-4-[3-(3-pyridinyl)-5-difluoromethylisoxazol-4-yl]benezenesulfonamide;

2,6-difluoro-4-[3-(5-methylpyridin-3-yl)-5-difluoromethylisoxazol-4-yl]benezenesulfonamide;

2,6-difluoro-4-[3-(2-methylpyridin-3-yl)-5-difluoromethylisoxazol-4-yl]benezenesulfonamide;

3-phenyl-4-[3,5-difluoro-4-(methylsulfonyl)phenyl]-5-hydroxymethylisoxazole;

3-(3-chlorophenyl)-4-[3,5-difluoro-4-(methylsulfonyl)phenyl]-5-hydroxymethylisoxazole;

3-(4-chlorophenyl)-4-[3,5-difluoro-4-(methylsulfonyl)phenyl]-5-hydroxymethylisoxazole;

3-(3-bromophenyl)-4-[3,5-difluoro-4-(methylsulfonyl)phenyl]-5-hydroxymethylisoxazole;

3-(4-bromophenyl)-4-[3,5-difluoro-4-(methylsulfonyl)phenyl]-5-hydroxymethylisoxazole;

3-(3-fluorophenyl)-4-[3,5-difluoro-4-(methylsulfonyl)phenyl]-5-hydroxymethylisoxazole;

3-(4-fluorophenyl)-4-[3,5-difluoro-4-(methylsulfonyl)phenyl]-5-hydroxymethylisoxazole;

3-(3-methylphenyl)-4-[3,5-difluoro-4-(methylsulfonyl)phenyl]-5-hydroxymethylisoxazole;

3-(4-methylphenyl)-4-[3,5-difluoro-4-(methylsulfonyl)phenyl]-5-hydroxymethylisoxazole;

3-(3-cyanophenyl)-4-[3,5-difluoro-4-(methylsulfonyl)phenyl]-5-hydroxymethylisoxazole;

3-(4-cyanophenyl)-4-[3,5-difluoro-4-(methylsulfonyl)phenyl]-5-hydroxymethylisoxazole;

3-(3-trifluoromethylphenyl)-4-[3,5-difluoro-4-(methylsulfonyl)phenyl]-5-hydroxymethylisoxazole;

3-(4-trifluoromethylphenyl)-4-[3,5-difluoro-4-(methylsulfonyl)phenyl]-5-hydroxymethylisoxazole;

3-(3-trifluoromethoxyphenyl)-4-[3,5-difluoro-4-(methylsulfonyl)phenyl]-5-hydroxymethylisoxazole;

3-(4-trifluoromethoxyphenyl)-4-[3,5-difluoro-4-(methylsulfonyl)phenyl]-5-hydroxymethylisoxazole;

3-(3,4-dichlorophenyl)-4-[3,5-difluoro-4-(methylsulfonyl)phenyl]-5-hydroxymethylisoxazole;

3-(3,4-dibromophenyl)-4-[3,5-difluoro-4-(methylsulfonyl)phenyl]-5-hydroxymethylisoxazole;

3-(3,4-difluorophenyl)-4-[3,5-difluoro-4-(methylsulfonyl)phenyl]-5-hydroxymethylisoxazole;

3-(3,5-dichlorophenyl)-4-[3,5-difluoro-4-(methylsulfonyl)phenyl]-5-hydroxymethylisoxazole;

3-(3,5-dibromophenyl)-4-[3,5-difluoro-4-(methylsulfonyl)phenyl]-5-hydroxymethylisoxazole;

3-(3,5-difluorophenyl)-4-[3,5-difluoro-4-(methylsulfonyl)phenyl]-5-hydroxymethylisoxazole;

3-(3,4-dimethylphenyl)-4-[3,5-difluoro-4-(methylsulfonyl)phenyl]-5-hydroxymethylisoxazole;

3-(3,5-dimethylphenyl)-4-[3,5-difluoro-4-(methylsulfonyl)phenyl]-5-hydroxymethylisoxazole;

3-(3-methyl-4-chlorophenyl)-4-[3,5-difluoro-4-(methylsulfonyl)phenyl]-5-hydroxymethylisoxazole;

3-(4-methyl-3-chlorophenyl)-4-[3,5-difluoro-4-(methylsulfonyl)phenyl]-5-hydroxymethylisoxazole;

3-(3-methyl-4-fluorophenyl)-4-[3,5-difluoro-4-(methylsulfonyl)phenyl]-5-hydroxymethylisoxazole;

3-(4-methyl-3-fluorophenyl)-4-[3,5-difluoro-4-(methylsulfonyl)phenyl]-5-hydroxymethylisoxazole;

3-(3-methyl-4-bromophenyl)-4-[3,5-difluoro-4-(methylsulfonyl)phenyl]-5-hydroxymethylisoxazole;

3-(4-methyl-3-bromophenyl)-4-[3,5-difluoro-4-(methylsulfonyl)phenyl]-5-hydroxymethylisoxazole;

3-(3-methyl-4-trifluoromethylphenyl)-4-[3,5-difluoro-4-(methylsulfonyl)phenyl]-5-hydroxymethylisoxazole;

3-(4-methyl-3-trifluoromethylphenyl)-4-[3,5-difluoro-4-(methylsulfonyl)phenyl]-5-hydroxymethylisoxazole;

3-(3-methyl-4-trifluoromethoxyphenyl)-4-[3,5-difluoro-4-(methylsulfonyl)phenyl]-5-hydroxymethylisoxazole;

3-(4-methyl-3-trifluoromethoxyphenyl)-4-[3,5-difluoro-4-(methylsulfonyl)phenyl]-5-hydroxymethylisoxazole;

3-(3-cyano-4-methylphenyl)-4-[3,5-difluoro-4-(methylsulfonyl)phenyl]-5-hydroxymethylisoxazole;

3-(4-cyano-3-methylphenyl)-4-[3,5-difluoro-4-(methylsulfonyl)phenyl]-5-hydroxymethylisoxazole;

3-(3-chloro-4-methoxyphenyl)-4-[3,5-difluoro-4-(methylsulfonyl)phenyl]-5-hydroxymethylisoxazole;

3-(4-chloro-3-methoxyphenyl)-4-[3,5-difluoro-4-(methylsulfonyl)phenyl]-5-hydroxymethylisoxazole;

3-(2-methylpyridin-6-yl)-4-[3,5-difluoro-4-(methylsulfonyl)phenyl]-5-hydroxymethylisoxazole;

3-(2-methylthiazol-4-yl)-4-[3,5-difluoro-4-(methylsulfonyl)phenyl]-5-hydroxymethylisoxazole;

3-(4-methylthiazol-2-yl)-4-[3,5-difluoro-4-(methylsulfonyl)phenyl]-5-hydroxymethylisoxazole;

3-(2-methylpyridin-3-yl)-4-[3,5-difluoro-4-(methylsulfonyl)phenyl]-5-hydroxymethylisoxazole;

3-(2-methylpyridin-3-yl)-4-[3,5-difluoro-4-(methylsulfonyl)phenyl]-5-hydroxymethylisoxazole;

3-(3-pyridinyl)-4-[3,5-difluoro-4-(methylsulfonyl)phenyl]-5-hydroxymethylisoxazole;

3-(5-methylpyridin-3-yl)-4-[3,5-difluoro-4-(methylsulfonyl)phenyl]-5-hydroxymethylisoxazole;

3-(2-methylpyridin-3-yl)-4-[3,5-difluoro-4-(methylsulfonyl)phenyl]-5-hydroxymethylisoxazole;

3-cyclohexyl-4-[3,5-difluoro-4-(methylsulfonyl)phenyl]-5-hydroxymethylisoxazole;

3-cyclopentyl-4-[3,5-difluoro-4-(methylsulfonyl)phenyl]-5-hydroxymethylisoxazole;

3-phenyl-4-[3,5-difluoro-4-(methylsulfonyl)phenyl]-5-fluoromethylisoxazole;

3-(3-chlorophenyl)-4-[3,5-difluoro-4-(methylsulfonyl)phenyl]-5-fluoromethylisoxazole;

3-(4-chlorophenyl)-4-[3,5-difluoro-4-(methylsulfonyl)phenyl]-5-fluoromethylisoxazole;

3-(3-bromophenyl)-4-[3,5-difluoro-4-(methylsulfonyl)phenyl]-5-fluoromethylisoxazole;

3-(4-bromophenyl)-4-[3,5-difluoro-4-(methylsulfonyl)phenyl]-5-fluoromethylisoxazole;

3-(3-fluorophenyl)-4-[3,5-difluoro-4-(methylsulfonyl)phenyl]-5-fluoromethylisoxazole;

3-(4-fluorophenyl)-4-[3,5-difluoro-4-(methylsulfonyl)phenyl]-5-fluoromethylisoxazole;

3-(3-methylphenyl)-4-[3,5-difluoro-4-(methylsulfonyl)phenyl]-5-fluoromethylisoxazole;

3-(4-methylphenyl)-4-[3,5-difluoro-4-(methylsulfonyl)phenyl]-5-fluoromethylisoxazole;

3-(3-cyanophenyl)-4-[3,5-difluoro-4-(methylsulfonyl)phenyl]-5-fluoromethylisoxazole;

3-(4-cyanophenyl)-4-[3,5-difluoro-4-(methylsulfonyl)phenyl]-5-fluoromethylisoxazole;

3-(3-trifluoromethylphenyl)-4-[3,5-difluoro-4-(methylsulfonyl)phenyl]-5-fluoromethylisoxazole;

3-(4-trifluoromethylphenyl)-4-[3,5-difluoro-4-(methylsulfonyl)phenyl]-5-fluoromethylisoxazole;

3-(3-trifluoromethoxyphenyl)-4-[3,5-difluoro-4-(methylsulfonyl)phenyl]-5-fluoromethylisoxazole;

3-(4-trifluoromethoxyphenyl)-4-[3,5-difluoro-4-(methylsulfonyl)phenyl]-5-fluoromethylisoxazole;

3-(3,4-dichlorophenyl)-4-[3,5-difluoro-4-(methylsulfonyl)phenyl]-5-fluoromethylisoxazole;

3-(3,4-dibromophenyl)-4-[3,5-difluoro-4-(methylsulfonyl)phenyl]-5-fluoromethylisoxazole;

3-(3,4-difluorophenyl)-4-[3,5-difluoro-4-(methylsulfonyl)phenyl]-5-fluoromethylisoxazole;

3-(3,5-dichlorophenyl)-4-[3,5-difluoro-4-(methylsulfonyl)phenyl]-5-fluoromethylisoxazole;

3-(3,5-dibromophenyl)-4-[3,5-difluoro-4-(methylsulfonyl)phenyl]-5-fluoromethylisoxazole;

3-(3,5-difluorophenyl)-4-[3,5-difluoro-4-(methylsulfonyl)phenyl]-5-fluoromethylisoxazole;

3-(3,4-dimethylphenyl)-4-[3,5-difluoro-4-(methylsulfonyl)phenyl]-5-fluoromethylisoxazole;

3-(3,5-dimethylphenyl)-4-[3,5-difluoro-4-(methylsulfonyl)phenyl]-5-fluoromethylisoxazole;

3-(3-methyl-4-chlorophenyl)-4-[3,5-difluoro-4-(methylsulfonyl)phenyl]-5-fluoromethylisoxazole;

3-(4-methyl-3-chlorophenyl)-4-[3,5-difluoro-4-(methylsulfonyl)phenyl]-5-fluoromethylisoxazole;

3-(3-methyl-4-fluorophenyl)-4-[3,5-difluoro-4-(methylsulfonyl)phenyl]-5-fluoromethylisoxazole;

3-(4-methyl-3-fluorophenyl)-4-[3,5-difluoro-4-(methylsulfonyl)phenyl]-5-fluoromethylisoxazole;

3-(3-methyl-4-bromophenyl)-4-[3,5-difluoro-4-(methylsulfonyl)phenyl]-5-fluoromethylisoxazole;

3-(4-methyl-3-bromophenyl)-4-[3,5-difluoro-4-(methylsulfonyl)phenyl]-5-fluoromethylisoxazole;

3-(3-methyl-4-trifluoromethylphenyl)-4-[3,5-difluoro-4-(methylsulfonyl)phenyl]-5-fluoromethylisoxazole;

3-(4-methyl-3-trifluoromethylphenyl)-4-[3,5-difluoro-4-(methylsulfonyl)phenyl]-5-fluoromethylisoxazole;

3-(3-methyl-4-trifluoromethoxyphenyl)-4-[3,5-difluoro-4-(methylsulfonyl)phenyl]-5-fluoromethylisoxazole;

3-(4-methyl-3-trifluoromethoxyphenyl)-4-[3,5-difluoro-4-(methylsulfonyl)phenyl]-5-fluoromethylisoxazole;

3-(3-cyano-4-methylphenyl)-4-[3,5-difluoro-4-(methylsulfonyl)phenyl]-5-fluoromethylisoxazole;

3-(4-cyano-3-methylphenyl)-4-[3,5-difluoro-4-(methylsulfonyl)phenyl]-5-fluoromethylisoxazole;

3-(3-chloro-4-methoxyphenyl)-4-[3,5-difluoro-4-(methylsulfonyl)phenyl]-5-fluoromethylisoxazole;

3-(4-chloro-3-methoxyphenyl)-4-[3,5-difluoro-4-(methylsulfonyl)phenyl]-5-fluoromethylisoxazole;

3-(2-methylpyridin-6-yl)-4-[3,5-difluoro-4-(methylsulfonyl)phenyl]-5-fluoromethylisoxazole;

3-(2-methylthiazol-4-yl)-4-[3,5-difluoro-4-(methylsulfonyl)phenyl]-5-fluoromethylisoxazole;

3-(4-methylthiazol-2-yl)-4-[3,5-difluoro-4-(methylsulfonyl)phenyl]-5-fluoromethylisoxazole;

3-(2-methylpyridin-3-yl)-4-[3,5-difluoro-4-(methylsulfonyl)phenyl]-5-fluoromethylisoxazole;

3-(2-methylpyridin-3-yl)-4-[3,5-difluoro-4-(methylsulfonyl)phenyl]-5-fluoromethylisoxazole;

3-(3-pyridinyl)-4-[3,5-difluoro-4-(methylsulfonyl)phenyl]-5-fluoromethylisoxazole;

3-(5-methylpyridin-3-yl)-4-[3,5-difluoro-4-(methylsulfonyl)phenyl]-5-fluoromethylisoxazole;

3-(2-methylpyridin-3-yl)-4-[3,5-difluoro-4-(methylsulfonyl)phenyl]-5-fluoromethylisoxazole;

3-cyclohexyl-4-[3,5-difluoro-4-(methylsulfonyl)phenyl]-5-fluoromethylisoxazole;

3-cyclopentyl-4-[3,5-difluoro-4-(methylsulfonyl)phenyl]-5-fluoromethylisoxazole;

3-phenyl-4-[3,5-difluoro-4-(methylsulfonyl)phenyl]-5-difluoromethylisoxazole;

3-(3-chloro-5-methylphenyl)-4-[3,5-difluoro-4-(methylsulfonyl)phenyl]-5-difluoromethylisoxazole;

3-(3-fluoro-5-methylphenyl)-4-[3,5-difluoro-4-(methylsulfonyl)phenyl]-5-difluoromethylisoxazole;

3-(3-chlorophenyl)-4-[3,5-difluoro-4-(methylsulfonyl)phenyl]-5-difluoromethylisoxazole;

3-(4-chlorophenyl)-4-[3,5-difluoro-4-(methylsulfonyl)phenyl]-5-difluoromethylisoxazole;

3-(3-bromophenyl)-4-[3,5-difluoro-4-(methylsulfonyl)phenyl]-5-difluoromethylisoxazole;

3-(4-bromophenyl)-4-[3,5-difluoro-4-(methylsulfonyl)phenyl]-5-difluoromethylisoxazole;

3-(3,5-difluorophenyl)-4-[3,5-difluoro-4-(methylsulfonyl)phenyl]-5-difluoromethylisoxazole;

3-(4-fluorophenyl)-4-[3,5-difluoro-4-(methylsulfonyl)phenyl]-5-difluoromethylisoxazole;

3-(4-methylphenyl)-4-[3,5-difluoro-4-(methylsulfonyl)phenyl]-5-difluoromethylisoxazole;

3-(3-methylphenyl)-4-[3,5-difluoro-4-(methylsulfonyl)phenyl]-5-difluoromethylisoxazole;

3-(3-bromo-5-methylphenyl)-4-[3,5-difluoro-4-(methylsulfonyl)phenyl]-5-difluoromethylisoxazole;

3-(3,4-dichlorophenyl)-4-[3,5-difluoro-4-(methylsulfonyl)phenyl]-5-difluoromethylisoxazole;

3-(3,4-dibromophenyl)-4-[3,5-difluoro-4-(methylsulfonyl)phenyl]-5-difluoromethylisoxazole;

3-(3,4-difluorophenyl)-4-[3,5-difluoro-4-(methylsulfonyl)phenyl]-5-difluoromethylisoxazole;

3-(3,5-dichlorophenyl)-4-[3,5-difluoro-4-(methylsulfonyl)phenyl]-5-difluoromethylisoxazole;

3-(3,5-dibromophenyl)-4-[3,5-difluoro-4-(methylsulfonyl)phenyl]-5-difluoromethylisoxazole;

3-(3,5-difluorophenyl)-4-[3,5-difluoro-4-(methylsulfonyl)phenyl]-5-difluoromethylisoxazole;

3-(3-chloro-4-fluorophenyl)-4-[3,5-difluoro-4-(methylsulfonyl)phenyl]-5-difluoromethylisoxazole;

3-(3-chloro-4-methylphenyl)-4-[3,5-difluoro-4-(methylsulfonyl)phenyl]-5-difluoromethylisoxazole;

3-(3-bromo-4-methylphenyl)-4-[3,5-difluoro-4-(methylsulfonyl)phenyl]-5-difluoromethylisoxazole;

3-(3,5-difluoro-4-methylphenyl)-4-[3,5-difluoro-4-(methylsulfonyl)phenyl]-5-difluoromethylisoxazole;

3-(3,4-dimethylphenyl)-4-[3,5-difluoro-4-(methylsulfonyl)phenyl]-5-difluoromethylisoxazole;

3-(4-trifluoromethoxyphenyl)-4-[3,5-difluoro-4-(methylsulfonyl)phenyl]-5-difluoromethylisoxazole;

3-(3-methyl-4-trifluoromethoxyphenyl)-4-[3,5-difluoro-4-(methylsulfonyl)phenyl]-5-difluoromethylisoxazole;

3-(4-methyl-3-trifluoromethoxyphenyl)-4-[3,5-difluoro-4-(methylsulfonyl)phenyl]-5-difluoromethylisoxazole;

3-(3-methyl-4-trifluoromethoxyphenyl)-4-[3,5-difluoro-4-(methylsulfonyl)phenyl]-5-difluoromethylisoxazole;

3-(4-methyl-3-trifluoromethoxyphenyl)-4-[3,5-difluoro-4-(methylsulfonyl)phenyl]-5-difluoromethylisoxazole;

3-(3-cyano-4-methylphenyl)-4-[3,5-difluoro-4-(methylsulfonyl)phenyl]-5-difluoromethylisoxazole;

3-(4-cyano-3-methylphenyl)-4-[3,5-difluoro-4-(methylsulfonyl)phenyl]-5-difluoromethylisoxazole;

3-(3-cyanophenyl)-4-[3,5-difluoro-4-(methylsulfonyl)phenyl]-5-difluoromethylisoxazole;

3-(4-cyanophenyl)-4-[3,5-difluoro-4-(methylsulfonyl)phenyl]-5-difluoromethylisoxazole;

3-(3-chloro-4-methoxyphenyl)-4-[3,5-difluoro-4-(methylsulfonyl)phenyl]-5-difluoromethylisoxazole;

3-(4-chloro-3-methoxyphenyl)-4-[3,5-difluoro-4-(methylsulfonyl)phenyl]-5-difluoromethylisoxazole;

3-(2-methylpyridin-6-yl)-4-[3,5-difluoro-4-(methylsulfonyl)phenyl]-5-difluoromethylisoxazole;

3-(2-methylthiazol-4-yl)-4-[3,5-difluoro-4-(methylsulfonyl)phenyl]-5-difluoromethylisoxazole;

3-(4-methylthiazol-2-yl)-4-[3,5-difluoro-4-(methylsulfonyl)phenyl]-5-difluoromethylisoxazole;

3-(2-methylpyridin-3-yl)-4-[3,5-difluoro-4-(methylsulfonyl)phenyl]-5-difluoromethylisoxazole;

3-(2-methylpyridin-3-yl)-4-[3,5-difluoro-4-(methylsulfonyl)phenyl]-5-difluoromethylisoxazole;

3-(3-pyridinyl)-4-[3,5-difluoro-4-(methylsulfonyl)phenyl]-5-difluoromethylisoxazole;

3-(5-methylpyridin-3-yl)-4-[3,5-difluoro-4-(methylsulfonyl)phenyl]-5-difluoromethylisoxazole;

3-(2-methylpyridin-3-yl)-4-[3,5-difluoro-4-(methylsulfonyl)phenyl]-5-difluoromethylisoxazole;

3-cyclohexyl-4-[3,5-difluoro-4-(methylsulfonyl)phenyl]-5-difluoromethylisoxazole;

3-cyclopentyl-4-[3,5-difluoro-4-(methylsulfonyl)phenyl]-5-difluoromethylisoxazole;

3-phenyl-4-[3,5-difluoro-4-(methylsulfonyl)phenyl]-5-methylisoxazole;

3-(3-chlorophenyl)-4-[3,5-difluoro-4-(methylsulfonyl)phenyl]-5-methylisoxazole;

3-(4-chlorophenyl)-4-[3,5-difluoro-4-(methylsulfonyl)phenyl]-5-methylisoxazole;

3-(3-bromophenyl)-4-[3,5-difluoro-4-(methylsulfonyl)phenyl]-5-methylisoxazole;

3-(4-bromophenyl)-4-[3,5-difluoro-4-(methylsulfonyl)phenyl]-5-methylisoxazole;

3-(3-fluorophenyl)-4-[3,5-difluoro-4-(methylsulfonyl)phenyl]-5-methylisoxazole;

3-(4-fluorophenyl)-4-[3,5-difluoro-4-(methylsulfonyl)phenyl]-5-methylisoxazole;

3-(3-methylphenyl)-4-[3,5-difluoro-4-(methylsulfonyl)phenyl]-5-methylisoxazole;

3-(4-methylphenyl)-4-[3,5-difluoro-4-(methylsulfonyl)phenyl]-5-methylisoxazole;

3-(3-cyanophenyl)-4-[3,5-difluoro-4-(methylsulfonyl)phenyl]-5-methylisoxazole;

3-(4-cyanophenyl)-4-[3,5-difluoro-4-(methylsulfonyl)phenyl]-5-methylisoxazole;

3-(3-trifluoromethylphenyl)-4-[3,5-difluoro-4-(methylsulfonyl)phenyl]-5-methylisoxazole;

3-(4-trifluoromethylphenyl)-4-[3,5-difluoro-4-(methylsulfonyl)phenyl]-5-methylisoxazole;

3-(3-trifluoromethoxyphenyl)-4-[3,5-difluoro-4-(methylsulfonyl)phenyl]-5-methylisoxazole;

3-(4-trifluoromethoxyphenyl)-4-[3,5-difluoro-4-(methylsulfonyl)phenyl]-5-methylisoxazole;

3-(3,4-dichlorophenyl)-4-[3,5-difluoro-4-(methylsulfonyl)phenyl]-5-methylisoxazole;

3-(3,4-dibromophenyl)-4-[3,5-difluoro-4-(methylsulfonyl)phenyl]-5-methylisoxazole;

3-(3,4-difluorophenyl)-4-[3,5-difluoro-4-(methylsulfonyl)phenyl]-5-methylisoxazole;

3-(3,5-dichlorophenyl)-4-[3,5-difluoro-4-(methylsulfonyl)phenyl]-5-methylisoxazole;

3-(3,5-dibromophenyl)-4-[3,5-difluoro-4-(methylsulfonyl)phenyl]-5-methylisoxazole;

3-(3,5-difluorophenyl)-4-[3,5-difluoro-4-(methylsulfonyl)phenyl]-5-methylisoxazole;

3-(3,4-dimethylphenyl)-4-[3,5-difluoro-4-(methylsulfonyl)phenyl]-5-methylisoxazole;

3-(3,5-dimethylphenyl)-4-[3,5-difluoro-4-(methylsulfonyl)phenyl]-5-methylisoxazole;

3-(3-methyl-4-chlorophenyl)-4-[3,5-difluoro-4-(methylsulfonyl)phenyl]-5-methylisoxazole;

3-(4-methyl-3-chlorophenyl)-4-[3,5-difluoro-4-(methylsulfonyl)phenyl]-5-methylisoxazole;

3-(3-methyl-4-fluorophenyl)-4-[3,5-difluoro-4-(methylsulfonyl)phenyl]-5-methylisoxazole;

3-(4-methyl-3-fluorophenyl)-4-[3,5-difluoro-4-(methylsulfonyl)phenyl]-5-methylisoxazole;

3-(3-methyl-4-bromophenyl)-4-[3,5-difluoro-4-(methylsulfonyl)phenyl]-5-methylisoxazole;

3-(4-methyl-3-bromophenyl)-4-[3,5-difluoro-4-(methylsulfonyl)phenyl]-5-methylisoxazole;

3-(3-methyl-4-trifluoromethylphenyl)-4-[3,5-difluoro-4-(methylsulfonyl)phenyl]-5-methylisoxazole;

3-(4-methyl-3-trifluoromethylphenyl)-4-[3,5-difluoro-4-(methylsulfonyl)phenyl]-5-methylisoxazole;

3-(3-methyl-4-trifluoromethoxyphenyl)-4-[3,5-difluoro-4-(methylsulfonyl)phenyl]-5-methylisoxazole;

3-(4-methyl-3-trifluoromethoxyphenyl)-4-[3,5-difluoro-4-(methylsulfonyl)phenyl]-5-methylisoxazole;

3-(3-cyano-4-methylphenyl)-4-[3,5-difluoro-4-(methylsulfonyl)phenyl]-5-methylisoxazole;

3-(4-cyano-3-methylphenyl)-4-[3,5-difluoro-4-(methylsulfonyl)phenyl]-5-methylisoxazole;

3-(3-chloro-4-methoxyphenyl)-4-[3,5-difluoro-4-(methylsulfonyl)phenyl]-5-methylisoxazole;

3-(4-chloro-3-methoxyphenyl)-4-[3,5-difluoro-4-(methylsulfonyl)phenyl]-5-methylisoxazole;

3-(2-methylpyridin-6-yl)-4-[3,5-difluoro-4-(methylsulfonyl)phenyl]-5-methylisoxazole;

3-(2-methylthiazol-4-yl)-4-[3,5-difluoro-4-(methylsulfonyl)phenyl]-5-methylisoxazole;

3-(4-methylthiazol-2-yl)-4-[3,5-difluoro-4-(methylsulfonyl)phenyl]-5-methylisoxazole;

3-(2-methylpyridin-3-yl)-4-[3,5-difluoro-4-(methylsulfonyl)phenyl]-5-methylisoxazole;

3-(2-methylpyridin-3-yl)-4-[3,5-difluoro-4-(methylsulfonyl)phenyl]-5-methylisoxazole;

3-(3-pyridinyl)-4-[3,5-difluoro-4-(methylsulfonyl)phenyl]-5-methylisoxazole;

3-(5-methylpyridin-3-yl)-4-[3,5-difluoro-4-(methylsulfonyl)phenyl]-5-methylisoxazole;

3-(2-methylpyridin-3-yl)-4-[3,5-difluoro-4-(methylsulfonyl)phenyl]-5-methylisoxazole;

3-cyclohexyl-4-[3,5-difluoro-4-(methylsulfonyl)phenyl]-5-methylisoxazole;

3-cyclopentyl-4-[3,5-difluoro-4-(methylsulfonyl)phenyl]-5-methylisoxazole;

2,6-difluoro-4-[3-phenyl-5-hydroxymethylisoxazol-4-yl]benzenesulfonamide;

2,6-difluoro-4-[3-(3-chlorophenyl)-5-hydroxymethylisoxazol-4-yl]benzenesulfonamide;

2,6-difluoro-4-[3-(4-chlorophenyl)-5-hydroxymethylisoxazol-4-yl]benzenesulfonamide;

2,6-difluoro-4-[3-(3-bromophenyl)-5-hydroxymethylisoxazol-4-yl]benzenesulfonamide;

2,6-difluoro-4-[3-(4-bromophenyl)-5-hydroxymethylisoxazol-4-yl]benzenesulfonamide;

2,6-difluoro-4-[3-(3-fluorophenyl)-5-hydroxymethylisoxazol-4-yl]benzenesulfonamide;

2,6-difluoro-4-[3-(4-fluorophenyl)-5-hydroxymethylisoxazol-4-yl]benzenesulfonamide;

2,6-difluoro-4-[3-(3-methylphenyl)-5-hydroxymethylisoxazol-4-yl]benzenesulfonamide;

2,6-difluoro-4-[3-(4-methylphenyl)-5-hydroxymethylisoxazol-4-yl]benzenesulfonamide;

2,6-difluoro-4-[3-(3-cyanophenyl)-5-hydroxymethylisoxazol-4-yl]benzenesulfonamide;

2,6-difluoro-4-[3-(4-cyanophenyl)-5-hydroxymethylisoxazol-4-yl]benzenesulfonamide;

2,6-difluoro-4-[3-(3-trifluoromethylphenyl)-5-hydroxymethylisoxazol-4-yl]benzenesulfonamide;

2,6-difluoro-4-[3-(4-trifluoromethylphenyl)-5-hydroxymethylisoxazol-4-yl]benzenesulfonamide;

2,6-difluoro-4-[3-(3-trifluoromethoxyphenyl)-5-hydroxymethylisoxazol-4-yl]benzenesulfonamide;

2,6-difluoro-4-[3-(4-trifluoromethoxyphenyl)-5-hydroxymethylisoxazol-4-yl]benzenesulfonamide;

2,6-difluoro-4-[3-(3,4-dichlorophenyl)-5-hydroxymethylisoxazol-4-yl]benzenesulfonamide;

2,6-difluoro-4-[3-(3,4-dibromophenyl)-5-hydroxymethylisoxazol-4-yl]benzenesulfonamide;

2,6-difluoro-4-[3-(3,4-difluorophenyl)-5-hydroxymethylisoxazol-4-yl]benzenesulfonamide;

2,6-difluoro-4-[3-(3,5-dichlorophenyl)-5-hydroxymethylisoxazol-4-yl]benzenesulfonamide;

2,6-difluoro-4-[3-(3,5-dibromophenyl)-5-hydroxymethylisoxazol-4-yl]benzenesulfonamide;

2,6-difluoro-4-[3-(3,5-difluorophenyl)-5-hydroxymethylisoxazol-4-yl]benzenesulfonamide;

2,6-difluoro-4-[3-(3,4-dimethylphenyl)-5-hydroxymethylisoxazol-4-yl]benzenesulfonamide;

2,6-difluoro-4-[3-(3,5-dimethylphenyl)-5-hydroxymethylisoxazol-4-yl]benzenesulfonamide;

2,6-difluoro-4-[3-(3-methyl-4-chlorophenyl)-5-hydroxymethylisoxazol-4-yl]benzenesulfonamide;

2,6-difluoro-4-[3-(4-methyl-3-chlorophenyl)-5-hydroxymethylisoxazol-4-yl]benzenesulfonamide;
2,6-difluoro-4-[3-(3-methyl-4-fluorophenyl)-5-hydroxymethylisoxazol-4-yl]benzenesulfonamide;
2,6-difluoro-4-[3-(4-methyl-3-fluorophenyl)-5-hydroxymethylisoxazol-4-yl]benzenesulfonamide;
2,6-difluoro-4-[3-(3-methyl-4-bromophenyl)-5-hydroxymethylisoxazol-4-yl]benzenesulfonamide;
2,6-difluoro-4-[3-(4-methyl-3-bromophenyl)-5-hydroxymethylisoxazol-4-yl]benzenesulfonamide;
2,6-difluoro-4-[3-(3-methyl-4-trifluoromethylphenyl)-5-hydroxymethylisoxazol-4-yl]benzenesulfonamide;
2,6-difluoro-4-[3-(4-methyl-3-trifluoromethylphenyl)-5-hydroxymethylisoxazol-4-yl]benzenesulfonamide;
2,6-difluoro-4-[3-(3-methyl-4-trifluoromethoxyphenyl)-5-hydroxymethylisoxazol-4-yl]benzenesulfonamide;
2,6-difluoro-4-[3-(4-methyl-3-trifluoromethoxyphenyl)-5-hydroxymethylisoxazol-4-yl]benzenesulfonamide;
2,6-difluoro-4-[3-(3-cyano-4-methylphenyl)-5-hydroxymethylisoxazol-4-yl]benzenesulfonamide;
2,6-difluoro-4-[3-(4-cyano-3-methylphenyl)-5-hydroxymethylisoxazol-4-yl]benzenesulfonamide;
2,6-difluoro-4-[3-(3-chloro-4-methoxyphenyl)-5-hydroxymethylisoxazol-4-yl]benzenesulfonamide;
2,6-difluoro-4-[3-(4-chloro-3-methoxyphenyl)-5-hydroxymethylisoxazol-4-yl]benzenesulfonamide;
2,6-difluoro-4-[3-(2-methylpyridin-6-yl)-5-hydroxymethylisoxazol-4-yl]benzenesulfonamide;
2,6-difluoro-4-[3-(2-methylthiazol-4-yl)-5-hydroxymethylisoxazol-4-yl]benzenesulfonamide;
2,6-difluoro-4-[3-(4-methylthiazol-2-yl)-5-hydroxymethylisoxazol-4-yl]benzenesulfonamide;
2,6-difluoro-4-[3-(2-methylpyridin-3-yl)-5-hydroxymethylisoxazol-4-yl]benzenesulfonamide;
2,6-difluoro-4-[3-(2-methylpyridin-3-yl)-5-hydroxymethylisoxazol-4-yl]benzenesulfonamide;
2,6-difluoro-4-[3-(3-pyridinyl)-5-hydroxymethylisoxazol-4-yl]benzenesulfonamide;
2,6-difluoro-4-[3-(5-methylpyridin-3-yl)-5-hydroxymethylisoxazol-4-yl]benzenesulfonamide;
2,6-difluoro-4-[3-(2-methylpyridin-3-yl)-5-hydroxymethylisoxazol-4-yl]benzenesulfonamide;
2,6-difluoro-4-[3-phenyl-5-5-methylisoxazol-4-yl]benzenesulfonamide;
2,6-difluoro-4-[3-(3-chlorophenyl)-5-methylisoxazol-4-yl]benzenesulfonamide;
2,6-difluoro-4-[3-(4-chlorophenyl)-5-methylisoxazol-4-yl]benzenesulfonamide;
2,6-difluoro-4-[3-(3-bromophenyl)-5-methylisoxazol-4-yl]benzenesulfonamide;
2,6-difluoro-4-[3-(4-bromophenyl)-5-methylisoxazol-4-yl]benzenesulfonamide;
2,6-difluoro-4-[3-(3-fluorophenyl)-5-methylisoxazol-4-yl]benzenesulfonamide;
2,6-difluoro-4-[3-(4-fluorophenyl)-5-methylisoxazol-4-yl]benzenesulfonamide;
2,6-difluoro-4-[3-(3-methylphenyl)-5-methylisoxazol-4-yl]benzenesulfonamide;
2,6-difluoro-4-[3-(4-methylphenyl)-5-methylisoxazol-4-yl]benzenesulfonamide;
2,6-difluoro-4-[3-(3-cyanophenyl)-5-methylisoxazol-4-yl]benzenesulfonamide;
2,6-difluoro-4-[3-(4-cyanophenyl)-5-methylisoxazol-4-yl]benzenesulfonamide;
2,6-difluoro-4-[3-(3-trifluoromethylphenyl)-5-methylisoxazol-4-yl]benzenesulfonamide;
2,6-difluoro-4-[3-(4-trifluoromethylphenyl)-5-methylisoxazol-4-yl]benzenesulfonamide;
2,6-difluoro-4-[3-(3-trifluoromethoxyphenyl)-5-methylisoxazol-4-yl]benzenesulfonamide;
2,6-difluoro-4-[3-(4-trifluoromethoxyphenyl)-5-methylisoxazol-4-yl]benzenesulfonamide;
2,6-difluoro-4-[3-(3,4-dichlorophenyl)-5-methylisoxazol-4-yl]benzenesulfonamide;
2,6-difluoro-4-[3-(3,4-dibromophenyl)-5-methylisoxazol-4-yl]benzenesulfonamide;
2,6-difluoro-4-[3-(3,4-difluorophenyl)-5-methylisoxazol-4-yl]benzenesulfonamide;
2,6-difluoro-4-[3-(3,5-dichlorophenyl)-5-methylisoxazol-4-yl]benzenesulfonamide;
2,6-difluoro-4-[3-(3,5-dibromophenyl)-5-methylisoxazol-4-yl]benzenesulfonamide;
2,6-difluoro-4-[3-(3,5-difluorophenyl)-5-methylisoxazol-4-yl]benzenesulfonamide;
2,6-difluoro-4-[3-(3,4-dimethylphenyl)-5-methylisoxazol-4-yl]benzenesulfonamide;
2,6-difluoro-4-[3-(3,5-dimethylphenyl)-5-methylisoxazol-4-yl]benzenesulfonamide;
2,6-difluoro-4-[3-(3-methyl-4-chlorophenyl)-5-methylisoxazol-4-yl]benzenesulfonamide;
2,6-difluoro-4-[3-(4-methyl-3-chlorophenyl)-5-methylisoxazol-4-yl]benzenesulfonamide;
2,6-difluoro-4-[3-(3-methyl-4-fluorophenyl)-5-methylisoxazol-4-yl]benzenesulfonamide;
2,6-difluoro-4-[3-(4-methyl-3-fluorophenyl)-5-methylisoxazol-4-yl]benzenesulfonamide;
2,6-difluoro-4-[3-(3-methyl-4-bromophenyl)-5-methylisoxazol-4-yl]benzenesulfonamide;
2,6-difluoro-4-[3-(4-methyl-3-bromophenyl)-5-methylisoxazol-4-yl]benzenesulfonamide;
2,6-difluoro-4-[3-(3-methyl-4-trifluoromethylphenyl)-5-methylisoxazol-4-yl]benzenesulfonamide;
2,6-difluoro-4-[3-(4-methyl-3-trifluoromethylphenyl)-5-methylisoxazol-4-yl]benzenesulfonamide;
2,6-difluoro-4-[3-(3-methyl-4-trifluoromethoxyphenyl)-5-methylisoxazol-4-yl]benzenesulfonamide;
2,6-difluoro-4-[3-(4-methyl-3-trifluoromethoxyphenyl)-5-methylisoxazol-4-yl]benzenesulfonamide;
2,6-difluoro-4-[3-(3-cyano-4-methylphenyl)-5-methylisoxazol-4-yl]benzenesulfonamide;
2,6-difluoro-4-[3-(4-cyano-3-methylphenyl)-5-methylisoxazol-4-yl]benzenesulfonamide;
2,6-difluoro-4-[3-(3-chloro-4-methoxyphenyl)-5-methylisoxazol-4-yl]benzenesulfonamide;
2,6-difluoro-4-[3-(4-chloro-3-methoxyphenyl)-5-methylisoxazol-4-yl]benzenesulfonamide;
2,6-difluoro-4-[3-(2-methylpyridin-6-yl)-5-methylisoxazol-4-yl]benzenesulfonamide;
2,6-difluoro-4-[3-(2-methylthiazol-4-yl)-5-methylisoxazol-4-yl]benzenesulfonamide;
2,6-difluoro-4-[3-(4-methylthiazol-2-yl)-5-methylisoxazol-4-yl]benzenesulfonamide;
2,6-difluoro-4-[3-(2-methylpyridin-3-yl)-5-methylisoxazol-4-yl]benzenesulfonamide;

2,6-difluoro-4-[3-(2-methylpyridin-3-yl)-5-methylisoxazol-4-yl]benzenesulfonamide;

2,6-difluoro-4-[3-(3-pyridinyl)-5-methylisoxazol-4-yl]benezenesulfonamide;

2,6-difluoro-4-[3-(5-methylpyridin-3-yl)-5-methylisoxazol-4-yl]benezenesulfonamide;

2,6-difluoro-4-[3-(2-methylpyridin-3-yl)-5-methylisoxazol-4-yl]benezenesulfonamide;

2,6-difluoro-4-[3-phenyl-5-trifluoromethylisoxazol-4-yl]benzenesulfonamide;

2,6-difluoro-4-[3-(3-chlorophenyl)-5-trifluoromethylisoxazol-4-yl]benezenesulfonamide;

2,6-difluoro-4-[3-(4-chlorophenyl)-5-trifluoromethylisoxazol-4-yl]benezenesulfonamide;

2,6-difluoro-4-[3-(3-bromophenyl)-5-trifluoromethylisoxazol-4-yl]benezenesulfonamide;

2,6-difluoro-4-[3-(4-bromophenyl)-5-trifluoromethylisoxazol-4-yl]benezenesulfonamide;

2,6-difluoro-4-[3-(3-fluorophenyl)-5-trifluoromethylisoxazol-4-yl]benezenesulfonamide;

2,6-difluoro-4-[3-(4-fluorophenyl)-5-trifluoromethylisoxazol-4-yl]benezenesulfonamide;

2,6-difluoro-4-[3-(3-methylphenyl)-5-trifluoromethylisoxazol-4-yl]benezenesulfonamide;

2,6-difluoro-4-[3-(4-methylphenyl)-5-trifluoromethylisoxazol-4-yl]benezenesulfonamide;

2,6-difluoro-4-[3-(3-cyanophenyl)-5-trifluoromethylisoxazol-4-yl]benezenesulfonamide;

2,6-difluoro-4-[3-(4-cyanophenyl)-5-trifluoromethylisoxazol-4-yl]benezenesulfonamide;

2,6-difluoro-4-[3-(3-trifluoromethylphenyl)-5-trifluoromethylisoxazol-4-yl]benezenesulfonamide;

2,6-difluoro-4-[3-(4-trifluoromethylphenyl)-5-trifluoromethylisoxazol-4-yl]benezenesulfonamide;

2,6-difluoro-4-[3-(3-trifluoromethoxyphenyl)-5-trifluoromethylisoxazol-4-yl]benezenesulfonamide;

2,6-difluoro-4-[3-(4-trifluoromethoxyphenyl)-5-trifluoromethylisoxazol-4-yl]benezenesulfonamide;

2,6-difluoro-4-[3-(3,4-dichlorophenyl)-5-trifluoromethylisoxazol-4-yl]benezenesulfonamide;

2,6-difluoro-4-[3-(3,4-dibromophenyl)-5-trifluoromethylisoxazol-4-yl]benezenesulfonamide;

2,6-difluoro-4-[3-(3,4-difluorophenyl)-5-trifluoromethylisoxazol-4-yl]benezenesulfonamide;

2,6-difluoro-4-[3-(3,5-dichlorophenyl)-5-trifluoromethylisoxazol-4-yl]benezenesulfonamide;

2,6-difluoro-4-[3-(3,5-dibromophenyl)-5-trifluoromethylisoxazol-4-yl]benezenesulfonamide;

2,6-difluoro-4-[3-(3,5-difluorophenyl)-5-trifluoromethylisoxazol-4-yl]benezenesulfonamide;

2,6-difluoro-4-[3-(3,4-dimethylphenyl)-5-trifluoromethylisoxazol-4-yl]benezenesulfonamide;

2,6-difluoro-4-[3-(3,5-dimethylphenyl)-5-trifluoromethylisoxazol-4-yl]benezenesulfonamide;

2,6-difluoro-4-[3-(3-methyl-4-chlorophenyl)-5-trifluoromethylisoxazol-4-yl]benezenesulfonamide;

2,6-difluoro-4-[3-(4-methyl-3-chlorophenyl)-5-trifluoromethylisoxazol-4-yl]benezenesulfonamide;

2,6-difluoro-4-[3-(3-methyl-4-fluorophenyl)-5-trifluoromethylisoxazol-4-yl]benezenesulfonamide;

2,6-difluoro-4-[3-(4-methyl-3-fluorophenyl)-5-trifluoromethylisoxazol-4-yl]benezenesulfonamide;

2,6-difluoro-4-[3-(3-methyl-4-bromophenyl)-5-trifluoromethylisoxazol-4-yl]benezenesulfonamide;

2,6-difluoro-4-[3-(4-methyl-3-bromophenyl)-5-trifluoromethylisoxazol-4-yl]benezenesulfonamide;

2,6-difluoro-4-[3-(3-methyl-4-trifluoromethylphenyl)-5-trifluoromethylisoxazol-4-yl]benezenesulfonamide;

2,6-difluoro-4-[3-(4-methyl-3-trifluoromethylphenyl)-5-trifluoromethylisoxazol-4-yl]benezenesulfonamide;

2,6-difluoro-4-[3-(3-methyl-4-trifluoromethoxyphenyl)-5-trifluoromethylisoxazol-4-yl]benezenesulfonamide;

2,6-difluoro-4-[3-(4-methyl-3-trifluoromethoxyphenyl)-5-trifluoromethylisoxazol-4-yl]benezenesulfonamide;

2,6-difluoro-4-[3-(3-cyano-4-methylphenyl)-5-trifluoromethylisoxazol-4-yl]benezenesulfonamide;

2,6-difluoro-4-[3-(4-cyano-3-methylphenyl)-5-trifluoromethylisoxazol-4-yl]benezenesulfonamide;

2,6-difluoro-4-[3-(3-chloro-4-methoxyphenyl)-5-trifluoromethylisoxazol-4-yl]benezenesulfonamide;

2,6-difluoro-4-[3-(4-chloro-3-methoxyphenyl)-5-trifluoromethylisoxazol-4-yl]benezenesulfonamide;

2,6-difluoro-4-[3-(2-methylpyridin-6-yl)-5-trifluoromethylisoxazol-4-yl]benezenesulfonamide;

2,6-difluoro-4-[3-(2-methylthiazol-4-yl)-5-trifluoromethylisoxazol-4-yl]benezenesulfonamide;

2,6-difluoro-4-[3-(4-methylthiazol-2-yl)-5-trifluoromethylisoxazol-4-yl]benezenesulfonamide;

2,6-difluoro-4-[3-(2-methylpyridin-3-yl)-5-trifluoromethylisoxazol-4-yl]benezenesulfonamide;

2,6-difluoro-4-[3-(2-methylpyridin-3-yl)-5-trifluoromethylisoxazol-4-yl]benezenesulfonamide;

2,6-difluoro-4-[3-(3-pyridinyl)-5-trifluoromethylisoxazol-4-yl]benezenesulfonamide;

2,6-difluoro-4-[3-(5-methylpyridin-3-yl)-5-trifluoromethylisoxazol-4-yl]benezenesulfonamide;

2,6-difluoro-4-[3-(2-methylpyridin-3-yl)-5-trifluoromethylisoxazol-4-yl]benezenesulfonamide;

2,5-difluoro-4-[3-phenyl-5-fluoromethylisoxazol-4-yl]benzenesulfonamide;

2,5-difluoro-4-[3-(3-chlorophenyl)-5-fluoromethylisoxazol-4-yl]benezenesulfonamide;

2,5-difluoro-4-[3-(4-chlorophenyl)-5-fluoromethylisoxazol-4-yl]benezenesulfonamide;

2,5-difluoro-4-[3-(3-bromophenyl)-5-fluoromethylisoxazol-4-yl]benezenesulfonamide;

2,5-difluoro-4-[3-(4-bromophenyl)-5-fluoromethylisoxazol-4-yl]benezenesulfonamide;

2,5-difluoro-4-[3-(3-fluorophenyl)-5-fluoromethylisoxazol-4-yl]benezenesulfonamide;

2,5-difluoro-4-[3-(4-fluorophenyl)-5-fluoromethylisoxazol-4-yl]benezenesulfonamide;

2,5-difluoro-4-[3-(3-methylphenyl)-5-fluoromethylisoxazol-4-yl]benezenesulfonamide;

2,5-difluoro-4-[3-(4-methylphenyl)-5-fluoromethylisoxazol-4-yl]benezenesulfonamide;

2,5-difluoro-4-[3-(3-cyanophenyl)-5-fluoromethylisoxazol-4-yl]benezenesulfonamide;

2,5-difluoro-4-[3-(4-cyanophenyl)-5-fluoromethylisoxazol-4-yl]benezenesulfonamide;

2,5-difluoro-4-[3-(3-trifluoromethylphenyl)-5-fluoromethylisoxazol-4-yl]benezenesulfonamide;

2,5-difluoro-4-[3-(4-trifluoromethylphenyl)-5-fluoromethylisoxazol-4-yl]benezenesulfonamide;

2,5-difluoro-4-[3-(3-trifluoromethoxyphenyl)-5-fluoromethylisoxazol-4-yl]benezenesulfonamide;
2,5-difluoro-4-[3-(4-trifluoromethoxyphenyl)-5-fluoromethylisoxazol-4-yl]benezenesulfonamide;
2,5-difluoro-4-[3-(3,4-dichlorophenyl)-5-fluoromethylisoxazol-4-yl]benezenesulfonamide;
2,5-difluoro-4-[3-(3,4-dibromophenyl)-5-fluoromethylisoxazol-4-yl]benezenesulfonamide;
2,5-difluoro-4-[3-(3,4-difluorophenyl)-5-fluoromethylisoxazol-4-yl]benezenesulfonamide;
2,5-difluoro-4-[3-(3,5-dichlorophenyl)-5-fluoromethylisoxazol-4-yl]benezenesulfonamide;
2,5-difluoro-4-[3-(3,5-dibromophenyl)-5-fluoromethylisoxazol-4-yl]benezenesulfonamide;
2,5-difluoro-4-[3-(3,5-difluorophenyl)-5-fluoromethylisoxazol-4-yl]benezenesulfonamide;
2,5-difluoro-4-[3-(3,4-dimethylphenyl)-5-fluoromethylisoxazol-4-yl]benezenesulfonamide;
2,5-difluoro-4-[3-(3,5-dimethylphenyl)-5-fluoromethylisoxazol-4-yl]benezenesulfonamide;
2,5-difluoro-4-[3-(3-methyl-4-chlorophenyl)-5-fluoromethylisoxazol-4-yl]benezenesulfonamide;
2,5-difluoro-4-[3-(4-methyl-3-chlorophenyl)-5-fluoromethylisoxazol-4-yl]benezenesulfonamide;
2,5-difluoro-4-[3-(3-methyl-4-fluorophenyl)-5-fluoromethylisoxazol-4-yl]benezenesulfonamide;
2,5-difluoro-4-[3-(4-methyl-3-fluorophenyl)-5-fluoromethylisoxazol-4-yl]benezenesulfonamide;
2,5-difluoro-4-[3-(3-methyl-4-bromophenyl)-5-fluoromethylisoxazol-4-yl]benezenesulfonamide;
2,5-difluoro-4-[3-(4-methyl-3-bromophenyl)-5-fluoromethylisoxazol-4-yl]benezenesulfonamide;
2,5-difluoro-4-[3-(3-methyl-4-trifluoromethylphenyl)-5-fluoromethylisoxazol-4-yl]benezenesulfonamide;
2,5-difluoro-4-[3-(4-methyl-3-trifluoromethylphenyl)-5-fluoromethylisoxazol-4-yl]benezenesulfonamide;
2,5-difluoro-4-[3-(3-methyl-4-trifluoromethoxyphenyl)-5-fluoromethylisoxazol-4-yl]benezenesulfonamide;
2,5-difluoro-4-[3-(4-methyl-3-trifluoromethoxyphenyl)-5-fluoromethylisoxazol-4-yl]benezenesulfonamide;
2,5-difluoro-4-[3-(3-cyano-4-methylphenyl)-5-fluoromethylisoxazol-4-yl]benezenesulfonamide;
2,5-difluoro-4-[3-(4-cyano-3-methylphenyl)-5-fluoromethylisoxazol-4-yl]benezenesulfonamide;
2,5-difluoro-4-[3-(3-chloro-4-methoxyphenyl)-5-fluoromethylisoxazol-4-yl]benezenesulfonamide;
2,5-difluoro-4-[3-(4-chloro-3-methoxyphenyl)-5-fluoromethylisoxazol-4-yl]benezenesulfonamide;
2,5-difluoro-4-[3-(2-methylpyridin-6-yl)-5-fluoromethylisoxazol-4-yl]benezenesulfonamide;
2,5-difluoro-4-[3-(2-methylthiazol-4-yl)-5-fluoromethylisoxazol-4-yl]benezenesulfonamide;
2,5-difluoro-4-[3-(4-methylthiazol-2-yl)-5-fluoromethylisoxazol-4-yl]benezenesulfonamide;
2,5-difluoro-4-[3-(2-methylpyridin-3-yl)-5-fluoromethylisoxazol-4-yl]benezenesulfonamide;
2,5-difluoro-4-[3-(2-methylpyridin-3-yl)-5-fluoromethylisoxazol-4-yl]benezenesulfonamide;
2,5-difluoro-4-[3-(3-pyridinyl)-5-fluoromethylisoxazol-4-yl]benezenesulfonamide;
2,5-difluoro-4-[3-(5-methylpyridin-3-yl)-5-fluoromethylisoxazol-4-yl]benezenesulfonamide;
2,5-difluoro-4-[3-(2-methylpyridin-3-yl)-5-fluoromethylisoxazol-4-yl]benezenesulfonamide;
2,5-difluoro-4-[3-cyclohexyl-5-fluoromethylisoxazol-4-yl]benezenesulfonamide;
2,5-difluoro-4-[3-cyclopentyl-5-fluoromethylisoxazol-4-yl]benezenesulfonamide;
2,5-difluoro-4-[3-phenyl-5-difluoromethylisoxazol-4-yl]benezenesulfonamide;
2,5-difluoro-4-[3-(3-chloro-5-methylphenyl)-5-difluoromethylisoxazol-4-yl]benezenesulfonamide;
2,5-difluoro-4-[3-(3-fluoro-5-methylphenyl)-5-difluoromethylisoxazol-4-yl]benezenesulfonamide;
2,5-difluoro-4-[3-(3-chlorophenyl)-5-difluoromethylisoxazol-4-yl]benezenesulfonamide;
2,5-difluoro-4-[3-(4-chlorophenyl)-5-difluoromethylisoxazol-4-yl]benezenesulfonamide;
2,5-difluoro-4-[3-(3-bromophenyl)-5-difluoromethylisoxazol-4-yl]benezenesulfonamide;
2,5-difluoro-4-[3-(4-bromophenyl)-5-difluoromethylisoxazol-4-yl]benezenesulfonamide;
2,5-difluoro-4-[3-(3-fluorophenyl)-5-difluoromethylisoxazol-4-yl]benezenesulfonamide;
2,5-difluoro-4-[3-(4-fluorophenyl)-5-difluoromethylisoxazol-4-yl]benezenesulfonamide;
2,5-difluoro-4-[3-(4-methylphenyl)-5-difluoromethylisoxazol-4-yl]benezenesulfonamide;
2,5-difluoro-4-[3-(3-methylphenyl)-5-difluoromethylisoxazol-4-yl]benezenesulfonamide;
2,5-difluoro-4-[3-(3-bromo-5-methylphenyl)-5-difluoromethylisoxazol-4-yl]benezenesulfonamide;
2,5-difluoro-4-[3-(3,4-dichlorophenyl)-5-difluoromethylisoxazol-4-yl]benezenesulfonamide;
2,5-difluoro-4-[3-(3,4-dibromophenyl)-5-difluoromethylisoxazol-4-yl]benezenesulfonamide;
2,5-difluoro-4-[3-(3,4-difluorophenyl)-5-difluoromethylisoxazol-4-yl]benezenesulfonamide;
2,5-difluoro-4-[3-(3,5-dichlorophenyl)-5-difluoromethylisoxazol-4-yl]benezenesulfonamide;
2,5-difluoro-4-[3-(3,5-dibromophenyl)-5-difluoromethylisoxazol-4-yl]benezenesulfonamide;
2,5-difluoro-4-[3-(3,5-difluorophenyl)-5-difluoromethylisoxazol-4-yl]benezenesulfonamide;
2,5-difluoro-4-[3-(3-chloro-4-fluorophenyl)-5-difluoromethylisoxazol-4-yl]benezenesulfonamide;
2,5-difluoro-4-[3-(3-chloro-4-methylphenyl)-5-difluoromethylisoxazol-4-yl]benezenesulfonamide;
2,5-difluoro-4-[3-(3-bromo-4-methylphenyl)-5-difluoromethylisoxazol-4-yl]benezenesulfonamide;
2,5-difluoro-4-[3-(3-fluoro-4-methylphenyl)-5-difluoromethylisoxazol-4-yl]benezenesulfonamide;
2,5-difluoro-4-[3-(3,4-dimethylphenyl)-5-difluoromethylisoxazol-4-yl]benezenesulfonamide;
2,5-difluoro-4-[3-(4-trifluoromethoxyphenyl)-5-difluoromethylisoxazol-4-yl]benezenesulfonamide;
2,5-difluoro-4-[3-(3-methyl-4-trifluoromethoxyphenyl)-5-difluoromethylisoxazol-4-yl]benezenesulfonamide;
2,5-difluoro-4-[3-(4-methyl-3-trifluoromethoxyphenyl)-5-difluoromethylisoxazol-4-yl]benezenesulfonamide;
2,5-difluoro-4-[3-(3-trifluoromethylphenyl)-5-difluoromethylisoxazol-4-yl]benezenesulfonamide;
2,5-difluoro-4-[3-(4-trifluoromethylphenyl)-5-difluoromethylisoxazol-4-yl]benezenesulfonamide;

2,5-difluoro-4-[3-(3-methyl-4-trifluoromethylphenyl)-5-difluoromethylisoxazol-4-yl]benzenesulfonamide;
2,5-difluoro-4-[3-(4-methyl-3-trifluoromethylphenyl)-5-difluoromethylisoxazol-4-yl]benzenesulfonamide;
2,5-difluoro-4-[3-(3-cyano-4-methylphenyl)-5-difluoromethylisoxazol-4-yl]benzenesulfonamide;
2,5-difluoro-4-[3-(4-cyano-3-methylphenyl)-5-difluoromethylisoxazol-4-yl]benzenesulfonamide;
2,5-difluoro-4-[3-(3-cyanophenyl)-5-difluoromethylisoxazol-4-yl]benzenesulfonamide;
2,5-difluoro-4-[3-(4-cyanophenyl)-5-difluoromethylisoxazol-4-yl]benzenesulfonamide;
2,5-difluoro-4-[3-(3-chloro-4-methoxyphenyl)-5-difluoromethylisoxazol-4-yl]benzenesulfonamide;
2,5-difluoro-4-[3-(4-chloro-3-methoxyphenyl)-5-difluoromethylisoxazol-4-yl]benzenesulfonamide;
2,5-difluoro-4-[3-(2-methylpyridin-6-yl)-5-difluoromethylisoxazol-4-yl]benzenesulfonamide;
2,5-difluoro-4-[3-(2-methylthiazol-4-yl)-5-difluoromethylisoxazol-4-yl]benzenesulfonamide;
2,5-difluoro-4-[3-(4-methylthiazol-2-yl)-5-difluoromethylisoxazol-4-yl]benzenesulfonamide;
2,5-difluoro-4-[3-(2-methylpyridin-3-yl)-5-difluoromethylisoxazol-4-yl]benzenesulfonamide;
2,5-difluoro-4-[3-(2-methylpyridin-3-yl)-5-difluoromethylisoxazol-4-yl]benzenesulfonamide;
2,5-difluoro-4-[3-(3-pyridinyl)-5-difluoromethylisoxazol-4-yl]benzenesulfonamide;
2,5-difluoro-4-[3-(5-methylpyridin-3-yl)-5-difluoromethylisoxazol-4-yl]benzenesulfonamide;
2,5-difluoro-4-[3-(2-methylpyridin-3-yl)-5-difluoromethylisoxazol-4-yl]benezenesulfonamide;
3-phenyl-4-[3,6-difluoro-4-(methylsulfonyl)phenyl]-5-hydroxymethylisoxazole;
3-(3-chlorophenyl)-4-[3,6-difluoro-4-(methylsulfonyl)phenyl]-5-hydroxymethylisoxazole;
3-(4-chlorophenyl)-4-[3,6-difluoro-4-(methylsulfonyl)phenyl]-5-hydroxymethylisoxazole;
3-(3-bromophenyl)-4-[3,6-difluoro-4-(methylsulfonyl)phenyl]-5-hydroxymethylisoxazole;
3-(4-bromophenyl)-4-[3,6-difluoro-4-(methylsulfonyl)phenyl]-5-hydroxymethylisoxazole;
3-(3-fluorophenyl)-4-[3,6-difluoro-4-(methylsulfonyl)phenyl]-5-hydroxymethylisoxazole;
3-(4-fluorophenyl)-4-[3,6-difluoro-4-(methylsulfonyl)phenyl]-5-hydroxymethylisoxazole;
3-(3-methylphenyl)-4-[3,6-difluoro-4-(methylsulfonyl)phenyl]-5-hydroxymethylisoxazole;
3-(4-methylphenyl)-4-[3,6-difluoro-4-(methylsulfonyl)phenyl]-5-hydroxymethylisoxazole;
3-(3-cyanophenyl)-4-[3,6-difluoro-4-(methylsulfonyl)phenyl]-5-hydroxymethylisoxazole;
3-(4-cyanophenyl)-4-[3,6-difluoro-4-(methylsulfonyl)phenyl]-5-hydroxymethylisoxazole;
3-(3-trifluoromethylphenyl)-4-[3,6-difluoro-4-(methylsulfonyl)phenyl]-5-hydroxymethylisoxazole;
3-(4-trifluoromethylphenyl)-4-[3,6-difluoro-4-(methylsulfonyl)phenyl]-5-hydroxymethylisoxazole;
3-(3-trifluoromethoxyphenyl)-4-[3,6-difluoro-4-(methylsulfonyl)phenyl]-5-hydroxymethylisoxazole;
3-(4-trifluoromethoxyphenyl)-4-[3,6-difluoro-4-(methylsulfonyl)phenyl]-5-hydroxymethylisoxazole;
3-(3,4-dichlorophenyl)-4-[3,6-difluoro-4-(methylsulfonyl)phenyl]-5-hydroxymethylisoxazole;
3-(3,4-dibromophenyl)-4-[3,6-difluoro-4-(methylsulfonyl)phenyl]-5-hydroxymethylisoxazole;
3-(3,4-difluorophenyl)-4-[3,6-difluoro-4-(methylsulfonyl)phenyl]-5-hydroxymethylisoxazole;
3-(3,5-dichlorophenyl)-4-[3,6-difluoro-4-(methylsulfonyl)phenyl]-5-hydroxymethylisoxazole;
3-(3,5-dibromophenyl)-4-[3,6-difluoro-4-(methylsulfonyl)phenyl]-5-hydroxymethylisoxazole;
3-(3,5-difluorophenyl)-4-[3,6-difluoro-4-(methylsulfonyl)phenyl]-5-hydroxymethylisoxazole;
3-(3,4-dimethylphenyl)-4-[3,6-difluoro-4-(methylsulfonyl)phenyl]-5-hydroxymethylisoxazole;
3-(3,5-dimethylphenyl)-4-[3,6-difluoro-4-(methylsulfonyl)phenyl]-5-hydroxymethylisoxazole;
3-(3-methyl-4-chlorophenyl)-4-[3,6-difluoro-4-(methylsulfonyl)phenyl]-5-hydroxymethylisoxazole;
3-(4-methyl-3-chlorophenyl)-4-[3,6-difluoro-4-(methylsulfonyl)phenyl]-5-hydroxymethylisoxazole;
3-(3-methyl-4-fluorophenyl)-4-[3,6-difluoro-4-(methylsulfonyl)phenyl]-5-hydroxymethylisoxazole;
3-(4-methyl-3-fluorophenyl)-4-[3,6-difluoro-4-(methylsulfonyl)phenyl]-5-hydroxymethylisoxazole;
3-(3-methyl-4-bromophenyl)-4-[3,6-difluoro-4-(methylsulfonyl)phenyl]-5-hydroxymethylisoxazole;
3-(4-methyl-3-bromophenyl)-4-[3,6-difluoro-4-(methylsulfonyl)phenyl]-5-hydroxymethylisoxazole;
3-(3-methyl-4-trifluoromethylphenyl)-4-[3,6-difluoro-4-(methylsulfonyl)phenyl]-5-hydroxymethylisoxazole;
3-(4-methyl-3-trifluoromethylphenyl)-4-[3,6-difluoro-4-(methylsulfonyl)phenyl]-5-hydroxymethylisoxazole;
3-(3-methyl-4-trifluoromethoxyphenyl)-4-[3,6-difluoro-4-(methylsulfonyl)phenyl]-5-hydroxymethylisoxazole;
3-(4-methyl-3-trifluoromethoxyphenyl)-4-[3,6-difluoro-4-(methylsulfonyl)phenyl]-5-hydroxymethylisoxazole;
3-(3-cyano-4-methylphenyl)-4-[3,6-difluoro-4-(methylsulfonyl)phenyl]-5-hydroxymethylisoxazole;
3-(4-cyano-3-methylphenyl)-4-[3,6-difluoro-4-(methylsulfonyl)phenyl]-5-hydroxymethylisoxazole;
3-(3-chloro-4-methoxyphenyl)-4-[3,6-difluoro-4-(methylsulfonyl)phenyl]-5-hydroxymethylisoxazole;
3-(4-chloro-3-methoxyphenyl)-4-[3,6-difluoro-4-(methylsulfonyl)phenyl]-5-hydroxymethylisoxazole;
3-(2-methylpyridin-6-yl)-4-[3,6-difluoro-4-(methylsulfonyl)phenyl]-5-hydroxymethylisoxazole;
3-(2-methylthiazol-4-yl)-4-[3,6-difluoro-4-(methylsulfonyl)phenyl]-5-hydroxymethylisoxazole;
3-(4-methylthiazol-2-yl)-4-[3,6-difluoro-4-(methylsulfonyl)phenyl]-5-hydroxymethylisoxazole;
3-(2-methylpyridin-3-yl)-4-[3,6-difluoro-4-(methylsulfonyl)phenyl]-5-hydroxymethylisoxazole;
3-(2-methylpyridin-3-yl)-4-[3,6-difluoro-4-(methylsulfonyl)phenyl]-5-hydroxymethylisoxazole;
3-(3-pyridinyl)-4-[3,6-difluoro-4-(methylsulfonyl)phenyl]-5-hydroxymethylisoxazole;
3-(5-methylpyridin-3-yl)-4-[3,6-difluoro-4-(methylsulfonyl)phenyl]-5-hydroxymethylisoxazole;
3-(2-methylpyridin-3-yl)-4-[3,6-difluoro-4-(methylsulfonyl)phenyl]-5-hydroxymethylisoxazole;
3-cyclohexyl-4-[3,6-difluoro-4-(methylsulfonyl)phenyl]-5-hydroxymethylisoxazole;

3-cyclopentyl-4-[3,6-difluoro-4-(methylsulfonyl)phenyl]-5-hydroxymethylisoxazole;

3-phenyl-4-[3,6-difluoro-4-(methylsulfonyl)phenyl]-5-fluoromethylisoxazole;

3-(3-chlorophenyl)-4-[3,6-difluoro-4-(methylsulfonyl)phenyl]-5-fluoromethylisoxazole;

3-(4-chlorophenyl)-4-[3,6-difluoro-4-(methylsulfonyl)phenyl]-5-fluoromethylisoxazole;

3-(3-bromophenyl)-4-[3,6-difluoro-4-(methylsulfonyl)phenyl]-5-fluoromethylisoxazole;

3-(4-bromophenyl)-4-[3,6-difluoro-4-(methylsulfonyl)phenyl]-5-fluoromethylisoxazole;

3-(3-fluorophenyl)-4-[3,6-difluoro-4-(methylsulfonyl)phenyl]-5-fluoromethylisoxazole;

3-(4-fluorophenyl)-4-[3,6-difluoro-4-(methylsulfonyl)phenyl]-5-fluoromethylisoxazole;

3-(3-methylphenyl)-4-[3,6-difluoro-4-(methylsulfonyl)phenyl]-5-fluoromethylisoxazole;

3-(4-methylphenyl)-4-[3,6-difluoro-4-(methylsulfonyl)phenyl]-5-fluoromethylisoxazole;

3-(3-cyanophenyl)-4-[3,6-difluoro-4-(methylsulfonyl)phenyl]-5-fluoromethylisoxazole;

3-(4-cyanophenyl)-4-[3,6-difluoro-4-(methylsulfonyl)phenyl]-5-fluoromethylisoxazole;

3-(3-trifluoromethylphenyl)-4-[3,6-difluoro-4-(methylsulfonyl)phenyl]-5-fluoromethylisoxazole;

3-(4-trifluoromethylphenyl)-4-[3,6-difluoro-4-(methylsulfonyl)phenyl]-5-fluoromethylisoxazole;

3-(3-trifluoromethoxyphenyl)-4-[3,6-difluoro-4-(methylsulfonyl)phenyl]-5-fluoromethylisoxazole;

3-(4-trifluoromethoxyphenyl)-4-[3,6-difluoro-4-(methylsulfonyl)phenyl]-5-fluoromethylisoxazole;

3-(3,4-dichlorophenyl)-4-[3,6-difluoro-4-(methylsulfonyl)phenyl]-5-fluoromethylisoxazole;

3-(3,4-dibromophenyl)-4-[3,6-difluoro-4-(methylsulfonyl)phenyl]-5-fluoromethylisoxazole;

3-(3,4-difluorophenyl)-4-[3,6-difluoro-4-(methylsulfonyl)phenyl]-5-fluoromethylisoxazole;

3-(3,5-dichlorophenyl)-4-[3,6-difluoro-4-(methylsulfonyl)phenyl]-5-fluoromethylisoxazole;

3-(3,5-dibromophenyl)-4-[3,6-difluoro-4-(methylsulfonyl)phenyl]-5-fluoromethylisoxazole;

3-(3,6-difluorophenyl)-4-[3,6-difluoro-4-(methylsulfonyl)phenyl]-5-fluoromethylisoxazole;

3-(3,4-dimethylphenyl)-4-[3,6-difluoro-4-(methylsulfonyl)phenyl]-5-fluoromethylisoxazole;

3-(3,5-dimethylphenyl)-4-[3,6-difluoro-4-(methylsulfonyl)phenyl]-5-fluoromethylisoxazole;

3-(3-methyl-4-chlorophenyl)-4-[3,6-difluoro-4-(methylsulfonyl)phenyl]-5-fluoromethylisoxazole;

3-(4-methyl-3-chlorophenyl)-4-[3,6-difluoro-4-(methylsulfonyl)phenyl]-5-fluoromethylisoxazole;

3-(3-methyl-4-fluorophenyl)-4-[3,6-difluoro-4-(methylsulfonyl)phenyl]-5-fluoromethylisoxazole;

3-(4-methyl-3-fluorophenyl)-4-[3,6-difluoro-4-(methylsulfonyl)phenyl]-5-fluoromethylisoxazole;

3-(3-methyl-4-bromophenyl)-4-[3,6-difluoro-4-(methylsulfonyl)phenyl]-5-fluoromethylisoxazole;

3-(4-methyl-3-bromophenyl)-4-[3,6-difluoro-4-(methylsulfonyl)phenyl]-5-fluoromethylisoxazole;

3-(3-methyl-4-trifluoromethylphenyl)-4-[3,6-difluoro-4-(methylsulfonyl)phenyl]-5-fluoromethylisoxazole;

3-(4-methyl-3-trifluoromethylphenyl)-4-[3,6-difluoro-4-(methylsulfonyl)phenyl]-5-fluoromethylisoxazole;

3-(3-methyl-4-trifluoromethoxyphenyl)-4-[3,6-difluoro-4-(methylsulfonyl)phenyl]-5-fluoromethylisoxazole;

3-(4-methyl-3-trifluoromethoxyphenyl)-4-[3,6-difluoro-4-(methylsulfonyl)phenyl]-5-fluoromethylisoxazole;

3-(3-cyano-4-methylphenyl)-4-[3,6-difluoro-4-(methylsulfonyl)phenyl]-5-fluoromethylisoxazole;

3-(4-cyano-3-methylphenyl)-4-[3,6-difluoro-4-(methylsulfonyl)phenyl]-5-fluoromethylisoxazole;

3-(3-chloro-4-methoxyphenyl)-4-[3,6-difluoro-4-(methylsulfonyl)phenyl]-5-fluoromethylisoxazole;

3-(4-chloro-3-methoxyphenyl)-4-[3,6-difluoro-4-(methylsulfonyl)phenyl]-5-fluoromethylisoxazole;

3-(2-methylpyridin-6-yl)-4-[3,6-difluoro-4-(methylsulfonyl)phenyl]-5-fluoromethylisoxazole;

3-(2-methylthiazol-4-yl)-4-[3,6-difluoro-4-(methylsulfonyl)phenyl]-5-fluoromethylisoxazole;

3-(4-methylthiazol-2-yl)-4-[3,6-difluoro-4-(methylsulfonyl)phenyl]-5-fluoromethylisoxazole;

3-(2-methylpyridin-3-yl)-4-[3,6-difluoro-4-(methylsulfonyl)phenyl]-5-fluoromethylisoxazole;

3-(2-methylpyridin-3-yl)-4-[3,6-difluoro-4-(methylsulfonyl)phenyl]-5-fluoromethylisoxazole;

3-(3-pyridinyl)-4-[3,6-difluoro-4-(methylsulfonyl)phenyl]-5-fluoromethylisoxazole;

3-(5-methylpyridin-3-yl)-4-[3,6-difluoro-4-(methylsulfonyl)phenyl]-5-fluoromethylisoxazole;

3-(2-methylpyridin-3-yl)-4-[3,6-difluoro-4-(methylsulfonyl)phenyl]-5-fluoromethylisoxazole;

3-cyclohexyl-4-[3,6-difluoro-4-(methylsulfonyl)phenyl]-5-fluoromethylisoxazole;

3-cyclopentyl-4-[3,6-difluoro-4-(methylsulfonyl)phenyl]-5-fluoromethylisoxazole;

3-phenyl-4-[3,5-difluoro-4-(methylsulfonyl)phenyl]-5-difluoromethylisoxazole;

3-(3-chloro-5-methylphenyl)-4-[3,5-difluoro-4-(methylsulfonyl)phenyl]-5-difluoromethylisoxazole;

3-(3-fluoro-5-methylphenyl)-4-[3,5-difluoro-4-(methylsulfonyl)phenyl]-5-difluoromethylisoxazole;

3-(3-chlorophenyl)-4-[3,5-difluoro-4-(methylsulfonyl)phenyl]-5-difluoromethylisoxazole;

3-(4-chlorophenyl)-4-[3,5-difluoro-4-(methylsulfonyl)phenyl]-5-difluoromethylisoxazole;

3-(3-bromophenyl)-4-[3,5-difluoro-4-(methylsulfonyl)phenyl]-5-difluoromethylisoxazole;

3-(4-bromophenyl)-4-[3,5-difluoro-4-(methylsulfonyl)phenyl]-5-difluoromethylisoxazole;

3-(3,5-difluorophenyl)-4-[3,5-difluoro-4-(methylsulfonyl)phenyl]-5-difluoromethylisoxazole;

3-(4-fluorophenyl)-4-[3,5-difluoro-4-(methylsulfonyl)phenyl]-5-difluoromethylisoxazole;

3-(4-methylphenyl)-4-[3,5-difluoro-4-(methylsulfonyl)phenyl]-5-difluoromethylisoxazole;

3-(3-methylphenyl)-4-[3,5-difluoro-4-(methylsulfonyl)phenyl]-5-difluoromethylisoxazole;

3-(3-bromo-5-methylphenyl)-4-[3,5-difluoro-4-(methylsulfonyl)phenyl]-5-difluoromethylisoxazole;

3-(3,4-dichlorophenyl)-4-[3,5-difluoro-4-(methylsulfonyl)phenyl]-5-difluoromethylisoxazole;

3-(3,4-dibromophenyl)-4-[3,5-difluoro-4-(methylsulfonyl)phenyl]-5-difluoromethylisoxazole;

3-(3,4-difluorophenyl)-4-[3,5-difluoro-4-(methylsulfonyl)phenyl]-5-difluoromethylisoxazole;

3-(3,5-dichlorophenyl)-4-[3,5-difluoro-4-(methylsulfonyl)phenyl]-5-difluoromethylisoxazole;

3-(3,5-dibromophenyl)-4-[3,5-difluoro-4-(methylsulfonyl)phenyl]-5-difluoromethylisoxazole;

3-(3,5-difluorophenyl)-4-[3,5-difluoro-4-(methylsulfonyl)phenyl]-5-difluoromethylisoxazole;

3-(3-chloro-4-fluorophenyl)-4-[3,5-difluoro-4-(methylsulfonyl)phenyl]-5-difluoromethylisoxazole;

3-(3-chloro-4-methylphenyl)-4-[3,5-difluoro-4-(methylsulfonyl)phenyl]-5-difluoromethylisoxazole;

3-(3-bromo-4-methylphenyl)-4-[3,5-difluoro-4-(methylsulfonyl)phenyl]-5-difluoromethylisoxazole;

3-(3,5-difluoro-4-methylphenyl)-4-[3,5-difluoro-4-(methylsulfonyl)phenyl]-5-difluoromethylisoxazole;

3-(3,4-dimethylphenyl)-4-[3,5-difluoro-4-(methylsulfonyl)phenyl]-5-difluoromethylisoxazole;

3-(4-trifluoromethoxyphenyl)-4-[3,5-difluoro-4-(methylsulfonyl)phenyl]-5-difluoromethylisoxazole;

3-(3-methyl-4-trifluoromethoxyphenyl)-4-[3,5-difluoro-4-(methylsulfonyl)phenyl]-5-difluoromethylisoxazole;

3-(4-methyl-3-trifluoromethoxyphenyl)-4-[3,5-difluoro-4-(methylsulfonyl)phenyl]-5-difluoromethylisoxazole;

3-(3-methyl-4-trifluoromethoxyphenyl)-4-[3,5-difluoro-4-(methylsulfonyl)phenyl]-5-difluoromethylisoxazole;

3-(4-methyl-3-trifluoromethoxyphenyl)-4-[3,5-difluoro-4-(methylsulfonyl)phenyl]-5-difluoromethylisoxazole;

3-(3-cyano-4-methylphenyl)-4-[3,5-difluoro-4-(methylsulfonyl)phenyl]-5-difluoromethylisoxazole;

3-(4-cyano-3-methylphenyl)-4-[3,5-difluoro-4-(methylsulfonyl)phenyl]-5-difluoromethylisoxazole;

3-(3-cyanophenyl)-4-[3,5-difluoro-4-(methylsulfonyl)phenyl]-5-difluoromethylisoxazole;

3-(4-cyanophenyl)-4-[3,5-difluoro-4-(methylsulfonyl)phenyl]-5-difluoromethylisoxazole;

3-(3-chloro-4-methoxyphenyl)-4-[3,5-difluoro-4-(methylsulfonyl)phenyl]-5-difluoromethylisoxazole;

3-(4-chloro-3-methoxyphenyl)-4-[3,5-difluoro-4-(methylsulfonyl)phenyl]-5-difluoromethylisoxazole;

3-(2-methylpyridin-6-yl)-4-[3,5-difluoro-4-(methylsulfonyl)phenyl]-5-difluoromethylisoxazole;

3-(2-methylthiazol-4-yl)-4-[3,5-difluoro-4-(methylsulfonyl)phenyl]-5-difluoromethylisoxazole;

3-(4-methylthiazol-2-yl)-4-[3,5-difluoro-4-(methylsulfonyl)phenyl]-5-difluoromethylisoxazole;

3-(2-methylpyridin-3-yl)-4-[3,5-difluoro-4-(methylsulfonyl)phenyl]-5-difluoromethylisoxazole;

3-(2-methylpyridin-3-yl)-4-[3,5-difluoro-4-(methylsulfonyl)phenyl]-5-difluoromethylisoxazole;

3-(3-pyridinyl)-4-[3,5-difluoro-4-(methylsulfonyl)phenyl]-5-difluoromethylisoxazole;

3-(5-methylpyridin-3-yl)-4-[3,5-difluoro-4-(methylsulfonyl)phenyl]-5-difluoromethylisoxazole;

3-(2-methylpyridin-3-yl)-4-[3,5-difluoro-4-(methylsulfonyl)phenyl]-5-difluoromethylisoxazole;

3-cyclohexyl-4-[3,5-difluoro-4-(methylsulfonyl)phenyl]-5-difluoromethylisoxazole;

3-cyclopentyl-4-[3,5-difluoro-4-(methylsulfonyl)phenyl]-5-difluoromethylisoxazole;

3-phenyl-4-[3,6-difluoro-4-(methylsulfonyl)phenyl]-5-methylisoxazole;

3-(3-chlorophenyl)-4-[3,6-difluoro-4-(methylsulfonyl)phenyl]-5-methylisoxazole;

3-(4-chlorophenyl)-4-[3,6-difluoro-4-(methylsulfonyl)phenyl]-5-methylisoxazole;

3-(3-bromophenyl)-4-[3,6-difluoro-4-(methylsulfonyl)phenyl]-5-methylisoxazole;

3-(4-bromophenyl)-4-[3,6-difluoro-4-(methylsulfonyl)phenyl]-5-methylisoxazole;

3-(3-fluorophenyl)-4-[3,6-difluoro-4-(methylsulfonyl)phenyl]-5-methylisoxazole;

3-(4-fluorophenyl)-4-[3,6-difluoro-4-(methylsulfonyl)phenyl]-5-methylisoxazole;

3-(3-methylphenyl)-4-[3,6-difluoro-4-(methylsulfonyl)phenyl]-5-methylisoxazole;

3-(4-methylphenyl)-4-[3,6-difluoro-4-(methylsulfonyl)phenyl]-5-methylisoxazole;

3-(3-cyanophenyl)-4-[3,6-difluoro-4-(methylsulfonyl)phenyl]-5-methylisoxazole;

3-(4-cyanophenyl)-4-[3,6-difluoro-4-(methylsulfonyl)phenyl]-5-methylisoxazole;

3-(3-trifluoromethylphenyl)-4-[3,6-difluoro-4-(methylsulfonyl)phenyl]-5-methylisoxazole;

3-(4-trifluoromethylphenyl)-4-[3,6-difluoro-4-(methylsulfonyl)phenyl]-5-methylisoxazole;

3-(3-trifluoromethoxyphenyl)-4-[3,6-difluoro-4-(methylsulfonyl)phenyl]-5-methylisoxazole;

3-(4-trifluoromethoxyphenyl)-4-[3,6-difluoro-4-(methylsulfonyl)phenyl]-5-methylisoxazole;

3-(3,4-dichlorophenyl)-4-[3,6-difluoro-4-(methylsulfonyl)phenyl]-5-methylisoxazole;

3-(3,4-dibromophenyl)-4-[3,6-difluoro-4-(methylsulfonyl)phenyl]-5-methylisoxazole;

3-(3,4-difluorophenyl)-4-[3,6-difluoro-4-(methylsulfonyl)phenyl]-5-methylisoxazole;

3-(3,5-dichlorophenyl)-4-[3,6-difluoro-4-(methylsulfonyl)phenyl]-5-methylisoxazole;

3-(3,5-dibromophenyl)-4-[3,6-difluoro-4-(methylsulfonyl)phenyl]-5-methylisoxazole;

3-(3,6-difluorophenyl)-4-[3,6-difluoro-4-(methylsulfonyl)phenyl]-5-methylisoxazole;

3-(3,4-dimethylphenyl)-4-[3,6-difluoro-4-(methylsulfonyl)phenyl]-5-methylisoxazole;

3-(3,5-dimethylphenyl)-4-[3,6-difluoro-4-(methylsulfonyl)phenyl]-5-methylisoxazole;

3-(3-methyl-4-chlorophenyl)-4-[3,6-difluoro-4-(methylsulfonyl)phenyl]-5-methylisoxazole;

3-(4-methyl-3-chlorophenyl)-4-[3,6-difluoro-4-(methylsulfonyl)phenyl]-5-methylisoxazole;

3-(3-methyl-4-fluorophenyl)-4-[3,6-difluoro-4-(methylsulfonyl)phenyl]-5-methylisoxazole;

3-(4-methyl-3-fluorophenyl)-4-[3,6-difluoro-4-(methylsulfonyl)phenyl]-5-methylisoxazole;

3-(3-methyl-4-bromophenyl)-4-[3,6-difluoro-4-(methylsulfonyl)phenyl]-5-methylisoxazole;

3-(4-methyl-3-bromophenyl)-4-[3,6-difluoro-4-(methylsulfonyl)phenyl]-5-methylisoxazole;

3-(3-methyl-4-trifluoromethylphenyl)-4-[3,6-difluoro-4-(methylsulfonyl)phenyl]-5-methylisoxazole;

3-(4-methyl-3-trifluoromethylphenyl)-4-[3,6-difluoro-4-(methylsulfonyl)phenyl]-5-methylisoxazole;

3-(3-methyl-4-trifluoromethoxyphenyl)-4-[3,6-difluoro-4-(methylsulfonyl)phenyl]-5-methylisoxazole;

3-(4-methyl-3-trifluoromethoxyphenyl)-4-[3,6-difluoro-4-(methylsulfonyl)phenyl]-5-methylisoxazole;

3-(3-cyano-4-methylphenyl)-4-[3,6-difluoro-4-(methylsulfonyl)phenyl]-5-methylisoxazole;

3-(4-cyano-3-methylphenyl)-4-[3,6-difluoro-4-(methylsulfonyl)phenyl]-5-methylisoxazole;

3-(3-chloro-4-methoxyphenyl)-4-[3,6-difluoro-4-(methylsulfonyl)phenyl]-5-methylisoxazole;

3-(4-chloro-3-methoxyphenyl)-4-[3,6-difluoro-4-(methylsulfonyl)phenyl]-5-methylisoxazole;

3-(2-methylpyridin-6-yl)-4-[3,6-difluoro-4-(methylsulfonyl)phenyl]-5-methylisoxazole;

3-(2-methylthiazol-4-yl)-4-[3,6-difluoro-4-(methylsulfonyl)phenyl]-5-methylisoxazole;

3-(4-methylthiazol-2-yl)-4-[3,6-difluoro-4-(methylsulfonyl)phenyl]-5-methylisoxazole;

3-(2-methylpyridin-3-yl)-4-[3,6-difluoro-4-(methylsulfonyl)phenyl]-5-methylisoxazole;

3-(2-methylpyridin-3-yl)-4-[3,6-difluoro-4-(methylsulfonyl)phenyl]-5-methylisoxazole;

3-(3-pyridinyl)-4-[3,6-difluoro-4-(methylsulfonyl)phenyl]-5-methylisoxazole;

3-(5-methylpyridin-3-yl)-4-[3,6-difluoro-4-(methylsulfonyl)phenyl]-5-methylisoxazole;

3-(2-methylpyridin-3-yl)-4-[3,6-difluoro-4-(methylsulfonyl)phenyl]-5-methylisoxazole;

3-cyclohexyl-4-[3,6-difluoro-4-(methylsulfonyl)phenyl]-5-methylisoxazole;

3-cyclopentyl-4-[3,6-difluoro-4-(methylsulfonyl)phenyl]-5-methylisoxazole;

2,5-difluoro-4-[3-phenyl-5-hydroxymethylisoxazol-4-yl]benezenesulfonamide;

2,5-difluoro-4-[3-(3-chlorophenyl)-5-hydroxymethylisoxazol-4-yl]benezenesulfonamide;

2,5-difluoro-4-[3-(4-chlorophenyl)-5-hydroxymethylisoxazol-4-yl]benezenesulfonamide;

2,5-difluoro-4-[3-(3-bromophenyl)-5-hydroxymethylisoxazol-4-yl]benezenesulfonamide;

2,5-difluoro-4-[3-(4-bromophenyl)-5-hydroxymethylisoxazol-4-yl]benezenesulfonamide;

2,5-difluoro-4-[3-(3-fluorophenyl)-5-hydroxymethylisoxazol-4-yl]benezenesulfonamide;

2,5-difluoro-4-[3-(4-fluorophenyl)-5-hydroxymethylisoxazol-4-yl]benezenesulfonamide;

2,5-difluoro-4-[3-(3-methylphenyl)-5-hydroxymethylisoxazol-4-yl]benezenesulfonamide;

2,5-difluoro-4-[3-(4-methylphenyl)-5-hydroxymethylisoxazol-4-yl]benezenesulfonamide;

2,5-difluoro-4-[3-(3-cyanophenyl)-5-hydroxymethylisoxazol-4-yl]benezenesulfonamide;

2,5-difluoro-4-[3-(4-cyanophenyl)-5-hydroxymethylisoxazol-4-yl]benezenesulfonamide;

2,5-difluoro-4-[3-(3-trifluoromethylphenyl)-5-hydroxymethylisoxazol-4-yl]benezenesulfonamide;

2,5-difluoro-4-[3-(4-trifluoromethylphenyl)-5-hydroxymethylisoxazol-4-yl]benezenesulfonamide;

2,5-difluoro-4-[3-(3-trifluoromethoxyphenyl)-5-hydroxymethylisoxazol-4-yl]benezenesulfonamide;

2,5-difluoro-4-[3-(4-trifluoromethoxyphenyl)-5-hydroxymethylisoxazol-4-yl]benezenesulfonamide;

2,5-difluoro-4-[3-(3,4-dichlorophenyl)-5-hydroxymethylisoxazol-4-yl]benezenesulfonamide;

2,5-difluoro-4-[3-(3,4-dibromophenyl)-5-hydroxymethylisoxazol-4-yl]benezenesulfonamide;

2,5-difluoro-4-[3-(3,4-difluorophenyl)-5-hydroxymethylisoxazol-4-yl]benezenesulfonamide;

2,5-difluoro-4-[3-(3,5-dichlorophenyl)-5-hydroxymethylisoxazol-4-yl]benezenesulfonamide;

2,5-difluoro-4-[3-(3,5-dibromophenyl)-5-hydroxymethylisoxazol-4-yl]benezenesulfonamide;

2,5-difluoro-4-[3-(3,5-difluorophenyl)-5-hydroxymethylisoxazol-4-yl]benezenesulfonamide;

2,5-difluoro-4-[3-(3,4-dimethylphenyl)-5-hydroxymethylisoxazol-4-yl]benezenesulfonamide;

2,5-difluoro-4-[3-(3,5-dimethylphenyl)-5-hydroxymethylisoxazol-4-yl]benezenesulfonamide;

2,5-difluoro-4-[3-(3-methyl-4-chlorophenyl)-5-hydroxymethylisoxazol-4-yl]benezenesulfonamide;

2,5-difluoro-4-[3-(4-methyl-3-chlorophenyl)-5-hydroxymethylisoxazol-4-yl]benezenesulfonamide;

2,5-difluoro-4-[3-(3-methyl-4-fluorophenyl)-5-hydroxymethylisoxazol-4-yl]benezenesulfonamide;

2,5-difluoro-4-[3-(4-methyl-3-fluorophenyl)-5-hydroxymethylisoxazol-4-yl]benezenesulfonamide;

2,5-difluoro-4-[3-(3-methyl-4-bromophenyl)-5-hydroxymethylisoxazol-4-yl]benezenesulfonamide;

2,5-difluoro-4-[3-(4-methyl-3-bromophenyl)-5-hydroxymethylisoxazol-4-yl]benezenesulfonamide;

2,5-difluoro-4-[3-(3-methyl-4-trifluoromethylphenyl)-5-hydroxymethylisoxazol-4-yl]benezenesulfonamide;

2,5-difluoro-4-[3-(4-methyl-3-trifluoromethylphenyl)-5-hydroxymethylisoxazol-4-yl]benezenesulfonamide;

2,5-difluoro-4-[3-(3-methyl-4-trifluoromethoxyphenyl)-5-hydroxymethylisoxazol-4-yl]benezenesulfonamide;

2,5-difluoro-4-[3-(4-methyl-3-trifluoromethoxyphenyl)-5-hydroxymethylisoxazol-4-yl]benezenesulfonamide;

2,5-difluoro-4-[3-(3-cyano-4-methylphenyl)-5-hydroxymethylisoxazol-4-yl]benezenesulfonamide;

2,5-difluoro-4-[3-(4-cyano-3-methylphenyl)-5-hydroxymethylisoxazol-4-yl]benezenesulfonamide;

2,5-difluoro-4-[3-(3-chloro-4-methoxyphenyl)-5-hydroxymethylisoxazol-4-yl]benezenesulfonamide;

2,5-difluoro-4-[3-(4-chloro-3-methoxyphenyl)-5-hydroxymethylisoxazol-4-yl]benezenesulfonamide;

2,5-difluoro-4-[3-(2-methylpyridin-6-yl)-5-hydroxymethylisoxazol-4-yl]benezenesulfonamide;

2,5-difluoro-4-[3-(2-methylthiazol-4-yl)-5-hydroxymethylisoxazol-4-yl]benezenesulfonamide;

2,5-difluoro-4-[3-(4-methylthiazol-2-yl)-5-hydroxymethylisoxazol-4-yl]benezenesulfonamide;

2,5-difluoro-4-[3-(2-methylpyridin-3-yl)-5-hydroxymethylisoxazol-4-yl]benezenesulfonamide;

2,5-difluoro-4-[3-(2-methylpyridin-3-yl)-5-hydroxymethylisoxazol-4-yl]benezenesulfonamide;

2,5-difluoro-4-[3-(3-pyridinyl)-5-hydroxymethylisoxazol-4-yl]benezenesulfonamide;

2,5-difluoro-4-[3-(5-methylpyridin-3-yl)-5-hydroxymethylisoxazol-4-yl]benezenesulfonamide;

2,5-difluoro-4-[3-(2-methylpyridin-3-yl)-5-hydroxymethylisoxazol-4-yl]benezenesulfonamide;

2,5-difluoro-4-[3-phenyl-5-methylisoxazol-4-yl]benezenesulfonamide;

2,5-difluoro-4-[3-(3-chlorophenyl)-5-methylisoxazol-4-yl]benezenesulfonamide;

2,5-difluoro-4-[3-(4-chlorophenyl)-5-methylisoxazol-4-yl]benezenesulfonamide;
2,5-difluoro-4-[3-(3-bromophenyl)-5-methylisoxazol-4-yl]benezenesulfonamide;
2,5-difluoro-4-[3-(4-bromophenyl)-5-methylisoxazol-4-yl]benezenesulfonamide;
2,5-difluoro-4-[3-(3-fluorophenyl)-5-methylisoxazol-4-yl]benezenesulfonamide;
2,5-difluoro-4-[3-(4-fluorophenyl)-5-methylisoxazol-4-yl]benezenesulfonamide;
2,5-difluoro-4-[3-(3-methylphenyl)-5-methylisoxazol-4-yl]benezenesulfonamide;
2,5-difluoro-4-[3-(4-methylphenyl)-5-methylisoxazol-4-yl]benezenesulfonamide;
2,5-difluoro-4-[3-(3-cyanophenyl)-5-methylisoxazol-4-yl]benezenesulfonamide;
2,5-difluoro-4-[3-(4-cyanophenyl)-5-methylisoxazol-4-yl]benezenesulfonamide;
2,5-difluoro-4-[3-(3-trifluoromethylphenyl)-5-methylisoxazol-4-yl]benezenesulfonamide;
2,5-difluoro-4-[3-(4-trifluoromethylphenyl)-5-methylisoxazol-4-yl]benezenesulfonamide;
2,5-difluoro-4-[3-(3-trifluoromethoxyphenyl)-5-methylisoxazol-4-yl]benezenesulfonamide;
2,5-difluoro-4-[3-(4-trifluoromethoxyphenyl)-5-methylisoxazol-4-yl]benezenesulfonamide;
2,5-difluoro-4-[3-(3,4-dichlorophenyl)-5-methylisoxazol-4-yl]benezenesulfonamide;
2,5-difluoro-4-[3-(3,4-dibromophenyl)-5-methylisoxazol-4-yl]benezenesulfonamide;
2,5-difluoro-4-[3-(3,4-difluorophenyl)-5-methylisoxazol-4-yl]benezenesulfonamide;
2,5-difluoro-4-[3-(3,5-dichlorophenyl)-5-methylisoxazol-4-yl]benezenesulfonamide;
2,5-difluoro-4-[3-(3,5-dibromophenyl)-5-methylisoxazol-4-yl]benezenesulfonamide;
2,5-difluoro-4-[3-(3,5-difluorophenyl)-5-methylisoxazol-4-yl]benezenesulfonamide;
2,5-difluoro-4-[3-(3,4-dimethylphenyl)-5-methylisoxazol-4-yl]benezenesulfonamide;
2,5-difluoro-4-[3-(3,5-dimethylphenyl)-5-methylisoxazol-4-yl]benezenesulfonamide;
2,5-difluoro-4-[3-(3-methyl-4-chlorophenyl)-5-methylisoxazol-4-yl]benezenesulfonamide;
2,5-difluoro-4-[3-(4-methyl-3-chlorophenyl)-5-methylisoxazol-4-yl]benezenesulfonamide;
2,5-difluoro-4-[3-(3-methyl-4-fluorophenyl)-5-methylisoxazol-4-yl]benezenesulfonamide;
2,5-difluoro-4-[3-(4-methyl-3-fluorophenyl)-5-methylisoxazol-4-yl]benezenesulfonamide;
2,5-difluoro-4-[3-(3-methyl-4-bromophenyl)-5-methylisoxazol-4-yl]benezenesulfonamide;
2,5-difluoro-4-[3-(4-methyl-3-bromophenyl)-5-methylisoxazol-4-yl]benezenesulfonamide;
2,5-difluoro-4-[3-(3-methyl-4-trifluoromethylphenyl)-5-methylisoxazol-4-yl]benezenesulfonamide;
2,5-difluoro-4-[3-(4-methyl-3-trifluoromethylphenyl)-5-methylisoxazol-4-yl]benezenesulfonamide;
2,5-difluoro-4-[3-(3-methyl-4-trifluoromethoxyphenyl)-5-methylisoxazol-4-yl]benezenesulfonamide;
2,5-difluoro-4-[3-(4-methyl-3-trifluoromethoxyphenyl)-5-methylisoxazol-4-yl]benezenesulfonamide;
2,5-difluoro-4-[3-(3-cyano-4-methylphenyl)-5-methylisoxazol-4-yl]benezenesulfonamide;
2,5-difluoro-4-[3-(4-cyano-3-methylphenyl)-5-methylisoxazol-4-yl]benezenesulfonamide;
2,5-difluoro-4-[3-(3-chloro-4-methoxyphenyl)-5-methylisoxazol-4-yl]benezenesulfonamide;
2,5-difluoro-4-[3-(4-chloro-3-methoxyphenyl)-5-methylisoxazol-4-yl]benezenesulfonamide;
2,5-difluoro-4-[3-(2-methylpyridin-6-yl)-5-methylisoxazol-4-yl]benezenesulfonamide;
2,5-difluoro-4-[3-(2-methylthiazol-4-yl)-5-methylisoxazol-4-yl]benezenesulfonamide;
2,5-difluoro-4-[3-(4-methylthiazol-2-yl)-5-methylisoxazol-4-yl]benezenesulfonamide;
2,5-difluoro-4-[3-(2-methylpyridin-3-yl)-5-methylisoxazol-4-yl]benezenesulfonamide;
2,5-difluoro-4-[3-(2-methylpyridin-3-yl)-5-methylisoxazol-4-yl]benezenesulfonamide;
2,5-difluoro-4-[3-(3-pyridinyl)-5-methylisoxazol-4-yl]benezenesulfonamide;
2,5-difluoro-4-[3-(5-methylpyridin-3-yl)-5-methylisoxazol-4-yl]benezenesulfonamide;
2,5-difluoro-4-[3-(2-methylpyridin-3-yl)-5-methylisoxazol-4-yl]benezenesulfonamide;
2,5-difluoro-4-[3-phenyl-5-trifluoromethylisoxazol-4-yl]benezenesulfonamide;
2,5-difluoro-4-[3-(3-chlorophenyl)-5-trifluoromethylisoxazol-4-yl]benezenesulfonamide;
2,5-difluoro-4-[3-(4-chlorophenyl)-5-trifluoromethylisoxazol-4-yl]benezenesulfonamide;
2,5-difluoro-4-[3-(3-bromophenyl)-5-trifluoromethylisoxazol-4-yl]benezenesulfonamide;
2,5-difluoro-4-[3-(4-bromophenyl)-5-trifluoromethylisoxazol-4-yl]benezenesulfonamide;
2,5-difluoro-4-[3-(3-fluorophenyl)-5-trifluoromethylisoxazol-4-yl]benezenesulfonamide;
2,5-difluoro-4-[3-(4-fluorophenyl)-5-trifluoromethylisoxazol-4-yl]benezenesulfonamide;
2,5-difluoro-4-[3-(3-methylphenyl)-5-trifluoromethylisoxazol-4-yl]benezenesulfonamide;
2,5-difluoro-4-[3-(4-methylphenyl)-5-trifluoromethylisoxazol-4-yl]benezenesulfonamide;
2,5-difluoro-4-[3-(3-cyanophenyl)-5-trifluoromethylisoxazol-4-yl]benezenesulfonamide;
2,5-difluoro-4-[3-(4-cyanophenyl)-5-trifluoromethylisoxazol-4-yl]benezenesulfonamide;
2,5-difluoro-4-[3-(3-trifluoromethylphenyl)-5-trifluoromethylisoxazol-4-yl]benezenesulfonamide;
2,5-difluoro-4-[3-(4-trifluoromethylphenyl)-5-trifluoromethylisoxazol-4-yl]benezenesulfonamide;
2,5-difluoro-4-[3-(3-trifluoromethoxyphenyl)-5-trifluoromethylisoxazol-4-yl]benezenesulfonamide;
2,5-difluoro-4-[3-(4-trifluoromethoxyphenyl)-5-trifluoromethylisoxazol-4-yl]benezenesulfonamide;
2,5-difluoro-4-[3-(3,4-dichlorophenyl)-5-trifluoromethylisoxazol-4-yl]benezenesulfonamide;
2,5-difluoro-4-[3-(3,4-dibromophenyl)-5-trifluoromethylisoxazol-4-yl]benezenesulfonamide;
2,5-difluoro-4-[3-(3,4-difluorophenyl)-5-trifluoromethylisoxazol-4-yl]benezenesulfonamide;
2,5-difluoro-4-[3-(3,5-dichlorophenyl)-5-trifluoromethylisoxazol-4-yl]benezenesulfonamide;

2,5-difluoro-4-[3-(3,5-dibromophenyl)-5-trifluoromethylisoxazol-4-yl]benzenesulfonamide;
2,5-difluoro-4-[3-(3,5-difluorophenyl)-5-trifluoromethylisoxazol-4-yl]benzenesulfonamide;
2,5-difluoro-4-[3-(3,4-dimethylphenyl)-5-trifluoromethylisoxazol-4-yl]benzenesulfonamide;
2,5-difluoro-4-[3-(3,5-dimethylphenyl)-5-trifluoromethylisoxazol-4-yl]benzenesulfonamide;
2,5-difluoro-4-[3-(3-methyl-4-chlorophenyl)-5-trifluoromethylisoxazol-4-yl]benzenesulfonamide;
2,5-difluoro-4-[3-(4-methyl-3-chlorophenyl)-5-trifluoromethylisoxazol-4-yl]benzenesulfonamide;
2,5-difluoro-4-[3-(3-methyl-4-fluorophenyl)-5-trifluoromethylisoxazol-4-yl]benzenesulfonamide;
2,5-difluoro-4-[3-(4-methyl-3-fluorophenyl)-5-trifluoromethylisoxazol-4-yl]benzenesulfonamide;
2,5-difluoro-4-[3-(3-methyl-4-bromophenyl)-5-trifluoromethylisoxazol-4-yl]benzenesulfonamide;
2,5-difluoro-4-[3-(4-methyl-3-bromophenyl)-5-trifluoromethylisoxazol-4-yl]benzenesulfonamide;
2,5-difluoro-4-[3-(3-methyl-4-trifluoromethylphenyl)-5-trifluoromethylisoxazol-4-yl]benzenesulfonamide;
2,5-difluoro-4-[3-(4-methyl-3-trifluoromethylphenyl)-5-trifluoromethylisoxazol-4-yl]benzenesulfonamide;
2,5-difluoro-4-[3-(3-methyl-4-trifluoromethoxyphenyl)-5-trifluoromethylisoxazol-4-yl]benzenesulfonamide;
2,5-difluoro-4-[3-(4-methyl-3-trifluoromethoxyphenyl)-5-trifluoromethylisoxazol-4-yl]benzenesulfonamide;
2,5-difluoro-4-[3-(3-cyano-4-methylphenyl)-5-trifluoromethylisoxazol-4-yl]benzenesulfonamide;
2,5-difluoro-4-[3-(4-cyano-3-methylphenyl)-5-trifluoromethylisoxazol-4-yl]benzenesulfonamide;
2,5-difluoro-4-[3-(3-chloro-4-methoxyphenyl)-5-trifluoromethylisoxazol-4-yl]benzenesulfonamide;
2,5-difluoro-4-[3-(4-chloro-3-methoxyphenyl)-5-trifluoromethylisoxazol-4-yl]benzenesulfonamide;
2,5-difluoro-4-[3-(2-methylpyridin-6-yl)-5-trifluoromethylisoxazol-4-yl]benzenesulfonamide;
2,5-difluoro-4-[3-(2-methylthiazol-4-yl)-5-trifluoromethylisoxazol-4-yl]benzenesulfonamide;
2,5-difluoro-4-[3-(4-methylthiazol-2-yl)-5-trifluoromethylisoxazol-4-yl]benzenesulfonamide;
2,5-difluoro-4-[3-(2-methylpyridin-3-yl)-5-trifluoromethylisoxazol-4-yl]benzenesulfonamide;
2,5-difluoro-4-[3-(2-methylpyridin-3-yl)-5-trifluoromethylisoxazol-4-yl]benzenesulfonamide;
2,5-difluoro-4-[3-(3-pyridinyl)-5-trifluoromethylisoxazol-4-yl]benzenesulfonamide;
2,5-difluoro-4-[3-(5-methylpyridin-3-yl)-5-trifluoromethylisoxazol-4-yl]benzenesulfonamide;
2,5-difluoro-4-[3-(2-methylpyridin-3-yl)-5-trifluoromethylisoxazol-4-yl]benzenesulfonamide;
and the pharmaceutically-acceptable salts, tautomers and prodrugs thereof.

Furanones

In still another embodiment, the present method of treating cyclooxygenase-2 mediated disorders comprises administering to the subject a therapeutically-effective amount of one or more compounds selected from a subclass of compounds of Formula I corresponding to Formula V:

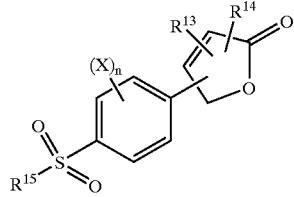

wherein substituents X, n, $R^{13}$, $R^{14}$ and $R^{15}$ have the same definitions and sub-definitions as substituents X, n, $R^1$, $R^3$ and $R^2$, respectively, set forth above for the compounds of Formula I, and the pharmaceutically-acceptable salts, tautomers and prodrugs thereof.

Within this subclass of compounds, a preferred group of compounds consists of those compounds of Formula VA and VB:

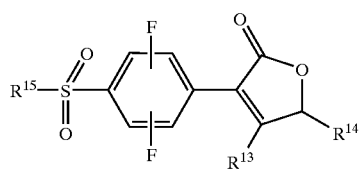

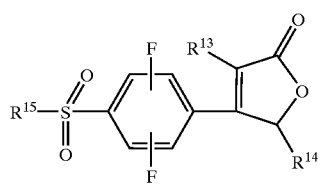

wherein $R^{13}$, $R^{14}$ and $R^{15}$ are as defined above, and the pharmaceutically-acceptable salts, tautomers and prodrugs thereof.

Within this subclass of compounds, a more preferred group of compounds consists of those compounds of Formula VC:

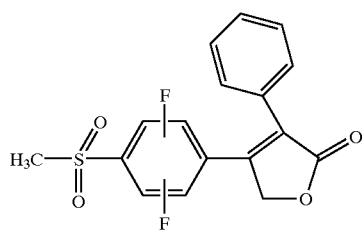

and the pharmaceutically-acceptable salts, tautomers and prodrugs thereof. Preferably, (a) one fluoro radical is present at the 2-position and the other fluoro radical is present at the 5-position, or (b) one fluoro radical is present at the 2-position and the other fluoro radical is present at the 3-position, or (c) one fluoro radical is present at the 3-position and the other fluoro radical is present at the 5-position.

Preferred species within this subclass include, but are not limited to:

2,5-difluoro-4-[4-5-oxo-2,5-dihydro-3-furanyl]benzenesulfonamide;
2,5-difluoro-4-[4-(3-chlorophenyl)-5-oxo-2,5-dihydro-3-furanyl]benzenesulfonamide;

2,5-difluoro-4-[4-(4-chlorophenyl)-5-oxo-2,5-dihydro-3-furanyl]benzenesulfonamide;
2,5-difluoro-4-[4-(3-bromophenyl)-5-oxo-2,5-dihydro-3-furanyl]benzenesulfonamide;
2,5-difluoro-4-[4-(4-bromophenyl)-5-oxo-2,5-dihydro-3-furanyl]benzenesulfonamide;
2,5-difluoro-4-[4-(3-fluorophenyl)-5-oxo-2,5-dihydro-3-furanyl]benzenesulfonamide;
2,5-difluoro-4-[4-(4-fluorophenyl)-5-oxo-2,5-dihydro-3-furanyl]benzenesulfonamide;
2,5-difluoro-4-[4--(3-methylphenyl)-5-oxo-2,5-dihydro-3-furanyl]benzenesulfonamide;
2,5-difluoro-4-[4-(4-methylphenyl)-5-oxo-2,5-dihydro-3-furanyl]benzenesulfonamide;
2,5-difluoro-4-[4-(3-cyanophenyl)-5-oxo-2,5-dihydro-3-furanyl]benzenesulfonamide;
2,5-difluoro-4-[4-(4-cyanophenyl)-5-oxo-2,5-dihydro-3-furanyl]benzenesulfonamide;
2,5-difluoro-4-[4-(3-trifluoromethoxyphenyl)-5-oxo-2,5-dihydro-3-furanyl]benzenesulfonamide;
2,5-difluoro-4-[4-(4-trifluoromethoxyphenyl)-5-oxo-2,5-dihydro-3-furanyl]benzenesulfonamide;
2,5-difluoro-4-[4-(3-trifluoromethoxyphenyl)-5-oxo-2,5-dihydro-3-furanyl]benzenesulfonamide;
2,5-difluoro-4-[4-(4-trifluoromethoxyphenyl)-5-oxo-2,5-dihydro-3-furanyl]benzenesulfonamide;
2,5-difluoro-4-[4-(3,4-dichlorophenyl)-5-oxo-2,5-dihydro-3-furanyl]benzenesulfonamide;
2,5-difluoro-4-[4-(3,4-dibromophenyl)-5-oxo-2,5-dihydro-3-furanyl]benzenesulfonamide;
2,5-difluoro-4-[4-(3,4-difluorophenyl)-5-oxo-2,5-dihydro-3-furanyl]benzenesulfonamide;
2,5-difluoro-4-[4-(3,5-dichlorophenyl)-5-oxo-2,5-dihydro-3-furanyl]benzenesulfonamide;
2,5-difluoro-4-[4-(3,5-dibromophenyl)-5-oxo-2,5-dihydro-3-furanyl]benzenesulfonamide;
2,5-difluoro-4-[4-(3,5-difluorophenyl)-5-oxo-2,5-dihydro-3-furanyl]benzenesulfonamide;
2,5-difluoro-4-[4-(3,4-dimethylphenyl)-5-oxo-2,5-dihydro-3-furanyl]benzenesulfonamide;
2,5-difluoro-4-[4-(3,5-dimethylphenyl)-5-oxo-2,5-dihydro-3-furanyl]benzenesulfonamide;
2,5-difluoro-4-[4-(3-methyl-4-chlorophenyl)-5-oxo-2,5-dihydro-3-furanyl]benzenesulfonamide;
2,5-difluoro-4-[4-(4-methyl-3-chlorophenyl)-5-oxo-2,5-dihydro-3-furanyl]benzenesulfonamide;
2,5-difluoro-4-[4-(3-methyl-4-fluorophenyl)-5-oxo-2,5-dihydro-3-furanyl]benzenesulfonamide;
2,5-difluoro-4-[4-(4-methyl-3-fluorophenyl)-5-oxo-2,5-dihydro-3-furanyl]benzenesulfonamide;
2,5-difluoro-4-[4-(3-methyl-4-bromophenyl)-5-oxo-2,5-dihydro-3-furanyl]benzenesulfonamide;
2,5-difluoro-4-[4-(4-methyl-3-bromophenyl)-5-oxo-2,5-dihydro-3-furanyl]benzenesulfonamide;
2,5-difluoro-4-[4-(3-methyl-4-trifluoromethylphenyl)-5-oxo-2,5-dihydro-3-furanyl]benzenesulfonamide;
2,5-difluoro-4-[4-(4-methyl-3-trifluoromethylphenyl)-5-oxo-2,5-dihydro-3-furanyl]benzenesulfonamide;
2,5-difluoro-4-[4-(3-methyl-4-trifluoromethoxyphenyl)-5-oxo-2,5-dihydro-3-furanyl]benzenesulfonamide;
2,5-difluoro-4-[4-(4-methyl-3-trifluoromethoxyphenyl)-5-oxo-2,5-dihydro-3-furanyl]benzenesulfonamide;
2,5-difluoro-4-[4-(3-cyano-4-methylphenyl)-5-oxo-2,5-dihydro-3-furanyl]benzenesulfonamide;
2,5-difluoro-4-[4-(4-cyano-3-methylphenyl)-5-oxo-2,5-dihydro-3-furanyl]benzenesulfonamide;
2,5-difluoro-4-[4-(3-chloro-4-methoxyphenyl)-5-oxo-2,5-dihydro-3-furanyl]benzenesulfonamide;
2,5-difluoro-4-[4-(4-chloro-3-methoxyphenyl)-5-oxo-2,5-dihydro-3-furanyl]benzenesulfonamide;
2,5-difluoro-4-[4-(2-methylpyridin-6-yl)-5-oxo-2,5-dihydro-3-furanyl]benzenesulfonamide;
2,5-difluoro-4-[4-(2-methylthiazol-4-yl)-5-oxo-2,5-dihydro-3-furanyl]benzenesulfonamide;
2,5-difluoro-4-[4-(4-methylthiazol-2-yl)-5-oxo-2,5-dihydro-3-furanyl]benzenesulfonamide;
2,5-difluoro-4-[4-(2-methylpyridin-3-yl)-5-oxo-2,5-dihydro-3-furanyl]benzenesulfonamide;
2,5-difluoro-4-[4-(2-methylpyridin-3-yl)-5-oxo-2,5-dihydro-3-furanyl]benzenesulfonamide;
2,5-difluoro-4-[4-(3-pyridinyl)-5-oxo-2,5-dihydro-3-furanyl]benzenesulfonamide;
2,5-difluoro-4-[4-(5-methylpyridin-3-yl)-5-oxo-2,5-dihydro-3-furanyl]benzenesulfonamide;
2,5-difluoro-4-[4-(2-methylpyridin-3-yl)-s-oxo-2,5-dihydro-3-furanyl]benzenesulfonamide;
2,5-difluoro-4-[4-cyclohexyl-5-oxo-2,5-dihydro-3-furanyl]benzenesulfonamide;
2,5-difluoro-4-[4-cyclopentyl-5-oxo-2,5-dihydro-3-furanyl]benzenesulfonamide;
3-phenyl-4-[3,5-difluoro-4-(methylsulfonyl)phenyl]-2(5H)-furanone;
3-(3-chlorophenyl)-4-[3,5-difluoro-4-(methylsulfonyl)phenyl]-2 (5H)-furanone;
3-(4-chlorophenyl)-4-[3,5-difluoro-4-(methylsulfonyl)phenyl]-2 (5H)-furanone;
3-(3-bromophenyl)-4-[3,5-difluoro-4-(methylsulfonyl)phenyl]-2 (5H)-furanone;
3-(4-bromophenyl)-4-[3,5-difluoro-4-(methylsulfonyl)phenyl]-2 (5H)-furanone;
3-(3-fluorophenyl)-4-[3,5-difluoro-4-(methylsulfonyl)phenyl]-2 (5H)-furanone;
3-(4-ifluorophenyl)-4-[3,5-difluoro-4-(methylsulfonyl)phenyl]-2 (5H)-furanone;
3-(3-methylphenyl)-4-[3,5-difluoro-4-(methylsulfonyl)phenyl]-2 (5H)-furanone;
3-(4-methylphenyl)-4-[3,5-difluoro-4-(methylsulfonyl)phenyl]-2 (5H)-furanone;
3-(3-cyanophenyl)-4-[3,5-difluoro-4-(methylsulfonyl)phenyl]-2 (5H)-furanone;
3-(4-cyanophenyl)-4-[3,5-difluoro-4-(methylsulfonyl)phenyl]-2 (5H)-furanone;
3-(3-triifluoromethylphenyl)-4-[3,5-difluoro-4-(methylsulfonyl) phenyl]-2 (5H)-furanone;
3-(4-trifluoromethylphenyl)-4-[3,5-difluoro-4-(methylsulfonyl) phenyl]-2 (5H)-furanone;
3-(3-trifluoromethoxyphenyl)-4-[3,5-difluoro-4-(methylsulfonyl) phenyl]-2 (5H)-furanone;
3-(4-trifluoromethoxyphenyl)-4-[3,5-difluoro-4-(methylsulfonyl) phenyl]-2 (5H)-furanone;
3-(3,4-dichlorophenyl)-4-[3,5-difluoro-4-(methylsulfonyl) phenyl]-2 (5H)-furanone;
3-(3,4-dibromophenyl)-4-[3,5-difluoro-4-(methylsulfonyl) phenyl]-2 (5H)-furanone;

3-(3,4-difluorophenyl)-4-[3,5-difluoro-4-(methylsulfonyl) phenyl]-2 (5H)-furanone;

3-(3,5-dichlorophenyl)-4-[3,5-difluoro-4-(methylsulfonyl) phenyl]-2 (5H)-furanone;

3-(3,5-dibromophenyl)-4-[3,5-difluoro-4-(methylsulfonyl) phenyl]-2 (5H)-furanone;

3-(3,5-difluorophenyl)-4-[3,5-difluoro-4-(methylsulfonyl) phenyl]-2 (5H)-furanone;

3-(3,4-dimethylphenyl)-4-[3,5-difluoro-4-(methylsulfonyl) phenyl]-2 (5H)-furanone;

3-(3,5-dimethylphenyl)-4-[3,5-difluoro-4-(methylsulfonyl) phenyl]-2 (5H)-furanone;

3-(3-methyl-4-chlorophenyl)-4-[3,5-difluoro-4-(methylsulfonyl) phenyl]-2 (5H)-furanone;

3-(4-methyl-3-chlorophenyl)-4-[3,5-difluoro-4-(methylsulfonyl) phenyl]-2 (5H)-furanone;

3-(3-methyl-4-fluorophenyl)-4-[3,5-difluoro-4-(methylsulfonyl) phenyl]-2 (5H)-furanone;

3-(4-methyl-3-fluorophenyl)-4-[3,5-difluoro-4-(methylsulfonyl) phenyl]-2 (5H)-furanone;

3-(3-methyl-4-bromophenyl)-4-[3,5-difluoro-4-(methylsulfonyl) phenyl]-2 (5H)-furanone;

3-(4-methyl-3-bromophenyl)-4-[3,5-difluoro-4-(methylsulfonyl) phenyl]-2 (5H)-furanone;

3-(3-methyl-4-trifluoromethylphenyl)-4-[3,5-difluoro-4-(methylsulfonyl) phenyl]-2 (5H)-furanone;

3-(4-methyl-3-trifluoromethylphenyl)-4-[3,5-difluoro-4-(methylsulfonyl) phenyl]-2 (5H)-furanone;

3-(3-methyl-4-trifluoromethoxyphenyl)-4-[3,5-difluoro-4-(methylsulfonyl) phenyl]-2 (5H)-furanone;

3-(4-methyl-3-trifluoromethoxyphenyl)-4-[3,5-difluoro-4-(methylsulfonyl) phenyl]-2 (5H)-furanone;

3-(3-cyano-4-methylphenyl)-4-[3,5-difluoro-4-(methylsulfonyl) phenyl]-2 (5H)-furanone;

3-(4-cyano-3-methylphenyl)-4-[3,5-difluoro-4-(methylsulfonyl) phenyl]-2 (5H)-furanone;

3-(3-chloro-4-methoxyphenyl)-4-[3,5-difluoro-4-(methylsulfonyl) phenyl]-2 (5H)-furanone;

3-(4-chloro-3-methoxyphenyl)-4-[3,5-difluoro-4-(methylsulfonyl) phenyl]-2 (5H)-furanone;

3-(2-methylpyridin-G-yl)-4-[3,5-difluoro-4-(methylsulfonyl) phenyl]-2 (5H)-furanone;

3-(2-methylthiazol-4-yl)-4-[3,5-difluoro-4-(methylsulfonyl) phenyl]-2 (5H)-furanone;

3-(4-methylthiazol-2-yl)-4-[3,5-difluoro-4-(methylsulfonyl) phenyl]-2 (5H)-furanone;

3-(2-methylpyridin-3-yl)-4-[3,5-difluoro-4-(methylsulfonyl) phenyl]-2 (5H)-furanone;

3-(2-methylpyridin-3-yl)-4-[3,5-difluoro-4-(methylsulfonyl) phenyl]-2 (5H)-furanone;

3-(3-pyridinyl)-4-[3,5-difluoro-4-(methylsulfonyl) phenyl]-2 (5H)-furanone;

3-(5-methylpyridin-3-yl)-4-[3,5-difluoro-4-(methylsulfonyl) phenyl]-2 (5H)-furanone;

3-(2-methylpyridin-3-yl)-4-[3,5-difluoro-4-(methylsulfonyl) phenyl]-2 (5H)-furanone;

3-cyclohexyl-4-[3,5-difluoro-4-(methylsulfonyl) phenyl]-2 (5H)-furanone;

3-cyclopentyl-4-[3,5-difluoro-4-(methylsulfonyl) phenyl]-2 (5H)-furanone;

2,6-difluoro-4-[4-5-oxo-2,5-dihydro-3-furanyl] benzenesulfonamide;

2,6-difluoro-4-[4-(3-chlorophenyl)-5-oxo-2,5-dihydro-3-furanyl]benzenesulfonamide;

2,6-difluoro-4-[4-(4-chlorophenyl)-5-oxo-2,5-dihydro-3-furanyl]benzenesulfonamide;

2,6-difluoro-4-[4-(3-bromophenyl)-5-oxo-2,5-dihydro-3-furanyl]benzenesulfonamide;

2,6-difluoro-4-[4-(4-bromophenyl)-5-oxo-2,5-dihydro-3-furanyl]benzenesulfonamide;

2,6-difluoro-4-[4-(3-fluorophenyl)-5-oxo-2,5-dihydro-3-furanyl]benzenesulfonamide;

2,6-difluoro-4-[4-(4-fluorophenyl)-5-oxo-2,5-dihydro-3-furanyl]benzenesulfonamide;

2,6-difluoro-4-[4-(3-methylphenyl)-5-oxo-2,5-dihydro-3-furanyl]benzenesulfonamide;

2,6-difluoro-4-[4-(4-methylphenyl)-5-oxo-2,5-dihydro-3-furanyl]benzenesulfonamide;

2,6-difluoro-4-[4-(3-cyanophenyl)-5-oxo-2,5-dihydro-3-furanyl]benzenesulfonamide;

2,6-difluoro-4-[4-(4-cyanophenyl)-5-oxo-2,5-dihydro-3-furanyl]benzenesulfonamide;

2,6-difluoro-4-[4-(3-trifluoromethylphenyl)-5-oxo-2,5-dihydro-3-furanyl]benzenesulfonamide;

2,6-difluoro-4-[4-(4-trifluoromethylphenyl)-s-oxo-2,5-dihydro-3-furanyl]benzenesulfonamide;

2,6-difluoro-4-[4-(3-trifluoromethoxyphenyl)-5-oxo-2,5-dihydro-3-furanyl]benzenesulfonamide;

2,6-difluoro-4-[4-(4-trifluoromethoxyphenyl)-5-oxo-2,5-dihydro-3-furanyl]benzenesulfonamide;

2,6-difluoro-4-[4-(3,4-dichlorophenyl)-5-oxo-2,5-dihydro-3-furanyl]benzenesulfonamide;

2,6-difluoro-4-[4-(3,4-dibromophenyl)-5-oxo-2,5-dihydro-3-furanyl]benzenesulfonamide;

2,6-difluoro-4-[4-(3,4-difluorophenyl)-5-oxo-2,5-dihydro-3-furanyl]benzenesulfonamide;

2,6-difluoro-4-[4-(3,5-dichlorophenyl)-5-oxo-2,5-dihydro-3-furanyl]benzenesulfonamide;

2,6-difluoro-4-[4-(3,5-dibromophenyl)-5-oxo-2,5-dihydro-3-furanyl]benzenesulfonamide;

2,6-difluoro-4-[4-(3,5-difluorophenyl)-5-oxo-2,5-dihydro-3-furanyl]benzenesulfonamide;

2,6-difluoro-4-[4-(3,4-dimethylphenyl)-5-oxo-2,5-dihydro-3-furanyl]benzenesulfonamide;

2,6-difluoro-4-[4-(3,5-dimethylphenyl)-5-oxo-2,5-dihydro-3-furanyl]benzenesulfonamide;

2,6-difluoro-4-[4-(3-methyl-4-chlorophenyl)-5-oxo-2,5-dihydro-3-furanyl]benzenesulfonamide;

2,6-difluoro-4-[4-(4-methyl-3-chlorophenyl)-5-oxo-2,5-dihydro-3-furanyl]benzenesulfonamide;

2,6-difluoro-4-[4-(3-methyl-4-fluorophenyl)-5-oxo-2,5-dihydro-3-furanyl]benzenesulfonamide;

2,6-difluoro-4-[4-(4-methyl-3-fluorophenyl)-5-oxo-2,5-dihydro-3-furanyl]benzenesulfonamide;

2,6-difluoro-4-[4-(3-methyl-4-bromophenyl)-5-oxo-2,5-dihydro-3-furanyl]benzenesulfonamide;

2,6-difluoro-4-[4-(4-methyl-3-bromophenyl)-5-oxo-2,5-dihydro-3-furanyl]benzenesulfonamide;

2,6-difluoro-4-[4-(3-methyl-4-trifluoromethylphenyl)-5-oxo-2,5-dihydro-3-furanyl]benzenesulfonamide;

2,6-difluoro-4-[4-(4-methyl-3-trifluoromethylphenyl)-5-oxo-2,5-dihydro-3-furanyl]benzenesulfonamide;

2,6-difluoro-4-[4-(3-methyl-4-trifluoromethoxyphenyl)-5-oxo-2,5-dihydro-3-furanyl]benzenesulfonamide;

2,6-difluoro-4-[4-(4-methyl-3-trifluoromethoxyphenyl)-5-oxo-2,5-dihydro-3-furanyl]benzenesulfonamide;

2,6-difluoro-4-[4-(3-cyano-4-methylphenyl)-5-oxo-2,5-dihydro-3-furanyl]benzenesulfonamide;

2,6-difluoro-4-[4-(4-cyano-3-methylphenyl)-5-oxo-2,5-dihydro-3-furanyl]benzenesulfonamide;

2,6-difluoro-4-[4-(3-chloro-4-methoxyphenyl)-5-oxo-2,5-dihydro-3-furanyl]benzenesulfonamide;

2,6-difluoro-4-[4-(4-chloro-3-methoxyphenyl)-5-oxo-2,5-dihydro-3-furanyl]benzenesulfonamide;

2,6-difluoro-4-[4-(2-methylpyridin-6-yl)-5-oxo-2,5-dihydro-3-furanyl]benzenesulfonamide;

2,6-difluoro-4-[4-(2-methylthiazol-4-yl)-5-oxo-2,5-dihydro-3-furanyl]benzenesulfonamide;

2,6-difluoro-4-[4-(4-methylthiazol-2-yl)-5-oxo-2,5-dihydro-3-furanyl]benzenesulfonamide;

2,6-difluoro-4-[4-(2-methylpyridin-3-yl)-5-oxo-2,5-dihydro-3-furanyl]benzenesulfonamide;

2,6-difluoro-4-[4-(2-methylpyridin-3-yl)-5-oxo-2,5-dihydro-3-furanyl]benzenesulfonamide;

2,6-difluoro-4-[4-(3-pyridinyl)-5-oxo-2,5-dihydro-3-furanyl]benzenesulfonamide;

2,6-difluoro-4-[4-(5-methylpyridin-3-yl)-5-oxo-2,5-dihydro-3-furanyl]benzenesulfonamide;

2,6-difluoro-4-[4-(2-methylpyridin-3-yl)-5-oxo-2,5-dihydro-3-furanyl]benzenesulfonamide;

2,6-difluoro-4-[4-cyclohexyl-5-oxo-2,5-dihydro-3-furanyl]benzenesulfonamide;

2,6-difluoro-4-[4-cyclopentyl-5-oxo-2,5-dihydro-3-furanyl]benzenesulfonamide;

3-phenyl-4-[3,6-difluoro-4-(methylsulfonyl)phenyl]-2 (5H)-furanone;

3-(3-chlorophenyl)-4-[3,6-difluoro-4-(methylsulfonyl) phenyl]-2 (5H)-furanone;

3-(4-chlorophenyl)-4-[3,6-difluoro-4-(methylsulfonyl) phenyl]-2 (5H)-furanone;

3-(3-bromophenyl)-4-[3,6-difluoro-4-(methylsulfonyl) phenyl]-2 (5H)-furanone;

3-(4-bromophenyl)-4-[3,6-difluoro-4-(methylsulfonyl) phenyl]-2 (5H)-furanone;

3-(3-ifluorophenyl)-4-[3,6-difluoro-4-(methylsulfonyl) phenyl]-2 (5H)-furanone;

3-(4-ifluorophenyl)-4-[3,6-difluoro-4-(methylsulfonyl) phenyl]-2 (5H)-furanone;

3-(3-methylphenyl)-4-[3,6-difluoro-4-(methylsulfonyl) phenyl]-2 (5H)-furanone;

3-(4-methylphenyl)-4-[3,6-difluoro-4-(methylsulfonyl) phenyl]-2 (5H)-furanone;

3-(3-cyanophenyl)-4-[3,6-difluoro-4-(methylsulfonyl) phenyl]-2 (5H)-furanone;

3-(4-cyanophenyl)-4-[3,6-difluoro-4-(methylsulfonyl) phenyl]-2 (5H)-furarione;

3-(3-trifluoromethylphenyl)-4-[3,6-difluoro-4-(methylsulfonyl) phenyl]-2 (5H)-furanone;

3-(4-trifluoromethylphenyl)-4-[3,6-difluoro-4-(methylsulfonyl) phenyl]-2 (5H)-furanone;

3-(3-trifluoromethoxyphenyl)-4-[3,6-difluoro-4-(methylsulfonyl) phenyl]-2 (5H)-furanone;

3-(4-trifluoromethoxyphenyl)-4-[3,6-difluoro-4-(methylsulfonyl) phenyl]-2 (5H)-furanone;

3-(3,4-dichlorophenyl)-4-[3,6-difluoro-4-(methylsulfonyl) phenyl]-2 (5H)-furanone;

3-(3,4-dibromophenyl)-4-[3,6-difluoro-4-(methylsulfonyl) phenyl]-2 (5H)-furanone;

3-(3,4-difluorophenyl)-4-[3,6-difluoro-4-(methylsulfonyl) phenyl]-2 (5H)-furanone;

3-(3,5-dichlorophenyl)-4-[3,6-difluoro-4-(methylsulfonyl) phenyl]-2 (5H)-furanone;

3-(3,5-dibromophenyl)-4-[3,6-difluoro-4-(methylsulfonyl) phenyl]-2 (5H)-furanone;

3-(3,5-difluorophenyl)-4-[3,6-difluoro-4-(methylsulfonyl) phenyl]-2 (5H)-furanone;

3-(3,4-dimethylphenyl)-4-[3,6-difluoro-4-(methylsulfonyl) phenyl]-2 (5H)-furanone;

3-(3,5-dimethylphenyl)-4-[3,6-difluoro-4-(methylsulfonyl) phenyl]-2 (5H)-furanone;

3-(3-methyl-4-chlorophenyl)-4-[3,6-difluoro-4-(methylsulfonyl) phenyl]-2 (5H)-furanone;

3-(4-methyl-3-chlorophenyl)-4-[3,6-difluoro-4-(methylsulfonyl) phenyl]-2 (5H)-furanone;

3-(3-methyl-4-fluorophenyl)-4-[3,6-difluoro-4-(methylsulfonyl) phenyl]-2 (5H)-furanone;

3-(4-methyl-3-fluorophenyl)-4-[3,6-difluoro-4-(methylsulfonyl) phenyl]-2 (5H)-furanone;

3-(3-methyl-4-bromophenyl)-4-[3,6-difluoro-4-(methylsulfonyl) phenyl]-2 (5H)-furanone;

3-(4-methyl-3-bromophenyl)-4-[3,6-difluoro-4-(methylsulfonyl) phenyl]-2 (5H)-furanone;

3-(3-methyl-4-trifluoromethylphenyl)-4-[3,6-difluoro-4-(methylsulfonyl) phenyl]-2 (5H)-furanone;

3-(4-methyl-3-trifluoromethylphenyl)-4-[3,6-difluoro-4-(methylsulfonyl) phenyl]-2 (5H)-furanone;

3-(3-methyl-4-trifluoromethoxyphenyl)-4-[3,6-difluoro-4-(methylsulfonyl) phenyl]-2 (5H)-furanone;

3-(4-methyl-3-trifluoromethoxyphenyl)-4-[3,6-difluoro-4-(methylsulfonyl) phenyl]-2 (5H)-furanone;

3-(3-cyano-4-methylphenyl)-4-[3,6-difluoro-4-(methylsulfonyl) phenyl]-2 (5H)-furanone;

3-(4-cyano-3-methylphenyl)-4-[3,6-difluoro-4-(methylsulfonyl) phenyl]-2 (5H)-furanone;

3-(3-chloro-4-methoxyphenyl)-4-[3,6-difluoro-4-(methylsulfonyl) phenyl]-2 (5H)-furanone;

3-(4-chloro-3-methoxyphenyl)-4-[3,6-difluoro-4-(methylsulfonyl) phenyl]-2 (5H)-furanone;

3-(2-methylpyridin-6-yl)-4-[3,6-difluoro-4-(methylsulfonyl) phenyl]-2 (5H)-furanone;

3-(4-methylthiazol-2-yl)-4-[3,6-difluoro-4-(methylsulfonyl) phenyl]-2 (5H)-furanone;

3-(2-methylpyridin-3-yl)-4-[3,6-difluoro-4-(methylsulfonyl) phenyl]-2 (5H)-furanone;

3-(2-methylpyridin-3-yl)-4-[3,6-difluoro-4-(methylsulfonyl) phenyl]-2 (5H)-furanone;

3-(3-pyridinyl)-4-[3,6-difluoro-4-(methylsulfonyl) phenyl]-2 (5H)-furanone;

3-(5-methylpyridin-3-yl)-4-[3,6-difluoro-4-(methylsulfonyl) phenyl]-2 (5H)-furanone;

3-(2-methylpyridin-3-yl)-4-[3,6-difluoro-4-(methylsulfonyl) phenyl]-2 (5H)-furanone;

3-cyclohexyl-4-[3,6-difluoro-4-(methylsulfonyl) phenyl]-2 (5H)-furanone;

3-cyclopentyl-4-[3,6-difluoro-4-(methylsulfonyl) phenyl]-2 (5H)-furanone;

and the pharmaceutically-acceptable salts, tautomers and prodrugs thereof.

Cyclopentenes

In still another embodiment, the present method of treating cyclooxygenase-2 mediated disorders comprises administering to the subject a therapeutically-effective amount of one or more compounds selected from a subclass of compounds of Formula I corresponding to Formula VI:

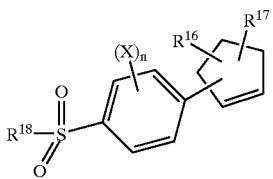

VI wherein substituents X, n, $R^{16}$, $R^{17}$ and $R^{18}$ have the same definitions and sub-definitions as substituents X, n, $R^1$, $R^3$ and $R^2$, respectively, set forth above for the compounds of Formula I, and the pharmaceutically-acceptable salts, tautomers and prodrugs thereof.

Within this subclass of compounds, a preferred group of compounds consists of those compounds of Formula VIA:

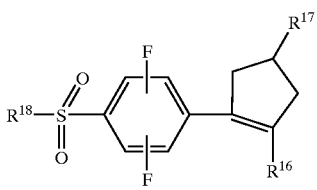

VIA wherein $R^{16}$, $R^{17}$ and $R^{18}$ are as defined above, and the pharmaceutically acceptable salts, tautomers and prodrugs thereof.

Within this subclass of compounds, a more preferred group of compounds consists of those compounds of Formula VIB:

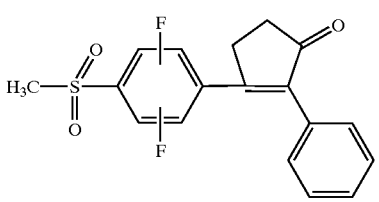

VIB and the pharmaceutically-acceptable salts, tautomers and prodrugs thereof. Preferably, (a) one fluoro radical is present at the 2-position and the other fluoro radical is present at the 5-position, or (b) one fluoro radical is present at the 2-position and the other fluoro radical is present at the 3-position, or (c) one fluoro radical is present at the 3-position and the other fluoro radical is present at the 5-position.

Preferred species within this subclass include, but are not limited to:

2,6-difluoro-4-[2-phenylcyclopenten-1-yl] benezenesulfonamide;

2,6-difluoro-4-[2-(3-chlorophenyl)cyclopenten-1-yl] benezenesulfonamide;

2,6-difluoro-4-[2-(4-chlorophenyl)cyclopenten-1-yl] benezenesulfonamide;

2,6-difluoro-4-[2-(3-bromophenyl)cyclopenten-1-yl] benezenesulfonamide;

2,6-difluoro-4-[2-(4-bromophenyl)cyclopenten-1-yl] benezenesulfonamide;

2,6-difluoro-4-[2-(3-fluorophenyl)cyclopenten-1-yl] benezenesulfonamide;

2,6-difluoro-4-[2-(4-fluorophenyl)cyclopenten-1-yl] benezenesulfonamide;

2,6-difluoro-4-[2-(3-methylphenyl)cyclopenten-1-yl] benezenesulfonamide;

2,6-difluoro-4-[2-(4-methylphenyl)cyclopenten-1-yl] benezenesulfonamide;

2,6-difluoro-4-[2-(3-cyanophenyl)cyclopenten-1-yl] benezenesulfonamide;

2,6-difluoro-4-[2-(4-cyanophenyl)cyclopenten-1-yl] benezenesulfonamide;

2,6-difluoro-4-[2-(3-trifluoromethylphenyl)cyclopenten-1-yl]benezenesulfonamide;

2,6-difluoro-4-[2-(4-trifluoromethylphenyl)cyclopenten-1-yl]benezenesulfonamide;

2,6-difluoro-4-[2-(3-trifluoromethoxyphenyl) cyclopenten-1-yl]benezenesulfonamide;

2,6-difluoro-4-[2-(4-trifluoromethoxyphenyl) cyclopenten-1-yl]benezenesulfonamide;

2,6-difluoro-4-[2-(3,4-dichlorophenyl)cyclopenten-1-yl] benezenesulfonamide;

2,6-difluoro-4-[2-(3,4-dibromophenyl)cyclopenten-1-yl] benezenesulfonamide;

2,6-difluoro-4-[2-(3,4-difluorophenyl)cyclopenten-1-yl] benezenesulfonamide;

2,6-difluoro-4-[2-(3,5-dichlorophenyl)cyclopenten-1-yl] benezenesulfonamide;

2,6-difluoro-4-[2-(3,5-dibromophenyl)cyclopenten-1-yl] benezenesulfonamide;

2,6-difluoro-4-[2-(3,5-difluorophenyl)cyclopenten-1-yl] benezenesulfonamide;

2,6-difluoro-4-[2-(3,4-dimethylphenyl)cyclopenten-1-yl] benezenesulfonamide;

2,6-difluoro-4-[2-(3,5-dimethylphenyl)cyclopenten-1-yl] benezenesulfonamide;

2,6-difluoro-4-[2-(3-methyl-4-chlorophenyl) cyclopenten-1-yl]benezenesulfonamide;

2,6-difluoro-4-[2-(4-methyl-3-chlorophenyl) cyclopenten-1-yl]benezenesulfonamide;

2,6-difluoro-4-[2-(3-methyl-4-fluorophenyl)cyclopenten-1-yl]benezenesulfonamide;

2,6-difluoro-4-[2-(4-methyl-3-fluorophenyl)cyclopenten-1-yl]benezenesulfonamide;

2,6-difluoro-4-[2-(3-methyl-4-bromophenyl) cyclopenten-1-yl]benezenesulfonamide;

2,6-difluoro-4-[2-(4-methyl-3-bromophenyl) cyclopenten-1-yl]benezenesulfonamide;

2,6-difluoro-4-[2-(3-methyl-4-trifluoromethylphenyl) cyclopenten-1-yl]benezenesulfonamide;

2,6-difluoro-4-[2-(4-methyl-3-trifluoromethylphenyl) cyclopenten-1-yl]benezenesulfonamide;

2,6-difluoro-4-[2-(3-methyl-4-trifluoromethoxyphenyl) cyclopenten-1-yl]benezenesulfonamide;

2,6-difluoro-4-[2-(4-methyl-3-trifluoromethoxyphenyl) cyclopenten-1-yl]benezenesulfonamide;

2,6-difluoro-4-[2-(3-cyano-4-methylphenyl) cyclopenten-1-yl]benezenesulfonamide;

2,6-difluoro-4-[2-(4-cyano-3-methylphenyl)cyclopenten-1-yl]benezenesulfonamide;

2,6-difluoro-4-[2-(3-chloro-4-methoxyphenyl)cyclopenten-1-yl]benezenesulfonamide;

2,6-difluoro-4-[2-(4-chloro-3-methoxyphenyl)cyclopenten-1-yl]benezenesulfonamide;

2,6-difluoro-4-[2-(2-methylpyridin-6-yl)cyclopenten-1-yl]benezenesulfonamide;

2,6-difluoro-4-[2-(2-methylthiazol-4-yl)cyclopenten-1-yl]benezenesulfonamide;

2,6-difluoro-4-[2-(4-methylthiazol-2-yl)cyclopenten-1-yl]benezenesulfonamide;

2,6-difluoro-4-[2-(2-methylpyridin-3-yl)cyclopenten-1-yl]benezenesulfonamide;

2,6-difluoro-4-[2-(2-methylpyridin-3-yl)cyclopenten-1-yl]benezenesulfonamide;

2,6-difluoro-4-[2-(3-pyridinyl)cyclopenten-1-yl]benezenesulfonamide;

2,6-difluoro-4-[2-(5-methylpyridin-3-yl)cyclopenten-1-yl]benezenesulfonamide;

2,6-difluoro-4-[2-(2-methylpyridin-3-yl)cyclopenten-1-yl]benezenesulfonamide;

2,6-difluoro-4-[2-cyclohexylcyclopenten-1-yl]benezenesulfonamide;

2,6-difluoro-4-[2-cyclopentylcyclopenten-1-yl]benezenesulfonamide;

4-[5-phenyl-1,4-cyclopentadienyl]-2,6-difluorophenyl methyl sulfone;

4-[5-(3-chlorophenyl)-1,4-cyclopentadienyl]-2,6-difluorophenyl methyl sulfone;

4-[5-(4-chlorophenyl)-1,4-cyclopentadienyl]-2,6-difluorophenyl methyl sulfone;

4-[5-(3-bromophenyl)-1,4-cyclopentadienyl]-2,6-difluorophenyl methyl sulfone;

4-[5-(4-bromophenyl)-1,4-cyclopentadienyl]-2,6-difluorophenyl methyl sulfone;

4-[5-(3-fluorophenyl)-1,4-cyclopentadienyl]-2,6difluorophenyl methyl sulfone;

4-[5-(4-fluorophenyl)-1,4-cyclopentadienyl]-2,6-difluorophenyl methyl sulfone;

4-[5-(3-methylphenyl)-1,4-cyclopentadienyl]-2,6-difluorophenyl methyl sulfone;

4-[5-(4-methylphenyl)-1,4-cyclopentadienyl]-2,6-difluorophenyl methyl sulfone;

4-[5-(3-cyanophenyl)-1,4-cyclopentadienyl]-2,6difluorophenyl methyl sulfone;

4-[5-(4-cyanophenyl)-1,4-cyclopentadienyl]-2,6-difluorophenyl methyl sulfone;

4-[5-(3-trifluoromethylphenyl)-1,4-cyclopentadienyl]-2,6-difluorophenyl methyl sulfone;

4-[5-(4-trifluoromethylphenyl)-1,4-cyclopentadienyl]-2,6-difluorophenyl methyl sulfone;

4-[5-(3-trifluoromethoxyphenyl)-1,4-cyclopentadienyl]-2,6-difluorophenyl methyl sulfone;

4-[5-(4-trifluoromethoxyphenyl)-1,4-cyclopentadienyl]-2,6-difluorophenyl methyl sulfone;

4-[5-(3,4-dichlorophenyl)-1,4-cyclopentadienyl]-2,6-difluorophenyl methyl sulfone;

4-[5-(3,4-dibromophenyl)-1,4-cyclopentadienyl]-2,6-difluorophenyl methyl sulfone;

4-[5-(3,4-difluorophenyl)-1,4-cyclopentadienyl]-2,6-difluorophenyl methyl sulfone;

4-[5-(3,5-dichlorophenyl)-1,4-cyclopentadienyl]-2,6-difluorophenyl methyl sulfone;

7,4-[5-(3,5-dibromophenyl)-1,4-cyclopentadienyl]-2,6-difluorophenyl methyl sulfone;

4-[5-(3,5-difluorophenyl)-1,4-cyclopentadienyl]-2,6-difluorophenyl methyl sulfone;

4-[5-(3,4-dimethylphenyl)-1,4-cyclopentadienyl]-2,6difluorophenyl methyl sulfone;

4-[5-(3,5-dimethylphenyl)-1,4-cyclopentadienyl]-2,6difluorophenyl methyl sulfone;

4-[5-(3-methyl-4-chlorophenyl)-1,4-cyclopentadienyl]-2,6-difluorophenyl methyl sulfone;

4-[5-(4-methyl-3-chlorophenyl)-1,4-cyclopentadienyl]-2,6-difluorophenyl methyl sulfone;

4-[5-(3-methyl-4-fluorophenyl)-1,4-cyclopentadienyl]-2,6-difluorophenyl methyl sulfone;

4-[5-(4-methyl-3-fluorophenyl)-1,4-cyclopentadienyl]-2,6-difluorophenyl methyl sulfone;

4-[5-(3-methyl-4-bromophenyl)-1,4-cyclopentadienyl]-2,6-difluorophenyl methyl sulfone;

4-[5-(4-methyl-3-bromophenyl)-1,4-cyclopentadienyl]-2,6-difluorophenyl methyl sulfone;

4-[5-(3-methyl-4-trifluoromethylphenyl)-1,4-cyclopentadienyl]-2,6-difluorophenyl methyl sulfone;

4-[5-(4-methyl-3-trifluoromethylphenyl)-1,4-cyclopentadienyl]-2,6-difluorophenyl methyl sulfone;

4-[5-(3-methyl-4-trifluoromethoxyphenyl)-1,4-cyclopentadienyl]-2,6-difluorophenyl methyl sulfone;

4-[5-(4-methyl-3-trifluoromethoxyphenyl)-1,4-cyclopentadienyl]-2,6-difluorophenyl methyl sulfone;

4-[5-(3-cyano-4-methylphenyl)-1,4-cyclopentadienyl]-2,6difluorophenyl methyl sulfone;

4-[5-(4-cyano-3-methylphenyl)-1,4-cyclopentadienyl]2,6difluorophenyl methyl sulfone;

4-[5-(3-chloro-4-methoxyphenyl)-1,4-cyclopentadienyl]-2,6-difluorophenyl methyl sulfone;

4-[5-(4-chloro-3-methoxyphenyl)-1,4-cyclopentadienyl]-2,6-difluorophenyl methyl sulfone;

4-[5-(2-methylpyridin-6-yl)-1,4-cyclopentadienyl]-2,6-difluorophenyl methyl sulfone;

4-[5-(2-methylthiazol-4-yl)-1,4-cyclopentadienyl]-2,6-difluorophenyl methyl sulfone;

4-[5-(4-methylthiazol-2-yl)-1,4-cyclopentadienyl]-2,6-difluorophenyl methyl sulfone;

4-[5-(2-methylpyridin-3-yl)-1,4-cyclopentadienyl]-2,6-difluorophenyl methyl sulfone;

4-[5-(2-methylpyridin-3-yl)-1,4-cyclopentadienyl]-2,6-difluorophenyl methyl sulfone;

4-[5-(3-pyridinyl)-1,4-cyclopentadienyl]-2,6-difluorophenyl methyl sulfone;

4-[5-(5-methylpyridin-3-yl)-1,4-cyclopentadienyl]-2,6-difluorophenyl methyl sulfone;

4-[5-(2-methylpyridin-3-yl)-1,4-cyclopentadienyl]-2,6-difluorophenyl methyl sulfone;

4-[5-cyclohexyl-1,4-cyclopentadienyl]-2,6-difluorophenyl methyl sulfone;

4-[5-cyclopentyl-1,4-cyclopentadienyl]-2,6-difluorophenyl methyl sulfone;

2,5-difluoro-4-[2-phenylcyclopenten-1-yl]benezenesulfonamide;

2,5-difluoro-4-[2-(3-chlorophenyl)cyclopenten-1-yl]benezenesulfonamide;

2,5-difluoro-4-[2-(4-chlorophenyl)cyclopenten-1-yl]benezenesulfonamide;

2,5-difluoro-4-[2-(3-bromophenyl)cyclopenten-1-yl]benezenesulfonamide;
2,5-difluoro-4-[2-(4-bromophenyl)cyclopenten-1-yl]benezenesulfonamide;
2,5-difluoro-4-[2-(3-fluorophenyl)cyclopenten-1-yl]benezenesulfonamide;
2,5-difluoro-4-[2-(4-fluorophenyl)cyclopenten-1-yl]benezenesulfonamide;
2,5-difluoro-4-[2-(3-methylphenyl)cyclopenten-1-yl]benezenesulfonamide;
2,5-difluoro-4-[2-(4-methylphenyl)cyclopenten-1-yl]benezenesulfonamide;
2,5-difluoro-4-[2-(3-cyanophenyl)cyclopenten-1-yl]benezenesulfonamide;
2,5-difluoro-4-[2-(4-cyanophenyl)cyclopenten-1-yl]benezenesulfonamide;
2,5-difluoro-4-[2-(3-trifluoromethylphenyl)cyclopenten-1-yl]benezenesulfonamide;
2,5-difluoro-4-[2-(4-trifluoromethylphenyl)cyclopenten-1-yl]benezenesulfonamide;
2,5-difluoro-4-[2-(3-trifluoromethoxyphenyl)cyclopenten-1-yl]benezenesulfonamide;
2,5-difluoro-4-[2-(4-trifluoromethoxyphenyl)cyclopenten-1-yl]benezenesulfonamide;
2,5-difluoro-4-[2-(3,4-dichlorophenyl)cyclopenten-1-yl]benezenesulfonamide;
2,5-difluoro-4-[2-(3,4-dibromophenyl)cyclopenten-1-yl]benezenesulfonamide;
2,5-difluoro-4-[2-(3,4-difluorophenyl)cyclopenten-1-yl]benezenesulfonamide;
2,5-difluoro-4-[2-(3,5-dichlorophenyl)cyclopenten-1-yl]benezenesulfonamide;
2,5-difluoro-4-[2-(3,5-dibromophenyl)cyclopenten-1-yl]benezenesulfonamide;
2,5-difluoro-4-[2-(3,5-difluorophenyl)cyclopenten-1-yl]benezenesulfonamide;
2,5-difluoro-4-[2-(3,4-dimethylphenyl)cyclopenten-1-yl]benezenesulfonamide;
2,5-difluoro-4-[2-(3,5-dimethylphenyl)cyclopenten-1-yl]benezenesulfonamide;
2,5-difluoro-4-[2-(3-methyl-4-chlorophenyl)cyclopenten-1-yl]benezenesulfonamide;
2,5-difluoro-4-[2-(4-methyl-3-chlorophenyl)cyclopenten-1-yl]benezenesulfonamide;
2,5-difluoro-4-[2-(3-methyl-4-fluorophenyl)cyclopenten-1-yl]benezenesulfonamide;
2,5-difluoro-4-[2-(4-methyl-3-fluorophenyl)cyclopenten-1-yl]benezenesulfonamide;
2,5-difluoro-4-[2-(3-methyl-4-bromophenyl)cyclopenten-1-yl]benezenesulfonamide;
2,5-difluoro-4-[2-(4-methyl-3-bromophenyl)cyclopenten-1-yl]benezenesulfonamide;
2,5-difluoro-4-[2-(3-methyl-4-trifluoromethylphenyl)cyclopenten-1-yl]benezenesulfonamide;
2,5-difluoro-4-[2-(4-methyl-3-trifluoromethylphenyl)cyclopenten-1-yl]benezenesulfonamide;
2,5-difluoro-4-[2-(3-methyl-4-trifluoromethoxyphenyl)cyclopenten-1-yl]benezenesulfonamide;
2,5-difluoro-4-[2-(4-methyl-3-trifluoromethoxyphenyl)cyclopenten-1-yl]benezenesulfonamide;
2,5-difluoro-4-[2-(3-cyano-4-methylphenyl)cyclopenten-1-yl]benezenesulfonamide;
2,5-difluoro-4-[2-(4-cyano-3-methylphenyl)cyclopenten-1-yl]benezenesulfonamide;
2,5-difluoro-4-[2-(3-chloro-4—methoxyphenyl)cyclopenten-1-yl]benezenesulfonamide;
2,5-difluoro-4-[2-(4-chloro-3-methoxyphenyl)cyclopenten-1-yl]benezenesulfonamide;
2,5-difluoro-4-[2-(2-methylpyridin-6-yl)cyclopenten-1-yl]benezenesulfonamide;
2,5-difluoro-4-[2-(2-methylthiazol-4-yl)cyclopenten-1-yl]benezenesulfonamide;
2,5-difluoro-4-[2-(4-methylthiazol-2-yl)cyclopenten-1-1]benezenesulfonamide;
2,5-difluoro-4-[2-(2-methylpyridin-3-yl)cyclopenten-1-yl]benezenesulfonamide;
2,5-difluoro-4-[2-(2-methylpyridin-3-yl)cyclopenten-1-yl]benezenesulfonamide;
2,5-difluoro-4-[2-(3-pyridinyl)cyclopenten-1-yl]benezenesulfonamide;
2,5-difluoro-4-[2-(5-methylpyridin-3-yl)cyclopenten-1-yl]benezenesulfonamide;
2,5-difluoro-4-[2-(2-methylpyridin-3-yl)cyclopenten-1-yl]benezenesulfonamide;
2, 5-difluoro-4-[2-cyclohexylcyclopenten-1-yl]benezenesulfonamide;
2, 5-difluoro-4-[2-cyclopentylcyclopenten-1-yl]benezenesulfonamide;
4-[5-phenyl-1,4-cyclopentadienyl]-2,5-difluorophenyl methyl sulfone;
4-[5-(3-chlorophenyl)-1,4-cyclopentadienyl]-2,5-difluorophenyl methyl sulfone;
4-[5-(4-chlorophenyl)-1,4-cyclopentadienyl]-2,5-difluorophenyl methyl sulfone;
4-[5-(3-bromophenyl)-1,4-cyclopentadienyl]-2,5-difluorophenyl methyl sulfone;
4-[5-(4-bromophenyl)-1,4-cyclopentadienyl]-2,5-difluorophenyl methyl sulfone;
4-[5-(3-fluorophenyl)-1,4-cyclopentadienyl]-2,5difluorophenyl methyl sulfone;
4-[5-(4-fluorophenyl)-1,4-cyclopentadienyl]-2,5-difluorophenyl methyl sulfone;
4-[5-(3-methylphenyl)-1,4-cyclopentadienyl]-2,5-difluorophenyl methyl sulfone;
4-[5-(4-methylphenyl)-1,4-cyclopentadienyl]-2,5-difluorophenyl methyl sulfone;
4-[5-(3-cyanophenyl)-1,4-cyclopentadienyl]-2,5-difluorophenyl methyl sulfone;
4-[5-(4-cyanophenyl)-1,4-cyclopentadienyl]-2,5difluorophenyl methyl sulfone;
4-[5-(3-trifluoromethylphenyl)-1,4-cyclopentadienyl]-2,5-difluorophenyl methyl sulfone;
4-[5-(4-trifluoromethylphenyl)-1,4-cyclopentadienyl]-2,5-difluorophenyl methyl sulfone;
4-[5-(3-trifluoromethoxyphenyl)-1,4-cyclopentadienyl]-2,5-difluorophenyl methyl sulfone;
4-[5-(4-trifluoromethoxyphenyl)-1,4-cyclopentadienyl]-2,5-difluorophenyl methyl sulfone;
4-[5-(3,4-dichlorophenyl)-1,4-cyclopentadienyl]-2,5difluorophenyl methyl sulfone;
4-[5-(3,4-dibromophenyl)-1,4-cyclopentadienyl]-2,5-difluorophenyl methyl sulfone;
4-[5-(3,4-difluorophenyl)-1,4-cyclopentadienyl]-25, difluorophenyl methyl sulfone;

4-[5-(3,5-dichlorophenyl)-1,4-cyclopentadienyl]-2,5difluorophenyl methyl sulfone;
4-[5-(3,5-dibromophenyl)-1,4-cyclopentadienyl]-2,5difluorophenyl methyl sulfone;
4-[5-(3,5-difluorophenyl)-1,4-cyclopentadienyl]-2,5difluorophenyl methyl sulfone;
4-[5-(3,4-dimethylphenyl)-1,4-cyclopentadienyl]-2,5difluorophenyl methyl sulfone;
4-[5-(3,5-dimethylphenyl)-1,4-cyclopentadienyl]-2,5-difluorophenyl methyl sulfone;
4-[5-(3-methyl-4-chlorophenyl)-1,4-cyclopentadienyl]-2,5-difluorophenyl methyl sulfone;
4-[5-(4-methyl-3-chlorophenyl)-1,4-cyclopentadienyl]-2,5-difluorophenyl methyl sulfone;
4-[5-(3-methyl-4-fluorophenyl)-1,4-cyclopentadienyl]-2,5-difluorophenyl methyl sulfone;
4-[5-(4-methyl-3-fluorophenyl)-1,4-cyclopentadienyl]-2,5-difluorophenyl methyl sulfone;
4[5(3-methyl-4-bromophenyl)-1,4-cyclopentadienyl]-2,5-difluorophenyl methyl sulfone;
4-[5-(4-methyl-3-bromophenyl)-1,4-cyclopentadienyl]-2,5-difluorophenyl methyl sulfone;
4-[5-(3-methyl-4-trifluoromethylphenyl)-1,4-cyclopentadienyl]-2,5-difluorophenyl methyl sulfone;
4-[5-(4-methyl-3-trifluoromethylphenyl)-1,4-cyclopentadienyl]-2,5-difluorophenyl methyl sulfone;
4-[5-(3-methyl-4-trifluoromethoxyphenyl)-1,4-cyclopentadienyl]-2,5-difluorophenyl methyl sulfone;
4-[5-(4-methyl-3-trifluoromethoxyphenyl)-1,4-cyclopentadienyl]-2,5-difluorophenyl methyl sulfone;
4-[5-(3-cyano-4-methylphenyl)-1,4-cyclopentadienyl]-2,5-difluorophenyl methyl sulfone;
4-[5-(4-cyano-3-methylphenyl)-1,4-cyclopentadienyl]-2,5-difluorophenyl methyl sulfone;
4-[5-(3-chloro-4-methoxyphenyl)-1,4-cyclopentadienyl]-2,5-difluorophenyl methyl sulfone;
4-[5-(4-chloro-3-methoxyphenyl)-1,4-cyclopentadienyl]-2,5-difluorophenyl methyl sulfone;
4-[5-(2-methylpyridin-6-yl)-1,4-cyclopentadienyl]-2,5-difluorophenyl methyl sulfone;
4-[5-(2-methylthiazol-4-yl)-1,4-cyclopentadienyl]-2,5-difluorophenyl methyl sulfone;
4-[5-(4-methylthiazol-2-yl)-1,4-cyclopentadienyl]-2,5-difluorophenyl methyl sulfone;
4-[5-(2-methylpyridin-3-yl)-1,4-cyclopentadienyl]-2,5-difluorophenyl methyl sulfone;
4-[5-(2-methylpyridin-3-yl)-1,4-cyclopentadienyl]-2,5-difluorophenyl methyl sulfone;
4-[5-(3-pyridinyl)-1,4-cyclopentadienyl]-2,5-difluorophenyl methyl sulfone;
4-[5-(5-methylpyridin-3-yl)-1,4-cyclopentadienyl]-2,5-difluorophenyl methyl sulfone;
4-[5-(2-methylpyridin-3-yl)-1,4-cyclopentadienyl]-2,5-difluorophenyl methyl sulfone;
4-[5-cyclohexyl-1,4-cyclopentadienyl]-2,5-difluorophenyl methyl sulfone;
4-[5-cyclopentyl-1,4-cyclopentadienyl]-2,5-difluorophenyl methyl sulfone; and the pharmaceutically-acceptable salts, tautomers and prodrugs thereof.

Pyridines

In still another embodiment, the present method of treating cyclooxygenase-2 mediated disorders comprises administering to the subject a therapeutically-effective amount of one or more compounds selected from a subclass of compounds of Formula I corresponding to Formula VII:

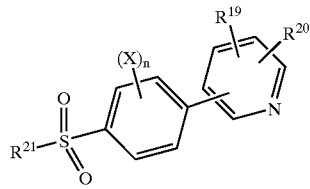

VII wherein substituents X, n, $R^{19}$, $R^{20}$ and $R^{21}$ have the same definitions and sub-definitions as substituents X, n, $R^1$, $R^3$ and $R^2$, respectively, set forth above for the compounds of Formula I, and the pharmaceutically-acceptable salts, tautomers and prodrugs thereof.

Within this subclass of compounds, a preferred group of compounds consists of those compounds of Formula VIIA:

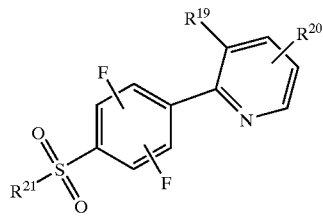

VIIA wherein $R^{19}$, $R^{20}$ and $R^{21}$ are as defined above, and the pharmaceutically-acceptable salts, tautomers and prodrugs thereof.

Within this subclass of compounds, a more preferred group of compounds consists of those compounds of Formula VIIB and VIIC:

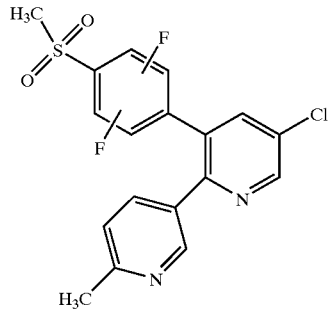

VIIB

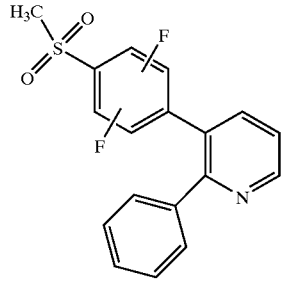

VIIC and the pharmaceutically-acceptable salts, tautomers and prodrugs thereof. Preferably, (a) one fluoro radical is present at the 2-position and the other fluoro radical is present at the 5-position, or (b) one fluoro is present at the 2-position and the other fluoro radical is present at the 3-position, or (c) one fluoro radical is present at the 3-position and the other fluoro radical is present at the 5-position.

Preferred species within this subclass include, but are not limited to:

2,6-difluoro-4-[3-phenyl-2-pyridinyl]-benezenesulfonamide;
2,6-difluoro-4-[3-(3-chlorophenyl)-2-pyridinyl]-benezenesulfonamide;
2,6-difluoro-4-[3-(4-chlorophenyl)-2-pyridinyl]-benezenesulfonamide;
2,6-difluoro-4-[3-(3-bromophenyl)-2-pyridinyl]-benezenesulfonamide;
2,6-difluoro-4-[3-(4-bromophenyl)-2-pyridinyl]-benezenesulfonamide;
2,6-difluoro-4-[3-(3-fluorophenyl)-2-pyridinyl]-benezenesulfonamide;
2,6-difluoro-4-[3-(4-fluorophenyl)-2-pyridinyl]-benezenesulfonamide;
2,6-difluoro-4-[3-(3-methylphenyl)-2-pyridinyl]-benezenesulfonamide;
2,6-difluoro-4-[3-(4-methylphenyl)-2-pyridinyl]-benezenesulfonamide;
2,6-difluoro-4-[3-(3-cyanophenyl)-2-pyridinyl]-benezenesulfonamide;
2,6-difluoro-4-[3-(4-cyanophenyl)-2-pyridinyl]-benezenesulfonamide;
2,6-difluoro-4-[3-(3-trifluoromethylphenyl)-2-pyridinyl]-benezenesulfonamide;
2,6-difluoro-4-[3-(4-trifluoromethylphenyl)-2-pyridinyl]-benezenesulfonamide;
2,6-difluoro-4-[3-(3-trifluoromethoxyphenyl)-2-pyridinyl]-benezenesulfonamide;
2,6-difluoro-4-[3-(4-trifluoromethoxyphenyl)-2-pyridinyl]-benezenesulfonamide;
2,6-difluoro-4-[3-(3,4-dichlorophenyl)-2-pyridinyl]-benezenesulfonamide;
2,6-difluoro-4-[3-(3,4-dibromophenyl)-2-pyridinyl]-benezenesulfonamide;
2,6-difluoro-4-[3-(3,4-difluorophenyl)-2-pyridinyl]-benezenesulfonamide;
2,6-difluoro-4-[3-(3,5-dichlorophenyl)-2-pyridinyl]-benezenesulfonamide;
2,6-difluoro-4-[3-(3,5-dibromophenyl)-2-pyridinyl]-benezenesulfonamide;
2,6-difluoro-4-[3-(3,5-difluorophenyl)-2-pyridinyl]-benezenesulfonamide;
2,6-difluoro-4-[3-(3,4-dimethylphenyl)-2-pyridinyl]-benezenesulfonamide;
2,6-difluoro-4-[3-(3,5-dimethylphenyl)-2-pyridinyl]-benezenesulfonamide;
2,6-difluoro-4-[3-(3-methyl-4-chlorophenyl)-2-pyridinyl]-benezenesulfonamide;
2,6-difluoro-4-[3-(4-methyl-3-chlorophenyl)-2-pyridinyl]-benezenesulfonamide;
2,6-difluoro-4-[3-(3-methyl-4-fluorophenyl)-2-pyridinyl]-benezenesulfonamide;
2,6-difluoro-4-[3-(4-methyl-3-fluorophenyl)-2-pyridinyl]-benezenesulfonamide;
2,6-difluoro-4-[3-(3-methyl-4-bromophenyl)-2-pyridinyl]-benezenesulfonamide;
2,6-difluoro-4-[3-(4-methyl-3-bromophenyl)-2-pyridinyl]-benezenesulfonamide;
2,6-difluoro-4-[3-(3-methyl-4-trifluoromethylphenyl)-2-pyridinyl]-benezenesulfonamide;
2,6-difluoro-4-[3-(4-methyl-3-trifluoromethylphenyl)-2-pyridinyl]-benezenesulfonamide;
2,6-difluoro-4-[3-(3-methyl-4-trifluoromethoxyphenyl)-2-pyridinyl]-benezenesulfonamide;
2,6-difluoro-4-[3-(4-methyl-3-trifluoromethoxyphenyl)-2-pyridinyl]-benezenesulfonamide;
2,6-difluoro-4-[3-(3-cyano-4-methylphenyl)-2-pyridinyl]-benezenesulfonamide;
2,6-difluoro-4-[3-(4-cyano-3-methylphenyl)-2-pyridinyl]-benezenesulfonamide;
2,6-difluoro-4-[3-(3-chloro-4-methoxyphenyl)-2-pyridinyl]-benezenesulfonamide;
2,6-difluoro-4-[3-(4-chloro-3-methoxyphenyl)-2-pyridinyl]-benezenesulfonamide;
2,6-difluoro-4-[3-(2-methylpyridin-G-yl)-2-pyridinyl]-benezenesulfonamide;
2,6-difluoro-4-[3-(2-methylthiazol-4-yl)-2-pyridinyl]-benezenesulfonamide;
2,6-difluoro-4-[3-(4-methylthiazol-2-yl)-2-pyridinyl]-benezenesulfonamide;
2,6-difluoro-4-[3-(2-methylpyridin-3-yl)-2-pyridinyl]-benezenesulfonamide;
2,6-difluoro-4-[3-(2-methylpyridin-3-yl)-2-pyridinyl]-benezenesulfonamide;
2,6-difluoro-4-[3-(3-pyridinyl)-2-pyridinyl]-benezenesulfonamide;
2,6-difluoro-4-[3-(5-methylpyridin-3-yl)-2-pyridinyl]-benezenesulfonamide;
2,6-difluoro-4-[3-(2-methylpyridin-3-yl)-2-pyridinyl]-benezenesulfonamide;
2,6-difluoro-4-[3-cyclohexyl-2-pyridinyl]-benezenesulfonamide;
2,6-difluoro-4-[3-cyclopentyl-2-pyridinyl]-benezenesulfonamide;
2, 6-difluoro-4-[3-phenyl-3-pyridinyl]-benezenesulfonamide;
2,6-difluoro-4-[3-(3-chlorophenyl)-3-pyridinyl]-benezenesulfonamide;
2,6-difluoro-4-[3-(4-chlorophenyl)-3-pyridinyl]-benezenesulfonamide;
2,6-difluoro-4-[3-(3-bromophenyl)-3-pyridinyl]-benezenesulfonamide;
2,6-difluoro-4-[3-(4-bromophenyl)-3-pyridinyl]-benezenesulfonamide;
2,6-difluoro-4-[3-(3-fluorophenyl)-3-pyridinyl]-benezenesulfonamide;
2,6-difluoro-4-[3-(4-fluorophenyl)-3-pyridinyl]-benezenesulfonamide;
2,6-difluoro-4-[3-(3-methylphenyl)-3-pyridinyl]-benezenesulfonamide;
2,6-difluoro-4-[3-(4-methylphenyl)-3-pyridinyl]-benezenesulfonamide;
2,6-difluoro-4-[3-(3-cyanophenyl)-3-pyridinyl]-benezenesulfonamide;
2,6-difluoro-4-[3-(4-cyanophenyl)-3-pyridinyl]-benezenesulfonamide;
2,6-difluoro-4-[3-(3-trifluoromethylphenyl)-3-pyridinyl]-benezenesulfonamide;
2,6-difluoro-4-[3-(4-trifluoromethylphenyl)-3-pyridinyl]-benezenesulfonamide;

2,6-difluoro-4-[3-(3-trifluoromethoxyphenyl)-3-pyridinyl]-benezenesulfonamide;
2,6-difluoro-4-[3-(4-trifluoromethoxyphenyl)-3-pyridinyl]-benezenesulfonamide;
2,6-difluoro-4-[3-(3,4-dichlorophenyl)-3-pyridinyl]-benezenesulfonamide;
2,6-difluoro-4-[3-(3,4-dibromophenyl)-3-pyridinyl]-benezenesulfonamide;
2,6-difluoro-4-[3-(3,4-difluorophenyl)-3-pyridinyl]-benezenesulfonamide;
2,6-difluoro-4-[3-(3,5-dichlorophenyl)-3-pyridinyl]-benezenesulfonamide;
2,6-difluoro-4-[3-(3,5-dibromophenyl)-3-pyridinyl]-benezenesulfonamide;
2,6-difluoro-4-[3-(3,5-difluorophenyl)-3-pyridinyl]-benezenesulfonamide;
2,6-difluoro-4-[3-(3,4-dimethylphenyl)-3-pyridinyl]-benezenesulfonamide;
2,6-difluoro-4-[3-(3,5-dimethylphenyl)-3-pyridinyl]-benezenesulfonamide;
2,6-difluoro-4-[3-(3-methyl-4-chlorophenyl)-3-pyridinyl]-benezenesulfonamide;
2,6-difluoro-4-[3-(4-methyl-3-chlorophenyl)-3-pyridinyl]-benezenesulfonamide;
2,6-difluoro-4-[3-(3-methyl-4-fluorophenyl)-3-pyridinyl]-benezenesulfonamide;
2,6-difluoro-4-[3-(4-methyl-3-fluorophenyl)-3-pyridinyl]-benezenesulfonamide;
2,6-difluoro-4-[3-(3-methyl-4-bromophenyl)-3-pyridinyl]-benezenesulfonamide;
2,6-difluoro-4-[3-(4-methyl-3-bromophenyl)-3-pyridinyl]-benezenesulfonamide;
2,6-difluoro-4-[3-(3-methyl-4-trifluoromethylphenyl)-3-pyridinyl]-benezenesulfonamide;
2,6-difluoro-4-[3-(4-methyl-3-trifluoromethylphenyl)-3-pyridinyl]-benezenesulfonamide;
2,6-difluoro-4-[3-(3-methyl-4-trifluoromethoxyphenyl)-3-pyridinyl]-benezenesulfonamide;
2,6-difluoro-4-[3-(4-methyl-3-trifluoromethoxyphenyl)-3-pyridinyl]-benezenesulfonamide;
2,6-difluoro-4-[3-(3-cyano-4-methylphenyl)-3-pyridinyl]-benezenesulfonamide;
2,6-difluoro-4-[3-(4-cyano-3-methylphenyl)-3-pyridinyl]-benezenesulfonamide;
2,6-difluoro-4-[3-(3-chloro-4-methoxyphenyl)-3-pyridinyl]-benezenesulfonamide;
2,6-difluoro-4-[3-(4-chloro-3-methoxyphenyl)-3-pyridinyl]-benezenesulfonamide;
2,6-difluoro-4-[3-(2-methylpyridin-6-yl)-3-pyridinyl]-benezenesulfonamide;
2,6-difluoro-4-[3-(2-methylthiazol-4-yl)-3-pyridinyl]-benezenesulfonamide;
2,6-difluoro-4-[3-(4-methylthiazol-2-yl)-3-pyridinyl]-benezenesulfonamide;
2,6-difluoro-4-[3-(2-methylpyridin-3-yl)-3-pyridinyl]-benezenesulfonamide;
2,6-difluoro-4-[3-(2-methylpyridin-3-yl)-3-pyridinyl]-benezenesulfonamide;
2,6-difluoro-4-[3-(3-pyridinyl)-3-pyridinyl]-benezenesulfonamide;
2,6-difluoro-4-[3-(5-methylpyridin-3-yl)-3-pyridinyl]-benezenesulfonamide;
2,6-difluoro-4-[3-(2-methylpyridin-3-yl)-3-pyridinyl]-benezenesulfonamide;
2,6-difluoro-4-[3-cyclohexyl-3-pyridinyl]-benezenesulfonamide;
2,6-difluoro-4-[3-cyclopentyl-3-pyridinyl]-benezenesulfonamide;
4-[4-phenyl-3-pyridinyl]-2,6-difluorophenyl methyl sulfone;
4-[4-(3-chlorophenyl)-3-pyridinyl]-2,6-difluorophenyl methyl sulfone;
4-[4-(4-chlorophenyl)-3-pyridinyl]-2,6-difluorophenyl methyl sulfone;
4-[4-(3-bromophenyl)-3-pyridinyl]-2,6-difluorophenyl methyl sulfone;
4-[4-(4-bromophenyl)-3-pyridinyl]-2,6-difluorophenyl methyl sulfone;
4-[4-(3-fluorophenyl)-3-pyridinyl]-2,6-difluorophenyl methyl sulfone;
4-[4-(4-fluorophenyl)-3-pyridinyl]-2,6-difluorophenyl methyl sulfone;
4-[4-(3-methylphenyl)-3-pyridinyl]-2,6-difluorophenyl methyl sulfone;
4-[4-(4-methylphenyl)-3-pyridinyl]-2,6-difluorophenyl methyl sulfone;
4-[4-(3-cyanophenyl)-3-pyridinyl]-2,6-difluorophenyl methyl sulfone;
4-[4-(4-cyanophenyl)-3-pyridinyl]-2,6-difluorophenyl methyl sulfone;
4-[4-(3-trifluoromethylphenyl)-3-pyridinyl]-2,6-difluorophenyl methyl sulfone;
4-[4-(4-trifluoromethylphenyl)-3-pyridinyl]-2,6-difluorophenyl methyl sulfone;
4-[4-(3-trifluoromethoxyphenyl)-3-pyridinyl]-2,6-difluorophenyl methyl sulfone;
4-[4-(4-trifluoromethoxyphenyl)-3-pyridinyl]-2,6-difluorophenyl methyl sulfone;
4-[4-(3,4-dichlorophenyl)-3-pyridinyl]-2,6-difluorophenyl methyl sulfone;
4-[4-(3,4-dibromophenyl)-3-pyridinyl]-2,6-difluorophenyl methyl sulfone;
4-[4-(3,4-difluorophenyl)-3-pyridinyl]-2,6-difluorophenyl methyl sulfone;
4-[4-(3,5-dichlorophenyl)-3-pyridinyl]-2,6-difluorophenyl methyl sulfone;
4-[4-(3,5-dibromophenyl)-3-pyridinyl]-2,6-difluorophenyl methyl sulfone;
4-[4-(3,5-difluorophenyl)-3-pyridinyl]-2,6-difluorophenyl methyl sulfone;
4-[4-(3,4-dimethylphenyl)-3-pyridinyl]-2,6-difluorophenyl methyl sulfone;
4-[4-(3,5-dimethylphenyl)-3-pyridinyl]-2,6-difluorophenyl methyl sulfone;
4-[4-(3-methyl-4-chlorophenyl)-3-pyridinyl]-2,6-difluorophenyl methyl sulfone;
4-[4-(4-methyl-3-chlorophenyl)-3-pyridinyl]-2,6-difluorophenyl methyl sulfone;
4-[4-(3-methyl-4-fluorophenyl)-3-pyridinyl]-2,6-difluorophenyl methyl sulfone;
4-[4-(4-methyl-3-fluorophenyl)-3-pyridinyl]-2,6-difluorophenyl methyl sulfone;
4-[4-(3-methyl-4-bromophenyl)-3-pyridinyl]-2,6-difluorophenyl methyl sulfone;

4-[4-(4-methyl-3-bromophenyl)-3-pyridinyl]-2,6-difluorophenyl methyl sulfone;
4-[4-(3-methyl-4-trifluoromethylphenyl)-3-pyridinyl]-2,6-difluorophenyl methyl sulfone;
4-[4-(4-methyl-3-trifluoromethylphenyl)-3-pyridinyl]-2,6-difluorophenyl methyl sulfone;
4-[4-(3-methyl-4-trifluoromethoxyphenyl)-3-pyridinyl]-2,6-difluorophenyl methyl sulfone;
4-[4-(4-methyl-3-trifluoromethoxyphenyl)-3-pyridinyl]-2,6-difluorophenyl methyl sulfone;
4-[4-(3-cyano-4-methylphenyl)-3-pyridinyl]-2,6-difluorophenyl methyl sulfone;
4-[4-(4-cyano-3-methylphenyl)-3-pyridinyl]-2,6-difluorophenyl methyl sulfone;
4-[4-(3-chloro-4-methoxyphenyl)-3-pyridinyl]-2,6-difluorophenyl methyl sulfone;
4-[4-(4-chloro-3-methoxyphenyl)-3-pyridinyl]-2,6-difluorophenyl methyl sulfone;
4-[4-(2-methylpyridin-6-yl)-3-pyridinyl]-2,6-difluorophenyl methyl sulfone;
4-[4-(2-methylthiazol-4-yl)-3-pyridinyl]-2,6-difluorophenyl methyl sulfone;
4-[4-(4-methylthiazol-2-yl)-3-pyridinyl]-2,6-difluorophenyl methyl sulfone;
4-[4-(2-methylpyridin-3-yl)-3-pyridinyl]-2,6-difluorophenyl methyl sulfone;
4-[4-(2-methylpyridin-3-yl)-3-pyridinyl]-2,6-difluorophenyl methyl sulfone;
4-[4-(3-pyridinyl)-3-pyridinyl]-2,6-difluorophenyl methyl sulfone;
4-[4-(5-methylpyridin-3-yl)-3-pyridinyl]-2,6-difluorophenyl methyl sulfone;
4-[4-(2-methylpyridin-3-yl)-3-pyridinyl]-2,6-difluorophenyl methyl sulfone;
4-[4-cyclohexyl-3-pyridinyl]-2,6-difluorophenyl methyl sulfone;
4-[4-cyclopentyl-3-pyridinyl]-2,6-difluorophenyl methyl sulfone;
2,5-difluoro-4-[3-phenyl-2-pyridinyl]-benezenesulfonamide;
2,5-difluoro-4-[3-(3-chlorophenyl)-2-pyridinyl]-benezenesulfonamide;
2,5-difluoro-4-[3-(4-chlorophenyl)-2-pyridinyl]-benezenesulfonamide;
2,5-difluoro-4-[3-(3-bromophenyl)-2-pyridinyl]-benezenesulfonamide;
2,5-difluoro-4-[3-(4-bromophenyl)-2-pyridinyl]-benezenesulfonamide;
2,5-difluoro-4-[3-(3-fluorophenyl)-2-pyridinyl]-benezenesulfonamide;
2,5-difluoro-4-[3-(4-fluorophenyl)-2-pyridinyl]-benezenesulfonamide;
2,5-difluoro-4-[3-(3-methylphenyl)-2-pyridinyl]-benezenesulfonamide;
2,5-difluoro-4-[3-(4-methylphenyl)-2-pyridinyl]-benezenesulfonamide;
2,5-difluoro-4-[3-(3-cyanophenyl)-2-pyridinyl]-benezenesulfonamide;
2,5-difluoro-4-[3-(4-cyanophenyl)-2-pyridinyl]-benezenesulfonamide;
2,5-difluoro-4-[3-(3-trifluoromethylphenyl)-2-pyridinyl]-benezenesulfonamide;
2,5-difluoro-4-[3-(4-trifluoromethylphenyl)-2-pyridinyl]-benezenesulfonamide;
2,5-difluoro-4-[3-(3-trifluoromethoxyphenyl)-2-pyridinyl]-benezenesulfonamide;
2,5-difluoro-4-[3-(4-trifluoromethoxyphenyl)-2-pyridinyl]-benezenesulfonamide;
2,5-difluoro-4-[3-(3,4-dichlorophenyl)-2-pyridinyl]-benezenesulfonamide;
2,5-difluoro-4-[3-(3,4-dibromophenyl)-2-pyridinyl]-benezenesulfonamide;
2,5-difluoro-4-[3-(3,4-difluorophenyl)-2-pyridinyl]-benezenesulfonamide;
2,5-difluoro-4-[3-(3,5-dichlorophenyl)-2-pyridinyl]-benezenesulfonamide;
2,5-difluoro-4-[3-(3,5-dibromophenyl)-2-pyridinyl]-benezenesulfonamide;
2,5-difluoro-4-[3-(3,5-difluorophenyl)-2-pyridinyl]-benezenesulfonamide;
2,5-difluoro-4-[3-(3,4-dimethylphenyl)-2-pyridinyl]-benezenesulfonamide;
2,5-difluoro-4-[3-(3,5-dimethylphenyl)-2-pyridinyl]-benezenesulfonamide;
2,5-difluoro-4-[3-(3-methyl-4-chlorophenyl)-2-pyridinyl]-benezenesulfonamide;
2,5-difluoro-4-[3-(4-methyl-3-chlorophenyl)-2-pyridinyl]-benezenesulfonamide;
2,5-difluoro-4-[3-(3-methyl-4-fluorophenyl)-2-pyridinyl]-benezenesulfonamide;
2,5-difluoro-4-[3-(4-methyl-3-fluorophenyl)-2-pyridinyl]-benezenesulfonamide;
2,5-difluoro-4-[3-(3-methyl-4-bromophenyl)-2-pyridinyl]-benezenesulfonamide;
2,5-difluoro-4-[3-(4-methyl-3-bromophenyl)-2-pyridinyl]-benezenesulfonamide;
2,5-difluoro-4-[3-(3-methyl-4-trifluoromethylphenyl)-2-pyridinyl]-benezenesulfonamide;
2,5-difluoro-4-[3-(4-methyl-3-trifluoromethylphenyl)-2-pyridinyl]-benezenesulfonamide;
2,5-difluoro-4-[3-(3-methyl-4-trifluoromethoxyphenyl)-2-pyridinyl]-benezenesulfonamide;
2,5-difluoro-4-[3-(4-methyl-3-trifluoromethoxyphenyl)-2-pyridinyl]-benezenesulfonamide;
2,5-difluoro-4-[3-(3-cyano-4—methylphenyl)-2-pyridinyl]-benezenesulfonamide;
2,5-difluoro-4-[3-(4-cyano-3-methylphenyl)-2-pyridinyl]-benezenesulfonamide;
2,5-difluoro-4-[3-(3-chloro-4-methoxyphenyl)-2-pyridinyl]-benezenesulfonamide;
2,5-difluoro-4-[3-(4-chloro-3-methoxyphenyl)-2-pyridinyl]-benezenesulfonamide;
2,5-difluoro-4-[3-(2-methylpyridin-6-yl)-2-pyridinyl]-benezenesulfonamide;
2,5-difluoro-4-[3-(2-methylthiazol-4-yl)-2-pyridinyl]-benezenesulfonamide;
2,5-difluoro-4-[3-(4-methylthiazol-2-yl)-2-pyridinyl]-benezenesulfonamide;
2,5-difluoro-4-[3-(2-methylpyridin-3-yl)-2-pyridinyl]-benezenesulfonamide;
2,5-difluoro-4-[3-(2-methylpyridin-3-yl)-2-pyridinyl]-benezenesulfonamide;
2,5-difluoro-4-[3-(3-pyridinyl)-2-pyridinyl]-benezenesulfonamide;

2,5-difluoro-4-[3-(5-methylpyridin-3-yl)-2-pyridinyl]-benezenesulfonamide;
2,5-difluoro-4-[3-(2-methylpyridin-3-yl)-2-pyridinyl]-benezenesulfonamide;
2,5-difluoro-4-[3-cyclohexyl-2-pyridinyl]-benezenesulfonamide;
2,5-difluoro-4-[3-cyclopentyl-2-pyridinyl]-benezenesulfonamide;
2,5-difluoro-4-[3-phenyl-3-pyridinyl]-benezenesulfonamide;
2,5-difluoro-4-[3-(3-chlorophenyl)-3-pyridinyl]-benezenesulfonamide;
2,5-difluoro-4-[3-(4-chlorophenyl)-3-pyridinyl]-benezenesulfonamide;
2,5-difluoro-4-[3-(3-bromophenyl)-3-pyridinyl]-benezenesulfonamide;
2,5-difluoro-4-[3-(4-bromophenyl)-3-pyridinyl]-benezenesulfonamide;
2,5-difluoro-4-[3-(3-fluorophenyl)-3-pyridinyl]-benezenesulfonamide;
2,5-difluoro-4-[3-(4-fluorophenyl)-3-pyridinyl]-benezenesulfonamide;
2,5-difluoro-4-[3-(3-methylphenyl)-3-pyridinyl]-benezenesulfonamide;
2,5-difluoro-4-[3-(4-methylphenyl)-3-pyridinyl]-benezenesulfonamide;
2,5-difluoro-4-[3-(3-cyanophenyl)-3-pyridinyl]-benezenesulfonamide;
2,5-difluoro-4-[3-(4-cyanophenyl)-3-pyridinyl]-benezenesulfonamide;
2,5-difluoro-4-[3-(3-trifluoromethylphenyl)-3-pyridinyl]-benezenesulfonamide;
2,5-difluoro-4-[3-(4-trifluoromethylphenyl)-3-pyridinyl]-benezenesulfonamide;
2,5-difluoro-4-[3-(3-trifluoromethoxyphenyl)-3-pyridinyl]-benezenesulfonamide;
2,5-difluoro-4-[3-(4-trifluoromethoxyphenyl)-3-pyridinyl]-benezenesulfonamide;
2,5-difluoro-4-[3-(3,4-dichlorophenyl)-3-pyridinyl]-benezenesulfonamide;
2,5-difluoro-4-[3-(3,4-dibromophenyl)-3-pyridinyl]-benezenesulfonamide;
2,5-difluoro-4-[3-(3,4-difluorophenyl)-3-pyridinyl]-benezenesulfonamide;
2,5-difluoro-4-[3-(3,5-dichlorophenyl)-3-pyridinyl]-benezenesulfonamide;
2,5-difluoro-4-[3-(3,5-dibromophenyl)-3-pyridinyl]-benezenesulfonamide;
2,5-difluoro-4-[3-(3,5-difluorophenyl)-3-pyridinyl]-benezenesulfonamide;
2,5-difluoro-4-[3-(3,4-dimethylphenyl)-3-pyridinyl]-benezenesulfonamide;
2,5-difluoro-4-[3-(3,5-dimethylphenyl)-3-pyridinyl]-benezenesulfonamide;
2,5-difluoro-4-[3-(3-methyl-4-chlorophenyl)-3-pyridinyl]-benezenesulfonamide;
2,5-difluoro-4-[3-(4-methyl-3-chlorophenyl)-3-pyridinyl]-benezenesulfonamide;
2,5-difluoro-4-[3-(3-methyl-4-fluorophenyl)-3-pyridinyl]-benezenesulfonamide;
2,5-difluoro-4-[3-(4-methyl-3-fluorophenyl)-3-pyridinyl]-benezenesulfonamide;
2,5-difluoro-4-[3-(3-methyl-4-bromophenyl)-3-pyridinyl]-benezenesulfonamide;
2,5-difluoro-4-[3-(4-methyl-3-bromophenyl)-3-pyridinyl]-benezenesulfonamide;
2,5-difluoro-4-[3-(3-methyl-4-trifluoromethylphenyl)-3-pyridinyl]-benezenesulfonamide;
2,5-difluoro-4-[3-(4-methyl-3-trifluoromethylphenyl)-3-pyridinyl]-benezenesulfonamide;
2,5-difluoro-4-[3-(3-methyl-4-trifluoromethoxyphenyl)-3-pyridinyl]-benezenesulfonamide;
2,5-difluoro-4-[3-(4-methyl-3-trifluoromethoxyphenyl)-3-pyridinyl]-benezenesulfonamide;
2,5-difluoro-4-[3-(3-cyano-4-methylphenyl)-3-pyridinyl]-benezenesulfonamide;
2,5-difluoro-4-[3-(4-cyano-3-methylphenyl)-3-pyridinyl]-benezenesulfonamide;
2,5-difluoro-4-[3-(3-chloro-4-methoxyphenyl)-3-pyridinyl]-benezenesulfonamide;
2,5-difluoro-4-[3-(4-chloro-3-methoxyphenyl)-3-pyridinyl]-benezenesulfonamide;
2,5-difluoro-4-[3-(2-methylpyridin-6-yl)-3-pyridinyl]-benezenesulfonamide;
2,5-difluoro-4-[3-(2-methylthiazol-4-yl)-3-pyridinyl]-benezenesulfonamide;
2,5-difluoro-4-[3-(4-methylthiazol-2-yl)-3-pyridinyl]-benezenesulfonamide;
2,5-difluoro-4-[3-(2-methylpyridin-3-yl)-3-pyridinyl]-benezenesulfonamide;
2,5-difluoro-4-[3-(2-methylpyridin-3-yl)-3-pyridinyl]-benezenesulfonamide;
2,5-difluoro-4-[3-(3-pyridinyl)-3-pyridinyl]-benezenesulfonamide;
2,5-difluoro-4-[3-(5-methylpyridin-3-yl)-3-pyridinyl]-benezenesulfonamide;
2,5-difluoro-4-[3-(2-methylpyridin-3-yl)-3-pyridinyl]-benezenesulfonamide;
2,5-difluoro-4-[3-cyclohexyl-3-pyridinyl]-benezenesulfonamide;
2,5-difluoro-4-[3-cyclopentyl-3-pyridinyl]-benezenesulfonamide;
4-[4-phenyl-3-pyridinyl]-2,5-difluorophenyl methyl sulfone;
4-[4-(3-chlorophenyl)-3-pyridinyl]-2,5-difluorophenyl methyl sulfone;
4-[4-(4-chlorophenyl)-3-pyridinyl]-2,5-difluorophenyl methyl sulfone;
4-[4-(3-bromophenyl)-3-pyridinyl]-2,5-difluorophenyl methyl sulfone;
4-[4-(4-bromophenyl)-3-pyridinyl]-2,5-difluorophenyl methyl sulfone;
4-[4-(3-fluorophenyl)-3-pyridinyl]-2,5-difluorophenyl methyl sulfone;
4-[4-(4-fluorophenyl)-3-pyridinyl]-2,5-difluorophenyl methyl sulfone;
4-[4-(3-methylphenyl)-3-pyridinyl]-2,5-difluorophenyl methyl sulfone;
4-[4-(4-methylphenyl)-3-pyridinyl]-2,5-difluorophenyl methyl sulfone;
4-[4-(3-cyanophenyl)-3-pyridinyl]-2,5-difluorophenyl methyl sulfone;
4-[4-(4-cyanophenyl)-3-pyridinyl]-2,5-difluorophenyl methyl sulfone;

4-[4-(3-trifluoromethylphenyl)-3-pyridinyl]-2,5-difluorophenyl methyl sulfone;
4-[4-(4-trifluoromethylphenyl)-3-pyridinyl]-2,5-difluorophenyl methyl sulfone;
4-[4-(3-trifluoromethoxyphenyl)-3-pyridinyl]-2,5-difluorophenyl methyl sulfone;
4-[4-(4-trifluoromethoxyphenyl)-3-pyridinyl]-2,5-difluorophenyl methyl sulfone;
4-[4-(3,4-dichlorophenyl)-3-pyridinyl]-2,5-difluorophenyl methyl sulfone;
4-[4-(3,4-dibromophenyl)-3-pyridinyl]-2,5-difluorophenyl methyl sulfone;
4-[4-(3,4-difluorophenyl)-3-pyridinyl]-2,5-difluorophenyl methyl sulfone;
4-[4-(3,5-dichlorophenyl)-3-pyridinyl]-2,5-difluorophenyl methyl sulfone;
4-[4-(3,5-dibromophenyl)-3-pyridinyl]-2,5-difluorophenyl methyl sulfone;
4-[4-(3,5-difluorophenyl)-3-pyridinyl]-2,5-difluorophenyl methyl sulfone;
4-[4-(3,4-dimethylphenyl)-3-pyridinyl]-2,5-difluorophenyl methyl sulfone;
4-[4-(3,5-dimethylphenyl)-3-pyridinyl]-2,5-difluorophenyl methyl sulfone;
4-[4-(3-methyl-4-chlorophenyl)-3-pyridinyl]-2,5-difluorophenyl methyl sulfone;
4-[4-(4-methyl-3-chlorophenyl)-3-pyridinyl]-2,5-difluorophenyl methyl sulfone;
4-[4-(3-methyl-4-fluorophenyl)-3-pyridinyl]-2,5-difluorophenyl methyl sulfone;
4-[4-(4-methyl-3-fluorophenyl)-3-pyridinyl]-2,5-difluorophenyl methyl sulfone;
4-[4-(3-methyl-4-bromophenyl)-3-pyridinyl]-2,5-difluorophenyl methyl sulfone;
4-[4-(4-methyl-3-bromophenyl)-3-pyridinyl]-2,5-difluorophenyl methyl sulfone;
4-[4-(3-methyl-4-trifluoromethylphenyl)-3-pyridinyl]-2,5-difluorophenyl methyl sulfone;
4-[4-(4-methyl-3-trifluoromethylphenyl)-3-pyridinyl]-2,5-difluorophenyl methyl sulfone;
4-[4-(3-methyl-4-trifluoromethoxyphenyl)-3-pyridinyl]-2,5-difluorophenyl methyl sulfone;
4-[4-(4-methyl-3-trifluoromethoxyphenyl)-3-pyridinyl]-2,5-difluorophenyl methyl sulfone;
4-[4-(3-cyano-4-methylphenyl)-3-pyridinyl]-2,5-difluorophenyl methyl sulfone;
4-[4-(4-cyano-3-methylphenyl)-3-pyridinyl]-2,5-difluorophenyl methyl sulfone;
4-[4-(3-chloro-4-methoxyphenyl)-3-pyridinyl]-2,5-difluorophenyl methyl sulfone;
4-[4-(4-chloro-3-methoxyphenyl)-3-pyridinyl]-2,5-difluorophenyl methyl sulfone;
4-[4-(2-methylpyridin-6-yl)-3-pyridinyl]-2,5-difluorophenyl methyl sulfone;
4-[4-(2-methylthiazol-4-yl)-3-pyridinyl]-2,5-difluorophenyl methyl sulfone;
4-[4-(4-methylthiazol-2-yl)-3-pyridinyl]-2,5-difluorophenyl methyl sulfone;
4-[4-(2-methylpyridin-3-yl)-3-pyridinyl]-2,5-difluorophenyl methyl sulfone;
4-[4-(2-methylpyridin-3-yl)-3-pyridinyl]-2,5-difluorophenyl methyl sulfone;
4-[4-(3-pyridinyl)-3-pyridinyl]-2,5-difluorophenyl methyl sulfone;
4-[4-(5-methylpyridin-3-yl)-3-pyridinyl]-2,5-difluorophenyl methyl sulfone;
4-[4-(2-methylpyridin-3-yl)-3-pyridinyl]-2,5-difluorophenyl methyl sulfone;
4-[4-cyclohexyl-3-pyridinyl]-2,5-difluorophenyl methyl sulfone;
4-[4-cyclopentyl-3-pyridinyl]-2,5-difluorophenyl methyl sulfone;

and the pharmaceutically-acceptable salts, tautomers and prodrugs thereof.

Additional Compounds

Within Formula I there is another subclass of compounds of interest that includes, but is not limited to:

5-phenyl-4-[3,5-difluoro-4-(methylsulfonyl)phenyl]-2-(difluoromethyl)-1H-imidazole;
5-(3-chlorophenyl)-4-[3,5-difluoro-4-(methylsulfonyl)phenyl]-2-(difluoromethyl)-1H-imidazole;
5-(4-chlorophenyl)-4-[3,5-difluoro-4-(methylsulfonyl)phenyl]-2-(difluoromethyl)-1H-imidazole;
5-(3-bromophenyl)-4-[3,5-difluoro-4-(methylsulfonyl)phenyl]-2-(difluoromethyl)-1H-imidazole;
5-(4-bromophenyl)-4-[3,5-difluoro-4-(methylsulfonyl)phenyl]-2-(difluoromethyl)-1H-imidazole;
5-(3-fluorophenyl)-4-[3,5-difluoro-4-(methylsulfonyl)phenyl]-2-(difluoromethyl)-1H-imidazole;
5-(4-fluorophenyl)-4-[3,5-difluoro-4-(methylsulfonyl)phenyl]-2-(difluoromethyl)-1H-imidazole;
5-(3-methylphenyl)-4-[3,5-difluoro-4-(methylsulfonyl)phenyl]-2-(difluoromethyl)-1H-imidazole;
5-(4-methylphenyl)-4-[3,5-difluoro-4-(methylsulfonyl)phenyl]-2-(difluoromethyl)-1H-imidazole;
5-(3-cyanophenyl)-4-[3,5-difluoro-4-(methylsulfonyl)phenyl]-2-(difluoromethyl)-1H-imidazole;
5-(4-cyanophenyl)-4-[3,5-difluoro-4-(methylsulfonyl)phenyl]-2-(difluoromethyl)-1H-imidazole;
5-(3-trifluoromethylphenyl)-4-[3,5-difluoro-4-(methylsulfonyl)phenyl]-2-(difluoromethyl)-1H-imidazole;
5-(4-trifluoromethylphenyl)-4-[3,5-difluoro-4-(methylsulfonyl)phenyl]-2-(difluoromethyl)-1H-imidazole;
5-(3-trifluoromethoxyphenyl)-4-[3,5-difluoro-4-(methylsulfonyl)phenyl]-2-(difluoromethyl)-1H-imidazole;
5-(4-trifluoromethoxyphenyl)-4-[3,5-difluoro-4-(methylsulfonyl)phenyl]-2-(difluoromethyl)-1H-imidazole;
5-(3,4-dichlorophenyl)-4-[3,5-difluoro-4-(methylsulfonyl)phenyl]-2-(difluoromethyl)-1H-imidazole;
5-(3,4-dibromophenyl)-4-[3,5-difluoro-4-(methylsulfonyl)phenyl]-2-(difluoromethyl)-1H-imidazole;
5-(3,4-difluorophenyl)-4-[3,5-difluoro-4-(methylsulfonyl)phenyl]-2-(difluoromethyl)-1H-imidazole;
5-(3,5-dichlorophenyl)-4-[3,5-difluoro-4-(methylsulfonyl)phenyl]-2-(difluoromethyl)-1H-imidazole;
5-(3,5-dibromophenyl)-4-[3,5-difluoro-4-(methylsulfonyl)phenyl]-2-(difluoromethyl)-1H-imidazole;

5-(3,5-difluorophenyl)-4-[3,5-difluoro-4-(methylsulfonyl)phenyl]-2-(difluoromethyl)-1H-imidazole;

5-(3,4-dimethylphenyl)-4-[3,5-difluoro-4-(methylsulfonyl)phenyl]-2-(difluoromethyl)-1H-imidazole;

5-(3,5-dimethylphenyl)-4-[3,5-difluoro-4-(methylsulfonyl)phenyl]-2-(difluoromethyl)-1H-imidazole;

5-(3-methyl-4-chlorophenyl)-4-[3,5-difluoro-4-(methylsulfonyl)phenyl]-2-(difluoromethyl)-1H-imidazole;

5-(4-methyl-3-chlorophenyl)-4-[3,5-difluoro-4-(methylsulfonyl)phenyl]-2-(difluoromethyl)-1H-imidazole;

5-(3-methyl-4-fluorophenyl)-4-[3,5-difluoro-4-(methylsulfonyl)phenyl]-2-(difluoromethyl)-1H-imidazole;

5-(4-methyl-3-fluorophenyl)-4-[3,5-difluoro-4-(methylsulfonyl)phenyl]-2-(difluoromethyl)-1H-imidazole;

5-(3-methyl-4-bromophenyl)-4-[3,5-difluoro-4-(methylsulfonyl)phenyl]-2-(difluoromethyl)-1H-imidazole;

5-(4-methyl-3-bromophenyl)-4-[3,5-difluoro-4-(methylsulfonyl)phenyl]-2-(difluoromethyl)-1H-imidazole;

5-(3-methyl-4-trifluoromethylphenyl)-4-[3,5-difluoro-4-(methylsulfonyl)phenyl]-2-(difluoromethyl)-1H-imidazole;

5-(4-methyl-3-trifluoromethylphenyl)-4-[3,5-difluoro-4-(methylsulfonyl)phenyl]-2-(difluoromethyl)-1H-imidazole;

5-(3-methyl-4-trifluoromethoxyphenyl)-4-[3,5-difluoro-4-(methylsulfonyl)phenyl]-2-(difluoromethyl)-1H-imidazole;

5-(4-methyl-3-trifluoromethoxyphenyl)-4-[3,5-difluoro-4-(methylsulfonyl)phenyl]-2-(difluoromethyl)-1H-imidazole;

5-(3-cyano-4-methylphenyl)-4-[3,5-difluoro-4-(methylsulfonyl)phenyl]-2-(difluoromethyl)-1H-imidazole;

5-(4-cyano-3-methylphenyl)-4-[3,5-difluoro-4-(methylsulfonyl)phenyl]-2-(difluoromethyl)-1H-imidazole;

5-(3-chloro-4-methoxyphenyl)-4-[3,5-difluoro-4-(methylsulfonyl)phenyl]-2-(difluoromethyl)-1H-imidazole;

5-(4-chloro-3-methoxyphenyl)-4-[3,5-difluoro-4-(methylsulfonyl)phenyl]-2-(difluoromethyl)-1H-imidazole;

5-(2-methylpyridin-6-yl)-4-[3,5-difluoro-4-(methylsulfonyl)phenyl]-2-(difluoromethyl)-1H-imidazole;

5-(2-methylthiazol-4-yl)-4-[3,5-difluoro-4-(methylsulfonyl)phenyl]-2-(difluoromethyl)-1H-imidazole;

5-(4-methylthiazol-2-yl)-4-[3,5-difluoro-4-(methylsulfonyl)phenyl]-2-(difluoromethyl)-1H-imidazole;

5-(2-methylpyridin-3-yl)-4-[3,5-difluoro-4-(methylsulfonyl)phenyl]-2-(difluoromethyl)-1H-imidazole;

5-(2-methylpyridin-3-yl)-4-[3,5-difluoro-4-(methylsulfonyl)phenyl]-2-(difluoromethyl)-1H-imidazole;

5-(3-pyridinyl)-4-[3,5-difluoro-4-(methylsulfonyl)phenyl]-2-(difluoromethyl)-1H-imidazole;

5-(5-methylpyridin-3-yl)-4-[3,5-difluoro-4-(methylsulfonyl)phenyl]-2-(difluoromethyl)-1H-imidazole;

5-(2-methylpyridin-3-yl)-4-[3,5-difluoro-4-(methylsulfonyl)phenyl]-2-(difluoromethyl)-1H-imidazole;

5-cyclohexyl-4-[3,5-difluoro-4-(methylsulfonyl)phenyl]-2-(difluoromethyl)-1H-imidazole;

5-cyclopentyl-4-[3,5-difluoro-4-(methylsulfonyl)phenyl]-2-(difluoromethyl)-1H-imidazole;

5-phenyl-4-[3,6-difluoro-4-(methylsulfonyl)phenyl]-2-(difluoromethyl)-1H-imidazole;

5-phenyl-4-[3,5-difluoro-4-(methylsulfonyl)phenyl]-2-(trifluoromethyl)-1H-imidazole;

5-(3-chlorophenyl)-4-[3,5-difluoro-4-(methylsulfonyl)phenyl]-2-(trifluoromethyl)-1H-imidazole;

5-(4-chlorophenyl)-4-[3,5-difluoro-4-(methylsulfonyl)phenyl]-2-(trifluoromethyl)-1H-imidazole;

5-(3-bromophenyl)-4-[3,5-difluoro-4-(methylsulfonyl)phenyl]-2-(trifluoromethyl)-1H-imidazole;

5-(4-bromophenyl)-4-[3,5-difluoro-4-(methylsulfonyl)phenyl]-2-(trifluoromethyl)-1H-imidazole;

5-(2-fluorophenyl)-4-[3,5-difluoro-4-(methylsulfonyl)phenyl]-2-(trifluoromethyl)-1H-imidazole;

5-(4-fluorophenyl)-4-[3,5-difluoro-4-(methylsulfonyl)phenyl]-2-(trifluoromethyl)-1H-imidazole;

5-(3-methylphenyl)-4-[3,5-difluoro-4-(methylsulfonyl)phenyl]-2-(trifluoromethyl)-1H-imidazole;

5-(4-methylphenyl)-4-[3,5-difluoro-4-(methylsulfonyl)phenyl]-2-(trifluoromethyl)-1H-imidazole;

5-(3-cyanophenyl)-4-[3,5-difluoro-4-(methylsulfonyl)phenyl]-2-(trifluoromethyl)-1H-imidazole;

5-(4-cyanophenyl)-4-[3,5-difluoro-4-(methylsulfonyl)phenyl]-2-(trifluoromethyl)-1H-imidazole;

5-(3-trifluoromethylphenyl)-4-[3,5-difluoro-4-(methylsulfonyl)phenyl]-2-(trifluoromethyl)-1H-imidazole;

5-(4-trifluoromethylphenyl)-4-[3,5-difluoro-4-(methylsulfonyl)phenyl]-2-(trifluoromethyl)-1H-imidazole;

5-(3-trifluoromethoxyphenyl)-4-[3,5-difluoro-4-(methylsulfonyl)phenyl]-2-(trifluoromethyl)-1H-imidazole;

5-(4-trifluoromethoxyphenyl)-4-[3,5-difluoro-4-(methylsulfonyl)phenyl]-2-(trifluoromethyl)-1H-imidazole;

5-(3,4-dichlorophenyl)-4-[3,5-difluoro-4-(methylsulfonyl)phenyl]-2-(trifluoromethyl)-1H-imidazole;

5-(3,4-dibromophenyl)-4-[3,5-difluoro-4-(methylsulfonyl)phenyl]-2-(trifluoromethyl)-1H-imidazole;

5-(3,4-difluorophenyl)-4-[3,5-difluoro-4-(methylsulfonyl)phenyl]-2-(trifluoromethyl)-1H-imidazole;

5-(3,5-dichlorophenyl)-4-[3,5-difluoro-4-(methylsulfonyl)phenyl]-2-(trifluoromethyl)-1H-imidazole;

5-(3,5-dibromophenyl)-4-[3,5-difluoro-4-(methylsulfonyl)phenyl]-2-(trifluoromethyl)-1H-imidazole;

5-(3,5-difluorophenyl)-4-[3,5-difluoro-4-(methylsulfonyl)phenyl]-2-(trifluoromethyl)-1H-imidazole;

5-(3,4-dimethylphenyl)-4-[3,5-difluoro-4-(methylsulfonyl)phenyl]-2-(trifluoromethyl)-1H-imidazole;

5-(3,5-dimethylphenyl)-4-[3,5-difluoro-4-(methylsulfonyl)phenyl]-2-(trifluoromethyl)-1H-imidazole;

5-(3-methyl-4-chlorophenyl)-4-[3,5-difluoro-4-(methylsulfonyl)phenyl]-2-(trifluoromethyl)-1H-imidazole;

5-(4-methyl-3-chlorophenyl)-4-[3,5-difluoro-4-(methylsulfonyl)phenyl]-2-(trifluoromethyl)-1H-imidazole;

5-(3-methyl-4-fluorophenyl)-4-[3,5-difluoro-4-(methylsulfonyl)phenyl]-2-(trifluoromethyl)-1H-imidazole;

5-(4-methyl-2-fluorophenyl)-4-[3,5-difluoro-4-(methylsulfonyl)phenyl]-2-(trifluoromethyl)-1H-imidazole;

5-(3-methyl-4-bromophenyl)-4-[3,5-difluoro-4-(methylsulfonyl)phenyl]-2-(trifluoromethyl)-1H-imidazole;

5-(4-methyl-3-bromophenyl)-4-[3,5-difluoro-4-(methylsulfonyl)phenyl]-2-(trifluoromethyl)-1H-imidazole;

5-(3-methyl-4-trifluoromethylphenyl)-4-[3,5-difluoro-4-(methylsulfonyl)phenyl]-2-(trifluoromethyl)-1H-imidazole;

5-(4-methyl-3-trifluoromethylphenyl)-4-[3,5-difluoro-4-(methylsulfonyl)phenyl]-2-(trifluoromethyl)-1H-imidazole;

5-(3-methyl-4-trifluoromethoxyphenyl)-4-[3,5-difluoro-4-(methylsulfonyl)phenyl]-2-(trifluoromethyl)-1H-imidazole;

5-(4-methyl-3-trifluoromethoxyphenyl)-4-[3,5-difluoro-4-(methylsulfonyl)phenyl]-2-(trifluoromethyl)-1H-imidazole;

5-(3-cyano-4-methylphenyl)-4-[3,5-difluoro-4-(methylsulfonyl)phenyl]-2-(trifluoromethyl)-1H-imidazole;

5-(4-cyano-3-methylphenyl)-4-[3,5-difluoro-4-(methylsulfonyl)phenyl]-2-(trifluoromethyl)-1H-imidazole;

5-(3-chloro-4-methoxyphenyl)-4-[3,5-difluoro-4-(methylsulfonyl)phenyl]-2-(trifluoromethyl)-1H-imidazole;

5-(4-chloro-3-methoxyphenyl)-4-[3,5-difluoro-4-(methylsulfonyl)phenyl]-2-(trifluoromethyl)-1H-imidazole;

5-(2-methylpyridin-6-yl)-4-[3,5-difluoro-4-(methylsulfonyl)phenyl]-2-(trifluoromethyl)-1H-imidazole;

5-(2-methylthiazol-4-yl)-4-[3,5-difluoro-4-(methylsulfonyl)phenyl]-2-(trifluoromethyl)-1H-imidazole;

5-(4-methylthiazol-2-yl)-4-[3,5-difluoro-4-(methylsulfonyl)phenyl]-2-(trifluoromethyl)-1H-imidazole;

5-(2-methylpyridin-3-yl)-4-[3,5-difluoro-4-(methylsulfonyl)phenyl]-2-(trifluoromethyl)-1H-imidazole;

5-(2-methylpyridin-3-yl)-4-[3,5-difluoro-4-(methylsulfonyl)phenyl]-2-(trifluoromethyl)-1H-imidazole;

5-(3-pyridinyl)-4-[3,5-difluoro-4-(methylsulfonyl)phenyl]-2-(trifluoromethyl)-1H-imidazole;

5-(5-methylpyridin-3-yl)-4-[3,5-difluoro-4-(methylsulfonyl)phenyl]-2-(trifluoromethyl)-1H-imidazole;

5-(2-methylpyridin-3-yl)-4-[3,5-difluoro-4-(methylsulfonyl)phenyl]-2-(trifluoromethyl)-1H-imidazole;

5-cyclohexyl-4-[3,5-difluoro-4-(methylsulfonyl)phenyl]-2-(trifluoromethyl)-1H-imidazole;

5-cyclopentyl-4-[3,5-difluoro-4-(methylsulfonyl)phenyl]-2-(trifluoromethyl)-1H-imidazole;

5-(3-chlorophenyl)-4-[3,6-difluoro-4-(methylsulfonyl)phenyl]-2-(difluoromethyl)-1H-imidazole;

5-(4-chlorophenyl)-4-[3,6-difluoro-4-(methylsulfonyl)phenyl]-2-(difluoromethyl)-1H-imidazole;

5-(3-bromophenyl)-4-[3,6-difluoro-4-(methylsulfonyl)phenyl]-2-(difluoromethyl)-1H-imidazole;

5-(4-bromophenyl)-4-[3,6-difluoro-4-(methylsulfonyl)phenyl]-2-(difluoromethyl)-1H-imidazole;

5-(3-fluorophenyl)-4-[3,6-difluoro-4-(methylsulfonyl)phenyl]-2-(difluoromethyl)-1H-imidazole;

5-(4-fluorophenyl)-4-[3,6-difluoro-4-(methylsulfonyl)phenyl]-2-(difluoromethyl)-1H-imidazole;

5-(3-methylphenyl)-4-[3,6-difluoro-4-(methylsulfonyl)phenyl]-2-(difluoromethyl)-1H-imidazole;

5-(4-methylphenyl)-4-[3,6-difluoro-4-(methylsulfonyl)phenyl]-2-(difluoromethyl)-1H-imidazole;

5-(3-cyanophenyl)-4-[3,6-difluoro-4-(methylsulfonyl)phenyl]-2-(difluoromethyl)-1H-imidazole;

5-(4-cyanophenyl)-4-[3,6-difluoro-4-(methylsulfonyl)phenyl]-2-(difluoromethyl)-1H-imidazole;

5-(3-trifluoromethylphenyl)-4-[3,6-difluoro-4-(methylsulfonyl)phenyl]-2-(difluoromethyl)-1H-imidazole;

5-(4-trifluoromethylphenyl)-4-[3,6-difluoro-4-(methylsulfonyl)phenyl]-2-(difluoromethyl)-1H-imidazole;

5-(3-trifluoromethoxyphenyl)-4-[3,6-difluoro-4-(methylsulfonyl)phenyl]-2-(difluoromethyl)-1H-imidazole;

5-(4-trifluoromethoxyphenyl)-4-[3,6-difluoro-4-(methylsulfonyl)phenyl]-2-(difluoromethyl)-1H-imidazole;

5-(3,4-dichlorophenyl)-4-[3,6-difluoro-4-(methylsulfonyl)phenyl]-2-(difluoromethyl)-1H-imidazole;

5-(3,4-dibromophenyl)-4-[3,6-difluoro-4-(methylsulfonyl)phenyl]-2-(difluoromethyl)-1H-imidazole;

5-(3,4-difluorophenyl)-4-[3,6-difluoro-4-(methylsulfonyl)phenyl]-2-(difluoromethyl)-1H-imidazole;

5-(3,5-dichlorophenyl)-4-[3,6-difluoro-4-(methylsulfonyl)phenyl]-2-(difluoromethyl)-1H-imidazole;

5-(3,5-dibromophenyl)-4-[3,6-difluoro-4-(methylsulfonyl)phenyl]-2-(difluoromethyl)-1H-imidazole;

5-(3,5-difluorophenyl)-4-[3,6-difluoro-4-(methylsulfonyl)phenyl]-2-(difluoromethyl)-1H-imidazole;

5-(3,4-dimethylphenyl)-4-[3,6-difluoro-4-(methylsulfonyl)phenyl]-2-(difluoromethyl)-1H-imidazole;

5-(3,5-dimethylphenyl)-4-[3,6-difluoro-4-(methylsulfonyl)phenyl]-2-(difluoromethyl)-1H-imidazole;

5-(3-methyl-4-chlorophenyl)-4-[3,6-difluoro-4-(methylsulfonyl)phenyl]-2-(difluoromethyl)-1H-imidazole;

5-(4-methyl-3-chlorophenyl)-4-[3,6-difluoro-4-(methylsulfonyl)phenyl]-2-(difluoromethyl)-1H-imidazole;

5-(3-methyl-4-fluorophenyl)-4-[3,6-difluoro-4-(methylsulfonyl)phenyl]-2-(difluoromethyl)-1H-imidazole;

5-(4-methyl-3-fluorophenyl)-4-[3,6-difluoro-4-(methylsulfonyl)phenyl]-2-(difluoromethyl)-1H-imidazole;

5-(3-methyl-4-bromophenyl)-4-[3,6-difluoro-4-(methylsulfonyl)phenyl]-2-(difluoromethyl)-1H-imidazole;

5-(4-methyl-3-bromophenyl)-4-[3,6-difluoro-4-(methylsulfonyl)phenyl]-2-(difluoromethyl)-1H-imidazole;

5-(3-methyl-4-trifluoromethylphenyl)-4-[3,6-difluoro-4-(methylsulfonyl)phenyl]-2-(difluoromethyl)-1H-imidazole;

5-(4-methyl-3-trifluoromethylphenyl)-4-[3,6-difluoro-4-(methylsulfonyl)phenyl]-2-(difluoromethyl)-1H-imidazole;

5-(3-methyl-4-trifluoromethoxyphenyl)-4-[3,6-difluoro-4-(methylsulfonyl)phenyl]-2-(difluoromethyl)-1H-imidazole;

5-(4-methyl-3-trifluoromethoxyphenyl)-4-[3,6-difluoro-4-(methylsulfonyl)phenyl]-2-(difluoromethyl)-1H-imidazole;

5-(3-cyano-4-methylphenyl)-4-[3,6-difluoro-4-(methylsulfonyl)phenyl]-2-(difluoromethyl)-1H-imidazole;

5-(4-cyano-3-methylphenyl)-4-[3,6-difluoro-4-(methylsulfonyl)phenyl]-2-(difluoromethyl)-1H-imidazole;

5-(3-chloro-4-methoxyphenyl)-4-[3,6-difluoro-4-(methylsulfonyl)phenyl]-2-(difluoromethyl)-1H-imidazole;

5-(4-chloro-3-methoxyphenyl)-4-[3,6-difluoro-4-(methylsulfonyl)phenyl]-2-(difluoromethyl)-1H-imidazole;

5-(2-methylpyridin-6-yl)-4-[3,6-difluoro-4-(methylsulfonyl)phenyl]-2-(difluoromethyl)-1H-imidazole;

5-(2-methylthiazol-4-yl)-4-[3,6-difluoro-4-(methylsulfonyl)phenyl]-2-(difluoromethyl)-1H-imidazole;

5-(4-methylthiazol-2-yl)-4-[3,6-difluoro-4-(methylsulfonyl)phenyl]-2-(difluoromethyl)-1H-imidazole;

5-(2-methylpyridin-3-yl)-4-[3,6-difluoro-4-(methylsulfonyl)phenyl]-2-(difluoromethyl)-1H-imidazole;

5-(2-methylpyridin-3-yl)-4-[3,6-difluoro-4-(methylsulfonyl)phenyl]-2-(difluoromethyl)-1H-imidazole;

5-(3-pyridinyl)-4-[3,6-difluoro-4-(methylsulfonyl)phenyl]-2-(difluoromethyl)-1H-imidazole;

5-(5-methylpyridin-3-yl)-4-[3,6-difluoro-4-(methylsulfonyl)phenyl]-2-(difluoromethyl)-1H-imidazole;

5-(2-methylpyridin-3-yl)-4-[3,6-difluoro-4-(methylsulfonyl)phenyl]-2-(difluoromethyl)-1H-imidazole;

5-cyclohexyl-4-[3,6-difluoro-4-(methylsulfonyl)phenyl]-2-(difluoromethyl)-1H-imidazole;

5-cyclopentyl-4-[3,6-difluoro-4-(methylsulfonyl)phenyl]-2-(difluoromethyl)-1H-imidazole;

5-phenyl-4-[3,6-difluoro-4-(methylsulfonyl)phenyl]-2-(trifluoromethyl)-1H-imidazole;

5-(3-chlorophenyl)-4-[3,6-difluoro-4-(methylsulfonyl)phenyl]-2-(trifluoromethyl)-1H-imidazole;

5-(4-chlorophenyl)-4-[3,6-difluoro-4-(methylsulfonyl)phenyl]-2-(trifluoromethyl)-1H-imidazole;

5-(3-bromophenyl)-4-[3,6-difluoro-4-(methylsulfonyl)phenyl]-2-(trifluoromethyl)-1H-imidazole;

5-(4-bromophenyl)-4-[3,6-difluoro-4-(methylsulfonyl)phenyl]-2-(trifluoromethyl)-1H-imidazole;

5-(2-fluorophenyl)-4-[3,6-difluoro-4-(methylsulfonyl)phenyl]-2-(trifluoromethyl)-1H-imidazole;

5-(4-fluorophenyl)-4-[3,6-difluoro-4-(methylsulfonyl)phenyl]-2-(trifluoromethyl)-1H-imidazole;

5-(3-methylphenyl)-4-[3,6-difluoro-4-(methylsulfonyl)phenyl]-2-(trifluoromethyl)-1H-imidazole;

5-(4-methylphenyl)-4-[3,6-difluoro-4-(methylsulfonyl)phenyl]-2-(trifluoromethyl)-1H-imidazole;

5-(3-cyanophenyl)-4-[3,6-difluoro-4-(methylsulfonyl)phenyl]-2-(trifluoromethyl)-1H-imidazole;

5-(4-cyanophenyl)-4-[3,6-difluoro-4-(methylsulfonyl)phenyl]-2-(trifluoromethyl)-1H-imidazole;

5-(3-trifluoromethylphenyl)-4-[3,6-difluoro-4-(methylsulfonyl)phenyl]-2-(trifluoromethyl)-1H-imidazole;

5-(4-trifluoromethylphenyl)-4-[3,6-difluoro-4-(methylsulfonyl)phenyl]-2-(trifluoromethyl)-1H-imidazole;

5-(3-trifluoromethoxyphenyl)-4-[3,6-difluoro-4-(methylsulfonyl)phenyl]-2-(trifluoromethyl)-1H-imidazole;

5-(4-trifluoromethoxyphenyl)-4-[3,6-difluoro-4-(methylsulfonyl)phenyl]-2-(trifluoromethyl)-1H-imidazole;

5-(3,4-dichlorophenyl)-4-[3,6-difluoro-4-(methylsulfonyl)phenyl]-2-(trifluoromethyl)-1H-imidazole;

5-(3,4-dibromophenyl)-4-[3,6-difluoro-4-(methylsulfonyl)phenyl]-2-(trifluoromethyl)-1H-imidazole;

5-(3,4-difluorophenyl)-4-[3,6-difluoro-4-(methylsulfonyl)phenyl]-2-(trifluoromethyl)-1H-imidazole;

5-(3,5-dichlorophenyl)-4-[3,6-difluoro-4-(methylsulfonyl)phenyl]-2-(trifluoromethyl)-1H-imidazole;

5-(3,5-dibromophenyl)-4-[3,6-difluoro-4-(methylsulfonyl)phenyl]-2-(trifluoromethyl)-1H-imidazole;

5-(3,6-difluorophenyl)-4-[3,6-difluoro-4-(methylsulfonyl)phenyl]-2-(trifluoromethyl)-1H-imidazole;

5-(3,4-dimethylphenyl)-4-[3,6-difluoro-4-(methylsulfonyl)phenyl]-2-(trifluoromethyl)-1H-imidazole;

5-(3,5-dimethylphenyl)-4-[3,6-difluoro-4-(methylsulfonyl)phenyl]-2-(trifluoromethyl)-1H-imidazole;

5-(3-methyl-4-chlorophenyl)-4-[3,6-difluoro-4-(methylsulfonyl)phenyl]-2-(trifluoromethyl)-1H-imidazole;

5-(4-methyl-3-chlorophenyl)-4-[3,6-difluoro-4-(methylsulfonyl)phenyl]-2-(trifluoromethyl)-1H-imidazole;

5-(3-methyl-4-fluorophenyl)-4-[3,6-difluoro-4-(methylsulfonyl)phenyl]-2-(trifluoromethyl)-1H-imidazole;

5-(4-methyl-2-fluorophenyl)-4-[3,6-difluoro-4-(methylsulfonyl)phenyl]-2-(trifluoromethyl)-1H-imidazole;

5-(3-methyl-4-bromophenyl)-4-[3,6-difluoro-4-(methylsulfonyl)phenyl]-2-(trifluoromethyl)-1H-imidazole;

5-(4-methyl-3-bromophenyl)-4-[3,6-difluoro-4-(methylsulfonyl)phenyl]-2-(trifluoromethyl)-1H-imidazole;

5-(3-methyl-4-trifluoromethylphenyl)-4-[3,6-difluoro-4-(methylsulfonyl)phenyl]-2-(trifluoromethyl)-1H-imidazole;

5-(4-methyl-3-trifluoromethylphenyl)-4-[3,6-difluoro-4-(methylsulfonyl)phenyl]-2-(trifluoromethyl)-1H-imidazole;

5-(3-methyl-4-trifluoromethoxyphenyl)-4-[3,6-difluoro-4-(methylsulfonyl)phenyl]-2-(trifluoromethyl)-1H-imidazole;

5-(4-methyl-3-trifluoromethoxyphenyl)-4-[3,6-difluoro-4-(methylsulfonyl)phenyl]-2-(trifluoromethyl)-1H-imidazole;

5-(3-cyano-4-methylphenyl)-4-[3,6-difluoro-4-(methylsulfonyl)phenyl]-2-(trifluoromethyl)-1H-imidazole;

5-(4-cyano-3-methylphenyl)-4-[3,6-difluoro-4-(methylsulfonyl)phenyl]-2-(trifluoromethyl)-1H-imidazole;

5-(3-chloro-4-methoxyphenyl)-4-[3,6-difluoro-4-(methylsulfonyl)phenyl]-2-(trifluoromethyl)-1H-imidazole;

5-(4-chloro-3-methoxyphenyl)-4-[3,6-difluoro-4-(methylsulfonyl)phenyl]-2-(trifluoromethyl)-1H-imidazole;

5-(2-methylpyridin-6-yl)-4-[3,6-difluoro-4-(methylsulfonyl)phenyl]-2-(trifluoromethyl)-1H-imidazole;

5-(2-methylthiazol-4-yl)-4-[3,6-difluoro-4-(methylsulfonyl)phenyl]-2-(trifluoromethyl)-1H-imidazole;

5-(4-methylthiazol-2-yl)-4-[3,6-difluoro-4-(methylsulfonyl)phenyl]-2-(trifluoromethyl)-1H-imidazole;

5-(2-methylpyridin-3-yl)-4-[3,6-difluoro-4-(methylsulfonyl)phenyl]-2-(trifluoromethyl)-1H-imidazole;

5-(2-methylpyridin-3-yl)-4-[3,6-difluoro-4-(methylsulfonyl)phenyl]-2-(trifluoromethyl)-1H-imidazole;

5-(3-pyridinyl)-4-[3,6-difluoro-4-(methylsulfonyl)phenyl]-2-(trifluoromethyl)-1H-imidazole;

5-(5-methylpyridin-3-yl)-4-[3,6-difluoro-4-(methylsulfonyl)phenyl]-2-(trifluoromethyl)-1H-imidazole;

5-(2-methylpyridin-3-yl)-4-[3,6-difluoro-4-(methylsulfonyl)phenyl]-2-(trifluoromethyl)-1H-imidazole;

5-cyclohexyl-4-[3,6-difluoro-4-(methylsulfonyl)phenyl]-2-(trifluoromethyl)-1H-imidazole;

5-cyclopentyl-4-[3,6-difluoro-4-(methylsulfonyl)phenyl]-2-(trifluoromethyl)-1H-imidazole;

and the pharmaceutically-acceptable salts, tautomers and prodrugs thereof.

Within Formula I there is another subclass or coumpounds of interest that includes, but is not limited to:

3-phenyl-4-[3,5-difluoro-4-(methylsulfonyl)phenyl]-1,3-oxazol-2 (3H)-one;

3-(3-chlorophenyl)-4-[3,5-difluoro-4-(methylsulfonyl)phenyl]-1,3-oxazol-2 (3H)-one;

3-(4-chlorophenyl)-4-[3,5-difluoro-4-(methylsulfonyl)phenyl]-1,3-oxazol-2 (3H)-one;

3-(3-bromophenyl)-4-[3,5-difluoro-4-(methylsulfonyl)phenyl]-1,3-oxazol-2 (3H)-one;

3-(4-bromophenyl)-4-[3,5-difluoro-4-(methylsulfonyl)phenyl]-1,3-oxazol-2 (3H)-one;

3-(3-fluorophenyl)-4-[3,5-difluoro-4-(methylsulfonyl)phenyl]-1,3-oxazol-2 (3H)-one;

3-(4-fluorophenyl)-4-[3,5-difluoro-4-(methylsulfonyl)phenyl]-1,3-oxazol-2 (3H)-one;

3-(3-methylphenyl)-4-[3,5-difluoro-4-(methylsulfonyl)phenyl]-1,3-oxazol-2 (3H)-one;

3-(4-methylphenyl)-4-[3,5-difluoro-4-(methylsulfonyl)phenyl]-1,3-oxazol-2 (3H)-one;

3-(3-cyanophenyl)-4-[3,5-difluoro-4-(methylsulfonyl)phenyl]-1,3-oxazol-2 (3H)-one;

3-(4-cyanophenyl)-4-[3,5-difluoro-4-(methylsulfonyl)phenyl]-1,3-oxazol-2 (3H)-one;

3-(3-trifluoromethylphenyl)-4-[3,5-difluoro-4-(methylsulfonyl)phenyl]-1,3-oxazol-2 (3H)-one;

3-(4-trifluoromethylphenyl)-4-[3,5-difluoro-4-(methylsulfonyl)phenyl]-1,3-oxazol-2 (3H)-one;

3-(3-trifluoromethoxyphenyl)-4-[3,5-difluoro-4-(methylsulfonyl)phenyl]-1,3-oxazol-2 (3H)-one;

3-(4-trifluoromethoxyphenyl)-4-[3,5-difluoro-4-(methylsulfonyl)phenyl]-1,3-oxazol-2 (3H)-one;

3-(3,4-dichlorophenyl)-4-[3,5-difluoro-4-(methylsulfonyl)phenyl]-1,3-oxazol-2 (3H)-one;

3-(3,4-dibromophenyl)-4-[3,5-difluoro-4-(methylsulfonyl)phenyl]-1,3-oxazol-2 (3H)-one;

3-(3,4-difluorophenyl)-4-[3,5-difluoro-4-(methylsulfonyl)phenyl]-1,3-oxazol-2 (3H)-one;

3-(3,5-dichlorophenyl)-4-[3,5-difluoro-4-(methylsulfonyl)phenyl]-1,3-oxazol-2 (3H)-one;

3-(3,5-dibromophenyl)-4-[3,5-difluoro-4-(methylsulfonyl)phenyl]-1,3-oxazol-2 (3H)-one;

3-(3,5-difluorophenyl)-4-[3,5-difluoro-4-(methylsulfonyl)phenyl]-1,3-oxazol-2 (3H)-one;

3-(3,4-dimethylphenyl)-4-[3,5-difluoro-4-(methylsulfonyl)phenyl]-1,3-oxazol-2 (3H)-one;

3-(3,5-dimethylphenyl)-4-[3,5-difluoro-4-(methylsulfonyl)phenyl]-1,3-oxazol-2 (3H)-one;

3-(3-methyl-4-chlorophenyl)-4-[3,5-difluoro-4-(methylsulfonyl)phenyl]-1,3-oxazol-2 (3H)-one;

3-(4-methyl-3-chlorophenyl)-4-[3,5-difluoro-4-(methylsulfonyl)phenyl]-1,3-oxazol-2 (3H)-one;

3-(3-methyl-4-fluorophenyl)-4-[3,5-difluoro-4-(methylsulfonyl)phenyl]-1,3-oxazol-2 (3H)-one;

3-(4-methyl-3-fluorophenyl)-4-[3,5-difluoro-4-(methylsulfonyl)phenyl]-1,3-oxazol-2 (3H)-one;

3-(3-methyl-4-bromophenyl)-4-[3,5-difluoro-4-(methylsulfonyl)phenyl]-1,3-oxazol-2 (3H)-one;

3-(4-methyl-3-bromophenyl)-4-[3,5-difluoro-4-(methylsulfonyl)phenyl]-1,3-oxazol-2 (3H)-one;

3-(3-methyl-4-trifluoromethylphenyl)-4-[3,5-difluoro-4-(methylsulfonyl)phenyl]-1,3-oxazol-2 (3H)-one;

3-(4-methyl-3-trifluoromethylphenyl)-4-[3,5-difluoro-4-(methylsulfonyl)phenyl]-1,3-oxazol-2 (3H)-one;

3-(3-methyl-4-trifluoromethoxyphenyl)-4-[3,5-difluoro-4-(methylsulfonyl)phenyl]-1,3-oxazol-2 (3H)-one;

3-(4-methyl-3-trifluoromethoxyphenyl)-4-[3,5-difluoro-4-(methylsulfonyl)phenyl]-1,3-oxazol-2 (3H)-one;

3-(3-cyano-4-methylphenyl)-4-[3,5-difluoro-4-(methylsulfonyl)phenyl]-1,3-oxazol-2 (3H)-one;

3-(4-cyano-3-methylphenyl)-4-[3,5-difluoro-4-(methylsulfonyl)phenyl]-1,3-oxazol-2 (3H)-one;

3-(3-chloro-4-methoxyphenyl)-4-[3,5-difluoro-4-(methylsulfonyl)phenyl]-1,3-oxazol-2 (3H)-one;

3-(4-chloro-3-methoxyphenyl)-4-[3,5-difluoro-4-(methylsulfonyl)phenyl]-1,3-oxazol-2 (3H)-one;

3-(2-methylpyridin-6-yl)-4-[3,5-difluoro-4-(methylsulfonyl)phenyl]-1,3-oxazol-2 (3H)-one;

3-(2-methylthiazol-4-yl)-4-[3,5-difluoro-4-(methylsulfonyl)phenyl]-1,3-oxazol-2 (3H)-one;

3-(4-methylthiazol-2-yl)-4-[3,5-difluoro-4-(methylsulfonyl)phenyl]-1,3-oxazol-2 (3H)-one;

3-(2-methylpyridin-3-yl)-4-[3,5-difluoro-4-(methylsulfonyl)phenyl]-1,3-oxazol-2 (3H)-one;

3-(2-methylpyridin-3-yl)-4-[3,5-difluoro-4-(methylsulfonyl)phenyl]-1,3-oxazol-2 (3H)-one;

3-(3-pyridinyl)-4-[3,5-difluoro-4-(methylsulfonyl)phenyl]-1,3-oxazol-2 (3H)-one;

3-(5-methylpyridin-3-yl)-4-[3,5-difluoro-4-(methylsulfonyl)phenyl]-1,3-oxazol-2 (3H)-one;

3-(2-methylpyridin-3-yl)-4-[3,5-difluoro-4-(methylsulfonyl)phenyl]-1,3-oxazol-2 (3H)-one;

3-cyclohexyl-4-[3,5-difluoro-4-(methylsulfonyl)phenyl]-1,3-oxazol-2 (3H)-one;

3-cyclopentyl-4-[3,5-difluoro-4-(methylsulfonyl)phenyl]-1,3-oxazol-2 (3H)-one;

2,6-difluoro-4-[3-2-oxo-2,3-dihydro-1,3-oxazol-1-4-yl]benzenesulfonamide;

2,6-difluoro-4-[3-(3-chlorophenyl)-2-oxo-2,3-dihydro-1,3-oxazol-4-yl]benzenesulfonamide;

2,6-difluoro-4-[3-(4-chlorophenyl)-2-oxo-2,3-dihydro-1,3-oxazol-4-yl]benzenesulfonamide;

2,6-difluoro-4-[3-(3-bromophenyl)-2-oxo-2,3-dihydro-1,3-oxazol-4-yl]benzenesulfonamide;

2,6-difluoro-4-[3-(4-bromophenyl)-2-oxo-2,3-dihydro-1,3-oxazol-4-yl]benzenesulfonamide;

2,6-difluoro-4-[3-(3-fluorophenyl)-2-oxo-2,3-dihydro-1,3-oxazol-4-yl]benzenesulfonamide;

2,6-difluoro-4-[3-(4-fluorophenyl)-2-oxo-2,3-dihydro-> oxazol-4-yl]benzenesulfonamide;

2,6-difluoro-4-[3-(3-methylphenyl)-4-[3-fluoro-4-(methylsulfonyl)phenyl]-1,3-oxazol-2 (3H)-one;

2,6-difluoro-4-[3-(4-methylphenyl)-2-oxo-2,3-dihydro-1,3-oxazol-4-yl]benzenesulfonamide;

2,6-difluoro-4-[3-(3-cyanophenyl)-2-oxo-2,3-dihydro-1,3-oxazol-4-yl]benzenesulfonamide;

2,6-difluoro-4-[3-(4-cyanophenyl)-2-oxo-2,3-dihydro-1,3-oxazol-4-yl]benzenesulfonamide;

2,6-difluoro-4-[3-(3-trifluoromethylphenyl)-2-oxo-2,3-dihydro-1,3-oxazol-4-yl]benzenesulfonamide;

2,6-difluoro-4-[3-(4-trifluoromethylphenyl)-2-oxo-2,3-dihydro-1,3-oxazol-4-yl]benzenesulfonamide;

2,6-difluoro-4-[3-(3-trifluoromethoxyphenyl)-2-oxo-2,3-dihydro-1,3-oxazol-4-yl]benzenesulfonamide;

2,6-difluoro-4-[3-(4-trifluoromethoxyphenyl)-2-oxo-2,3-dihydro-1,3-oxazol-4-yl]benzenesulfonamide;

2,6-difluoro-4-[3-(3,4-dichlorophenyl)-2-oxo-2,3-dihydro-1,3-oxazol-4-yl]benzenesulfonamide;

2,6-difluoro-4-[3-(3,4-dibromophenyl)-2-oxo-23-dihydro-1,3-oxazol-4-yl]benzenesulfonamide;

2,6-difluoro-4-[3-(3,4-difluorophenyl)-2-oxo-2,3-dihydro-1,3-oxazol-4-yl]benzenesulfonamide;

2,6-d±fluoro-4-[3-(3,5-dichlorophenyl)-2-oxo-2,3-dihydro-1,3-oxazol-4-yl]benzenesulfonamide;

2,6-difluoro-4-[3-(3,5-dibromophenyl)-2-oxo-2,3-dihydro-1,3-oxazol-4-yl]benzenesulfonamide;

2,6-difluoro-4-[3-(3,5-difluorophenyl)-2-oxo-2,3-dihydro-1,3-oxazol-4-yl]benzenesulfonamide;

2,6-difluoro-4-[3-(3,4-dimethylphenyl)-2-oxo-2,3-dihydro-1,3-oxazol-4-yl]benzenesulfonamide;

2,6-difluoro-4-[3-(3,5-dimethylphenyl)-2-oxo-2,3-dihydro-1,3-oxazol-4-yl]benzenesulfonamide;

2,6-difluoro-4-[3-(3-methyl-4-chlorophenyl)-2-oxo-23 dihydro-1,3-oxazol-4-yl]benzenesulfonamide;

2,6-difluoro-4-[3-(4-methyl-3-chlorophenyl-2-oxo-2,3 dihydro-1,3-oxazol-4-yl]benzenesulfonamide;

2,6-difluoro-4-[3-(3-methyl-4-fluorophenyl)- 2-oxo-2,3-dihydro-1,3-oxazol-4-yl]benzenesulfonamide;

2,6-difluoro-4-[3-(4-methyl-3-fluorophenyl-2-oxo-2,3 dihydro-1,3-oxazol-4-yl]benzenesulfonamide;

2,6-difluoro-4-[3-(3-methyl-4-bromophenyl)-2-oxo-2,3-dihydro-1,3-oxazol-4-yl]benzenesulfonamide;

2,6-difluoro-4-[3-(4-methyl-3-bromophenyl-2-oxo-2,3 dihydro-1,3-oxazol-4-yl]benzenesulfonamide;

2,6-difluoro-4-[3-(3-methyl-4-trifluoromethylphenyl)-2-oxo-2,3-dihydro -1,3-oxazol-4-yl]benzenesulfonamide;

2,6-difluoro-4-[3-(4-methyl-3-trifluoromethylphenyl)-2-oxo-2,3-dihydro-1,3-oxazol-4-yl]benzenesulfonamide;

2,6-difluoro-4-[3-(3-methyl-4-trifluoromethoxyphenyl)-2-oxo -2,3-dihydro-1,3-oxazol-4-yl]benzenesulfonamide;

2,6-difluoro-4-[3-(4-methyl-3-trifluoromethoxyphenyl)-2-oxo-2,3-dihydro-1,3-oxazol-4-yl]benzenesulfonamide;

2,6-difluoro-4-[3-(3-cyano-4-methylphenyl)-2-oxo-2,3 dihydro-1,3-oxazol-4-yl]benzenesulfonamide;

2,6-difluoro-4-[3-(4-cyano-3-methylphenyl)-2-oxo-2,3-dihydro-1,3-oxazol-4-yl]benzenesulfonamide;

2,6-difluoro-4-[3-(3-chloro-4-methoxyphenyl)-2-oxo-2,3-dihydro-1,3-oxazol-4-yl]benzenesulfonamide;

2,6-difluoro-4-[3-(4-chloro-3-methoxyphenyl)-2-oxo-2,3-dihydro-1,3-oxazol-4-yl]benzenesulfonamide;
2,6-difluoro-4-[3-(2-methylpyridin-6-yl)-2-oxo-2,3-dihydro-1,3-oxazol-4-yl]benzenesulfonamide;
2,6-difluoro-4-[3-(2-methylthiazol-4-yl)-2-oxo-2,3-dihydro-1,3-oxazol-4-yl]benzenesulfonamide;
2,6-difluoro-4-[3-(4-methylthiazol-2-yl)-2-oxo-2,3-dihydro-1,3-oxazol-4-yl]benzenesulfonamide;
2,6-difluoro-4-[3-(2-methylpyridin-3-yl)-2-oxo-2,3-dihydro-1,3-oxazol-4-yl]benzenesulfonamide;
2,6-difluoro-4-[3-(2-methylpyridin-3-yl)-2-oxo-2,3-dihydro-1,3-oxazol-4-yl]benzenesulfonamide;
2,6-difluoro-4-[3-(3-pyridinyl)-2-oxo-2,3-dihydro-1,3-oxazol-4-yl]benzenesulfonamide;
2,6-difluoro-4-[3-(5-methylpyridin-3-yl)-2-oxo-2,3-dihydro-1,3-oxazol-4-yl]benzenesulfonamide;
2,6-difluoro-4-[3-(2-methylpyridin-3-yl)-2-oxo-2,3-dihydro-1,3-oxazol-4-yl]benzenesulfonamide;
3-cyclohexyl-2-oxo-2,3-dihydro-1,3-oxazol-4-yl]benzenesulfonamide;
3-cyclopentyl-2-oxo-2,3-dihydro-1,3-oxazol-4-yl]benzenesulfonamide;
3-phenyl-4-[3,6-difluoro-4-(methylsulfonyl)phenyl]-1,3-oxazol-2 (3H)-one;
3-(3-chlorophenyl)-4-[3,6-difluoro-4-(methylsulfonyl)phenyl]-1,3-oxazol-2 (3H)-one;
3-(4-chlorophenyl)-4-[3,6-difluoro-4-(methylsulfonyl)phenyl]-1,3-oxazol-2 (3H)-one;
3-(3-bromophenyl)-4-[3,6-difluoro-4-(methylsulfonyl)phenyl]1,3-oxazol-2 (3H)-one;
3-(4-bromophenyl)-4-[3,6-difluoro-4-(methylsulfonyl)phenyl]-1,3-oxazol-2 (3H)-one;
3-(3-fluorophenyl)-4-[3,6-difluoro-4-(methylsulfonyl)phenyl]-1,3-oxazol-2 (3H)-one;
3-(4-fluorophenyl)-4-[3,6-difluoro-4-(methylsulfonyl)phenyl]-1,3-oxazol-2 (3H)-one;
3-(3-methylphenyl)-4-[3,6-difluoro-4-(methylsulfonyl)phenyl]-1,3-oxazol-2 (3H)-one;
3-(4-methylphenyl)-4-[3,6-difluoro-4-(methylsulfonyl)phenyl]-1,3-oxazol-2 (3H)-one;
3-(3-cyanophenyl)-4-[3,6-difluoro-4-(methylsulfonyl)phenyl]-1,3-oxazol-2 (3H)-one;
3-(4-cyanophenyl)-4-[3,6-difluoro-4-(methylsulfonyl)phenyl]-1,3-oxazol-2 (3H)-one;
3-(3-trifluoromethylphenyl)-4-[3,6-difluoro-4-(methylsulfonyl)phenyl]-1,3-oxazol-2 (3H)-one;
3-(4-trifluoromethylphenyl)-4-[3,6-difluoro-4-(methylsulfonyl)phenyl]-1,3-oxazol-2 (3H)-one;
3-(3-trifluoromethoxyphenyl)-4-[3,6-difluoro-4-(methylsulfonyl)phenyl]-1,3-oxazol-2 (3H)-one;
3-(4-trifluoromethoxyphenyl)-4-[3,6-difluoro-4-(methylsulfonyl)phenyl]-1,3-oxazol-2 (3H)-one;
3-(3,4-dichlorophenyl)-4-[3,6-difluoro-4-(methylsulfonyl)phenyl]-1,3-oxazol-2 (3H)-one;
3-(3,4-dibromophenyl)-4-[3,6-difluoro-4-(methylsulfonyl)phenyl]-1,3-oxazol-2 (3H)-one;
3-(3,4-difluorophenyl)-4-[3,6-difluoro-4-(methylsulfonyl)phenyl]-1,3-oxazol-2 (3H)-one;
3-(3,5-dichlorophenyl)-4-[3,6-difluoro-4-(methylsulfonyl)phenyl]-1,3-oxazol-2 (3H)-one;
3-(3,5-dibromophenyl)-4-[3,6-difluoro-4-(methylsulfonyl)phenyl]-1,3-oxazol-2 (3H)-one;
3-(3-fluorophenyl)-4-[3,6-difluoro-4-(methylsulfonyl)phenyl]-1,3-oxazol-2 (3H)-one;
3-(3,4-dimethylphenyl)-4-[3,6-difluoro-4-(methylsulfonyl)phenyl]-1,3-oxazol-2 (3H)-one;
3-(3,5-dimethylphenyl)-4-[3,6-difluoro-4-(methylsulfonyl)phenyl]-1,3-oxazol-2 (3H)-one;
3-(3-methyl-4-chlorophenyl)-4-[3,6-difluoro-4-(methylsulfonyl)phenyl]-1,3-oxazol-2 (3H)-one;
3-(4-methyl-3-chlorophenyl)-4-[3,6-difluoro-4-(methylsulfonyl)phenyl]-1,3-oxazol-2 (3H)-one;
3-(3-methyl-4-fluorophenyl)-4-[3,6-difluoro-4-(methylsulfonyl)phenyl]-1,3-oxazol-2 (3H)-one;
3-(4-methyl-3-fluorophenyl)-4-[3,6-difluoro-4-(methylsulfonyl)phenyl]-1,3-oxazol-2 (3H)-one;
3-(3-methyl-4-bromophenyl)-4-[3,6-difluoro-4-(methylsulfonyl)phenyl]-1,3-oxazol-2 (3H)-one;
3-(4-methyl-3-bromophenyl)-4-[3,6-difluoro-4-(methylsulfonyl)phenyl]-1,3-oxazol-2 (3H)-one;
3-(3-methyl-4-trifluoromethylphenyl)-4-[3,6-difluoro-4-(methylsulfonyl)phenyl]-1,3-oxazol-2 (3H)-one;
3-(4-methyl-3-trifluoromethylphenyl)-4-[3,6-difluoro-4-(methylsulfonyl)phenyl]-1,3-oxazol-2 (3H)-one;
3-(3-methyl-4-trifluoromethoxyphenyl)-4-[3,6-difluoro-4-(methylsulfonyl)phenyl]-1,3-oxazol-2 (3H)-one;
3-(4-methyl-3-trifluoromethoxyphenyl)-4-[3,6-difluoro-4-(methylsulfonyl)phenyl]-1,3-oxazol-2 (3H)-one;
3-(3-cyano-4-methylphenyl)-4-[3,6,-difluoro-4-(methylsulfonyl)phenyl]-1,3-oxazol-2 (3H)-one;
3-(4-cyano-3-methylphenyl)-4-[3,6,-difluoro-4-(methylsulfonyl)phenyl]-1,3-oxazol-2 (3H)-one;
3-(3-chloro-4-methoxyphenyl)-4-[3,6-difluoro-4-(methylsulfonyl)phenyl]-1,3-oxazol-2 (3H)-one;
3-(4-chloro-3-methoxyphenyl)-4-[3,6-difluoro-4-(methylsulfonyl)phenyl]-1,3-oxazol-2 (3H)-one;
3-(2-methylpyridin-6-yl)-4-[3,6-difluoro-4-(methylsulfonyl)phenyl]-1,3-oxazol-2 (3H)-one;
3-(2-methylthiazol-4-yl)-4-[3,6,-difluoro-4-(methylsulfonyl)phenyl]-1,3-oxazol-2 (3H)-one;
3-(4-methylthiazol-2-yl)-4-[3,6-difluoro-4-(methylsulfonyl)phenyl]-1,3-oxazol-2 (3H)-one;
3-(2-methylpyridin-3-yl)-4-[3,6-difluoro-4-(methylsulfonyl)phenyl]-1,3-oxazol-2 (3H)-one;
3-(2-methylpyridin-3-yl)-4-[3,6-difluoro-4-(methylsulfonyl)phenyl]-1,3-oxazol-2 (3H)-one;
3-(3-pyridinyl)-4-[3,6-difluoro-4-(methylsulfonyl)phenyl]-1,3-oxazol-2 (3H)-one;
3-(5-methylpyridin-3-yl)-4-[3,6-difluoro-4-(methylsulfonyl)phenyl]-1,3-oxazol-2 (3H)-one;
3-(2-methylpyridin-3-yl)-4-[3,6-difluoro-4-(methylsulfonyl)phenyl]-1,3-oxazol-2 (3H)-one;
3-cyclohexyl-4-[3,6-difluoro-4-(methylsulfonyl)phenyl]-1,3-oxazol-2 (3H)-one;
3-cyclopentyl-4-[3,6-difluoro-4-(methylsulfonyl)phenyl]-1,3-oxazol-2 (3H)-one;
2,5-difluoro-4-[3,2-oxo-2,3-dihydro-1,3-oxazol-4-yl]benzenesulfonamide;
2,5-difluoro-4-[3-(3-chlorophenyl)-2-oxo-23-dihydrol-2,3-oxazol-4-yl]benzenesulfonamide;
2,5-difluoro-4-[3-(4-chlorophenyl)-2-oxo-2,3-dihydro-1,3-oxazol-4-yl]benzenesulfonamide;
2,5-difluoro-4-[3-(3-bromophenyl)-2-oxo-2,3-dihydro-1,3-oxazol-4-yl]benzenesulfonamide;

2,5-difluoro-4-[3-(4-bromophenyl)-2-oxo-2,3-dihydro-1,3-oxazol-4-yl]benzenesulfonamide;
2,5-difluoro-4-[3-(3-fluorophenyl)-2-oxo-2,3-dihydro-1,3-oxazol-4-yl]benzenesulfonamide;
2,5-difluoro-4-[3-(4-fluorophenyl)-2-oxo-2,3-dihydro-1,3-oxazol-4-yl]benzenesulfonamide;
2,5-difluoro-4-[3-(3-methylphenyl)-4-[3-fluoro-4-(methylsulfonyl)phenyl]-1,3-oxazol-2 (3H)-one;
2,5-difluoro-4-[3-(4-methylphenyl)-2-oxo-2,3-dihydro-1,3-oxazol-4-yl]benzenesulfonamide;
2,5-difluoro-4-[3-(3-cyanophenyl)-2-oxo-2,3-dihydro-1,3-oxazol-4-yl]benzenesulfonamide;
2,5-difluoro-4-[3-(4-cyanophenyl)-2-oxo-2,3-dihydro-1,3-oxazol-4-yl]benzenesulfonamide;
2,5-difluoro-4-[3-(3-trifluoromethylphenyl)-2-oxo-2,3-dihydro-1,3-oxazol-4-yl]benzenesulfonamide;
2,5-difluoro-4-[3-(4-trifluoromethylphenyl)-2-oxo-2,3-dihydro-1,3-oxazol-4-yl]benzenesulfonamide;
2,5-difluoro-4-[3-(3-trifluoromethoxyphenyl)-2-oxo-2,3-dihydro-1,3-oxazol-4-yl]benzenesulfonamide;
2,5-difluoro-4-[3-(4-trifluoromethoxyphenyl)-2-oxo-2,3-dihydro-1,3-oxazol-4-yl]benzenesulfonamide;
2,5-difluoro-4-[3-(3,4-dichlorophenyl)-2-oxo-2,3-dihydro-1,3-oxazol-4-yl]benzenesulfonamide;
2,5-difluoro-4-[3-(3,4-dibromophenyl)-2-oxo-2dihydro-1,3-oxazol-4-yl]benzenesulfonamide;
2,5-difluoro-4-[3-(3,4-difluorophenyl)-2-oxo2,3dihydro-1,3-oxazol-4-yl]benzenesulfonamide;
2,5-difluoro-4-[3-(3,5-dichlorophenyl)-2-oxo-2,3-dihydro-1,3-oxazol-4-yl]benzenesulfonamide;
215-difluoro-4-[3-(3,5-dibromophenyl)-2-oxo2,3-dihydro1,3-oxazol-4-yl]benzenesulfonamide;
2,5-difluoro-4-[3-(3,5-difluorophenyl)-2-oxo-2,3-dihydro-1,3-oxazol-4-yl]benzenesulfonamide;
2,5-difluoro-4-[3-(3,4-dimethylphenyl)-2-oxo-2,3-dihydro-1,3-oxazol-4-yl]benzenesulfonamide;
2,5-difluoro-4-[3-(3,5-dimethylphenyl)-2-oxo-2,3-dihydro-1,3-oxazol-4-yl]benzenesulfonamide;
2,5-difluoro-4-[3-(3-methyl-4-chlorophenyl)2oxo2,3-dihydro-1,3-oxazol-4-yl]benzenesulfonamide;
2,5-difluoro-4-[3-(4-methyl-3-chlorophenyl)-2-oxo23dihydro-1,3-oxazol-4-yl]benzenesulfonamide;
2,5-difluoro-4-[3-(3-methyl-4-fluorophenyl)-2-oxo-2,3-dihydro-1,3-oxazol-4-yl]benzenesulfonamide;
2,5-difluoro-4-[3-(4-methyl-3-fluorophenyl)>oxo23dihydro-1,3-oxazol-4-yl]benzenesulfonamide;
2,5-difluoro-4-[3-(3-methyl-4-bromophenyl]-2-oxo-2,3-dihydro-1,3-oxazol-4-yl]benzenesulfonamide;
2,5-difluoro-4-[3-(4-methyl-3-bromophenyl)-2-oxo-2,3-dihydro-1,3-oxazol-4-yl]benzenesulfonamide;
2,5-difluoro-4-[3-(3-methyl-4-trifluoromethylphenyl)-2-oxo-2,3-dihydro-1,3-oxazol-4-yl]benzenesulfonamide;
2,5-difluoro-4-[3-(4-methyl-3-trifluoromethylphenyl)-2-oxo-2,3-dihydro-1,3-oxazol-4-yl]benzenesulfonamide;
2,5-difluoro-4-[3-(3-methyl-4-trifluoromethoxyphenyl)-2-oxo-2,3-dihydro-1,3-oxazol-4-yl]benzenesulfonamide;
2,5-difluoro-4-[3-(4-methyl-3-trifluoromethoxyphenyl)-2-oxo-2,3-dihydro-1,3-oxazol-4-yl]benzenesulfonamide;
2,5-difluoro-4-[3-(3-cyano-4-methylphenyl)2-oxo2,3dihydro-1,3-oxazol-4-yl]benzenesulfonamide;
2,5-difluoro-4-[3-(4-cyano-3-methylphenyl)2 oxo2,3dihydro-1,3-oxazol-4-yl]benzenesulfonamide;
2,5-difluoro-4-[3-(3-chloro-4-methoxyphenyl)-2-oxo-2,3-dihydro-1,3-oxazol-4-yl]benzenesulfonamide;
2,5-difluoro-4-[3-(4-chloro-3-methoxyphenyl)-2-oxo-2,3-dihydro-1,3-oxazol-4-yl]benzenesulfonamide;
2,5-difluoro-4-[3-(2-methylpyridin-5-yl)-2-oxo-2,3-dihydro-1,3-oxazol-4-yl]benzenesulfonamide;
2,5-difluoro-4-[3-(2-methylthiazol-4-yl)-2-oxo-2,3-dihydro-1,3-oxazol-4-yl]benzenesulfonamide;
2,5-difluoro-4-[3-(4-methylthiazol-2-yl)-2-oxo-2,3-dihydro-1,3-oxazol-4-yl]benzenesulfonamide;
2,5-difluoro-4-[3-(2-methylpyridin-3-yl)-2-oxo-2,3-dihydro-1,3-oxazol-4-yl]benzenesulfonamide;
2,5-difluoro-4-[3-(2-methylpyridin-3-yl)-2-oxo-2,3-dihydro-1,3-oxazol-4-yl]benzenesulfonamide;
2,5-difluoro-4-[3-(3-pyridinyl)-2-oxo-2,3-dihydro-1,3-oxazol-4-yl]benzenesulfonamide;
2,5-difluoro-4-[3-(5-methylpyridin-3-yl)-2-oxo-2,3-dihydro-1,3-oxazol-4-yl]benzenesulfonamide;
2,5-difluoro-4-[3-(2-methylpyridin-3-yl)-2-oxo-2,3-dihydro-1,3-oxazol-4-yl]benzenesulfonamide;
2,5-difluoro-4-[3-cyclohexyl-2-oxo-2,3-dihydro-1,3-oxazol-4-yl]benzenesulfonamide;
2,5-difluoro-4-[3-cyclopentyl-2-oxo-2,3-dihydro-1,3-oxazol-4-yl]benzenesulfonamide; and the pharmaceutically-acceptable salts, tautomers and prodrugs thereof.

Within Formula I there is another subclass of compounds of interest that includes, but is not limited to:

2,6-difluoro-4-[2-oxo-2,3-dihydro-1,3-thiazol-4-yl]benzenesulfonamide;
2,6-difluoro-4-[3-(3-chlorophenyl)-2-oxo-2,3-dihydro-1,3 thiazol-4-yl]benzenesulfonamide;
2,6-difluoro-4-[3-(4-chlorophenyl)-2-oxo-2,3-dihydro-1,3-thiazol-4-yl]benzenesulfonamide;
2,6-difluoro-4-[3-(3-bromophenyl)-2-oxo-2,3-dihydro-1,3-thiazol-4-yl]benzenesulfonamide;
2,6-difluoro-4-[3-(4-bromophenyl)-2-oxo-2,3-dihydro-1,3-thiazol-4-yl]benzenesulfonamide;
2,6-difluoro-4-[3-(3-fluorophenyl)-2-oxo-2,3-dihydro-1,3-thiazol-4-yl]benzenesulfonamide;
2,6-difluoro-4-[3-(4-fluorophenyl)-2-oxo-2,3-dihydro-1,3-thiazol-4-yl]benzenesulfonamide;
2,6-difluoro-4-[3-(3-methylphenyl)-4-[3-fluoro-4-(methylsulfonyl)phenyl]-1,3-thiazol-2 (3H)-one;
Image Page 52
2,6-difluoro-4-[3-(4-methylphenyl)-2-oxo-2,3-dihydro-1,3-thiazol-4-yl]benzenesulfonamide;
2,6-difluoro-4-[3-(3-cyanophenyl)-2-oxo-2,3-dihydro-1,3-thiazol-4-yl]benzenesulfonamide;
2,6-difluoro-4-[3-(4-cyanophenyl)-2-oxo-2,3-dihydro-1,3-thiazol-4-yl]benzenesulfonamide;
2,6-difluoro-4-[3-(3-trifluoromethylphenyl)-2-oxo-2,3-dihydro-1,3-thiazol-4-yl]benzenesulfonamide;
2,6-difluoro-4-[3-(4-trifluoromethylphenyl)-2-oxo-2,3-dihydro-1,3-thiazol-4-yl]benzenesulfonamide;
2,6-difluoro-4-[3-(3-trifluoromethoxyphenyl)-2-oxo-2,3-dihydro-1,3-thiazol-4-yl]benzenesulfonamide;
2,6-difluoro-4-[3-(4-trifluoromethoxyphenyl)-2-oxo-2,3-dihydro-1,3-thiazol-4-yl]benzenesulfonamide;
2,6-difluoro-4-[3-(3,4-dichlorophenyl)-2-oxo-2,3-dihydro-1,3-thiazol-4-yl]benzenesulfonamide;

2,6-difluoro-4-[3-(3,4-dibromophenyl)-2-oxo-2,3-dihydro-1,3thiazol-4-yl]benzenesulfonamide;
2,6-difluoro-4-[3-(3,4-difluorophenyl)-2-oxo-2,3-dihydro-1,3-thiazol-4-yl]benzenesulfonamide;
2,6-difluoro-4-[3-(3,5-dichlorophenyl)-2-oxo-2,3-dihydro-1,3-thiazol-4-yl]benzenesulfonamide;
2,6-difluoro-4-[3-(3,5-dibromophenyl)-2-oxo-2,3-dihydro-1,3 thiazol-4-yl]benzenesulfonamide;
2,6-difluoro-4-[3-(3,5-difluorophenyl)-2-oxo-2,3-dihydro-1,3-thiazol-4-yl]benzenesulfonamide;
2,6-difluoro-4-[3-(3,4-dimethylphenyl)-2-oxo-2,3-dihydro-1,3-thiazol-4-yl]benzenesulfonamide;
2,6-difluoro-4-[3-(3,5-dimethylphenyl)-2-oxo-2,3-dihydro-1,3-thiazol-4-yl]benzenesulfonamide;
2,6-difluoro-4-[3-(3-methyl-4-chlorophenyl)-2-oxo-2,3-dihydro-1,3-thiazol-4-yl]benzenesulfonamide;
2,6-difluoro-4-[3-(4-methyl-3-chlorophenyl)-2-oxo-2,3-dihydro-1,3-thiazol-4-yl]benzenesulfonamide;
2,6-difluoro-4-[3-(3-methyl-4—fluorophenyl)-2-oxo-2,3-dihydro-1,3-thiazol-4-yl]benzenesulfonamide;
2,6-difluoro-4-[3-(4-methyl-3-fluorophenyl)-2-oxo-2,3-dihydro-1,3-thiazol-4-yl]benzenesulfonamide;
2,6-difluoro-4-[3-(3-methyl-4-bromophenyl)-2-oxo-2,3-dihydro-1,3-thiazol-4-yl]benzenesulfonamide;
2,6-difluoro-4-[3-(4-methyl-3-bromophenyl)-2-oxo-2,3-dihydro-1,3-thiazol-4-yl]benzenesulfonamide;
2,6-difluoro-4-[3-(3-methyl-4-trifluoromethylphenyl)-2-oxo-2,3-dihydro-1,3-thiazol-4-yl]benzenesulfonamide;
2,6-difluoro-4-[3-(4-methyl-3-trifluoromethylphenyl)-2-oxo-2,3-dihydro-1,3-thiazol-4-yl]benzenesulfonamide;
2,6-difluoro-4-[3-(3-methyl-4-trifluoromethoxyphenyl)-2-oxo-2,3-dihydro-1,3-thiazol-4-yl] benzenesulfonamide;
2,6-difluoro-4-[3-(4-methyl-3-trifluoromethoxyphenyl)-2-oxo-2,3-dihydro-1,3-thiazol-4-yl] benzenesulfonamide;
2,6-difluoro-4-[3-(3-cyano-4-methylphenyl)-2-oxo-2,3-dihydro-1,3-thiazol-4-yl]benzenesulfonamide;
2,6-difluoro-4-[3-(4-cyano-3-methylphenyl)-2-oxo-2,3-dihydro-1,3-thiazol-4-yl]benzenesulfonamide;
2,6-difluoro-4-[3-(3-chloro-4-methoxyphenyl)-2-oxo-2,3-dihydro-1,3-thiazol-4-yl]benzenesulfonamide;
2,6-difluoro-4-[3-(4-chloro-3-methoxyphenyl)-2-oxo-2,3-dihydro-1,3-thiazol-4-yl]benzenesulfonamide;
2,6-difluoro-4-[3-(2-methylpyridin-6-yl)-2-oxo-2,3-dihydro-1,3-thiazol-4-yl]benzenesulfonamide;
2,6-difluoro-4-[3-(2-methylthiazol-4-yl)-2-oxo-2,3-dihydro-1,3-thiazol-4-yl]benzenesulfonamide;
2,6-difluoro-4-[3-(4-methylthiazol-2-yl)-2-oxo-2,3-dihydro-1,3-thiazol-4-yl]benzenesulfonamide;
2,6-difluoro-4-[3-(2-methylpyridin-3-yl)-2-oxo-2,3-dihydro-1,3-thiazol-4-yl]benzenesulfonamide;
2,6-difluoro-4-[3-(2-methylpyridin-3-yl)-2-oxo-2,3-dihydro-1,3-thiazol-4-yl]benzenesulfonamide;
2,6-difluoro-4-[3-(3-pyridinyl)-2-oxo-2,3—dihydro-1,3-thiazol-4-yl]benzenesulfonamide;
2,6-difluoro-4-[3-(5-methylpyridin-3-yl)-2-oxo-2,3-dihydro-1,3-thiazol-4-yl]benzenesulfonamide;
2,6-difluoro-4-[3-(2-methylpyridin-3-yl)-2-oxo-2,3-dihydro-1,3-thiazol-4-yl]benzenesulfonamide;
2,6-difluoro-4-[3-cyclohexyl-2-oxo-2,3-dihydro-1,3-thiazol-4-yl]benzenesulfonamide;

2,6-difluoro-4-[3-cyclohexyl-2-oxo-2,3-dihydro-1,3-thiazol-4-yl]benzenesulfonamide;
2,5-difluoro-4-[3-2-oxo-2,3-dihydro-1,3-thiazol-4-yl]benzenesulfonamide;
2,5-difluoro-4-[3-(3-chlorophenyl)-2-oxo-2,3-dihydro-1,3-thiazol-4-yl]benzenesulfonamide;
2,5-difluoro-4-[3-(4-chlorophenyl)-2-oxo-2,3-dihydro-1,3-thiazol-4-yl]benzenesulfonamide;
2,5-difluoro-4-[3-(3-bromophenyl)-2-oxo-2,3-dihydro-1,3-thiazol-4—yl]benzenesulfonamide;
2,5-difluoro-4-[3-(4-bromophenyl)-2-oxo-2,3-dihydro-1,3-thiazol-4-yl]benzenesulfonamide;
2,5-difluoro-4-[3-(3-fluorophenyl)-2-oxo-2,3-dihydro-1,3-thiazol-4-yl]benzenesulfonamide;
2,5-difluoro-4-[3-(4-fluorophenyl)-2-oxo-2,3-dihydro-1,3-thiazol-4-yl]benzenesulfonamide;
2,5-difluoro-4-[3-(3-methylphenyl)-4-[3-fluoro-4-(methylsulfonyl)phenyl]-1,3-thiazol-2 (3H)-one;
2,5-difluoro-4-[3-(4-methylphenyl)-2-oxo-2,3-dihydro-1,3-thiazol-4-yl]benzenesulfonamide;
2,5-difluoro-4-[3-(3-cyanophenyl)-2-oxo-2,3-dihydro-1,3-thiazol-4-yl]benzenesulfonamide;
2,5-difluoro-4-[3-(4-cyanophenyl)-2-oxo-2,3-dihydro-1,3-thiazol-4-yl]benzenesulfonamide;
2,5-difluoro-4-[3-(3-trifluoromethylphenyl)-2-oxo-2,3-dihydro-1,3-thiazol-4-yl]benzenesulfonamide; Image Page 55
2,5-difluoro-4-[3-(4-trifluoromethylphenyl)-2-oxo-2,3-dihydro-1,3-thiazol-4-yl]benzenesulfonamide;
2,5-difluoro-4-[3-(3-trifluoromethoxyphenyl)-2-oxo-2,3-dihydro-1,3—thiazol-4-yl]benzenesulfonamide;
2,5-difluoro-4-[3-(4-trifluoromethoxyphenyl)-2-oxo-2,3-dihydro-1,3-thiazol-4-yl]benzenesulfonamide;
2,5-difluoro-4-[3-(3,4-dichlorophenyl)-2-oxo-2,3-dihydro-1,3-thiazol-4-yl]benzenesulfonamide;
2,5-difluoro-4-[3-(3,4-dibromophenyl)-2-oxo-2,3-dihydro1,3 thiazol-4-yl]benzenesulfonamide;
2,5-difluoro-4-[3-(3,4-difluorophenyl)-2-oxo-2,3-dihydro-1,3-thiazol-4-yl]benzenesulfonamide;
2,5-difluoro-4-[3-(3,5-dichlorophenyl)-2-oxo-2,3-dihydro-1,3-thiazol-4-yl]benzenesulfonamide;
2,5-difluoro-4-[3-(3,5-dibromophenyl)-2-oxo-2,3-dihydro-1,3-thiazol-4-yl]benzenesulfonamide;
2,5-difluoro-4-[3-(3,5-difluorophenyl)-2-oxo-2,3-dihydro-1,3-thiazol-4-yl]benzenesulfonamide;
2,5-difluoro-4-[3-(3,4-dimethylphenyl)-2-oxo-2,3-dihydro-1,3-thiazol-4-yl]benzenesulfonamide;
2,5-difluoro-4-[3-(3,5-dimethylphenyl)-2-oxo-2,3-dihydro-1,3-thiazol-4-yl]benzenesulfonamide;
2,5-difluoro-4-[3-(3-methyl-4-chlorophenyl)-2-oxo-2,3-dihydro-1,3-thiazol-4-yl]benzenesulfonamide;
2,5-difluoro-4-[3—(4-methyl-3—chlorophenyl)-2-oxo-2,3-dihydro-1,3-thiazol-4-yl]benzenesulfonamide;
2,5-difluoro-4-[3-(3-methyl-4-fluorophenyl)-2-oxo-2,3-dihydro-1,3-thiazol-4-yl]benzenesulfonamide;
2,5-difluoro-4-[3-(4-methyl-3-fluorophenyl)-2-oxo-2,3-dihydro-1,3-thiazol-4-yl]benzenesulfonamide;
2,5-difluoro-4-[3-(3-methyl-4-bromophenyl)-2-oxo-2,3-dihydro-1,3—thiazol-4-yl]benzenesulfonamide;
2,5-difluoro-4-[3-(4-methyl-3-bromophenyl)-2-oxo-2,3-dihydro-1,3-thiazol-4-yl]benzenesulfonamide;
2,5-difluoro-4-[3-(3-methyl-4-trifluoromethylphenyl)-2-oxo-2,3-dihydro-1,3-thiazol-4-yl I benzenesulfonamide;

2,5-difluoro-4-[3-(4-methyl-3-trifluoromethylphenyl)-2-oxo-2,3-dihydro-1,3-thiazol-4-yl]benzenesulfonamide;
2,5-difluoro-4-[3-(3-methyl-4-trifluoromethoxyphenyl)-2-oxo-2,3-dihydro-1,3-thiazol-4-yl]benzenesulfonamide;
2,5-difluoro-4-[3-(4-methyl-3-trifluoromethoxyphenyl)-2-oxo-2,3-dihydro-1,3-thiazol-4-yl]benzenesulfonamide;
2,5-difluoro-4-[3-(3-cyano-4-methylphenyl)-2-oxo-2,3-dihydro-1,3-thiazol-4-yl]benzenesulfonamide;
2,5-difluoro-4-[3-(4-cyano-3-methylphenyl)-2-oxo-2,3-dihydro-1,3-thiazol-4-yl]benzenesulfonamide;
2,5-difluoro-4-[3-(3-chloro-4-methoxyphenyl)-2-oxo-2,3-dihydro-1,3-thiazol-4-yl]benzenesulfonamide;
2,5-difluoro-4-[3-(4-chloro-3-methoxyphenyl)-2-oxo-2,3-dihydro-1,3-thiazol-4-yl]benzenesulfonamide;
2,5-difluoro-4-[3-(2-methylpyridin-6-yl)-2-oxo-2,3-dihydro-1,3-thiazol-4-yl]benzenesulfonamide;
2,5-difluoro-4-[3-(2-methylthiazol-4-yl)-2-oxo-2,3-dihydro-1,3-thiazol-4-yl]benzenesulfonamide;
2,5-difluoro-4-[3-(4-methylthiazol-2-yl)-2-oxo-2,3-dihydro-1,3-thiazol-4-yl]benzenesulfonamide;
2,5-difluoro-4-[3-(2-methylpyridin-3-yl)-2-oxo-2,3-dihydro-1,3-thiazol-4-yl]benzenesulfonamide;
2,5-difluoro-4-[3-(2-methylpyridin-3-yl)-2-oxo-2,3-dihydro-1,3-thiazol-4-yl]benzenesulfonamide;
2,5-difluoro-4-[3-(3-pyridinyl)-2-oxo-2,3-dihydro-1,3-thiazol-4-yl]benzenesulfonamide;
2,5-difluoro-4-[3-(5-methylpyridin-3-yl)-2-oxo-2,3-dihydro-1,3-thiazol-4-yl]benzenesulfonamide;
2,5-difluoro-4-[3-(2-methylpyridin-3-yl)-2-oxo-2,3-dihydro-1,3-thiazol-4-yl]benzenesulfonamide;
2,5-difluoro-4-[3-cyclohexyl-2-oxo-2,3-dihydro-1,3-thiazol-4-yl]benzenesulfonamide;
2,5-difluoro-4-[3-cyclopentyl-2-oxo-2,3-dihydro-1,3-thiazol-4-yl]benzenesulfonamide;
3-phenyl-4-[3,6-difluoro-4-(methylsulfonyl)phenyl]-1,3-thiazol-2 (3H)-one;
3-(3-chlorophenyl)-4-[3,6-difluoro-4-(methylsulfonyl)phenyl]-1,3-thiazol-2 (3H)-one;
3-(4-chlorophenyl)-4-[3,6-difluoro-4-(methylsulfonyl)phenyl]-1,3-thiazol-2 (3H)-one;
3-(3-bromophenyl)-4-[3,6-difluoro-4-(methylsulfonyl)phenyl]-1,3-thiazol-2 (3H)-one;
3-(4-bromophenyl)-4-[3,6-difluoro-4-(methylsulfonyl)phenyl]-1,3-thiazol-2 (3H)-one;
3-(3-fluorophenyl)-4-[3,6-difluoro-4-(methylsulfonyl)phenyl]-1,3-thiazol-2 (3H)-one;
3-(4-fluorophenyl)-4-[3,6-difluoro-4-(methylsulfonyl)phenyl]-1,3-thiazol-2 (3H)-one;
3-(3-methylphenyl)-4-[3,6-difluoro-4-(methylsulfonyl)phenyl]-1,3-thiazol-2 (3H)-one;
3-(4-methylphenyl)-4-[3,6-difluoro-4-(methylsulfonyl)phenyl]-1,3-thiazol-2 (3H)-one;
3-(3-cyanophenyl)-4-[3,6-difluoro-4-(methylsulfonyl)phenyl]-1,3-thiazol-2 (3H)-one;
3-(4-cyanophenyl)-4-[3,6-difluoro-4-(methylsulfonyl)phenyl]-1,3-thiazol-2 (3H)-one;
3-(3-trifluoromethylphenyl)-4-[3,6-difluoro-4-(methylsulfonyl)phenyl]-1,3-thiazol-2 (3H)-one;
3-(4-trifluoromethylphenyl)-4-[3,6-difluoro-4-(methylsulfonyl)phenyl]-1,3-thiazol-2 (3H)-one;
3-(3-trifluoromethoxyphenyl)-4-[3,6-difluoro-4-(methylsulfonyl)phenyl]-1,3-thiazol-2 (3H)-one;
3-(4-trifluoromethoxyphenyl)-4-[3,6-difluoro-4-(methylsulfonyl)phenyl]-1,3-thiazol-2 (3H)-one;
3-(3,4-dichlorophenyl)-4-[3,6-difluoro-4-(methylsulfonyl)phenyl]-1,3-thiazol-2 (3H)-one; Image Page 58
3-(3,4-dibromophenyl)-4-[3,6-difluoro-4-(methylsulfonyl)phenyl]-1,3-thiazol-2 (3H)-one;
3-(3,4-difluorophenyl)-4-[3,6-difluoro-4-(methylsulfonyl)phenyl]-1,3-thiazol-2 (3H)-one;
3-(3,5-dichlorophenyl)-4-[3,6-difluoro-4-(methylsulfonyl)phenyl]-1,3-thiazol-2 (3H)-one;
3-(3,5-dibromophenyl)-4-[3,6-difluoro-4-(methylsulfonyl)phenyl]-1,3-thiazol-2 (3H)-one;
3-(3-fluorophenyl)-4-[3,6-difluoro-4-(methylsulfonyl)phenyl]-1,3-thiazol-2 (3H)-one;
3-(3,4-dimethylphenyl)-4-[3,6-difluoro-4-(methylsulfonyl)phenyl]-1,3-thiazol-2 (3H)-one;
3-(3,5-dimethylphenyl)-4-[3,6-difluoro-4-(methylsulfonyl)phenyl]-1,3-thiazol-2 (3H)-one;
3-(3-methyl-4-chlorophenyl)-4-[3,6-difluoro-4-(methylsulfonyl)phenyl]-1,3-thiazol-2 (3H)-one;
3-(4-methyl-3-chlorophenyl)-4-[3,6-difluoro-4-(methylsulfonyl)phenyl]-1,3-thiazol-2 (3H)-one;
3-(3-methyl-4-fluorophenyl)-4-[3,6-difluoro-4-(methylsulfonyl)phenyl]-1,3-thiazol-2 (3H)-one;
3-(4-methyl-3-fluorophenyl)-4-[3,6-difluoro-4-(methylsulfonyl)phenyl]-1,3-thiazol-2 (3H)-one;
3-(3-methyl-4-bromophenyl)-4-[3,6-difluoro-4-(methylsulfonyl)phenyl]-1,3-thiazol-2 (3H)-one;
3-(4-methyl-3-bromophenyl)-4-[3,6-difluoro-4-(methylsulfonyl)phenyl]-1,3-thiazol-2 (3H)-one;
3-(3-methyl-4-trifluoromethylphenyl)-4-[3,6-difluoro-4-(methylsulfonyl)phenyl]-1,3-thiazol-2 (3H)-one;
3-(4-methyl-3-trifluoromethylphenyl)-4-[3,6-difluoro-4-(methylsulfonyl)phenyl]-1,3-thiazol-2 (3H)-one;
3-(3-methyl-4-trifluoromethoxyphenyl)-4-[3,6-difluoro-4-(methylsulfonyl)phenyl]-1,3-thiazol-2 (3H)-one;
3-(4-methyl-3-trifluoromethoxyphenyl)-4-[3,6-difluoro-4-(methylsulfonyl)phenyl]-1,3-thiazol-2 (3H)-one;
3-(3-cyano-4-methylphenyl)-4-[3,6-difluoro-4-(methylsulfonyl)phenyl]-1,3-thiazol-2 (3H)-one;
3-(4-cyano-3-methylphenyl)-4-[3,6-difluoro-4-(methylsulfonyl)phenyl]-1,3-thiazol-2 (3H)-one;
3-(3-chloro-4-methoxyphenyl)-4-[3,6-difluoro-4-(methylsulfonyl)phenyl]-1,3-thiazol-2 (3H)-one;
3-(4-chloro-3-methoxyphenyl)-4-[3,6-difluoro-4-(methylsulfonyl)phenyl]-1,3-thiazol-2 (3H)-one;
3-(2-methylpyridin-6-yl)-4-[3,6-difluoro-4-(methylsulfonyl)phenyl]-1,3-thiazol-2 (3H)-one;
3-(2-methylthiazol-4-yl)-4-[3,6-difluoro-4-ethylsulfonyl)phenyl]-1,3-thiazol-2 (3H)-one; -(methysulfonyl)phenyl]-3-(4-methylthiazol-2-yl)-4-[3,6-difluoro-4-1,3-thiazol-2 (3H)-one;
3-(2-methylpyridin-3-yl)-4-[3,6-difluoro-4-(methylsulfonyl)phenyl]-1,3-thiazol-2 (3H)-one;
3-(2-methylpyridin-3-yl)-4-[3,6-difluoro-4-(methylsulfonyl)phenyl]-1,3-thiazol-2 (3H)-one;
3-(3-pyridinyl)-4-[3,6-difluoro-4-(methylsulfonyl)phenyl]-1,3-thiazol-2 (3H)-one;
3-(5-methylpyridin-3-yl)-4-[3,6-difluoro-4-(methylsulfonyl)phenyl]-1,3-thiazol-2 (3H)-one;

3-(2-methylpyridin-3-yl)-4-[3,6-difluoro-4-(methylsulfonyl)phenyl]-1,3-thiazol-2 (3H)-one;
3-cyclohexyl-4-[3,6-difluoro-4-(methylsulfonyl)phenyl]-1,3-thiazol-2 (3H)-one;
3-cyclopentyl-4-[3,6-difluoro-4-(methylsulfonyl)phenyl]-1,3-thiazol-2 (3H)-one;
3-phenyl-4-[3,6-difluoro-4-(methylsulfonyl)phenyl]-1,3-thiazol-2 (3H)-one;
3-(3-chlorophenyl)-4-[3,6-difluoro-4-(methylsulfonyl)phenyl]-1,3-thiazol-2 (3H)-one;
3-(4-chlorophenyl)-4-[3,6-difluoro-4-(methylsulfonyl)phenyl]-1,3-thiazol-2 (3H)-one;
3-(3-brornophenyl)-4-[3,6-difluoro-4-(methylsulfonyl)phenyl]-1,3-thiazol-2 (3H)-one;
3-(4-bromophenyl)-4-[3,6-difluoro-4-(methylsulfonyl)phenyl]-1,3-thiazol-2 (3H)-one;
3-(3-fluorophenyl)-4-[3,6-difluoro-4-(methylsulfonyl)phenyl]-1,3-thiazol-2 (3H)-one;
3-(4-fluorophenyl)-4-[3,6-difluoro-4-(methylsulfonyl)phenyl]-1,3-thiazol-2 (3H)-one;
3-(3-methylphenyl)-4-[3,6-difluoro-4-(methylsulfonyl)phenyl]-1,3-thiazol-2 (3H)-one;
3-(4-methylphenyl)-4-[3,6-difluoro-4-1,3-thiazol-2 (3H)-one; -(methylsulfonyl)phenyl ]cyanophenyl)-4-[3,6-difluoro-4-(methylsulfonyl)phenyl]-1,3-thiazol-2 (3H)-one;
3-(4-cyanophenyl)-4-[3,6-difluoro-4-(methylsulfonyl)phenyl]-1,3-thiazol-2 (3H)-one;
3-(3-trifluoromethylphenyl)-4-[3,6-difluoro-4-(methylsulfonyl)phenyl]-1,3-thiazol-2 (3H)-one;
3-(4-trifluoromethylphenyl)-4-[3,6-difluoro-4-(methylsulfonyl)phenyl]-1,3-thiazol-2 (3H)-one;
3-(3-trifluoromethoxyphenyl)-4-[3,6-difluoro-4-(methylsulfonyl)phenyl]-1,3-thiazol-2 (3H)-one;
3-(4-trifluoromethoxyphenyl)-4-[3,6-difluoro-4-(methylsulfonyl)phenyl]-1,3-thiazol-2 (3H)-one;
3-(3,4-dichlorophenyl)-4-[3,6-difluoro-4-(methylsulfonyl)phenyl]-1,3-thiazol-2 (3H)-one;
3-(3,4-dibromophenyl)-4-[3,6-difluoro-4-(methylsulfonyl)phenyl]-1,3-thiazol-2 (3H)-one;
3-(3,4-difluorophenyl)-4-[3,6-difluoro-4-(methylsulfonyl)phenyl]-1,3-thiazol-2 (3H)-one;
3-(3,5-dichlorophenyl)-4-[3,6-difluoro-4-(methylsulfonyl)phenyl]-1,3-thiazol-2 (3H)-one;
3-(3,5-dibromophenyl)-4-[3,6-difluoro-4-(methylsulfonyl)phenyl]-1,3-thiazol-2 (3H)-one;
Image Page 61
3-(3-fluorophenyl)-4-[3,6-difluoro-4-(methylsulfonyl)phenyl]-1,3-thiazol-2 (3H)-one;
3-(3,4-dimethylphenyl)-4-[3,6-difluoro-4-(methylsulfonyl)phenyl]-1,3-thiazol-2 (3H)-one;
3-(3,5-dimethylphenyl)-4-[3,6-difluoro-4-(methylsulfonyl)phenyl]-1,3-thiazol-2 (3H)-one;
3-(3-methyl-4-chlorophenyl)-4-[3,6-difluoro-4-(methylsulfonyl)phenyl]-1,3-thiazol-2 (3H)-one;
3-(4-methyl-3-chlorophenyl)-4-[3,6-difluoro-4-(methylsulfonyl)phenyl]-1,3-thiazol-2 (3H)-one;
3-(3-methyl-4-fluorophenyl)-4-[3,6-difluoro-4-(methylsulfonyl)phenyl]-1,3-thiazol-2 (3H)-one;
3-(4-methyl-3-fluorophenyl)-4-[3,6-difluoro-4-(methylsulfonyl)phenyl]-1,3-thiazol-2 (3H)-one;
3-(3-methyl-4-bromophenyl)-4-[3,6-difluoro-4-(methylsulfonyl)phenyl]-1,3-thiazol-2 (3H)-one;
3-(4-methyl-3-bromophenyl)-4-[3,6-difluoro-4-(methylsulfonyl)phenyl]-1,3-thiazol-2 (3H)-one;
3-(3-methyl-4-trifluoromethylphenyl)-4-[3,6-difluoro-4-(methylsulfonyl)phenyl]-1,3-thiazol-2 (3H)-one;
3-(4-methyl-3-trifluoromethylphenyl)-4-[3,6-difluoro-4-(methylsulfonyl)phenyl]-1,3-thiazol-2 (3H)-one;
3-(3-methyl-4-trifluoromethoxyphenyl)-4-[3,6-difluoro-4-(methylsulfonyl)phenyl]-1,3-thiazol-2 (3H)-one;
3-(4-methyl-3-trifluoromethoxyphenyl)-4-[3,6-difluoro-4-(methylsulfonyl)phenyl]-1,3-thiazol-2 (3H)-one;
3-(3-cyano-4-methylphenyl)-4-[3,6-difluoro-4-(methylsulfonyl)phenyl]-1,3-thiazol-2 (3H)-one;
3-(4-cyano-3-methylphenyl)-4-[3,6-difluoro-4-(methylsulfonyl)phenyl]-1,3-thiazol-2 (3H)-one;
3-(3-chloro-4-methoxyphenyl)-4-[3,6-difluoro-4-(methylsulfonyl)phenyl]-1,3-thiazol-2 (3H)-one;
3-(4-chloro-3-methoxyphenyl)-4-[3,6-difluoro-4-(methylsulfonyl)phenyl]-1,3-thiazol-2 (3H)-one;
3-(2-methylpyridin-6-yl)-4-[3,6-difluoro-4-(methylsulfonyl)phenyl]-1,3-thiazol-2 (3H)-one;
3-(2-methylthiazol-4-yl)-4-[3,6-difluoro-4-(methylsulfonyl)phenyl]-1,3-thiazol-2 (3H)-one;
3-(4-methylthiazol-2-yl)-4-[3,6-difluoro-4-(methylsulfonyl)phenyl]-1,3-thiazol-2 (3H)-one;
3-(2-methylpyridin-3-yl)-4-[3,6-difluoro-4-(methylsulfonyl)phenyl]-1,3-thiazol-2 (3H)-one;
3-(2-methylpyridin-3-yl)-4-[3,6-difluoro-4-(methylsulfonyl)phenyl]-1,3-thiazol-2 (3H)-one;
3-(3-pyridinyl)-4-[3,6-difluoro-4-(methylsulfonyl)phenyl]-1,3-thiazol-2 (3H)-one; 1,3-(5-methylpyridin-3-yl)-4-[3,6-difluoro-4-(methylsulfonyl)phenyl]-1,3-thiazol-2(3H)-one;
3 (2-methylpyridin-3-yl)-4-[3,6-difluoro-4-(methylsulfonyl)phenyl]-1,3-thiazol-2 (3H)-one;
3-cyclohexyl-4-[3,6-difluoro-4-(methylsulfonyl)phenyl]-1,3-thiazol-2 (3H)-one;
3-cyclopentyl-4-[3,6-difluoro-4-(methylsulfonyl)phenyl]-1,3-thiazol-2 (3H)-one; and the pharmaceutically-acceptable salts, tautomers and pro-drugs thereof.

Definitions

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical.

Where the term "alkyl" is used, either alone or within other terms such as "haloalkyl", "alkylsulfonyl" and "alkoxyalkyl", it embraces linear or branched radicals having one to about twenty carbon atoms or, preferably, one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl pentyl, iso-amyl, hexyl and the like. Even more preferred are lower alkyl radicals having one to three carbon atoms.

Where the term "alkenyl" is used, either alone or within other terms such as "arylalkenyl", it embraces linear or branched radicals having at least one carbon—carbon double bond of two to about twenty carbon atoms or, preferably, two to about twelve carbon atoms. More preferred alkenyl radicals are "lower alkenyl" radicals having two to about six carbon atoms. Examples of alkenyl radicals include ethenyl, propenyl, allyl, propenyl, butenyl and 4-methylbutenyl.

The terms "alkenyl" and "lower alkenyl", embrace radicals having "cis" and "trans" orientations, or alternatively, "E" and "Z" orientations.

The term "alkynyl" denotes linear or branched radicals having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about six carbon atoms. Examples of such radicals include propargyl, butynyl, and the like.

The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl.

The term "cycloalkenyl" embraces partially saturated carbocyclic radicals having three to twelve carbon atoms. Cycloalkenyl radicals that are partially saturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "halo" and "halogen" means halogens such as fluorine, chlorine, bromine or iodine atoms. The term "haloalklyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo-and polyhaloalkyl radicals may have two or more of the same halo atoms or a combination of different halo radicals. "Lower haloalkyl" embraces radicals having one to six carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The terms "hydroxyalkyl" and "hydroxylalkyl" embrace linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "cyanoalkyl" embraces linear or branched alkyl radicals having one to about ten carbon atoms any one of which may be substituted with one or more cyano radicals. More preferred cyanoalkyl radicals are "lower cyanoalkyl" radicals having one to six carbon atoms and one cyano radical. Even more preferred are lower cyanoalkyl radicals having one to three carbon atoms. Examples of such radicals include cyanomethyl.

The term "aryl", alone or in combination, means a carbocyclic aromatic system containing one or two rings wherein such rings may be attached together in a pendent manner or may be fused. The term "aryl" embraces aromatic radicals such as phenyl, naphthyl, tetrahydronaphthyl, indane and biphenyl. More preferred aryl is phenyl. Said "aryl" group may have one to three substituents such as lower alkyl, hydroxy, halo, haloalkyl, nitro, cyano, alkoxy and lower alkylamino.

The term "heterocyclyl" or "heterocyclo" embraces 3- to 10-membered saturated, partially saturated and unsaturated heteroatom-containing ring-shaped radicals, where the heteroatoms may be selected from nitrogen, sulfur and oxygen. More preferred heterocyclyl are 5- to 8-membered ring heterocyclyl. Examples of saturated heterocyclic radicals include saturated 3- to 6-membered heteromonocyclic groups containing 1 to 4 nitrogen atoms [e.g., pyrrolidinyl, imidazolidinyl, piperidino, piperazinyl]; saturated 3- to 6-membered heteromonocyclic groups containing 1 to 2 oxygen atoms and 1 to 3 nitrogen atoms [e.g., morpholinyl]; saturated 3- to 6-membered heteromonocyclic groups containing 1 to 2 sulfur atoms and 1 to 3 nitrogen atoms [e.g., thiazolidinyl]. Examples of partially saturated heterocyclyl radicals include dihydrothiophene, dihydropyran, dihydrofuran and dihydrothiazole. Examples of unsaturated heterocyclic radicals, also termed "heteroaryl" radicals, include unsaturated 5- to 6-membered heteromonocyclyl groups containing 1 to 4 nitrogen atoms, for example, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated condensed heterocyclic groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl]; unsaturated 3- to 6-membered heteromonocyclic groups containing an oxygen atom, for example, pyranyl, 2-furyl, 3-furyl, etc., unsaturated 5- to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, isoxazolyl, oxadiazolyl [e.g., 1,2,4-oxadiazolyl, 1,3,4-oxadiazolyl, 1,2,5-oxadiazolyl]; unsaturated condensed heterocyclic groups containing 1 to 2 oxygen atoms and 1 to 3 nitrogen atoms [e.g., benzoxazolyl, benzoxadiazolyl]; unsaturated 5-to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]; unsaturated condensed heterocyclic groups containing 1 to 2 sulfur atoms and 1 to 3 nitrogen atoms [e.g., benzothiazolyl, benzothiadiazolyl] and the like. The term also embraces radicals where heterocyclic radicals are fused with aryl radicals. Examples of such fused bicyclic radicals include benzofuran, benzothiophene, and the like. Said "heterocyclyl" group may have 1 to 3 substituents such as lower alkyl, hydroxy, oxo, amino and lower alkylamino.

Heterocyclic radicals can include 3- to 10-membered fused or unfused radicals. Preferred examples of heteroaryl radicals include benzofuryl, 2,3-dihydrobenzofuryl, benzothienyl, indolyl, dihydroindolyl, chromanyl, benzopyran, thiochromanyl, benzothiopyran, benzodioxolyl, benzodioxanyl, pyridyl, thienyl, thiazolyl, furyl, and pyrazinyl. More preferred heteroaryl radicals are 5- or 6-membered heteroaryl, containing one or two heteroatoms selected from sulfur nitrogen and oxygen, selected from thienyl, furanyl, thiazolyl, imidazolyl, pyrazolyl, isoxazolyl, isothiazolyl, pyridyl, piperidinyl and pyrazinyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are lower aralkyl radicals having phenyl attached to alkyl portions having one to three carbon atoms. Examples of such radicals include benzyl, diphenylmethyl and phenylethyl. The aryl in said aralkyl may be additionally substituted with halo, alkyl, alkoxy, haloalkyl and haloalkoxy. The term "arylalkenyl" embraces aryl-substituted alkenyl radicals. Preferable arylalkenyl radicals are "lower arylalkenyl" radicals having aryl radicals attached to alkenyl radicals having two to six carbon atoms. Examples of such radicals include phenylethenyl. The aryl in said arylalkenyl may be additionally substituted with halo, alkyl, alkoxy, haloalkyl and haloalkoxy. The aryl in said aralkyl and arylalkenyl may be additionally substituted with halo, alkyl, alkoxy, haloalkyl and haloalkoxy.

The terms benzyl and phenylmethyl are interchangeable.

The term "heterocyclylalkyl" embraces heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkyl radicals having alkyl portions of one to three carbon atoms. Examples include such radicals as pyridylmethyl and thienylmethyl.

The terms "alkoxy" and "alkyloxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. The "alkoxy" radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy. The term "alkoxyalkyl" embraces alkyl radicals having one or more alkoxy radicals attached to the alkyl radical, that is, to form monoalkoxyalkyl and dialkoxyalkyl radicals.

The term "aryloxy" embraces aryl radicals attached through an oxygen atom to other radicals. The term "aralkoxy" embraces aralkyl radicals attached through an oxygen atom to other radicals. The term "aryloxyalkyl" embraces aryloxy radicals as described above attached through the oxygen atom to an alkyl radical. The term "heterocyclyloxy" embraces heterocyclyl radicals attached through an oxygen atom to other radicals.

The term "alkylsulfinyl" embraces radicals containing a linear or branched alkyl radical, of one to ten carbon atoms, attached to a divalent —S(=O)— atom. More preferred are lower alkylsulfinyl radicals having one to three carbon atoms.

The term "sulfonyl", whether used alone or linked to other terms such as "alkylsulfonyl" and "arylsulfonyl", denotes respectively divalent radicals —SO$_2$. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Even more preferred are lower alkylsulfonyl radicals having one to three carbon atoms. Examples of such lower alkylsulfonyl radicals include methylsulfonyl, ethylsulfonyl and propylsulfonyl. "Arylsulfonyl" embraces aryl radicals attached to a sulfonyl radical, where aryl is defined as above. A preferred arylsulfonyl radical is phenylsulfonyl.

The terms "sulfamyl," "aminosulfonyl" and "sulfonamidyl," whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide (—SO$_2$NH$_2$). The term "alkylaminosulfonyl" includes "N-alkylaminosulfonyl" and "N,N-dialkylaminosulfonyl" where sulfamyl radicals are substituted, respectively, with one alkyl radical, or two alkyl radicals. More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, N-ethylaminosulfonyl and N-methyl-N-ethylaminosulfonyl. The terms "N-arylaminosulfonyl" and "N-alkyl-N-arylaminosulfonyl" denote sulfamyl radicals substituted, respectively, with one aryl radical, or one alkyl and one aryl radical. More preferred N-alkyl-N-arylaminosulfonyl radicals are "lower N-alkyl-N-arylsulfonyl" radicals having alkyl radicals of one to six carbon atoms. Even more preferred are lower N-alkyl-N-arylsulfonyl radicals having one to three carbon atoms. Examples of such lower N-alkyl-N-arylaminosulfonyl radicals include N-methyl-N-phenylaminosulfonyl and N-ethyl-N-phenylaminosulfonyl. Examples of such N-aryl-aminosulfonyl radicals include N-phenylaminosulfonyl.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, (CH$_3$—S—). The term "alkylthioalkyl" embraces radicals containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include methylthiomethyl.

The term "arylthio" embraces aryl radicals of six to ten carbon atoms, attached to a divalent sulfur atom. An example of "arylthio" is phenylthio. The term "aralkylthio" embraces aralkyl radicals as described above, attached to a divalent sulfur atom. More preferred are phenyl-C$_1$-C$_3$-alkylthio radicals. An example of "aralkylthio" is benzylthio. The term "arylthioalkyl" embraces arylthio radicals as described above, through the sulfur atom to an alkyl radical.

The terms "carboxy" or "carboxyl", whether used alone or with other terms, such as "carboxyalkyl", denotes —CO$_2$H. The term "carboxyalkyl" embraces radicals having a carboxy radical as defined above, attached to an alkyl radical.

The term "carbonyl", whether used alone or with other terms, such as "alkylcarbonyl", denotes —(C=O)—.

The term "alkylcarbonyl" embraces radicals having a carbonyl radical substituted with an alkyl radical. More preferred alkylcarbonyl radicals are "lower alkylcarbonyl" radicals having one to six carbon atoms. Even more preferred are lower alkylcarbonyl radicals having one to three carbon atoms. The term "alkylcarbonyl" includes radicals having alkyl, hydroxylalkyl, radicals, as defined herein, attached to a carbonyl radical. Examples of such radicals include substituted or unsubstituted methylcarbonyl, ethylcarbonyl, propylcarbonyl, butylcarbonyl, pentylcarbonyl, hydroxymethylcarbonyl, hydroxyethylcarbonyl.

The term "arylcarbonyl" embraces radicals having a carbonyl radical substituted with an aryl radical. More preferred arylcarbonyl radicals include phenylcarbonyl. The term "arylalkylcarbonyl" embraces radicals having a carbonyl radical substituted with an arylalkyl radical. More preferred radicals are phenyl-C$_1$-C$_3$-alkylcarbonyl, including benzyl-carbonyl.

The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl. Even more preferred are lower alkoxycarbonyl radicals having alkoxy portions of one to three carbon atoms. The term "alkoxycarbonylalkyl" embraces alkyl radicals substituted with an alkoxycarbonyl radical as defined above. More preferred are "lower alkoxycarbonylalkyl" radicals with alkyl portions having one to six carbons. Examples of such lower alkoxycarbonylalkyl radicals include substituted or unsubstituted methoxycarbonylmethyl, ethoxycarbonylmethyl, methoxycarbonylethyl and ethoxycarbonylethyl.

The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula $—C(=O)NH_2$. The terms "N-alkylaminocarbonyl" and "N,N-dialkylaminocarbonyl" denote aminocarbonyl radicals which have been substituted with one alkyl radical and with two alkyl radicals, respectively. More preferred are "lower alkylaminocarbonyl" having lower alkyl radicals as described above attached to an aminocarbonyl radical. The terms "N-arylaminocarbonyl" and "N-alkyl-N-arylaminocarbonyl" denote aminocarbonyl radicals substituted, respectively, with one aryl radical, or one alkyl and one aryl radical.

The term "aminoalkyl" embraces alkyl radicals substituted with amino radicals. The term "alkylaminoalkyl" embraces aminoalkyl radicals having the nitrogen atom substituted with an alkyl radical. Even more preferred are lower alkylaminoalkyl radicals having one to three carbon atoms.

The terms "N-alkylamino" and "N,N-dialkylamino" denote amino groups which have been substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable "alkylamino" may be mono or dialkylamino such as N-methylamino, N-ethylamino, N,N-dimethylamino, N,N-diethylamino or the like. The term "arylamino" denotes amino groups which have been substituted with one or two aryl radicals, such as N-phenylamino. The "arylamino" radicals may be further substituted on the aryl ring portion of the radical. The term "aralkylamino" denotes amino groups that have been substituted with one or two aralkyl radicals. More preferred are phenyl-$C_1$-$C_3$-alkylamino radicals, such as N-benzylamino. The "aralkylamino" radicals may be further substituted on the aryl ring portion of the radical. The terms "N-alkyl-N-arylamino" and "N-aralkyl-N-alkylamino" denote amino groups which have been substituted with one aralkyl and one alkyl radical, or one aryl and one alkyl radical, respectively, to an amino group.

The additional terms used to describe the substituents of the compounds of Formulae I–VII and not specifically defined herein are defined in a similar manner to that illustrated in the above definitions.

The terms "treatment" and "treating" refers to any process, action, application, therapy, or the like, wherein a subject, including a human being, is provided medical aid with the object of improving the subject's condition, directly or indirectly, or slowing the progression of a condition or disorder in the subject.

The term "prevention" or "prophylaxis" includes either preventing the onset of clinically evident inflammation or inflammation related disorders altogether or preventing the onset of a preclinically evident stage of inflammation or an inflammation related disorder in individuals.

The term "therapeutically-effective" is intended to qualify the amount of each agent that will achieve the goal of improvement in disease severity and the frequency of incidence while avoiding adverse side effects typically associated with alternative therapies.

The term "prodrug" refers to a compound that is a drug precursor that, following administration to a subject and subsequent absorption, is converted to an active species in vivo via some process, such as metabolic conversion. Other products from the conversion process are easily disposed of by the body. More preferred prodrugs produce products from the conversion process that are generally accepted as safe. By way of illustration and not limitation, U.S. Pat. No. 5,932,598 describes prodrug forms of compounds that are substituted sulfonamide compounds that selectively inhibit cyclooxygenase-2. For example, the prodrug may be an acylated form of the active compound such as an acylated sulfonamide.

The term "co-therapy" (or "combination-therapy"), in defining use of a cyclooxygenase-2 inhibitor agent and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Stereoisomers, Tautomers, Protected Acids and Salts

Also included in the family of compounds of Formulae I through VII are the stereoisomers thereof including, but not limited to enantiomers, diastereomers, racemic mixtures and other mixtures thereof.

Also included in the family of compounds of Formulae I through VII are the tautomeric forms of those compounds.

Also included in the family of compounds of Formulae I through VII are the protected acids thereof, such as the esters, hydroxyamino derivatives, amides and sulfonamides. Thus, for example, primary and secondary amines can be reacted with carboxylic acid substituted forms of Formulae I–VII to form amides which can be useful as prodrugs. Preferred amines are heterocyclic amines, including optionally substituted aminothiazoles, optionally substituted amino-isoxazoles, and optionally substituted aminopyridines; aniline derivatives; sulfonamides; aminocarboxylic acids; and the like. The esters, hydroxyamino derivatives and sulfonamides can be prepared from the acids by methods known to one skilled in the art.

Also included in the family of compounds of Formulae I–VII are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formulae I–VII may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, N-hydroxybutyric, salicyclic, galactaric and galacturonic acid. Suitable pharmaceutically-acceptable base addition salts of compounds of Formulae I–VII include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, trimethylamine. All of these salts may be prepared by conventional means from the corresponding compounds of the invention by reacting, for example, the appropriate acid or base with the compounds of Formulae I–VII.

Pharmaceutical Compositions

Also embraced within this invention is a class of pharmaceutical compositions comprising the one or more of the active compounds of Formulae I–VII in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and compositions may, for example, be administered orally, pulmonary, mucosally, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredients in the range of about 0.1 to 2000 mg, preferably in the range of about 0.5 to 500 mg and most preferably between about 1 and 100 mg. A daily dose of about 0.01 to 100 mg/kg body weight, preferably between about 0.5 and about 20 mg/kg body weight and most preferably between about 0.1 to 10 mg/kg body weight, may be appropriate. The daily dose can be administered in one to four doses per day.

In the case of psoriasis and other skin conditions, it may be preferable to apply a topical preparation of compounds of this invention to the affected area two to four times a day.

For inflammations of the eye or other external tissues, e.g., mouth and skin, the formulations are preferably applied as a topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol such as propylene glycol, butane-1,3- diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

For pulmonary administration, the pharmaceutical composition may be administered in the form of an aerosol or with an inhaler including dry powder aerosol.

General Synthetic Procedures

The compounds of the invention can be synthesized according to the procedures set forth below. The substituents of the compounds shown in the following procedures generally have the same definition as the substituents at the corresponding position in the compounds of Formulae I–VII, except where further noted. For example, unless otherwise noted, $R^1$, $R^2$ and $R^3$ as used in the procedures below correspond to $R^1$, $R^2$ and $R^3$ as previously defined; $R^{3A}$ and $R^{3B}$ correspond to substituents independently selected from $R^3$ as previously defined; and $R^S$ corresponds to a functional group selected from the group consisting of hydrogen and the optional substituents previously defined for the $R^1$ cyclohexyl, pyridinyl and phenyl moieties. Unless otherwise noted, $X^H$ as used in the procedures below corresponds to halogen. Although the discussion of the synthetic methodology outlined below focuses primarily on difluoro compounds (i.e., wherein one of $X^1$ and $X^2$ is fluoro and the other of $X^1$ and $X^2$ is hydrogen), it also is applicable to the preparation of trifluoro compounds (i.e., wherein both of $X^1$ and $X^2$ are fluoro).

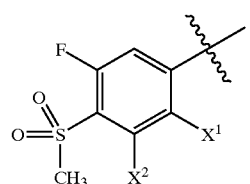

1. $X^1$ = H, $X^2$ = F
2. $X^1$ = F, $X^2$ = H

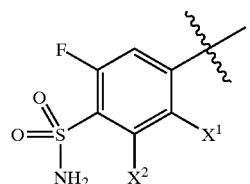

3. $X^1$ = H, $X^2$ = F
4. $X^1$ = F, $X^2$ = H

The 3,5-difluoro-4-methylsulfonylphenyl 1, 2,5-difluoro-4-methylsulfonylphenyl 2, 3,5-difluoro-4-aminosulfonylphenyl 3, and 2,5-difluoro-4-amino-sulfonylphenyl 4 are specific regiochemically substituted aromatic rings present in the cyclooxygenase-2 inhibiting diaryl-heterocycles disclosed in this application. The described difluoro-4-methylsulfonylphenyl 1 or 2 and difluoro-4-amino-sulfonylphenyl 3 or 4 ring functionality can be prepared using the synthetic methodology outlined below for the various diaryl substituted heterocycles disclosed in this application.

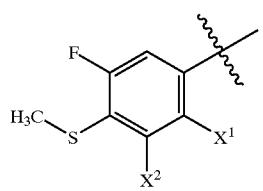

5. $X^1$ = H, $X^2$ = F
6. $X^1$ = F, $X^2$ = H

[O] →

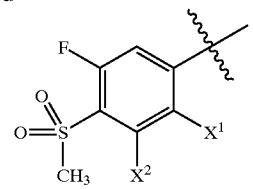

1. $X^1$ = H, $X^2$ = F
2. $X^1$ = F, $X^2$ = H

The methylthio 5 or 6 group can be converted to the corresponding methylsulfone 1 or 2, respectively, through treatment with at least two molar oxidizing equivalents of a reagent such as m-chloroperbenzoic acid, monoperoxyphthalic acid, or OXONE®.

Scheme I

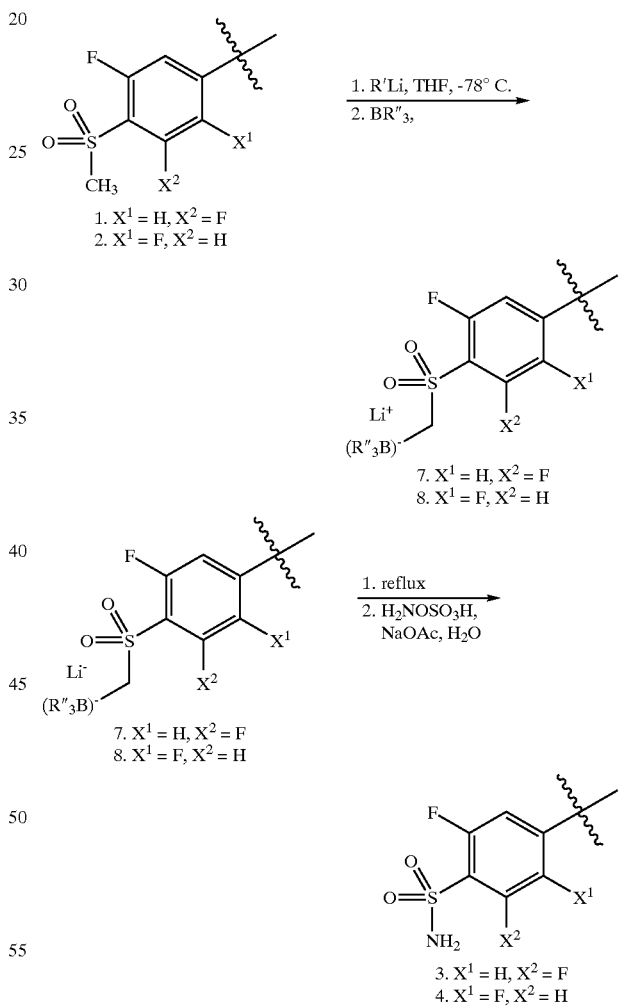

The sulfonamide 3 or 4 can be obtained from the corresponding sulfone 1 or 2 by treatment with an alkyl base such as butyllithium, methyllithium, and the like in ethereal solvents such as tetrahydrofuran at approximately −78° C. In a second step, a trialkyl-borane such as triethylborane or tributylborane is added affording the corresponding intermediate borate 7 or 8 which is warmed to room temperature prior to refluxing for 16 hours or an appropriate period of time. The solution is cooled to room temperature. Water, sodium acetate and hydroxylamine-O-sulfonic acid are then added to yield the sufonamide 3 or 4 [Hwang, *Tetrahedron Letters*, 35, 7201–04 (1994)].

followed by in situ ethylene extrusion affords the sulfinic acid 13 or 14 [Vhu, *Steroids*, 67, 543–45 (1997)]. Sulfinic acid 13 or 14 can be converted to the corresponding sul-

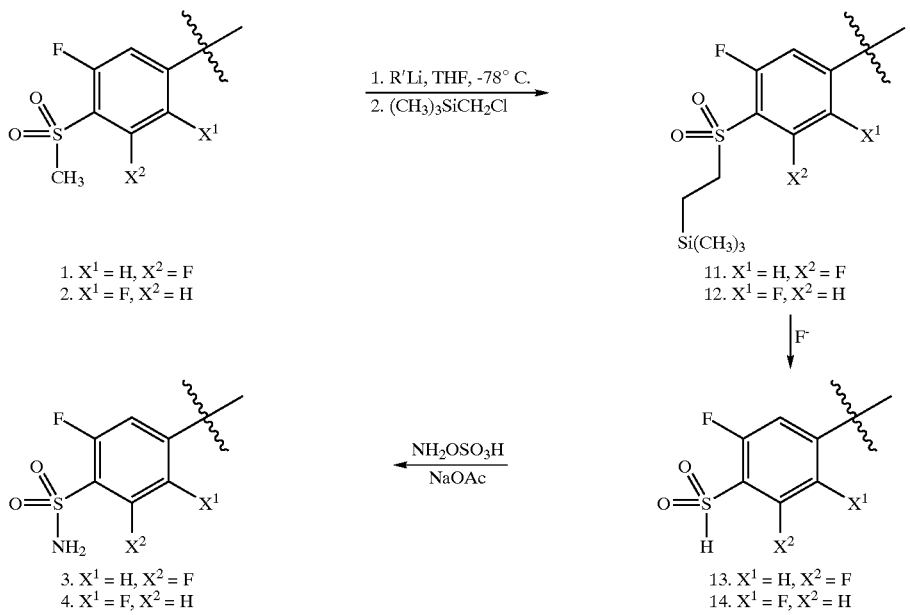

In Scheme II, sulfonamide 3 or 4 can be obtained by treatment of the corresponding sulfone 1 or 2 with an alkyl base such as butyllithium. Addition of trimethylsilylmethylchloride affords the corresponding trimethylsilylethylsulfone 11 or 12. Desilylation by a reagent such as tetra-n-butyl ammonium fluoride to a solution of the sulfone 11 or 12 fonamide 3 or 4 by the addition of sodium acetate and hydroxylamine-O-sulfonic acid.

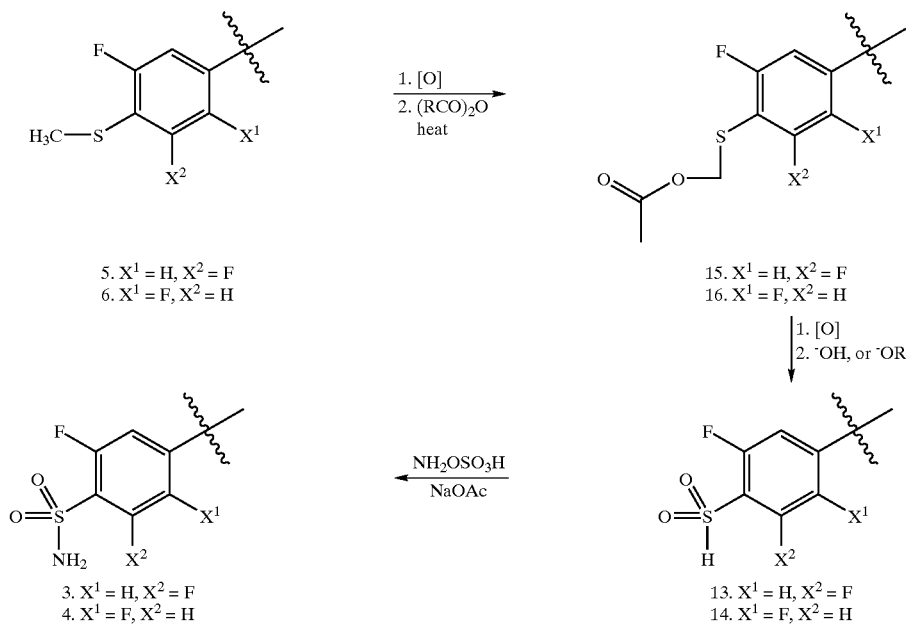

In Scheme III sulfonamides 3 or 4 can be prepared from the methylthio group from the corresponding ring substitution in 5 or 6 by conversion of the methylthio moiety to the sulfoxide by careful addition of one equivalent of an oxidizing agent such as m-chloroperbenzoic acid, monoperoxyphthalic acid, or OXONE®. A Pummer rearrangement performed by mixing the resulting sulfoxide in anhydrides followed by heating provides the corresponding thioacetal 15 or 16. Oxidation to the sulfone as described earlier followed by treatment with either hydroxide or an alkoxide provides the corresponding sulfinic acid 13 or 14 [Vleeschauwer, *Syn. Lett.,* 4, 375–77, (1997)]. The sulfinic acid 13 or 14 can be converted to the desired sulfonamide 3 or 4 by the addition of a suitable base such as sodium acetate and hydroxylamine-O-sulfonic acid in aqueous alcoholic solvents such as methanol-water or ethanol-water.

Scheme IV

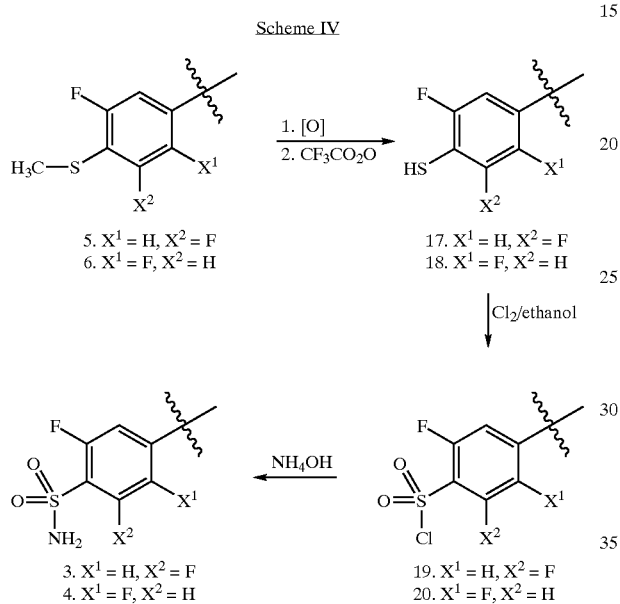

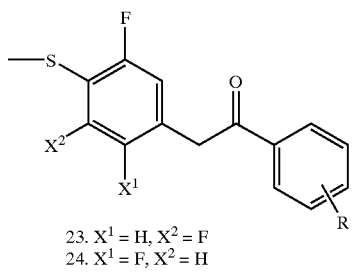

23. $X^1 = H, X^2 = F$
24. $X^1 = F, X^2 = H$

Difluoro-4-methylthiophenyl-substituted-phenyl-ethanones 21, 22, 23 and 24 are intermediates used in the preparation of many of the diaryl-heterocycles disclosed in this application. The following is a description of several methods for their preparation.

Scheme V

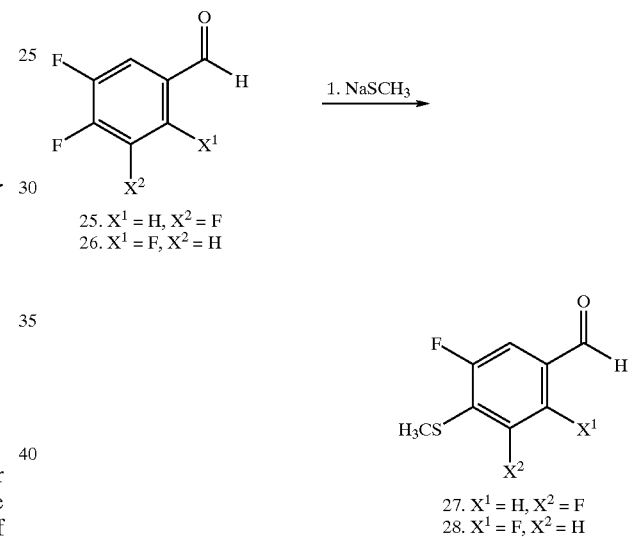

Alternatively, Scheme IV illustrates another procedure for the preparation of sulfonamides 3 or 4 starting with the corresponding methylthio moiety 5 or 6. First, conversion of the methylthio moiety to the methylsulfoxide is accomplished by careful addition of one equivalent of an oxidizing agent such as m-chloro-perbenzoic acid, monoperoxyphthalic acid, or OXONE®. The methylsulfoxide is then mixed in a variety of inert solvents such as dichloromethane with trifluoroacetic anhydride which, after aqueous workup, provides the corresponding sulfide 17 or 18, respectively. The sulfide 17 or 18 is treated with chlorine providing the corresponding sulfonyl-chloride 19 or 20. Finally, addition of ammonia to the sulfonylchloride 19 or 20 affords the desired sulfonamide 3 or 4 [Kharash, *J. Am. Chem. Soc.,* 73, 3240 (1951)].

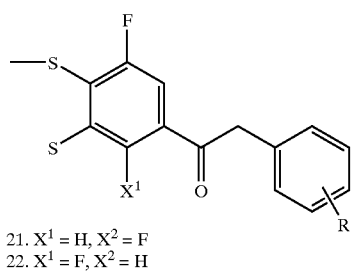

21. $X^1 = H, X^2 = F$
22. $X^1 = F, X^2 = H$

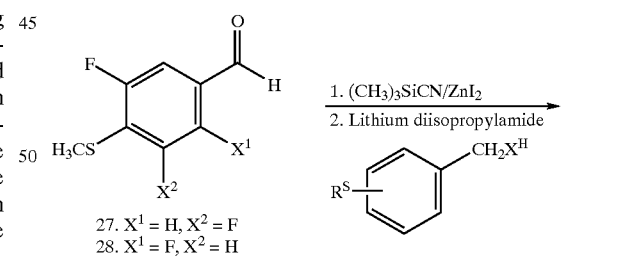

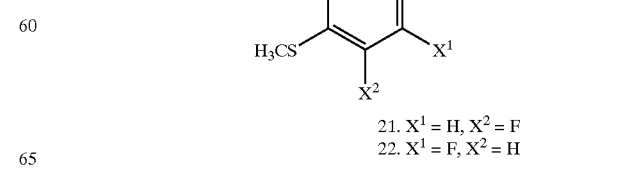

21. $X^1 = H, X^2 = F$
22. $X^1 = F, X^2 = H$

Scheme V illustrates the preparation of a deoxybenzoin 21 or 22. Mixing trifluorobenzaldehyde 25 or 26 with sodium thiomethoxide in polar solvents such as acetonitrile or dimethylformamide produces the corresponding difluoro-4-methylthiobenzaldehyde 27 or 28. A solution of the aldehyde, zinc iodide, and trimethylsilyl cyanide in a halogenated solvent such as dichloromethane is mixed at room temperature affording a trimethylsilylcyanohydrin. Deprotonation of the cyanohydrin with a base such as lithium diisopropylamide or lithium hexamethyl-disilylamide followed by addition of an appropriately substituted benzylhalide and acid-base workup of the reaction yields the corresponding 1-(difluoro-4-methylthiophenyl)-2-(substituted-phenyl)-ethanone 21 or 22.

desired 1-(substituted-phenyl)-2-(difluoro-4-methylthiophenyl)-ethanone 23 or 24.

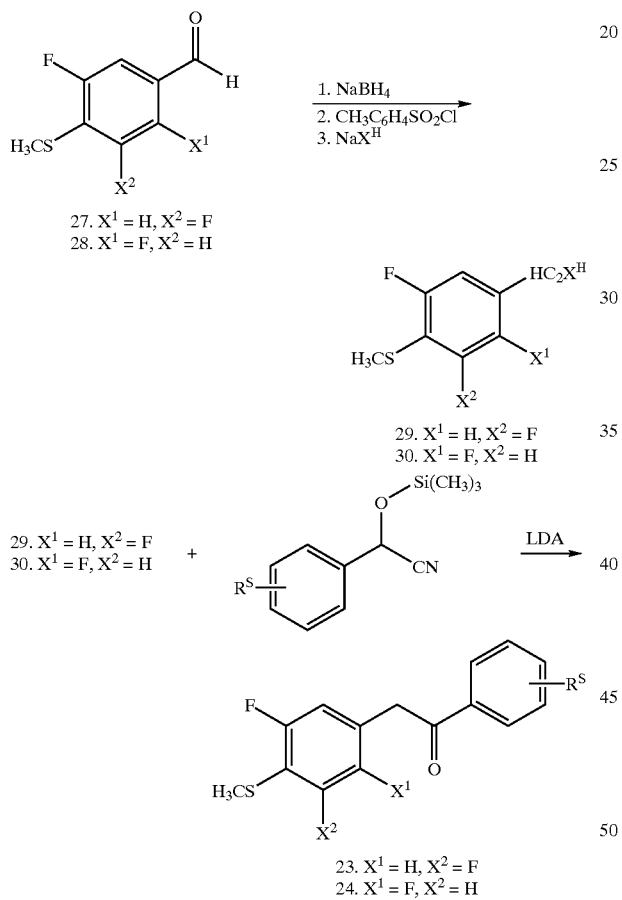

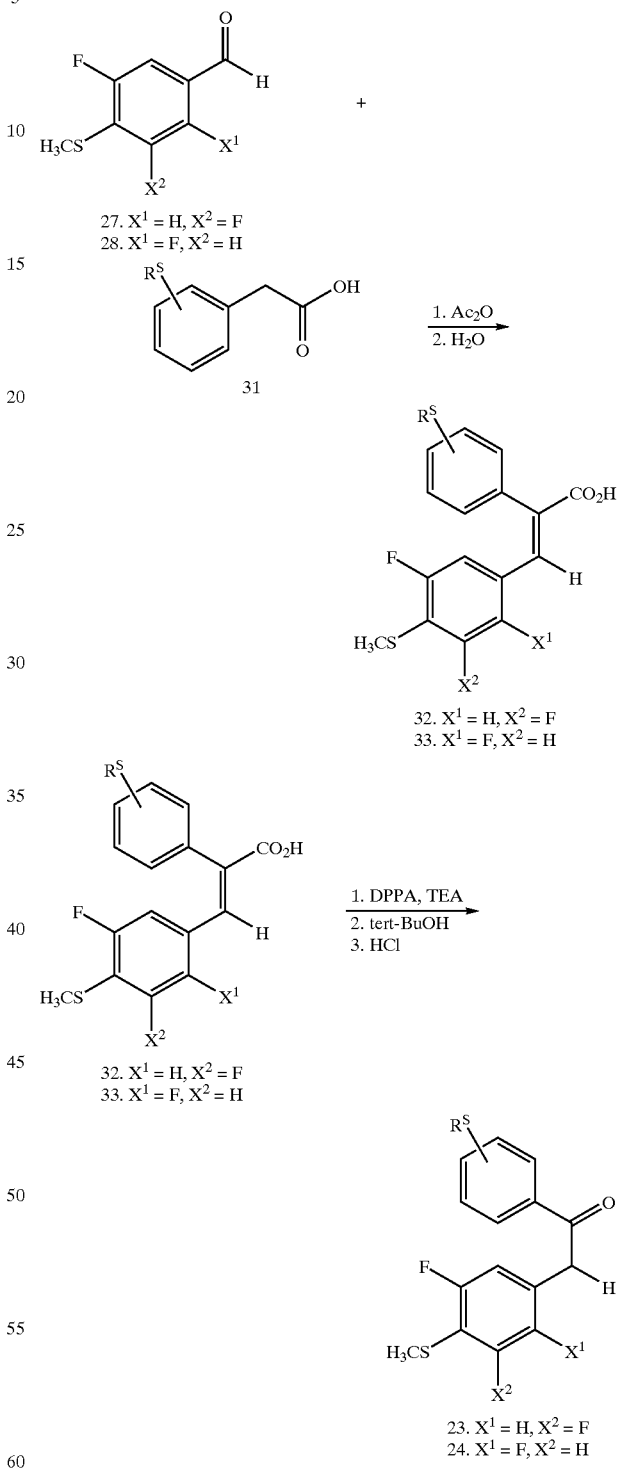

A synthetic scheme for the preparation of difluoro-4-methylthiophenyl-substituted-phenyl-ethanone 23 or 24, which has the alternative regiochemistry, is outlined in Scheme VI. Reduction of the difluoro-4 methylthiobenzaldehyde 27 or 28 with hydride reagents such as sodium borohydride, lithium aluminum hydride, and the like affords the benzyl alcohol. Conversion of the benzyl alcohol to the corresponding benzyl halide 29 or 30 can be accomplished through the preparation of the tosylate followed by displacement with chloride or bromide ion (represented by $X^H$ in Scheme VI). These compounds can be utilized in the synthetic methodology described previously to afford the Scheme VII illustrates a procedure that can be used to prepare 1-(substituted-phenyl)-2-(difluoro-4-methylthiophenyl)-ethanone 23 or 24 from the corresponding difluoro-4-methylthiobenzaldehyde 27 or 28. In step one, the aldehyde 27 or 28 and substituted phenylacetic acid 31 are heated in acetic anhydride and triethylamine which, upon aqueous quenching, affords the corresponding 2,3-disubstituted acrylic acid 32 or 33. Mixing of acrylic acid 32 or 33 with diphenylphosphorylazide (DPPA) and triethylamine produces an acylazide. The acylazide undergoes a Curtius rearrangement to an isocyanate which is trapped with tert-butanol yielding a N-tert-butylcarboxy-carbamate. Treatment of the carbamate with concentrated aqueous hydrochloric acid provides the desired substituted ketone 23 or 24.

substituted-phenyl ethanone 21 or 22 and an acetal of dimethylformamide are refluxed together in toluene. Upon removal of the solvent and excess acetal, the enamine 33 or 34 is obtained. The enamine 33 or 34 is refluxed in 1,2 dichloroethane with esters of thioacetic acid affording a mixture of Michael addition products 35 or 36. The 1,2-dichloroethane is removed at reduced pressure and the residue is taken up in an alcoholic solvent and the related sodium alkoxide added. Upon mixing at room temperature

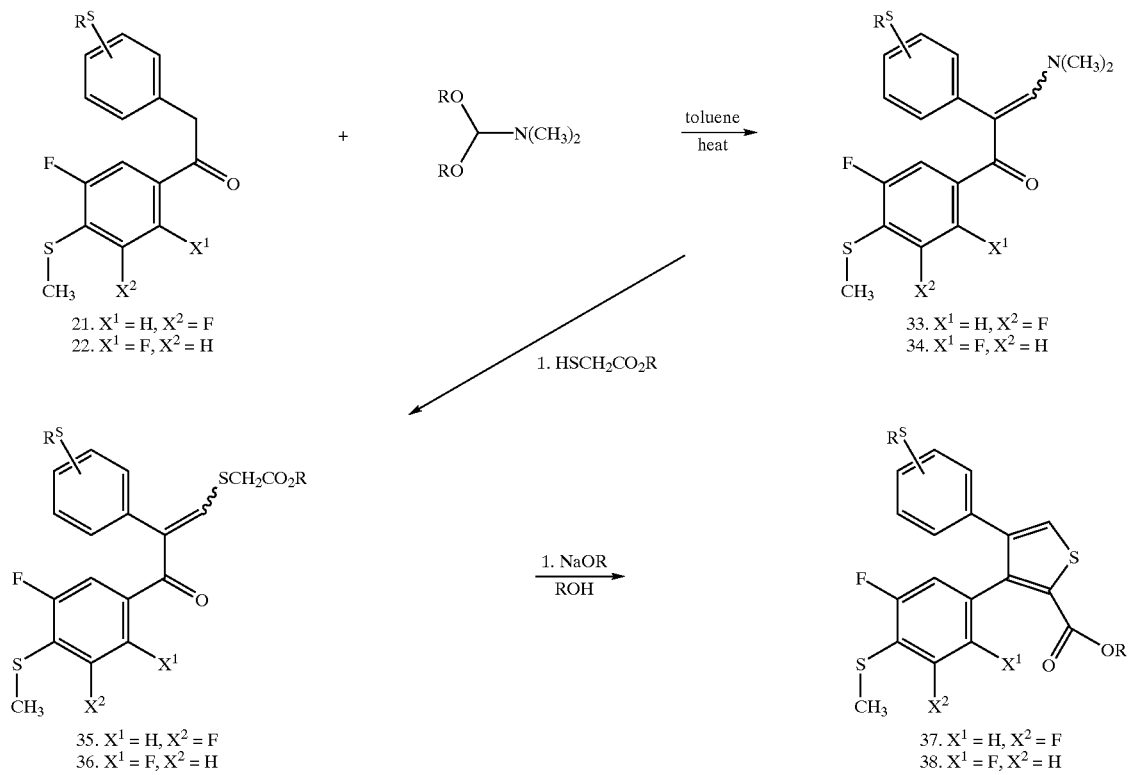

The preparation of 3,4-diarylthiophene 37 or 38 is illustrated in Scheme VIII. Difluoro-4-methylthiophenylthe desired trisubstituted thiophene 37 or 38 is obtained after purification.

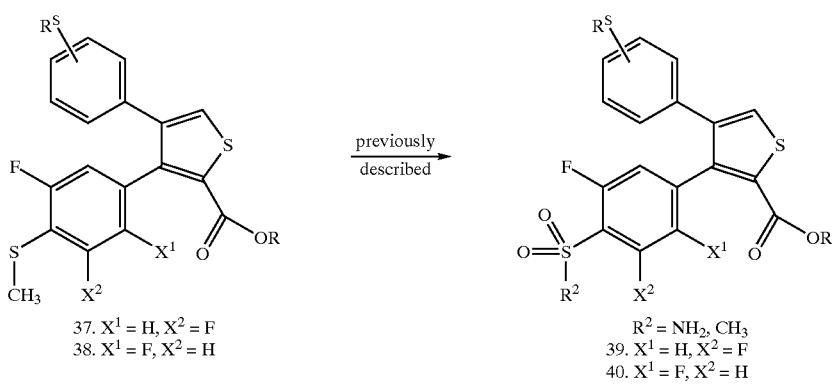

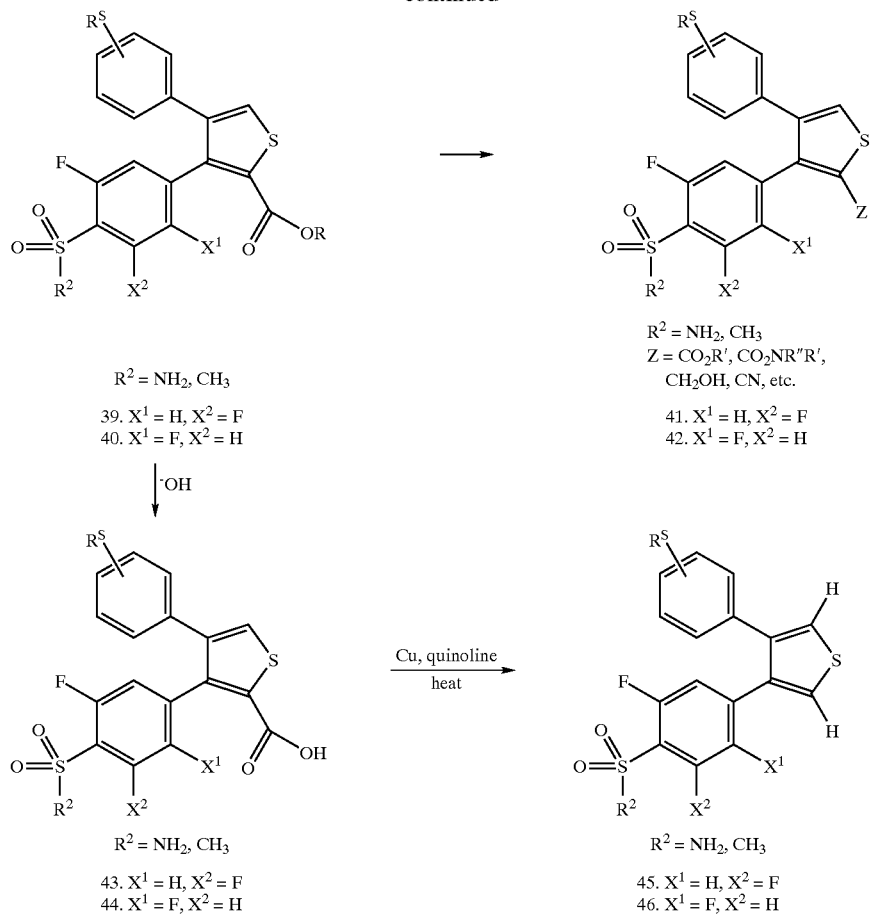

As illustrated in Scheme IX, the methylthio moiety 37 or 38 can be converted to the corresponding difluoronated methyl sulphone or sulfonamide 39 or 40 as described previously. The ester group of thiophene 39 or 40 then can be manipulated using conventional organic laboratory procedures into a number functional groups such as alcohol, alkyl, alkene, alkyne, amide, cyano, etc. The ester group also can be saponified and the resulting carboxylic acid 43 or 44 removed through a copper-mediated decarboxylation affording the desired 3,4-substituted diphenylthiophene 45 or 46.

Scheme X

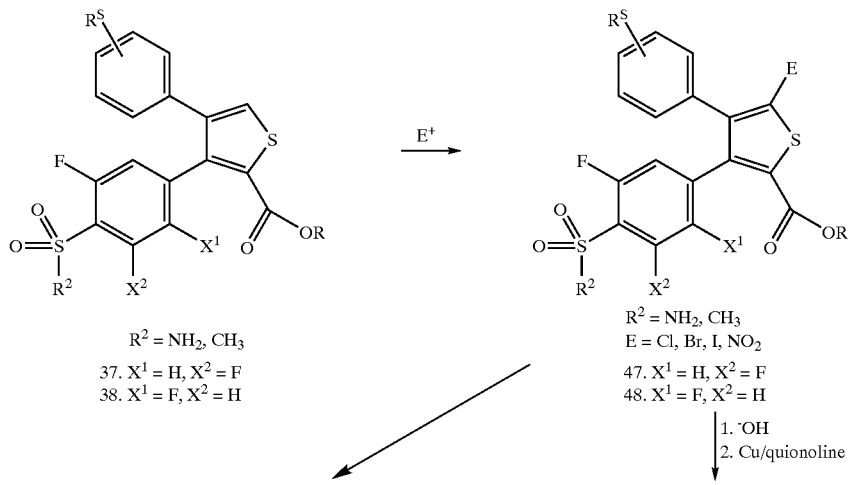

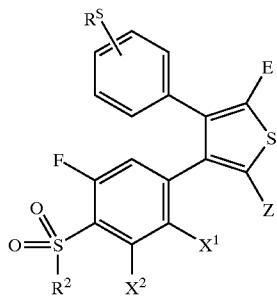

$R^2 = NH_2, CH_3$
$E = Cl\ Br, I, NO_2$
$Z = CO_2R, CO_2NR''R'$,
  $CH_2OH, CN$, etc.

49. $X^1 = H, X^2 = F$
50. $X^1 = F, X^2 = H$

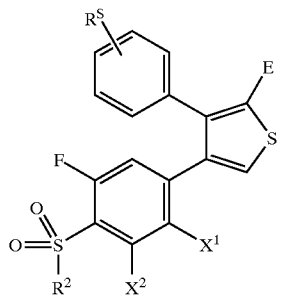

$R^2 = NH_2, CH_3$
$E = Cl, Br, I, NO_2$

51. $X^1 = H, X^2 = F$
52. $X^1 = F, X^2 = H$

Alternatively, as illustrated in Scheme X, the remaining hydrogen of the thiophene ring 37 or 38 can be converted to functional groups as in the corresponding difluoronated compounds 49, 50, 51 or 52, respectively.

Scheme XI

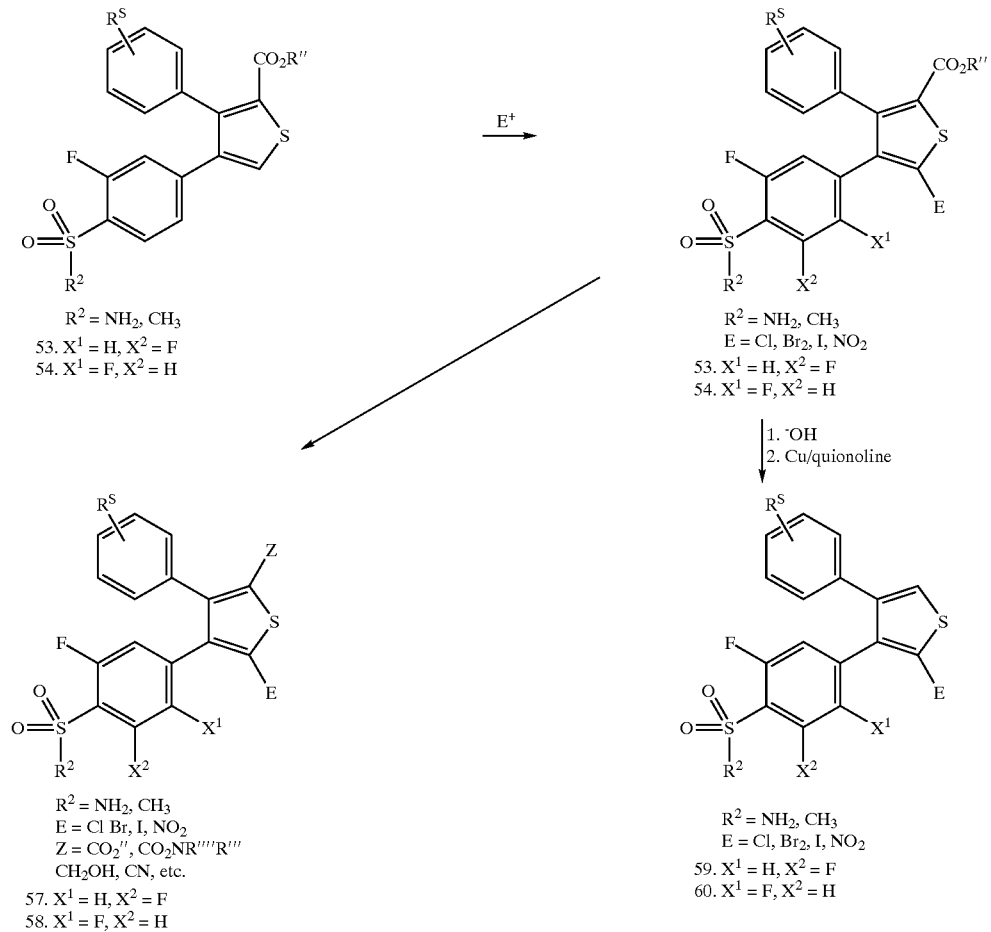

a halogen or nitro group in the corresponding 47 or 48 and the ester once more manipulated as described to a variety of Initiation of the thiophene protocol with the second regioisomer of the difluoro-4-methylthiophenyl-substitutedphenyl ethanone 21 or 22 and implementation of the thiophene chemistry described in Scheme X affords thiophenes with the regiosubstitution shown in Scheme XI.

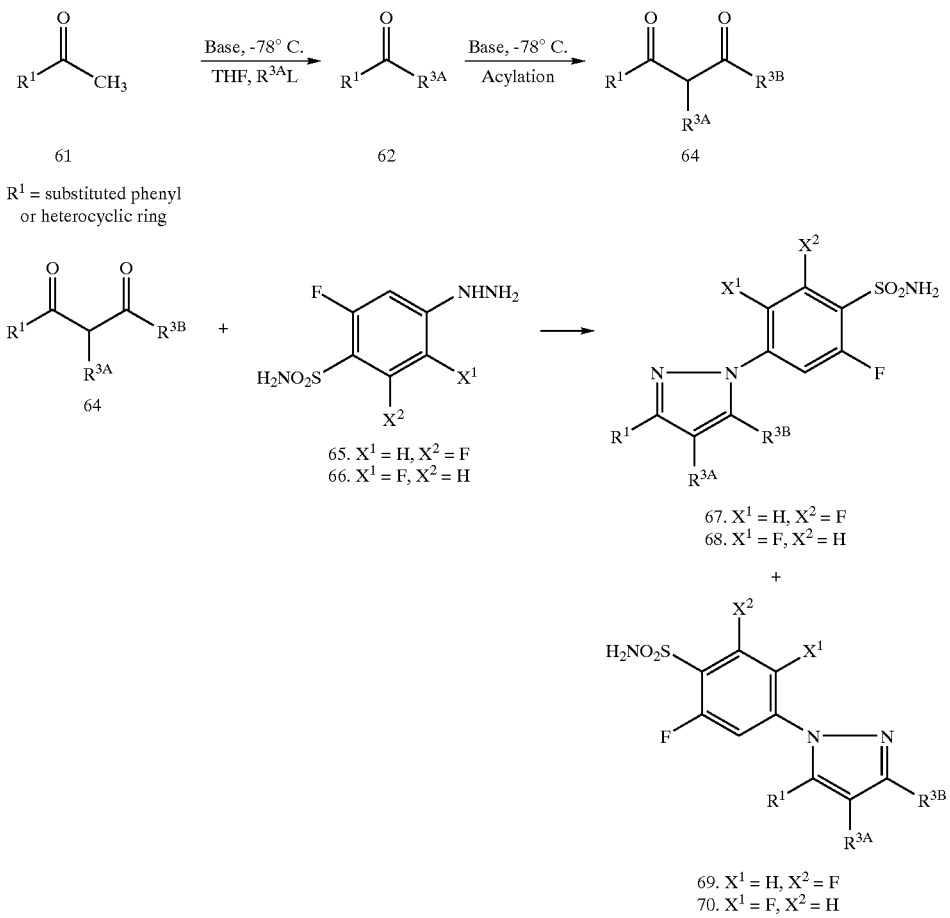

Synthetic Scheme XII illustrates the preparation of tetra-substituted pyrazoles from acetophenone 61. In step 1 of synthetic Scheme XII, the phenyl-methyl ketone 61 is treated with a base and an alkylating reagent ($R^{3A}L$, where L represents a leaving group such as tosyl) to give the substituted ketone 62. In step 2, the substituted ketone 62 is treated with base, such as sodium methoxide, and an acylating reagent such as an ester ($R^{3B}CO_2CH_3$), or ester equivalent ($R^{3B}CO$-imidazole) to give the intermediate diketone 64 [Reid, Calvin, *J. Amer. Chem. Soc.*, 72, 2948–52 (1950)]. In step 3, the diketone 64 is reacted with a substituted hydrazine 65 or 66 in acetic acid or an alcoholic solvent to give a mixture of corresponding pyrazoles 67 and 69, or 68 and 70, respectively. Separation of the desired pyrazole 69 or 70 can be achieved by chromatography or recrystallization.

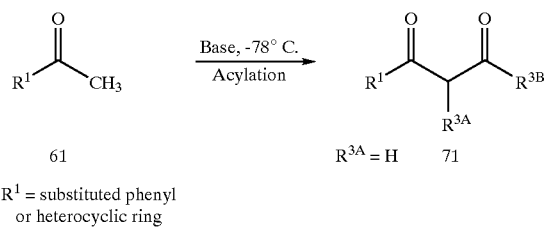

-continued

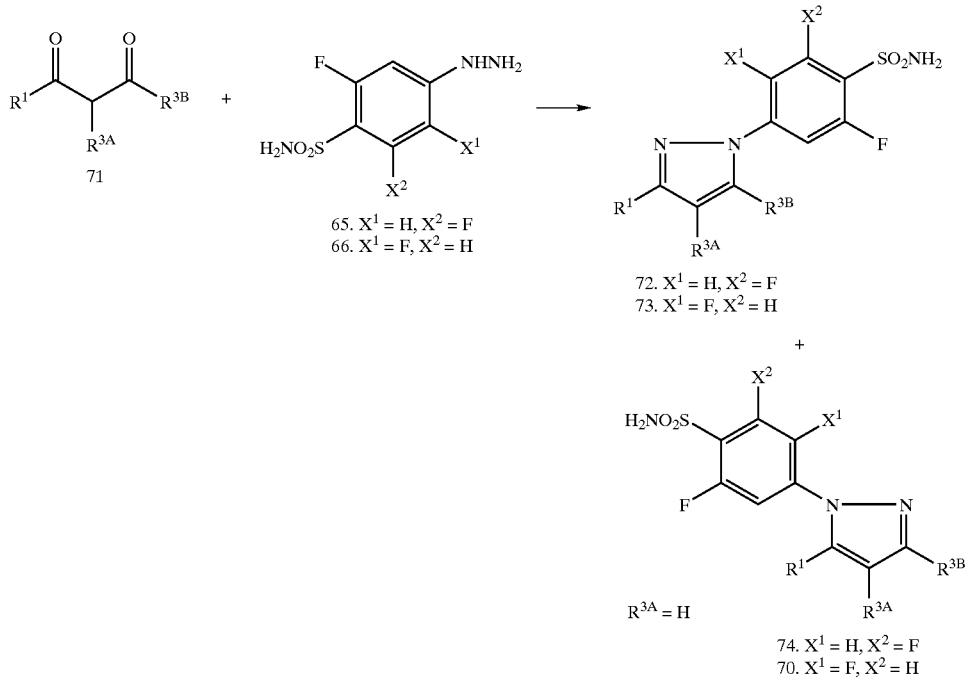

65. $X^1 = H, X^2 = F$
66. $X^1 = F, X^2 = H$

72. $X^1 = H, X^2 = F$
73. $X^1 = F, X^2 = H$

74. $X^1 = H, X^2 = F$
70. $X^1 = F, X^2 = H$

Synthetic Scheme XIII illustrates the preparation of 4-unsubstituted pyrazoles (i.e., $R^{3A}$ as used in Scheme XIII is hydrogen). In step 1, ketone 61 is treated with a base, preferably sodium methoxide or sodium hydride, and an ester, or ester equivalent, to form the intermediate diketone 71 which is used without further purification. In step 2, diketone 71 in an anhydrous protic solvent, such as absolute ethanol or acetic acid, is treated with the hydrochloride salt or the free base of a substituted hydrazine 65 or 66 at reflux for 10 to 24 hours to afford a mixture of pyrazoles 72 and 74, or 73 and 75, respectively. Recrystallization from diethyl ether/hexane or chromatography affords the corresponding desired compound 74 or 75, usually as a light yellow or tan solid. Additional pyrazoles can be prepared in accordance with the methods described in U.S. Pat. Nos. 5,401,765, 5,434,178, 4,146,721, 5,051,518, 5,134,142, and 4,914,121, which are incorporated by reference.

Scheme XIV

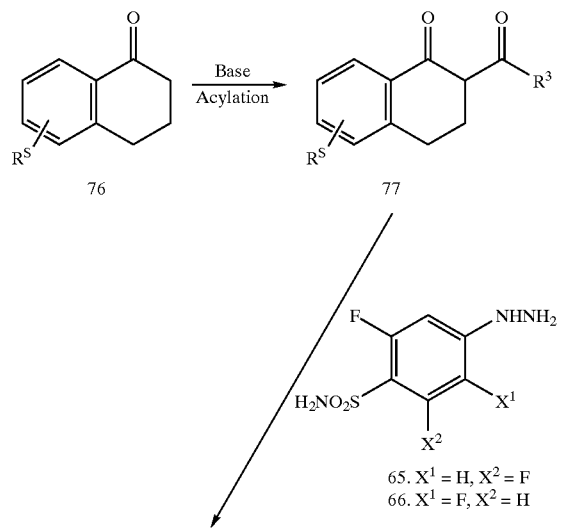

65. $X^1 = H, X^2 = F$
66. $X^1 = F, X^2 = H$

-continued

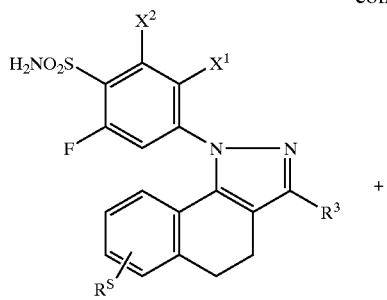
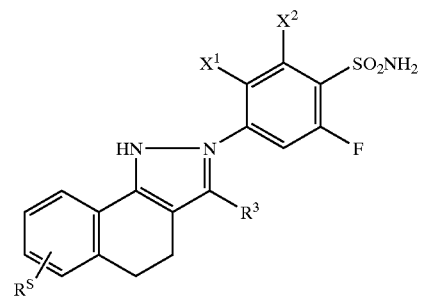

78. $X^1 = H, X^2 = F$
79. $X^1 = F, X^2 = H$

80. $X^1 = H, X^2 = F$
81. $X^1 = F, X^2 = H$

Synthetic Scheme XIV illustrates the preparation of 4,5-dihydrobenz[g]indazole compounds. In step 1, ethyl esters of acetates are mixed with base, such as 25% sodium methoxide in a protic solvent, such as methanol, and 1-tetralone derivative 76 to give the intermediate diketone 77. In step 2, the diketone 77 in an anhydrous protic solvent, such as absolute ethanol or acetic acid, is treated with the free base or hydrochloride salt of a substituted hydrazine 65 or 66 at reflux for 24 hours to afford a mixture of corresponding pyrazoles 78 and 80, or 79 and 81. Recrystallization gives the 4,5-dihydrobenz[g]indazolyl-benzenesulfonamide 78 or 79.

Scheme XV

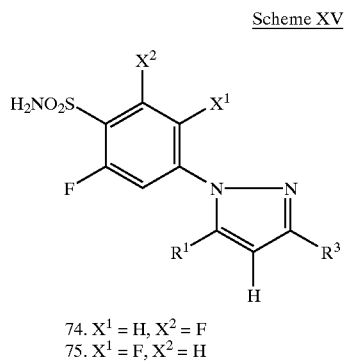

74. $X^1 = H, X^2 = F$
75. $X^1 = F, X^2 = H$ $R^1$ = Substituted phenyl or heterocycle

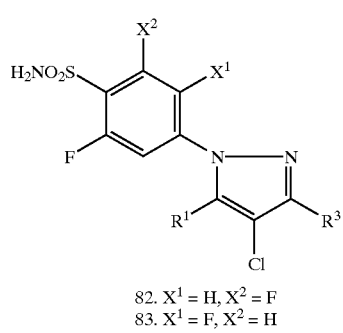

82. $X^1 = H, X^2 = F$
83. $X^1 = F, X^2 = H$

Synthetic Scheme XV illustrates the preparation of 4-chloro-pyrazole compound 82 or 83, from the pyrazole compound 74 or 75 wherein $R^{3A}$ is hydrogen. Chlorination results from passing a stream of chlorine gas at room temperature through a solution containing 74 or 75.

Scheme XVI

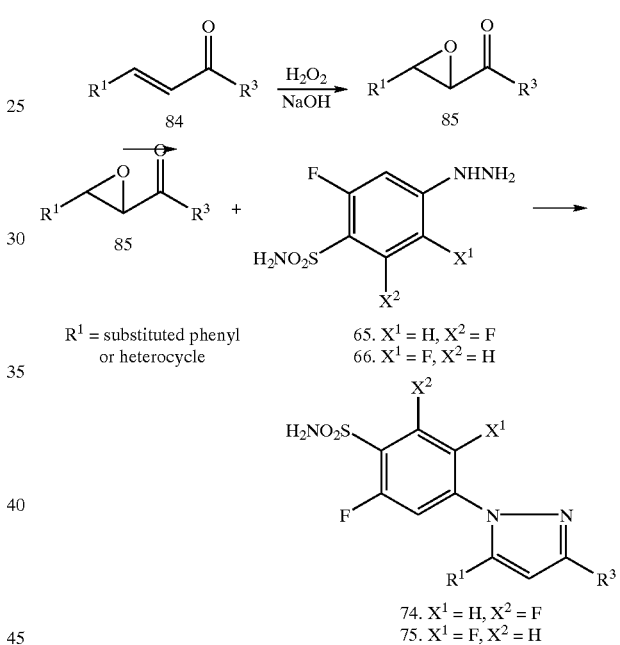

$R^1$ = substituted phenyl or heterocycle

65. $X^1 = H, X^2 = F$
66. $X^1 = F, X^2 = H$

74. $X^1 = H, X^2 = F$
75. $X^1 = F, X^2 = H$

Scheme XVI illustrates an alternative regioselective method of constructing pyrazole 74 or 75. Commercially available enones 84 can be epoxidized to give epoxyketones 85, which are treated with the appropriate difluoro-4-sulfonamido-phenylhydrazine hydrochloride 65 or 66, to provide the desired pyrazole 74 or 75, respectively.

Scheme XVII

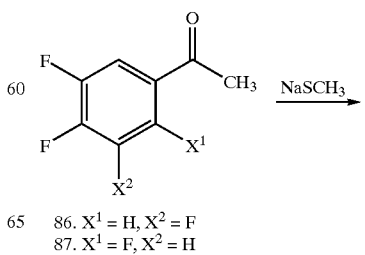

86. $X^1 = H, X^2 = F$
87. $X^1 = F, X^2 = H$

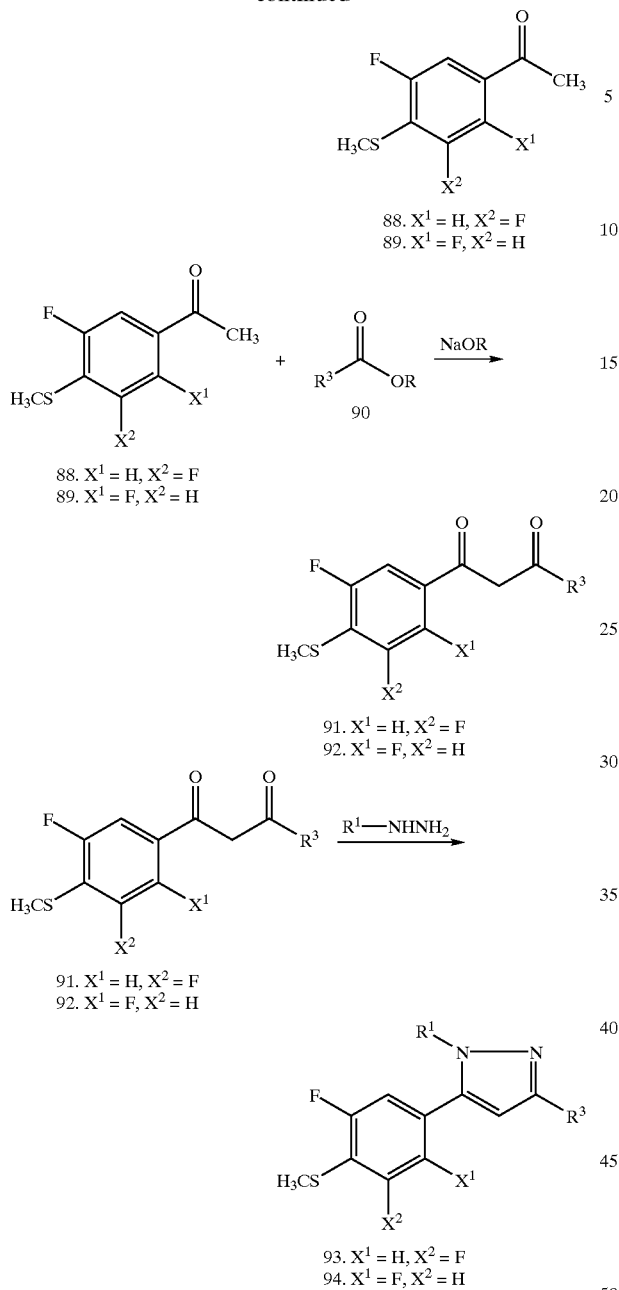

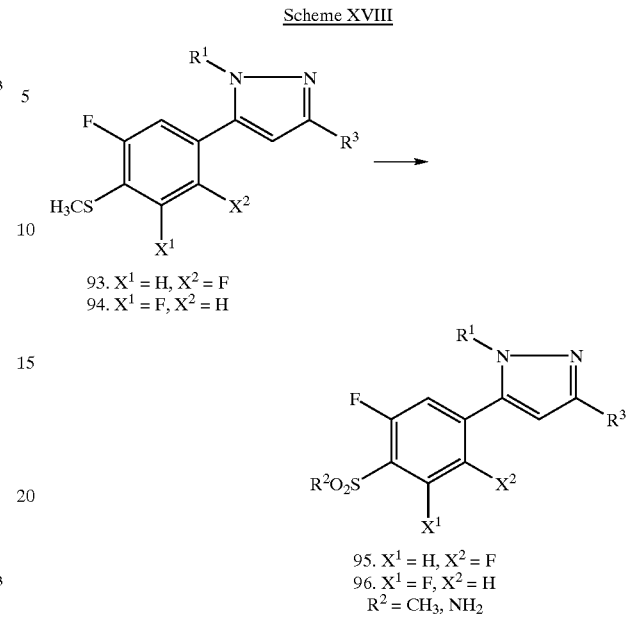

95. $X^1$ = H, $X^2$ = F
96. $X^1$ = F, $X^2$ = H
$R^2$ = $CH_3$, $NH_2$

The methylthiopyrazole 93 or 94 can be converted to the desired difluoro-4-methylsulfonylpyrazole or difluoro-4-sulfonamidylpyrazoles 95 or 96, respectively, using procedures described earlier. Similar pyrazoles can be prepared by methods described in U.S. Pat. No. 5,486,534 which is incorporated by reference. WO96/37476 describes methods for the preparation of 3-haloalkyl-1H-pyrazoles and also is incorporated by reference.

Scheme XIX

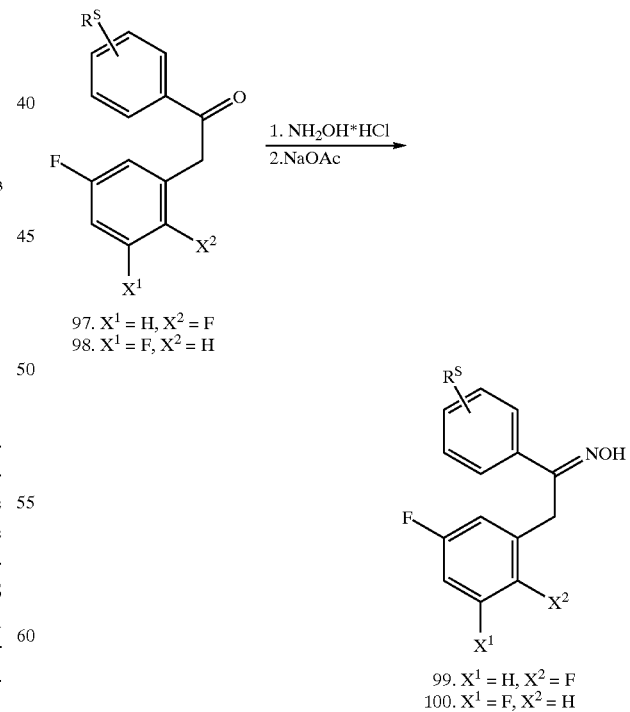

Scheme XVII illustrates a regioselective method of preparing methylthiopyrazole 93 or 94. The trifluoroacetophenone 86 or 87 is mixed with sodium thiomethoxide in a polar solvent such as acetonitrile of dimethylformamide to afford the corresponding difluoro-4-methylsulfonylacetophenone 88 or 89. Mixing the acetophenone 88 or 89 with a base, such as sodium methoxide, and an acylating reagent 90 such as an ester ($R^1CO_2CH_3$), or activated ester equivalent ($R^1$CO-imidazole), gives the corresponding intermediate diketone 91 or 92 [*J. Amer. Chem. Soc.*, 72, 2948–52, (1950)]. This diketone 91 or 92 is refluxed with a substituted hydrazine in alcoholic solvents under acid conditions to afford the methylthiopyrazole 93 or 94 after purification by chromatography or crystallization.

Synthetic Scheme XIX illustrates a procedure that can be used for the preparation of oxime intermediate 99 or 100. Treatment of ketone intermediate 97 or 98 with hydroxylamine, generally prepared from hydroxylamine hydrochloride by sodium acetate, provides the corresponding oxime intermediate 99 or 100 respectively. A wide variety of solvents can be used for this reaction including ethanol, toluene, and tetrahydrofuran.

Scheme XX

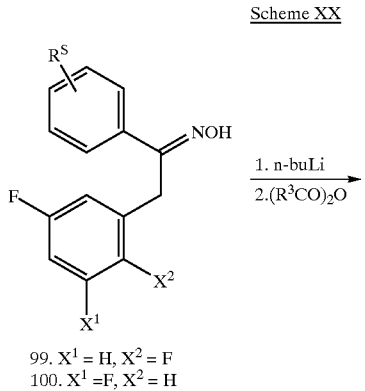

99. $X^1$ = H, $X^2$ = F
100. $X^1$ = F, $X^2$ = H 1. n-buLi
2. $(R^3CO)_2O$

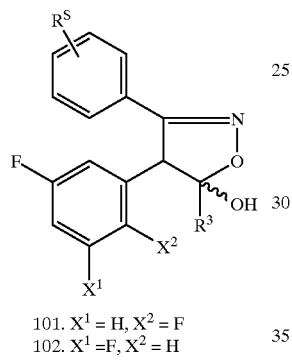

101. $X^1$ = H, $X^2$ = F
102. $X^1$ = F, $X^2$ = H

Synthetic Scheme XX illustrates a procedure that can be used for the preparation of hydrated isoxazole derivatives 101 or 102. The substituted oxime 99 or 100 is treated with at least two equivalents of a base such as n-butyllithium in hexanes to produce a dianion which is subsequently acylated. Suitable acylating agents are anhydrides, acyl imidazoles, esters and the like. Upon quenching the reaction mixture with dilute aqueous acid, the corresponding hydrated isoxazole derivative 101 or 102 can be isolated by crystallization or chromatography.

Scheme XXI

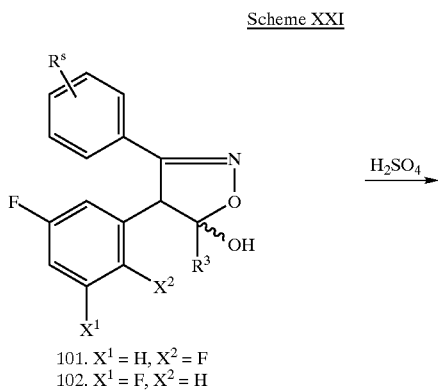

101. $X^1$ = H, $X^2$ = F
102. $X^1$ = F, $X^2$ = H $H_2SO_4$

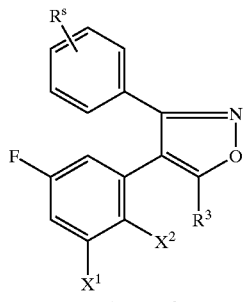

103. $X^1$ = H, $X^2$ = F
104. $X^1$ = F, $X^2$ = H

Synthetic Scheme XXI illustrates a procedure that can be used for the preparation of isoxazole analog 103 or 104 through dehydration of the corresponding hydrated isoxazole derivative 101 or 102. Substituted hydrated isoxazole 101 or 102 is dissolved in an appropriate solvent such as toluene and then treated with a catalytic to stoichiometric amount of concentrated sulfuric acid to effect dehydration and thereby produce isoxazole derivative 103 or 104. Other acids also can be employed to effect this transformation such as concentrated HCl, concentrated HBr and many others.

Scheme XXII

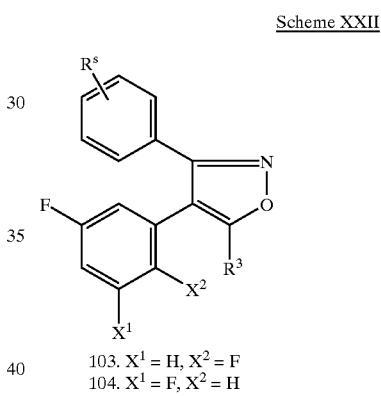

103. $X^1$ = H, $X^2$ = F
104. $X^1$ = F, $X^2$ = H

1. ClSO$_3$H
2. NH$_4$OH

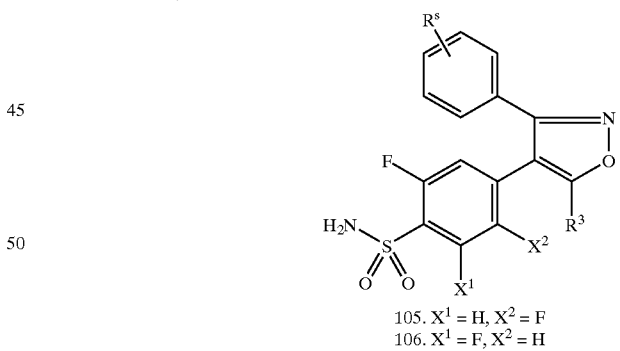

105. $X^1$ = H, $X^2$ = F
106. $X^1$ = F, $X^2$ = H

Synthetic Scheme XXII illustrates a procedure that can be used for the preparation of substituted difluoro-(4-sulfonamidyl)phenylisoxazole analog 105 or 106 from the corresponding difluorophenylisoxazole 103 or 104. The procedure is a two step process for the direct introduction of the sulfonamide moiety into difluorophenylisoxazole 103 or 104 or hydrated isoxazole 101 or 102. In step one, isoxazole 103 or 104 or hydrated isoxazole 101 or 102 is treated at about 0° C. with two or three equivalents of chlorosulfonic acid to form the corresponding sulfonyl chloride. In step two, the sulfonyl chloride thus formed is treated with concentrated ammonia to provide the sulfonamide derivative 105 or 106.

Scheme XXIII

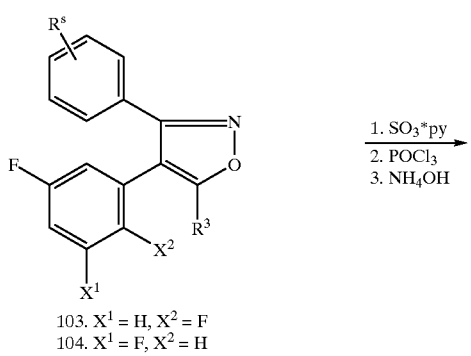

103. $X^1 = H, X^2 = F$
104. $X^1 = F, X^2 = H$

1. SO$_3$*py
2. POCl$_3$
3. NH$_4$OH

105. $X^1 = H, X^2 = F$
106. $X^1 = F, X^2 = H$

Synthetic Scheme XXIII illustrates a three step procedure used to prepare sulfonamide 105 or 106 from the corresponding difluorophenyl isoxazole 103 or 104. In step one, the difluorophenyl isoxazole 103 or 104 is converted into the corresponding sulfonic acid by treatment with sulfur trioxide pyridine complex at about 100° C. In step two, the sulfonic acid is converted into the sulfonyl chloride by the action of phosphorus oxychloride. In step three, the sulfonyl chloride is treated with excess concentrated ammonia to provide difluoro-4-sulfonamidyl-phenylisoxazole 105 or 106.

Scheme XXIV

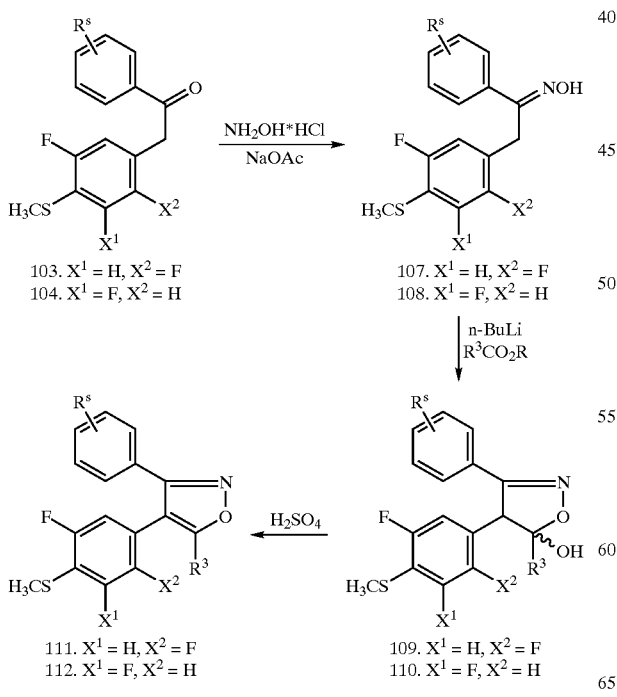

Scheme XXIV illustrates a five step procedure for the preparation of substituted isoxazole derivatives. In the first step substituted phenyl-2-(difluoro-4-methylthiophenyl)-ethanone 21 or 22 is converted to the corresponding oxime 107 or 108 by treatment with hydroxylamine hydrochloride in the presence of sodium acetate in aqueous ethanol. The oxime 107 or 108 is treated with slightly more than two equivalents of n-butyl lithium and then the resulting dianion is quenched by a suitable acylating agent such as an anhydride, acid chloride, ester, acyl imidazole and the like to afford a hydrated isoxazole 109 or 110, respectively. In the last step, the hydrated isoxazole is dehydrated by an acid and the sulfonamide unmasked by treatment with aqueous sulfuric acid to form the isoxazole derivative 111 or 112 as desired.

Scheme XXV

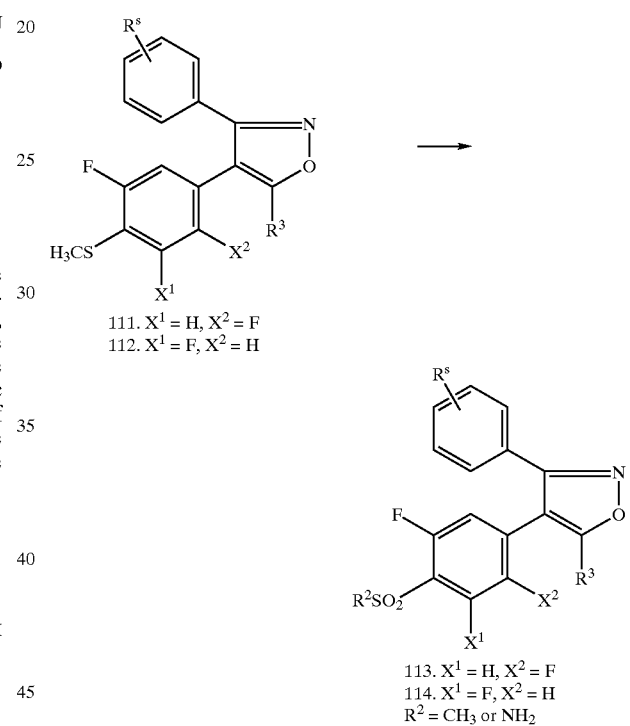

111. $X^1 = H, X^2 = F$
112. $X^1 = F, X^2 = H$

113. $X^1 = H, X^2 = F$
114. $X^1 = F, X^2 = H$
$R^2 = CH_3$ or $NH_2$

As illustrated in Scheme XXV, the methylsulfide moiety 111 or 112 prepared in Scheme XXIV can be converted to the sulfonamide or methylsulfone diarylisoxazole 113 or 114.

Scheme XXVI

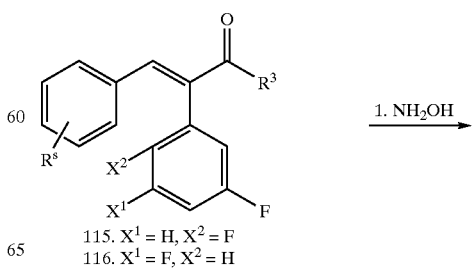

115. $X^1 = H, X^2 = F$
116. $X^1 = F, X^2 = H$

1. NH$_2$OH

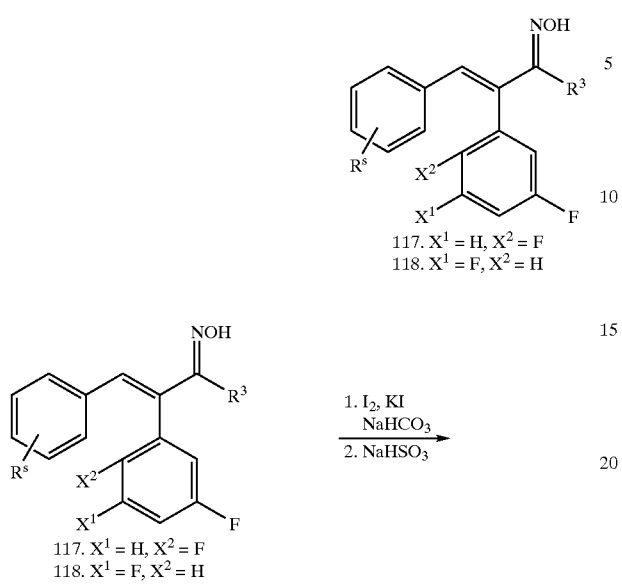

117. $X^1 = H, X^2 = F$
118. $X^1 = F, X^2 = H$

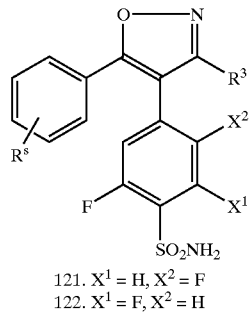

121. $X^1 = H, X^2 = F$
122. $X^1 = F, X^2 = H$

Treatment of the isoxazole 119 or 120 with chlorosulfonic acid provides, after workup, the intermediate sulfonyl chloride which can be converted to the corresponding sulfonamide 121 or 122 by mixing with ammonia in various solvents. In addition, difluoro-4-sulfonamidyl-phenyl type diaryl/heteroaryl isoxazoles can be prepared by the methods described in PCT Application Serial No. US96/01869, PCT documents WO92/05162 and WO92/19604, and European Publication EP 26928, which are incorporated by reference.

Scheme XXVIII

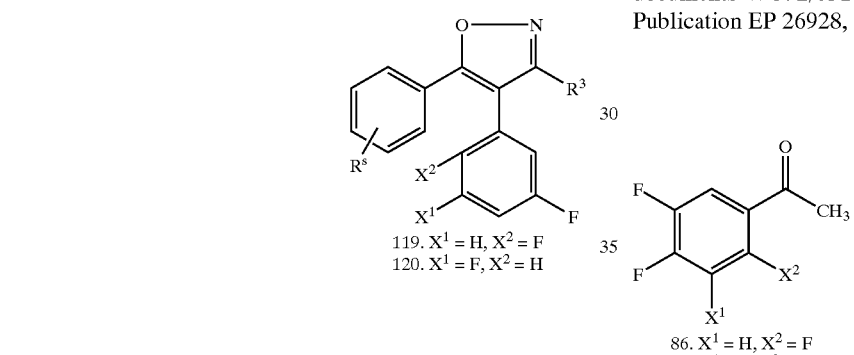

86. $X^1 = H, X^2 = F$
87. $X^1 = F, X^2 = H$

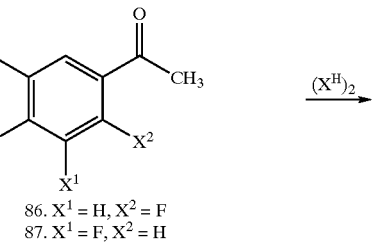

$X^H$ = Cl, Br, I

123. $X^1 = H, X^2 = F$
124. $X^1 = F, X^2 = H$

Scheme XXVI illustrates a three-step procedure for the preparation of another isoxazole isomer. In step one, substituted 1,2-diphenylbutenone 115 or 116 is converted to the corresponding oxime 117 or 118 by treatment with hydroxylamine hydrochloride in the presence of sodium acetate in aqueous ethanol. The oxime 117 or 118 is then reacted with potassium iodide and iodine in the presence of base, such as sodium bicarbonate, to afford a halo intermediate. Sodium bisulfite is added to form the corresponding isoxazole 119 or 120.

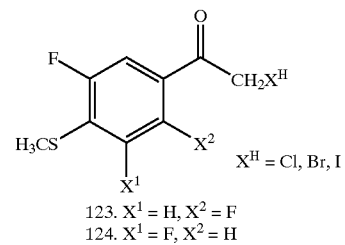

123. $X^1 = H, X^2 = F$
124. $X^1 = F, X^2 = H$

+

Scheme XXVII

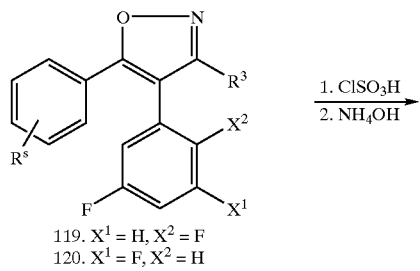

119. $X^1 = H, X^2 = F$
120. $X^1 = F, X^2 = H$

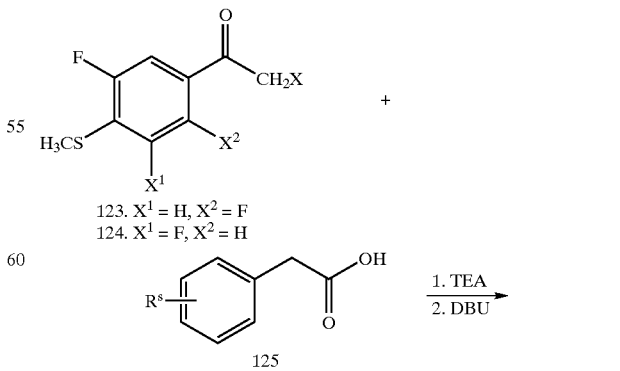

125

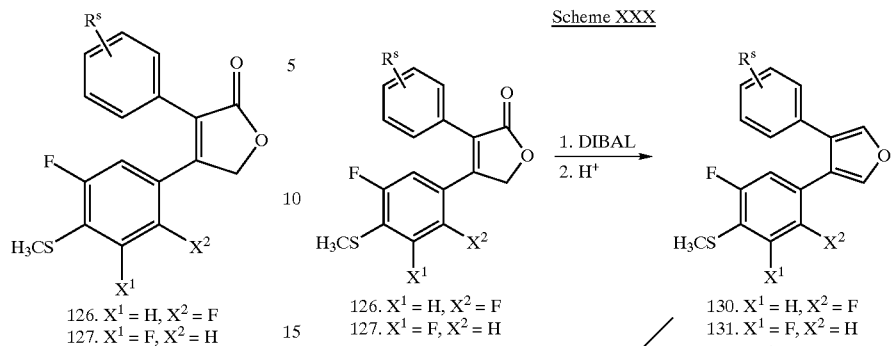

Scheme XXVIII illustrates a synthetic pathway for preparation of furanones. The acetophenone 86 or 87 is halogenated in acetic acid to afford the corresponding acylhalide 123 or 124. Displacement of the halide 123 or 124 with phenylacetic acid 125 in the presence of triethylamine in acetonitrile followed by addition of diazobi-cyclo[5.4.0]undec-7-ene affords the corresponding furanone 126 or 127 as desired [Ahluwalia, *Synth. Commun.* 19, 619–26 (1989)].

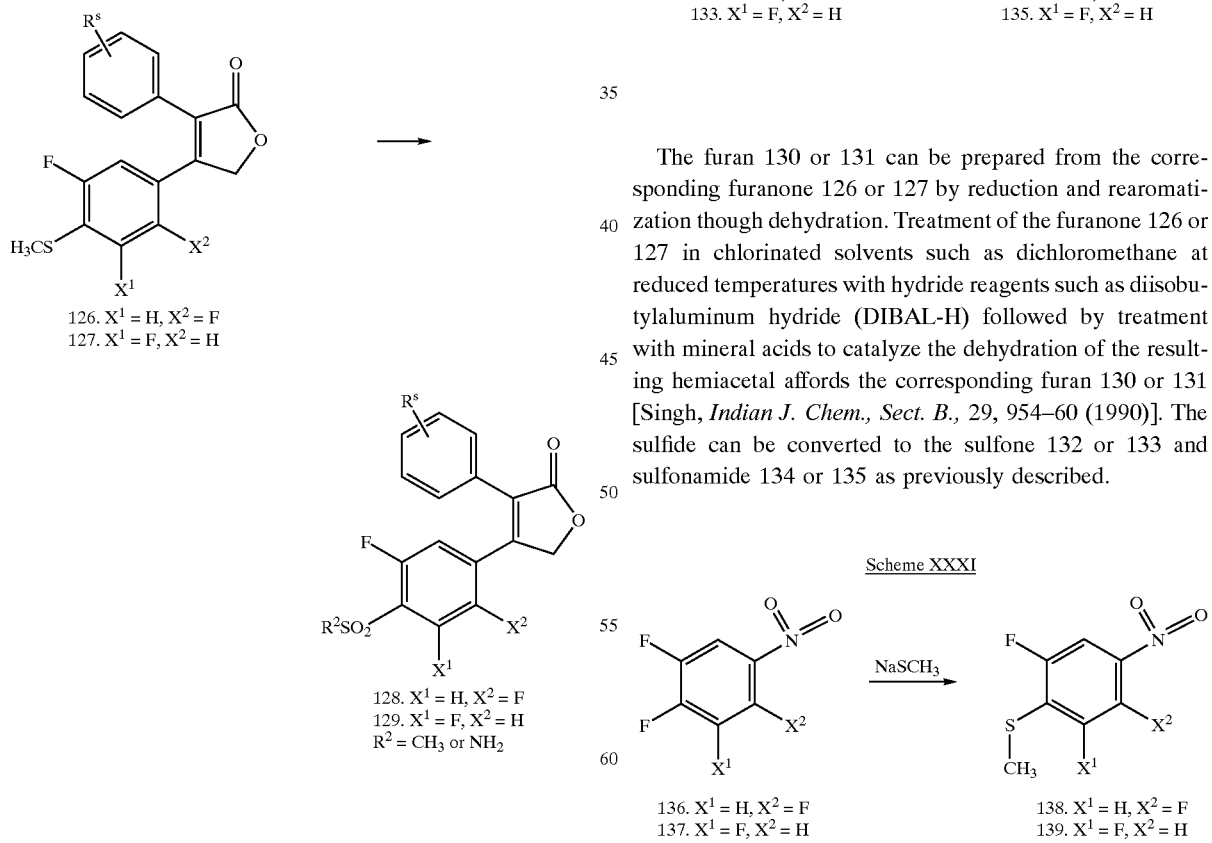

The methylthiofuranones 126 or 127 can be converted to the corresponding methylsulfonyl and sulfonamide furanones 128 or 129 as previously outlined.

The furan 130 or 131 can be prepared from the corresponding furanone 126 or 127 by reduction and rearomatization though dehydration. Treatment of the furanone 126 or 127 in chlorinated solvents such as dichloromethane at reduced temperatures with hydride reagents such as diisobutylaluminum hydride (DIBAL-H) followed by treatment with mineral acids to catalyze the dehydration of the resulting hemiacetal affords the corresponding furan 130 or 131 [Singh, *Indian J. Chem., Sect. B.*, 29, 954–60 (1990)]. The sulfide can be converted to the sulfone 132 or 133 and sulfonamide 134 or 135 as previously described.

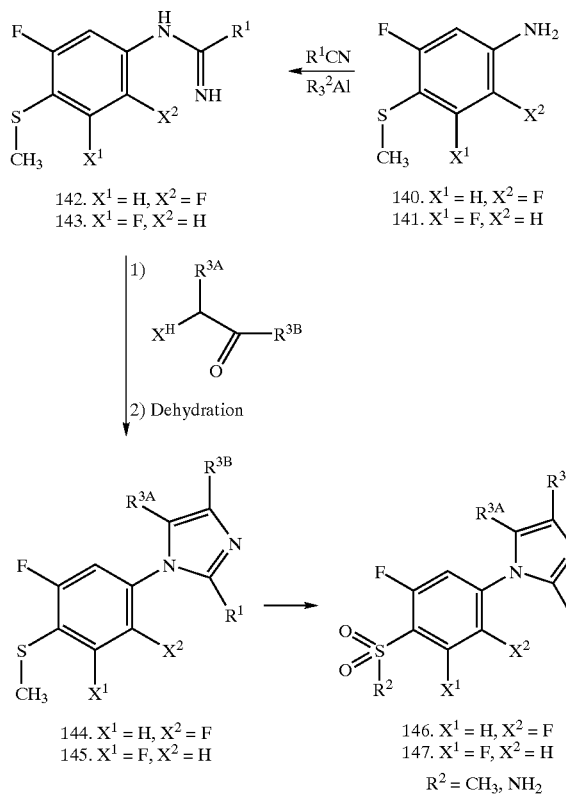

Scheme XXXI illustrates the preparation of the difluoro-4-sulfonylphenyl-imidazole 146 or 147. Substitution of the 4-fluorine in trifluoro-nitrobenzene 136 or 137 with sodium thiomethoxide provides the corresponding difluoro-4-methylthio-nitrobenzene 138 or 139. Reduction of the nitro group to an amine can be accomplished through hydrogenation over a metallic catalyst such as palladium or platinum on various supports. The resulting phenylamine 140 or 141 can be reacted with substituted nitriles in the presence of alkylaluminum reagents such a trimethylaluminum in inert solvents such as toluene or benzene affording the corresponding amidine 142 or 143. Mixing of the amidine with a 2-haloketone in the presence of mild inorganic or organic bases such as triethylamine, diisopropylamine, or sodium bicarbonate in solvents such as acetone, acetonitrile, or dimethylformamide gives a 4,5-dihydroimidazole that can be dehydrated in the presence of catalytic mineral acids to afford the corresponding 1,2-disubstituted imidazole 144 or 145.

These types of diaryl/heteroaryl imidazoles also can be prepared by the methods described in U.S. Pat. No. 4,822,805 and PCT documents WO93/14082 and WO96/03388, which are incorporated by reference. The methylsulfide can be converted to the sulfones or sulfonamide affording substituted diarylimidazole 146 or 147 as previously described.

Scheme XXXII

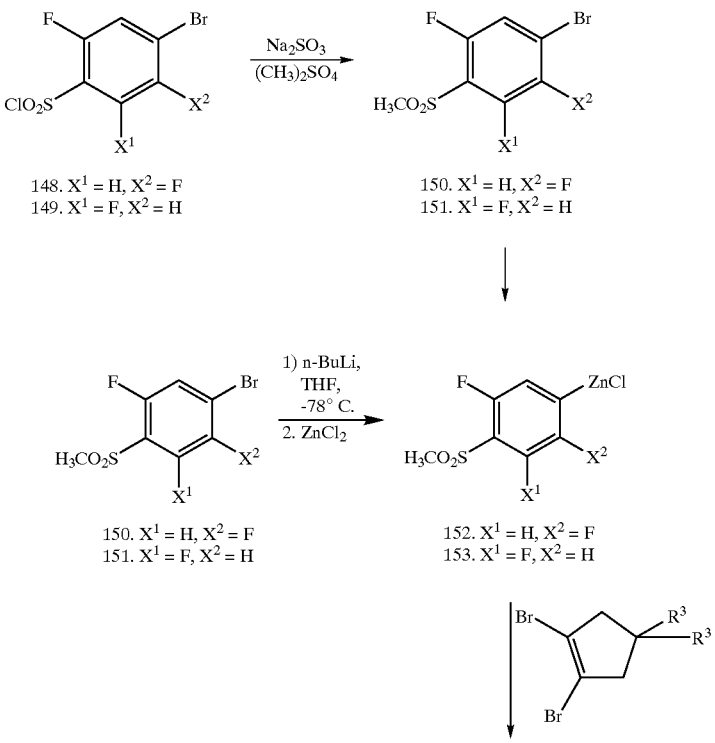

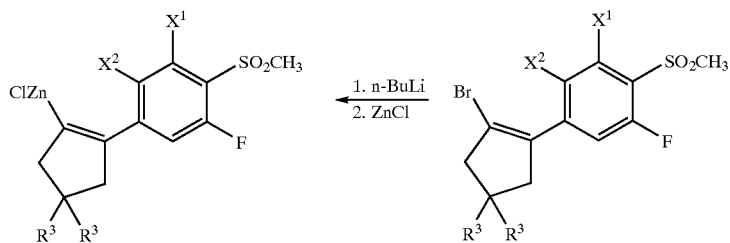

156. $X^1$ = H, $X^2$ = F
157. $X^1$ = F, $X^2$ = H

154. $X^1$ = H, $X^2$ = F
155. $X^1$ = F, $X^2$ = H

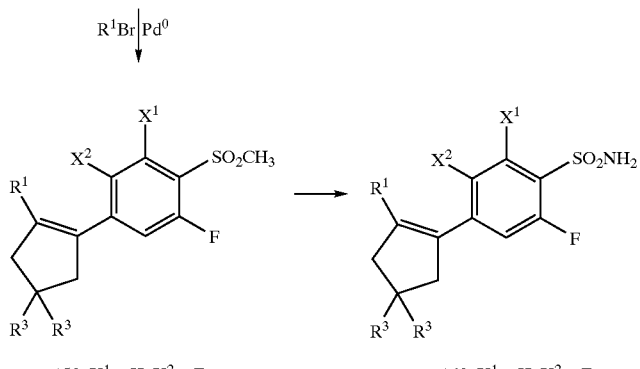

158. $X^1$ = H, $X^2$ = F
159. $X^1$ = F, $X^2$ = H

160. $X^1$ = H, $X^2$ = F
161. $X^1$ = F, $X^2$ = H

The 4-bromo-difluorobenzenesufonyl chloride 148 or 149 can be treated with sodium sulfite followed by treatment with dimethylsulfate to afford the corresponding 4-bromo-difluoromethylsulfonyl-benzene 150 or 151 [*Organic Synthesis, Vol. IV*, p. 674]. Diaryl/heteroaryl cyclopentene 158 or 159 comprising the difluorosulfonyl functional group can be prepared in accordance with the general methods described in U.S. Pat. No. 5,344,991 and PCT document WO95/00501 starting from the 4-bromo-difluoromethylsulfonyl-benzene, as outlined in Scheme XXXII. U.S. Pat. No. 5,344,991 and PCT document WO95/0050 are incorporated by reference. The sulfone can be converted to the cyclopentenylphenylsulfonamide 160 or 161 as described previously.

Scheme XXXIII

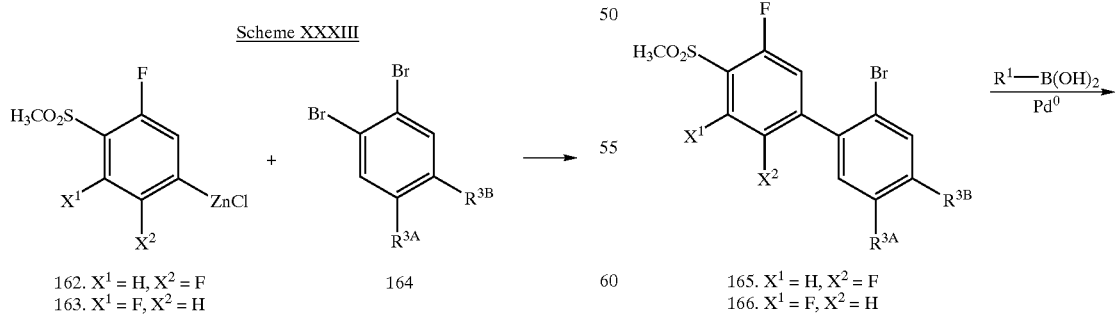

162. $X^1$ = H, $X^2$ = F
163. $X^1$ = F, $X^2$ = H

164

165. $X^1$ = H, $X^2$ = F
166. $X^1$ = F, $X^2$ = H

-continued

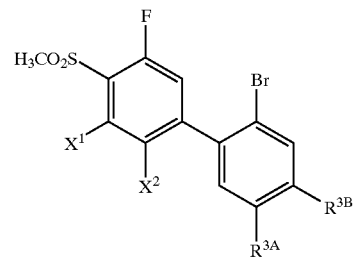

165. $X^1$ = H, $X^2$ = F
166. $X^1$ = F, $X^2$ = H

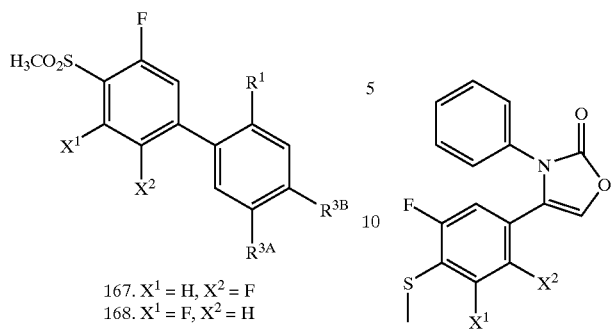

167. $X^1 = H, X^2 = F$
168. $X^1 = F, X^2 = H$

↓

169. $X^1 = H, X^2 = F$
170. $X^1 = F, X^2 = H$

Synthetic Scheme XXXIII similarly illustrates a procedure for the preparation of 1,2 diarylbenzene 169 or 170 comprising the difluorosulfonyl functional group from 2-bromo-biphenyl intermediate 167 or 168 (prepared similarly to the procedure described in Synthetic Scheme XXXII) and the appropriate substituted phenyl boronic acid utilizing a Suzuki coupling procedure [Synth. Commun., 11, 513 (1981)]. Sulfonamides can be prepared from the sulfones as described earlier in this application. U.S. application Ser. No. 08/346,533 generally describes the preparation of terphenyl compounds and is incorporated by reference.

Scheme XXXIV

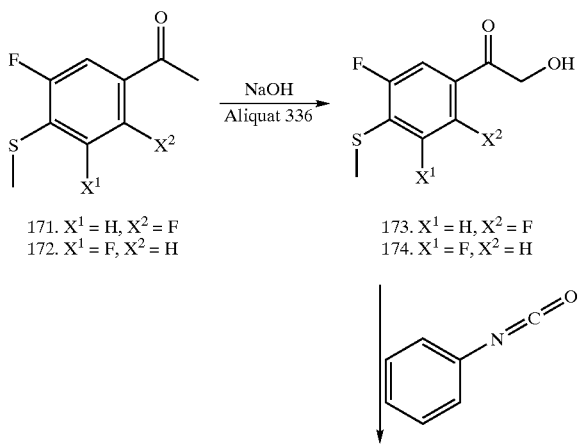

171. $X^1 = H, X^2 = F$
172. $X^1 = F, X^2 = H$

173. $X^1 = H, X^2 = F$
174. $X^1 = F, X^2 = H$

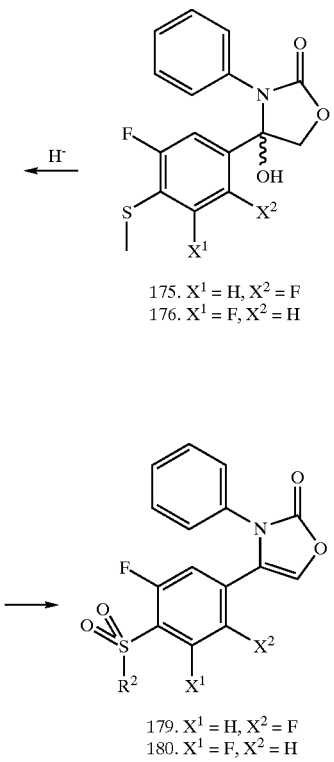

175. $X^1 = H, X^2 = F$
176. $X^1 = F, X^2 = H$

177. $X^1 = H, X^2 = F$
178. $X^1 = F, X^2 = H$

177. $X^1 = H, X^2 = F$
178. $X^1 = F, X^2 = H$

179. $X^1 = H, X^2 = F$
180. $X^1 = F, X^2 = H$ $R^2 = NH_2, CH_3$

Scheme XXXIV illustrates the preparation of 3,4-diaryloxazol-2-one 179 or 180 and derivatives. Oxidation of the methyl group adjacent to the carbonyl carbon to an alcohol can be accomplished using base, aliquat 336 and oxygen (see, e.g., EP 197,704, which is incorporated by reference). Treatment of the resulting alcohol 173 or 174 with an isocyanate followed by dehydration of the hydroxy intermediate 175 or 176 in the presence of acid affords the corresponding oxazolone compound 177 or 178. The methylsulfide group of oxazolone compound 177 or 178 can be converted to the sulfone or sulfonamide affording the corresponding substituted 3,4 diaryloxazol-2-one 179 or 180 as previously described. Other 3,4-diaryloxazol-2-one compounds with the basic structure of substituted 3,4 diaryloxazol-2-ones 179 or 180 that comprise the difluorosulfonyl functional group can be prepared starting from the 2-hydroxy-1'-[difluoro-4-methylsulfidophenyl]-ethanone 173 or 174 in accordance with the methods described in PCT documents WO98/11080 and WO99/14205 which are incorporated by reference.

Scheme XXXV

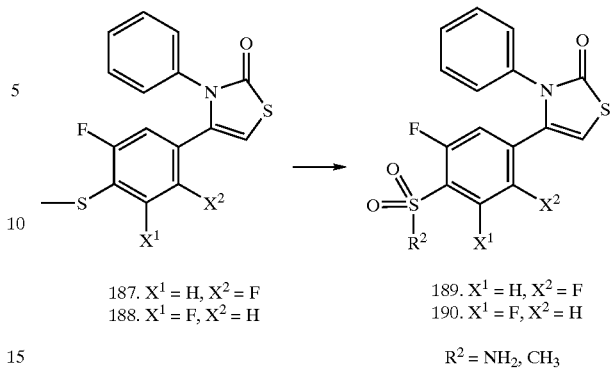

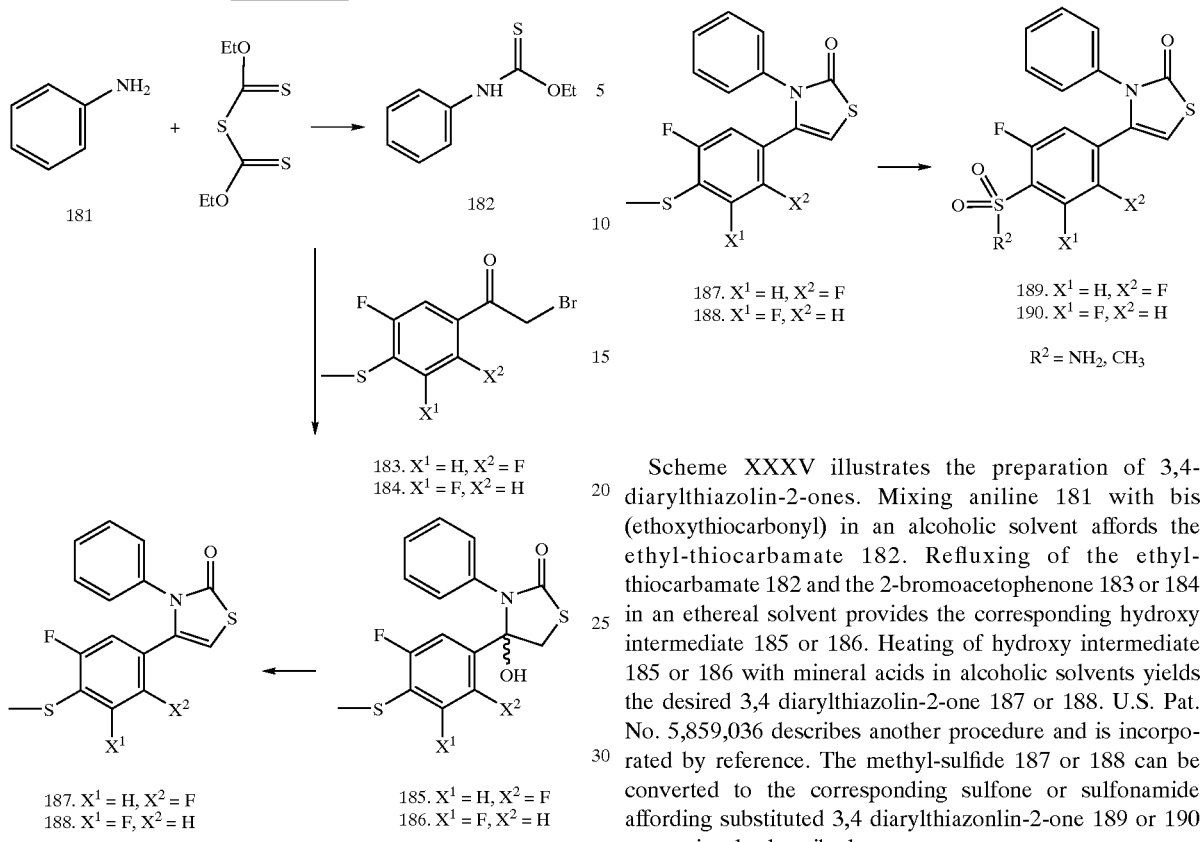

Scheme XXXV illustrates the preparation of 3,4-diarylthiazolin-2-ones. Mixing aniline 181 with bis(ethoxythiocarbonyl) in an alcoholic solvent affords the ethyl-thiocarbamate 182. Refluxing of the ethyl-thiocarbamate 182 and the 2-bromoacetophenone 183 or 184 in an ethereal solvent provides the corresponding hydroxy intermediate 185 or 186. Heating of hydroxy intermediate 185 or 186 with mineral acids in alcoholic solvents yields the desired 3,4 diarylthiazolin-2-one 187 or 188. U.S. Pat. No. 5,859,036 describes another procedure and is incorporated by reference. The methyl-sulfide 187 or 188 can be converted to the corresponding sulfone or sulfonamide affording substituted 3,4 diarylthiazonlin-2-one 189 or 190 as previously described.

Scheme XXXVI

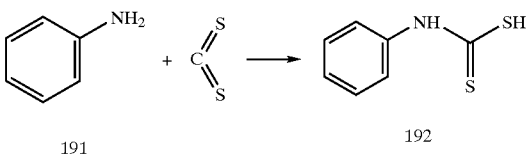

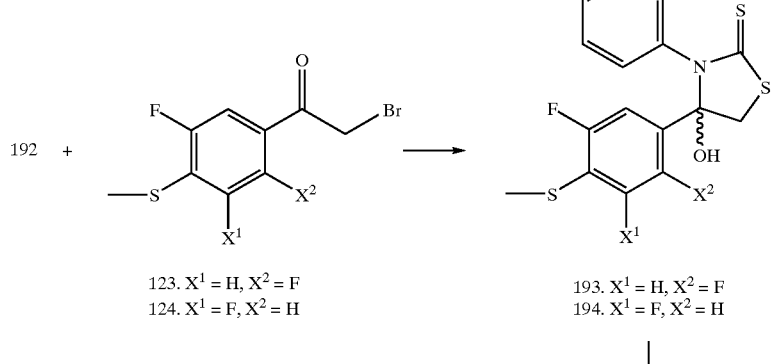

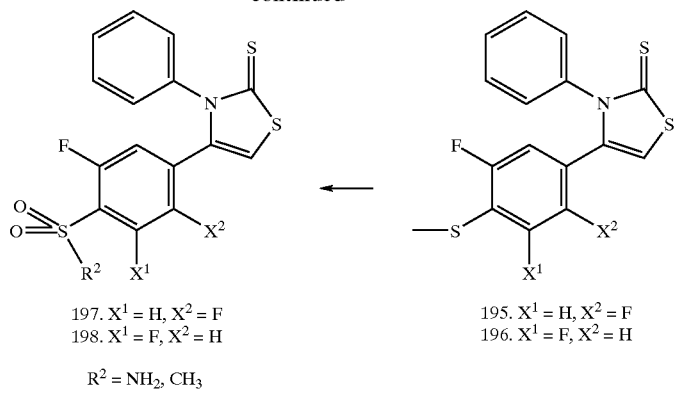

197. $X^1$ = H, $X^2$ = F
198. $X^1$ = F, $X^2$ = H

195. $X^1$ = H, $X^2$ = F
196. $X^1$ = F, $X^2$ = H $R^2$ = $NH_2$, $CH_3$

Scheme XXXVI illustrates the preparation of 3,4-diarylthiazolin-2-thione 197 or 198. Mixing of aniline with carbon disulfide in an alcoholic solvent affords the dithiocarbamate 192. Refluxing of dithiocarbamate 192 and the 2-bromoacetophenone 123 or 124 in an ethereal solvent provides the corresponding hydroxy intermediate 193 or 194. Heating of hydroxy intermediate 193 or 194 with mineral acids in alcoholic solvents yields the desired 3,4 diarylthiazonlin-2-thione 195 or 196. U.S. Pat. No. 5,859,036 describes another procedure that can be appropriately modified and used. U.S. Pat. No. 5,859,036 is incorporated by reference. The methylsulfide 195 or 196 can be converted to the corresponding sulfone or sulfonamide affording substituted 3,4 diarylthiazonlin-2-thione 197 or 198 as previously described.

EXAMPLES

The following examples contain detailed descriptions of the methods of preparation of compounds of Formulae I–VII. These detailed descriptions fall within the scope, and serve to exemplify, the above-described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

The following abbreviations are used:
DMSO—dimethylsulfoxide
$DMSOd_6$—deuterated dimethylsulfoxide
$CDCl_3$—deuterated chloroform
DMF—dimethylformamide
BOC—tert-butyloxycarbonyl
$CD_3OD$—deuterated methanol
EtOH—ethanol
h—hour
hr—hour
min—minutes
THF—tetrahydrofuran
TLC—thin layer chromatography
TEA or $Et_3N$—triethylamine
DBU—1,8-diazabicyclo[5.4.0]undec-7-ene
DMAP—4-dimethylaminopyridine
DPPA—diphenylphosphorylazide
NaOAc—sodium acetate
$AC_2O$—acetic anhydride
Tert-BuOH—tert-butanol
LDA—lithium diisopropylamide
DIBAL—diisobutylaluminum hydride Example 1

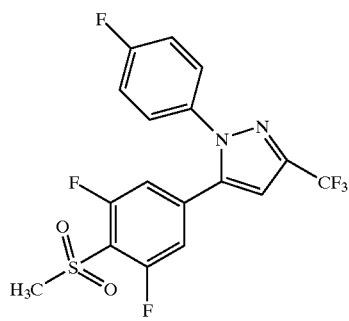

5-[3,5-difluoro-4-(methylsulfonyl)phenyl]-1-(4-fluorophenyl)-3-(trifluoromethyl)-1H-pyrazole

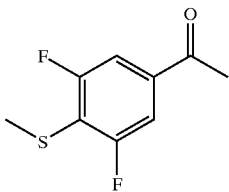

Step 1: Preparation of 1-[3,5-difluoro-4-(methylthio)phenyl]ethanone

The 3,4,5-triflouroacetophenone (9.50 g, 54.6 mmol) and sodium thiomethoxide (4.60 g) were mixed together in acetonitrile (80 mL). The solution was stirred for 2 hour at ambient temperature. Solvent was removed in vacuo and the residue dissolved in ethyl acetate. The solution was extracted with water (2×100 mL), saturated ammonium chloride (2×100 mL) and dried over sodium sulfate. Solvent was removed in vacuo to yield 1-[3,5-difluoro-4-(methylthio)phenyl]ethanone as a yellow oil (8.08 g, 73%). $^1$H NMR ($CDCl_3$/300 MHz) 7.46–7.43 (m, 2H), 2.58 (s, 3H), 2.56 (t, 3H, J=1). ESHRMS m/z 203.0357 (M+H$^+$, Calcd 203.0342).

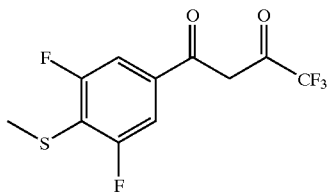

Step 2: Preparation of 1-[3,5-difluoro-4-(methylthio)phenyl]-4,4,4-trifluorobutane-1,3-dione 1-[3,5-difluoro-4-(methylthio)phenyl]ethanone (4.84 g, 23.9 mmol) was dissolved in diethyl ether (200 mL). Sodium methoxide (24 mL of 25% in methanol, 30 mmol) was added and stirred 10 min at ambient temperature. Ethyl trifluoroacetate (3.79 g, 23.9 mmol) was added. The solution was stirred for 1 hour then aqueous hydrochloric acid was added (100 mL, 1 M). The layers were separated and the organic layer collected. The organic layer was washed with water (2×100 mL), saturated ammonium chloride (2×200 mL) and dried over sodium sulfate. The solvent was removed in vacuo to afford a yellow oil. The 1-[3,5-difluoro-4-(methylthio)phenyl]-4,4,4-trifluorobutane-1,3-dione was isolated by crystallization from ethyl acetate and hexanes (5.50 g, 77%). $^1$H NMR (CDCl$_3$/300 MHz) 7.49 (m, 2H), 6.50 (s, 1H), 2.62 (s, 3H). ESHRMS m/z 297.0012 (M+H$^+$, Calcd 297.0009). Anal. Calcd for C$_{11}$H$_7$F$_5$O$_2$S: C, 44.30; H, 2.37. Found: C, 44.36; H, 2.26.

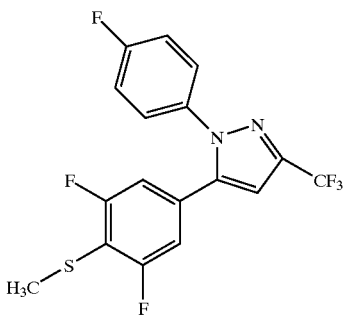

Step 3: Preparation of 5-[3,5-difluoro-4-(methylthio)-phenyl]-1-(4-fluorophenyl)-3-(trifluoromethyl)-1H-pyrazole 1-[3,5-difluoro-4-(methylthio)phenyl]-4,4,4-trifluorobutane-1,3-dione (1.09 g, 3.6 mmol) dissolved in ethanol (150 mL). One drop of concentrated hydrochloric acid was added and 4-fluorophenylhydrazine hydrochloride (0.69 g, 4.0 mmol). The reaction was stirred at ambient temperature for 72 hours. Solvent was removed in vacuo and the residue was dissolved in ethyl acetate (100 mL) extracted with water (2×100 mL), saturated ammonium chloride (2×150 mL) and dried over sodium sulfate. The solvent was removed in vacuo and the 5-[3,5-difluoro-4-(methylthio)-phenyl]-1-(4-fluorophenyl)-3-(trifluoromethyl)-1H-pyrazole was obtained by crystallization from ethyl acetate and hexanes (0.71 g, 50%). $^1$H NMR (CDCl$_3$/300 MHz) 7.36–7.29 (m, 2H), 7.18–7.13 (m, 2H), 6.81–6.77 (m, 3H), 2.53 (s, 3H). ESHRMS m/z 389.0557 (M+H$^+$, Calcd 389.0547). Anal. Calcd for C$_{17}$H$_{10}$F$_6$N$_2$S: C, 52.58; H, 2.34; N, 7.21. Found: C, 52.45; H, 2.34; N, 7.15.

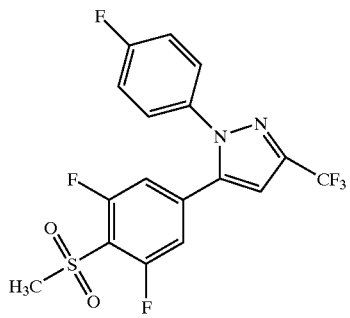

Step 4: Preparation of 5-[3,5-difluoro-4-(methylsulfonyl)-phenyl]-1-(4-fluorophenyl)-3-(trifluoromethyl)-1H-pyrazole 5-[3,5-difluoro-4-(methylthio)phenyl]-1-(4-fluorophenyl)-3-(trifluoromethyl)-1H-pyrazole was dissolved in methyelene chloride:methanol (25 mL, 3:1). Monoperoxyphthalic acid, magnesium salt hexahydrate (2.27 g, 1.84 mmol) was added and the reaction stirred at ambient temperature for 16 hours. Solvent was removed in vacuo and the residue was dissolved in ethyl acetate (100 mL) extracted with aqueous sodium hydroxide (2×100 mL), water (2×100 mL), saturated ammonium chloride solution (2×150 mL) and dried over sodium sulfate. The solvent was removed in vacuo and the 5-[3,5-difluoro-4-(methylsulfonyl)-phenyl]-1-(4-fluorophenyl)-3-(trifluoromethyl)-1H-pyrazole obtained by crystallization from ethyl acetate and hexanes, (0.74 g, 96%). $^1$H NMR (CD$_3$OD/300 MHz) 6.96–6.91 (m, 2H), 6.82–6.75 (m, 2H), 6.63–6.32 (m, 3H), 2.83 (s, 3H). ESHRMS m/z 438.0705 (M+NH$_4^+$, Calcd 438.0711). Anal. Calcd for C$_{17}$H$_{10}$F$_6$N$_2$O$_2$S: C, 48.58; H, 2.40; N, 6.66. Found: C, 48.10; H, 2.29; N, 6.74.

Examples 2 through 11 were prepared utilizing a similar synthetic sequence to Example 1.

Example 2

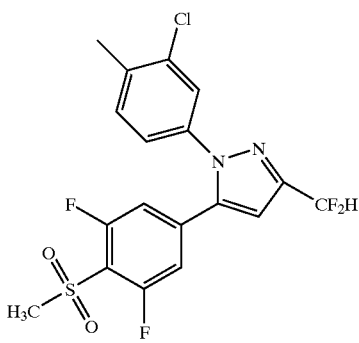

1-(3-chloro-4-methylphenyl)-3-(difluoromethyl)-5-[3,5-difluoro-4-(methylsulfonyl)phenyl]-1H-pyrazole $^1$H NMR (CDCl$_3$/300 MHz) 7.46–7.29 (m, 2H), 7.02–6.78 (m, 4H), 3.34 (s, 3H), 2.46 (s, 3H). ESHRMS m/z 433.0425 (M+H, Calcd 433.0401). Anal. Calcd for C$_{18}$H$_{13}$ClF$_4$N$_2$O$_2$S: C, 49.95; H, 3.03; N, 6.47. Found: C, 49.84; H, 2.78; N, 6.44.

Example 3

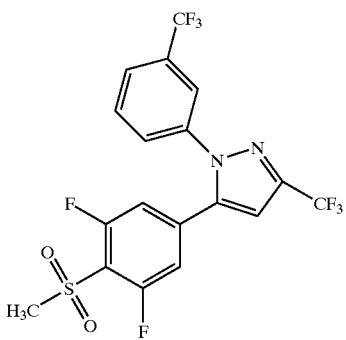

5-[3,5-difluoro-4-(methylsulfonyl)phenyl]-3-(trifluoromethyl)-1-[3-(trifluoromethyl)phenyl]-1H-pyrazole (86%)

$^1$H NMR (CDCl$_3$/300 MHz) 7.79–7.73 (m, 2H), 7.66–7.60 (m, 1H), 7.47–7.45 (m, 1H), 6.97–6.93 (m, 3H), 3.34 (s, 3H). Anal. Calcd for C$_{18}$H$_{10}$F$_8$N$_2$O$_2$S: C, 45.97; H, 2.14; N, 5.96. Found: C, 46.01; H, 2.33; N, 5.94.

Example 4

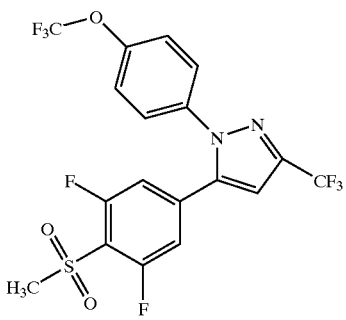

5-[3,5-difluoro-4-(methylsulfonyl)phenyl]-1-[4-(trifluoromethoxy)phenyl]-3-(trifluoromethyl)-1H-pyrazole $^1$H NMR (CDCl$_3$/300 MHz) 7.42–7.29 (m, 4H), 6.96 (s, 1H), 6.93–6.91 (m, 2H), 3.35 (s, 3H). ESHRMS m/z 504.0631 (M+NH$_4$, Calcd 504.0628). Anal. Calcd for C$_{18}$H$_{13}$F$_8$N$_2$O$_3$S: C, 44.45; H, 2.07; N, 5.76. Found: C, 44.75; H, 1.78; N, 5.68.

Example 5

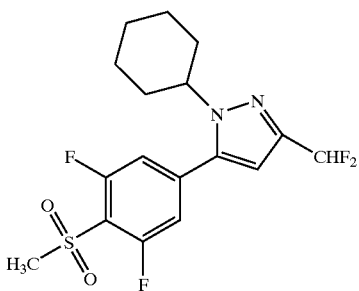

1-cyclohexyl-3-(difluoromethyl)-5-[3,5-difluoro-4-(methylsulfonyl)phenyl]-1H-pyrazole $^1$H NMR (CDCl$_3$/300 MHz) 7.12–7.08 (m, 2H), 6.56 (s, 1H), 4.08 (m, 1H), 3.39 (s, 3H), 1.93–1.28 (m, 11H). ESHRMS m/z 391.1116 (M+H, Calcd 391.1103).

Example 6

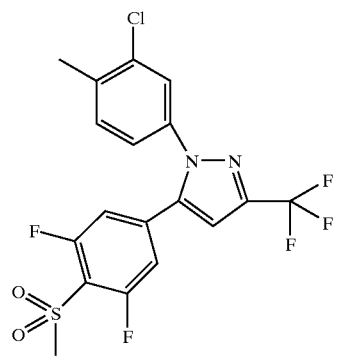

1-(3-chloro-4-methylphenyl)-5-[3,5-difluoro-4-(methylsulfonyl)phenyl]-3-(trifluoromethyl)-1H-pyrazole MP 134.2–134.6° C. MS m/z (m+H) 451.4

Example 7

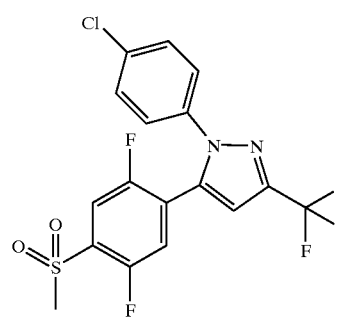

1-(4-chlorophenyl)-5-[2,5-difluoro-4-(methylsulfonyl)-phenyl]-3-(trifluoromethyl)-1H-pyrazole MP 188.0–188.9° C. MS m/z (m+H) 437.7

Example 8

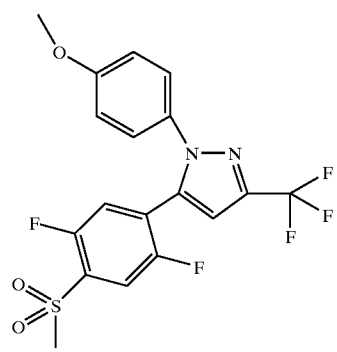

5-[2,5-difluoro-4-(methylsulfonyl)phenyl]-1-(4-methoxyphenyl)-3-(trifluoromethyl)-1H-pyrazole MP 135.0–138.0° C. MS m/z (m+H) 433.4.

Example 9

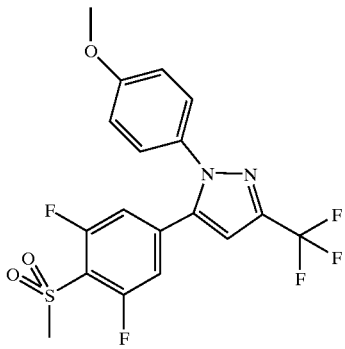

5-[3,5-difluoro-4-(methylsulfonyl)phenyl]-1-(4-methoxyphenyl)-3-(trifluoromethyl)-1H-pyrazole MP 172.5–173.7° C. MS m/z (m+H) 433.4

Example 10

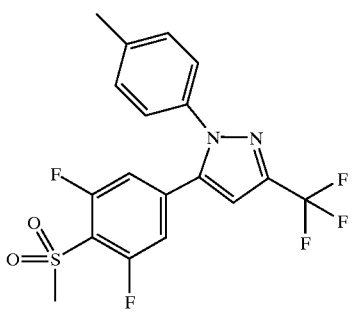

5-[3,5-difluoro-4-(methylsulfonyl)phenyl]-1-(4-methylphenyl)-3-(trifluoromethyl)-1H-pyrazole MP 151.0–152.0° C. MS m/z (m+H) 417.4

Example 11

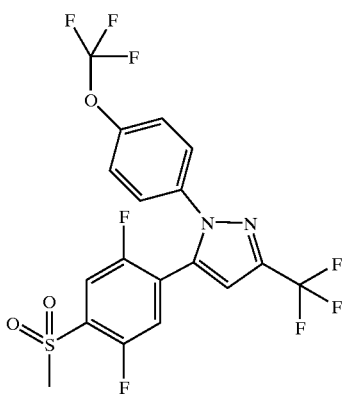

5-[2,5-difluoro-4-(methylsulfonyl)phenyl]-1-[4-(trifluoromethoxy)phenyl]-3-(trifluoromethyl)-1H-pyrazole MP 138.1–139.7° C. MS m/z (m+H) 487.3

Example 12

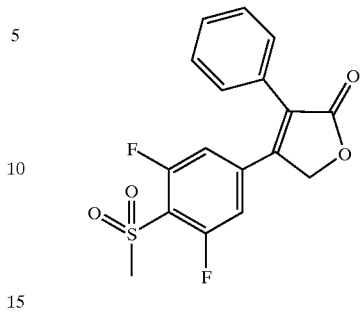

4-[3,5-difluoro-4-(methylsulfonyl)phenyl]-3-phenylfuran-2(5H)-one

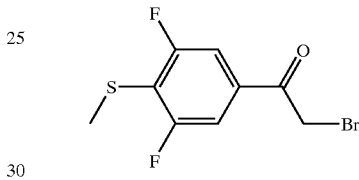

Step 1: Preparation of 2-bromo-1-[3,5-difluoro-4-(methylthio)phenyl]ethanone

To a solution of 1-[3,5-difluoro-4-(methylthio)-phenyl]ethanone (prepared in Step 1 of Example 1) (6.2 g, 30 mmol) in 30% HBr in acetic acid (10 mL) was added bromine (4.8 g, 30 mmol) dropwise, and the reaction mixture stirred at room temperature for 45 minutes. The mixture was treated with water and extracted with ethyl acetate (1×250 mL, 1×100 mL). The combined extracts were washed with dilute sodium chloride solution, dried with magnesium sulfate, and concentrated. To the residue was added hexanes (100 mL) and the mixture concentrated. The residue was dissolved in 30% HBr in acetic acid (10 mL) and treated with bromine (0.80 g, 5.0 mmol). After stirring at room temperature for 30 minutes, the mixture was treated with water and extracted with dichloromethane (1×200 mL, 1×100 mL). The combined extracts were washed with water, dried with magnesium sulfate and concentrated. To the residue was added hexanes (100 mL), and the mixture concentrated. Purification of the product by silica gel chromatography using 10% ethyl acetate in hexanes gave 2-bromo-1-[3,5-difluoro-4-(methylthio)-phenyl]ethanone as an orange solid (7.2 g, 86%), MP 30.5–33.2° C. $^1$H NMR (CDCl$_3$/400 MHz) 7.46–7.50 (m, 2H), 4.33 (s, 2H), 2.57 (t, 3H, J=1.1). ESHRMS m/z 278.9260 (M–H$^+$, Calcd 278.9291). Anal. Calcd for C$_9$H$_7$BrF$_2$OS: C, 38.45; H, 2.52. Found: C, 38.19; H, 2.34.

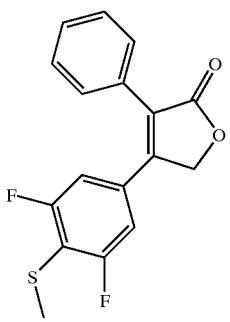

Step 2: Preparation of 4-[3,5-difluoro-4-(methylthio)-phenyl]-3-phenylfuran-2(5H)-one To a mixture of phenylacetic acid (4.2 g, 0.030 mol) and crude 2-bromo-1-[3,5-difluoro-4-(methylthio)-phenyl] ethanone (8.6 g, 0.030 mol) in anhydrous acetonitrile (100 mL) was added diisopropylethylamine (3.9 g, 0.030 mol). The reaction mixture was stirred for one hour at room temperature and 1,8-diazabicyclo[5.4.0]undec-7-ene (5.0 g, 0.032 mol) was added. After 2 hours the mixture was poured into dilute HCl and extracted with dichloromethane (1×200 mL, 2×75 mL). The combined extracts were dried using magnesium sulfate, and concentrated. The residue was treated with anhydrous acetonitrile (100 mL) and DBU (10.0 g, 0.065 mol), stirring at room temperature for 3 hours. The mixture was poured into dilute HCl and extracted with dichloromethane (1×200 mL, 2×50 mL). The combined extracts were dried using magnesium sulfate, and concentrated. Purification by silica gel chromatography using 5% dichloromethane/10% ethyl acetate in hexanes afforded 4-[3,5-difluoro-4-(methylthio)-phenyl]-3-phenylfuran-2 (5H)-one as an orange liquid (7.2 g, 76%). $^1$H NMR (CDCl$_3$/400 MHz) 7.37–7.41 (m, 5H), 6.97 (m, 2H), 5.09 (s, 2H), 2.48 (s, 3H). ESHRMS m/z 319.0601 (M+H$^+$, Calcd 319.0604). Anal. Calcd for C$_{17}$H$_{12}$F$_2$O$_2$S: C, 64.14; H, 3.80. Found: C, 63.56; H, 3.54.

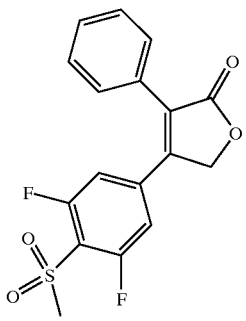

Step 3: Preparation of 4-[3,5-difluoro-4-(methylsulfonyl)phenyl]-3-phenylfuran-2(5H)-one Unpurified 4-[3,5-difluoro-4-(methylthio)-phenyl]-3-phenylfuran-2(5H)-one (8.9 g, 27 mmol) and magnesum monoperoxyphthalate hexahydrate (17.2 g, 27 mmol) were combined in a mixture of dichloromethane (200 mL) and methanol (60 mL), and stirred overnight at room temperature. The slurry was poured into water, and extracted with dichloromethane (1×200 mL, 2×50 mL). The combined extracts were washed with water and dilute sodium bicarbonate, and the aqueous sodium bicarbonate wash extracted with dichloromethane (50 mL). The combined extracts were dried with magnesium sulfate, filtered and concentrated. The residue was treated again with magnesium monoperoxyphthalate hexahydrate (8.5 g., 25 mmol), in a mixture of dichloromethane (120 mL) and methanol (30 mL), stirring overnight at room temperature. The reaction mixture was poured into water, and extracted with dichloromethane (2×200 mL). The combined extracts were washed with dilute ammonium chloride (100 mL), and dilute sodium chloride (100 mL), dried with magnesium sulfate, and concentrated to give 6.7 g yellow solids. The crude product was dissolved in dichloromethane (20 mL), and crystallized by adding a mixture of 40% ethyl acetate/60% hexanes (15 mL). The product was filtered, and the filtrate purified by silica gel chromatography using 40% ethyl acetate/60% hexanes to give a total of 5.3 g yellow solids (56%). The 4-[3,5-difluoro-4-(methylsulfonyl)phenyl]-3-phenylfuran-2 (5H)-one was recrystallized from ethyl acetate to give white solids. MP 203.5–203.8° C. $^1$H NMR (CDCl$_3$/400 MHz) 7.35–7.44 (m, 5H), 6.97 (d, 2H, J=9.0), 5.11 (s, 2H), 3.29 (s, 3H). ESHRMS m/z 351.0536 (M+H$^+$, Calcd 351.0502). Anal. Calcd for C$_{17}$H$_{12}$F$_2$O$_4$S: C, 58.28; H, 3.45. Found: C, 57.69; H, 3.72.

Example 13 was prepared utilizing a similar synthetic sequence to example 12.

Example 13

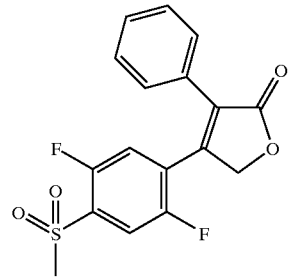

4-[2,5-difluoro-4-(methylsulfonyl)phenyl]-3-phenylfuran-2(5H)-one $^1$H NMR (CDCl$_3$/400 MHz) 7.74–7.78 (m, 1H), 7.35–7.41 (m, 1H), 7.05–7.09 (m, 1H), 5.18 (d, 2H, J=1.4), 3.22 (s, 3H). ESHRMS m/z 368.0783 (M+NH$_4^+$, Calcd 368.0768).

Example 14

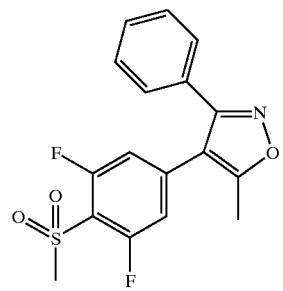

4-[3,5-difluoro-4-(methylsulfonyl)phenyl]-5-methyl-3-phenylisoxazole

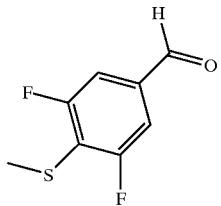

Step 1: Preparation of 3,5-difluoro-4-(methylthio)-benzaldehyde

To a solution of 3,4,5-trifluorobenzaldehyde (30.0 g, 0.187 mol) in anhydrous THF (400 mL) cooled in a cold water bath was added sodium thiomethoxide (14.4 g, 0.20 mol) in portions over 30 minutes. The mixture was stirred at room temperature for 18 hours, then poured into water and extracted with dichloromethane (1×500 mL, 2×200 mL). The combined extracts were washed with water, dried using magnesium sulfate, and concentrated. Purification of the product by silica gel chromatography using 2% dichloromethane/5% ethyl acetate in hexanes gave the 3,5-difluoro-4-(methylthio)-benzaldehyde as a clear colorless liquid (22.0 g, 62%). $^1$H NMR (CDCl$_3$/400 MHz) 9.86 (t, J=1.5, 1H), 7.34–7.39 (m, 2H), 2.55 (s, 3H). HRMS m/z 188.0099 (M$^+$, calcd 188.0107).

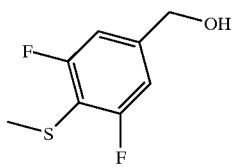

Step 2: Preparation of [3,5-difluoro-4-(methylthio)-phenyl]methanol

To a solution of 3,5-difluoro-4-(methylthio)-benzaldehyde (31.3 g, 0.166 mol) in anhydrous THF (200 mL) cooled with a cold water bath was added sodium borohydride (1.6 g, 0.042 mol) in portions over 30 minutes. After stirring 1 hour at room temperature, excess dilute HCl was added, until gas evolution ceased. Water (600 mL) was added and the mixture extracted with dichloromethane (1×500 mL, 1×100 mL). The combined extracts were washed once with water, dried with magnesium sulfate, and concentrated. Purification by silica gel chromatography using 3% ethyl acetate/10% dichloromethane in hexanes initially, and eluting product with 60% ethyl acetate in hexanes gave [3,5-difluoro-4-(methylthio)-phenyl]methanol as a light yellow liquid (24.8 g, 78%). $^1$H NMR (CDCl$_3$/400 MHz) 6.88–6.93 (m, 2H), 4.65 (s, 2H), 2.42 (s, 3H). HRMS m/z 190.0266 (M+H$^+$, calcd 190.0264).

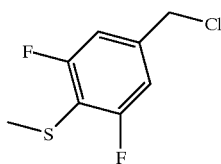

Step 3: Preparation of 5-(chloromethyl)-1,3-difluoro-2-(methylthio)benzene

To a solution of [3,5-difluoro-4-(methylthio)-phenyl]methanol (24.0 g, 0.126 mol) in dichloromethane (300 mL) cooled in an ice bath was added methanesulfonylchloride (16.9 g, 0.147 mol) in portions followed by diisopropylethylamine in portions. The mixture was allowed to warm to room temperature, and stirred for 18 hours. 4-dimethylaminopyridine was added and the mixture was heated to reflux for 2 hours, cooled, and stirred at room temperature for 18 hours. The mixture was poured into dilute HCl and extracted with dichloromethane once (75 mL) after separating. The combined extracts were washed with dilute sodium chloride, dried using magnesium sulfate, and concentrated. Purification by silica gel chromatography using 5% ethyl acetate in hexanes gave 5-(chloromethyl)-1,3-difluoro-2-(methylthio)benzene as a clear colorless liquid (24.9 g, 95%). $^1$H NMR (CDCl$_3$/400 MHz) 6.92–6.96 (m, 2H), 4.49 (s, 2H), 2.44 (s, 3H). HRMS m/z 207.9893 (M$^+$, calcd 207.9925).

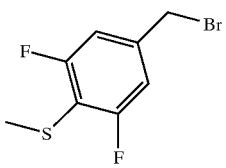

Step 4: Preparation of 5-(bromomethyl)-1,3-difluoro-2-(methylthio)benzene

A mixture of 5-(chloromethyl)-1,3-difluoro-2-(methylthio)benzene (21.3 g, 0.10 mol), lithium bromide (15 g, 0.17 mol), and acetone (200 mL) was heated and held at reflux for 18 hours. The cool mixture was poured into water and extracted with dichloromethane (1×200 mL, 2×50 mL). The combined extracts were dried using magnesium sulfate, and concentrated. The residue was dissolved in acetone (200 mL), lithium bromide (30 g, 0.34 mol) and sodium bromide (20 g, 0.19 mol) were added and the mixture heated and held at reflux for 42 hours. The mixture was cooled, added to water, and extracted with dichloromethane (1×150 mL, 1×50 mL). The combined extracts were washed with dilute sodium chloride, dried with magnesium sulfate, and concentrated. The 5-(bromomethyl)-1,3-difluoro-2-(methylthio)benzene was purified using silica gel chromatography using hexanes as a yellow solid (20.5 g, 80%). $^1$H NMR (CDCl$_3$/400 MHz) 6.92–6.95 (m, 2H), 4.37 (s, 2H), 2.45 (s, 3H). HRMS m/z 251.9432 (M$^+$, calcd 251.9420).

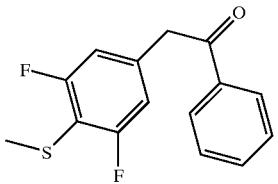

Step 5: Preparation of 2-[3,5-difluoro-4-(methylthio)-phenyl]-1-phenylethanone To a solution of phenyl[(trimethylsilyl)-oxy]aceto-nitrile (13.7 g, 60.7 mmol) in anhydrous THF (140 mL) cooled in a dry ice/acetone bath, was added a THF solution of lithium bis(trimethylsilyl)amide (62 mL 1.0M) slowly over 15 minutes. The reaction mixture was stirred for 45 minutes cooling at −78° C., then a solution of 5-(bromomethyl)-1,3-difluoro-2-(methylthio)benzene (14.7 g, 58 mmol) in anhydrous THF (20 mL) was added over 10 minutes. The reaction mixture was allowed to warm to room temperature, and stirred for 18 hours. To this mixture was added 5% HCl (300 mL) and the mixture stirred for one hour. The resulting oil was extracted with ethyl acetate (1×400 mL, 2×100 mL). To the combined extracts was added 5% sodium hydroxide (200 mL), and the mixture stirred for one hour. Additional water (200 mL) was added, the organic phase was separated, and the aqueous phase extracted with ethyl acetate (2×150 mL). The combined extracts were dried using magnesium sulfate, and concentrated. Chromatography on silica gel with 15% dichloromethane in hexanes initially and eluting the product with 30% gave 2-[3,5-difluoro-4-(methylthio)phenyl]-1-phenylethanone as light yellow solid (11.0 g, 68%). MP 71.8–71.9° C. $^1$H NMR (CDCl$_3$/400 MHz) 7.96–7.99 (m, 2H), 7.57–7.61 (m, 1H), 7.24–7.50 (m, 2H), 6.80–6.85 (m, 2H), 4.24 (s, 2H), 2.42 (s, 3H). HRMS m/z 279.0667 (M+H$^+$, calcd 279.0655). Anal. Calcd for C$_{15}$H$_{12}$F$_2$OS: C, 64.73; H, 4.35. Found: C, 64.70; H, 4.38.

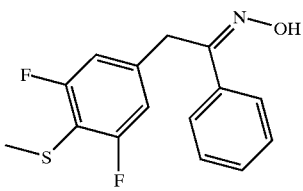

Step 6: Preparation of 2-[3,5-difluoro-4-(methylthio)-phenyl]-1-phenylethanone Oxime Hydroxylamine hydrochloride (5.5 g, 0.079 mol) and sodium acetate (6.5 g, 0.079 mol) were added to a slurry of 2-[3,5-difluoro-4-(methylthio)phenyl]-1-phenylethanone in ethanol (120 mL) and water (30 mL). The mixture was heated and held at reflux for 1 hour, then cooled and allowed to stir for 18 hours at room temperature. Additional water (50 mL) was added, and the mixture concentrated to half its volume. Dilute HCl was added, and the mixture extracted with dichloromethane (1×100 mL), 3×50 mL). The combined extracts were washed with dilute sodium bicarbonate, dried with magnesium sulfate, and concentrated to give a light yellow oil, that was crystallized from ethyl acetate/hexanes to afford 2-[3,5-difluoro-4-(methylthio)phenyl]-1-phenylethanone oxime as white solid (6.2 g, 53%). A second crop (2.3 g, 73% net yield) was also collected. $^1$H NMR (CDCl$_3$/400 MHz) 7.57–7.60 (m, 2H), 7.35–7.37 (m, 3H), 6.80–6.84 (m, 1.7H), 6.75–6.77 (m, 0.3H), 4.14 (s, 1.7H), 3.83 (s, 0.3H), 2.39 (s, 3H). HRMS m/z 244.0773 (M+H$^+$, calcd 244.0764). Anal. Calcd for C$_{15}$H$_{13}$F$_2$NOS: C, 61.42; H, 4.47; N, 4.78. Found: C, 61.44; H, 4.50; N, 4.84.

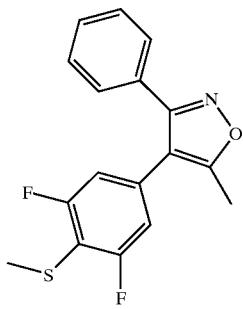

Step 7: Preparation of 4-[3,5-difluoro-4-(methylthio)-phenyl]-5-methyl-3-phenylisoxazole To a solution of lithium diisopropylamide (82 mmol) in anhydrous THF (200 mL), cooled to −45° C., was added a solution of 2-[3,5-difluoro-4-(methylthio)-phenyl]-1-phenylethanone oxime (5.7 g, 19 mmol) in anhydrous THF (15 mL), controlling the reaction temperature between −40 and −50° C. The mixture was allowed to warm to −25±5° C., held there for 1 hour, and cooled to −55° C. Excess ethyl acetate (20 g, 220 mmol) was gradually added to the mixture, and the mixture allowed to warm to 10° C. Dilute ammonium chloride solution was added, and the mixture extracted with dichloromethane (1×500 mL, 2×100 mL). The combined extracts were washed with dilute ammonium chloride, dried using magnesium sulfate, and concentrated. The residue was dissolved in dichloromethane (100 mL). The P-toluenesulfonic acid (1.0 g, 6.4 mmol) was added, and the mixture heated and held at reflux for 1 hour. The cool mixture was washed with dilute sodium bicarbonate, and the aqueous wash extracted with dichloromethane. The combined organic phases were dried using magnesium sulfate, and concentrated. The product was isolated by silica gel chromatography using 5% ethyl acetate in hexanes to give 4-[3,5-difluoro-4-(methylthio)phenyl]-5-methyl-3-phenylisoxazole as a yellow solid (2.9 g, 47%). $^1$H NMR (CDCl$_3$/400 MHz) 7.33–7.42 (m, 5H), 6.68–6.73 (m, 2H), 2.48 (s, 3H) 2.47 (s, 3H). HRMS m/z 318.0769 (M+H$^+$, calcd 318.0764). Anal. Calcd for C$_{17}$H$_{13}$F$_2$NOS: C, 64.34; H, 4.13; N, 4.41. Found: C, 64.22; H, 4.16; N, 4.28.

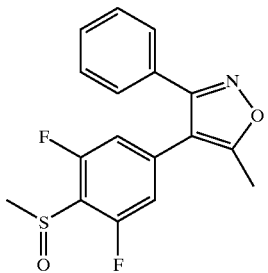

Step 8: Preparation of 4-[3,5-difluoro-4-(methylsulfinyl)phenyl]-5-methyl-3-phenylisoxazole To a solution of 4-[3,5-difluoro-4-(methylthio)phenyl]-5-methyl-3-phenylisoxazole in dichloromethane (75 mL) and methanol (15 mL) cooled in an ice bath was added magnesium monoperoxyphthalate hexahydrate (4.4 g 80%, 7.1 mmol) in portions over 5 minutes. The reaction mixture was stirred for 90 minutes, then poured into water and extracted with dichloromethane (1×250 mL, 1×75 mL). The combined extracts were washed with dilute ammonium chloride, dried with magnesium sulfate, and concentrated. Purification by silica gel chromatography using 25% ethyl acetate/25% hexanes/50% dichloromethane gave 4-[3,5-difluoro-4-(methylsulfinyl)phenyl]-5-methyl-3-phenylisoxazole as a white solid. $^1$H NMR (CDCl$_3$/400 MHz) 7.37–7.44 (m, 5H), 6.77–6.81 (m, 2H), 3.13 (s, 3H) 2.50 (s, 3H). HRMS m/z 334.0698 (M+H$^+$, calcd 334.0713). Anal. Calcd for C$_{17}$H$_{13}$F$_2$NO$_2$S: C, 61.25; H, 3.93; N, 4.20. Found: C, 61.22; H, 4.00; N, 4.02.

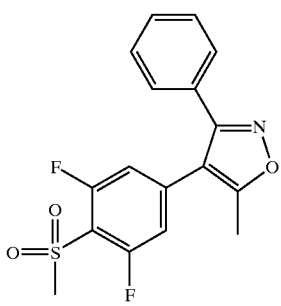

Step 9: Preparation of 4-[3,5-difluoro-4-(methylsulfonyl)-phenyl]-5-methyl-3-phenylisoxazole Potassium peroxymonosulfate (0.25 g, 0.40 mmol) and water (7 mL) were added to a mixture of 4-[3,5-difluoro-4-(methyl-sulfinyl)phenyl]-5-methyl-3-phenylisoxazole (0.10 g, 0.30 mmol), dichloromethane (4 mL), and methanol (4 mL). The mixture was stirred for four days at room temperature. To the mixture was added magnesium monoperoxyphathalate hexahydrate (0.50 g, 0.80 mmol), dichloromethane (20 mL), methanol (10 mL). The mixture was stirred vigorously for 18 hours. To the mixture was added potassium peroxymonosulfate (0.35 g, 0.57 mmol), and the reaction continued for 18 hours. The mixture was poured into water and extracted with dichloromethane (4×75 mL). The combined extracts were dried with magnesium sulfate, concentrated, and the residue purified by silica gel chromatography using 30% ethyl acetate in hexanes. A white solid (98 mg, 93%) was obtained. MP 140.4–143.4° C. $^1$H NMR (CDCl$_3$/400 MHz) 7.35–7.45 (m, 5H), 6.84 (d, 2H, J=9.4), 3.32 (s, 3H) 2.52 (s, 3H). ESHRMS m/z 350.0642 (M+H$^+$, Calcd 350.0662).

Example 15

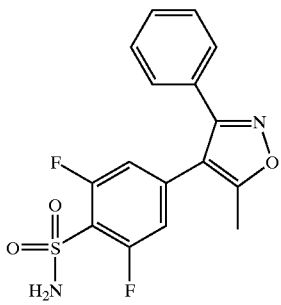

2,6-difluoro-4-(5-methyl-3-phenylisoxazol-4-yl)benzene-sulfonamide

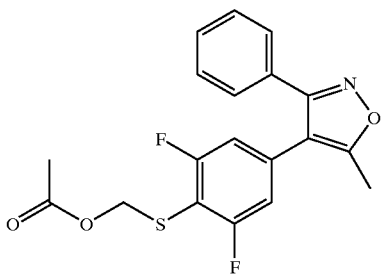

Step 1: Preparation of {[2,6-difluoro-4-(5-methyl-3-phenylisoxazol-4-yl)phenyl]thio}methyl Acetate A slurry of 4-[3,5-difluoro-4-(methylsulfinyl)phenyl]-5-methyl-3-phenylisoxazole (2.3 g, 6.8 mmol) (step 9 example 14), sodium acetate (3.4 g, 41 mmol) in acetic anhydride (30 mL) was heated and held at reflux for 9 hours. The mixture was concentrated on at reduced pressure and the residue was treated with dilute aqueous sodium bicarbonate and extracted with dichloromethane (1×200 mL, 2×75 mL). The combined extracts were washed with dilute sodium bicarbonate, dilute ammonium chloride, dried with magnesium sulfate and concentrated. The product was purified by silica gel chromatography using 1% ethyl acetate/50% dichloromethane in hexanes to give {[2,6-difluoro-4-(5-methyl-3-phenylisoxazol-4-yl)phenyl]thio}methyl acetate as a white solid (2.1 g, 82%), MP 130.3–130.3° C. $^1$H NMR (CDCl$_3$/400 MHz) 7.34–7.43 (m, 5H), 6.73–6.79 (m, 2H), 5.29 (s, 2H), 2.49 (s, 3H) 2.05 (s, 3H). HRMS m/z 376.0822 (M+H$^+$, Calcd 376.0819). Anal. Calcd for C$_{19}$H$_{15}$F$_2$NO$_3$S: C, 60.79; H, 4.03; N, 3.73. Found: C, 60.44; H, 4.09; N, 3.66.

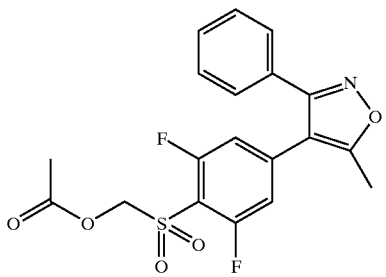

Step 2: Preparation of {[2,6-difluoro-4-(5-methyl-3-phenylisoxazol-4-yl)phenyl]sulfonyl}methyl Acetate To a solution of {[2,6-difluoro-4-(5-methyl-3-phenyl-isoxazol-4-yl)phenyl]thio}methyl acetate in methanol (30 mL) and dichloromethane (70 mL) was added magnesium monoperoxyphthalate hexahydrate (8.6 g 80%, 14 mmol). The slurry was heated and held at reflux for 4 hours, then poured into water and extracted with dichloromethane (1×150 mL, 3×75 mL). The combined extracts were washed with dilute sodium chloride twice, dried with magnesium sulfate, and concentrated. The residue was dissolved in dichloromethane (40 mL) and methanol (20 mL), magnesium monoperoxyphthalate hexahydrate (4.5 g, 7.3 mmol) was added, and the mixture heated and held at reflux for 5 hours. Additional magnesium monoperoxyphthalate hexahydrate was added and the mixture heated and held at reflux for 18 hours. The reaction mixture was poured into dilute ammonium chloride and extracted with dichloromethane (1×200 mL, 2×50 mL). The combined extracts were washed twice with dilute ammonium chloride, dried with magnesium sulfate, and concentrated. Purification by silica gel chromatography using 30% ethyl acetate in hexanes gave white solids, which were dissolved in dichloromethane, washed with dilute sodium bicarbonate, dried with magnesium sulfate, and concentrated to provide {[2,6-difluoro-4-(5-methyl-3-phenylisoxazol-4-yl)phenyl]sulfonyl}methyl acetate as a white solid (1.4 g, 54%). Recrystallization from ethyl acetate/hexanes gave an analytical sample of the product, MP 164.6–165.6° C. $^1$H NMR (CDCl$_3$/400 MHz) 7.35–7.46 (m, 5H), 6.82–6.86 (m, 2H), 5.33 (s, 2H), 2.54 (s, 3H) 2.12 (s, 3H). HRMS m/z 408.0725 (M+H$^+$, calcd 408.0717). Anal. Calcd for C$_{19}$H$_{15}$F$_2$NO$_5$S: C, 56.02; H, 3.71; N, 3.44. Found: C, 56.07; H, 3.61; N, 3.58.

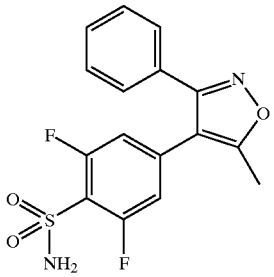

Step 3: Preparation of 2,6-difluoro-4-(5-methyl-3-phenylisoxazol-4-yl)benzenesulfonamide To a mixture of {[2,6-difluoro-4-(5-methyl-3-phenylisoxazol-4-yl)phenyl]sulfonyl}methyl acetate (1.5 g, 3.9 mmol) in THF (25 mL) and methanol (25 mL) was added a solution of lithium hydroxide (0.50 g, 12 mmol) in water (4 mL). The resulting solution was stirred at room temperature for 1 hour. Additional solution of lithium hydroxide (0.60 g, 14 mmol) in water (8 mL) was added, followed by solid hydroxylamine sulfonic acid (1.6 g, 14.1 mmol) and methanol (5 mL). The reaction mixture was stirred overnight and poured into water (250 mL). The 2,6-difluoro-4-(5-methyl-3-phenyl-isoxazol-4-yl)benzenesulfonamide was isolated as a white solid (1.08 g, 85%). MP 226.1–226.2° C. $^1$H NMR (CD$_3$OD/400 MHz) 7.36–7.46 (m, 5H), 6.95 (d, 2H, J=9.4), 2.51 (s, 3H). ESHRMS m/z 351.0621 (M+H$^+$, Calcd 351.0615). Anal. Calcd for C$_{16}$H$_{12}$F$_2$N$_2$O$_3$S: C, 54.85; H, 3.45; N, 8.00. Found: C, 54.95; H, 3.51; N, 7.81.

Biological Evaluation
Evaluation of COX-1 and COX-2 Activity In Vitro

The compounds of this invention exhibited inhibition in vitro of COX-2. The COX-2 inhibition activity of the compounds of this invention illustrated in the Examples was determined by the following methods.

A. Preparation of Recombinant COX Baculoviruses

Recombinant COX-1 and COX-2 were prepared as described by Gierse et al. [*J. Biochem.*, 305, 479–84 (1995)]. A 2.0 kb fragment containing the coding region of either human or murine COX-1 or human or murine COX-2 was cloned into a BamH1 site of the baculovirus transfer vector pVL1393 (Invitrogen) to generate the baculovirus transfer vectors for COX-1 and COX-2 in a manner similar to the method of D. R. O'Reilly et al. [*Baculovirus Expression Vectors: A Laboratory Manual* (1992)]. Recombinant baculoviruses were isolated by transfecting 4 µg of baculovirus transfer vector DNA into SF9 insect cells (2×10$^8$) along with 200 ng of linearized baculovirus plasmid DNA by the calcium phosphate method. See M. D. Summers and G. E. Smith, *A Manual of Methods for Baculovirus Vectors and Insect Cell Culture Procedures, Texas Agric. Exp. Station Bull.* 1555 (1987). Recombinant viruses were purified by three rounds of plaque purification and high titer (10$^{7-108}$ pfu/mL) stocks of virus were prepared. For large scale production, SF9 insect cells were infected in 10 liter fermentors (0.5×10$^6$/mL) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000×G for 30 minutes, and the resultant supernatant was stored at −80° C. before being assayed for COX activity.

B. Assay for COX-1 and COX-2 Activity

COX activity was assayed as PGE$_2$ formed/µg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 µM). Compounds were pre-incubated with the enzyme for 10–20 minutes prior to the addition of arachidonic acid. Any reaction between the arachidonic acid and the enzyme was stopped after ten minutes at 37° C. room temperature by transferring 40 µl of reaction mix into 160 µl ELISA buffer and 25 µM indomethacin. The PGE$_2$ formed was measured by standard ELISA technology (Cayman Chemical).

C. Fast assay for COX-1 and COX-2 Activity

COX activity was assayed as PGE$_2$ formed/µg protein/time using an ELISA to detect the prostaglandin released. CHAPS-solubilized insect cell membranes containing the appropriate COX enzyme were incubated in a potassium phosphate buffer (0.05 M Potassium phosphate, pH 7.5, 2 µM phenol, 1 µM heme, 300 µM epinephrine) with the addition of 20 µl of 100 µM arachidonic acid (10 µM). Compounds were pre-incubated with the enzyme for 10 minutes at 25° C. prior to the addition of arachidonic acid. Any reaction between the arachidonic acid and the enzyme was stopped after two minutes at 37° C./room temperature by transferring 40 µl of reaction mix into 160 µl ELISA buffer and 25 µM indomethacin. The PGE$_2$ formed was measured by standard ELISA technology (Cayman Chemical). Results are shown in Table I.

TABLE I

| Example | Human COX-2 IC$_{50}$ (µM) | Human COX-1 IC$_{50}$ (µM) |
|---|---|---|
| 1 | 3.44 | >100 |
| 2 | 0.55 | >100 |
| 3 | 0.3 | >100 |
| 4 | 0.1 | >100 |
| 5 | 1.21 | >100 |
| 6 | 0.09 | >100 |
| 7 | 0.09 | 56.7 |
| 8 | 0.25 | 14.85 |
| 14 | 1.21 | >100 |
| 15 | 0.12 | >100 |

Rat Carrageenan Foot Pad Edema Test

The carrageenan foot edema test is performed with materials, reagents and procedures essentially as described by Winter et al. [*Proc. Soc. Exp. Biol. Med.*, 111, 544 (1962)]. Male Sprague-Dawley rats are selected in each group so that the average body weight is as close as possible. Rats are fasted with free access to water for over sixteen hours prior to the test. The rats are dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline is administered and the volume of the injected foot is measured with a displacement plethysmometer connected to a pressure transducer with a digital indicator. Three hours after the injection of the carrageenan, the volume of the foot is again measured. The average foot swelling in a group of drug-treated animals is compared with that of a group of placebo-treated animals and the percentage inhibition of edema is determined (Otterness and Bliven, *Laboratory Models for Testing NSAIDs*, in *Non-steroidal Anti-Inflammatory Drugs*, (J. Lombardino, ed. 1985)).

Rat Carrageenan-Induced Analgesia Test

The rat carrageenan analgesia test is performed with materials, reagents and procedures essentially as described by Hargreaves et al. [*Pain*, 32, 77 (1988)]. Male Sprague-Dawley rats are treated as previously described for the Carrageenan Foot Pad Edema test. Three hours after the injection of the carrageenan, the rats are placed in a special plexiglass container with a transparent floor having a high intensity lamp as a radiant heat source, positionable under the floor. After an initial twenty minute period, thermal stimulation is begun on either the injected foot or on the contralateral uninjected foot. A photoelectric cell turns off the lamp and timer when light is interrupted by paw withdrawal. The time until the rat withdraws its foot is then measured. The withdrawal latency in seconds is determined for the control and drug-treated groups, and percent inhibition of the hyperalgesic foot withdrawal is determined.

As various changes could be made in the above methods and apparatus without departing from the scope of the invention, it is intended that all matter contained in the above description be interpreted as illustrative and not in a limiting sense. All documents mentioned in this application are expressly incorporated by reference as if fully set forth at length.

All mentioned references are incorporated by reference as if here written. When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

What is claimed is:

1. A compound, or a pharmaceutically-acceptable salt, tautomer or prodrug thereof, selected from the group consisting of:

2,5-difluoro-4-[5-oxo-2,5-dihydro-3-furanyl]benzenesulfonamide;

2,5-difluoro-4-[4-(3-chlorophenyl)-5-oxo-2,5-dihydro-3-furanyl]benzenesulfonamide;

2,5-difluoro-4-[4-(4-chlorophenyl)-5-oxo-2,5-dihydro-3-furanyl]benzenesulfonamide;

2,5-difluoro-4-[4-(3-bromophenyl)-5-oxo-2,5-dihydro-3-furanyl]benzenesulfonamide;

2,5-difluoro-4-[4-(4-bromophenyl)-5-oxo-2,5-dihydro-3-furanyl]benzenesulfonamide;

2,5-difluoro-4-[4-(3-fluorophenyl)-5-oxo-2,5-dihydro-3-furanyl]benzenesulfonamide;

2,5-difluoro-4-[4-(4-fluorophenyl)-5-oxo-2,5-dihydro-3-furanyl]benzenesulfonamide;

2,5-difluoro-4-[4-(3-methylphenyl)-5-oxo-2,5-dihydro-3-furanyl]benzenesulfonamide;

2,5-difluoro-4-[4-(4-methylphenyl)-5-oxo-2,5-dihydro-3-furanyl]benzenesulfonamide;

2,5-difluoro-4-[4-(3-cyanophenyl)-5-oxo-2,5-dihydro-3-furanyl]benzenesulfonamide;

2,5-difluoro-4-[4-(4-cyanophenyl)-5—oxo-2,5-dihydro-3-furanyl]benzenesulfonamide;

2,5-difluoro-4-[4-(3-trifluoromethylphenyl)-5-oxo-2,5-dihydro-3-furanyl]benzenesulfonamide;

2,5-difluoro-4-[4-(4-trifluoromethylphenyl)-5-oxo-2,5-dihydro-3-furanyl]benzenesulfonamide;

2,5-difluoro-4-[4-(3-trifluoromethoxyphenyl)-5-oxo-2,5-dihydro-3-furanyl]benzenesulfonamide;

2,5-difluoro-4-[4-(4-trifluoromethoxyphenyl)-5-oxo-2,5-dihydro-3-furanyl]benzenesulfonamide;

2,5-difluoro-4-[4-(3,4-dichlorophenyl)-5-oxo-2,5-dihydro-3-furanyl]benzenesulfonamide;

2,5-difluoro-4-[4-(3,4-dibromophenyl)-5-oxo-2,5-dihydro-3-furanyl]benzenesulfonamide;

2,5-difluoro-4-[4-(3,4-difluorophenyl)-5-oxo-2,5-dihydro-3-furanyl]benzenesulfonamide;

2,5-difluoro-4-[4-(3,5-dichlorophenyl)-5-oxo-2,5-dihydro-3-furanyl]benzenesulfonamide;

2,5-difluoro-4-[4-(3,5-dibromophenyl)-5-oxo-2,5-dihydro-3-furanyl]benzenesulfonamide;

2,5-difluoro-4-[4-(3,5-difluorophenyl)-5-oxo-2,5-dihydro-3-furanyl]benzenesulfonamide;

2,5-difluoro-4-[4-(3,4-dimethylphenyl)-5-oxo-2,5-dihydro-3-furanyl]benzenesulfonamide;

2,5-difluoro-4-[4-(3,5-dimethylphenyl)-5-oxo-2,5-dihydro-3 furanyl]benzenesulfonamide;

2,5-difluoro-4-[4-(3-methyl-4-chlorophenyl)-5-oxo-2,5-dihydro-3-furanyl]benzenesulfonamide;

2,5-difluoro-4-[4-(4-methyl-3-chlorophenyl)-5-oxo-2,5 dihydro-3-furanyl]benzenesulfonamide;

2,5-difluoro-4-[4-(3-methyl-4-fluorophenyl)-5-oxo-2,5 dihydro-3-furanyl]benzenesulfonamide;

2,5-difluoro-4-[4-(4-methyl-3-fluorophenyl)-5-oxo-2,5-dihydro-3-furanyl]benzenesulfonamide;

2,5-difluoro-4-[4-(3-methyl-4-bromophenyl)-5-oxo-2,5-dihydro-3-furanyl]benzenesulfonamide;

2,5-difluoro-4-[4-(4-methyl-3-bromophenyl)-s-oxo-2,5-dihydro-3-furanyl]benzenesulfonamide;

2,5-difluoro-4-[4-(3-methyl-4-trifluoromethylphenyl)-5-oxo-2,5-dihydro-3-furanyl]benzenesulfonamide;

2,5-difluoro-4-[4-(4-methyl-3-trifluoromethylphenyl)-5-oxo-2,5-dihydro-3-furanyl]benzenesulfonamide;

2,5-difluoro-4-[4-(3-methyl-4-trifluoromethoxyphenyl)-5-oxo-2,5-dihydro-3-furanyl]benzenesulfonamide;

2,5-difluoro-4-[4-(4-methyl-3-trifluoromethoxyphenyl)-5-oxo-2,5-dihydro-3-furanyl]benzenesulfonamide;

2,5-difluoro-4-[4-(3-cyano-4-methylphenyl)-5-oxo-2,5-dihydro-3-furanyl]benzenesulfonamide;

2,5-difluoro-4-[4-(4-cyano-3-methylphenyl)-5-oxo-2,5-dihydro-3-furanyl]benzenesulfonamide;

2,5-difluoro-4-[4-(3-chloro-4-methoxyphenyl)-5-oxo-2,5-dihydro-3-furanyl]benzenesulfonamide;

2,5-difluoro-4-[4-(4-chloro-3-methoxyphenyl)-5-oxo-2,5-dihydro-3-furanyl]benzenesulfonamide;

2,5-difluoro-4-[4-(2-methylpyridin-6-yl)-5-oxo-2,5-dihydro-3-furanyl]benzenesulfonamide;

2,5-difluoro-4-[4-(2-methylthiazol-4-yl)-5-oxo-2,5-dihydro-3-furanyl]benzenesulfonamide;

2,5-difluoro-4-[4-(4-methylthiazol-2-yl)-5-oxo-2,5-dihydro-3-furanyl]benzenesulfonamide;

2,5-difluoro-4-[4-(2-methylpyridin-3-yl)-5-oxo-2,5-dihydro-3-furanyl]benzenesulfonamide;

2,5-difluoro-4-[4-(2-methylpyridin-3-yl)-5-oxo-2,5-dihydro-3-furanyl]benzenesulfonamide;

2,5-difluoro-4-[4-(3-pyridinyl)-5-oxo-2,5-dihydro-3-furanyl]benzenesulfonamide;

2,5-difluoro-4-[4-(5-methylpyridin-3-yl)-5-oxo-2,5-dihydro-3-furanyl]benzenesulfonamide;

2,5-difluoro-4-[4-(2-methylpyridin-3-yl)-5-oxo-2,5-dihydro-3-furanyl]benzenesulfonamide;

2,5-difluoro-4-[4-cyclohexyl-5-oxo-2,5-dihydro-3-furanyl]benzenesulfonamide;

2,5-difluoro-4-[4-cyclopentyl-5-oxo-2,5-dihydro-3-furanyl]benzenesulfonamide;

3-phenyl-4-[3,5-difluoro-4-(methylsulfonyl)phenyl]-2 (5H)-furanone;

3-(3-chlorophenyl)-4-[3,5-difluoro-4-(methylsulfonyl)phenyl]-2 (5H)-furanone;

3-(4-chlorophenyl)-4-[3,5-difluoro-4-(methylsulfonyl)phenyl]-2 (5H)-furanone;

3-(3-bromophenyl)-4-[3,5-difluoro-4-(methylsulfonyl)phenyl]-2 (5H)-furanone;

3-(4-bromophenyl)-4-[3,5-difluoro-4-(methylsulfonyl)phenyl]-2 (5H)-furanone;

3-(3-fluorophenyl)-4-[3,5-difluoro-4-(methylsulfonyl)phenyl]-2 (5H)-furanone;

3-(4-fluorophenyl)-4-[3,5-difluoro-4-(methylsulfonyl)phenyl]-2 (5H)-furanone;

3-(3-methylphenyl)-4-[3,5-difluoro-4-(methylsulfonyl)phenyl]-2 (5H)-furanone;

3-(4-methylphenyl)-4-[3,5-difluoro-4-(methylsulfonyl)phenyl]-2 (5H)-furanone;

3-(3-cyanophenyl)-4-[3,5-difluoro-4-(methylsulfonyl)phenyl]-2 (5H)-furanone;

3-(4-cyanophenyl)-4-[3,5-difluoro-4-(methylsulfonyl)phenyl]-2 (5H)-furanone;

3-(3-trifluoromethylphenyl)-4-[3,5-difluoro-4-(methylsulfonyl) phenyl]-2 (5H)-furanone;

3-(4-trifluoromethylphenyl)-4-[3,5-difluoro-4-(methylsulfonyl) phenyl]-2 (5H)-furanone;

3-(3-trifluoromethoxyphenyl)-4-[3,5-difluoro-4-(methylsulfonyl) phenyl]-2 (5H)-furanone;

3-(4-trifluoromethoxyphenyl)-4-[3,5-difluoro-4-(methylsulfonyl) phenyl]-2 (5H)-furanone;

3-(3,4-dichlorophenyl)-4-[3,5-difluoro-4-(methylsulfonyl) phenyl]-2 (5H)-furanone;

3-(3,4-dibromophenyl)-4-[3,5-difluoro-4-(methylsulfonyl) phenyl]-2 (5H)-furanone;

3-(3,4-difluorophenyl)-4-[3,5-difluoro-4-(methylsulfonyl) phenyl]-2 (5H)-furanone;

3-(3,5-dichlorophenyl)-4-[3,5-difluoro-4-(methylsulfonyl)phenyl]-2 (5H)-furanone;

3-(3,5-dibromophenyl)-4-[3,5-difluoro-4-(methylsulfonyl) phenyl]-2 (5H)-furanone;

3-(3,5-difluorophenyl)-4-[3,5-difluoro-4-methylsulfonyl) phenyl]-2 (5H)-furanone;

3-(3,4-dimethylphenyl)-4-[3,5-difluoro-4-(methylsulfonyl)phenyl]-2 (5H)-furanone;

3-(3,5-dimethylphenyl)-4-[3,5-difluoro-4-(methylsulfonyl) phenyl]-2 (5H)-furanone;

3-(3-methyl-4-chlorophenyl)-4-[3,5-difluoro-4-(methylsulfonyl) phenyl]-2 (5H)-furanone;

3-(4-methyl-3-chlorophenyl)-4-[3,5-difluoro-4-(methylsulfonyl) phenyl]-2 (5H)-furanone;

3-(3-methyl-4-fluorophenyl)-4-[3,5-difluoro-4-(methylsulfonyl)phenyl]-2 (5H)-furanone;

3-(4-methyl-3-fluorophenyl)-4-[3,5-difluoro-4-(methylsulfonyl) phenyl]-2 (5H)-furanone;

3-(3-methyl-4-bromophenyl)-4-[3,5-difluoro-4-(methylsulfonyl) phenyl]-2 (5H)-furanone;

3-(4-methyl-3-bromophenyl)-4-[3,5-difluoro-4-(methylsulfonyl) phenyl]-2 (5H)-furanone;

3-(3-methyl-4-trifluoromethylphenyl)-4-[3,5-difluoro-4-(methylsulfonyl)phenyl]-2 (5H)-furanone;

3-(4-methyl-3-trifluoromethylphenyl)-4-[3,5-difluoro-4-(methylsulfonyl) phenyl]-2 (5H)-furanone;

3-(3-methyl-4-trifluoromethoxyphenyl)-4-[3,5-difluoro-4-(methylsulfonyl)phenyl]-2 (5H)-furanone;

3-(4-methyl-3-trifluoromethoxyphenyl)-4-[3,5-difluoro-4-(methylsulfonyl) phenyl]-2 (5H)-furanone;

3-(3-cyano-4-methylphenyl)-4-[3,5-difluoro-4-(methylsulfonyl) phenyl]-2 (5H)-furanone;

3-(4-cyano-3-methylphenyl)-4-[3,5-difluoro-4-(methylsulfonyl) phenyl]-2 (5H)-furanone;

3-(3-chloro-4-methoxyphenyl)-4-[3,5-difluoro-4-(methylsulfonyl) phenyl]-2 (5H)-furanone;

3-(4-chloro-3-methoxyphenyl)-4-[3,5-difluoro-4-(methylsulfonyl) phenyl]-2 (5H)-furanone;

3-(2-methylpyridin-6-yl)-4-[3,5-difluoro-4-(methylsulfonyl) phenyl]-2 (5H)-furanone;

3-(2-methylthiazol-4-yl)-4-[3,5-difluoro-4-(methylsulfonyl)phenyl]-2 (5H)-furanone;

3-(4-methylthiazol-2-yl)-4-[3,5-difluoro-4-(methylsulfonyl) phenyl]-2 (5H)-furanone;

3-(2-methylpyridin-3-yl)-4-[3,5-difluoro-4-(methylsulfonyl) phenyl]-2 (5H)-furanone;

3-(2-methylpyridin-3-yl)-4-[3,5-difluoro-4-(methylsulfonyl)phenyl]-2 (5H)-furanone;

3-(3-pyridinyl)-4-[3,5-difluoro-4-(methylsulfonyl) phenyl]-2 (5H)-furanone;

3-(5-methylpyridin-3-yl)-4-[3,5-difluoro-4-(methylsulfonyl) phenyl]-2 (5H)-furanone;

3-(2-methylpyridin-3-yl)-4-[3,5-difluoro-4-(methylsulfonyl)phenyl]-2 (5H)-furanone;

3-cyclohexyl-4-[3,5-difluoro-4-(methylsulfonyl) phenyl]-2 (5H)-furanone;

3-cyclopentyl-4-[3,5-difluoro-4-(methylsulfonyl) phenyl]-2 (5H)-furanone;

2,6-difluoro-4-[4,5-oxo-2,5-dihydro-3-furanyl]benzenesulfonamide;

2,6-difluoro-4-[4-(3-chlorophenyl)-5-oxo-2,5-dihydro-3-furanyl]benzenesulfonamide;

2,6-difluoro-4-[4-(4-chlorophenyl)-5-oxo-2,5-dihydro-3-furanyl]benzenesulfonamide;

2,6-difluoro-4-[4-(3-bromophenyl)-5-oxo-2,5-dihydro-3-furanyl]benzenesulfonamide;

2,6-difluoro-4-[4-(4-bromophenyl)-5-oxo-2,5-dihydro-3-furanyl]benzenesulfonamide;

2,6-difluoro-4-[4-(3-fluorophenyl)-5-oxo2,5-dihydro-3-furanyl]benzenesulfonamide;

2,6-difluoro-4-[4-(4-fluorophenyl)-5-oxo-2,5-dihydro-3-furanyl]benzenesulfonamide;

2,6-difluoro-4-[4-(3-methylphenyl)-5-oxo-2,5-dihydro-3-furanyl]benzenesulfonamide;

2,6-difluoro-4-[4-(4-methylphenyl)-5-oxo-2,5-dihydro-3-furanyl]benzenesulfonamide;

2,6-difluoro-4-[4-(3-cyanophenyl)-5-oxo-2,5-dihydro-3-furanyl]benzenesulfonamide;

2,5-difluoro-4-[4-(4-cyanophenyl)-5-oxo-2,5-dihydro-3-furanyl]benzenesulfonamide;

2,6-difluoro-4-[4-(3-trifluoromethylphenyl)-5-oxo-2,5-dihydro-3-furanyl]benzenesulfonamide;
2,6-difluoro-4-[4-(4-trifluoromethylphenyl)-5-oxo-2,5-dihydro-3-furanyl]benzenesulfonamide;
2,6-difluoro-4-[4-(3-trifluoromethoxyphenyl)-5-oxo-2,5-dihydro-3-furanyl]benzenesulfonamide;
2,6-difluoro-4-[4-(4-trifluoromethoxyphenyl)-5-oxo-2,5-dihydro-3-furanyl]benzenesulfonamide;
2,6-difluoro-4-[4-(3,4-dichlorophenyl)-5-oxo-2,5-dihydro-3-furanyl]benzenesulfonamide;
2,6-difluoro-4-[4-(3,4-dibromophenyl)-5-oxo-2,5-dihydro-3-furanyl]benzenesulfonamide;
2,6-difluoro-4-[4-(3,4-difluorophenyl)-5-oxo-2,5-dihydro-3-furanyl]benzenesulfonamide;
2,5-difluoro-4-[4-(3,5-dichlorophenyl)-5-oxo-2,5-dihydro-3-furanyl]benzenesulfonamide;
2,6-difluoro-4-[4-(3,5-dibromophenyl)-5-oxo-2,5-dihydro-3-furanyl]benzenesulfonamide;
2,6-difluoro-4-[4-(3,5-difluorophenyl)-5-oxo-2,5-dihydro-3-furanyl]benzenesulfonamide;
2,6-difluoro-4-[4-(3,4-dimethylphenyl)-5-oxo-2,5-dihydro-3-furanyl]benzenesulfonamide;
2,6-difluoro-4-[4-(3,5-dimethylphenyl)-5-oxo-2,6-dihydro-3-furanyl]benzenesulfonamide;
2,6-difluoro-4-[4-(3-methyl-4-chlorophenyl)-s-oxo-2,5-dihydro-3-furanyl]benzenesulfonamide;
2,6-difluoro-4-[4-(4-methyl-3-chlorophenyl)-5-oxo-25-dihydro-3-furanyl]benzenesulfonamide;
2,6-difluoro-4-[4-(3-methyl-4-fluorophenyl)-5-oxo-2,5-dihydro-3-furanyl]benzenesulfonamide;
2,6-difluoro-4-[4-(4-methyl-3-fluorophenyl)5-oxo-2,5-dihydro-3-furanyl]benzenesulfonamide;
2,6-difluoro-4-[4-(3-methyl-4-bromophenyl)-5-oxo-2,5-dihydro-3-furanyl]benzenesulfonamide;
2,6-difluoro-4-[4-(4-methyl-3-bromophenyl)-5-oxo-2,5-dihydro-3-furanyl]benzenesulfonamide;
2,6-difluoro-4-[4-(3-methyl-4-trifluoromethylphenyl)-5-oxo-2,5-dihydro-3-furanyl]benzenesulfonamide;
2,6-difluoro-4-[4-(4-methyl-3-trifluoromethylphenyl)-5-oxo-2,5-dihydro-3-furanyl]benzenesulfonamide;
2,6-difluoro-4-[4-(3-methyl-4-trifluoromethoxyphenyl)-5-oxo-2,5-dihydro-3-furanyl]benzenesulfonamide;
2,6-difluoro-4-[4-(4-methyl-3-trifluoromethoxyphenyl)-5-oxo-2,5-dihydro-3-furanyl]benzenesulfonamide;
2,6-difluoro-4-[4-(3-cyano-4-methylphenyl)-5-oxo-2,5-dihydro-3-furanyl]benzenesulfonamide;
2,6-difluoro-4-[4-(4-cyano-3-methylphenyl)-5-oxo-2,5-dihydro-3-furanyl]benzenesulfonamide;
2,6-difluoro-4-[4-(3-chloro-4-methoxyphenyl)-5-oxo-2,5-dihydro-3-furanyl]benzenesulfonamide;
2,6-difluoro-4-[4-(4-chloro-3-methoxyphenyl)-5-oxo-2,5-dihydro-3-furanyl]benzenesulfonamide;
2,6-difluoro-4-[4-(2-methylpyridin-6-yl)-5-oxo-2,5-dihydro-3-furanyl]benzenesulfonamide;
2,6-difluoro-4-[4-(2-methylthiazol-4-yl)-5-oxo-2,5-dihydro-3-furanyl]benzenesulfonamide;
2,6-difluoro-4-[4-(4-methylthiazol-2-yl)-5-oxo-2,5-dihydro-3-furanyl]benzenesulfonamide;
2,6-difluoro-4-[4-(2-methylpyridin-3-yl)-5-oxo-2,5-dihydro-3-furanyl]benzenesulfonamide;
2,6-difluoro-4-[4-(2-methylpyridin-3-yl)-5-oxo-2,5-dihydro-3-furanyl]benzenesulfonamide;
2,6-difluoro-4-[4-(3-pyridinyl)-5-oxo-2-dihydro-3-furanyl]benzenesulfonamide;
2,6-difluoro-4-[4-(5-methylpyridin-3-yl)-5-oxo-2,5-dihydro-3-furanyl]benzenesulfonamide;
2,6-difluoro-4-[4-(2-methylpyridin-3-yl)-5-oxo-2,5-dihydro-3-furanyl]benzenesulfonamide;
2,6-difluoro-4-[4-cyclohexyl-5-oxo-2,5-dihydro-3-furanyl]benzenesulfonamide;
2,6-difluoro-4-[4-cyclopentyl-5-oxo-2,5-dihydro-3-furanyl]benzenesulfonamide;
3-phenyl-4-[3,6-difluoro-4-(methylsulfonyl)phenyl]-2(5H)-furanone;
3-(3-chlorophenyl)-4-[3,6-difluoro-4-(methylsulfonyl)phenyl]-2(5H)-furanone;
3-(4-chlorophenyl)-4-[3,6-difluoro-4-(methylsulfonyl)phenyl]-2(5H)-furanone;
3-(3-bromophenyl)-4-[3,6-difluoro-4-(methylsulfonyl)phenyl]-2(5H)-furanone;
3-(4-bromophenyl)-4-[3,6-difluoro-4-(methylsulfonyl)phenyl]-2(5H)-furanone;
3-(3-fluorophenyl)-4-[3,6-difluoro-4-(methylsulfonyl)phenyl]-2(5H)-furanone;
3-(4-fluorophenyl)-4-[3,6-difluoro-4-(methylsulfonyl)phenyl]-2(5H)-furanone;
3-(3-methylphenyl)-4-[3,6-difluoro-4-(methylsulfonyl)phenyl]-2(5H)-furanone;
3-(4-methylphenyl)-4-[3,6-difluoro-4-(methylsulfonyl)phenyl]-2(5H)-furanone;
3-(3-cyanophenyl)-4-[3,6-difluoro-4-(methylsulfonyl)phenyl]-2(5H)-furanone;
3-(4-cyanophenyl)-4-[3,6-difluoro-4-(methylsulfonyl)phenyl]-2(5H)-furanone;
3-(3-trifluoromethylphenyl)-4-[3,6-difluoro-4-(methylsulfonyl)phenyl]-2(5H)-furanone;
3-(4-trifluoromethylphenyl)-4-[3,6-difluoro-4-(methylsulfonyl)phenyl]-2(5H)-furanone;
3-(3-trifluoromethoxyphenyl)-4-[3,6-difluoro-4-(methylsulfonyl)phenyl]-2(5H)-furanone;
3-(4-trifluoromethoxyphenyl)-4-[3,6-difluoro-4-(methylsulfonyl)phenyl]-2(5H)-furanone;
3-(3,4-dichlorophenyl)-4-[3,6-difluoro-4-(methylsulfonyl)phenyl]-2(5H)-furanone;
3-(3,4-dibromophenyl)-4-[3,6-difluoro-4-(methylsulfonyl)phenyl]-2(5H)-furanone;
3-(3,4-difluorophenyl)-4-[3,6-difluoro-4-(methylsulfonyl)phenyl]-2(5H)-furanone;
3-(3,5-dichlorophenyl)-4-[3,6-difluoro-4-(methylsulfonyl)phenyl]-2(5H)-furanone;
3-(3,5-dibromophenyl)-4-[3,6-difluoro-4-(methylsulfonyl)phenyl]-2(5H)-furanone;
3-(3,5-difluorophenyl)-4-[3,6-difluoro-4-(methylsulfonyl)phenyl]-2(5H)-furanone;
3-(3,4-dimethylphenyl)-4-[3,6-difluoro-4-(methylsulfonyl)phenyl]-2(5H)-furanone;
3-(3,5-dimethylphenyl)-4-[3,6-difluoro-4-(methylsulfonyl)phenyl]-2(5H)-furanone;
3-(3-methyl-4-chlorophenyl)-4-[3,6-difluoro-4(methylsulfonyl)phenyl]-2(5H)-furanone;
3-(4-methyl-3-chlorophenyl)-4-[3,6-difluoro-4-(methylsulfonyl)phenyl]-2(5H)-furanone;
3-(3-methyl-4-fluorophenyl)-4-[3,6-difluoro-4-(methylsulfonyl)phenyl]-2(5H)-furanone;

3-(4-methyl-3-fluorophenyl)-4-[3,6-difluoro-4-(methylsulfonyl) phenyl]-2 (5H)-furanone;

3-(3-methyl-4-bromophenyl)-4-[3,6-difluoro-4-(methylsulfonyl) phenyl]-2 (5H)-furanone;

3-(4-methyl-3-bromophenyl)-4-[3,6-difluoro-4-(methylsulfonyl)phenyl]-2 (5H)-furanone;

3-(3-methyl-4-trifluoromethylphenyl)-4-[3,6-difluoro-4-(methylsulfonyl) phenyl]-2 (5H)-furanone;

3-(4-methyl-3-trifluoromethylphenyl)-4-[3,6-difluoro-4-(methylsulfonyl)phenyl]-2 (5H)-furanone;

3-(3-methyl-4-trifluoromethoxyphenyl)-4-[3,6-difluoro-4-(methylsulfonyl)phenyl]-2 (5H)-furanone;

3-(4-methyl-3-trifluoromethoxyphenyl)-4-[3,6-difluoro-4-(methylsulfonyl) phenyl]-2 (5H)-furanone;

3-(3-cyano-4-methylphenyl)-4-[3,6-difluoro-4-(methylsulfonyl) phenyl]-2 (5H)-furanone;

3-(4-cyano-3-methylphenyl)-4-[3,6-difluoro-4-(methylsulfonyl) phenyl]-2 (5H)-furanone;

3-(3-chloro-4-methoxyphenyl)-4-[3,6-difluoro-4-(methylsulfonyl)phenyl]-2 (5H)-furanone;

3-(4-chloro-3-methoxyphenyl)-4-[3,6-difluoro-4-(methylsulfonyl) phenyl]-2 (5H)-furanone;

3-(2-methylpyridin-6-yl)-4-[3,6-difluoro-4-(methylsulfonyl) phenyl]-2 (5H)-furanone;

3-(2-methylthiazol-4-yl)-4-[3,6-difluoro-4-(methylsulfonyl) phenyl]-2 (5H)-furanone;

3-(4-methylthiazol-2-yl)-4-[3,6-difluoro-4-(methylsulfonyl)phenyl]-2 (5H)-furanone;

3-(2-methylpyridin-3-yl)-4-[3,6-difluoro-4-(methylsulfonyl) phenyl]-2 (5H)-furanone;

3-(2-methylpyridin-3-yl)-4-[3,6-difluoro-4-(methylsulfonyl) phenyl]-2 (5H)-furanone;

3-(3-pyridinyl)-4-[3,6-difluoro-4-(methylsulfonyl) phenyl]-2 (5H)-furanone;

3-(5-methylpyridin-3-yl)-4-[3,6-difluoro-4-(methylsulfonyl) phenyl]-2 (5H)-furanone;

3-(2-methylpyridin-3-yl)-4-[3,6-difluoro-4-(methylsulfonyl) phenyl]-2 (5H)-furanone;

3-cyclohexyl-4-[3,6-difluoro-4-(methylsulfonyl) phenyl]-2 (5H)-furanone;

3-cyclopentyl-4-[3,6-difluoro-4-(methylsulfonyl) phenyl]-2 (5H)-furanone.

2. A compound, or a pharmaceutically-acceptable salt, tautomer or prodrug thereof, selected from the group consisting of:

2,6-difluoro-4-[2-phenylcyclopenten-1-yl]benezenesulfonamide;

2,6-difluoro-4-[2-(3-chlorophenyl)cyclopenten-1-yl]benezenesulfonamide;

2,6-difluoro-4-[2-(4-chlorophenyl)cyclopenten-1-yl]benezenesulfonamide;

2,6-difluoro-4-[2-(3-bromophenyl)cyclopenten-1-yl]benezenesulfonamide;

2,6-difluoro-4-[2-(4-bromophenyl)cyclopenten-1-yl]benezenesulfonamide;

2,6-difluoro-4-[2-(3-fluorophenyl)cyclopenten-1-yl]benezenesulfonamide;

2,6-difluoro-4-[2-(4-fluorophenyl)cyclopenten-1-yl]benezenesulfonamide;

2,6-difluoro-4-[2-(3-methylphenyl)cyclopenten-1-yl]benezenesulfonamide;

2,6-difluoro-4-[2-(4-methylphenyl)cyclopenten-1-yl]benezenesulfonamide;

2,6-difluoro-4-[2-(3-cyanophenyl)cyclopenten-1-yl]benezenesulfonamide;

2,6-difluoro-4-[2-(4-cyanophenyl)cyclopenten-1-yl]benezenesulfonamide;

2,6-difluoro-4-[2-(3-trifluoromethylphenyl)cyclopenten-1-yl]benezenesulfonamide;

2,6-difluoro-4-[2-(4-trifluoromethylphenyl)cyclopenten-1-yl]benezenesulfonamide;

2,6-difluoro-4-[2-(3-trifluoromethoxyphenyl)cyclopenten-1-yl]benezenesulfonamide;

2,6-difluoro-4-[2-(4-trifluoromethoxyphenyl)cyclopenten-1-yl]benezenesulfonamide;

2,6-difluoro-4-[2-(3,4-dichlorophenyl)cyclopenten-1-yl]benezenesulfonamide;

2,6-difluoro-4-[2-(3,4-dibromophenyl)cyclopenten-1-yl]benezenesulfonamide;

2,6-difluoro-4-[2-(3,4-difluorophenyl)cyclopenten-1-yl]benezenesulfonamide;

2,6-difluoro-4-[2-(3,5-dichlorophenyl)cyclopenten-1-yl]benezenesulfonamide;

2,6-difluoro-4-[2-(3,5-dibromophenyl)cyclopenten-1-yl]benezenesulfonamide;

2,6-difluoro-4-[2-(3,5-difluorophenyl)cyclopenten-1-yl]benezenesulfonamide;

2,6-difluoro-4-[2-(3,4-dimethylphenyl)cyclopenten-1-yl]benezenesulfonamide;

2,6-difluoro-4-[2-(3,5-dimethylphenyl)cyclopenten-1-yl]benezenesulfonamide;

2,6-difluoro-4-[2-(3-methyl-4-chlorophenyl)cyclopenten-1-yl]benezenesulfonamide;

2,6-difluoro-4-[2-(4-methyl-3-chlorophenyl)cyclopenten-1-yl]benezenesulfonamide;

2,6-difluoro-4-[2-(3-methyl-4-fluorophenyl)cyclopenten-1-yl]benezenesulfonamide;

2,6-difluoro-4-[2-(4-methyl-3-fluorophenyl)cyclopenten-1-yl]benezenesulfonamide;

2,6-difluoro-4-[2-(3-methyl-4-bromophenyl)cyclopenten-1-yl]benezenesulfonamide;

2,6-difluoro-4-[2-(4-methyl-3-bromophenyl)cyclopenten-1-yl]benezenesulfonamide;

2,6-difluoro-4-[2-(3-methyl-4-trifluoromethylphenyl)cyclopenten-1-yl]benezenesulfonamide;

2,6-difluoro-4-[2-(4-methyl-3-trifluoromethylphenyl)cyclopenten-1-yl]benezenesulfonamide;

2,6-difluoro-4-[2-(3-methyl-4-trifluoromethoxyphenyl)cyclopenten-1-yl]benezenesulfonamide;

2,6-difluoro-4-[2-(4-methyl-3-trifluoromethoxyphenyl)cyclopenten-1-yl]benezenesulfonamide;

2,6-difluoro-4-[2-(3-cyano-4-methylphenyl)cyclopenten-1-yl]benezenesulfonamide;

2,6-difluoro-4-[2-(4-cyano-3-methylphenyl)cyclopenten-1-yl]benezenesulfonamide;

2,6-difluoro-4-[2-(3-chloro-4-methoxyphenyl)cyclopenten-1-yl]benezenesulfonamide;

2,6-difluoro-4-[2-(4-chloro-3-methoxyphenyl)cyclopenten-1-yl]benezenesulfonamide;

2,6-difluoro-4-[2-(2-methylpyridin-6-yl)cyclopenten-1-yl]benezenesulfonamide;

2,6-difluoro-4-[2-(2-methylthiazol-4-yl)cyclopenten-1-yl]benezenesulfonamide;

2,6-difluoro-4-[2-(4-methylthiazol-2-yl)cyclopenten-1-yl]benezenesulfonamide;

2,6-difluoro-4-[2-(2-methylpyridin-3-yl)cyclopenten-1-yl]benezenesulfonamide;
2,6-difluoro-4-[2-(2-methylpyridin-3-yl)cyclopenten-1-yl]benezenesulfonamide;
2,6-difluoro-4-[2-(3-pyridinyl)cyclopenten-1-yl]benezenesulfonamide;
2,6-difluoro-4-[2-(5-methylpyridin-3-yl)cyclopenten-1-yl]benezenesulfonamide;
2,6-difluoro-4-[2-(2-methylpyridin-3-yl)cyclopenten-1-yl]benezenesulfonamide;
2,6-difluoro-4-[2-cyclohexylcyclopenten-1-yl]benezenesulfonamide;
2,6-difluoro-4-[2-cyclopentylcyclopenten-1-yl]benezenesulfonamide;
4-[5-phenyl-1,4-cyclopentadienyl]-2,6-difluorophenyl methyl sulfone;
4-[5-(3-chlorophenyl)-1,4-cyclopentadienyl]-2,6-difluorophenyl methyl sulfone;
4-[5-(4-chlorophenyl)-1,4-cyclopentadienyl]-2,6-difluorophenyl methyl sulfone;
4-[5-(3-bromophenyl)-1,4-cyclopentadienyl]-2,6-difluorophenyl methyl sulfone;
4-[5-(4-bromophenyl)-1,4-cyclopentadienyl]-2,6-difluorophenyl methyl sulfone;
4-[5-(3-fluorophenyl)-1,4-cyclopentadienyl]-2,6-difluorophenyl methyl sulfone;
4-[5-(4-fluorophenyl)-1,4-cyclopentadienyl]-2,6-difluorophenyl methyl sulfone;
4-[5-(3-methylphenyl)-1,4-cyclopentadienyl]-2,6-difluorophenyl methyl sulfone;
4-[5-(4-methylphenyl)-1,4-cyclopentadienyl]-2,6-difluorophenyl methyl sulfone;
4-[5-(3-cyanophenyl)-1,4-cyclopentadienyl]-2,6-difluorophenyl methyl sulfone;
4-[5-(4-cyanophenyl)-1,4-cyclopentadienyl]-2,6-difluorophenyl methyl sulfone;
4-[5-(3-trifluoromethylphenyl)-1,4-cyclopentadienyl]-2,6-difluorophenyl methyl sulfone;
4-[5-(4-trifluoromethylphenyl)-1,4-cyclopentadienyl]-2,6-di fluorophenyl methyl sulfone;
4-[5-(3-trifluoromethoxyphenyl)-1,4-cyclopentadienyl]-2,6-difluorophenyl methyl sulfone;
4-[5-(4-trifluoromethoxyphenyl)-1,4-cyclopentadienyl]-2,6-difluorophenyl methyl sulfone;
4-[5-(3,4-dichlorophenyl)-1,4-cyclopentadienyl]-2,6-difluorophenyl methyl sulfone;
4-[5-(3,4-dibromophenyl)-1,4-cyclopentadienyl]-2,6-difluorophenyl methyl sulfone;
4-[5-(3,4-difluorophenyl)-1,4-cyclopentadienyl]-2,5-difluorophenyl methyl sulfone;
4-[5-(3,5-dichlorophenyl)-1,4-cyclopentadienyl]-2,6-difluorophenyl methyl sulfone;
4-[5-(3,5-dibromophenyl)-1,4-cyclopentadienyl]-2,6-difluorophenyl methyl sulfone;
4-[5-(3,5-difluorophenyl)-1,4-cyclopentadienyl]-2,6-difluorophenyl methyl sulfone;
4-[5-(3,4-dimethylphenyl)-1,4-cyclopentadienyl]-2,6-difluorophenyl methyl sulfone;
4-[5-(3,5-dimethylphenyl)-1,4-cyclopentadienyl]-2,6-difluorophenyl methyl sulfone;
4-[5-(3-methyl-4-chlorophenyl)-1,4-cyclopentadienyl]-2,6-difluorophenyl methyl sulfone;
4-[5-(4-methyl-3-chlorophenyl)-1,4-cyclopentadienyl]-2,6-difluorophenyl methyl sulfone;
4-[5-(3-methyl-4-fluorophenyl)-1,4-cyclopentadienyl]-2,6-difluorophenyl methyl sulfone;
4-[5-(4-methyl-3-fluorophenyl)-1,4-cyclopentadienyl]-2,6-difluorophenyl methyl sulfone;
4-[5-(3-methyl-4-bromophenyl)-1,4-cyclopentadienyl]-2,6-difluorophenyl methyl sulfone;
4-[5-(4-methyl-3-bromophenyl)-1,4-cyclopentadienyl]-2,6-difluorophenyl methyl sulfone;
4-[5-(3-methyl-4-trifluoromethylphenyl)-1,4-cyclopentadienyl]-2,6-difluorophenyl methyl sulfone;
4-[5-(4-methyl-3-trifluoromethylphenyl)-1,4-cyclopentadienyl]-2,6-fluorophenyl methyl sulfone;
4-[5-(3-methyl-4-trifluoromethoxyphenyl)-1,4-cyclopentadienyl]-2,6-difluorophenyl methyl sulfone;
4-[5-(4-methyl-3-trifluoromethoxyphenyl)-1,4-cyclopentadienyl]-2,6-difluorophenyl methyl sulfone;
4-[5-(3-cyano-4-methylphenyl)-1,4-cyclopentadienyl]-2,6-difluorophenyl methyl sulfone;
4-[5-(4-cyano-3-methylphenyl)-1,4-cyclopentadienyl]-2,6-difluorophenyl methyl sulfone;
4-[5-(3-chloro-4-methoxyphenyl)-1,4-cyclopentadienyl]-2,6 difluorophenyl methyl sulfone;
4-[5-(4-chloro-3-methoxyphenyl)-1,4-cyclopentadienyl]-2,6-difluorophenyl methyl sulfone;
4-[5-(2-methylpyridin-6-yl)-1,4-cyclopentadienyl]-2,6-difluorophenyl methyl sulfone;
4-[5-(2-methylthiazol-4-yl)-1,4-cyclopentadienyl]-2,6-difluorophenyl methyl sulfone;
4-[5-(4-methylthiazol-2-yl)-1,4-cyclopentadienyl]-2,6difluorophenyl methyl sulfone;
4-[5-(2-methylpyridin-3-yl)-1,4-cyclopentadienyl]-2,6-difluorophenyl methyl sulfone;
4-[5-(2-methylpyridin-3-yl)-1,4-cyclopentadienyl]-2,6-difluorophenyl methyl sulfone;
4-[5-(3-pyridinyl)-1,4-cyclopentadienyl]-2,6-difluorophenyl methyl sulfone;
4-[5-(5-methylpyridin-3-yl)-1,4-cyclopentadienyl]-2,6-difluorophenyl methyl sulfone;
4-[5-(2-methylpyridin-3-yl)-1,4-cyclopentadienyl]-2,6-difluorophenyl methyl sulfone;
4-[5-cyclohexyl-1,4-cyclopentadienyl]-2,6-difluorophenyl methyl sulfone;
4-[5-cyclopentyl-1,4-cyclopentadienyl]-2,6-difluorophenyl methyl sulfone;
2,5-difluoro-4-[2-phenylcyclopenten-1-yl]benezenesulfonamide;
2,5-difluoro-4-[2-(3-chlorophenyl)cyclopenten-1-yl]benezenesulfonamide;
2,5-difluoro-4-[2-(4-chlorophenyl)cyclopenten-1-yl]benezenesulfonamide;
2,5-difluoro-4-[2-(3-bromophenyl)cyclopenten-1-yl]benezenesulfonamide;
2,5-difluoro-4-[2-(4-bromophenyl)cyclopenten-1-yl]benezenesulfonamide;
2,5-difluoro-4-[2-(3-fluorophenyl)cyclopenten-1-yl]benezenesulfonamide;
2,5-difluoro-4-[2-(4-fluorophenyl)cyclopenten-1-yl]benezenesulfonamide;
2,5-difluoro-4-[2-(3-methylphenyl)cyclopenten-1-yl]benezenesulfonamide;

2,5-difluoro-4-[2-(4-methylphenyl)cyclopenten-1-yl]benezenesulfonamide;
2,5-difluoro-4-[2-(3-cyanophenyl)cyclopenten-1-yl]benezenesulfonamide;
2,5-difluoro-4-[2-(4-cyanophenyl)cyclopenten-1-yl]benezenesulfonamide;
2,5-difluoro-4-[2-(3-trifluoromethylphenyl)cyclopenten-1-yl]benezenesulfonamide;
2,5-difluoro-4-[2-(4-trifluoromethylphenyl)cyclopenten-1-yl]benezenesulfonamide;
2,5-difluoro-4-[2-(3-trifluoromethoxyphenyl)cyclopenten-1-yl]benezenesulfonamide;
2,5-difluoro-4-[2-(4-trifluoromethoxyphenyl)cyclopenten-1-yl]benezenesulfonamide;
2,5-difluoro-4-[2-(3,4-dichlorophenyl)cyclopenten-1-yl]benezenesulfonamide;
2,5-difluoro-4-[2-(3,4-dibromophenyl)cyclopenten-1-yl]benezenesulfonamide;
2,5-difluoro-4-[2-(3,4-difluorophenyl)cyclopenten-1-yl]benezenesulfonamide;
2,5-difluoro-4-[2-(3,5-dichlorophenyl)cyclopenten-1-yl]benezenesulfonamide;
2,5-difluoro-4-[2-(3,5-dibromophenyl)cyclopenten-1-yl]benezenesulfonamide;
2,5-difluoro-4-[2-(3,5-difluorophenyl)cyclopenten-1-yl]benezenesulfonamide;
2,5-difluoro-4-[2-(3,4-dimethylphenyl)cyclopenten-1-yl]benezenesulfonamide;
2,5-difluoro-4-[2-(3,5-dimethylphenyl)cyclopenten-1-yl]benezenesulfonamide;
2,5-difluoro-4-[2-(3-methyl-4-chlorophenyl)cyclopenten-1-yl]benezenesulfonamide;
2,5-difluoro-4-[2-(4-methyl-3-chlorophenyl)cyclopenten-1-yl]benezenesulfonamide;
2,5-difluoro-4-[2-(3-methyl-4-fluorophenyl)cyclopenten-1-yl]benezenesulfonamide;
2,5-difluoro-4-[2-(4-methyl-3-fluorophenyl)cyclopenten-1-yl]benezenesulfonamide;
2,5-difluoro-4-[2-(3-methyl-4-bromophenyl)cyclopenten-1-yl]benezenesulfonamide;
2,5-difluoro-4-[2-(4-methyl-3-bromophenyl)cyclopenten-1-yl]benezenesulfonamide;
2,5-difluoro-4-[2-(3-methyl-4-trifluoromethylphenyl)cyclopenten-1-yl]benezenesulfonamide;
2,5-difluoro-4-[2-(4-methyl-3-trifluoromethylphenyl)cyclopenten-1-yl]benezenesulfonamide;
2,5-difluoro-4-[2-(3-methyl-4-trifluoromethoxyphenyl)cyclopenten-1-yl]benezenesulfonamide;
2,5-difluoro-4-[2-(4-methyl-3-trifluoromethoxyphenyl)cyclopenten-1-yl]benezenesulfonamide;
2,5-difluoro-4-[2-(3-cyano-4-methylphenyl)cyclopenten-1-yl]benezenesulfonamide;
2,5-difluoro-4-[2-(4-cyano-3-methylphenyl)cyclopenten-1-yl]benezenesulfonamide;
2,5-difluoro-4-[2-(3-chloro-4-methoxyphenyl)cyclopenten-1-yl]benezenesulfonamide;
2,5-difluoro-4-[2-(4-chloro-3-methoxyphenyl)cyclopenten-1-yl]benezenesulfonamide;
2,5-difluoro-4-[2-(2-methylpyridin-G-yl)cyclopenten-1-yl]benezenesulfonamide;
2,5-difluoro-4-[2-(2-methylthiazol-4-yl)cyclopenten-1-yl]benezenesulfonamide;
2,5-difluoro-4-[2-(4-methylthiazol-2-yl)cyclopenten-1-yl]benezenesulfonamide;
2,5-difluoro-4-[2-(2-methylpyridin-3-yl)cyclopenten-1-yl]benezenesulfonamide;
2,5-difluoro-4-[2-(2-methylpyridin-3-yl)cyclopenten-1-yl]benezenesulfonamide;
2,5-difluoro-4-[2-(3-pyridinyl)cyclopenten-1—yl]benezenesulfonamide;
2,5-difluoro-4-[2-(5-methylpyridin-3-yl)cyclopenten-1-yl]benezenesulfonamide;
2,5-difluoro-4-[2-(2-methylpyridin-3-yl)cyclopenten-1-yl]benezenesulfonamide;
2,5-difluoro-4-[2-cyclohexylcyclopenten-1-yl]benezenesulfonamide;
2,5-difluoro-4-[2-cyclopentylcyclopenten-1-yl]benezenesulfonamide;
4-[5-phenyl-1,4-cyclopentadienyl]-2,5-difluorophenyl methyl sulfone;
4-[5-(3-chlorophenyl)-1,4-cyclopentadienyl]-2,5-difluorophenyl methyl sulfone;
4-[5-(4-chlorophenyl)-1,4-cyclopentadienyl]-2,5-difluorophenyl methyl sulfone;
4-[5-(3-bromophenyl)-1,4-cyclopentadienyl]-2,5-difluorophenyl methyl sulfone;
4-[5-(4-bromophenyl)-1,4-cyclopentadienyl]-2,5-difluorophenyl methyl sulfone;
4-[5-(3-fluorophenyl)-1,4-cyclopentadienyl]-2,5-difluorophenyl methyl sulfone;
4-[5-(4-fluorophenyl)-1,4-cyclopentadienyl]-2,5-difluorophenyl methyl sulfone;
4-[5-(3-methylphenyl)-1,4-cyclopentadienyl]-2,5-difluorophenyl methyl sulfone;
4-[5-(4-methylphenyl)-1,4-cyclopentadienyl]-2,5-difluorophenyl methyl sulfone;
4-[5-(3-cyanophenyl)-1,4-cyclopentadienyl]-2,5-difluorophenyl methyl sulfone;
4-[5-(4-cyanophenyl)-1,4-cyclopentadienyl]-2,5-difluorophenyl methyl sulfone;
4-[5-(3-trifluoromethylphenyl)-1,4-cyclopentadienyl]-2,5-difluorophenyl methyl sulfone;
4-[5-(4-trifluoromethylphenyl)-1,4-cyclopentadienyl]-2,5-difluorophenyl methyl sulfone;
4-[5-(3-trifluoromethoxyphenyl)-1,4-cyclopentadienyl]-2,5-difluorophenyl methyl sulfone;
4-[5-(4-trifluoromethoxyphenyl)-1,4-cyclopentadienyl]-2,5-difluorophenyl methyl sulfone;
4-[5-(3,4-dichlorophenyl)-1,4-cyclopentadienyl]-2,5-difluorophenyl methyl sulfone;
4-[5-(3,4-dibromophenyl)-1,4-cyclopentadienyl]-2,5-difluorophenyl methyl sulfone;
4-[5-(3,4-difluorophenyl)-1,4-cyclopentadienyl]-2,5-difluorophenyl methyl sulfone;
4-[5-(3,5-dichlorophenyl)-1,4-cyclopentadienyl]-2,5-difluorophenyl methyl sulfone;
4-[5-(3,5-dibromophenyl)-1,4-cyclopentadienyl]-2,5-difluorophenyl methyl sulfone;
4-[5-(3,5-difluorophenyl)-1,4-cyclopentadienyl]-2,5-difluorophenyl methyl sulfone;
4-[5-(3,4-dimethylphenyl)-1,4-cyclopentadienyl]-2,5-difluorophenyl methyl sulfone;
4-[5-(3,5-dimethylphenyl)-1,4-cyclopentadienyl]-2,5-difluorophenyl methyl sulfone;

4-[5-(3-methyl-4-chlorophenyl)-1,4-cyclopentadienyl]-2,5-difluorophenyl methyl sulfone;
4-[s-(4-methyl-3-chlorophenyl)-1,4-cyclopentadienyl]-2,5-difluorophenyl methyl sulfone;
4-[5-(3-methyl-4-fluorophenyl)-1,4-cyclopentadienyl]-2,5-difluorophenyl methyl sulfone;
4-[5-(4-methyl-3-fluorophenyl)-1,4-cyclopentadienyl]-2,5-difluorophenyl methyl sulfone;
4-[5-(3-methyl-4-bromophenyl)-1,4-cyclopentadienyl]-2,5-difluorophenyl methyl sulfone;
4-[5-(4-methyl-3-bromophenyl)-1,4-cyclopentadienyl]-2,5-difluorophenyl methyl sulfone;
4-[5-(3-methyl-4-trifluoromethylphenyl)-1,4-cyclopentadienyl]-2,5-difluorophenyl methyl sulfone;
4-[5-(4-methyl-3-trifluoromethylphenyl)-1,4-cyclopentadienyl]-2,5-difluorophenyl methyl sulfone;
4-[5-(3-methyl-4-trifluoromethoxyphenyl)-1,4-cyclopentadienyl]-2,5-difluorophenyl methyl sulfone;
4-[5-(4-methyl-3-trifluoromethoxyphenyl)-1,4-cyclopentadienyl]-2,5-difluorophenyl methyl sulfone;
4-[5-(3-cyano-4-methylphenyl)-1,4-cyclopentadienyl]2,5-difluorophenyl methyl sulfone;
4-[5-(4-cyano-3-methylphenyl)-1,4-cyclopentadienyl]-2,5-difluorophenyl methyl sulfone;
4-[5-(3-chloro-4-methoxyphenyl)-1,4-cyclopentadienyl]-2,5-difluorophenyl methyl sulfone;
4-[5-(4-chloro-3-methoxyphenyl)-1,4-cyclopentadienyl]-2,5-difluorophenyl methyl sulfone;
4-[5-(2-methylpyridin-6-yl)-1,4-cyclopentadienyl]-2,5-difluorophenyl methyl sulfone;
4-[5-(2-methylthiazol-4-yl)-1,4-cyclopentadienyl]-2,5-difluorophenyl methyl sulfone;
4-[5-(4-methylthiazol-2-yl)-1,4-cyclopentadienyl]-2,5-difluorophenyl methyl sulfone;
4-[5-(2-methylpyridin-3-yl)-1,4-cyclopentadienyl]-2,5-difluorophenyl methyl sulfone;
4-[5-(2-methylpyridin-3-yl)-1,4-cyclopentadienyl]-2,5-difluorophenyl methyl sulfone;
4-[5-(3-pyridinyl)-1,4-cyclopentadienyl]-2,5-difluorophenyl methyl sulfone;
4-[5-(5-methylpyridin-3-yl)-1,4-cyclopentadienyl]-2,5-difluorophenyl methyl sulfone;
4-[5-(2-methylpyridin-3-yl)-1,4-cyclopentadienyl]-2,5-difluorophenyl methyl sulfone;
4-[5-cyclohexyl-1,4-cyclopentadienyl]-2,5-difluorophenyl methyl sulfone;
4-[5-cyclopentyl-1,4-cyclopentadienyl]-2,5-difluorophenyl methyl sulfone.

3. A compound, or a pharmaceutically-acceptable salt, tautomer or prodrug thereof, selected from the group consisting of:
2,6-difluoro-4-[3-phenyl-2-pyridinyl]-benezenesulfonamide;
2,6-difluoro-4-[3-(3-chlorophenyl)-2-pyridinyl]-benezenesulfonamide;
2,6-difluoro-4-[3-(4-chlorophenyl)-2-pyridinyl]-benezenesulfonamide;
2,6-difluoro-4-[3-(3-bromophenyl)-2—pyridinyl]-benezenesulfonamide;
2,6-difluoro-4-[3-(4-bromophenyl)-2-pyridinyl]-benezenesulfonamide;
2,6-difluoro-4-[3-(3-fluorophenyl)-2-pyridinyl]-benezenesulfonamide;
2,6-difluoro-4-[3-(4-fluorophenyl)-2-pyridinyl]-benezenesulfonamide;
2 G-difluoro-4-[3-(3-methylphenyl)-2-pyridinyl]-benezenesulfonamide;
2,6-difluoro-4-[3-(4-methylphenyl)-2-pyridinyl]-benezenesulfonamide;
2 G-difluoro-4-[3-(3-cyanophenyl)-2-pyridinyl]-benezenesulfonamide;
2,6-difluoro-4-[3-(4-cyanophenyl)-2-pyridinyl]-benezenesulfonamide;
2,6-difluoro-4-[3-(3-trifluoromethylphenyl)-2-pyridinyl]-benezenesulfonamide;
2,6-difluoro-4-[3-(4-trifluoromethylphenyl)-2-pyridinyl]-benezenesulfonamide;
2,6-difluoro-4-[3-(3-trifluoromethoxyphenyl)-2-pyridinyl]-benezenesulfonamide;
2,6-difluoro-4-[3-(4-trifluoromethoxyphenyl)-2-pyridinyl]-benezenesulfonamide;
2,6-difluoro-4-[3-(3,4-dichlorophenyl)-2-pyridinyl]-benezenesulfonamide;
2,6-difluoro-4-[3-(3,4-dibromophenyl)-2-pyridinyl]-benezenesulfonamide;
2,6-difluoro-4-[3-(3,4-difluorophenyl)-2-pyridinyl]-benezenesulfonamide;
2,6-difluoro-4-[3-(3,5-dichlorophenyl)-2-pyridinyl]-benezenesulfonamide;
2,6-difluoro-4-[3-(3,5-dibromophenyl)-2-pyridinyl]-benezenesulfonamide;
2,6-difluoro-4-[3-(3,5-difluorophenyl)-2-pyridinyl]-benezenesulfonamide;
2,6-difluoro-4-[3-(3,4-dimethylphenyl)-2-pyridinyl]-benezenesulfonamide;
2,6-difluoro-4-[3-(3,5-dimethylphenyl)-2-pyridinyl]-benezenesulfonamide;
2,6-difluoro-4-[3-(3-methyl-4-chlorophenyl)-2-pyridinyl]-benezenesulfonamide;
2,6-difluoro-4-[3-(4-methyl-3-chlorophenyl)-2-pyridinyl]-benezenesulfonamide;
2,6-difluoro-4-[3-(3-methyl-4-fluorophenyl)-2-pyridinyl]-benezenesulfonamide;
2,6-difluoro-4-[3-(4-methyl-3-fluorophenyl)-2-pyridinyl]-benezenesulfonamide;
2,6-difluoro-4-[3-(3-methyl-4-bromophenyl)-2-pyridinyl]-benezenesulfonamide;
2,6-difluoro-4-[3-(4-methyl-3-bromophenyl)-2-pyridinyl]-benezenesulfonamide;
2,6-difluoro-4-[3-(3-methyl-4-trifluoromethylphenyl)-2-pyridinyl]-benezenesulfonamide;
2,6-difluoro-4-[3-(4-methyl-3-trifluoromethylphenyl)-2-pyridinyl]-benezenesulfonamide;
2,6-difluoro-4-[3-(3-methyl-4-trifluoromethoxyphenyl)-2-pyridinyl]-benezenesulfonamide;
2,6-difluoro-4-[3-(4-methyl-3-trifluoromethoxyphenyl)-2-pyridinyl]-benezenesulfonamide;
2,6-difluoro-4-[3-(3-cyano-4-methylphenyl)-2-pyridinyl]-benezenesulfonamide;
2,6-difluoro-4-[3-(4-cyano-3-methylphenyl)-2-pyridinyl]-benezenesulfonamide;
2,6-difluoro-4-[3-(3-chloro-4-methoxyphenyl)-2-pyridinyl]-benezenesulfonamide;
2,6-difluoro-4-[3-(4-chloro-3-methoxyphenyl)-2-pyridinyl]-benezenesulfonamide;

2,6-difluoro-4-[3-(2-methylpyridin-6-yl)-2-pyridinyl]-benezenesulfonamide;
2,6-difluoro-4-[3-(2-methylthiazol-4-yl)-2-pyridinyl]-benezenesulfonamide;
2,6-difluoro-4-[3-(4-methylthiazol-2-yl)-2-pyridinyl]-benezenesulfonamide;
2,6-difluoro-4-[3-(2-methylpyridin-3-yl)-2-pyridinyl]-benezenesulfonamide;
2,6-difluoro-4-[3-(2-methylpyridin-3-yl)-2-pyridinyl]-benezenesulfonamide;
2,6-difluoro-4-[3-(3-pyridinyl)-2-pyridinyl]-benezenesulfonamide;
2,6-difluoro-4-[3-(5-methylpyridin-3-yl)-2-pyridinyl]-benezenesulfonamide;
2,6-difluoro-4-[3-(2-methylpyridin-3-yl)-2-pyridinyl]-benezenesulfonamide;
2,6-difluoro-4-[3-cyclohexyl-2-pyridinyl]-benezenesulfonamide;
2,6-difluoro-4-[3-cyclopentyl-2-pyridinyl]-benezenesulfonamide;
2,6-difluoro-4-[3-phenyl-3-pyridinyl]-benezenesulfonamide;
2,6-difluoro-4-[3-(3-chlorophenyl)-3-pyridinyl]-benezenesulfonamide;
2,6-difluoro-4-[3-(4-chlorophenyl)-3-pyridinyl]-benezenesulfonamide;
2,6-difluoro-4-[3-(3-bromophenyl)-3-pyridinyl]-benezenesulfonamide;
2,6-difluoro-4-[3-(4-bromophenyl)-3-pyridinyl]-benezenesulfonamide;
2,6-difluoro-4-[3-(3-fluorophenyl)-3-pyridinyl]-benezenesulfonamide;
2,6-difluoro-4-[3-(4-fluorophenyl)-3-pyridinyl]]-benezenesulfonamide;
2,6-difluoro-4-[3-(3-methylphenyl)-3-pyridinyl]-benezenesulfonamide;
2,6-difluoro-4-[3-(4-methylphenyl)-3-pyridinyl]-benezenesulfonamide;
2,6-difluoro-4-[3-(3-cyanophenyl)-3-pyridinyl]-benezenesulfonamide;
2,6-difluoro-4-[3-(4-cyanophenyl)-3-pyridinyl]-benezenesulfonamide;
2,6-difluoro-4-[3-(3-trifluoromethylphenyl)-3-pyridinyl]-benezenesulfonamide;
2,6-difluoro-4-[3-(4-trifluoromethylphenyl)-3-pyridinyl]-benezenesulfonamide;
2,6-difluoro-4-[3-(3-trifluoromethoxyphenyl)-3-pyridinyl]-benezenesulfonamide;
2,6-difluoro-4-[3-(4-trifluoromethoxyphenyl)-3-pyridinyl]-benezenesulfonamide;
2,6-difluoro-4-[3-(3,4-dichlorophenyl)-3-pyridinyl]-benezensulfonamide;
2,6-difluoro-4-[3-(3,4-dibromophenyl)-3-pyridinyl]-benezenesulfonamide;
2,6-difluoro-4-[3-(3,4-difluorophenyl)-3-pyridinyl]-benezenesulfonamide;
2,6-difluoro-4-[3-(3,5-dichlorophenyl)-3-pyridinyl]-benezenesulfonamide;
2,6-difluoro-4-[3-(3,5-dibromophenyl)-3-pyridinyl]-benezenesulfonamide;
2,6-difluoro-4-[3-(3,5-difluorophenyl)-3-pyridinyl]-benezenesulfonamide;
2,6-difluoro-4-[3-(3,4-dimethylphenyl)-3-pyridinyl]-benezenesulfonamide;
2,6-difluoro-4-[3-(3,5-dimethylphenyl)-3-pyridinyl]-benezenesulfonamide;
2,6-difluoro-4-[3-(3-methyl-4-chlorophenyl)-3-pyridinyl]-benezenesulfonamide;
2,6-difluoro-4-[3-(4-methyl-3-chlorophenyl)-3-pyridinyl]-benezenesulfonamide;
2,6-difluoro-4-[3-(3-methyl-4-fluorophenyl)-3-pyridinyl]-benezenesulfonamide;
2,6-difluoro-4-[3-(4-methyl-3-fluorophenyl)-3-pyridinyl]-benezenesulfonamide;
2,6-difluoro-4-[3-(3-methyl-4-bromophenyl)-3-pyridinyl]-benezenesulfonamide;
2,6-difluoro-4-[3-(4-methyl-3-bromophenyl)-3-pyridinyl]-benezenesulfonamide;
2,6-difluoro-4-[3-(3-methyl-4-trifluoromethylphenyl)-3-pyridinyl]-benezenesulfonamide;
2,6-difluoro-4-[3-(4-methyl-3-trifluoromethylphenyl)-3-pyridinyl]-benezenesulfonamide;
2,6-difluoro-4-[3-(3-methyl-4-trifluoromethoxyphenyl)-3-4-pyridinyl]-benezenesulfonamide;
2,6-difluoro-4-[3-(4-methyl-3-trifluoromethoxyphenyl)-3-pyridinyl]-benezenesulfonamide;
2,6-difluoro-4-[3-(3-cyano-4-methylphenyl)-3-pyridinyl]-benezenesulfonamide;
2,6-difluoro-4-[3-(4-cyano-3-methylphenyl)-3-pyridinyl]-benezenesulfonamide;
2,6-difluoro-4-[3-(3-chloro-4-methoxyphenyl)-3-pyridinyl]-benezenesulfonamide;
2,6-difluoro-4-[3-(4-chloro-3-methoxyphenyl)-3-pyridinyl]-benezenesulfonamide;
2,6-difluoro-4-[3-(2-methylpyridin-3-yl)-3-pyridinyl]-benezenesulfonamide;
2,6-difluoro-4-[3-(2-methylthiazol-4-yl)-3-pyridinyl]-benezenesulfonamide;
2,6-difluoro-4-[3-(4-methylthiazol-2-yl)-3-pyridinyl]-benezenesulfonamide;
2,6-difluoro-4-[3-(2-methylpyridin-3-yl)-3-pyridinyl]-benezenesulfonamide;
2,6-difluoro-4-[3-(2-methylpyridin-3-yl)-3-pyridinyl]-benezenesulfonamide;
2,6-difluoro-4-[3-(3-pyridinyl)-3-pyridinyl]-benezenesulfonamide;
2,6-difluoro-4-[3-(5-methylpyridin-3-yl)-3-pyridinyl]-benezenesulfonamide;
2,6-difluoro-4-[3-(2-methylpyridin-3-yl)-3-pyridinyl]-benezenesulfonamide;
2,6-difluoro-4-[3-cyclohexyl-3-pyridinyl]-benezenesulfonamide;
2,6-difluoro-4-[3-cyclopentyl-3-pyridinyl]-benezenesulfonamide;
4-[4-phenyl-3-pyridinyl]-2,6-difluorophenyl methyl sulfone;
4-[4-(3-chlorophenyl)-3-pyridinyl]-2,6-difluorophenyl methyl sulfone;
4-[4-(4-chlorophenyl)-3-pyridinyl]-2,6-difluorophenyl methyl sulfone;
4-[4-(3-bromophenyl)-3-pyridinyl]-2,6-difluorophenyl methyl sulfone;
4-[4-(4-bromophenyl)-3-pyridinyl]-2,6-difluorophenyl methyl sulfone;

4-[4-(3-fluorophenyl)-3-pyridinyl]-2,6-difluorophenyl methyl sulfone;
4-[4-(4-fluorophenyl)-3-pyridinyl]-2,6-difluorophenyl methyl sulfone;
4-[4-(3-methylphenyl)-3-pyridinyl]-2,6-difluorophenyl methyl sulfone;
4-[4-(4-methylphenyl)-3-pyridinyl]-2,6-difluorophenyl methyl sulfone;
4-[4-(3-cyanophenyl)-3-pyridinyl]-2,6-difluorophenyl methyl sulfone;
4-[4-(4-cyanophenyl)-3-pyridinyl]-2,6-difluorophenyl methyl sulfone;
4-[4-(3-trifluoromethylphenyl)-3-pyridinyl]-2,6-difluorophenyl methyl sulfone;
4-[4-(4-trifluoromethylphenyl)-3-pyridinyl]-2,6-difluorophenyl methyl sulfone;
4-[4-(3-trifluoromethoxyphenyl)-3-pyridinyl]-2,6-difluorophenyl methyl sulfone;
4-[4-(4-trifluoromethoxyphenyl)-3-pyridinyl]-2,6-difluorophenyl methyl sulfone;
4-[4-(3,4-dichlorophenyl)-3-pyridinyl]-2,6-difluorophenyl methyl sulfone;
4-[4-(3,4-dibromophenyl)-3-pyridinyl]-2,6-difluorophenyl methyl sulfone;
4-[4-(3,4-difluorophenyl)-3-pyridinyl]-2,6-difluorophenyl methyl sulfone;
4-[4-(3,5-dichlorophenyl)-3-pyridinyl]-2,6-difluorophenyl methyl sulfone;
4-[4-(3,5-dibromophenyl)-3-pyridinyl]-2,6-difluorophenyl methyl sulfone;
4-[4-(3,5-difluorophenyl)-3-pyridinyl]-2,6-difluorophenyl methyl sulfone;
4-[4-(3,4-dimethylphenyl)-3-pyridinyl]-2,6-difluorophenyl methyl sulfone;
4-[4-(3,5-dimethylphenyl)-3-pyridinyl]-2,6-difluorophenyl methyl sulfone;
4-[4-(3-methyl-4-chlorophenyl)-3-pyridinyl]-2,6-difluorophenyl methyl sulfone;
4-[4-(4-methyl-3-chlorophenyl)-3-pyridinyl]-2,6-difluorophenyl methyl sulfone;
4-[4-(3-methyl-4-fluorophenyl)-3-pyridinyl]-2,6-difluorophenyl methyl sulfone;
4-[4-(4-methyl-3-fluorophenyl)-3-pyridinyl]-2,6-difluorophenyl methyl sulfone;
4-[4-(3-methyl-4-bromophenyl)-3-pyridinyl]-2,6-difluorophenyl methyl sulfone;
4-[4-(4-methyl-3-bromophenyl)-3-pyridinyl]-2,6-difluorophenyl methyl sulfone;
4-[4-(3-methyl-4-trifluoromethylphenyl)-3-pyridinyl]-2,6-difluorophenyl methyl sulfone;
4-[4-(4-methyl-3-trifluoromethylphenyl)-3-pyridinyl]-2,6-difluorophenyl methyl sulfone;
4-[4-(3-methyl-4-trifluoromethoxyphenyl)-3-pyridinyl]-2,6-difluorophenyl methyl sulfone;
4-[4-(4-methyl-3-trifluoromethoxyphenyl)-3-pyridinyl]-2,6-difluorophenyl methyl sulfone;
4-[4-(3-cyano-4-methylphenyl)-3—pyridinyl]-2,6-difluorophenyl methyl sulfone;
4-[4-(4-cyano-3-methylphenyl)-3-pyridinyl]-2,6-difluorophenyl methyl sulfone;
4-[4-(3-chloro-4-methoxyphenyl)-3-pyridinyl]-2,6-difluorophenyl methyl sulfone;
4-[4-(4-chloro-3-methoxyphenyl)-3-pyridinyl]-2,6-difluorophenyl methyl sulfone;
4-[4-(2-methylpyridin-6-yl)-3-pyridinyl]-2,6-difluorophenyl methyl sulfone;
4-[4-(2-methylthiazol-4-yl)-3-pyridinyl]-2,6-difluorophenyl methyl sulfone;
4-[4-(4-methylthiazol-2-yl)-3-pyridinyl]-2,6-difluorophenyl methyl sulfone;
4-[4-(2-methylpyridin-3-yl)-3-pyridinyl]-2,6-difluorophenyl methyl sulfone;
4-[4-(2-methylpyridin-3-yl)-3-pyridinyl]-2,6-difluorophenyl methyl sulfone;
4-[4-(3-pyridinyl)-3-pyridinyl]-2,6-difluorophenyl methyl sulfone;
4-[4-(5-methylpyridin-3-yl)-3-pyridinyl]-2,6-difluorophenyl methyl sulfone;
4-[4-(2-methylpyridin-3-yl)-3-pyridinyl]-2,6-difluorophenyl methyl sulfone;
4-[4-cyclohexyl-3-pyridinyl]-2,6-difluorophenyl methyl sulfone;
4-[4-cyclopentyl-3-pyridinyl]-2,6-difluorophenyl methyl sulfone;
2,5-difluoro-4-[3-phenyl-2-pyridinyl]-benezenesulfonamide;
2,5-difluoro-4-[3-(3-chlorophenyl)-2-pyridinyl]-benezenesulfonamide;
2,5-difluoro-4-[3-(4-chlorophenyl)-2-pyridinyl]-benezenesulfonamide;
2,5-difluoro-4-[3-(3-bromophenyl)-2—pyridinyl]-benezenesulfonamide;
2,5-difluoro-4-[3-(4-bromophenyl)-2-pyridinyl]-benezenesulfonamide;
2,5-difluoro-4-[3-(3-fluorophenyl)-2-pyridinyl]-benezenesulfonamide;
2,5-difluoro-4-[3-(4-fluorophenyl)-2-pyridinyl]-benezenesulfonamide;
2,5-difluoro-4-[3-(3-methylphenyl)-2-pyridinyl]-benezenesulfonamide;
2,5-difluoro-4-[3-(4-methylphenyl)-2-pyridinyl]-benezenesulfonamide;
2,5-difluoro-4-[3-(3-cyanophenyl)-2-pyridinyl]-benezenesulfonamide;
2,5-difluoro-4-[3-(4-cyanophenyl)-2-pyridinyl]-benezenesulfonamide;
2,5-difluoro-4-[3-(3-trifluoromethylphenyl)-2-pyridinyl]-benezenesulfonamide;
2,5-difluoro-4-[3-(4-trifluoromethylphenyl)-2-pyridinyl]-benezenesulfonamide;
2,5-difluoro-4-[3-(3-trifluoromethoxyphenyl)-2-pyridinyl]-benezenesulfonamide;
2,5-difluoro-4-[3-(4-trifluoromethoxyphenyl)-2-pyridinyl]-benezenesulfonamide;
2,5-difluoro-4-[3-(3,4-dichlorophenyl)-2-pyridinyl]-benezenesulfonamide;
2,5-difluoro-4-[3-(3,4-dibromophenyl)-2-pyridinyl]-benezenesulfonamide;
2,5-difluoro-4-[3-(3,4-difluorophenyl)-2-pyridinyl]-benezenesulfonamide;
2,5-difluoro-4-[3-(3,5-dichlorophenyl)-2-pyridinyl]-benezenesulfonamide;
2,5-difluoro-4-[3-(3,5-dibromophenyl)-2-pyridinyl]-benezenesulfonamide;

2,5-difluoro-4-[3-(3,5-difluorophenyl)-2-pyridinyl]-benezenesulfonamide;
2,5-difluoro-4-[3-(3,4-dimethylphenyl)-2-pyridinyl]-benezenesulfonamide;
2,5-difluoro-4-[3-(3,5-dimethylphenyl)-2-pyridinyl]-benezenesulfonamide;
2,5-difluoro-4-[3-(3-methyl-4-chlorophenyl)-2-pyridinyl]-benezenesulfonamide;
2,5-difluoro-4-[3-(4-methyl-3-chlorophenyl)-2-pyridinyl]-benezenesulfonamide;
2,5-difluoro-4-[3-(3-methyl-4-fluorophenyl)-2-pyridinyl]-benezenesulfonamide;
2,5-difluoro-4-[3-(4-methyl-3-fluorophenyl)-2-pyridinyl]-benezenesulfonamide;
2,5-difluoro-4-[3-(3-methyl-4-bromophenyl)-2-pyridinyl]-benezenesulfonamide;
2,5-difluoro-4-[3-(4-methyl-3-bromophenyl)-2-pyridinyl]-benezenesulfonamide;
2,5-difluoro-4-[3-(3-methyl-4-trifluoromethylphenyl)-2-pyridinyl]-benezenesulfonamide;
2,5-difluoro-4-[3-(4-methyl-3-trifluoromethylphenyl)-2-pyridinyl]-benezenesulfonamide;
2,5-difluoro-4-[3-(3-methyl-4-trifluoromethoxyphenyl)-2-pyridinyl]-benezenesulfonamide;
2,5-difluoro-4-[3-(4-methyl-3-trifluoromethoxyphenyl)-2-pyridinyl]-benezenesulfonamide;
2,5-difluoro-4-[3-(3-cyano-4-methylphenyl)-2-pyridinyl]-benezenesulfonamide;
2,5-difluoro-4-[3-(4-cyano-3-methylphenyl)-2-pyridinyl]-benezenesulfonamide;
2,5-difluoro-4-[3-(3-chloro-4-methoxyphenyl)-2-pyridinyl]-benezenesulfonamide;
2,5-difluoro-4-[3-(4-chloro-3-methoxyphenyl)-2-pyridinyl]-benezenesulfonamide;
2,5-difluoro-4-[3-(2-methylpyridin-6-yl)-2-pyridinyl]-benezenesulfonamide;
2,5-difluoro-4-[3-(2-methylthiazol-4-yl)-2-pyridinyl]-benezenesulfonamide;
2,5-difluoro-4-[3-(4-methylthiazol-2-yl)-2-pyridinyl]-benezenesulfonamide;
2,5-difluoro-4-[3-(2-methylpyridin-3-yl)-2-pyridinyl]-benezenesulfonamide;
2,5-difluoro-4-[3-(2-methylpyridin-3-yl)-2-pyridinyl]-benezenesulfonamide;
2,5-difluoro-4-[3-(3-pyridinyl)-2-pyridinyl]-benezenesulfonamide;
2,5-difluoro-4-[3-(5-methylpyridin-3-yl)-2-pyridinyl]-benezenesulfonamide;
2,5-difluoro-4-[3-(2-methylpyridin-3-yl)-2-pyridinyl]-benezenesulfonamide;
2,5-difluoro-4-[3-cyclohexyl-2-pyridinyl]-benezenesulfonamide;
2,5-difluoro-4-[3-cyclopentyl-2-pyridinyl]-benezenesulfonamide;
2,5-difluoro-4-[3-phenyl-3-pyridinyl]-benezenesulfonamide;
2,5-difluoro-4-[3-(3-chlorophenyl)-3-pyridinyl]-benezenesulfonamide;
2,5-difluoro-4-[3-(4-chlorophenyl)-3-pyridinyl]-benezenesulfonamide;
2,5-difluoro-4-[3-(3-bromophenyl)-3-pyridinyl]-benezenesulfonamide;
2,5-difluoro-4-[3-(4-bromophenyl)-3-pyridinyl]-benezenesulfonamide;
2,5-difluoro-4-[3-(3-fluorophenyl)-3-pyridinyl]-benezenesulfonamide;
2,5-difluoro-4-[3-(4-fluorophenyl)-3-pyridinyl]-benezenesulfonamide;
2,5-difluoro-4-[3-(3-methylphenyl)-3-pyridinyl]-benezenesulfonamide;
2,5-difluoro-4-[3-(4-methylphenyl)-3-pyridinyl]-benezenesulfonamide;
2,5-difluoro-4-[3-(3-cyanophenyl)-3-pyridinyl]-benezenesulfonamide;
2,5-difluoro-4-[3-(4-cyanophenyl)-3-pyridinyl]-benezenesulfonamide;
2,5-difluoro-4-[3-(3-trifluoromethylphenyl)-3-pyridinyl]-benezenesulfonamide;
2,5-difluoro-4-[3-(4-trifluoromethylphenyl)-3-pyridinyl]-benezenesulfonamide;
2,5-difluoro-4-[3-(3-trifluoromethoxyphenyl)-3-pyridinyl]-benezenesulfonamide;
2,5-difluoro-4-[3-(4-trifluoromethoxyphenyl)-3-pyridinyl]-benezenesulfonamide;
2,5-difluoro-4-[3-(3,4-dichlorophenyl)-3-pyridinyl]-benezenesulfonamide;
2,5-difluoro-4-[3-(3,4-dibromophenyl)-3-pyridinyl]-benezenesulfonamide;
2,5-difluoro-4-[3-(3,4-difluorophenyl)-3-pyridinyl]-benezenesulfonamide;
2,5-difluoro-4-[3-(3,5-dichlorophenyl)-3-pyridinyl]-benezenesulfonamide;
2,5-difluoro-4-[3-(3,5-dibromophenyl)-3-pyridinyl]-benezenesulfonamide;
2,5-difluoro-4-[3-(3,5-difluorophenyl)-3-pyridinyl]-benezenesulfonamide;
2,5-difluoro-4-[3-(3,4-dimethylphenyl)-3-pyridinyl]-benezenesulfonamide;
2,5-difluoro-4-[3-(3,5-dimethylphenyl)-3-pyridinyl]-benezenesulfonamide;
2,5-difluoro-4-[3-(3-methyl-4-chlorophenyl)-3-pyridinyl]-benezenesulfonamide;
2,5-difluoro-4-[3-(4-methyl-3-chlorophenyl)-3-pyridinyl]-benezenesulfonamide;
2,5-difluoro-4-[3-(3-methyl-4-fluorophenyl)-3-pyridinyl]-benezenesulfonamide;
2,5-difluoro-4-[3-(4-methyl-3-fluorophenyl)-3-pyridinyl]-benezenesulfonamide;
2,5-difluoro-4-[3-(3-methyl-4-bromophenyl)-3-pyridinyl]-benezenesulfonamide;
2,5-difluoro-4-[3-(4-methyl-3-bromophenyl)-3-pyridinyl]-benezenesulfonamide;
2,5-difluoro-4-[3-(3-methyl-4-trifluoromethylphenyl)-3-pyridinyl]-benezenesulfonamide;
2,5-difluoro-4-[3-(4-methyl-3-trifluoromethylphenyl)-3-pyridinyl]-benezenesulfonamide;
2,5-difluoro-4-[3-(3-methyl-4-trifluoromethoxyphenyl)-3-pyridinyl]-benezenesulfonamide;
2,5-difluoro-4-[3-(4-methyl-3-trifluoromethoxyphenyl)-3-pyridinyl]-benezenesulfonamide;
2,5-difluoro-4-[3-(3-cyano-4-methylphenyl)-3-pyridinyl]-benezenesulfonamide;
2,5-difluoro-4-[3-(4-cyano-3-methylphenyl)-3-pyridinyl]-benezenesulfonamide;

2,5-difluoro-4-[3-(3-chloro-4-methoxyphenyl)-3-pyridinyl]-benezenesulfonamide;
2,5-difluoro-4-[3-(4-chloro-3-methoxyphenyl)-3-pyridinyl]-benezenesulfonamide;
2,5-difluoro-4-[3-(2-methylpyridin-G-yl)-3-pyridinyl]-benezenesulfonamide;
2,5-difluoro-4-[3-(2-methylthiazol-4-yl)-3-pyridinyl]-benezenesulfonamide;
2,5-difluoro-4-[3-(4-methylthiazol-2-yl)-3-pyridinyl]-benezenesulfonamide;
2,5-difluoro-4-[3-(2-methylpyridin-3-yl)-3-pyridinyl]-benezenesulfonamide;
2,5-difluoro-4-[3-(2-methylpyridin-3-yl)-3-pyridinyl]-benezenesulfonamide;
2,5-difluoro-4-[3-(3-pyridinyl)-3-pyridinyl]-benezenesulfonamide;
2,5-difluoro-4-[3-(5-methylpyridin-3-yl)-3-pyridinyl]-benezenesulfonamide;
2,5-difluoro-4-[3-(2-methylpyridin-3-yl)-3-pyridinyl]-benezenesulfonamide;
2,5-difluoro-4-[3-cyclohexyl-3-pyridinyl]-benezenesulfonamide;
2,5-difluoro-4-[3-cyclopentyl-3-pyridinyl]-benezenesulfonamide; ±7,4-[4-phenyl-3-pyridinyl]-2,5-difluorophenyl methyl sulfone;
4-[4-(3-chlorophenyl)-3-pyridinyl]-2,5-difluorophenyl methyl sulfone;
4-[4-(4-chlorophenyl)-3-pyridinyl]-2,5-difluorophenyl methyl sulfone;
4-[4-(3-bromophenyl)-3-pyridinyl]-2,5-difluorophenyl methyl sulfone;
4-[4-(4-bromophenyl)-3-pyridinyl]-2,5-difluorophenyl methyl sulfone;
4-[4-(3-fluorophenyl)-3-pyridinyl]-2,5-difluorophenyl methyl sulfone;
4-[4-(4-fluorophenyl)-3-pyridinyl]-2,5-difluorophenyl methyl sulfone;
4-[4-(3-methylphenyl)-3-pyridinyl]-2,5-difluorophenyl methyl sulfone;
4-[4-(4-methylphenyl)-3-pyridinyl]-2,5-difluorophenyl methyl sulfone;
4-[4-(3-cyanophenyl)-3-pyridinyl]-2,5-difluorophenyl methyl sulfone;
4-[4-(4-cyanophenyl)-3-pyridinyl]-2,5-difluorophenyl methyl sulfone;
4-[4-(3-trifluoromethylphenyl)-3-pyridinyl]-2,5-difluorophenyl methyl sulfone;
4-[4-(4-trifluoromethylphenyl)-3-pyridinyl]-2,5-difluorophenyl methyl sulfone;
4-[4-(3-trifluoromethoxyphenyl)-3-pyridinyl]-2,5-difluorophenyl methyl sulfone;
4-[4-(4-trifluoromethoxyphenyl)-3-pyridinyl]-2,5-difluorophenyl methyl sulfone;
4-[4-(3,4-dichlorophenyl)-3-pyridinyl]-2,5-difluorophenyl methyl sulfone;
4-[4-(3,4-dibromophenyl)-3-pyridinyl]-2,5-difluorophenyl methyl sulfone;
4-[4-(3,4-difluorophenyl)-3-pyridinyl]-2,5-difluorophenyl methyl sulfone;
4-[4-(3,5-dichlorophenyl)-3-pyridinyl]-2,5-difluorophenyl methyl sulfone;
4-[4-(3,5-dibromophenyl)-3-pyridinyl]-2,5-difluorophenyl methyl sulfone;
4-[4-(3,5-difluorophenyl)-3-pyridinyl]-2,5-difluorophenyl methyl sulfone;
4-[4-(3,4-dimethylphenyl)-3-pyridinyl]-2,5-difluorophenyl methyl sulfone;
4-[4-(3,5-dimethylphenyl)-3-pyridinyl]-2,5-difluorophenyl methyl sulfone;
4-[4-(3-methyl-4-chlorophenyl)-3-pyridinyl]-2,5-difluorophenyl methyl sulfone;
4-[4-(4-methyl-3-chlorophenyl)-3-pyridinyl]-2,5-difluorophenyl methyl sulfone;
4-[4-(3-methyl-4-fluorophenyl)-3-pyridinyl]-2,5-difluorophenyl methyl sulfone;
4-[4-(4-methyl-3-fluorophenyl)-3-pyridinyl]-2,5-difluorophenyl methyl sulfone;
4-[4-(3-methyl-4-bromophenyl)-3-pyridinyl]-2,5-difluorophenyl methyl sulfone;
4-[4-(4-methyl-3-bromophenyl)-3-pyridinyl]-2,5-difluorophenyl methyl sulfone;
4-[4-(3-methyl-4-trifluoromethylphenyl)-3-pyridinyl]-2,5-difluorophenyl methyl sulfone;
4-[4-(4-methyl-3-trifluoromethylphenyl)-3-pyridinyl]-2,5-difluorophenyl methyl sulfone;
4-[4-(3-methyl-4-trifluoromethoxyphenyl)-3-pyridinyl]-2,5-difluorophenyl methyl sulfone;
4-[4-(4-methyl-3-trifluoromethoxyphenyl)-3-pyridinyl]-2,5-difluorophenyl methyl sulfone;
4-[4-(3-cyano-4-methylphenyl)-3-pyridinyl]-2,5-difluorophenyl methyl sulfone;
4-[4-(4-cyano-3-methylphenyl)-3-pyridinyl]-2,5-difluorophenyl methyl sulfone;
4-[4-(3-chloro-4-methoxyphenyl)-3-pyridinyl]-2,5-fluorophenyl methyl sulfone;
4-[4-(4-chloro-3-methoxyphenyl)-3-pyridinyl]-2,5-difluorophenyl methyl sulfone;
4-[4-(2-methylpyridin-6-yl)-3-pyridinyl]-2,5-difluorophenyl methyl sulfone;
4-[4-(2-methylthiazol-4-yl)-3-pyridinyl]-2,5-difluorophenyl methyl sulfone;
4-[4-(4-methylthiazol-2-yl)-3-pyridinyl]-2,5-difluorophenyl methyl sulfone;
4-[4-(2-methylpyridin-3-yl)-3-pyridinyl]-2,5-difluorophenyl methyl sulfone;
4-[4-(2-methylpyridin-3-yl)-3-pyridinyl]-2,5-difluorophenyl methyl sulfone;
4-[4-(3-pyridinyl)-3-pyridinyl]-2,5-difluorophenyl methyl sulfone;
4-[4-(5-methylpyridin-3-yl)-3-pyridinyl]-2,5-difluorophenyl methyl sulfone;
4-[4-(2-methylpyridin-3-yl)-3-pyridinyl]-2,5-difluorophenyl methyl sulfone;
4-[4-cyclohexyl-3-pyridinyl]-2,5-difluorophenyl methyl sulfone;
4-[4-cyclopentyl-3-pyridinyl]-2,5-difluorophenyl methyl sulfone.

4. A compound, or a pharmaceutically-acceptable salt, tautomer or prodrug thereof, selected from the group consisting of:
5-phenyl-4-[3,5-difluoro-4-(methylsulfonyl)phenyl]-2-(difluoromethyl)-1H-imidazole;
5-(3-chlorophenyl)-4-[3,5-difluoro-4-(methylsulfonyl)phenyl]-2-(difluoromethyl)-1H-imidazole;
5-(4-chlorophenyl)-4-[3,5-difluoro-4-(methylsulfonyl)phenyl]-2-(difluoromethyl)-1H-imidazole;

5-(3-bromophenyl)-4-[3,5-difluoro-4-(methylsulfonyl)
phenyl]-2-(difluoromethyl)-1H-imidazole;

5-(4-bromophenyl)-4-[3,5-difluoro-4-(methylsulfonyl)
phenyl]-2-(difluoromethyl)-1H-imidazole;

5-(3-fluorophenyl)-4-[3,5-difluoro-4-(methylsulfonyl)
phenyl]-2-(difluoromethyl)-1H-imidazole;

5-(4-fluorophenyl)-4-[3,5-difluoro-4-(methylsulfonyl)
phenyl]-2-(difluoromethyl)-1H-imidazole;

5-(3-methylphenyl)-4-[3,5-difluoro-4-(methylsulfonyl)
phenyl]-2-(difluoromethyl)-1H-imidazole;

5-(4-methylphenyl)-4-[3,5-difluoro-4-(methylsulfonyl)
phenyl]-2-(difluoromethyl)-1H-imidazole;

5-(3-cyanophenyl)-4-[3,5-difluoro-4-(methylsulfonyl)
phenyl]-2-(difluoromethyl)-1H-imidazole;

5-(4-cyanophenyl)-4-[3,5-difluoro-4-(methylsulfonyl)
phenyl]-2-(difluoromethyl)-1H-imidazole;

5-(3-trifluoromethylphenyl)-4-[3,5-difluoro-4-
(methylsulfonyl)phenyl]-2-(difluoromethyl)-1H-
imidazole;

5-(4-trifluoromethylphenyl)-4-[3,5-difluoro-4-
(methylsulfonyl)phenyl]-2-(difluoromethyl)-1H-
imidazole;

5-(3-trifluoromethoxyphenyl)-4-[3,5-difluoro-4-
(methylsulfonyl)phenyl]-2-(difluoromethyl)-1H-
imidazole;

5-(4-trifluoromethoxyphenyl)-4-[3,5-difluoro-4-
(methylsulfonyl)phenyl]-2-(difluoromethyl)-1H-
imidazole;

5-(3,4-dichlorophenyl)-4-[3,5-difluoro-4-
(methylsulfonyl)phenyl]-2-(difluoromethyl)-1H-
imidazole; Image Page 104

5-(3,4-dibromophenyl)-4-[3,5-difluoro-4-
(methylsulfonyl)phenyl]-2-(difluoromethyl)-1H-
imidazole;

5-(3,4-difluorophenyl)-4-[3,5-difluoro-4-
(methylsulfonyl)phenyl]-2-(difluoromethyl)-1H-
imidazole;

5-(3,5-dichlorophenyl)-4-[3,5-difluoro-4-
(methylsulfonyl)phenyl]-2-(difluoromethyl)-1H-
imidazole;

5-(3,5-dibromophenyl)-4-[3,5-difluoro-4-
(methylsulfonyl)phenyl]-2-(difluoromethyl)-1H-
imidazole;

5-(3,5-difluorophenyl)-4-[3,5-difluoro-4-
(methylsulfonyl)phenyl]-2-(difluoromethyl)-1H-
imidazole;

5-(3,4-dimethylphenyl)-4-[3,5-difluoro-4-
(methylsulfonyl)phenyl]-2-(difluoromethyl)-1H-
imidazole;

7,5-(3,5-dimethylphenyl)-4-[3,5-difluoro-4-
(methylsulfonyl)phenyl]-2-(difluoromethyl)-1H-
imidazole;

5-(3-methyl-4-chlorophenyl)-4-[3,5-difluoro-4-
(methylsulfonyl)phenyl]-2-(difluoromethyl)-1H-
imidazole;

5-(4-methyl-3-chlorophenyl)-4-[3,5-difluoro-4-
(methylsulfonyl)phenyl]-2-(difluoromethyl)-1H-
imidazole;

5-(3-methyl-4-fluorophenyl)-4-[3,5-difluoro-4-
(methylsulfonyl)phenyl]-2-(difluoromethyl)-1H—
imidazole;

5-(4-methyl-3-fluorophenyl)-4-[3,5-difluoro-4-
(methylsulfonyl)phenyl]-2-(difluoromethyl)-1H-
imidazole;

5-(3-methyl-4-bromophenyl)-4-[3,5-difluoro-4-
(methylsulfonyl)phenyl]-2-(difluoromethyl)-1H-
imidazole;

5-(4-methyl-3-bromophenyl)-4-[3,5-difluoro-4-
(methylsulfonyl)phenyl]-2-(difluoromethyl)-1H-
imidazole;

5-(3-methyl-4-trifluoromethylphenyl)-4-[3,5-difluoro-4-
(methylsulfonyl)phenyl]-2-(difluoromethyl)-1H-
imidazole;

5-(4-methyl-3-trifluoromethylphenyl)-4-[3,5-difluoro-4-
(methylsulfonyl) phenyl]-2-(difluoromethyl)-1H-
imidazole;

5-(3-methyl-4-trifluoromethoxyphenyl)-4-[3,5-difluoro-
4-(methylsulfonyl)phenyl]-2-(difluoromethyl)-1H-
imidazole;

5-(4-methyl-3-trifluoromethoxyphenyl)-4-[3,5-difluoro-
4-(methylsulfonyl)phenyl]-2-(difluoromethyl)-1H-
imidazole;

5-(3-cyano-4-methylphenyl)-4-[3,5-difluoro-4-
(methylsulfonyl)phenyl]-2-(difluoromethyl)-1H-
imidazole;

5-(4-cyano-3-methylphenyl)-4-[3,5-difluoro-4-
(methylsulfonyl)phenyl]-2-(difluoromethyl)-1H-
imidazole;

5-(3-chloro-4-methoxyphenyl)-4-[3,5-difluoro-4-
(methylsulfonyl)phenyl]-2-(difluoromethyl)-1H-
imidazole;

5-(4-chloro-3-methoxyphenyl)-4-[3,5-difluoro-4-
(methylsulfonyl)phenyl]-2-(difluoromethyl)-1H-
imidazole;

5-(2-methylpyridin-G-yl)-4-[3,5-difluoro-4-
(methylsulfonyl)phenyl]-2-(difluoromethyl)-1H-
imidazole;

5-(2-methylthiazol-4-yl)-4-[3,5-difluoro-4-
(methylsulfonyl)phenyl]-2-(difluoromethyl)-1H-
imidazole;

5-(4-methylthiazol-2-yl)-4-[3,5-difluoro-4-
(methylsulfonyl)phenyl]-2-(difluoromethyl)-1H-
imidazole;

5-(2-methylpyridin-3-yl)-4-[3,5-difluoro-4-
(methylsulfonyl)phenyl]-2-(difluoromethyl)-1H-
imidazole; (met 5-(2-methylpyridin-3-yl)-4-[3,5-
difluoro-4-methylsulfonyl)phenyl]-2-(difluoromethyl)-
1H-imidazole;

5-(3-pyridinyl)-4-[3,5-difluoro-4-(methylsulfonyl)
phenyl]-2-(difluoromethyl)-1H-imidazole;

5-(5-methylpyridin-3-yl)-4-[3,5-difluoro-4-
(methylsulfonyl)phenyl]-2-(difluoromethyl)-1H-
imidazole;

5-(2-methylpyridin-3-yl)-4-[3,5-difluoro-4-
(methylsulfonyl)phenyl]-2-(difluoromethyl)-1H-
imidazole;

5-cyclohexyl-4-[3,5-difluoro-4-(methylsulfonyl)phenyl]-
2-(difluoromethyl)-1H-imidazole;

5-cyclopentyl-4-[3,5-difluoro-4-(methylsulfonyl)
phenyl]-2-(difluoromethyl)-1H-imidazole;

5-phenyl-4-[3,6-difluoro-4-(methylsulfonyl)phenyl]-2-
(difluoromethyl)-1H-imidazole;

5-phenyl-4-[3,5-difluoro-4-(methylsulfonyl)phenyl]-2-
(trifluoromethyl)-1H-imidazole;

5-(3-chlorophenyl)-4-[3,5-difluoro-4-(methylsulfonyl)
phenyl]-2-(trifluoromethyl)-1H-imidazole;

5-(4-chlorophenyl)-4-[3,5-difluoro-4-(methylsulfonyl)
phenyl]-2-(trifluoromethyl)-1H-imidazole;

5-(3-bromophenyl)-4-[3,5-difluoro-4-(methylsulfonyl)phenyl]-2-(trifluoromethyl)-1H-imidazole;

5-(4-bromophenyl)-4-[3,5-difluoro-4-(methylsulfonyl)phenyl]-2-(trifluoromethyl)-1H-imidazole;

5-(2-fluorophenyl)-4-[3,5-difluoro-4-(methylsulfonyl)phenyl]-2-(trifluoromethyl)-1H-imidazole;

5-(4-fluorophenyl)-4-[3,5-difluoro-4-(methylsulfonyl)phenyl]-2-(trifluoromethyl)-1H-imidazole;

5-(3-methylphenyl)-4-[3,5-difluoro-4-(methylsulfonyl)phenyl]-2-(trifluoromethyl)-1H-imidazole;

5-(4-methylphenyl)-4-[3,5-difluoro-4-(methylsulfonyl)phenyl]-2-(trifluoromethyl)-1H-imidazole;

5-(3-cyanophenyl)-4-[3,5-difluoro-4-(methylsulfonyl)phenyl]-2-(trifluoromethyl)-1H-imidazole;

5-(4-cyanophenyl)-4-[3,5-difluoro-4-(methylsulfonyl)phenyl]-2-(trifluoromethyl)-1H-imidazole;

5-(3-trifluoromethylphenyl)-4-[3,5-difluoro-4-(methylsulfonyl)phenyl]-2-(trifluoromethyl)-1H-imidazole;

5-(4-trifluoromethylphenyl)-4-[3,5-difluoro-4-(methylsulfonyl)phenyl]-2-(trifluoromethyl)-1H-imidazole;

5-(3-trifluoromethoxyphenyl)-4-[3,5-difluoro-4-(methylsulfonyl)phenyl]-2-(trifluoromethyl)-1H-imidazole;

5-(4-trifluoromethoxyphenyl)-4-[3,5-difluoro-4-(methylsulfonyl)phenyl]-2-(trifluoromethyl)-1H-imidazole;

5-(3,4-dichlorophenyl)-4-[3,5-difluoro-4-(methylsulfonyl)phenyl]-2-(trifluoromethyl)-1H-imidazole;

5-(3,4-dibromophenyl)-4-[3,5-difluoro-4-(methylsulfonyl)phenyl]-2-(trifluoromethyl)-1H-imidazole;

5-(3,4-difluorophenyl)-4-[3,5-difluoro-4-(methylsulfonyl)phenyl]-2-(trifluoromethyl)-1H-imidazole;

5-(3,5-dichlorophenyl)-4-[3,5-difluoro-4-(methylsulfonyl)phenyl]-2-(trifluoromethyl)-1H-imidazole;

5-(3,5-dibromophenyl)-4-[3,5-difluoro-4-(methylsulfonyl)phenyl]-2-(trifluoromethyl)-1H-imidazole;

5-(3,5-difluorophenyl)-4-[3,5-difluoro-4-(methylsulfonyl)phenyl]-2-(trifluoromethyl)-1H-imidazole;

5-(3,4-dimethylphenyl)-4-[3,5-difluoro-4-(methylsulfonyl)phenyl]-2-(trifluoromethyl)-1H-imidazole;

5-(3,5-dimethylphenyl)-4-[3,5-difluoro-4-(methylsulfonyl)phenyl]-2-(trifluoromethyl)-1H-imidazole;

5-(3-methyl-4-chlorophenyl)-4-[3,5-difluoro-4-(methylsulfonyl)phenyl]-2-(trifluoromethyl)-1H-imidazole;

5-(4-methyl-3-chlorophenyl)-4-[3,5-difluoro-4-methylsulfonyl)phenyl]-2-(trifluoromethyl)-1H-imidazole;

5-(3-methyl-4-fluorophenyl)-4-[3,5-difluoro-4-(methylsulfonyl)phenyl]-2-(trifluoromethyl)-1H-imidazole;

5-(4-methyl-2-fluorophenyl)-4-[3,5-difluoro-4-(methylsulfonyl)phenyl]-2-(trifluoromethyl)-1H-imidazole;

5-(3-methyl-4-bromophenyl)-4-[3,5-difluoro-4-(methylsulfonyl)phenyl]-2-(trifluoromethyl)-1H-imidazole;

5-(4-methyl-3-bromophenyl)-4-[3,5-difluoro-4-(methylsulfonyl)phenyl]-2-(trifluoromethyl)-1H-imidazole;

5-(3-methyl-4-trifluoromethylphenyl)-4-[3,5-difluoro-4-(methylsulfonyl)phenyl]-2-(trifluoromethyl)-1H-imidazole;

5-(4-methyl-3-trifluoromethylphenyl)-4-[3,5-difluoro-4-(methylsulfonyl)phenyl]-2-(trifluoromethyl)-1H-imidazole;

5-(3-methyl-4-trifluoromethoxyphenyl)-4-[3,5-difluoro-4-(methylsulfonyl)phenyl]-2-(trifluoromethyl)-1H-imidazole;

5-(4-methyl-3-trifluoromethoxyphenyl)-4-[3,5-difluoro-4-(methylsulfonyl)phenyl]-2-(trifluoromethyl)-1H-imidazole;

5-(3-cyano-4-methylphenyl)-4-[3,5-difluoro-4-(methylsulfonyl)phenyl]-2-(trifluoromethyl)-1H-imidazole;

5-(4-cyano-3-methylphenyl)-4-[3,5-difluoro-4-(methylsulfonyl)phenyl]-2-(trifluoromethyl)-1H-imidazole;

5-(3-chloro-4-methoxyphenyl)-4-[3,5-difluoro-4-(methylsulfonyl)phenyl]-2-(trifluoromethyl)-1H-imidazole;

5-(4-chloro-3-methoxyphenyl)-4-[3,5-difluoro-4-(methylsulfonyl)phenyl]-2-(trifluoromethyl)-1H-imidazole;

5-(2-methylpyridin-6-yl)-4-[3,5-difluoro-4-(methylsulfonyl)phenyl]-2-(trifluoromethyl)-1H-imidazole;

5-(2-methylthiazol-4-yl)-4-[3,5-difluoro-4-(methylsulfonyl)phenyl]-2-(trifluoromethyl)-1H-imidazole;

5-(4-methylthiazol-2-yl)-4-[3,5-difluoro-4-(methylsulfonyl)phenyl]-2-(trifluoromethyl)-1H-imidazole;

5-(2-methylpyridin-3-yl)-4-[3,5-difluoro-4-(methylsulfonyl)phenyl]-2-(trifluoromethyl)-1H-imidazole;

5-(2-methylpyridin-3-yl)-4-[3,5-difluoro-4-(methylsulfonyl)phenyl]-2-(trifluoromethyl)-1H-imidazole;

7,5-(3-pyridinyl)-4-[3,5-difluoro-4-(methylsulfonyl)phenyl]-2-(trifluoromethyl)-1H-imidazole;

5-(5-methylpyridin-3-yl)-4-[3,5-difluoro-4-(methylsulfonyl)phenyl]-2-(trifluoromethyl)-1H-imidazole;

5-(2-methylpyridin-3-yl)-4-[3,5-difluoro-4-(methylsulfonyl)phenyl]-2-(trifluoromethyl)-1H-imidazole;

5-cyclohexyl-4-[3,5-difluoro-4-(methylsulfonyl)phenyl]-2-(trifluoromethyl)-1H-imidazole;

5-cyclopentyl-4-[3,5-difluoro-4-(methylsulfonyl)phenyl]-2-(trifluoromethyl)-1H-imidazole;

5-(3-chlorophenyl)-4-[3,6-difluoro-4-(methylsulfonyl)phenyl]-2-(difluoromethyl)-1H-imidazole;

5-(4-chlorophenyl)-4-[3,6-difluoro-4-(methylsulfonyl)phenyl]-2-(difluoromethyl)-1H-imidazole;

5-(3-bromophenyl)-4-[3,6-difluoro-4-(methylsulfonyl)phenyl]-2-(difluoromethyl)-1H-imidazole;

5-(4-bromophenyl)-4-[3,6-difluoro-4-(methylsulfonyl)phenyl]-2-(difluoromethyl)-1H-imidazole;

5-(3-fluorophenyl)-4-[3,6-difluoro-4-(methylsulfonyl)phenyl]-2-(difluoromethyl)-1H-imidazole;

5-(4-fluorophenyl)-4-[3,6-difluoro-4-(methylsulfonyl)phenyl]-2-(difluoromethyl)-1H-imidazole;

5-(3-methylphenyl)-4-[3,6-difluoro-4-(methylsulfonyl)phenyl]-2-(difluoromethyl)-1H-imidazole;

5-(4-methylphenyl)-4-[3,6-difluoro-4-(methylsulfonyl)phenyl]-2-(difluoromethyl)-1H-imidazole;

5-(3-cyanophenyl)-4-[3,6-difluoro-4-(methylsulfonyl)phenyl]-2-(difluoromethyl)-1H-imidazole;

5-(4-cyanophenyl)-4-[3,6-difluoro-4-(methylsulfonyl)phenyl]-2-(difluoromethyl)-1H-imidazole;

5-(3-trifluoromethylphenyl)-4-[3,6-difluoro-4-(methylsulfonyl)phenyl]-2-(difluoromethyl)-1H-imidazole;

5-(4-trifluoromethylphenyl)-4-[3,6-difluoro-4-(methylsulfonyl)phenyl]-2-(difluoromethyl)-1H-imidazole;

5-(3-trifluoromethoxyphenyl)-4-[3,6-difluoro-4-(methylsulfonyl)phenyl]-2-(difluoromethyl)-1H-imidazole;

5-(4-trifluoromethoxyphenyl)-4-[3,6-difluoro-4-(methylsulfonyl)phenyl]-2-(difluoromethyl)-1H-imidazole;

5-(3,4-dichlorophenyl)-4-[3,6-difluoro-4-(methylsulfonyl)phenyl]-2-(difluoromethyl)-1H-imidazole;

5-(3,4-dibromophenyl)-4-[3,6-difluoro-4-(methylsulfonyl)phenyl]-2-(difluoromethyl)-1H-imidazole;

5-(3,4-difluorophenyl)-4-[3,6-difluoro-4-(methylsulfonyl)phenyl]-2-(difluoromethyl)-1H-imidazole;

5-(3,5-dichlorophenyl)-4-[3,6-difluoro-4-(methylsulfonyl)phenyl]-2-(difluoromethyl)-1H-imidazole;

5-(3,5-dibromophenyl)-4-[3,6-difluoro-4-(methylsulfonyl)phenyl]-2-(difluoromethyl)-1H-imidazole;

5-(3,5-difluorophenyl)-4-[3,6-difluoro-4-(methylsulfonyl)phenyl]-2-(difluoromethyl)-1H-imidazole;

5-(3,4-dimethylphenyl)-4-[3,6-difluoro-4-(methylsulfonyl)phenyl]-2-(difluoromethyl)-1H-imidazole;

5-(3,5-dimethylphenyl)-4-[3,6-difluoro-4-(methylsulfonyl)phenyl]-2-(difluoromethyl)-1H-imidazole;

5-(3-methyl-4-chlorophenyl)-4-[3,6-difluoro-4-(methylsulfonyl)phenyl]-2-(difluoromethyl)-1H-imidazole;

5-(4-methyl-3-chlorophenyl)-4-[3,6-difluoro-4-(methylsulfonyl)phenyl]-2-(difluoromethyl)-1H-imidazole;

5-(3-methyl-4-fluorophenyl)-4-[3,6-difluoro-4-(methylsulfonyl)phenyl]-2-(difluoromethyl)-1H-imidazole;

5-(4-methyl-3-fluorophenyl)-4-[3,6-difluoro-4-(methylsulfonyl)phenyl]-2-(difluoromethyl)-1H-imidazole;

5-(3-methyl-4-bromophenyl)-4-[3,6-difluoro-4-(methylsulfonyl)phenyl]-2-(difluoromethyl)-1H-imidazole;

5-(4-methyl-3-bromophenyl)-4-[3,6-difluoro-4-(methylsulfonyl)phenyl]-2-(difluoromethyl)-1H-imidazole;

5-(3-methyl-4-trifluoromethylphenyl)-4-[3,6-difluoro-4-methylsulfonyl)phenyl]-2-(difluoromethyl)-1H-imidazole;

5-(4-methyl-3-trifluoromethylphenyl)-4-[3,6-difluoro-4-(methylsulfonyl)phenyl]-2-(difluoromethyl)-1H-imidazole;

5-(3-methyl-4-trifluoromethoxyphenyl)-4-[3,6-difluoro-4-(methylsulfonyl)phenyl]-2-(difluoromethyl)-1H-imidazole;

5-(4-methyl-3-trifluoromethoxyphenyl)-4-[3,6-difluoro-4-(methylsulfonyl)phenyl]-2-(difluoromethyl)-1H-imidazole;

5-(3-cyano-4-methylphenyl)-4-[3,6-difluoro-4-(methylsulfonyl)phenyl]-2-(difluoromethyl)-1H-imidazole;

5-(4-cyano-3-methylphenyl)-4-[3,6-difluoro-4-(methylsulfonyl)phenyl]-2-(difluoromethyl)-1H-imidazole;

5-(3-chloro-4-methoxyphenyl)-4-[3,6-difluoro-4-(methylsulfonyl)phenyl]-2-(difluoromethyl)-1H-imidazole;

5-(4-chloro-3-methoxyphenyl)-4-[3,6-difluoro-4-(methylsulfonyl)phenyl]-2-(difluoromethyl)-1H-imidazole;

5-(2-methylpyridin6-yl)-4-[3,6-difluoro-4-(methylsulfonyl)phenyl]-2-(difluoromethyl)-1H-imidazole;

5-(2-methylthiazol-4-yl)-4-[3,6-difluoro-4-(methylsulfonyl)phenyl]-2-(difluoromethyl)-1H-imidazole;

5-(4-methylthiazol-2-yl)-4-[3,6-difluoro-4-(methylsulfonyl)phenyl]-2-(difluoromethyl)-1H-imidazole;

5-(2-methylpyridin-3-yl)-4-[3,6-difluoro-4-(methylsulfonyl)phenyl]-2-(difluoromethyl)-1H-imidazole;

5-(2-methylpyridin-3-yl)-4-[3,6-difluoro-4-(methylsulfonyl)phenyl]-2-(difluoromethyl)-1H-imidazole;

5-(3-pyridinyl)-4-[3,6-difluoro-4-(methylsulfonyl)phenyl]-2-(difluoromethyl)-1H-imidazole;

5-(5-methylpyridin-3-yl)-4-[3,6-difluoro-4-(methylsulfonyl)phenyl]-2-(difluoromethyl)-1H-imidazole;

5-(2-methylpyridin-3-yl)-4-[3,6-difluoro-4-(methylsulfonyl)phenyl]-2-(difluoromethyl)-1H-imidazole;

5-cyclohexyl-4-[3,6-difluoro-4-(methylsulfonyl)phenyl]-2-(difluoromethyl)-1H-imidazole;

5-cyclopentyl-4-[3,6-difluoro-4-(methylsulfonyl)phenyl]-2-(difluoromethyl)-1H-imidazole;

5-phenyl-4-[3,6-difluoro-4-(methylsulfonyl)phenyl]-2-(trifluoromethyl)-1H-imidazole;

5-(3-chlorophenyl)-4-[3,6-difluoro-4-methylsulfonyl)phenyl]-2-(trifluoromethyl)-1H-imidazole; chlorophenyl)-4-[3,6-difluoro-4-(methylsulfonyl)phenyl]-2-(trifluoromethyl)-1H-imidazole;

5-(3-bromophenyl)-4-[3,6-difluoro-4-(methylsulfonyl)phenyl]-2-(trifluoromethyl)-1H-imidazole;

5-(4-bromophenyl)-4-[3,6-difluoro-4-(methylsulfonyl)phenyl]-2-(trifluoromethyl)-1H-imidazole;

5-(2-fluorophenyl)-4-[3,6-difluoro-4-(methylsulfonyl)phenyl]-2-(trifluoromethyl)-1H-imidazole;

5-(4-fluorophenyl)-4-[3,6-difluoro-4-(methylsulfonyl)phenyl]-2-(trifluoromethyl)-1H-imidazole;

5-(3-methylphenyl)-4-[3,6-difluoro-4-(methylsulfonyl)phenyl]-2-(trifluoromethyl)-1H-imidazole;

5-(4-methylphenyl)-4-[3,6-difluoro-4-(methylsulfonyl)phenyl]-2-(trifluoromethyl)-1H-imidazole;

5-(3-cyanophenyl)-4-[3,6-difluoro-4-(methylsulfonyl)phenyl]-2-(trifluoromethyl)-1H-imidazole;

5-(4-cyanophenyl)-4-[3,6-difluoro-4-(methylsulfonyl)phenyl]-2-(trifluoromethyl)-1H-imidazole;

5-(3-trifluoromethylphenyl)-4-[3,6-difluoro-4-(methylsulfonyl)phenyl]-2-(trifluoromethyl)-1H-imidazole;

5-(4-trifluoromethylphenyl)-4-[3,6-difluoro-4-(methylsulfonyl)phenyl]-2-(trifluoromethyl)-1H-imidazole;

5-(3-trifluoromethoxyphenyl)-4-[3,6-difluoro-4-(methylsulfonyl)phenyl]-2-(trifluoromethyl)-1H-imidazole;

5-(4-trifluoromethoxyphenyl)-4-[3,6-difluoro-4-(methylsulfonyl)phenyl]-2-(trifluoromethyl)-1H-imidazole;

5-(3,4-dichlorophenyl)-4-[3,6-difluoro-4-(methylsulfonyl)phenyl]-2-(trifluoromethyl)-1H-imidazole;

5-(3,4-dibromophenyl)-4-[3,6-difluoro-4-(methylsulfonyl)phenyl]-2-(trifluoromethyl)-1H-imidazole;

5-(3,4-difluorophenyl)-4-[3,6-difluoro-4-(methylsulfonyl)phenyl]-2-(trifluoromethyl)-1H-imidazole;

5-(3,5-dichlorophenyl)-4-[3,6-difluoro-4-(methylsulfonyl)phenyl]-2-(trifluoromethyl)-1H-imidazole;

5-(3,5-dibromophenyl)-4-[3,6-difluoro-4-(methylsulfonyl)phenyl]-2-(trifluoromethyl)-1H-imidazole;

5-(3,6-difluorophenyl)-4-[3,6-difluoro-4-(methylsulfonyl)phenyl]-2-(trifluoromethyl)-1H-imidazole;

5-(3,4-dimethylphenyl)-4-[3,6-difluoro-4-(methylsulfonyl)phenyl]-2-(trifluoromethyl)-1H-imidazole;

5-(3,5-dimethylphenyl)-4-[3,6-difluoro-4-(methylsulfonyl)phenyl]-2-(trifluoromethyl)-1H-imidazole;

5-(3-methyl-4-chlorophenyl)-4-[3,6-difluoro-4-(methylsulfonyl)phenyl]-2-(trifluoromethyl)-1H-imidazole;

5-(4-methyl-3-chlorophenyl)-4-[3,6-difluoro-4-(methylsulfonyl)phenyl]-2-(trifluoromethyl)-1H-imidazole;

5-(3-methyl-4-fluorophenyl)-4-[3,6-difluoro-4-(methylsulfonyl)phenyl]-2-(trifluoromethyl)-1H-imidazole;

5-(4-methyl-2-fluorophenyl)-4-[3,6-difluoro-4-(methylsulfonyl)phenyl]-2-(trifluoromethyl)-1H-imidazole;

5-(3-methyl-4-bromophenyl)-4-[3,6-difluoro-4-(methylsulfonyl)phenyl]-2-(trifluoromethyl)-1H-imidazole;

5-(4-methyl-3-bromophenyl)-4-[3,6-difluoro-4-(methylsulfonyl)phenyl]-2-(trifluoromethyl)-1H-imidazole;

5-(3-methyl-4-trifluoromethylphenyl)-4-[3,6-difluoro-4-(methylsulfonyl)phenyl]-2-(trifluoromethyl)-1H-imidazole;

5-(4-methyl-3-trifluoromethylphenyl)-4-[3,6-difluoro-4-(methylsulfonyl)phenyl]-2-(trifluoromethyl)-1H-imidazole;

5-(3-methyl-4-trifluoromethoxyphenyl)-4-[3,6-difluoro-4-(methylsulfonyl)phenyl]-2-(trifluoromethyl)-1H-imidazole;

5-(4-methyl-3-trifluoromethoxyphenyl)-4-[3,6-difluoro-4-(methylsulfonyl)phenyl]-2-(trifluoromethyl)-1H-imidazole; cyano-4-methylphenyl)-4-[3,6-difluoro-4-methylsulfonyl)phenyl]-2-(trifluoromethyl)-1H-imidazole;

5-(4-cyano-3-methylphenyl)-4-[3,6-difluoro-4-(methylsulfonyl)phenyl]-2-(trifluoromethyl)-1H-imidazole;

5-(3-chloro-4-methoxyphenyl)-4-113,6-difluoro-4-(methylsulfonyl)phenyl]-2-(trifluoromethyl)-1H-imidazole;

5-(4-chloro-3-methoxyphenyl)-4-[3,6-difluoro-4-(methylsulfonyl)phenyl]-2-(trifluoromethyl)-1H-imidazole;

5-(2-methylpyridin-6-yl)-4-[3,6-difluoro-4-(methylsulfonyl)phenyl]-2-(trifluoromethyl)-1H-imidazole;

5-(2-methylthiazol-4-yl)-4-[3,6-difluoro-4-(methylsulfonyl)phenyl]-2-(trifluoromethyl)-1H-imidazole;

5-(4-methylthiazol-2-yl)-4-[3,6-difluoro-4-(methylsulfonyl)phenyl]-2-(trifluoromethyl)-1H-imidazole;

5-(2-methylpyridin-3-yl)-4-[3,6-difluoro-4 (methylsulfonyl)phenyl]-2-(trifluoromethyl)-1H-imidazole;

5-(2-methylpyridin-3-yl)-4-[3,6-difluoro-4-(methylsulfonyl)phenyl]-2-(trifluoromethyl)-1H-imidazole;

5-(3-pyridinyl)-4-[3,6-difluoro-4-(methylsulfonyl)phenyl]-2-(trifluoromethyl)-1H-imidazole;

5-(5-methylpyridin-3-yl)-4-[3,6-difluoro-4-(methylsulfonyl)phenyl]-2-(trifluoromethyl)-1H-imidazole;

5-(2-methylpyridin-3-yl)-4-[3,6-difluoro-4-(methylsulfonyl)phenyl]-2-(trifluoromethyl)-1H-imidazole;

5-cyclohexyl-4-[3,6-difluoro-4-(methylsulfonyl)phenyl]-2-(trifluoromethyl)-1H-imidazole;

5-cyclopentyl-4-[3,6-difluoro-4-(methylsulfonyl)phenyl]-2-(trifluoromethyl)-1H-imidazole.

5. A compound, or a pharmaceutically-acceptable salt, tautomer or prodrug thereof, selected from the group consisting of:

3-phenyl-4-[3,5-difluoro-4-(methylsulfonyl)phenyl]-1,3-oxazol-2 (3H)-one;

3-(3-chlorophenyl)-4-[3,5-difluoro-4-(methylsulfonyl)phenyl]-1,3-oxazol-2 (3H)-one;

3-(4-chlorophenyl)-4-[3,5-difluoro-4-(methylsulfonyl)phenyl]-1,3-oxazol-2 (3H)-one;

3-(3-bromophenyl)-4-[3,5-difluoro-4-(methylsulfonyl)phenyl]-1,3-oxazol-2 (3H)-one;

3-(4-bromophenyl)-4-[3,5-difluoro-4-(methylsulfonyl)
phenyl]-1,3-oxazol-2 (3H)-one;

3-(3-fluorophenyl)-4-[3,5-difluoro-4-(methylsulfonyl)
phenyl]-1,3-oxazol-2 (3H)-one;

3-(4-fluorophenyl)-4-[3,5-difluoro-4-(methylsulfonyl)
phenyl]-1,3-oxazol-2 (3H)-one;

3-(3-methylphenyl)-4-[3,5-difluoro-4-(methylsulfonyl)
phenyl]-1,3-oxazol-2 (3H)-one;

3-(4-methylphenyl)-4-[3,5-difluoro-4-(methylsulfonyl)
phenyl]-1,3-oxazol-2 (3H)-one;

3-(3-cyanophenyl)-4-[3,5-difluoro-4-(methylsulfonyl)
phenyl]-1,3-oxazol-2 (3H)-one;

3-(4-cyanophenyl)-4-[3,5-difluoro-4-(methylsulfonyl)
phenyl]-1,3-oxazol-2 (3H)-one;

3-(3-trifluoromethylphenyl)-4-[3,5-difluoro-4-
(methylsulfonyl)phenyl]-1,3-oxazol-2 (3H)-one;

3-(4-trifluoromethylphenyl)-4-[3,5-difluoro-4-
(methylsulfonyl)phenyl]-1,3-oxazol-2 (3H)-one;

3-(3-trifluoromethoxyphenyl)-4-[3,5-difluoro-4-
(methylsulfonyl)phenyl]-1,3-oxazol-2 (3H)-one;

3-(4-trifluoromethoxyphenyl)-4-[3,5-difluoro-4-
(methylsulfonyl)phenyl]-1,3-oxazol-2 (3H)-one;

3-(3,4-dichlorophenyl)-4-[3,5-difluoro-4-
(methylsulfonyl)phenyl]-1,3-oxazol-2 (3H)-one;

3-(3,4-dibromophenyl)-4-[3,5-difluoro-4-
(methylsulfonyl)phenyl]-1,3-oxazol-2 (3H)-one;

3-(3,4-difluorophenyl)-4-[3,5-difluoro-4-
(methylsulfonyl)phenyl]-1,3-oxazol-2 (3H)-one;

3-(3,5-dichlorophenyl)-4-[3,5-difluoro-4-
(methylsulfonyl)phenyl]-1,3-oxazol-2(3H-one;

3-(3,5-dibromophenyl)-4-[3,5-difluoro-4-
(methylsulfonyl)phenyl]-1,3-oxazol-2 (3H)-one;

3-(3,5-difluorophenyl)-4-[3,5-difluoro-4-
(methylsulfonyl)phenyl]-1,3-oxazol-2 (3H)-one;

3-(3,4-dimethylphenyl)-4-[3,5-difluoro-4-
(methylsulfonyl)phenyl]-1,3-oxazol-2 (3H)-one;

3-(3,5-dimethylphenyl)-4-[3,5-difluoro-4-
(methylsulfonyl)phenyl]-1,3-oxazol-2 (3H)-one;

3-(3-methyl-4-chlorophenyl)-4-[3,5-difluoro-4-
(methylsulfonyl)phenyl]-1,3-oxazol-2 (3H)-one;

3-(4-methyl-3-chlorophenyl)-4-[3,5-difluoro-4
(methylsulfonyl)phenyl]-1,3-oxazol-2 (3H)-one;

3-(3-methyl-4-fluorophenyl)-4-[3,5-difluoro-4
(methylsulfonyl)phenyl]-1,3-oxazol-2 (3H)-one;

3-(4-methyl-3-fluorophenyl)-4-[3,5-difluoro-4-
(methylsulfonyl)phenyl]-1,3-oxazol-2 (3H)-one;

3-(3-methyl-4-bromophenyl)-4-[3,5-difluoro-4-
(methylsulfonyl)phenyl]-1,3-oxazol-2 (3H)-one;

3-(4-methyl-3-bromophenyl)-4-[3,5-difluoro-4-
(methylsulfonyl)phenyl]-1,3-oxazol-2 (3H)-one;

3-(3-methyl-4-trifluoromethylphenyl)-4-[3,5-difluoro-4-
(methylsulfonyl)phenyl]-1,3-oxazol-2 (3H)-one;

3-(4-methyl-3-trifluoromethylphenyl)-4-[3,5-difluoro-4-
(methylsulfonyl)phenyl]-1,3-oxazol-2 (3H)-one;

3-(3-methyl-4-trifluoromethoxyphenyl)-4-[3,5-difluoro-
4-(methylsulfonyl)phenyl]-1,3-oxazol-2 (3H)-one;

3-(4-methyl-3-trifluoromethoxyphenyl)-4-[3,5-difluoro-
4-(methylsulfonyl)phenyl]-1,3-oxazol-2 (3H)-one;

3-(3-cyano-4-methylphenyl)-4-[3,5-difluoro-4-
(methylsulfonyl)phenyl]-1,3-oxazol-2 (3H)-one;

3-(4-cyano-3-methylphenyl)-4-[3,5-difluoro-4-
(methylsulfonyl)phenyl]-1,3-oxazol-2 (3H)-one;

3-(3-chloro-4-methoxyphenyl)-4-[3,5-difluoro-4-
(methylsulfonyl)phenyl]-1,3-oxazol-2 (3H)-one;

7,3-(4-chloro-3-methoxyphenyl)-4-[3,5-difluoro-4-
(methylsulfonyl)phenyl]-1,3-oxazol-2 (3H)-one;

3-(2-methylpyridin-6-yl)-4-[3,5-difluoro-4-
(methylsulfonyl)phenyl]-1,3-oxazol-2 (3H)-one;

3-(2-methylthiazol-4-yl)-4-[3,5-difluoro-4-
(methylsulfonyl)phenyl]-1,3-oxazol-2 (3H)-one;

3-(4-methylthiazol-2-yl)-4-[3,5-difluoro-4-
(methylsulfonyl)phenyl]-1,3-oxazol-2 (3H)-one;

3-(2-methylpyridin-3-yl)-4-[3,5-difluoro-4-
(methylsulfonyl)phenyl]-1,3-oxazol-2 (3H)-one;

3-(2-methylpyridin-3-yl)-4-[3,5-difluoro-4-
(methylsulfonyl)phenyl]-1,3-oxazol-2 (3H)-one;

3-(3-pyridinyl)-4-[3,5-difluoro-4-(methylsulfonyl)
phenyl]-1,3-oxazol-2 (3H)-one;

3-(5-methylpyridin-3-yl)-4-[3,5-difluoro-4-
(methylsulfonyl)phenyl]-1,3-oxazol-2 (3H)-one;

3-(2-methylpyridin-3-yl)-4-[3,5-difluoro-4-
(methylsulfonyl)phenyl]-1,3-oxazol-2 (3H)-one;

3-cyclohexyl-4-[3,5-difluoro-4-(methylsulfonyl)phenyl]-
1,3-oxazol-2 (3H)-one;

3-cyclopentyl-4-[3,5-difluoro-4-(methylsulfonyl)
phenyl]-1,3-oxazol-2 (3H)-one;

2,6-difluoro-4-[3,5-oxo-2,3-dihydro-1,3-oxazol-4-yl]
benzenesulfonamide;

2,6-difluoro-4-[3-(3-chlorophenyl)-2-oxo-2,3-dihydro-1,
3-oxazol-4-yl]benzenesulfonamide;

2,6-difluoro-4-[3-(4-chlorophenyl)-2-oxo-2,3-dihydro-1,
3-oxazol-4-yl]benzenesulfonamide;

2,6-difluoro-4-[3-(3-bromophenyl)-2-oxo-2,3-dihydro-1,
3-oxazol-4-yl]benzenesulfonamide;

2,6-difluoro-4-[3-(4-bromophenyl)-2-oxo-2,3-dihydro-1,
3-oxazol-4-yl]benzenesulfonamide;

2,6-difluoro-4-[3-(3-fluorophenyl)-2-oxo-2,3-dihydro-1,
3-oxazol-4-yl]benzenesulfonamide;

2,6-difluoro-4-[3-(4-fluorophenyl)-2-oxo-2,3-dihydro-1,
3-oxazol-4-yl]benzenesulfonamide;

2,6-difluoro-4-[3-(3-methylphenyl)-4-[3-fluoro-4-
(methylsulfonyl)phenyl]-1,3-oxazol-2 (3H)-one;

2,6-difluoro-4-[3-(4-methylphenyl)-2-oxo-2,3-dihydro-1,
3-oxazol-4-yl]benzenesulfonamide;

2,6-difluoro-4-[3-(3-cyanophenyl)-2-oxo-2,3-dihydro-1,
3-oxazol-4-yl]benzenesulfonamide;

2,6-difluoro-4-[3-(4-cyanophenyl)-2-oxo-2,3-dihydro-1,
3-oxazol-4-yl]benzenesulfonamide;

2,6-difluoro-4-[3-(3-trifluoromethylphenyl)-2-oxo-2,3-
dihydro-1,3-oxazol-4-yl]benzenesulfonamide;

2,6-difluoro-4-[3-(4-trifluoromethylphenyl)-2-oxo-2,3-
dihydro-1,3-oxazol-4-yl]benzenesulfonamide;

2,6-difluoro-4-[3-(3-trifluoromethoxyphenyl)-2-oxo-2,3-
dihydro-1,3-oxazol-4-yl]benzenesulfonamide;

2,6-difluoro-4-[3-(4-trifluoromethoxyphenyl)-2-oxo-2,3-
dihydro-1,3-oxazol-4-yl]benzenesulfonamide;

2,3-difluoro-4-[3-(3,4-dichlorophenyl)-2-oxo-2,3-
dihydro-1,3-oxazol-4-yl]benzenesulfonamide;

2,6-difluoro-4-[3-(3,4-dibromophenyl)-2-oxo-2,3-
dihydro-1,3-oxazol-4-yl]benzenesulfonamide;

2,6-difluoro-4-[3-(3,4-difluorophenyl)-2-oxo-2,3-
dihydro-1,3-oxazol-4-yl]benzenesulfonamide;

2,6-difluoro-4-[3-(3,5-dichlorophenyl)-2-oxo-2,3-
dihydro-1,3-oxazol-4-yl]benzenesulfonamide;

2,6-difluoro-4-[3-(3,5-dibromophenyl)-2-oxo-2,3-dihydro-1,3-oxazol-4-yl]benzenesulfonamide;
2,6-difluoro-4-[3-(3,5-difluorophenyl)-2-oxo-2,3-dihydro-1,3-oxazol-4-yl]benzenesulfonamide;
2,3-difluoro-4-[3-(3,4-dimethylphenyl)-2-oxo-2,3-dihydro-1,3-oxazol-4-yl]benzenesulfonamide;
2,6-difluoro-4-[3-(3,5-dimethylphenyl)-2-oxo-2,3-dihydro-3-oxazol-4-yl]benzenesulfonamide;
2,3-difluoro-4-[3-(3-methyl-4-chlorophenyl)-2-oxo-2,3-dihydro-1,3-oxazol-4-yl]benzenesulfonamide;
2,6-difluoro-4-[3-(4-methyl-3-chlorophenyl)-2-oxo-2,3-dihydro-1,3-oxazol-4-yl]benzenesulfonamide;
2,6-difluoro-4-[3-(3-methyl-4-fluorophenyl)-2-oxo-2,3-dihydro-1,3-oxazol-4-yl]benzenesulfonamide;
2,6-difluoro-4-[3-(4-methyl-3-fluorophenyl)-2-oxo-2,3-dihydro-1,3-oxazol-4-yl]benzenesulfonamide;
2,6-difluoro-4-[3-(3-methyl-4-bromophenyl)-2-oxo-2,3-dihydro-1,3-oxazol-4-yl]benzenesulfonamide;
2,6-difluoro-4-[3-(4-methyl-3-bromophenyl)-2-oxo-2,3-dihydro-1,3-oxazol-4-yl]benzenesulfonamide;
2,6-difluoro-4-[3-(3-methyl-4-trifluoromethylphenyl)-2-oxo-2,3-dihydro-1,3-oxazol-4-yl]benzenesulfonamide;
2,6-difluoro-4-[3-(4-methyl-3-trifluoromethylphenyl)-2-oxo-2,3-dihydro-1,3-oxazol-4-yl]benzenesulfonamide;
2,6-difluoro-4-[3-(3-methyl-4-trifluoromethoxyphenyl)-2-oxo-2,3-dihydro-1,3-oxazol-4-yl]benzenesulfonamide;
2,6-difluoro-4-[3-(4-methyl-3-trifluoromethoxyphenyl)-2-oxo-2,3-dihydro-1,3-oxazol-4-yl]benzenesulfonamide;
2,6-difluoro-4-[3-(3-cyano-4-methylphenyl)-2-oxo-2,3-dihydro-1,3-oxazol-4-yl]benzenesulfonamide;
2,6-difluoro-4-[3-(4-cyano-3-methylphenyl)-2-oxo-2,3-dihydro-1,3-oxazol-4-yl]benzenesulfonamide;
2,6-difluoro-4-[3-(3-chloro-4-methoxyphenyl)-2-oxo-2,3-dihydro-1,3-oxazol-4-yl]benzenesulfonamide;
2,6-difluoro-4-[3-(4-chloro-3-methoxyphenyl)-2-oxo-2,3-dihydro-1,3-oxazol-4-yl]benzenesulfonamide;
2,6-difluoro-4-[3-(2-methylpyridin-6-yl)-2—oxo-2,3-dihydro-1,3-oxazol-4-yl]benzenesulfonamide;
2,6-difluoro-4-[3-(2-methylthiazol-4-yl)-2-oxo-2,3-dihydro-1,3-oxazol-4-yl]benzenesulfonamide;
2,6-difluoro-4-[3-(4-methylthiazol-2-yl)-2-oxo-2,3-dihydro-3-oxazol-4-yl]benzenesulfonamide;
2,6-difluoro-4-[3-(2-methylpyridin-3-yl)-2-oxo-2,3-dihydro-1,3-oxazol-4-yl]benzenesulfonamide;
2,6-difluoro-4-[3-(2-methylpyridin-3-yl)-2-oxo-2,3-dihydro-1,3-oxazol-4-yl]benzenesulfonamide;
2,6-difluoro-4-[3-(3-pyridinyl)-2-oxo-2,3-dihydro-1,3-oxazol-4-yl]benzenesulfonamide;
2,6-difluoro-4-[3-(5-methylpyridin-3-yl)-2-oxo-2,3-dihydro-1,3-oxazol-4-yl]benzenesulfonamide;
2,6-difluoro-4-[3-(2-methylpyridin-3-yl)-2-oxo-2,3-dihydro-1,3-oxazol-4-yl]benzenesulfonamide;
3-cyclohexyl-2-oxo-2,3-dihydro-1,3-oxazol-4-yl]benzenesulfonamide;
3-cyclopentyl-2-oxo-2,3-dihydro-1,3-oxazol-4-yl]benzenesulfonamide;
3-phenyl-4-[3,6-difluoro-4-(methylsulfonyl)phenyl]-1,3-oxazol-2 (3H)-one;
3-(3-chlorophenyl)-4-[3,6-difluoro-4-(methylsulfonyl)phenyl]-1,3-oxazol-2 (3H)-one;
3-(4-chlorophenyl)-4-[3,6-difluoro-4-(methylsulfonyl)phenyl]-1,3-oxazol-2 (3H)-one;
3-(3-bromophenyl)-4-[3,6-difluoro-4-(methylsulfonyl)phenyl]-1,3-oxazol-2 (3H)-one;
3-(4-bromophenyl)-4-[3,6-difluoro-4-(methylsulfonyl)phenyl]-1,3-oxazol-2 (3H)-one;
3-(3-fluorophenyl)-4-[3,6-difluoro-4-(methylsulfonyl)phenyl]-1,3-oxazol-2 (3H)-one;
3-(4-fluorophenyl)-4-[3,6-difluoro-4-(methylsulfonyl)phenyl]-1,3-oxazol-2 (3H)-one;
3-(3-methylphenyl)-4-[3,6-difluoro-4-(methylsulfonyl)phenyl]-1,3-oxazol-2 (3H)-one;
3-(4-methylphenyl)-4-[3,6-difluoro-4-(methylsulfonyl)phenyl]-1,3-oxazol-2 (3H)-one;
3-(3-cyanophenyl)-4-[3,6-difluoro-4-(methylsulfonyl)phenyl]-1,3-oxazol-2 (3H)-one;
3-(4-cyanophenyl)-4-[3,6-difluoro-4-(methylsulfonyl)phenyl]-1,3-oxazol-2 (3H)-one;
3-(3-trifluoromethylphenyl)-4-[3,6-difluoro-4-(methylsulfonyl)phenyl]-1,3-oxazol-2 (3H)-one;
3-(4-trifluoromethylphenyl)-4-[3,6-difluoro-4-(methylsulfonyl)phenyl]-1,3-oxazol-2 (3H)-one;
3-(3-trifluoromethoxyphenyl)-4-[3,6-difluoro-4-(methylsulfonyl)phenyl]-1,3-oxazol-2 (3H)-one;
3-(4-trifluoromethoxyphenyl)-4-(3,6-difluoro-4-(methylsulfonyl)phenyl]-1,3-oxazol-2 (3H)-one;
3-(3,4-dichlorophenyl)-4-[3,6-difluoro-4-(methylsulfonyl)phenyl]-1,3-oxazol-2 (3H)-one;
3-(3,4-dibromophenyl)-4-[3,6-difluoro-4-(methylsulfonyl)phenyl]-1,3-oxazol-2 (3H)-one;
3-(3,4-difluorophenyl)-4-[3,6-difluoro-4-(methylsulfonyl)phenyl]-1,3-oxazol-2 (3H)-one;
3-(3,5-dichlorophenyl)-4-[3,6-difluoro-4-(methylsulfonyl)phenyl]-1,3-oxazol-2 (3H)-one;
3-(3,5-dibromophenyl)-4-[3,6-difluoro-4-(methylsulfonyl)phenyl]-1,3-oxazol-2 (3H)-one;
3-(3-fluorophenyl)-4-[3,6-difluoro-4-(methylsulfonyl)phenyl]-1,3-oxazol-2 (3H)-one;
3-(3,4-dimethylphenyl)-4-[3,6-difluoro-4-(methylsulfonyl)phenyl]-1,3-oxazol-2 (3H)-one;
3-(3,5-dimethylphenyl)-4-[3,6-difluoro-4-(methylsulfonyl)phenyl]-1,3-oxazol-2 (3H)-one;
3-(3-methyl-4-chlorophenyl)-4-[3,6-difluoro-4-(methylsulfonyl)phenyl]-1,3-oxazol-2 (3H)-one;
3-(4-methyl-3-chlorophenyl)-4-[3,6-difluoro-4-(methylsulfonyl)phenyl]-1,3-oxazol-2 (3H)-one;
3-(3-methy1-4-[fluorophenyl)-4-[3,6-difluoro-4-(methylsulfonyl)phenyl]-1,3-oxazol-2 (3H)-one;
3-(4-methyl-3-fluorophenyl)-4-[3,6-difluoro-4-(methylsulfonyl)phenyl]-1,3-oxazol-2 (3H)-one;
3-(3-methyl-4-bromophenyl)-4-[3,6-difluoro-4-methylsulfonyl)phenyl]-1,3-oxazol-2 (3H)-one;
3-(4-methyl-3-bromophenyl)-4-[3,6-difluoro-4-t methylsulfonyl)phenyl]-1,3-oxazol-2 (3H)-one;
3-(3-methyl-4-trifluoromethylphenyl)-4-[3,6-difluoro-4-(methylsulfonyl)phenyl]-1,3-oxazol-2 (3H)-one;
3-(4-methyl-3-trifluoromethylphenyl)-4-[3,6-difluoro-4-(methylsulfonyl)phenyl]-1,3-oxazol-2 (3H)-one;
3-(3-methyl-4-trifluoromethoxyphenyl)-4-[3,6-difluoro-4-(methylsulfonyl)phenyl]-1,3-oxazol-2 (3H)-one;
3-(4-methyl-3-trifluoromethoxyphenyl)-4-[3,6-difluoro-4-(methylsulfonyl)phenyl]-1,3-oxazol-2 (3H)-one;

3-(3-cyano-4-methylphenyl)-4-[3,6-difluoro-4-(methylsulfonyl)phenyl]-1,3-oxazol-2 (3H)-one;

3-(4-cyano-3-methylphenyl)-4-[3,6-difluoro-4-(methylsulfonyl)phenyl]-1,3-oxazol-2 (3H)-one;

3-(3-chloro-4-methoxyphenyl)-4-[3,6-difluoro-4-(methylsulfonyl)phenyl]-1,3-oxazol-2 (3H)-one;

3-(4-chloro-3-methoxyphenyl)-4-[3,6-difluoro-4-(methylsulfonyl)phenyl]-1,3-oxazol-2 (3H)-one;

3-(2-methylpyridin-6-yl)-4-[3,6-difluoro-4-(methylsulfonyl)phenyl]-1,3-oxazol-2 (3H)-one;

3-(2-methylthiazol-4-yl)-4-[3,6-difluoro-4-(methylsulfonyl)phenyl]-1,3-oxazol-2 (3H)-one;

3-(4-methylthiazol-2-yl)-4-[3,6-difluoro-4-(methylsulfonyl)phenyl]-1,3-oxazol-2 (3H)-one;

3-(2-methylpyridin-3-yl)-4-[3,6-difluoro-4-(methylsulfonyl)phenyl]-1,3-oxazol-2 (3H)-one;

3-(2-methylpyridin-3-yl)-4-[3,6-difluoro-4-(methylsulfonyl)phenyl]-1,3-oxazol-2 (3H)-one;

3-(3-pyridinyl)-4-[3,6-difluoro-4-(methylsulfonyl)phenyl]-1,3-oxazol-2 (3H)-one;

3-(5-methylpyridin-3-yl)-4-[3,6-difluoro-4-(methylsulfonyl)phenyl]-1,3-oxazol-2 (3H)-one;

3-(2-methylpyridin-3-yl)-4-[3,6-difluoro-4-(methylsulfonyl)phenyl]-1,3-oxazol-2 (3H)-one;

3-cyclohexyl-4-[3,6-difluoro-4-(methylsulfonyl)phenyl]-1,3-oxazol-2 (3H)-one;

3-cyclopentyl-4-[3,6-difluoro-4-(methylsulfonyl)phenyl]-1,3-oxazol-2 (3H)-one;

2,5-difluoro-4-[2-oxo-2,3-dihydro-1,3-oxazol-4-yl]benzenesulfonamide;

2,5-difluoro-4-[3-(3-chlorophenyl)-2-oxo-2,3-dihydro-1,3-oxazol-4-yl]benzenesulfonamide;

2,5-difluoro-4-[3-(4-chlorophenyl)-2-oxo-2,3-dihydro-1,3-oxazol-4-yl]benzenesulfonamide;

2,5-difluoro-4-[3-(3-bromophenyl)-2-oxo-2,3-dihydro-1,3-oxazol-4-yl]benzenesulfonamide;

2,5-difluoro-4-[3-(4-bromophenyl)-2-oxo-2,3-dihydro-1,3-oxazol-4-yl]benzenesulfonamide;

2,5-difluoro-4-[3-(3-fluorophenyl)-2-oxo-2,3-dihydro-1,3-oxazol-4-yl]benzenesulfonamide;

2,5-difluoro-4-[3-(4-fluorophenyl)-2-oxo-2,3-dihydro-1,3-oxazol-4-yl]benzenesulfonamide;

2,5-difluoro-4-[3-(3-methylphenyl)-4-[3-fluoro-4-(methylsulfonyl)phenyl]-1,3-oxazol-2 (3H)-one;

2,5-difluoro-4-[3-(4-methylphenyl)-2-oxo-2,3-dihydro-1,3-oxazol-4-yl]benzenesulfonamide;

2,5-difluoro-4-[3-(3-cyanophenyl)-2-oxo-2,3-dihydro-1,3-oxazol-4-yl]benzenesulfonamide;

2,5-difluoro-4-[3-(4-cyanophenyl)-2-oxo-2,3-dihydro-1,3-oxazol-4-yl]benzenesulfonamide;

2,5-difluoro-4-[3-(3-trifluoromethylphenyl)-2-oxo-2,3-dihydro-1,3-oxazol-4-yl]benzenesulfonamide;

2,5-difluoro-4-[3-(4-trifluoromethylphenyl)-2-oxo-2,3-dihydro-1,3-oxazol-4-yl]benzenesulfonamide;

2,5-difluoro-4-[3-(3-trifluoromethoxyphenyl)-2-oxo-2,3-dihydro-1,3-oxazol-4-yl]benzenesulfonamide;

2,5-difluoro-4-[3-(4-trifluoromethoxyphenyl)-2-oxo-2,3-dihydro-1,3-oxazol-4-yl]benzenesulfonamide;

2,5-difluoro-4-[3-(3,4-dichlorophenyl)-2-oxo-2,3-dihydro-1,3-oxazol-4-yl]benzenesulfonamide;

2,5-difluoro-4-[3-(3,4-dibromophenyl)-2-oxo-2,3-dihydro-1,3-oxazol-4-yl]benzenesulfonamide;

2,5-difluoro-4-[3-(3,4-difluorophenyl)-2-oxo-2,3-dihydro-1,3-oxazol-4-yl]benzenesulfonamide;

2,5-difluoro-4-[3-(3,5-dichlorophenyl)-2-oxo-2,3-dihydro-1,3-oxazol-4-yl]benzenesulfonamide;

2,5-difluoro-4-[3-(3,5-dibromophenyl)-2-oxo-2,3-dihydro-1,3-oxazol-4-yl]benzenesulfonamide;

2,5-difluoro-4-[3-(3,5-difluorophenyl)-2-oxo-2,3-dihydro-1,3-oxazol-4-yl]benzenesulfonamide;

2,5-difluoro-4-[3-(3,4-dimethylphenyl)-2-oxo-2,3-dihydro-1,3-oxazol-4-yl]benzenesulfonamide;

2,5-difluoro-4-[3-(3,5-dimethylphenyl)-2-oxo-2,3-dihydro-1,3-oxazol-4-yl]benzenesulfonamide;

2,5-difluoro-4-[3-(3-methyl-4-chlorophenyl)-2-oxo-2,3-dihydro-1,3-oxazol-4-yl]benzenesulfonamide;

2,5-difluoro-4-[3-(4-methyl-3-chlorophenyl)-2-oxo-2,3-dihydro-1,3-oxazol-4-yl]benzenesulfonamide;

2,5-difluoro-4-[3-(3-methyl-4-fluorophenyl)-2-oxo-2,3-dihydro-1,3-oxazol-4-yl]benzenesulfonamide;

2,5-difluoro-4-[3-(4-methyl-3-fluorophenyl)-2-oxo-2,3-dihydro-1,3-oxazol-4-yl]benzenesulfonamide;

2,5-difluoro-4-[3-(3-methyl-4-bromophenyl)-2-oxo-2,3-dihydro-1,3-oxazol-4-yl]benzenesulfonamide;

2,5-difluoro-4-[3-(4-methyl-3-bromophenyl)-2-oxo-2,3-dihydro-1,3-oxazol-4-yl]benzenesulfonamide;

2,5-difluoro-4-[3-(3-methyl-4-trifluoromethylphenyl)-2-oxo-2,3-dihydro-1,3-oxazol-4-yl]benzenesulfonamide;

2,5-difluoro-4-[3-(4-methyl-3-trifluoromethylphenyl)-2-oxo-2,3-dihydro-1,3-oxazol-4-yl]benzenesulfonamide;

2,5-difluoro-4-[3-(3-methyl-4-trifluoromethoxyphenyl)-2-oxo-2,3-dihydro-1,3-oxazol-4-yl]benzenesulfonamide;

2,5-difluoro-4-[3-(4-methyl-3-trifluoromethoxyphenyl)-2-oxo-2,3-dihydro-1,3-oxazol-4-yl]benzenesulfonamide;

2,5-difluoro-4-[3-(3-cyano-4-methylphenyl)-2-oxo-2,3-dihydro-1,3-oxazol-4-yl]benzenesulfonamide;

2,5-difluoro-4-[3-(4-cyano-3-methylphenyl)-2-oxo-2,3-dihydro-1,3-oxazol-4-yl]benzenesulfonamide;

2,5-difluoro-4-[3-(3-chloro-4-methoxyphenyl)-2-oxo-2,3-dihydro-1,3-oxazol-4-yl]benzenesulfonamide;

2,5-difluoro-4-[3-(4-chloro-3-methoxyphenyl)-2-oxo-2,3-dihydro-1,3-oxazol-4-yl]benzenesulfonamide;

2,5-difluoro-4-[3-(2-methylpyridin-6-yl)-2-oxo-2,3-dihydro-1,3-oxazol-4-yl]benzenesulfonamide;

2,5-difluoro-4-[3-(2-methylthiazol-4-yl)-2-oxo-2,3-dihydro-1,3-oxazol-4-yl]benzenesulfonamide;

2,5-difluoro-4-[3-(4-methylthiazol-2-yl)-2-oxo-2,3-dihydro-1,3-oxazol-4-yl]benzenesulfonamide;

2,5-difluoro-4-[3-(2-methylpyridin-3-yl)-2-oxo-2,3-dihydro-1,3-oxazol-4-yl]benzenesulfonamide;

2,5-difluoro-4-[3-(2-methylpyridin-3-yl)-2-oxo-2,3-dihydro-1,3-oxazol-4-yl]benzenesulfonamide;

2,5-difluoro-4-[3-(3-pyridinyl)-2—oxo-2,3—dihydro-1,3-oxazol-4-yl]benzenesulfonamide;

2,5-difluoro-4-[3-(5-methylpyridin-3-yl)-2-oxo-2,3-dihydro-1,3-oxazol-4-yl]benzenesulfonamide;

2,5-difluoro-4-[3-(2-methylpyridin-3-yl)-2-oxo-2,3-dihydro-1,3-oxazol-4-yl]benzenesulfonamide;

2,5-difluoro-4-[3-cyclohexyl-2-oxo-2,3-dihydro-1,3-oxazol-4-yl]benzenesulfonamide;

2,5-difluoro-4-[3-cyclopentyl-2-oxo-2,3-dihydro-1,3-oxazol-4-yl]benzenesulfonamide.

6. A compound, or a pharmaceutically-acceptable salt, tautomer or prodrug thereof, selected from the group consisting of:

2,6-difluoro-4-[2-oxo-2,3-dihydro-1,3-thiazol-4-yl]benzenesulfonamide;
2,6-difluoro-4-[3-(3-chlorophenyl)-2-oxo-2,3-dihydro-1,3-thiazol-4-yl]benzenesulfonamide;
2,6-difluoro-4-[3-(4-chlorophenyl)-2-oxo-2,3-dihydro-1,3-thiazol-4-yl]benzenesulfonamide;
2,6-difluoro-4-[3-(3-bromophenyl)-2-oxo-2,3-dihydro-1,3-thiazol-4-yl]benzenesulfonamide;
2,6-difluoro-4-[3-(4-bromophenyl)-2-oxo-2,3-dihydro-1,3-thiazol-4—yl]benzenesulfonamide;
2,6-difluoro-4-[3-(3-fluorophenyl)-2-oxo-2,3-dihydro-1,3-thiazol-4-yl]benzenesulfonamide;
2,6-difluoro-4-[3-(4-fluorophenyl)-2-oxo-2,3-dihydro-1,3-thiazol-4-yl]benzenesulfonamide;
2,6-difluoro-4-[3-(3-methylphenyl)-4-[3-fluoro-4-(methylsulfonyl)phenyl]-1,3-thiazol-2 (3H)-one;
2,6-difluoro-4-[3-(4-methylphenyl)-2-oxo-2,3-dihydro-1,3-thiazol-4-yl]benzenesulfonamide;
2,6-difluoro-4-[3-(3-cyanophenyl)-2-oxo-2,3-dihydro-1,3-thiazol-4-yl]benzenesulfonamide;
2,6-difluoro-4-[3-(4-cyanophenyl)-2-oxo-2,3-dihydro-1,3-thiazol-4-yl]benzenesulfonamide;
2,6-difluoro-4-[3-(3-trifluoromethylphenyl)-2-oxo-2,3-dihydro-1,3-thiazol-4-yl]benzenesulfonamide;
2,6-difluoro-4-[3-(4-trifluoromethylphenyl)-2-oxo-2,3-dihydro-1,3-thiazol-4-yl]benzenesulfonamide;
2,6-difluoro-4-[3-(3-trifluoromethoxyphenyl)-2-oxo-2,3-dihydro-1,3-thiazol-4-yl]benzenesulfonamide;
2,6-difluoro-4-[3-(4-trifluoromethoxyphenyl)-2-oxo-2,3-dihydro-1,3-thiazol-4-yl]benzenesulfonamide;
2,6-difluoro-4-[3-(3,4-dichlorophenyl)-2-oxo-2,3-dihydro-1,3-thiazol-4-yl]benzenesulfonamide;
2,6-difluoro-4-[3-(3,4-dibromophenyl)-2-oxo-2,3-dihydro-1,3-thiazol-4-yl]benzenesulfonamide;
2,6-difluoro-4-[3-(3,4-difluorophenyl)-2-oxo-2,3-dihydro-1,3-thiazol-4-yl]benzenesulfonamide;
2,6-difluoro-4-[3-(3,5-dichlorophenyl)-2-oxo-2,3-dihydro-1,3-thiazol-4-yl]benzenesulfonamide;
2,6-difluoro-4-[3-(3,5-dibromophenyl)-2-oxo-2,3-dihydro-1,3-thiazol-4-yl]benzenesulfonamide;
2,6-difluoro-4-[3-(3,5-difluorophenyl)-2-oxo-2,3-dihydro-1,3-thiazol-4-yl]benzenesulfonamide;
2,6-difluoro-4-[3-(3,4-dimethylphenyl)-2-oxo-2,3-dihydro-1,3-thiazol-4-yl]benzenesulfonamide;
2,6-difluoro-4-[3-(3,5-dimethylphenyl)-2-oxo-2,3-dihydro-1,3-thiazol-4-yl]benzenesulfonamide;
2,6-difluoro-4-[3-(3-methyl-4-chlorophenyl)-2-oxo-2,3-dihydro-1,3-thiazol-4-yl]benzenesulfonamide;
2,6-difluoro-4-[3-(4-methyl-3-chlorophenyl)-2-oxo-2,3-dihydro-1,3-thiazol-4-yl]benzenesulfonamide;
2,6-difluoro-4-[3-(3-methyl-4-fluorophenyl)-2-oxo-2,3-dihydro-1,3-thiazol-4-yl]benzenesulfonamide;
2,6-difluoro-4-[3-(4-methyl-3-fluorophenyl)-2-oxo-2,3-dihydro-1,3-thiazol-4-yl]benzenesulfonamide;
2,6-difluoro-4-[3-(3-methyl-4-bromophenyl)-2-oxo-2,3-dihydro-1,3-thiazol-4-yl]benzenesulfonamide;
2,6-difluoro-4-[3-(4-methyl-3-bromophenyl)-2-oxo-2,3-dihydro-1,3-thiazol-4-yl]benzenesulfonamide;
2,6-difluoro-4-[3-(3-methyl-4-trifluoromethylphenyl)-2-oxo-2,3-dihydro-1,3-thiazol-4-yl]benzenesulfonamide;
2,6-difluoro-4-[3-(4-methyl-3-trifluoromethylphenyl)-2-oxo-2,3-dihydro-1,3-thiazol-4-yl]benzenesulfonamide;
2,6-difluoro-4-[3-(3-methyl-4-trifluoromethoxyphenyl)-2-oxo-2,3-dihydro-1,3-thiazol-4-yl]benzenesulfonamide;
2,6-difluoro-4-[3-(4-methyl-3-trifluoromethoxyphenyl)-2-oxo-2,3-dihydro-1,3-thiazol-4-yl]benzenesulfonamide;
2,6-difluoro-4-[3-(3-cyano-4-methylphenyl)-2-oxo-2,3-dihydro-1,3-thiazol-4-yl]benzenesulfonamide;
2,6-difluoro-4-[3-(4-cyano-3-methylphenyl)-2-oxo-2,3-dihydro-1,3-thiazol-4-yl]benzenesulfonamide;
2,6-difluoro-4-[3-(3-chloro-4-methoxyphenyl)-2-oxo-2,3-dihydro-1,3-thiazol-4-yl]benzenesulfonamide;
2,6-difluoro-4-[3-(4-chloro-3-methoxyphenyl)-2-oxo-2,3-dihydro-1,3-thiazol-4-yl]benzenesulfonamide;
2,6-difluoro-4-[3-(2-methylpyridin-6-yl)-2-oxo-2,3-dihydro-1,3-thiazol-4-yl]benzenesulfonamide;
2,6-difluoro-4-[3-(2-methylthiazol-4-yl)-2-oxo-2,3-dihydro-1,3-thiazol-4-yl]benzenesulfonamide;
2,6-difluoro-4-[3-(4-methylthiazol-2-yl)-2-oxo-2,3-dihydro-1,3-thiazol-4-yl]benzenesulfonamide;
2,6-difluoro-4-[3-(2-methylpyridin-3-yl)-2-oxo-2,3-dihydro-1,3-thiazol-4-yl]benzenesulfonamide;
2,6-difluoro-4-[3-(2-methylpyridin-3-yl)-2-oxo-2,3-dihydro-1,3-thiazol-4-yl]benzenesulfonamide;
2,6-difluoro-4-[3-(3-pyridinyl)-2-oxo-2,3-dihydro-1,3-thiazol-4-yl]benzenesulfonamide;
2,6-difluoro-4-[3-(5-methylpyridin-3-yl)-2-oxo-2,3-dihydro-1,3-thiazol-4-yl]benzenesulfonamide;
2,6-difluoro-4-[3-(2-methylpyridin-3-yl)-2-oxo-2,3-dihydro-1,3-thiazol-4-yl]benzenesulfonamide;
2,6-difluoro-4-[3-cyclohexyl-2-oxo-2,3-dihydro-1,3-thiazol-4-yl]benzenesulfonamide;
2,6-difluoro-4-[3-cyclopentyl-2-oxo-2,3-dihydro-1,3-thiazol-4-yl]benzenesulfonamide;
2,5-difluoro-4-[2-oxo-2,3-dihydro-1,3-thiazol-4-yl]benzenesulfonamide;
2,5-difluoro-4-[3-(3-chlorophenyl)-2-oxo-2,3-dihydro-1,3-thiazol-4-yl]benzenesulfonamide;
2,5-difluoro-4-[3-(4-chlorophenyl)-2-oxo-2,3-dihydro-1,3-thiazol-4-yl]benzenesulfonamide;
2,5-difluoro-4-[3-(3-bromophenyl)-2-oxo-2,3-dihydro-1,3-thiazol-4-yl]benzenesulfonamide;
2,5-difluoro-4-[3-(4—bromophenyl)-2-oxo-2,3-dihydro-1,3-thiazol-4-yl]benzenesulfonamide;
2,5-difluoro-4-[3-(3-fluorophenyl)-2-oxo-2,3-dihydro-1,3-thiazol-4-yl]benzenesulfonamide;
2,5-difluoro-4-[3-(4-fluorophenyl)-2-oxo-2,3-dihydro-1,3-thiazol-4-yl]benzenesulfonamide;
2,5-difluoro-4-[3-(3-methylphenyl)-4-[3-fluoro-4-(methylsulfonyl)phenyl]-1,3-thiazol-2 (3H)-one;
2,5-difluoro-4-[3-(4-methylphenyl)-2-oxo-2,3—dihydro-1,3-thiazol-4-yl]benzenesulfonamide;
2,5-difluoro-4-[3-(3-cyanophenyl)-2-oxo-2,3-dihydro-1,3-thiazol-4-yl]benzenesulfonamide;
2,5-difluoro-4-[3-(4-cyanophenyl)-2—oxo-2,3-dihydro-1,3-thiazol-4-yl]benzenesulfonamide;
2,5-difluoro-4-[3-(3-trifluoromethylphenyl)-2-oxo-2,3-dihydro-1,3-thiazol-4-yl]benzenesulfonamide;
2,5-difluoro-4-[3-(4-trifluoromethylphenyl)-2-oxo-2,3-dihydro-1,3-thiazol-4-yl]benzenesulfonamide;

2,5-difluoro-4-[3-(3-trifluoromethoxyphenyl)-2-oxo-2,3-dihydro-1,3-thiazol-4-yl]benzenesulfonamide;

2,5-difluoro-4-[3-(4-trifluoromethoxyphenyl)-2-oxo-2,3-dihydro-1,3-thiazol-4—yl]benzenesulfonamide;

2,5-difluoro-4-[3-(3,4-dichlorophenyl)-2-oxo-2,3-dihydro-1,3-thiazol-4-yl]benzenesulfonamide;

2,5-difluoro-4-[3-(3,4-dibromophenyl)-2-oxo-2,3-dihydro-1,3-thiazol-4-yl]benzenesulfonamide;

2,5-difluoro-4-[3-(3,4-difluorophenyl)-2-oxo-2,3-dihydro-1,3-thiazol-4-yl]benzenesulfonamide;

2,5-difluoro-4-[3-(3,5-dichlorophenyl)-2-oxo-2,3-dihydro-1,3-thiazol-4-yl]benzenesulfonamide;

2,5-difluoro-4-[3-(3,5-dibromophenyl)-2-oxo-2,3-dihydro-1,3-thiazol-4—yl]benzenesulfonamide;

2,5-difluoro-4-[3-(3,5-difluorophenyl)-2-oxo-2,3-dihydro-1,3-thiazol-4-yl]benzenesulfonamide;

2,5-difluoro-4-[3-(3,4-dimethylphenyl)-2-oxo-2,3—dihydro-1,3-thiazol-4-yl]benzenesulfonamide;

2,5-difluoro-4-[3-(3,5-dimethylphenyl)-2-oxo-2,3-dihydro-1,3-thiazol-4-yl]benzenesulfonamide;

2,5-difluoro-4-[3-(3-methyl-4-chlorophenyl)-2-oxo-2,3-dihydro-1,3-thiazol-4-yl]benzenesulfonamide;

2,5-difluoro-4-[3-(4-methyl-3-chlorophenyl)-2-oxo-2,3-dihydro-1,3-thiazol-4-yl]benzenesulfonamide;

2,5-difluoro-4-[3-(3-methyl-4-fluorophenyl)-2-oxo-2,3-dihydro-1,3-thiazol-4-yl]benzenesulfonamide;

2,5-difluoro-4-[3-(4-methyl-3-fluorophenyl)-2-oxo-2,3-dihydro-1,3-thiazol-4-yl]benzenesulfonamide;

2,5-difluoro-4-[3-(3-methyl-4-bromophenyl)-2-oxo-2,3-dihydro-1,3-thiazol-4-yl]benzenesulfonamide;

2,5-difluoro-4-[3-(4-methyl-3-bromophenyl)-2-oxo-2,3-dihydro-1,3-thiazol-4-yl]benzenesulfonamide;

2,5-difluoro-4-[3-(3-methyl-4-trifluoromethylphenyl)-2-oxo-2,3-dihydro-1,3-thiazol-4-yl]benzenesulfonamide;

2,5-difluoro-4-[3-(4-methyl-3-trifluoromethylphenyl)-2-oxo-2,3-dihydro-1,3-thiazol-4-yl]benzenesulfonamide;

2,5-difluoro-4-[3-(3-methyl-4-trifluoromethoxyphenyl)-2-oxo-2,3-dihydro-1,3-thiazol-4-yl]benzenesulfonamide;

2,5-difluoro-4-[3-(4-methyl-3-trifluoromethoxyphenyl)-2-oxo-2,3-dihydro-1,3-thiazol-4-yl]benzenesulfonamide;

2,5-difluoro-4-[3-(3-cyano-4-methylphenyl)-2-oxo-2,>dihydro-1,3-thiazol-4-yl]benzenesulfonamide;

2,5-difluoro-4-[3-(4-cyano-3-methylphenyl)-2-oxo-2,3-dihydro-1,3-thiazol-4-yl]benzenesulfonamide;

2,5-difluoro-4-[3-(3-chloro-4-methoxyphenyl)-2-oxo-2,3-dihydro-1,3-thiazol-4-yl]benzenesulfonamide;

2,5-difluoro-4-[3-(4-chloro-3-methoxyphenyl)-2-oxo-2,3-dihydro-1,3-thiazol-4-yl]benzenesulfonamide;

2,5-difluoro-4-[3-(2-methylpyridin-6-yl)-2-oxo-2,3-dihydro-1,3-thiazol-4-yl]benzenesulfonamide;

2,5-difluoro-4-[3-(2-methylthiazol-4-yl)-2-oxo-2,3-dihydro-1,3-thiazol-4-yl]benzenesulfonamide;

2,5-difluoro-4-[3-(4-methylthiazol-2-yl)-2-oxo-2,3-dihydro-1,3-thiazol-4-yl]benzenesulfonamide;

2,5-difluoro-4-[3-(2-methylpyridin-3-yl)-2-oxo-2,3-dihydro-1,3-thiazol-4-yl]benzenesulfonamide;

2,5-difluoro-4-[3-(2-methylpyridin-3-yl)-2-oxo-2,3-dihydro-1,3-thiazol-4-yl]benzenesulfonamide;

2,5-difluoro-4-[3-(3-pyridinyl)-2-oxo-2,3-dihydro-1,3-thiazol-4-yl]benzenesulfonamide;

2,5-difluoro-4-[3-(5-methylpyridin-3-yl)-2-oxo-2,3-dihydro-1,3-thiazol-4-yl]benzenesulfonamide;

2,5-difluoro-4-[3-(2-methylpyridin-3-yl)-2-oxo-2,3-dihydro-1,3-thiazol-4-yl]benzenesulfonamide;

2,5-difluoro-4-[3-cyclohexyl-2-oxo-2,3-dihydro-1,3-thiazol-4-yl]benzenesulfonamide;

2,5-difluoro-4-[3-cyclopentyl-2-oxo-2,3-dihydro-1,3-thiazol-4-yl]benzenesulfonamide;

3-phenyl-4-[3,6-difluoro-4-(methylsulfonyl)phenyl]-1,3-thiazol-2 (3H)-one;

3-(3-chlorophenyl)-4-[3,6-difluoro-4-(methylsulfonyl)phenyl]-1,3-thiazol-2 (3H)-one;

3-(4-chlorophenyl)-4-[3,6-difluoro-4-(methylsulfonyl)phenyl]-1,3-thiazol-2 (3H)-one;

3-(3-bromophenyl)-4-[3,6-difluoro-4-(methylsulfonyl)phenyl]-1,3-thiazol-2 (3H)-one;

3-(4-bromophenyl)-4-[3,6-difluoro-4-(methylsulfonyl)phenyl]-1,3-thiazol-2 (3H)-one;

3-(3-fluorophenyl)-4-[3,6-difluoro-4-(methylsulfonyl)phenyl]-1,3-thiazol-2 (3H)-one;

3-(4-fluorophenyl)-4-[3,6-difluoro-4-(methylsulfonyl)phenyl]-1,3-thiazol-2 (3H)-one;

3-(3-methylphenyl)-4-[3,6-difluoro-4-(methylsulfonyl)phenyl]-1,3-thiazol-2 (3H)-one;

3-(4-methylphenyl)-4-[3,6-difluoro-4-(methylsulfonyl)phenyl]-1,3-thiazol-2 (3H)-one;

3-(3-cyanophenyl)-4-[3,6-difluoro-4-(methylsulfonyl)phenyl]-1,3-thiazol-2 (3H)-one;

3-(4-cyanophenyl)-4-[3,5-difluoro-4-(methylsulfonyl)phenyl]-1,3-thiazol-2 (3H)-one;

3-(3-trifluoromethylphenyl)-4-[3,6-difluoro-4-(methylsulfonyl)phenyl]-1,3-thiazol-2 (3H)-one;

3-(4-trifluoromethylphenyl)-4-[3,6-difluoro-4-(methylsulfonyl)phenyl]-1,3-thiazol-2 (3H)-one;

3-(3-trifluoromethoxyphenyl)-4-[3,6-difluoro-4-(methylsulfonyl)phenyl]-1,3-thiazol-2 (3H)-one;

3-(4-trifluoromethoxyphenyl)-4-[3,6-difluoro-4-(methylsulfonyl)phenyl]-1,3-thiazol-2 (3H)-one;

3-(3,4-dichlorophenyl)-4-[3,6-difluoro-4-(methylsulfonyl)phenyl]-1,3-thiazol-2 (3H)-one;

3-(3,4-dibromophenyl)-4-[3,6-difluoro-4-(methylsulfonyl)phenyl]-1,3-thiazol-2 (3K)-one;

3-(3,4-difluorophenyl)-4-[3,6-difluoro-4-(methylsulfonyl)phenyl]-1,3-thiazol-2 (3K)-one;

3-(3,5-dichlorophenyl)-4-[3,6-difluoro-4-(methylsulfonyl)phenyl]-1,3-thiazol-2 (3H)-one;

3-(3,5-dibromophenyl)-4-[3,6-difluoro-4-(methylsulfonyl)phenyl]-1,3-thiazol-2 (3H)-one;

3-(3-fluorophenyl)-4-[3,6-difluoro-4-(methylsulfonyl)phenyl]-1,3-thiazol-2 (3H)-one;

3-(3,4-dimethylphenyl)-4-[3,6-difluoro-4-(methylsulfonyl)phenyl]-1,3-thiazol-2 (3H)-one;

3-(3,5-dimethylphenyl)-4-[3,6-difluoro-4-(methylsulfonyl)phenyl]-1,3-thiazol-2 (3H)-one;

3-(3-methyl-4-chlorophenyl)-4-[3,6-difluoro-4-(methylsulfonyl)phenyl]-1,3-thiazol-2 (3H)-one;

3-(4-methyl-3-chlorophenyl)-4-[3,6-difluoro-4-(methylsulfonyl)phenyl]-1,3-thiazol-2 (3H)-one;

3-(3-methyl-4-fluorophenyl)-4-[3,6-difluoro-4-(methylsulfonyl)phenyl]-1,3-thiazol-2 (3H)-one;

3-(4-methyl-3-fluorophenyl)-4-[3,6-difluoro-4-(methylsulfonyl)phenyl]-1,3-thiazol-2 (3H)-one;

3-(3-methyl-4-bromophenyl)-4-[3,6-difluoro-4-(methylsulfonyl)phenyl]-1,3-thiazol-2 (3H)-one;

3-(4-methyl-3-bromophenyl)-4-[3,6-difluoro-4-(methylsulfonyl)phenyl]-1,3-thiazol-2 (3H)-one;

3-(3-methyl-4-trifluoromethylphenyl)-4-[3,6-difluoro-4-(methylsulfonyl)phenyl]-1,3-thiazol-2 (3H)-one;

3-(4-methyl-3-trifluoromethylphenyl)-4-[3,6-difluoro-4-(methylsulfonyl)phenyl]-1,3-thiazol-2 (3H)-one;

3-(3-methyl-4-trifluoromethoxyphenyl)-4-[3,6-difluoro-4-(methylsulfonyl)phenyl]-1,3-thiazol-2 (3H)-one;

3-(4-methyl-3-trifluoromethoxyphenyl)-4-[3,6-difluoro-4-(methylsulfonyl)phenyl]-1,3-thiazol-2 (3H)-one;

3-(3-cyano-4-methylphenyl)-4-[3,5-difluoro-4-(methylsulfonyl)phenyl]-1,3-thiazol-2 (3H)-one;

3-(4-cyano-3-methylphenyl)-4-[3,6-difluoro-4-(methylsulfonyl)phenyl]-1,3-thiazol-2 (3H)-one;

3-(3-chloro-4-methoxyphenyl)-4-[3,6-difluoro-4-(methylsulfonyl)phenyl]-1,3-thiazol-2 (3H)-one;

3-(4-chloro-3-methoxyphenyl)-4-[3,6-difluoro-4-(methylsulfonyl)phenyl]-1,3-thiazol-2 (3H)-one;

3-(2-methylpyridin-6-yl)-4-[3,6-difluoro-4-(methylsulfonyl)phenyl]-1,3-thiazol-2 (3H)-one;

3-(2-methylthiazol-4-yl)-4-[3,6-difluoro-4-(methylsulfonyl)phenyl]-1,3-thiazol-2 (3H)-one;

3-(4-methylthiazol-2-yl)-4-[3,6-difluoro-4-(methylsulfonyl)phenyl]-1,3-thiazol-2 (3H)-one;

3-(2-methylpyridin-3-yl)-4-[3,6-difluoro-4-(methylsulfonyl)phenyl]-1,3-thiazol-2 (3H)-one;

3-(2-methylpyridin-3-yl)-4-[3,6-difluoro-4-(methylsulfonyl)phenyl]-1,3-thiazol-2 (3H)-one;

3-(3-pyridinyl)-4-[3,6-difluoro-4-(methylsulfonyl)phenyl]-1,3-thiazol-2 (3H)-one;

3-(5-methylpyridin-3-yl)-4-[3,6-difluoro-4-(methylsulfonyl)phenyl]-1,3-thiazol-2 (3H)-one;

3-(2-methylpyridin-3-yl)-4-[3,6-difluoro-4-(methylsulfonyl)phenyl]-1,3-thiazol-2 (3H)-one;

3-cyclohexyl-4-[3,6-difluoro-4-(methylsulfonyl)phenyl]-1,3-thiazol-2 (3H)-one;

3-cyclopentyl-4-[3,6-difluoro-4-(methylsulfonyl)phenyl]-1,3-thiazol-2 (3H)-one;

3-phenyl-4-[3,6-difluoro-4-(methylsulfonyl)phenyl]-1,3-thiazol-2 (3H)-one;

3-(3-chlorophenyl)-4-[3,6-difluoro-4-(methylsulfonyl)phenyl]-1,3-thiazol-2 (3H)-one;

3-(4-chlorophenyl)-4-[3,6-difluoro-4-(methylsulfonyl)phenyl]-1,3-thiazol-2 (3H)-one;

3-(3-bromophenyl)-4-[3,6-difluoro-4-(methylsulfonyl)phenyl]-1,3-thiazol-2 (3H)-one;

3-(4-bromophenyl)-4-[3,6-difluoro-4-(methylsulfonyl)phenyl]-1,3-thiazol-2 (3H)-one; Image Page 134

3-(3-fluorophenyl)-4-[3,6-difluoro-4-(methylsulfonyl)phenyl]-1,3-thiazol-2 (3H)-one;

3-(4-fluorophenyl)-4-[3,6-difluoro-4-(methylsulfonyl)phenyl]-1,3-thiazol-2 (3H)-one;

3-(3-methylphenyl)-4-[3,6-difluoro-4-(methylsulfonyl)phenyl]-1,3-thiazol-2 (3H)-one;

3-(4-methylphenyl)-4-[3,6-difluoro-4-(methylsulfonyl)phenyl]-1,3-thiazol-2 (3H)-one;

3-(3-cyanophenyl)-4-[3,6-difluoro-4-(methylsulfonyl)phenyl]-1,3-thiazol-2 (3H)-one;

3-(4-cyanophenyl)-4-[3,6-difluoro-4-(methylsulfonyl)phenyl]-1,3-thiazol-2 (3H)-one;

3-(3-trifluoromethylphenyl)-4-[3,6-difluoro-4-(methylsulfonyl)phenyl]-1,3-thiazol-2(3H)-one;

3-(4-trifluoromethylphenyl)-4-[3,6-difluoro-4-(methylsulfonyl)phenyl]-1,3-thiazol-2 (3H)-one;

3-(3-trifluoromethoxyphenyl)-4-[3,6-difluoro-4-(methylsulfonyl)phenyl]-1,3-thiazol-2 (3H)-one;

3-(4-trifluoromethoxyphenyl)-4-[3,6-difluoro-4-(methylsulfonyl)phenyl]-1,3-thiazol-2 (3H)-one;

3-(3,4-dichlorophenyl)-4-[3,6-difluoro-4-(methylsulfonyl)phenyl]-1,3-thiazol-2 (3H)-one;

3-(3,4-dibromophenyl)-4-[3,6-difluoro-4-(methylsulfonyl)phenyl]-1,3-thiazol-2 (3H)-one;

3-(3,4-difluorophenyl)-4-[3,6-difluoro-4-(methylsulfonyl)phenyl]-1,3-thiazol-2 (3H)-one;

3-(3,5-dichlorophenyl)-4-[3,6-difluoro-4-(methylsulfonyl)phenyl]-1,3-thiazol-2 (3H)-one;

3-(3,5-dibromophenyl)-4-[3,6-difluoro-4-(methylsulfonyl)phenyl]-1,3-thiazol-2 (3H)-one;

3-(3-fluorophenyl)-4-[3,6-difluoro-4-(methylsulfonyl)phenyl]-1,3-thiazol-2 (3H)-one;

3-(3,4-dimethylphenyl)-4-[3,5-difluoro-4-(methylsulfonyl)phenyl]-1,3-thiazol-2 (3H)-one;

3-(3,5-dimethylphenyl)-4-[3,6-difluoro-4-(methylsulfonyl)phenyl]-1,3-thiazol-2 (3H)-one;

3-(3-methyl-4-chlorophenyl)-4-[3,6-difluoro-4-(methylsulfonyl)phenyl]-1,3-thiazol-2 (3H)-one;

3-(4-methyl-3-chlorophenyl)-4-[3,6-difluoro-4-(methylsulfonyl)phenyl]-1,3-thiazol-2 (3H)-one;

3-(3-methyl-4-fluorophenyl)-4-[3,6-difluoro-4-(methylsulfonyl)phenyl]-1,3-thiazol-2 (3H)-one;

3-(4-methyl-3-fluorophenyl)-4-[3,6-difluoro-4-(methylsulfonyl)phenyl]-1,3-thiazol-2 (3H)-one;

3-(3-methyl-4-bromophenyl)-4-[3,6-difluoro-4-(methylsulfonyl)phenyl]-1,3-thiazol-2 (3H)-one;

7,3-(4-methyl-3-bromophenyl)-4-[3,6-difluoro-4-(methylsulfonyl)phenyl]-1,3-thiazol-2 (3H)-one;

3-(3-methyl-4-trifluoromethylphenyl)-4-[3,6-difluoro-4-(methylsulfonyl)phenyl]-1,3-thiazol-2 (3H)-one;

3-(4-methyl-3-trifluoromethylphenyl)-4-[3,6-difluoro-4-(methylsulfonyl)phenyl]-1,3-thiazol-2 (3H)-one;

3-(3-methyl-4-trifluoromethoxyphenyl)-4-[3,6-difluoro-4-(methylsulfonyl)phenyl]-1,3-thiazol-2 (3H)-one;

3-(4-methyl-3-trifluoromethoxyphenyl)-4-[3,6-difluoro-4-(methylsulfonyl)phenyl]-1,3-thiazol-2 (3H)-one;

3-(3-cyano-4-methylphenyl)-4-[3,6-difluoro-4-(methylsulfonyl)phenyl]-1,3-thiazol-2 (3H)-one;

3-(4-cyano-3-methylphenyl)-4-[3,6-difluoro-4-(methylsulfonyl)phenyl]-1,3-thiazol-2 (3H)-one;

3-(3-chloro-4-methoxyphenyl)-4-[3,6-difluoro-4-(methylsulfonyl)phenyl]-1,3-thiazol-2 (3H)-one;

3-(4-chloro-3-methoxyphenyl)-4-[3,6-difluoro-4-(methylsulfonyl)phenyl]-1,3-thiazol-2 (3H)-one;

3-(2-methylpyridin)-4-[3,6-difluoro-4-(methylsulfonyl)phenyl]-1,3-thiazol-2 (3H)-one;

3-(2-methylthiazol-4-yl)-4-[3,6-difluoro-4-(methylsulfonyl)phenyl]-1,3-thiazol-2 (3H)-one;

3-(4-methylthiazol-2-yl)-4-[3,6-difluoro-4-(methylsulfonyl)phenyl]-1,3-thiazol-2 (3H)-one;

3-(2-methylpyridin-3-yl)-4-[3,6-difluoro-4-(methylsulfonyl)phenyl]-1,3-thiazol-2 (3H)-one;

3-(2-methylpyridin-3-yl)-4-[3,6-difluoro-4-(methylsulfonyl)phenyl]-1,3-thiazol-2 (3H)-one;

93-(3-pyridinyl)-4-[3,6-difluoro-4-(methylsulfonyl)phenyl]-thiazol-2 (3H)-one;

3-(5-methylpyridin-3-yl)-4-[3,6-difluoro-4-(methylsulfonyl)phenyl]-1,3-thiazol-2 (3H)-one;

3-(2-methylpyridin-3-yl)-4-[3,6-difluoro-4-(methylsulfonyl)phenyl]-1,3-thiazol-2 (3H)-one;

3-cyclohexyl-4-[3,6-difluoro-4-(methylsulfonyl)phenyl]-1,3-thiazol-2 (3H)-one;

3-cyclopentyl-4-[3,6-difluoro-4-(methylsulfonyl)phenyl]-1,3-thiazol-2 (3H)-one.

7. A pharmaceutical composition comprising a therapeutically-effective amount of a compound of any one of claims 1–6, and at least one pharmaceutically-acceptable carrier, diluent, or adjuvant.

8. A method of treating inflammation, said method comprising administering to the subject having or susceptible to such inflammation or inflammation-associated disorder, a therapeutically-effective amount of a compound of any one of claims 1–6.

9. The method of claim 8 for use in the treatment of inflammation.

10. The method of claim 8, for use in the treatment of an inflammation-associated disorder.

11. The method of claim 10, wherein the inflammation-associated disorder is arthritis.

12. The method of claim 10, wherein the inflammation-associated disorder is pain.

13. The method of claim 10, wherein the inflammation-associated disorder is fever.

14. A method of treating cancer, said method comprising administering to the subject having or susceptible to such cancer, a therapeutically-effective amount of a compound of claim 8.

15. The method of claim 14 wherein the compound is administered intravenously.

16. The method of claim 14 wherein the compound is administered intramuscularly.

* * * * *

UNITED STATES PATENT AND TRADEMARK OFFICE
CERTIFICATE OF CORRECTION

PATENT NO.       : 6,699,884 B2                                    Page 1 of 6
APPLICATION NO.  : 10/319916
DATED            : March 2, 2004
INVENTOR(S)      : David L. Brown et al.

It is certified that error appears in the above-identified patent and that said Letters Patent is hereby corrected as shown below:

Column 178, claim 1
  Lines 27 and 30, that portion reading "oxo-2,5" should read -- oxo-2,5- --.
  Line 36, that portion reading "-s-oxo-2,5-" should read -- -5-oxo-2,5- --.

Column180, claim 1
  Line 44, that portion reading "[4,5-oxo" should read -- [5-oxo --.
  Line 55, that portion reading "oxo2,5-dihydro-3" should read
-- oxo-2,5-dihydro-3- --.
  Line 66, that portion reading "2,5-difluoro" should read -- 2,6-difluoro --.

Column 181, claim 1
  Line 16, that portion reading "2,5-difluoro" should read -- 2,6-difluoro --.
  Line 25, that portion reading "5-oxo-2,6-" should read -- 5-oxo-2,5- --.
  Line 27, that portion reading "-s-oxo-2,5-" should read -- -5-oxo-2,5- --.
  Line 29, that portion reading "-5-oxo-25" should read -- -5-oxo-2,5- --.
  Line 34, that portion reading "fluorophenyl)5-oxo-2,5" should read
-- fluorophenyl)-5-oxo-2,5- --.
  Line 38, that portion reading "oxo-2,5" should read -- oxo-2,5- --.
  Line 51, that portion reading "oxo-2,5" should read -- oxo-2,5- --.

Column 182, claim 1
  Line 1, that portion reading "oxo-2-dihydro-3" should read
--oxo-2,5-dihydro-3- --.

Column 183, claim 2
  Lines 50, 52, 54, 56, 59, 61, 63, 65, and 67, "benezenesulfonamide" should read
--benzenesulfonamide --.

Column 184, claim 2
  Lines 2, 4, 7, 9, 11, 13, 15, 17, 20, 22, 24, 26, 28, 30, 32, 35, 37, 39, 41, 43, 45, 48, 50, 52, 54, 56, 58, 60, 63, 65, and 67, "benezenesulfonamide" should read
-- benzenesulfonamide --.

Column 185, claim 2
  Lines 2, 4, 6, 9, 11, 13 and 15, "benezenesulfonamide" should read
-- benzenesulfonamide --.
  Line 43, that portion reading "6-di fulorophenyl" should read
-- 6-difluorophenyl --.
  Line 53, "that portion reading "]-2,5-" should read -- ]-2,6- --.

UNITED STATES PATENT AND TRADEMARK OFFICE
CERTIFICATE OF CORRECTION

PATENT NO. : 6,699,884 B2
APPLICATION NO. : 10/319916
DATED : March 2, 2004
INVENTOR(S) : David L. Brown et al.

It is certified that error appears in the above-identified patent and that said Letters Patent is hereby corrected as shown below:

Column 186, claim 2
    Line 15, that portion reading "-2,6-fluorophenyl" should read
-- -2,6-difluorophenyl --.
    Line 35, that portion reading "6difluorophenyl" should read
-- 6-difluorophenyl --.
    Lines 52, 54, 56, 58, 60, 62, 65 and 67, "benezenesulfonamide" should read
-- benzenesulfonamide --.

Column 187, claim 2
    Lines 2, 4, 6, 8, 11, 13, 15, 18, 20, 22, 24, 26, 28, 30, 33, 35, 37, 39, 41, 43, 45, 48, 50, 52, 54, 56, 58, 60, 63, 65, and 67, "benezenesulfonamide" should read
-- benzenesulfonamide --.

Column 188, claim 2
    Lines 2, 4, 6, 9, 11, 13, 15, and 17, "benezenesulfonamide" should read
-- benzenesulfonamide --.

Column 189, claim 2
    Line 3, that portion reading "4-[s-(4-" should read -- 4-[5-(4- --.
    Lines 23-24, that portion reading "cyclopentadienyl]2,5-" should read
-- cyclopentadienyl]-2,5- --.

Column 189, claim 3
    Lines 59, 61, 63, 65 and 67, "benezenesulfonamide" should read
-- benzenesulfonamide --.

Column 190, claim 3
    Line 3, that portion reading "2 G-difluoro" should read -- 2,6-difluoro --.
    Line 8, that portion reading '2-G-difluoro" should read -- 2,6-difluoro --.
    Lines 2, 4, 6, 9, 11, 13, 15, 17, 19, 21, 24, 26, 28, 30, 33, 35, 37, 39, 41, 43, 45, 48, 50, 52, 54, 56, 58, 60, 63, 65, and 67, "benezenesulfonamide" should read
-- benzenesulfonamide --.

Column 191, claim 3
    Lines 2, 4, 6, 9, 11, 13, 15, 18, 20, 22, 24, 26, 28, 30, 32, 35, 37, 39, 41, 43, 45, 48, 50, 52, 54, 56, 58, 61, 63, 65, and 67, "benezenesulfonamide" should read
-- benzenesulfonamide --.
    Line 36, that portion reading "pyridinyl]]-" should read -- pyridinyl]- --.

UNITED STATES PATENT AND TRADEMARK OFFICE
CERTIFICATE OF CORRECTION

PATENT NO. : 6,699,884 B2
APPLICATION NO. : 10/319916
DATED : March 2, 2004
INVENTOR(S) : David L. Brown et al.

It is certified that error appears in the above-identified patent and that said Letters Patent is hereby corrected as shown below:

Column 192 claim 3
    Lines 2, 4, 6, 9, 11, 13, 15, 18, 20, 22, 24, 26, 28, 30, 32, 35, 37, 39, 41, 43, 45, 48, 50, 52, 54, and 56, "benezenesulfonamide" should read
-- benzenesulfonamide --.
    Line 24, that portion reading "3-4-pyridinyl]" should read -- 3-pyridinyl] --.
    Line 36, that portion reading "methylpyridin-3-yl)" should read
--methylpyridin-6-yl) --.

Column 193, claim 3
    Line 2, that portion reading "sul f one;" should read -- sulfone; --.

Column 194, claim 3
    Lines 26, 28, 30, 32, 35, 37, 39, 41, 43, 45, 48, 50, 52, 54, 56, 59, 61, 63, 65 and 67, "benezenesulfonamide" should read -- benzenesulfonamide --.

Column 195, claim 3
    Lines 2, 4, 6, 9, 11, 13, 15, 17, 19, 21, 24, 26, 28, 30, 33, 35, 37, 39, 41, 43, 45, 48, 50, 52, 54, 56, 58, 60, 63, 65, and 67, "benezenesulfonamide" should read
-- benzenesulfonamide --.

Column 196, claim 3
    Lines 2, 4, 6, 9, 11, 13, 15, 17, 19, 21, 24, 26, 28, 30, 33, 35, 37, 39, 41, 43, 45, 48, 50, 52, 54, 56, 58, 60, 63, 65, and 67, "benezenesulfonamide" should read
-- benzenesulfonamide --.

Column 197, claim 3
    Lines 2, 4, 6, 9, 11, 13, 15, 17, 19, 21, 24, and 26, "benezenesulfonamide"
should read -- benzenesulfonamide --.
    Line 5, that portion reading "methylpyridin-G-yl)" should read
-- methylpyridin-6-yl) --.
    Lines 25-26 should read
    -- benzenesulfonamide;
        4-[4-phenyl-3-pyridinyl]-2,5-difluorophenyl methyl sulfone; --.

Column 198, claim 3
    Line 34, that portion reading "fluorophenyl" should read -- difluorophenyl --.

Column 199, claim 4
    Line 33, delete that portion reading "Image Page 104".
    Line 53, that portion reading "7,5-(3,5-" should read -- 5-(3,5- --.

UNITED STATES PATENT AND TRADEMARK OFFICE
CERTIFICATE OF CORRECTION

PATENT NO. : 6,699,884 B2
APPLICATION NO. : 10/319916
DATED : March 2, 2004
INVENTOR(S) : David L. Brown et al.

It is certified that error appears in the above-identified patent and that said Letters Patent is hereby corrected as shown below:

Column 200, claim 4
    Line 32, that portion reading "methylpyridin-G-yl)" should read
-- methylpyridin-6-yl) --.
    Lines 44-46, should read
-- imidazole;
        5-(2-methylpyridin-3-yl)-4-[3,5-difluoro-4-(methylsulfonyl))phenyl]-2-(difluoromethyl)-1H-imidazole; --

Column 201, claim 4
    Line 60, that portion reading "methylsulfonyl)phenyI]" should read
-- (methylsulfonyl)phenyl] --.

Column 202, claim 4
    Line 39, that portion reading "difluoro-4" should read -- difluoro-4- --.
    Line 49, that portion reading "7,5-(3-pyridinyl)" should read
-- 5-(3-pyridinyl) --.

Column 204, claim 4
    Line 62, that portion reading "chlorophenyl)-4-" should read
-- 5-(4-chlorophenyl)-4- --.

Column 206, claim 4
    Line 16 should read
-- imidazole;
        5-(3-cyano-4-methylphenyl)-4-[3,6-difluoro-4- --.
    Line 22, that portion reading "-4-113,6-difluoro-4-" should read
-- -4-[3,6-difluoro-4- --.

Column 207, claim 5
    Line 33, that portion reading "2(3H-one;" should read -- 2 (3H)-one; --.

Column 208, claim 5
    Line 3, that portion reading "7,3-(4-chloro" should read -- 3-(4-chloro --.
    Line 27, that portion reading "[3,5-oxo" should read -- [2-oxo --.
    Line 60, that portion reading "2,3-difluoro" should read -- 2,6-difluoro --.

Column 209, claim 5
    Line 5, that portion reading "2,3-difluoro" should read -- 2,6-difluoro --.
    Line 9, that portion reading "-3-oxazol" should read -- -1,3-oxazol --.
    Line 10, that portion reading "2,3-difluoro" should read -- 2,6-difluoro --.
    Line 47, that portion reading "-3-oxazol" should read -- -1,3-oxazol --.

UNITED STATES PATENT AND TRADEMARK OFFICE
CERTIFICATE OF CORRECTION

PATENT NO.        : 6,699,884 B2
APPLICATION NO. : 10/319916
DATED             : March 2, 2004
INVENTOR(S)      : David L. Brown et al.

It is certified that error appears in the above-identified patent and that said Letters Patent is hereby corrected as shown below:

Column 210, claim 5
    Line 51, that portion reading "-4-[flurophenyl)" should read
-- -4-fluorophenyl) --.
    Lines 57-58, that portion reading "-4-t-methylsulfonyl)" should read
-- -4-(methylsulfonyl) --.

Column 215, claim 6
    Line 46, that portion reading "oxo-2,>" should read -- oxo-2,3- --.

Column 216, claim 6
    Lines 45 and 47, that portion reading "(3K)-one;" should read -- (3H)-one; --.

Column 217, claim 6
    Line 14, that portion reading "[3,5-difluoro" should read -- [3,6-difluoro --.
    Line 54, delete that portion reading "Image Page 134".

Column 218, claim 6
    Line 1, that portion reading "difluoro-4" should read -- difluoro-4- --.
    Line 23, that portion reading "[3,5-difluoro" should read -- [3,6-difluoro --.
    Line 38, that portion reading "7,3-(4-methyl" should read -- 3-(4-methyl --.
    Line 57, that portion reading "(2-methylpyridin)" should read
-- (2-methylpyridin-6-yl) --.

UNITED STATES PATENT AND TRADEMARK OFFICE
CERTIFICATE OF CORRECTION

PATENT NO.         : 6,699,884 B2
APPLICATION NO. : 10/319916
DATED              : March 2, 2004
INVENTOR(S)        : David L. Brown et al.

It is certified that error appears in the above-identified patent and that said Letters Patent is hereby corrected as shown below:

<u>Column 219, claim 6</u>
    Line 1, that portion reading "93-(3-pyridinyl)" should read -- 3-(3-pyridinyl) --.
    Line 2, that portion reading "phenyl]-thiazol" should read
-- phenyl]-1,3-thiazol --.

Signed and Sealed this

Eighth Day of August, 2006

JON W. DUDAS
*Director of the United States Patent and Trademark Office*